US012735433B2

(12) United States Patent
Agejas Chicharro et al.

(10) Patent No.: US 12,735,433 B2
(45) Date of Patent: Sep. 15, 2026

(54) MACROCYCLIC GLUCAGON-LIKE PEPTIDE 1 RECEPTOR AGONISTS

(71) Applicant: Eli Lilly and Company, Indianapolis, IN (US)

(72) Inventors: Francisco Javier Agejas Chicharro, Alcobendas (ES); Renato Alejandro Bauer, Zionsville, IN (US); Michael Gregory Bell, Fishers, IN (US); Qi Chen, Carmel, IN (US); Graham Robert Cumming, Alcobendas (ES); Todd Fields, New Palestine, IN (US); Douglas Linn Gernert, Fishers, IN (US); Joseph Daniel Ho, San Diego, CA (US); Talbi Abelkader Kaoudi, Alcobendas (ES); Thierry Jean Masquelin, Sandy, UT (US); Jose Miguel Minguez Ortega, Alcobendas (ES); Julian Priego Soler, Alcobendas (ES); Antonio Rodriguez Hergueta, Alcobendas (ES); Eric Michael Woerly, Indianapolis, IN (US)

(73) Assignee: ELI LILLY AND COMPANY, Indianapolis, IN (US)

( * ) Notice: Subject to any disclaimer, the term of this patent is extended or adjusted under 35 U.S.C. 154(b) by 369 days.

(21) Appl. No.: 18/562,568

(22) PCT Filed: May 19, 2022

(86) PCT No.: PCT/US2022/029958

§ 371 (c)(1),
(2) Date: Nov. 20, 2023

(87) PCT Pub. No.: WO2022/246019

PCT Pub. Date: Nov. 24, 2022

(65) Prior Publication Data

US 2024/0343740 A1 Oct. 17, 2024

Related U.S. Application Data

(60) Provisional application No. 63/191,034, filed on May 20, 2021.

(30) Foreign Application Priority Data

Dec. 21, 2021 (EP) .................................... 21383172

(51) Int. Cl.

| | |
|---|---|
| *C07D 498/08* | (2006.01) |
| *A61K 31/40* | (2006.01) |
| *A61K 31/444* | (2006.01) |
| *A61K 31/529* | (2006.01) |
| *C07D 498/18* | (2006.01) |
| *C07D 519/00* | (2006.01) |

(52) U.S. Cl.

CPC ............ *C07D 498/08* (2013.01); *A61K 31/40* (2013.01); *A61K 31/444* (2013.01); *A61K 31/529* (2013.01); *C07D 498/18* (2013.01); *C07D 519/00* (2013.01)

(58) Field of Classification Search

None

See application file for complete search history.

(56) References Cited

U.S. PATENT DOCUMENTS

| | | | |
|---|---|---|---|
| 2004/0127504 | A1 | 7/2004 | Cowart et al. |
| 2023/0203023 | A1 | 6/2023 | Jiang et al. |

FOREIGN PATENT DOCUMENTS

| | | | |
|---|---|---|---|
| CN | 113480534 | A | 10/2021 |
| CN | 113493447 | A | 10/2021 |
| CN | 113801136 | A | 12/2021 |
| CN | 113816948 | A | 12/2021 |
| CN | 114478497 | A | 5/2022 |
| CN | 114591296 | A | 6/2022 |
| CN | 114634510 | A | 6/2022 |
| CN | 114763352 | A | 7/2022 |
| CN | 114805336 | A | 7/2022 |
| CN | 114907351 | A | 8/2022 |
| CN | 115594669 | A | 1/2023 |
| CN | 115703766 | A | 2/2023 |
| CN | 115703792 | A | 2/2023 |
| CN | 116102543 | A | 5/2023 |

(Continued)

OTHER PUBLICATIONS

Patent Cooperation Treaty International Search Report of the International Searching Authority pertaining to International Patent Application No. PCT/US2022/029958; International Filing Date: May 19, 2022; Date of Mailing: Aug. 29, 2022.

(Continued)

*Primary Examiner* — Adam C Milligan

*Assistant Examiner* — Jason M. Nolan

(74) *Attorney, Agent, or Firm* — Nicholas M. Kunz

(57) ABSTRACT

A compound of the formula: or a pharmaceutically acceptable salt thereof, and methods of using this compound for treating type II diabetes mellitus.

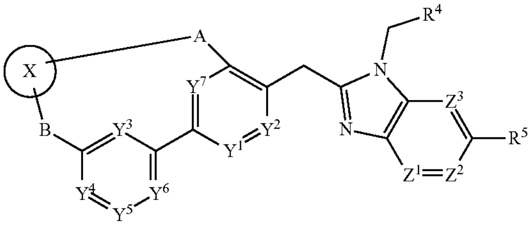

27 Claims, No Drawings

(56) References Cited

FOREIGN PATENT DOCUMENTS

| | | | |
|---|---|---|---|
| CN | 116120296 | A | 5/2023 |
| CN | 116217558 | A | 6/2023 |
| CN | 116354945 | A | 6/2023 |
| WO | 2011/143365 | A1 | 11/2011 |
| WO | 2013/090454 | A2 | 6/2013 |
| WO | 2018/109607 | A1 | 6/2018 |
| WO | 2019/239319 | A1 | 12/2019 |
| WO | 2019/239371 | A1 | 12/2019 |
| WO | 2020/103815 | A1 | 5/2020 |
| WO | 2020207474 | A1 | 10/2020 |
| WO | 2020/263695 | A1 | 12/2020 |
| WO | 2021/018023 | A1 | 2/2021 |
| WO | 2021081207 | A1 | 4/2021 |
| WO | 2021/096284 | A1 | 5/2021 |
| WO | 2021/096304 | A1 | 5/2021 |
| WO | 2021/112538 | A1 | 6/2021 |
| WO | 2021/154796 | A1 | 8/2021 |
| WO | 2021/160127 | A1 | 8/2021 |
| WO | 2021/187886 | A1 | 9/2021 |
| WO | 2021/197464 | A1 | 10/2021 |
| WO | 2021/219019 | A1 | 11/2021 |
| WO | 2021/244645 | A1 | 12/2021 |
| WO | 2021/249492 | A1 | 12/2021 |
| WO | 2021/254470 | A1 | 12/2021 |
| WO | 2021/259309 | A1 | 12/2021 |
| WO | 2022/007979 | A1 | 1/2022 |
| WO | 2022/028572 | A1 | 2/2022 |
| WO | 2022/031994 | A1 | 2/2022 |
| WO | 2022/040600 | A1 | 2/2022 |
| WO | 2022/042691 | A1 | 3/2022 |
| WO | 2022/068772 | A1 | 4/2022 |
| WO | 2022/078152 | A1 | 4/2022 |
| WO | 2022/078380 | A1 | 4/2022 |
| WO | 2022/078407 | A1 | 4/2022 |
| WO | 2022/109182 | A1 | 5/2022 |
| WO | 2022/111624 | A1 | 6/2022 |
| WO | 2022/116693 | A1 | 6/2022 |
| WO | 2022/135572 | A1 | 6/2022 |
| WO | 2022/165076 | A1 | 8/2022 |
| WO | 2022/184849 | A1 | 9/2022 |
| WO | 2022/192428 | A1 | 9/2022 |
| WO | 2022/192430 | A1 | 9/2022 |
| WO | 2022/199458 | A1 | 9/2022 |
| WO | 2022/199661 | A1 | 9/2022 |
| WO | 2022/202864 | A1 | 9/2022 |
| WO | 2022/216094 | A1 | 10/2022 |
| WO | 2022/219495 | A1 | 10/2022 |
| WO | 2022/225914 | A1 | 10/2022 |
| WO | 2022/225941 | A1 | 10/2022 |
| WO | 2022/228490 | A1 | 11/2022 |
| WO | 2022/235717 | A1 | 11/2022 |
| WO | 2022/268152 | A1 | 12/2022 |
| WO | 2023/000834 | A1 | 1/2023 |
| WO | 2023/001237 | A1 | 1/2023 |
| WO | 2023/011539 | A1 | 2/2023 |
| WO | 2023/025201 | A1 | 3/2023 |
| WO | 2023/029380 | A1 | 3/2023 |
| WO | 2023/049518 | A1 | 3/2023 |
| WO | 2023/057414 | A1 | 4/2023 |
| WO | 2023/057427 | A1 | 4/2023 |
| WO | 2023/057429 | A1 | 4/2023 |
| WO | 2023/066356 | A1 | 4/2023 |
| WO | 2023/111144 | A1 | 6/2023 |
| WO | 2023/111145 | A1 | 6/2023 |
| WO | 2023/138684 | A1 | 7/2023 |
| WO | 2023/151574 | A1 | 8/2023 |
| WO | 2023/151575 | A1 | 8/2023 |
| WO | 2023/164050 | A1 | 8/2023 |
| WO | 2023/164358 | A1 | 8/2023 |
| WO | 2023/169436 | A1 | 9/2023 |
| WO | 2023/179542 | A1 | 9/2023 |
| WO | 2023/198140 | A1 | 10/2023 |

OTHER PUBLICATIONS

Patent Cooperation Treaty Written Opinion of the International Searching Authority pertaining to International Patent Application No. PCT/US2022/029958; International Filing Date: May 19, 2022; Date of Mailing: Aug. 29, 2022.

MACROCYCLIC GLUCAGON-LIKE PEPTIDE 1 RECEPTOR AGONISTS

This invention relates to glucagon-like peptide-1 receptor agonists and therapeutic uses of the compounds to treat type II diabetes mellitus.

Glucagon-like peptide-1 (GLP-1) is a member of the incretin family of peptide hormones secreted by intestinal enteroendocrine L-cells. GLP-1 induces the release of insulin from beta cells in a glucose dependent manner. However, GLP-1 is rapidly metabolized so that only a small percentage of the GLP-1 can be utilized to induce insulin secretion. To offset this, GLP-1 receptor (GLP-1R) agonists have been developed to enhance insulin secretion as a treatment for type II diabetes mellitus.

The majority of GLP-1R agonists that have been approved to treat type II diabetes mellitus are injectable agents. Patients often prefer orally administered drugs because of the drawbacks associated with injection such as inconvenience, pain, and the potential for injection site irritation.

WO2018/109607 discloses certain benzimidazole derivatives, which are described as GLP-1R agonists. Further GLP-1 agonist compounds are disclosed in WO2019/239371, WO2019/239319, WO2020/103815, WO2020/207474, WO2020/263695, WO2021/018023, WO2021/081207, WO2021/096284, WO2021/096304, WO2021/112538, WO2021/154796, WO2021/160127, WO2021/187886, WO2021/197464, CN113480534, WO2021/219019, WO2021/244645, WO2021/249492, CN113801136, WO2021/254470, WO2021/259309, WO2022/007979, WO2022/031994, WO2022/028572, WO2022/040600, WO2022/042691, WO2022/068772, WO2022/078407, WO2022/078380 and WO2022/078152.

However, there is a need for alternative GLP-1R agonists. In particular, there is a need for GLP-1R agonists which can be administered orally. There is especially a need for potent GLP-1R agonists which have a favorable toxicology profile and/or a pharmacokinetic profile which supports once daily dosing.

Accordingly, the present invention provides a compound of the formula:

Formula IX

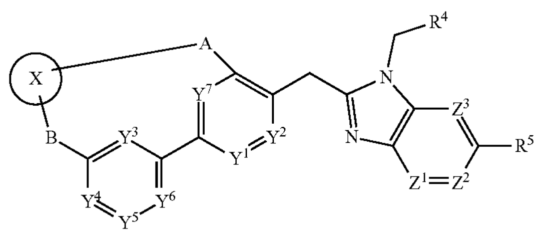

wherein -A- is —$CR^aR^bCR^aR^bCR^bR^bO$—, —$OCR^bR^bCR^aR^bCR^aR^b$—, —$OCR^bR^bCR^bR^b$, —$CR^aR^bCR^bR^bOCR^bR^b$—, —$CR^bR^bOCR^bR^bCR^aR^b$—, —$CR^bR^bOCR^bR^b$, —$CR^aR^bCR^bR^bO$—, or —$OCR^bR^bCR^aR^b$—.

$R^a$ at each occurrence is independently H, halo, $C_1$-$C_2$alkyl, OH or $C_1$-$C_3$alkoxy;

$R^b$ at each occurrence is independently H, halo or $C_1$-$C_2$alkyl;

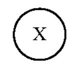

is

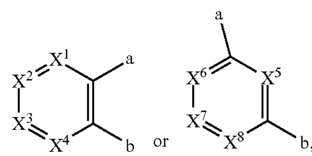

wherein a is the point of attachment to linker A;

b is the point of attachment of linker B;

$X^1$, $X^2$, $X^3$ and $X^4$ are independently N, CH or $CR^1$, wherein no more than two of $X^1$, $X^2$, $X^3$ and $X^4$ are N and no more than two of $X^1$, $X^2$, $X^3$ and $X^4$ are $CR^1$;

$X^5$ is N, CH or $CR^{1a}$, $X^6$, $X^7$ and $X^8$ are independently N, CH or $CR^1$, wherein no more than two of $X^5$, $X^6$, $X^7$ and $X^8$ are N and no more than two of $X^5$, $X^6$, $X^7$ and $X^8$ are $CR^{1a}$ or $CR^1$;

$R^1$ at each occurrence is independently CN; halo; $C_1$-$C_3$alkyl optionally substituted with OH; $C_1$-$C_3$haloalkyl; $C_1$-$C_3$alkoxy; $C_3$-$C_5$cycloalkyl; —$SO_2C_1$-$C_3$alkyl;

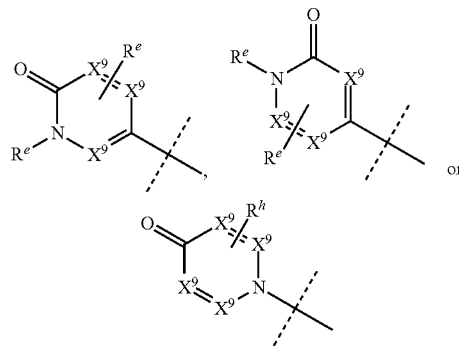

wherein each $X^9$ is independently CH or N and no more than one $X^9$ in the ring is N, each R is independently selected from: H, $C_1$-$C_3$haloalkyl, halo, $C_3$-$C_5$cycloalkyl and $C_1$-$C_3$alkyl optionally substituted with OH, $R^h$ is H, $C_1$-$C_3$haloalkyl, halo, $C_3$-$C_5$cycloalkyl, OH, —$NR^cR^d$ or $C_1$-$C_3$alkyl optionally substituted with OH;

5- or 6-membered heteroaryl or phenyl wherein the heteroaryl or phenyl is optionally substituted with one or two substituents independently selected from: $C_1$-$C_3$alkoxy, $C_3$-$C_5$cycloalkyl, —$CH_2$—$C_3$-$C_5$cycloalkyl, —$SO_2C_1$-$C_3$alkyl, $C_4$-$C_5$heterocyclyl, —$CH_2$—$C_4$-$C_5$heterocyclyl, halo, $C_1$-$C_3$haloalkyl, $C_1$-$C_3$haloalkoxy, CN, —$CONR^cR^d$, —$NR^cR^d$ or $C_1$-$C_3$alkyl optionally substituted with OH;

$R^{1a}$ is CN; halo; $C_1$-$C_3$alkyl optionally substituted with OH; $C_1$-$C_3$haloalkyl; or $C_1$-$C_3$alkoxy;

—B— is —$CH_2O$—, —$OCH_2$— or —$CH_2NH$—;

$Y^1$, $Y^2$ and $Y^7$ are independently N, CH or $CR^2$, wherein no more than one of $Y^1$, $Y^2$ and $Y^7$ is N and no more than two of $Y^1$, $Y^2$ and $Y^7$ is $CR^2$;

$Y^3$, $Y^4$, $Y^5$ and $Y^6$ are independently N, CH or $CR^2$, wherein no more than two of $Y^3$, $Y^4$, $Y^5$ and $Y^6$ are N and no more than two of $Y^3$, $Y^4$, $Y^5$ and $Y^6$ are $CR^2$;

$R^2$ at each occurrence is independently halo or methyl;

$Z^1$, $Z^2$ and $Z^3$ are independently N, CH or $CR^3$, wherein no more than two of $Z^1$, $Z^2$ and $Z^3$ are N and no more than two of $Z^1$, $Z^2$ and $Z^3$ are $CR^3$;

$R^3$ at each occurrence is independently halo; $C_1$-$C_4$alkyl; —$OC_4$-$C_6$cycloalkyl optionally substituted with $C_1$-$C_2$alkoxy, OH, $C_1$-$C_3$alkyl or $C_1$-$C_3$haloalkyl; —$OC_4$-$C_6$heterocyclyl optionally substituted with $C_1$-$C_2$alkoxy, OH, $C_1$-$C_3$alkyl or $C_1$-$C_3$haloalkyl; or $C_1$-$C_4$alkoxy optionally substituted with one or two substituents selected from: $C_1$-$C_2$alkoxy, OH, —$NR^fR^g$, —$CONR^cR^d$, CN, halo or 5- or 6-membered heteroaryl optionally substituted with $C_1$-$C_3$alkyl;

$R^4$ is

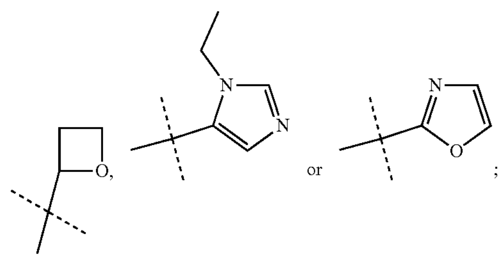

$R^5$ is —$CO_2H$,

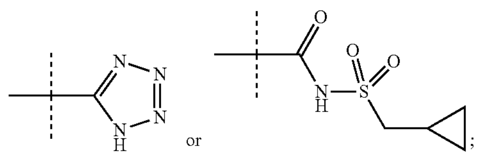

$R^c$ and $R^d$ are each independently H or $C_1$-$C_3$alkyl;

$R^f$ is H or $C_1$-$C_3$alkyl; and $R^g$ is H, $C_1$-$C_3$alkyl, $C_1$-$C_3$haloalkyl, $C_3$-$C_5$cycloalkyl, $C(O)C_1$-$C_3$alkyl, or $C_1$-$C_3$alkyl$C_3$-$C_5$cycloalkyl;

or a pharmaceutically acceptable salt thereof.

Formula IX includes all individual enantiomers, and mixtures thereof, as well as racemates.

In an embodiment, there is provided a compound of the formula:

Formula X

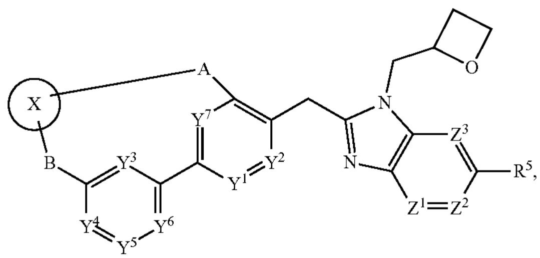

or a pharmaceutically acceptable salt thereof.

In an embodiment, there is provided a compound of the formula:

Formula Va

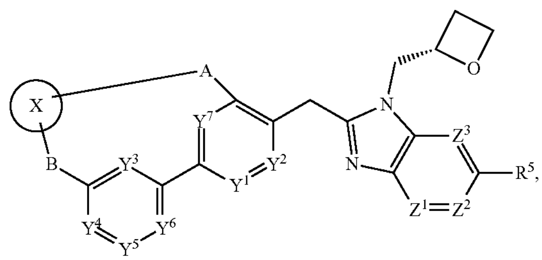

or a pharmaceutically acceptable salt thereof.

In an embodiment, there is provided a compound of the formula:

Formula VI

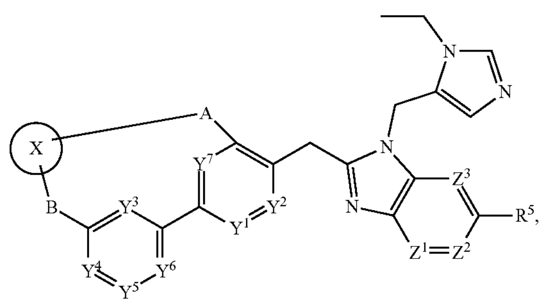

or a pharmaceutically acceptable salt thereof.

In an embodiment of Formula V, Va and VI, $Y^4$, $Y^5$, $Y^6$ and $Y^7$ are all CH.

In an embodiment,

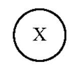

is

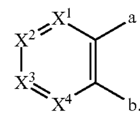

In one embodiment,

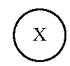

is

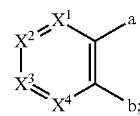

$X^1$, $X^3$ and $X^4$ are CH; and $X^2$ is $CR^1$. In an alternate embodiment,

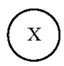

is

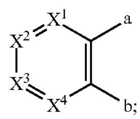

$X^1$ is N; $X^2$ is $CR^1$; and $X^3$ and $X^4$ are CH. In a further alternate embodiment,

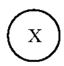

is

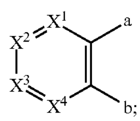

$X^1$, $X^3$ and $X^4$ are CH; and $X^2$ is N. In a further alternate embodiment,

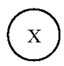

is

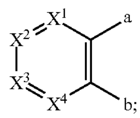

$X^1$ and $X^4$ are CH; $X^2$ is $CR^1$; and $X^3$ is N. In a further alternate embodiment,

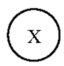

is

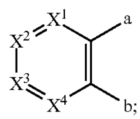

$X^1$ and $X^3$ are CH; $X^2$ is $CR^1$; and $X^4$ is N. In a further alternate embodiment,

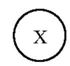

is

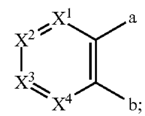

$X^1$ and $X^3$ are CH; and $X^2$ and $X^4$ are $CR^1$.

In an embodiment, only one of $X^1$, $X^2$, $X^3$ and $X^4$ is N.

In an alternate embodiment

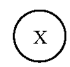

is

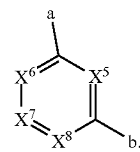

In one embodiment,

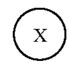

is

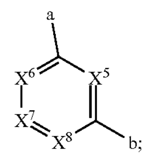

$X^5$, $X^7$ and $X^8$ are CH; and $X^6$ is $CR^1$. In an alternate embodiment,

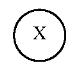

is

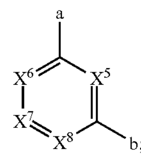

$X^5$ is N; $X^6$ is $CR^1$; and $X^7$ and $X^8$ are CH.

In an embodiment, only one of $X^5$, $X^6$, $X^7$ and $X^8$ is N.

In an embodiment, $R^1$ is CN; halo; $C_1$-$C_3$alkyl optionally substituted with OH; $C_1$-$C_3$haloalkyl;

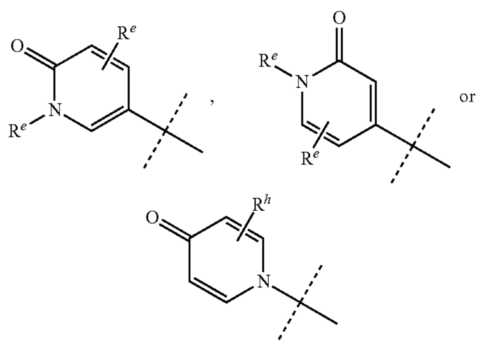

wherein each $R^e$ is independently selected from: H, $C_1$-$C_3$alkyl or halo, and $R^h$ is H or halo;

- 5- or 6-membered heteroaryl or phenyl wherein the heteroaryl or phenyl is optionally substituted with one substituent selected from: $C_1$-$C_3$alkoxy, $C_3$-$C_5$cycloalkyl, $-SO_2C_1$-$C_3$alkyl, $C_4$-$C_5$heterocyclyl, $-CH_2-C_4$-$C_5$heterocyclyl, halo, $-CONR^cR^d$, $-NR^cR^d$ or $C_1$-$C_3$alkyl optionally substituted with OH, wherein $R^c$ and $R^d$ are each independently H or $C_1$-$C_3$alkyl.

In an embodiment, $R^1$ is CN, halo, $CF_3$, $-CH_2OH$,

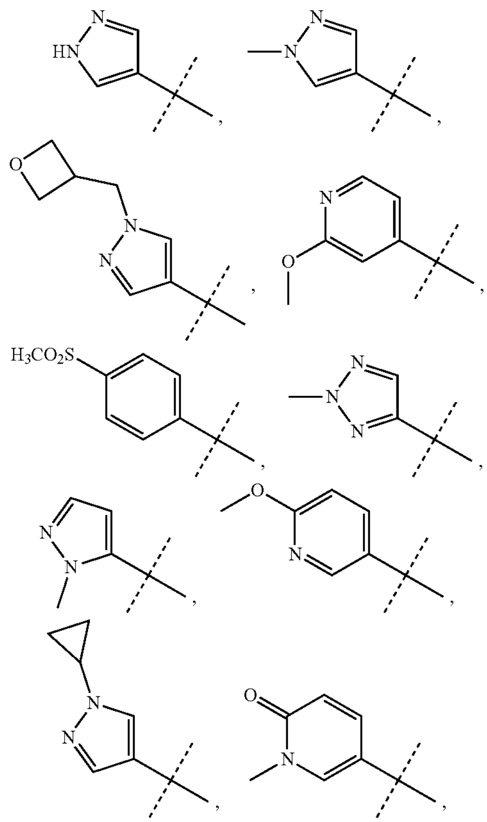

-continued

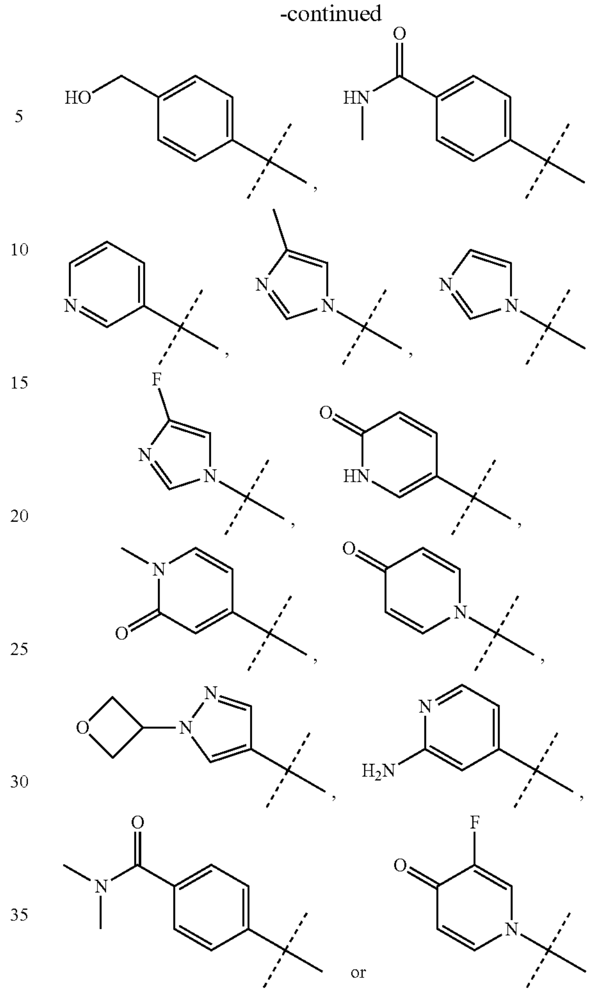

Preferably $R^1$ is CN, Cl, F, $CF_3$,

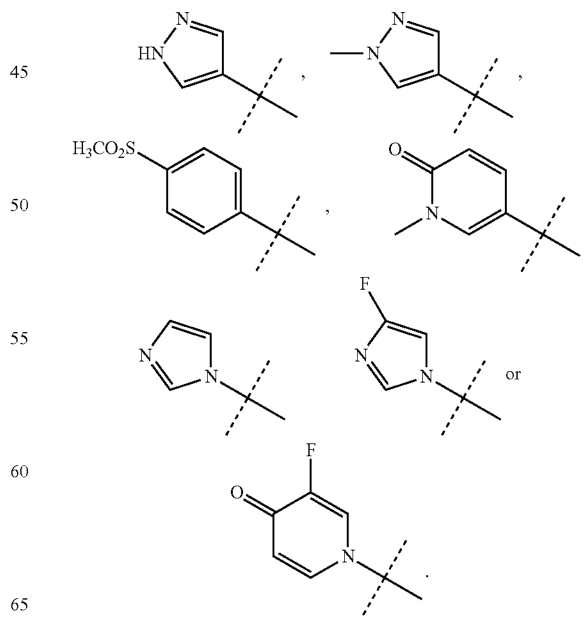

In an embodiment, $R^1$ is CN; halo; $C_1$-$C_3$alkyl optionally substituted with OH; $C_1$-$C_3$haloalkyl;

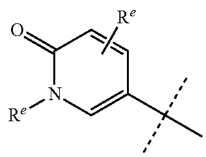

wherein each $R^e$ is independently selected from: H or $C_1$-$C_3$alkyl; 5- or 6-membered heteroaryl or phenyl wherein the heteroaryl or phenyl is optionally substituted with one substituent selected from: $C_1$-$C_3$alkoxy, $C_3$-$C_5$cycloalkyl, —$SO_2C_1$-$C_3$alkyl, —$CH_2$—$C_4$-$C_5$heterocyclyl, —$CONR^cR^d$ or $C_1$-$C_3$alkyl optionally substituted with OH, wherein $R^c$ and $R^d$ are each independently H or $C_1$-$C_3$alkyl. In an embodiment, $R^1$ is CN, halo, $CF_3$, —$CH_2OH$,

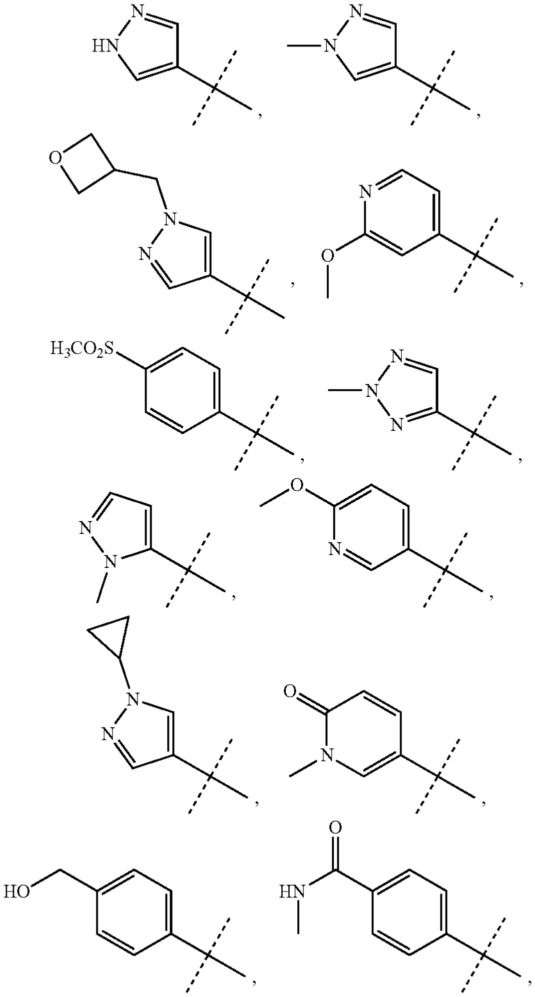

or

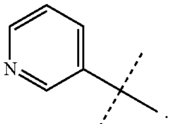

Preferably, $R^1$ is CN, Cl, F, $CF_3$,

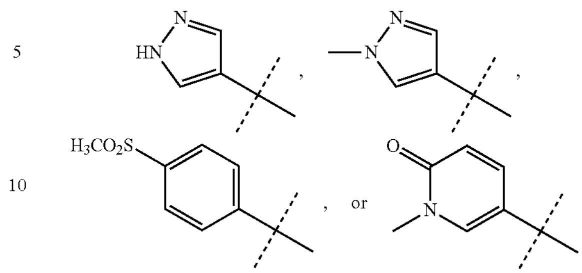

In a further embodiment, is $R^1$ is CN, halo, $C_1$-$C_3$alkyl or $C_1$-$C_3$haloalkyl. In an embodiment, $R^1$ is CN, halo or $CF_3$. In an embodiment, $R^1$ is CN or halo.

In one embodiment,

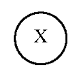

is

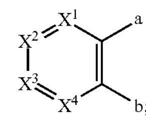

$X^1$, $X^3$ and $X^4$ are CH; $X^2$ is $CR^1$; and $R^1$ is CN; halo; $C_1$-$C_3$alkyl optionally substituted with OH; $C_1$-$C_3$haloalkyl;

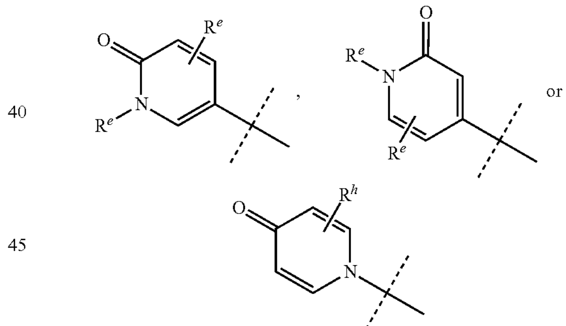

wherein each $R^e$ is independently selected from: H, $C_1$-$C_3$alkyl or halo, and $R^h$ is H or halo;

5- or 6-membered heteroaryl or phenyl wherein the heteroaryl or phenyl is optionally substituted with one substituent selected from: $C_1$-$C_3$alkoxy, $C_3$-$C_5$cycloalkyl, —$SO_2C_1$-$C_3$alkyl, $C_4$-$C_5$heterocyclyl, —$CH_2$—$C_4$-$C_5$heterocyclyl, halo, —$CONR^cR^d$, —$NR^cR^d$, or $C_1$-$C_3$alkyl optionally substituted with OH, wherein $R^c$ and $R^d$ are each independently H or $C_1$-$C_3$alkyl. Preferably, $R^1$ is CN, halo, $CF_3$, —$CH_2OH$,

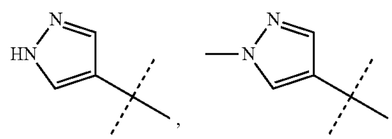

-continued

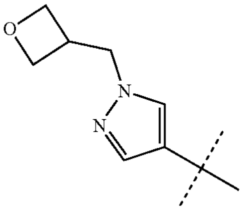, 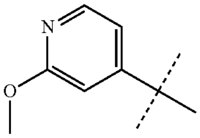,

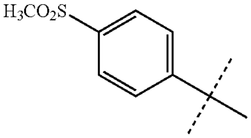, 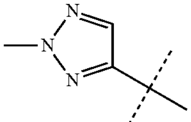,

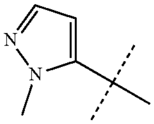, 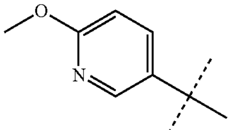,

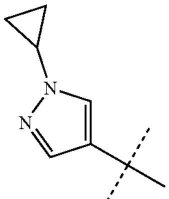, 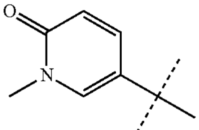,

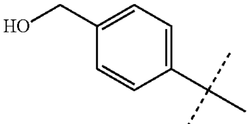, 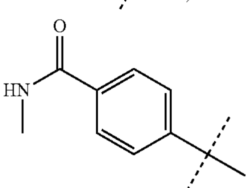,

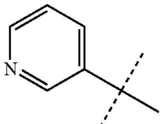, 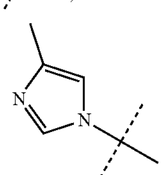, 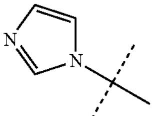,

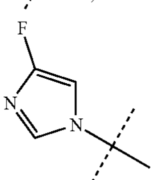, 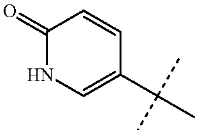,

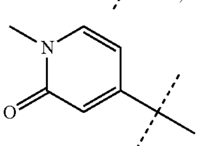, 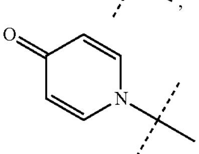,

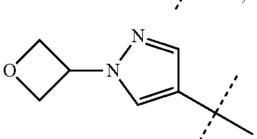, 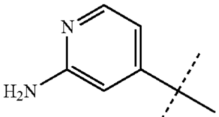,

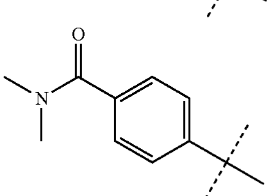 or 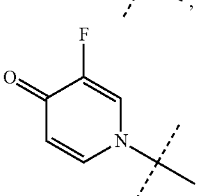.

More preferably, $R^1$ is CN, Cl, F, $CF_3$,

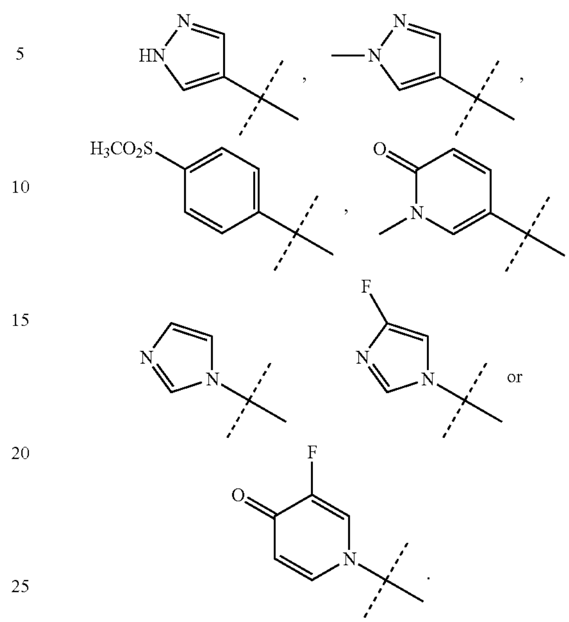

In one embodiment,

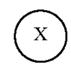

is

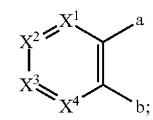

$X^1$, $X^3$ and $X^4$ are CH; $X^2$ is $CR^1$; and $R^1$ is CN; halo; $C_1$-$C_3$alkyl optionally substituted with OH; $C_1$-$C_3$haloalkyl;

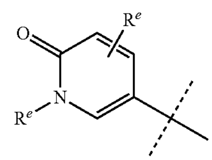

wherein each $R^e$ is independently selected from: H or $C_1$-$C_3$alkyl; 5- or 6-membered heteroaryl or phenyl wherein the heteroaryl or phenyl is optionally substituted with one substituent selected from: $C_1$-$C_3$alkoxy, $C_3$-$C_5$cycloalkyl, $—SO_2C_1$-$C_3$alkyl, $—CH_2—C_4$-$C_5$heterocyclyl, $—CONR^cR^d$ or $C_1$-$C_3$alkyl optionally substituted with OH, wherein $R^c$ and $R^d$ are each independently H or $C_1$-$C_3$alkyl. Preferably, $R^1$ is CN, halo, $CF_3$, $—CH_2OH$

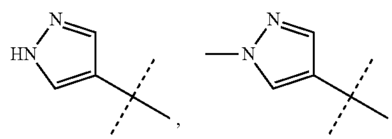

-continued

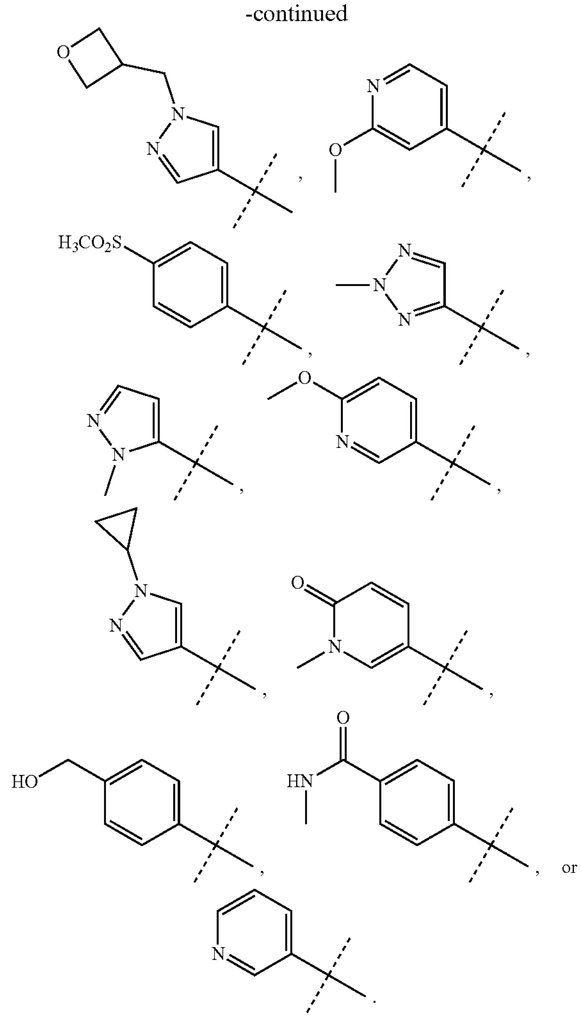

More preferably, $R^1$ is CN, Cl, F, $CF_3$,

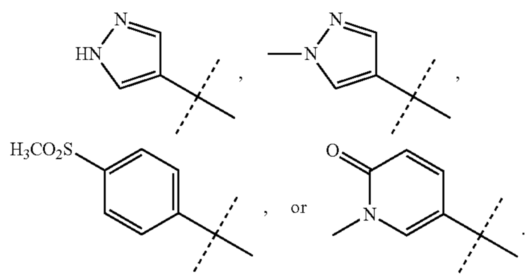

In a further embodiment, $X^1$, $X^3$ and $X^4$ are CH; $X^2$ is $CR^1$; and $R^1$ is CN. In a further embodiment, $X^1$, $X^3$ and $X^4$ are CH; $X^2$ is $CR^1$; and $R^1$ is Cl. In a further embodiment, $X^1$, $X^3$ and $X^4$ are CH; $X^2$ is $CR^1$; and $R^1$ is $CF_3$.

In an alternate embodiment,

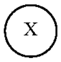

is

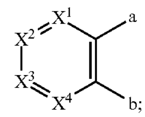

$X^1$ is N; $X^2$ is $CR^1$; $X^3$ and $X^4$ are CH; and $R^1$ is $CF_3$.

In an alternate embodiment,

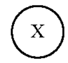

is

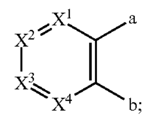

$X^1$ and $X^4$ are CH; $X^2$ is $CR^1$; $X^3$ is N; and $R^1$ is $CF_3$.

In an alternate embodiment,

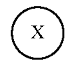

is

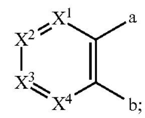

$X^1$ and $X^3$ are CH; $X^2$ is $CR^1$; $X^4$ is N; and $R^1$ is CN.

In an alternate embodiment,

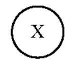

is

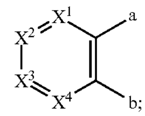

$X^1$ and $X^3$ are CH; $X^2$ and $X^4$ are $CR^1$; and each $R^1$ is independently selected from halo and CN. Preferably, each $R^1$ is independently selected from F, Cl and CN.

In an alternate embodiment,

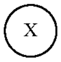

is

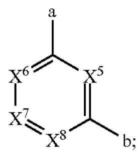

$X^5$, $X^7$ and $X^8$ are CH; $X^6$ is $CR^1$; and $R^1$ is CN or Cl. Particularly, $R^1$ is CN.

In an alternate embodiment,

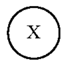

is

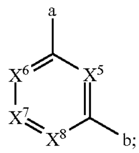

$X^5$ is N; $X^6$ is $CR^1$; $X^7$ and $X^8$ are CH; and $R^1$ is CN.

In an embodiment, -A- is —$CH_2CH_2CH_2O$—, —$OCH_2CH_2O$—, —$CH_2CH_2OCH_2$—, —$CH_2OCH_2CH_2$—, —$CH_2OCH_2$—, —$CH_2CH_2O$—, —$OCH_2CH_2$— or —$CF_2CH_2OCH_2$—. In a particular embodiment, -A- is —$CH_2CH_2CH_2O$—, —$CH_2OCH_2$—, —$CH_2CH_2OCH_2$—, $CH_2OCH_2CH_2$— or —$CF_2CH_2OCH_2$—.

In an embodiment, -A- is —$CHR^aCHR^aCHR^bO$—, —$CHR^bOCHR^b$— or —$OCHR^bCHR^bO$—. In a further embodiment, -A- is —$CHR^aCHR^aCHR^bO$—. In a particular embodiment, -A- is —$CHR^aCHR^aCHR^bO$— and each $R^a$ and $R^b$ is H. In an alternate embodiment, -A- is —$CHR^bO$-$CHR^b$—. In a particular embodiment, -A- is —$CHR^bO$-$CHR^b$— and each $R^b$ is H. In an alternate embodiment, -A- is —$OCHR^bCHR^bO$—. In a particular embodiment, -A- is —$OCHR^bCHR^bO$— and each $R^b$ is H. In a particular embodiment, -A- is —$CH_2CH_2CH_2O$—, —$OCH_2CH_2O$—, —$CH_2CH_2OCH_2$—, —$CH_2OCH_2$—, or —$CH_2CH_2O$—; preferably, A- is —$CH_2CH_2CH_2O$— or —$CH_2OCH_2$—.

In an embodiment, —B— is —$CH_2O$— or —$CH_2NH$—. In an alternate embodiment, B is —$CH_2O$— or —$OCH_2$—. In a further embodiment, —B— is —$CH_2O$—.

In an embodiment, $Y^3$ is N or CH. In an embodiment, $Y^3$ is N. In an alternate embodiment, $Y^3$ is CH.

In an embodiment, $Y^4$ is CH.

In an embodiment, $Y^5$ is CH.

In an embodiment, $Y^6$ is CH or $CR^2$.

In an embodiment, $Y^3$ is N; and $Y^4$, $Y^5$ are CH; and $Y^6$ is CH or $CR^2$. In a further embodiment, $Y^3$ is N; and $Y^4$, $Y^5$ are CH; and $Y^6$ is CH. In yet a further embodiment, $Y^3$ is N; and $Y^4$, $Y^5$ are CH; and $Y^6$ is $CR^2$, preferably $R^2$ is F. In an alternate embodiment, $Y^3$, $Y^4$, $Y^5$ and $Y^6$ are all CH. In a further alternate embodiment, $Y^3$ and $Y^6$ are N; and $Y^4$ and $Y^5$ are CH.

In an embodiment, $Y^1$ is CH or $CR^2$.

In an embodiment, $Y^2$ is CH.

In an embodiment, $Y^7$ is CH.

In an embodiment, $R^2$ is F or methyl.

In an embodiment, $Y^1$, $Y^2$ and $Y^7$ are all CH. In an alternate embodiment, $Y^1$ is $CR^2$; $Y^2$ is CH; $Y^7$ is CH; and $R^2$ is F. In a further alternate embodiment, $Y^1$ is $CR^2$; $Y^2$ is CH; $Y^7$ is CH; and $R^2$ is methyl.

In an embodiment, $Y^1$ and $Y^2$ are both CH. In an alternate embodiment, $Y^1$ is $CR^2$, $Y^2$ is CH and $R^2$ is F. In a further alternate embodiment, $Y^1$ is $CR^2$, $Y^2$ is CH and $R^2$ is methyl.

In an embodiment, $Y^4$, $Y^5$, $Y^6$ and $Y^7$ are all CH.

In an embodiment, $Z^1$ is CH or $CR^3$.

In an embodiment, $Z^2$ is CH.

In an embodiment, $Z^3$ is CH. In an alternate embodiment, $Z^3$ is N.

In a particular embodiment, $Z^2$ and $Z^3$ are both CH.

In an embodiment, $R^3$ is halo; —$OC_4$-$C_6$heterocyclyl optionally substituted with $C_1$-$C_3$alkyl; or $C_1$-$C_4$alkoxy optionally substituted with one or two substituents selected from: $C_1$-$C_2$alkoxy, OH, —$NR^fR^g$, —$CONR^cR^d$ or 5- or 6-membered heteroaryl optionally substituted with $C_1$-$C_3$alkyl; wherein $R^c$ and $R^d$ are each independently H or $C_1$-$C_3$alkyl, $R^f$ is H or $C_1$-$C_3$alkyl, and $R^g$ is H, $C_1$-$C_3$alkyl or $C_1$-$C_3$haloalkyl. In a particular embodiment, $R^3$ is halo or $C_1$-$C_4$alkoxy optionally substituted with one or two substituents selected from: $C_1$-$C_2$alkoxy, OH, or —$NR^fR^g$, wherein $R_f$ and $R_g$ are both $CH_3$; preferably, $R^3$ is F, —$OCH_3$, —$OCH_2CH_2OCH_3$, $OCH_2CH_2OH$ or $OCH_2CH_2N(CH_3)_2$.

In an embodiment, $R^3$ is halo, $C_1$-$C_4$alkoxy or —$C_1$-$C_3$alkoxy$C_1$-$C_2$alkoxy; preferably, $R^3$ is F, —$OCH_3$ or —$OCH_2CH_2OCH_3$. In an alternate embodiment, $R^3$ is halo, $C_1$-$C_2$alkyl or methoxy.

In an embodiment, $Z^1$ is $CR^3$ and $R^3$ is halo; —$OC_4$-$C_6$heterocyclyl optionally substituted with $C_1$-$C_3$alkyl; or $C_1$-$C_4$alkoxy optionally substituted with one or two substituents selected from: $C_1$-$C_2$alkoxy, OH, —$NR^fR^g$, —$CONR^cR^d$ or 5- or 6-membered heteroaryl optionally substituted with $C_1$-$C_3$alkyl; wherein $R^c$ and $R^d$ are each independently H or $C_1$-$C_3$alkyl, $R^f$ is H or $C_1$-$C_3$alkyl, and $R^g$ is H, $C_1$-$C_3$alkyl or $C_1$-$C_3$haloalkyl. In a further embodiment, $Z^1$ is $CR^3$ and $R^3$ is halo or $C_1$-$C_4$alkoxy optionally substituted with one or two substituents selected from: $C_1$-$C_2$alkoxy, OH, or —$NR^fR^g$, wherein $R_f$ and $R_g$ are both $CH_3$; preferably, $R^3$ is F, —$OCH_3$, —$OCH_2CH_2OCH_3$, $OCH_2CH_2OH$ or $OCH_2CH_2N(CH_3)_2$. In one embodiment, $Z^1$ is $CR^3$ and $R^3$ is F. In an alternate embodiment, $Z^1$ is CH. In a further alternate embodiment, $Z^1$ is $CR^3$ and $R^3$ is methoxy.

In an embodiment, $R^5$ is —$CO_2H$. In an alternate embodiment, $R^5$ is

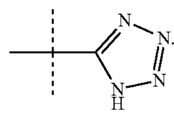

In an embodiment, there is provided a compound of the formula:

Formula VIII

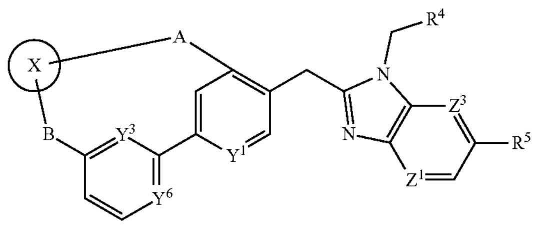

wherein -A- is $—CH_2CH_2CH_2O—$, $—OCH_2CH_2O—$, $—CH_2CH_2OCH_2—$, $—CH_2OCH_2CH_2—$, $—CH_2OCH_2—$, $—CH_2CH_2O—$, $—OCH_2CH_2—$ or $—CF_2CH_2OCH_2—$;

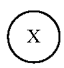

is

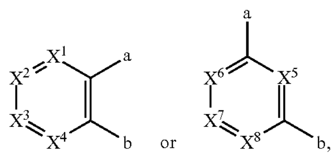

wherein a is the point of attachment to linker A; b is the point of attachment of linker B;

$X^1$, $X^2$, $X^3$ and $X^4$ are independently N, CH or $CR^1$, wherein no more than one of $X^1$, $X^2$, $X^3$ and $X^4$ is N and no more than two of $X^1$, $X^2$, $X^3$ and $X^4$ are $CR^1$;

$X^5$ is N or CH, $X^6$, $X^7$ and $X^8$ are independently N, CH or $CR^1$, wherein no more than one of $X^5$, $X^6$, $X^7$ and $X^8$ is N and no more than one of $X^6$, $X^7$ and $X^8$ is $CR^1$;

$R^1$ at each occurrence is independently CN; halo; $C_1$-$C_3$alkyl optionally substituted with OH; $C_1$-$C_3$haloalkyl;

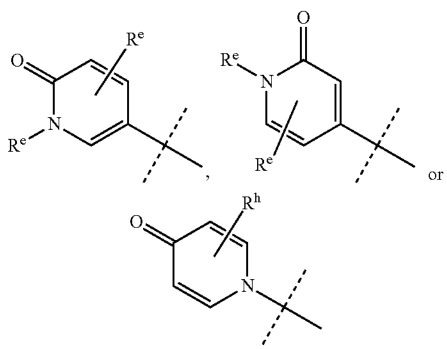

wherein each $R^e$ is independently selected from: H, $C_1$-$C_3$alkyl or halo, and $R^h$ is H or halo; 5- or 6-membered heteroaryl or phenyl wherein the heteroaryl or phenyl is optionally substituted with one substituent selected from: $C_1$-$C_3$alkoxy, $C_3$-$C_5$cycloalkyl, $—SO_2C_1$-$C_3$alkyl, $C_4$-$C_5$heterocyclyl, $—CH_2—C_4$-$C_5$heterocyclyl, halo, $—CONR^cR^d$, $—NR^eR^d$ or $C_1$-$C_3$alkyl optionally substituted with OH;

—B— is $—CH_2O—$, or $—CH_2NH—$;

$Y^1$ is CH or $CR^2$;

$Y^3$ is N or CH;

$Y^6$ is N, CH or $CR^2$;

$R^2$ at each occurrence is independently halo or methyl;

$Z^1$ is CH or $CR^3$;

$Z^3$ is N or CH;

$R^3$ is halo; $—OC_4$-$C_6$heterocyclyl optionally substituted with $C_1$-$C_3$alkyl; or $C_1$-$C_4$alkoxy optionally substituted with one or two substituents selected from: $C_1$-$C_2$alkoxy, OH, $—NR^fR^g$, $—CONR^cR^d$ or 5- or 6-membered heteroaryl optionally substituted with $C_1$-$C_3$alkyl;

$R^4$ is

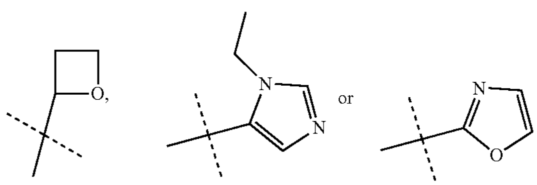

$R^5$ is $—CO_2H$,

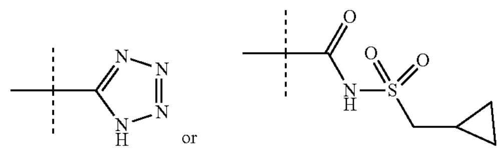

$R^c$ and $R^d$ are each independently H or $C_1$-$C_3$alkyl;

$R^f$ is H or $C_1$-$C_3$alkyl; and $R^g$ is H, $C_1$-$C_3$alkyl or $C_1$-$C_3$haloalkyl;

or a pharmaceutically acceptable salt thereof.

In one embodiment of Formula VIII, -A- is $—CH_2CH_2CH_2O—$, $—CH_2OCH_2—$, $—CH_2CH_2OCH_2—$, $CH_2OCH_2CH_2—$ or $—CF_2CH_2OCH_2—$.

In one embodiment of Formula VIII,

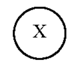

is

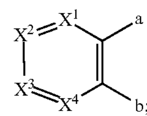

$X^1$, $X^3$ and $X^4$ are CH; and $X^2$ is $CR^1$. In an alternate embodiment of Formula VIII,

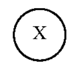

is

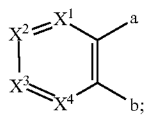

$X^1$ is N; $X^2$ is $CR^1$; and $X^3$ and $X^4$ are CH. In a further alternate embodiment of Formula VIII,

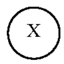

is

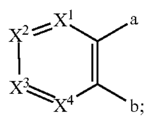

$X^1$, $X^3$ and $X^4$ are CH; and $X^2$ is N. In a further alternate embodiment of Formula VIII,

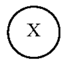

is

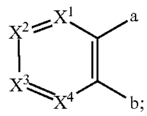

$X^1$ and $X^4$ are CH; $X^2$ is $CR^1$; and $X^3$ is N. In a further alternate embodiment of Formula VIII,

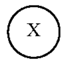

is

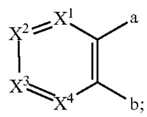

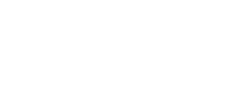

$X^1$ and $X^3$ are CH; $X^2$ is $CR^1$; and $X^4$ is N. In a further alternate embodiment of Formula VIII,

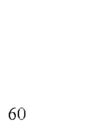

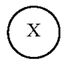

is

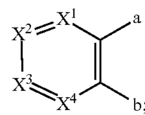

$X^1$ and $X^3$ are CH; and $X^2$ and $X^4$ are $CR^1$.

In one embodiment of Formula VIII,

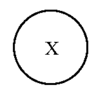

is

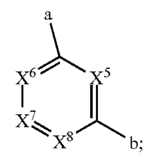

$X^5$, $X^7$ and $X^8$ are CH; and $X^6$ is $CR^1$. In an alternate embodiment of Formula VIII,

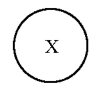

is

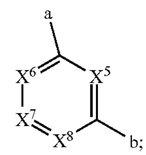

$X^5$ is N; $X^6$ is $CR^1$; and $X^7$ and $X^8$ are CH.

In one embodiment of Formula VIII, $R^1$ is CN, halo, $CF_3$, $-CH_2OH$,

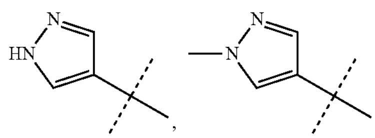

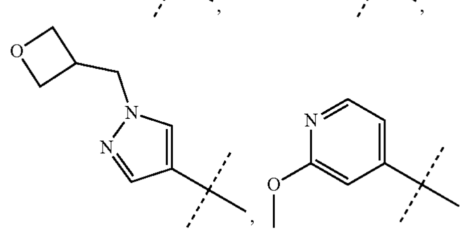

-continued
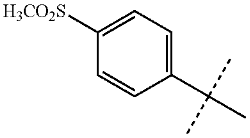,
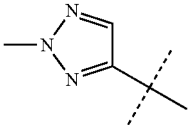,
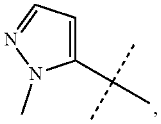,
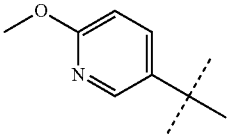,
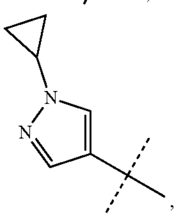,
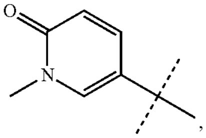,
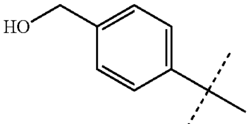,
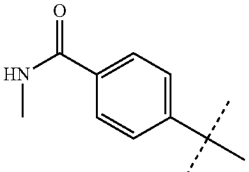,
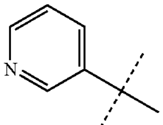,
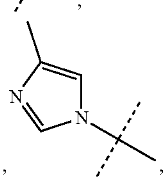,
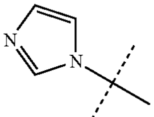,
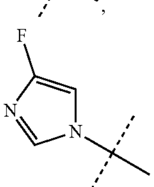,
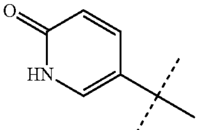,
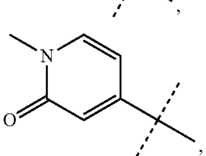,
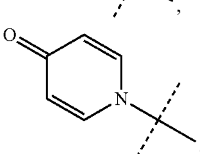,
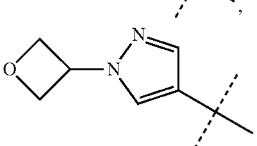,
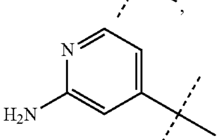,
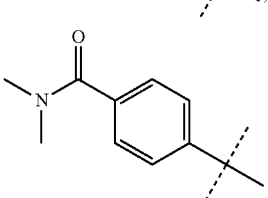 or
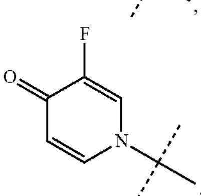.
Preferably, $R^1$ is CN, Cl, F, $CF_3$,
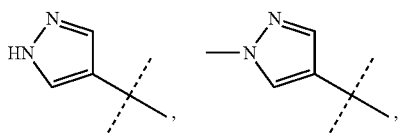
-continued
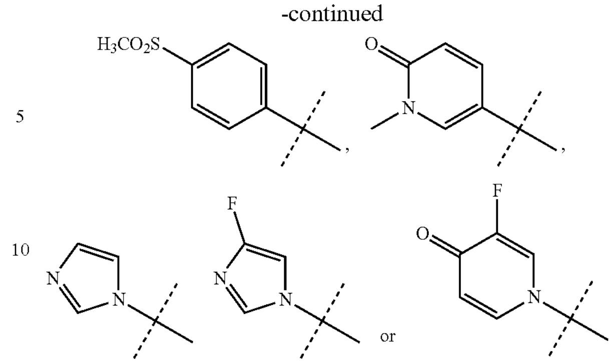
In one embodiment of Formula VIII,
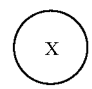
is
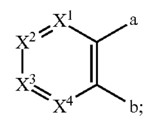
$X^1$, $X^3$ and $X^4$ are CH; $X^2$ is $CR^1$; and $R^1$ is CN, halo, $CF_3$, $—CH_2OH$,
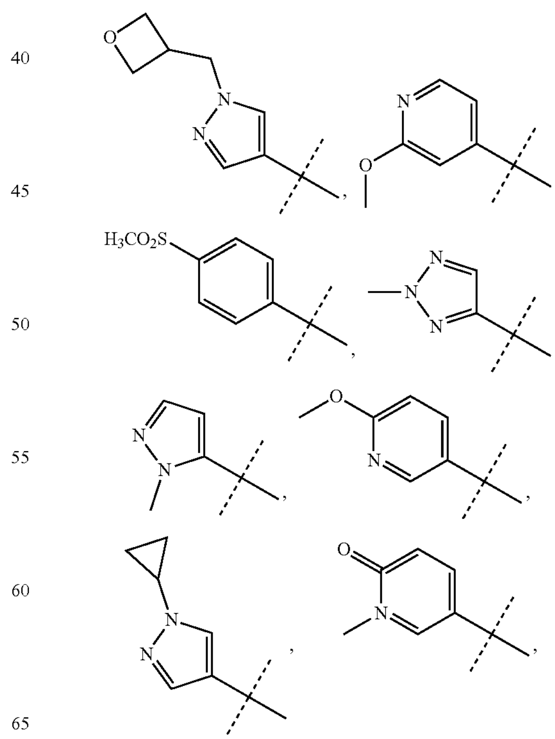

-continued

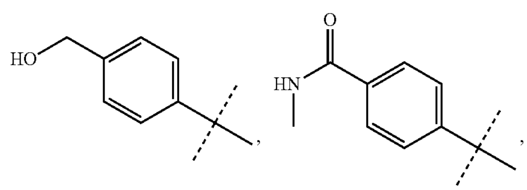

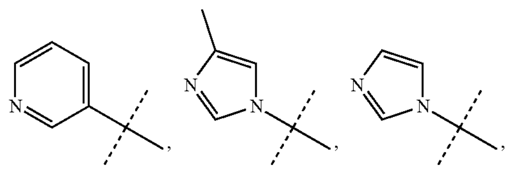

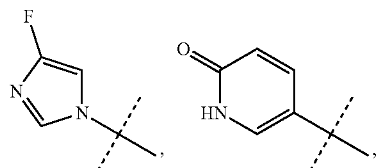

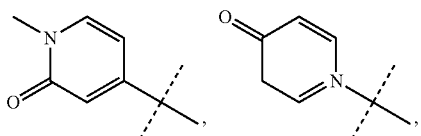

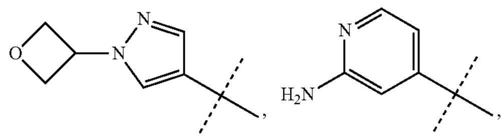

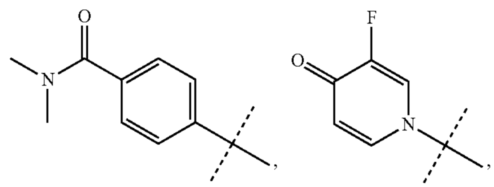

Preferably, $R^1$ is CN, Cl, F, $CF_3$,

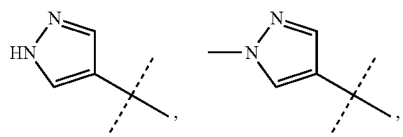

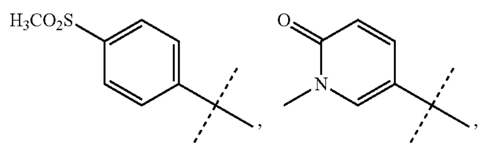

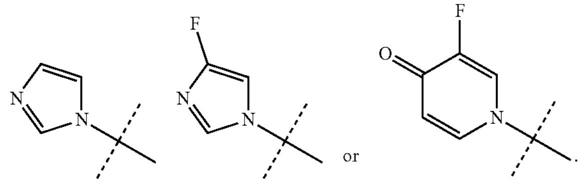

In an alternate embodiment of Formula VIII,

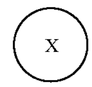

is

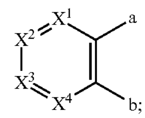

$X^1$ is N; $X^2$ is $CR^1$; $X^3$ and $X^4$ are CH; and $R^1$ is $CF_3$.

In an alternate embodiment of Formula VIII,

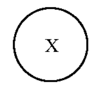

is

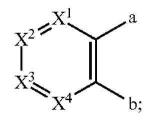

$X^1$, $X^3$ and $X^4$ are CH, and $X^2$ is N.

In an alternate embodiment of Formula VIII,

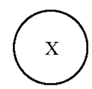

is

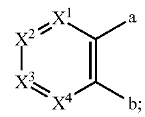

$X^1$ and $X^4$ are CH; $X^2$ is $CR^1$; $X^3$ is N; and $R^1$ is $CF_3$.

In an alternate embodiment of Formula VIII,

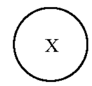

is

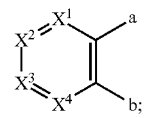

$X^1$ and $X^3$ are CH; $X^2$ is $CR^1$; $X^4$ is N; and $R^1$ is CN.

In an alternate embodiment of Formula VIII,

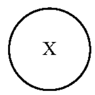

is

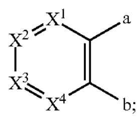

$X^1$ and $X^3$ are CH; $X^2$ and $X^4$ are $CR^1$; and each $R^1$ is independently selected from halo and CN. Preferably, each $R^1$ is independently selected from F, Cl and CN.

In an alternate embodiment of Formula VIII,

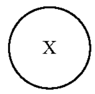

is

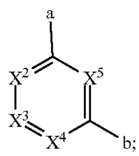

$X^5$, $X^7$ and $X^8$ are CH; $X^6$ is $CR^1$; and $R^1$ is CN or Cl. Particularly, $R^1$ is CN.

In an alternate embodiment of Formula VIII,

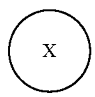

is

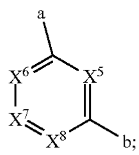

$X^5$ is N; $X^6$ is $CR^1$; $X^7$ and $X^8$ are CH; and $R^1$ is CN.

In one embodiment of Formula VIII, —B— is —$CH_2O$—.

In one embodiment of Formula VIII, $Y^6$ is CH or $CR^2$.

In one embodiment of Formula VIII, $R^2$ is F or methyl.

In one embodiment of Formula VIII, $Y^3$ is N and $Y^6$ is CH or $CR^2$. In a further embodiment of Formula VIII, $Y^3$ is N and $Y^6$ is CH. In yet a further embodiment, $Y^3$ is N and $Y^6$ is $CR^2$, preferably $R^2$ is F. In an alternate embodiment, $Y^3$ and $Y^6$ are both CH. In a further alternate embodiment, $Y^3$ and $Y^6$ are both N.

In one embodiment of Formula VIII, $Z^3$ is CH.

In one embodiment of Formula VIII, $R^3$ is halo or $C_1$-$C_4$alkoxy optionally substituted with one or two substituents selected from: $C_1$-$C_2$alkoxy, OH, or —$NR^fR^g$, wherein $R_f$ and $R_g$ are both $CH_3$; preferably, $R^3$ is F, —$OCH_3$, —$OCH_2CH_2OCH_3$, $OCH_2CH_2OH$ or $OCH_2CH_2N(CH_3)_2$.

In one embodiment of Formula VIII, $R^4$ is

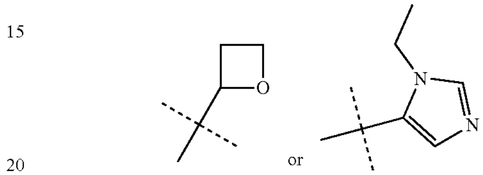

Certain compounds of Formula VIII have the following features:

i. -A- is —$CH_2CH_2CH_2O$—, —$CH_2OCH_2$—, —$CH_2CH_2OCH_2$—, $CH_2OCH_2CH_2$— or —$CF_2CH_2OCH_2$—;

ii.

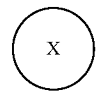

is

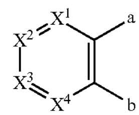

wherein $X^1$, $X^3$ and $X^4$ are CH, $X^2$ is $CR^1$, and $R^1$ is CN, Cl, F, $CF_3$,

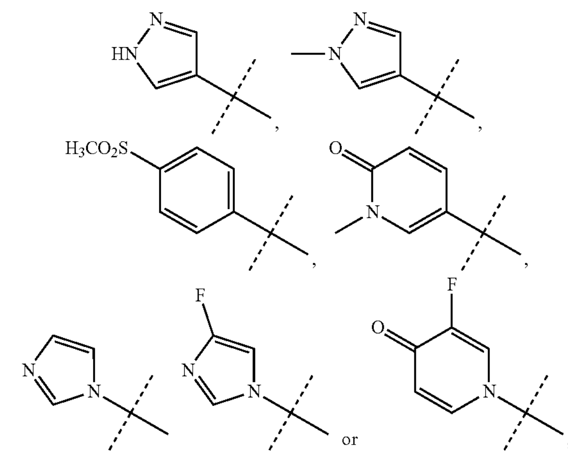

or wherein $X^1$ is N, $X^2$ is $CR^1$, $X^3$ and $X^4$ are CH, and $R^1$ is $CF_3$; or wherein $X^1$, $X^3$ and $X^4$ are CH, and $X^2$ is N;

or wherein $X^1$ and $X^4$ are CH, $X^2$ is $CR^1$, $X^3$ is N and $R^1$ is $CF_3$; or wherein $X^1$ and $X^3$ are CH, $X^2$ is $CR^1$, $X^4$ is N and $R^1$ is CN; or wherein $X^1$ and $X^3$ are CH, $X^2$ and $X^4$ are $CR^1$, and each $R^1$ is independently selected from F, Cl and CN;

or

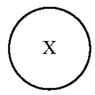

is

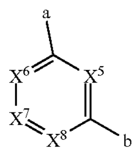

wherein $X^5$, $X^7$ and $X^8$ are CH, $X^6$ is $CR^1$, and $R^1$ is CN or $C_1$; or wherein $X^5$ is N, $X^6$ is $CR^1$, $X^7$ and $X^8$ are CH, and $R^1$ is CN;

iii. —B— is —$CH_2O$—;

iv. $Y^1$ is CH or $CR^2$, and $R^2$ is F or methyl;

v. $Y^6$ is CH or $CR^2$, and $R^2$ is F;

vi. $Z^3$ is CH;

vii. $Z^1$ is CH or $CR^3$, and $R^3$ is F, —$OCH_3$, —$OCH_2CH_2OCH_3$, $OCH_2CH_2OH$ or $OCH_2CH_2N(CH_3)_2$; and viii. $R^4$ is

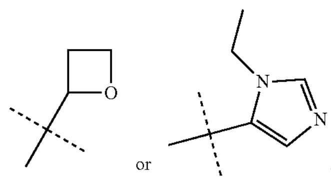

In an embodiment, there is provided a compound of the formula:

Formula VII

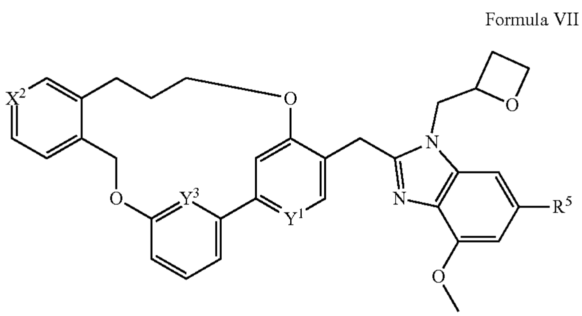

or a pharmaceutically acceptable salt thereof.

In a preferred embodiment, there is provided a compound of the formula:

Formula VIIa

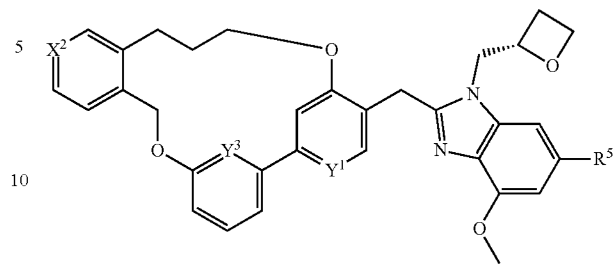

or a pharmaceutically acceptable salt thereof.

In one embodiment of Formula VII and VIIa, $X^2$ is $CR^1$ and $R^1$ is CN. In an alternate embodiment of Formula VII and VIIa, $X^2$ is $CR^1$ and $R^1$ is $CF_3$.

In one embodiment of Formula VII and VIIa, $Y^3$ is N. In an alternate embodiment, $Y^3$ is CH.

In one embodiment of Formula VII and VIIa, $Y^1$ is CH. In an alternate embodiment, $Y^1$ is $CR^2$ and $R^2$ is methyl.

In one embodiment of Formula VII and VIIa, $R^5$ is —$CO_2H$. In an alternate embodiment, $R^5$ is

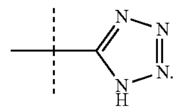

In an embodiment, there is provided a compound of the formula:

Formula IV

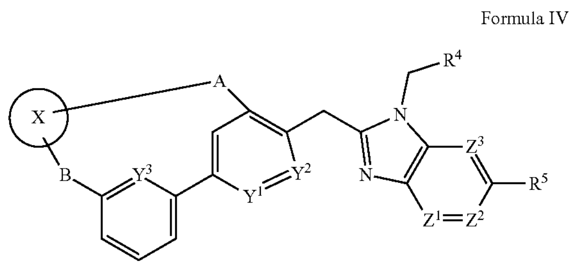

wherein -A- is —$CHR^aCHR^aCHR^bO$—, —$OCHR^bCHR^aCHR^a$—, —$OCHR^bCHR^bO$—, —$CHR^aCHR^bOCHR^b$—, —$CHR^bOCHR^bCHR^a$—, —$CHR^bOCHR^b$—, —$CHR^aCHR^bO$—, or —$OCHR^bCHR^a$—;

$R^a$ at each occurrence is independently H, halo, $C_1$-$C_2$alkyl or OH;

$R^b$ at each occurrence is independently H, halo or $C_1$-$C_2$alkyl;

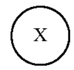

is

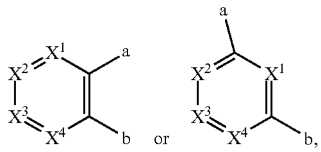

wherein a is the point of attachment to linker A; b is the point of attachment of linker B;

$X^1$, $X^2$, $X^3$ and $X^4$ are independently N, CH or $CR^1$, wherein no more than two of $X^1$, $X^2$, $X^3$ and $X^4$ are N and no more than two of $X^1$, $X^2$, $X^3$ and $X^4$ are $CR^1$;

$R^1$ is CN; halo; $C_1$-$C_3$alkyl optionally substituted with OH; $C_1$-$C_3$haloalkyl; $C_1$-$C_3$alkoxy; $C_3$-$C_5$cycloalkyl; —$SO_2C_1$-$C_3$alkyl;

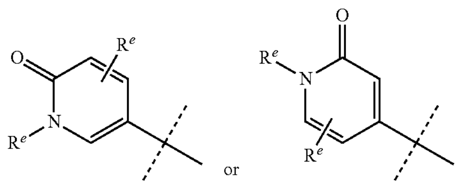

wherein each $R^e$ is independently selected from: H, $C_1$-$C_3$alkyl optionally substituted with OH, $C_1$-$C_3$haloalkyl, halo and $C_3$-$C_5$cycloalkyl; 5- or 6-membered heteroaryl or phenyl wherein the heteroaryl or phenyl is optionally substituted with one or two substituents independently selected from: $C_1$-$C_3$alkyl optionally substituted with OH, $C_1$-$C_3$alkoxy, $C_3$-$C_5$cycloalkyl, —$CH_2$—$C_3$-$C_5$cycloalkyl, —$SO_2C_1$-$C_3$alkyl, —$CH_2$—$C_4$-$C_5$heterocyclyl, halo, $C_1$-$C_3$haloalkyl, $C_1$-$C_3$haloalkoxy, CN or —$CONR^cR^d$ wherein $R^c$ and $R^d$ are each independently H or $C_1$-$C_3$alkyl;

—B— is —$CH_2O$—, —$OCH_2$— or —$CH_2NH$—;

$Y^1$ and $Y^2$ are independently N, CH or $CR^2$, wherein only one of $Y^1$ and $Y^2$ can be N;

$Y^3$ is N or CH;

$R^2$ is halo or methyl;

$Z^1$ is N, CH or $CR^3$;

$Z^2$ is CH or $CR^3$;

$Z^3$ is N, CH or $CR^3$;

$R^3$ is halo, $C_1$-$C_4$alkyl, $C_1$-$C_4$alkoxy or —$C_1$-$C_3$alkoxy$C_1$-$C_2$alkoxy;

$R^4$ is

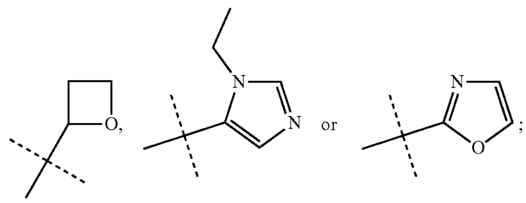

and $R^5$ is —$CO_2H$ or

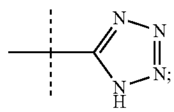

or a pharmaceutically acceptable salt thereof.

In an embodiment, there is provided a compound of Formula IV wherein -A- is —$CHR^aCHR^aCHR^bO$—, —$OCHR^bCHR^aCHR^a$—, —$OCHR^bCHR^bO$—, —$CHR^a$-$CHR^bOCHR^b$—, —$CHR^bOCHR^bCHR^a$—, —$CHR^bO$-$CHR^b$—, —$CHR^aCHR^bO$—, or —$OCHR^bCHR^a$;

$R^a$ at each occurrence is independently H, halo, $C_1$-$C_2$alkyl or OH;

$R^b$ at each occurrence is independently H, halo or $C_1$-$C_2$alkyl;

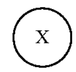

is

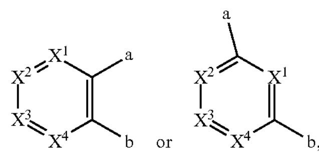

wherein a is the point of attachment to linker A; b is the point of attachment of linker B;

$X^1$, $X^2$, $X^3$ and $X^4$ are independently N, CH or $CR^1$, wherein no more than two of $X^1$, $X^2$, $X^3$ and $X^4$ can be N and no more than two of $X^1$, $X^2$, $X^3$ and $X^4$ can be $CR^1$;

$R^1$ is CN, halo, $C_1$-$C_3$alkyl or $C_1$-$C_3$haloalkyl;

—B— is —$CH_2O$—, —$OCH_2$— or —$CH_2NH$—;

$Y^1$ and $Y^2$ are independently N, CH or $CR^2$, wherein only one of $Y^1$ and $Y^2$ can be N;

$Y^3$ is N or CH;

$R^2$ is halo or methyl;

$Z^1$ is N, CH or $CR^3$;

$Z^2$ is CH or $CR^3$;

$Z^3$ is N, CH or $CR^3$;

$R^3$ is halo, $C_1$-$C_4$alkyl, $C_1$-$C_4$alkoxy or —$C_1$-$C_3$alkoxy$C_1$-$C_2$alkoxy; $R^4$ is

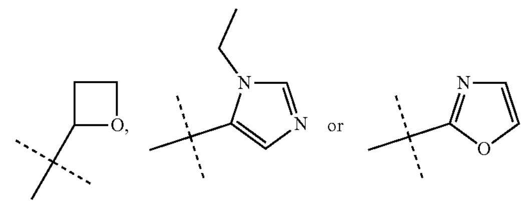

and $R^5$ is —$CO_2H$ or

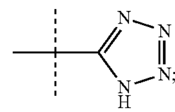

or a pharmaceutically acceptable salt thereof.

In an alternate embodiment, there is provided a compound of the formula:

Formula I

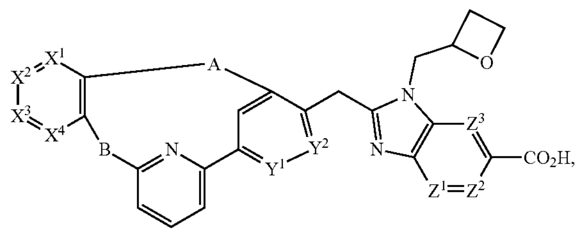

wherein

-A- is —$CHR^aCHR^aCHR^bO$—, —$OCHR^bCHR^a$-$CHR^a$—, —$OCHR^bCHR^bO$—, —$CHR^aCH R^bO$-$CHR^b$—, —$CHR^bOCHR^bCHR^a$—, —$CHR^bO$-$CHR^b$—, —$CHR^aCH R^bO$—, or —$OCHR^bCHR^a$—;

$R^a$ at each occurrence is independently H, halo, $C_1$-$C_2$alkyl or OH;

$R^b$ at each occurrence is independently H, halo or $C_1$-$C_2$alkyl;

$X^1$, $X^2$, $X^3$ and $X^4$ are independently N, CH or $CR^1$, wherein only one of $X^1$, $X^2$, $X^3$ and $X^4$ can be N and no more than two of $X^1$, $X^2$, $X^3$ and $X^4$ can be $CR^1$;

$R^1$ is CN or halo;

—B— is —$CH_2O$— or —$OCH_2$—;

$Y^1$ and $Y^2$ are independently N, CH or $CR^2$, wherein only one of $Y^1$ and $Y^2$ can be N;

$R^2$ is halo or methyl;

$Z^1$ is N, CH or $CR^3$;

$Z^2$ is CH or $CR^3$;

$Z^3$ is N, CH or $CR^3$; and $R^3$ is halo, $C_1$-$C_2$alkyl or methoxy;

or a pharmaceutically acceptable salt thereof.

In an embodiment, there is provided a compound of the formula:

Formula Ia

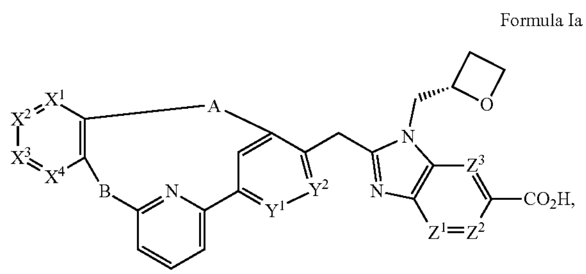

or a pharmaceutically acceptable salt thereof.

In an embodiment, there is provided a compound of the formula:

Formula II

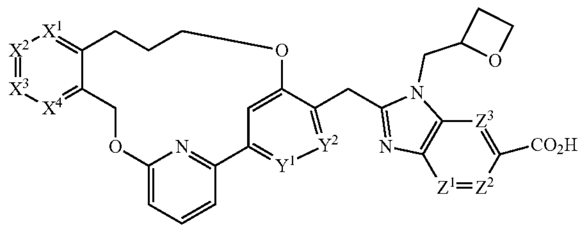

or a pharmaceutically acceptable salt thereof.

In a preferred embodiment, there is provided a compound of the formula:

Formula IIa

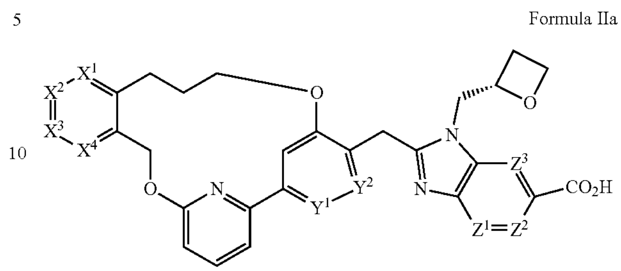

or a pharmaceutically acceptable salt thereof.

In an embodiment, there is provided a compound of the formula:

Formula III

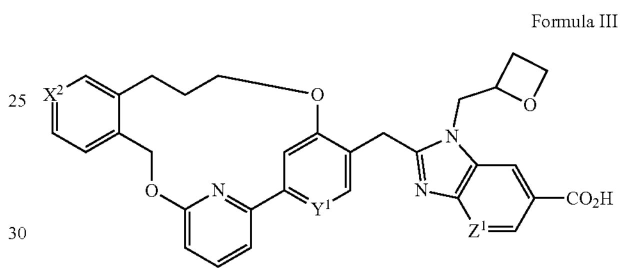

or a pharmaceutically acceptable salt thereof.

In a preferred embodiment, there is provided a compound of the formula:

Formula IIIa

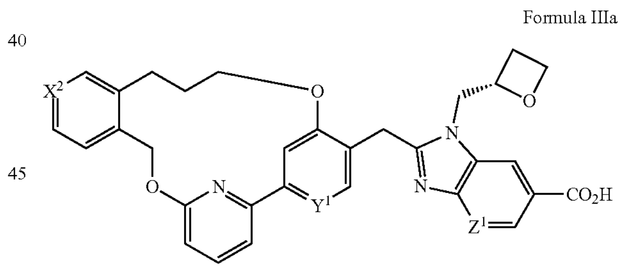

or a pharmaceutically acceptable salt thereof.

In an embodiment, -A- is —$CHR^aCHR^aCHR^bO$—. In a further embodiment, each $R^a$ and $R^b$ is H.

In an embodiment, $X^1$, $X^3$ and $X^4$ are CH and $X^2$ is $CR^1$. In one embodiment, $R^1$ is CN. In an alternate embodiment, $R^1$ is $C_1$.

In an embodiment, —B— is —$CH_2O$—.

In one embodiment, $Y^1$ and $Y^2$ are both CH. In an alternate embodiment, $Y^1$ is $CR^2$, $Y^2$ is CH and $R^2$ is F.

In an embodiment, $Z^2$ and $Z^3$ are both CH.

In an embodiment, $Z^1$ is CH or $CR^3$. In one embodiment, $Z^1$ is CH. In an alternate embodiment, $Z^1$ is $CR^3$ and $R^3$ is F.

In an embodiment, there is provided a compound selected from:

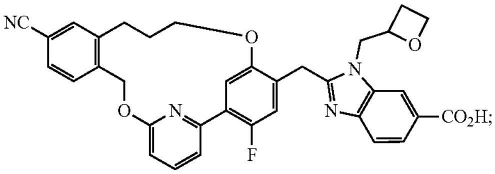
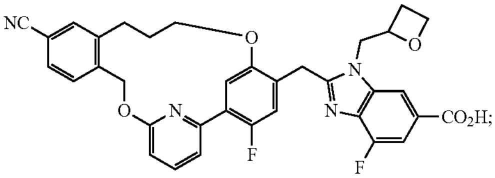
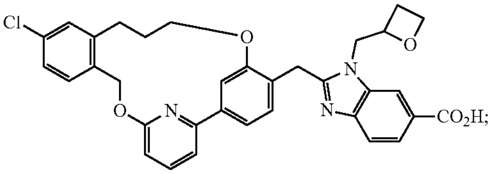
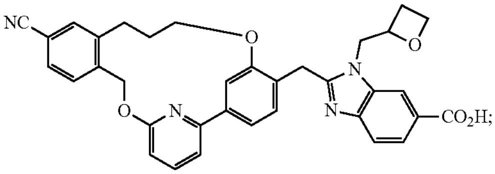
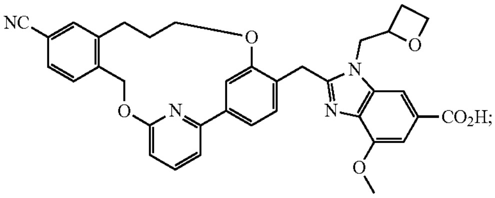
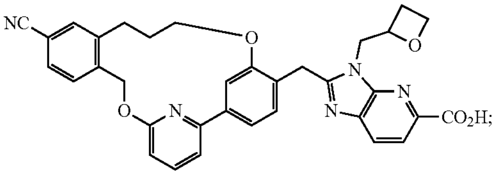
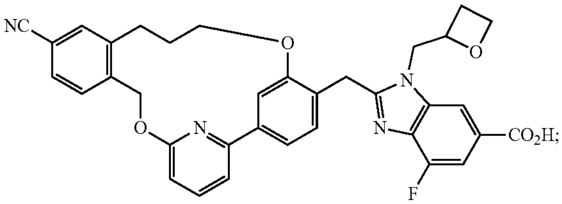
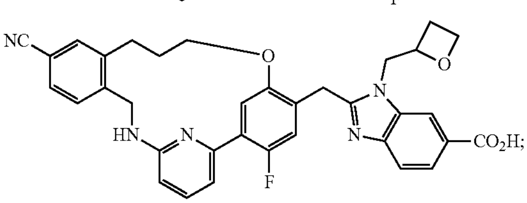
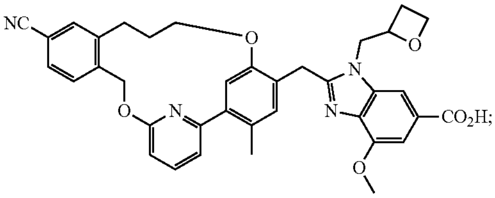
-continued
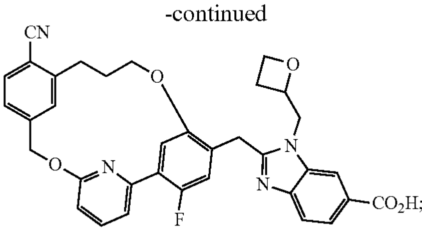
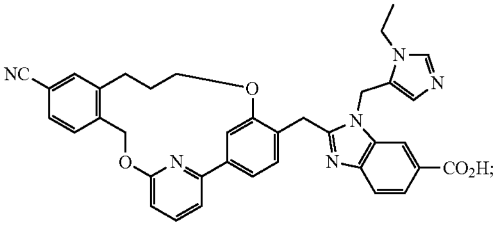
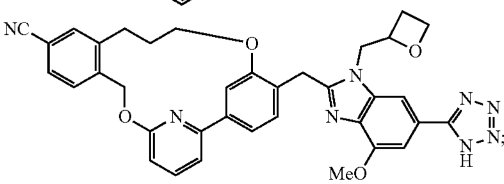
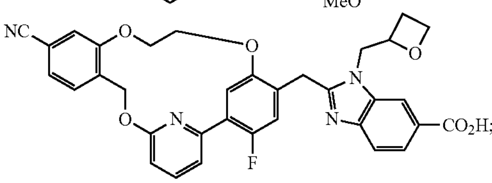
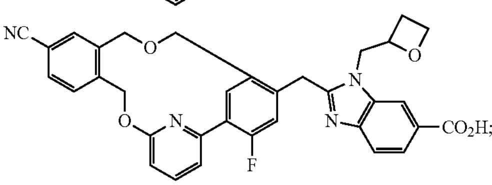
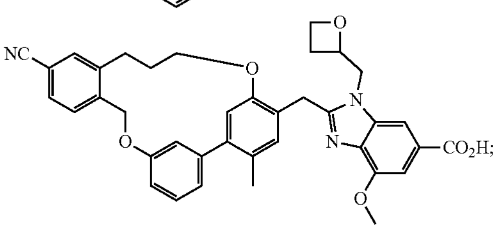
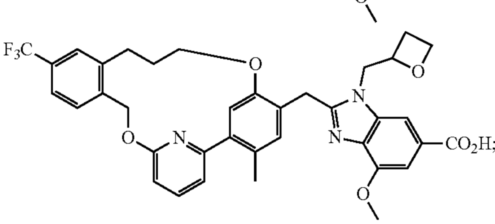
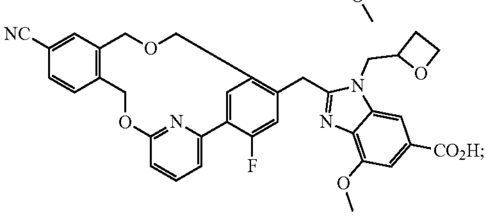
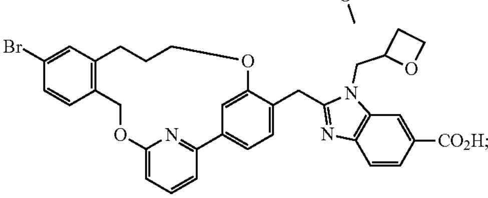

-continued
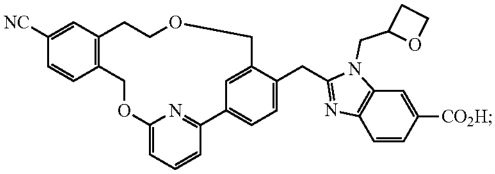
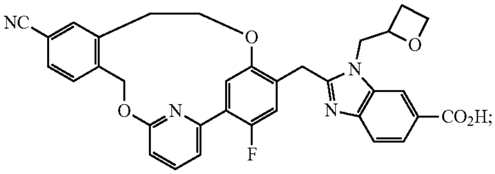
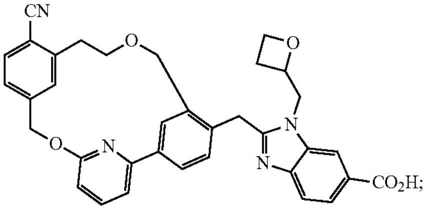
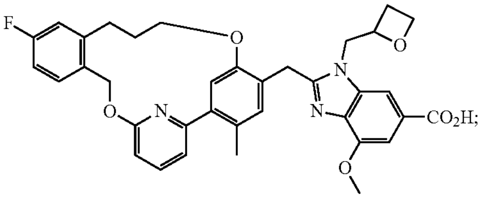
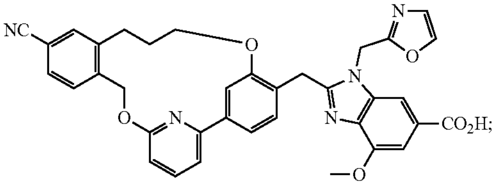
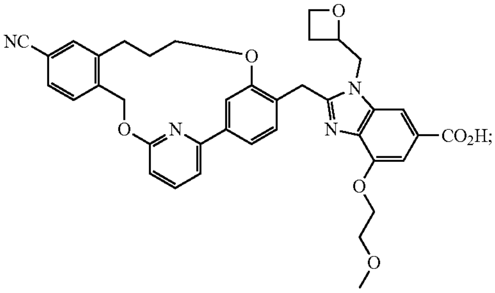
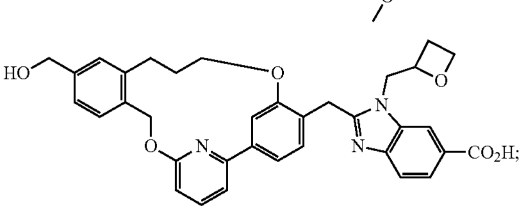
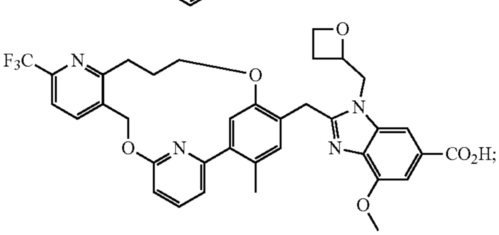
-continued
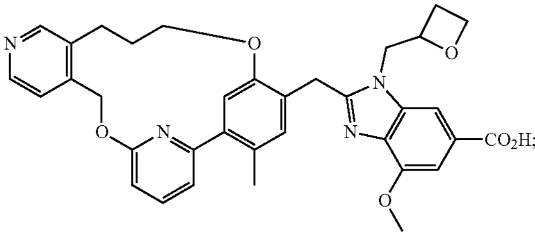
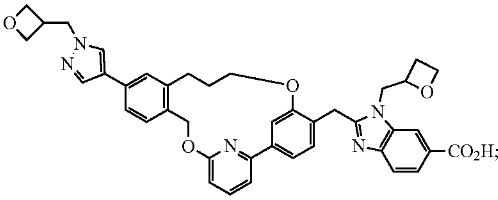
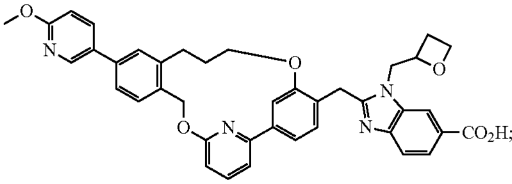
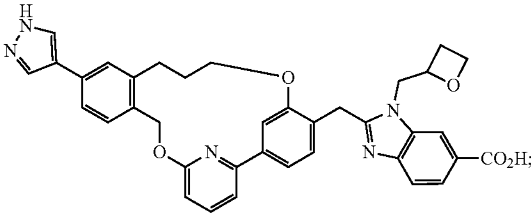
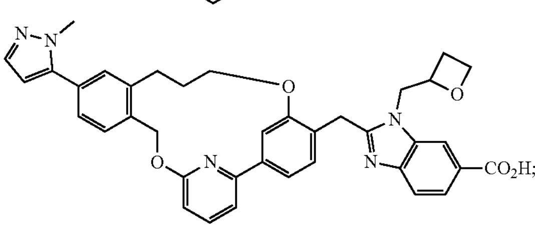
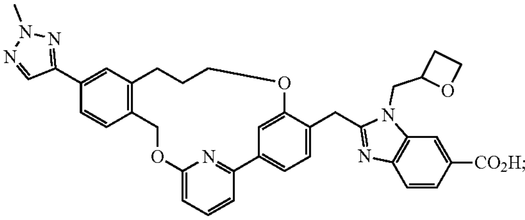
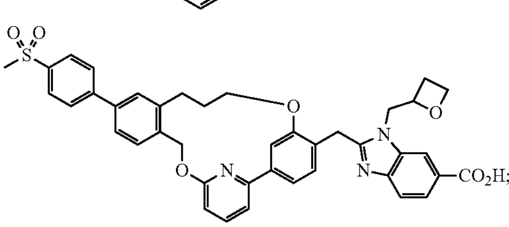
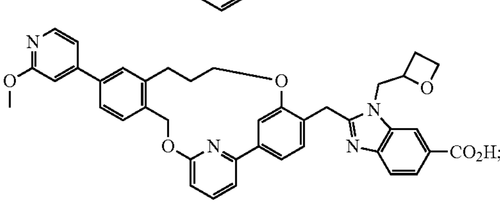

-continued
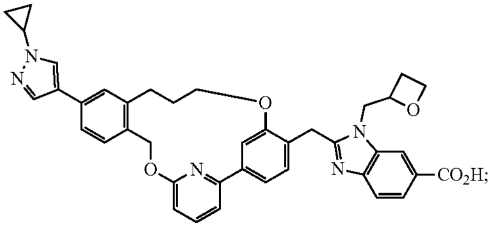
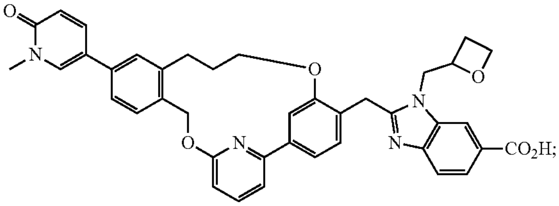
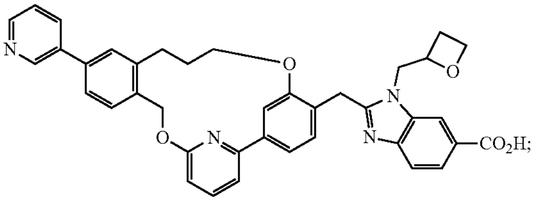
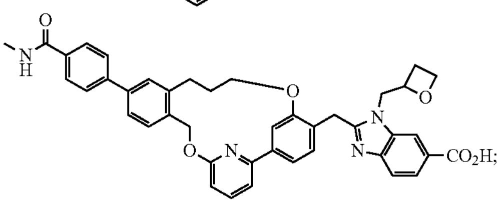
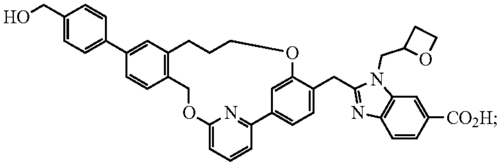
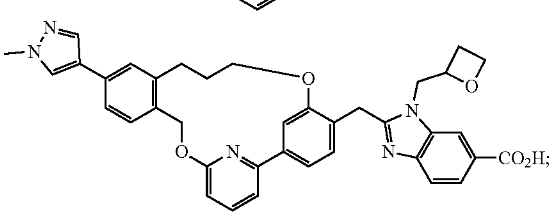
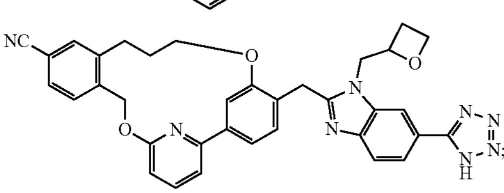
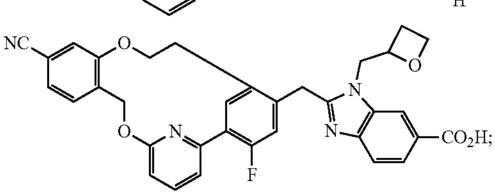
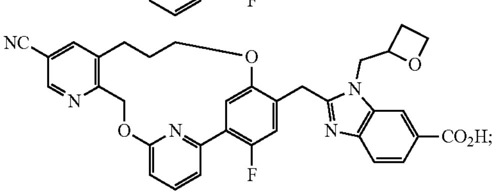
-continued
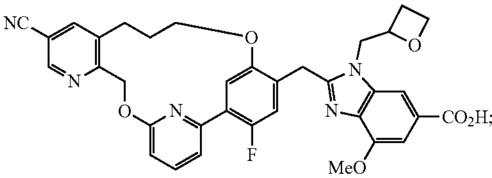
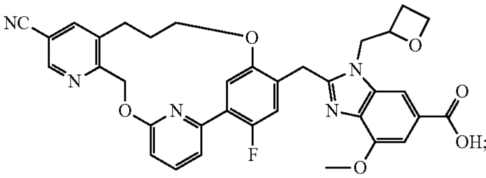
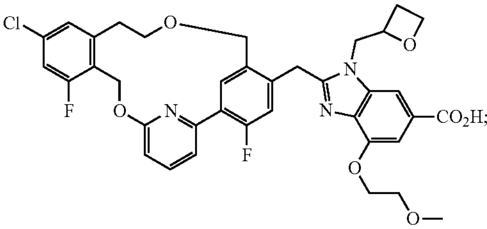
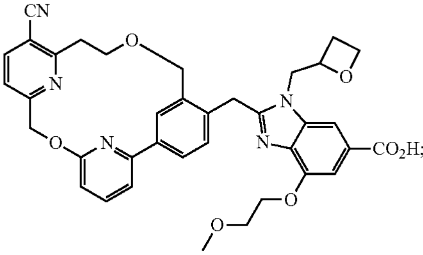
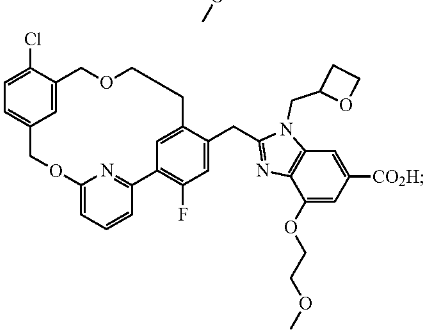
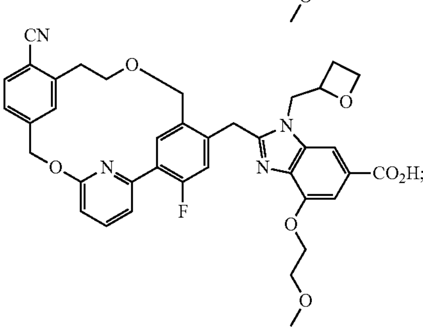
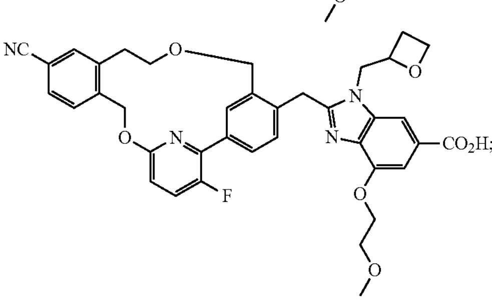

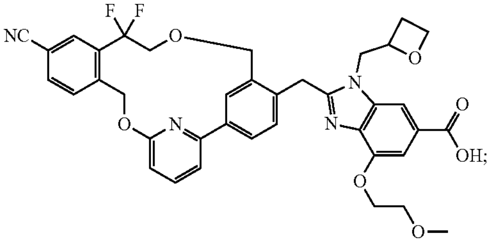
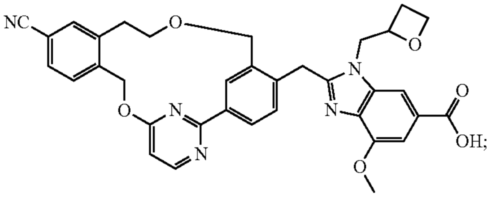
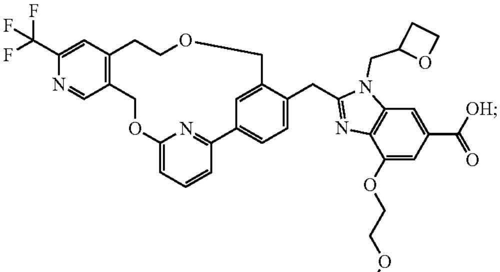
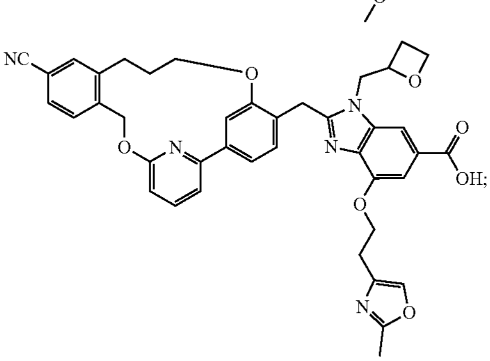
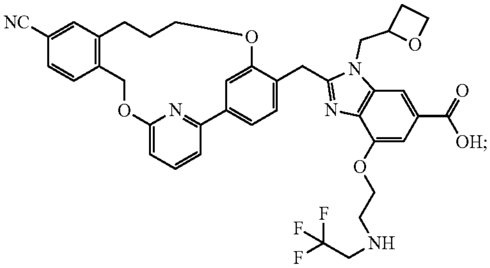
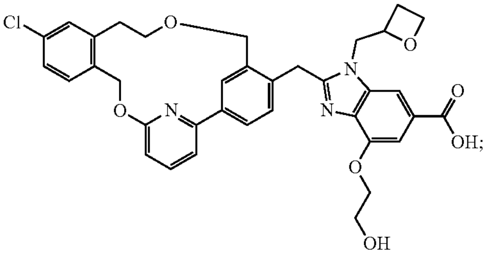
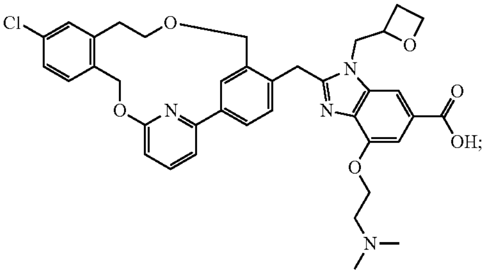
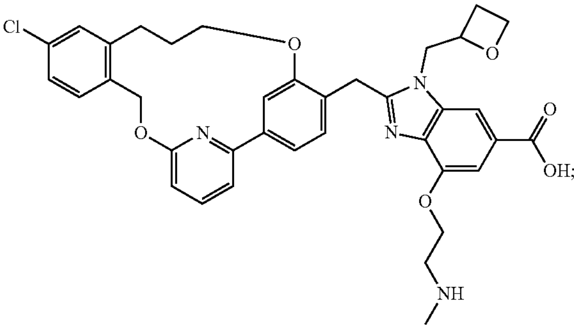
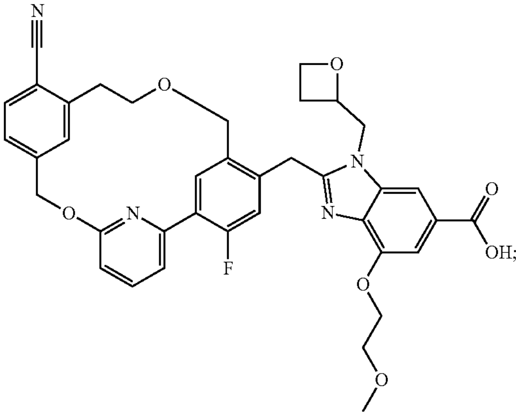
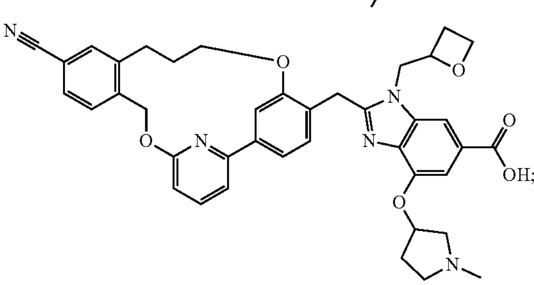
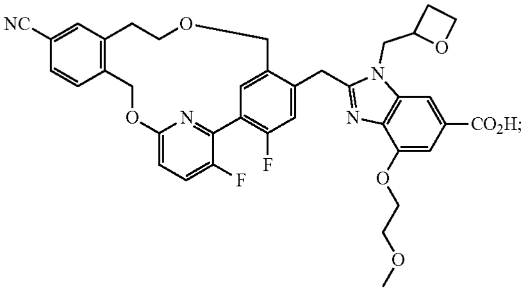

-continued
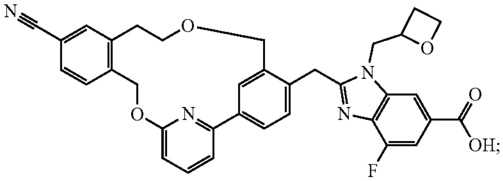
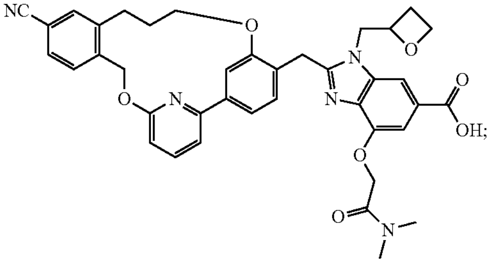
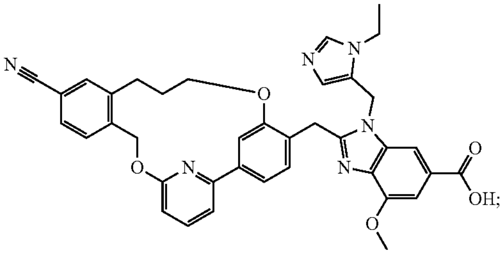
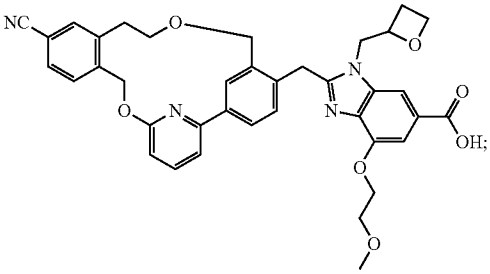
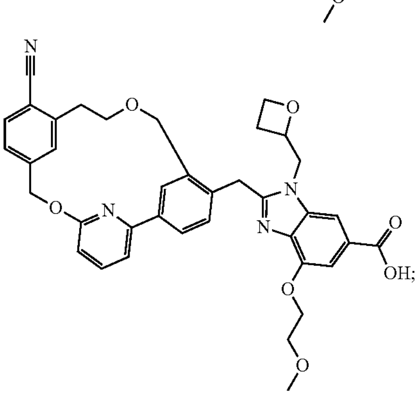
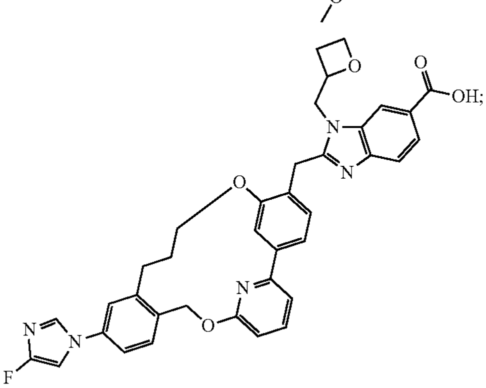
-continued
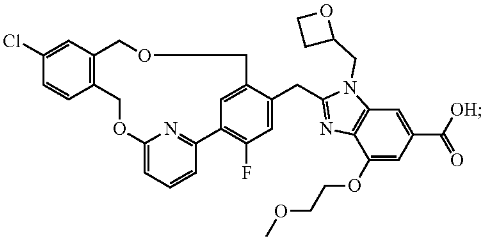
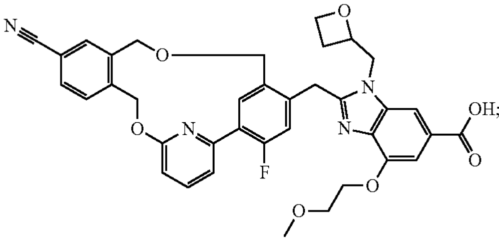
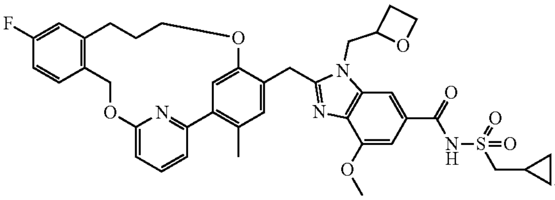
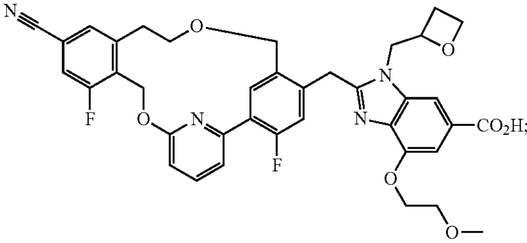
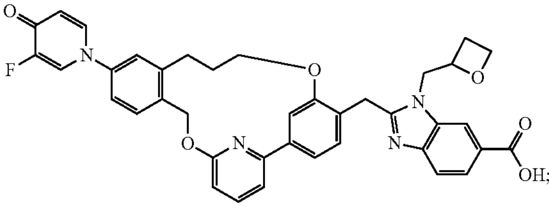
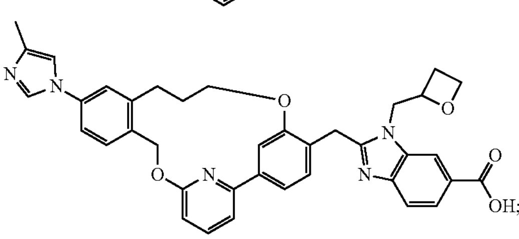
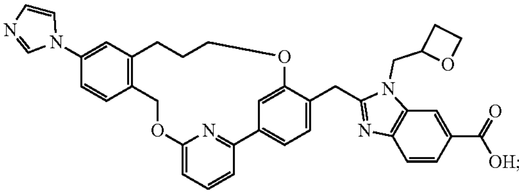

-continued

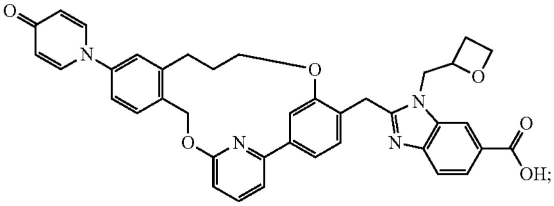

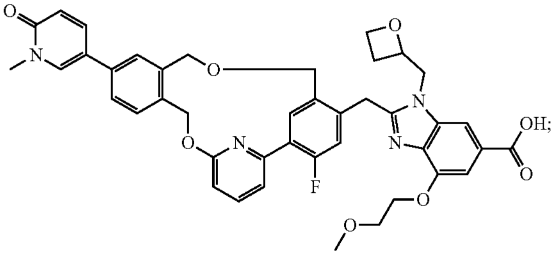

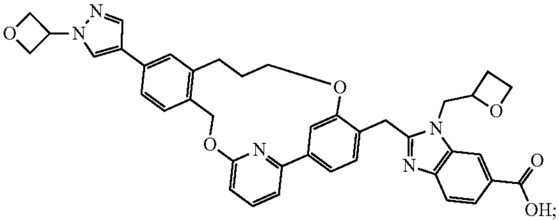

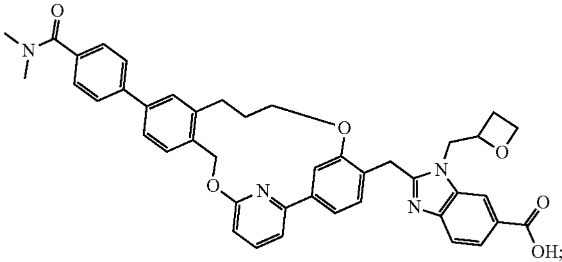

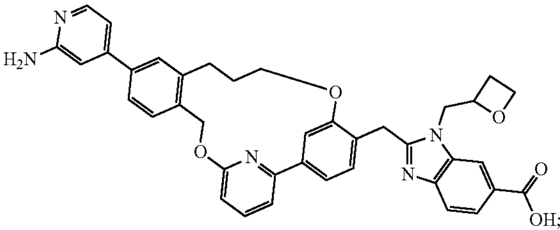

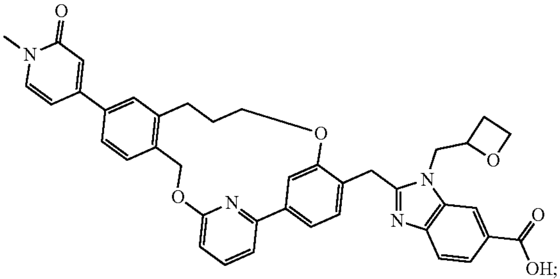

-continued and

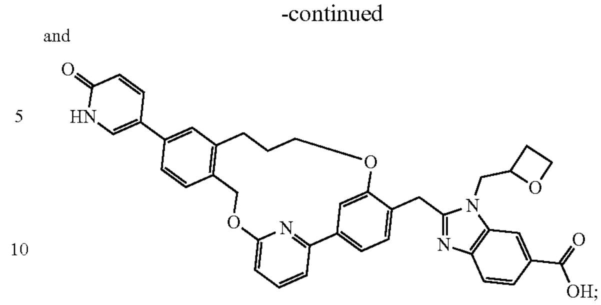

or a pharmaceutically acceptable salt thereof.

In linker A, the left hand terminal group as written is attached to the X ring and the right hand terminal group is attached to the $Y^1$, $Y^2$ and $Y^7$ containing ring. For example, in the group $—CR^aR^bCR^aR^bCR^bR^bO—$ the oxygen is attached to the $Y^1$, $Y^2$ and $Y^7$ containing ring. In linker B, the left hand terminal group is attached to the X ring and the right hand terminal group is attached the $Y^3$ containing ring.

The term "halogen" or "halo" refers to fluorine, chlorine, bromine, or iodine.

The term "$C_1$-$C_n$alkyl" refers to a straight, or branched chain saturated hydrocarbon containing 1 to n carbon atoms. Examples of a $C_1$-$C_4$alkyl group include, but are not limited to, methyl, ethyl, propyl, butyl, and tert-butyl. Examples of a $C_1$-$C_3$alkyl group include, but are not limited to, methyl, ethyl and propyl. A $C_1$-$C_2$alkyl group is methyl or ethyl.

The term "$C_1$-$C_n$haloalkyl" refers to a $C_1$-$C_n$alkyl group, as defined herein, which is substituted with one, or more halogen. Examples of $C_1$-$C_3$haloalkyl groups include, but are not limited to, trifluoromethyl, difluoromethyl and pentafluoroethyl.

The term "$C_1$-$C_n$alkoxy" refers to a straight, or branched chain saturated hydrocarbon containing 1 to n carbon atoms containing a terminal "O" in the chain, i.e., —O(alkyl). Examples of $C_1$-$C_4$alkoxy groups include, but are not limited to, methoxy, ethoxy, propoxy and butoxy.

The term "$C_1$-$C_n$haloalkoxy" refers to a $C_1$-$C_n$alkoxy group, as defined herein, which is substituted with one, or more halogen. Examples of $C_1$-$C_3$haloalkoxy groups include, but are not limited to, trifluoromethoxy, difluoromethoxy and pentafluoroethoxy.

The term "$C_3$-$C_5$cycloalkyl" refers to a monocyclic saturated carbon ring containing between 3 and 5 carbon atoms. Specifically, it refers to cyclopropyl, cyclobutyl or cyclopentyl.

The term "$C_4$-$C_6$cycloalkyl" refers to a monocyclic saturated carbon ring containing between 4 and 6 carbon atoms. Specifically, it refers to cyclobutyl, cyclopentyl or cyclohexyl.

The term "heteroaryl" refers to a monocyclic aromatic ring containing one or more heteroatoms, preferably selected from: N, S and O. Examples of 5-membered heteroaryls include, but are not limited to, pyrazole, triazole and thiazole. Examples of 6-membered heteroaryls include, but are not limited to, pyridine and pyridazine.

The term "$C_4$-$C_6$heterocyclyl" refers to a 4, 5 or 6 membered monocyclic saturated ring containing one or more heteroatoms, for example, pyrrolidine.

The term "$C_4$-$C_5$heterocyclyl" refers to a 4 or 5 membered monocyclic saturated ring containing one or more heteroatoms, for example, oxetane.

Formula IX encompasses Formulae I, Ia, Ib, II, IIa, IIb, III, IIIa, IIIb, IV, V, Va, Vb, VI, VII, VIIa and VIIb and reference to Formula IX below, for example in the methods of treatment and therapeutic uses, is also to be read as a reference to each and all of these sub-formulae.

In another embodiment, there is provided a pharmaceutically acceptable composition comprising a compound of Formula IX, or a pharmaceutically acceptable salt thereof, and at least one of a pharmaceutically acceptable carrier, diluent or excipient. In a preferred embodiment, the pharmaceutically acceptable composition is formulated for oral administration.

In another embodiment, there is provided a method of treating a patient for type II diabetes mellitus, the method comprises administering to the patient in need of treatment a pharmaceutically acceptable composition comprising an effective amount of a compound of Formula IX, or a pharmaceutically acceptable salt thereof, and at least one of a pharmaceutically acceptable carrier, diluent or excipient. In one embodiment, the pharmaceutically acceptable composition is formulated for oral administration. Preferably, the patient is a human.

In another embodiment, there is provided a method of treating a patient for type II diabetes mellitus, the method comprises administering to the patient in need of treatment an effective amount of a compound of Formula IX, or a pharmaceutically acceptable salt thereof. In a preferred embodiment, the patient is a human.

In another embodiment, there is provided a method of lowering blood glucose levels in a patient, the method comprises administering to the patient in need of treatment an effective amount of a compound of Formula IX, or a pharmaceutically acceptable salt thereof. In a preferred embodiment, the patient is a human.

In another embodiment, there is provided a method of treating hyperglycemia in a patient, the method comprises administering to the patient in need of treatment an effective amount of a compound of Formula IX, or a pharmaceutically acceptable salt thereof. In a preferred embodiment, the patient is a human.

In another embodiment, there is provided a method of treating obesity in a mammal, the method comprises administering to the patient in need of treatment an effective amount of a compound of Formula IX, or a pharmaceutically acceptable salt thereof. In a preferred embodiment, the patient is a human.

In another embodiment, there is provided a method of treating nonalcoholic steatohepatitis (NASH) in a patient, the method comprises administering to the patient in need of treatment an effective amount of a compound of Formula IX, or a pharmaceutically acceptable salt thereof. In a preferred embodiment, the patient is a human.

In an embodiment, there is provided a compound of Formula IX, or a pharmaceutically acceptable salt thereof, for use in therapy.

In another embodiment, there is provided a compound of Formula IX, or a pharmaceutically acceptable salt thereof, for use in the treatment of type II diabetes mellitus.

In another embodiment, there is provided a compound of Formula IX, or a pharmaceutically acceptable salt thereof, for use in lowering blood glucose levels.

In another embodiment, there is also provided a compound of Formula IX, or a pharmaceutically acceptable salt thereof, for use in treating hyperglycemia.

In another embodiment, there is provided a compound of Formula IX, or a pharmaceutically acceptable salt thereof, for use in treating obesity.

In another embodiment, there is also provided a compound of Formula IX, or a pharmaceutically acceptable salt thereof, for use in treating NASH.

In an embodiment, there is provided the use of a compound of Formula IX, or a pharmaceutically acceptable salt thereof, for the manufacture of a medicament for the treatment of type II diabetes mellitus.

In an embodiment, there is provided the use of a compound of Formula IX, or a pharmaceutically acceptable salt thereof, for the manufacture of a medicament for lowering blood glucose levels.

In an embodiment, there is provided the use of a compound of Formula IX, or a pharmaceutically acceptable salt thereof, for the manufacture of a medicament for the treatment of hyperglycemia.

In an embodiment, there is provided the use of a compound of Formula IX, or a pharmaceutically acceptable salt thereof, for the manufacture of a medicament for the treatment of obesity.

In an embodiment, there is provided the use of a compound of Formula IX, or a pharmaceutically acceptable salt thereof, for the manufacture of a medicament for the treatment of NASH.

The compounds of Formula IX may be used in simultaneous, separate, or sequential combination with one or more therapeutic agents. Examples of additional therapeutic agents include, but are not limited to, metformin, thiazolidinediones, sulfonylureas, dipeptidyl peptidase 4 inhibitors, sodium glucose co-transporters, and ketohexokinase inhibitors.

In a preferred embodiment, the compound of Formula IX is administered orally.

In a preferred embodiment, the compound of Formula IX is administered once daily. In another preferred embodiment, the therapeutic use is in a human.

The term "pharmaceutically acceptable salt" as used herein refers a salt of a compound of the invention considered to be acceptable for clinical and/or veterinary use.

Examples of pharmaceutically acceptable salts and common methodologies for preparing them can be found in "Handbook of Pharmaceutical Salts: Properties, Selection and Use" P. Stahl, et al., 2nd Revised Edition, Wiley-VCH, 2011 and S. M. Berge, et al., "Pharmaceutical Salts", *Journal of Pharmaceutical Sciences,* 1977, 66(1), 1-19.

The term "effective amount" refers to the amount or dose of a compound of Formula IX, or a pharmaceutically acceptable salt thereof, which, upon single or multiple dose administration to the patient, provides the desired effect in the patient under diagnosis or treatment. The attending physician, as one skilled in the art, can readily determine an effective amount by the use of conventional techniques and by observing results obtained under analogous circumstances. Factors considered in the determination of an effective amount or dose of a compound include: whether the compound or its salt will be administered; the co-administration of other agents, if used; the size, age, and general health of the patient; the degree of involvement or the severity of the disorder; the response of the individual patient; the mode of administration; the bioavailability characteristics of the preparation administered; the dose regimen selected; and other relevant circumstances. The compounds of the present invention are effective at a dosage per day that falls within the range of about 0.01 to about 15 mg/kg of body weight.

As used herein, the terms "treating", "to treat", or "treatment", refers to lowering, reducing, or reversing the progression or severity of an existing symptom, disorder, or condition, such as hyperglycemia, which can include increasing insulin secretion.

As used herein, the term "patient" includes mammals. The patient is preferably human.

The compounds of Formula IX can be formulated as pharmaceutical compositions administered by any route which makes the compound bioavailable. Preferably, such compositions are for oral administration. Preferably the pharmaceutical compositions are formulated as a tablet, capsule, or a solution. The tablet, capsule, or solution can include a compound of Formula IX in an amount effective for treating a patient in need of treatment. Such pharmaceutical compositions and processes for preparing same are well known in the art (See, e.g., "Remington: The Science and Practice of Pharmacy", A. Adejare Editor, $23^{rd}$ Ed., 2020, Elsevier Science).

The compounds of Formula IX and the pharmaceutically acceptable salts thereof are useful in the therapeutic uses of the invention, with certain configurations being preferred.

Compounds of the present invention include:

Formula Ia

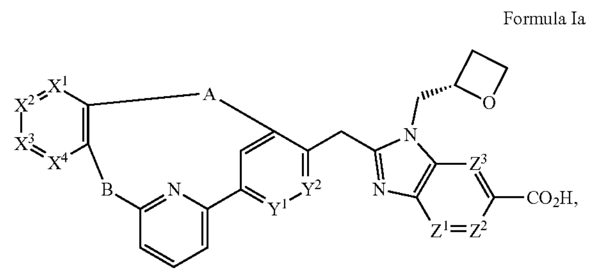

Formula Ib

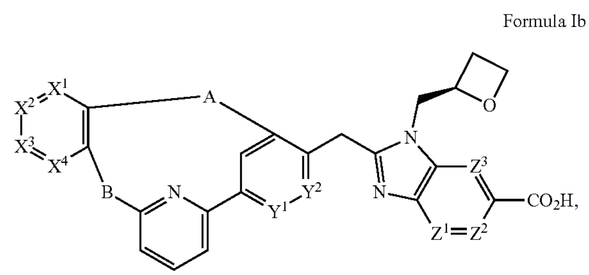

Formula IIa

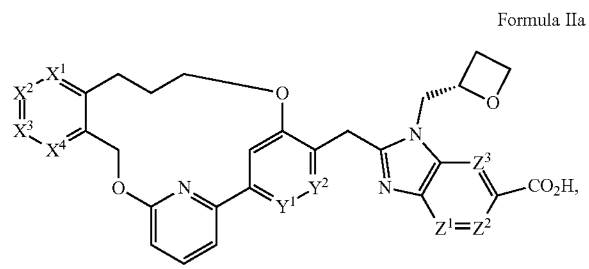

Formula IIb

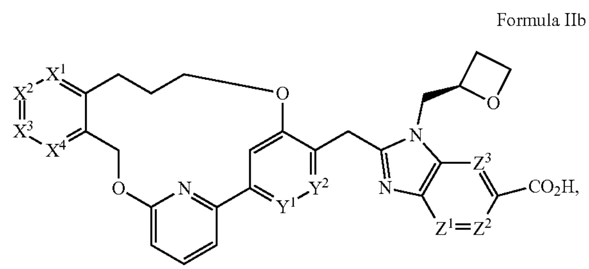

-continued

Formula IIIa

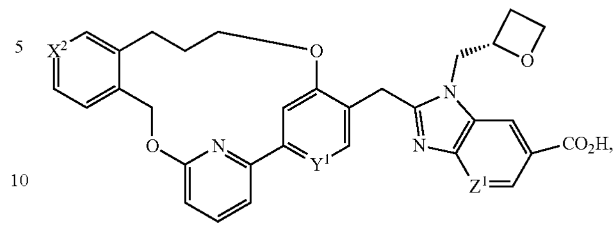

Formula IIIb

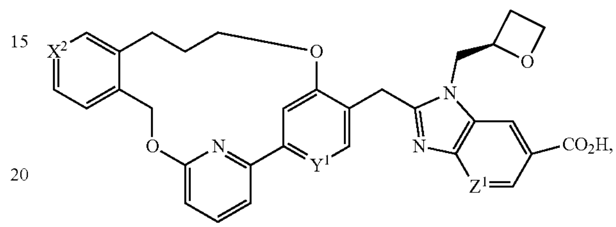

Formula Va

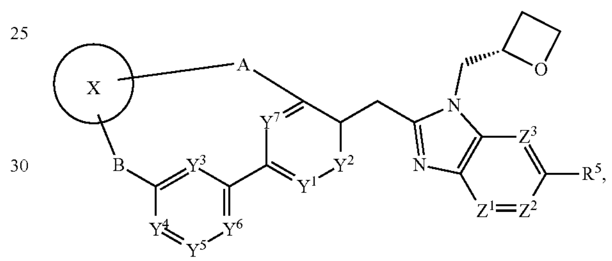

Formula Vb

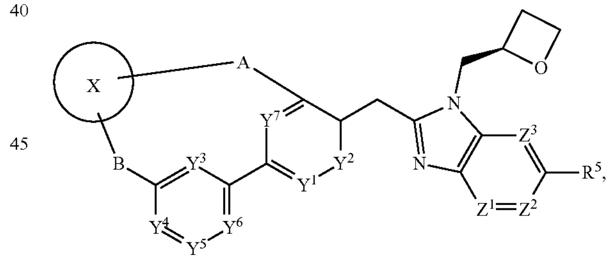

Formula VIIa

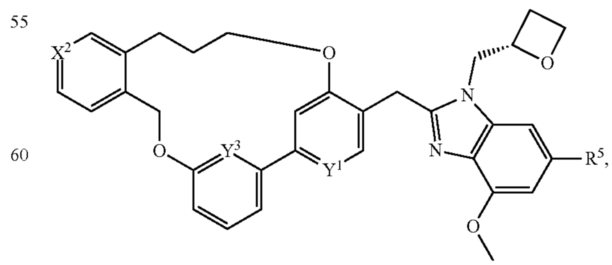

-continued

Formula VIIb

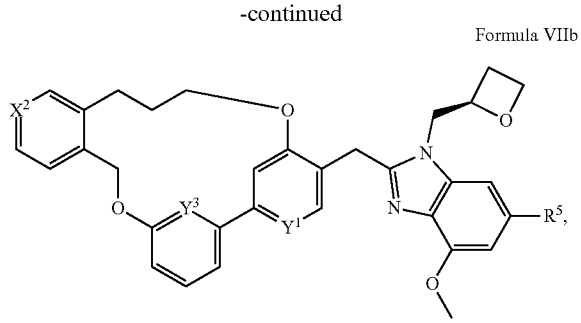

or pharmaceutically acceptable salts thereof.

Although the present invention contemplates all individual enantiomers, mixtures thereof, and racemates, compounds of Formula Ia, IIa, IIIa, Va and VIIa and pharmaceutically acceptable salts thereof, are particularly preferred.

Individual enantiomers may be separated or resolved by one of ordinary skill in the art at any convenient point in the synthesis of compounds of the invention, by methods such as selective crystallization techniques, chiral chromatography (See for example, J. Jacques, et al., "*Enantiomers, Racemates, and Resolutions*", John Wiley and Sons, Inc., 1981, and E. L. Eliel and S. H. Wilen," *Stereochemistry of Organic Compounds*", Wiley-Interscience, 1994), or supercritical fluid chromatography (SFC) (See for example, T. A. Berger; "*Supercritical Fluid Chromatography Primer*," Agilent Technologies, July 2015).

A pharmaceutically acceptable salt of the compounds of the invention can be formed, for example, by reaction of a compound of Formula IX and an appropriate pharmaceutically acceptable base in a suitable solvent under standard conditions well known in the art (See, for example, Bastin, R. J., et al.; *Org. Process. Res. Dev.,* 4, 427-435, 2000 and Berge, S. M., et al.; *J. Pharm. Sci.,* 66, 1-19, 1977).

Certain abbreviations used herein are defined according to Daub G. H., et al., "The Use of Acronyms in Organic Chemistry" *Aldrichimica Acta,* 1984, 17(1), 6-23. Certain abbreviations are defined as follows: "ACN" refers to acetonitrile; "Boc" refers to tert-butyloxycarbonyl; "cAMP" refers to cyclic adenosine-3',5'-monophosphate; "DCM" refers to dichloromethane or methylene chloride; "DEAD" refers to diethyl azodicarboxylate; "DIAD" refers to diisopropyl azodicarboxylate; "DIPEA" refers to N,N-diisopropylethylamine; "DMF" refers to N,N-dimethylformamide; "DMSO" refers to dimethyl sulfoxide; "$EC_{50}$" refers to the concentration of an agent which produces 50% response of the target activity compared to a predefined positive control compound (absolute $EC_{50}$); "EDC" refers to N-(3-dimethylaminopropyl)-N'-ethylcarbodiimide hydrochloride; "ES/MS" refers to electrospray mass spectrometry; "EtOAc" refers to ethyl acetate; "HATU" refers to 1-[bis(dimethylamino)methylene]-1H-1,2,3-triazolo[4,5-b]pyridinium 3-oxide hexafluorophosphate; "HEK" refers to human embryonic kidney; "HEPES" refers to 4-(2-hydroxyethyl)-1-piperazineethanesulfonic acid; "h" refers to hours or hour, respectively; Ir[dF(CF3)ppy]2(dthpy))PF6 refers to [4,4'-Bis(1,1-dimethylethyl)-2,2'-bipyridine-N1,N1']bis[3,5-difluoro-2-[5-(trifluoromethyl)-2-pyridinyl-N]phenyl-C] Iridium(II) hexafluorophosphate; "KOAc" refers to potassium acetate; "MeOH" refers to methanol or methyl alcohol; "min" refers to minute or minutes; "MTBE" refers to methyl tert-butyl ether; "$Pd(dppf)Cl_2$" refers to [1,1'-bis (diphenylphosphino)ferrocene]dichloropalladium(II); $PdCl_2$ (dtbpf) refers to [1,1'-Bis(di-tert-butylphosphino)ferrocene] dichlioropalladiurm(II); "RT" refers to room temperature; "$S_NAr$" refers to nucleophilic aromatic substitution; "TBAF" refers to tetrabutylammonium fluoride; "TBS" refers to tert-butyl dimethylsilyl; "TEA" refers triethylamine; "TFA" refers to trifluoroacetic acid; "THF" refers to tetrahydrofuran; "TMAD" refers to tetramethyl azodicarboxamide; and "TMSCN" refers to trimethylsilyl cyanide.

The compounds of the present invention may be prepared by a variety of procedures, some of which are illustrated in the Preparations and Examples below. The specific synthetic steps for each of the routes described may be combined in different ways, to prepare compounds of the invention, or salts thereof. The product of each step below can be recovered by conventional methods, including extraction, evaporation, precipitation, chromatography, filtration, trituration, and crystallization. The reagents and starting materials are readily available to one of ordinary skill in the art. Individual isomers, enantiomers, and diastereomers may be separated or resolved at any convenient point in the synthesis, by methods such as, selective crystallization techniques or chiral chromatography (See for example, J. Jacques, et al., "*Enantiomers, Racemates, and Resolutions*", John Wiley and Sons, Inc., 1981, and E. L. Eliel and S. H. Wilen," *Stereochemistry of Organic Compounds*", Wiley-Interscience, 1994). Without limiting the scope of the invention, the following preparations, and examples are provided to further illustrate the invention.

Scheme 1

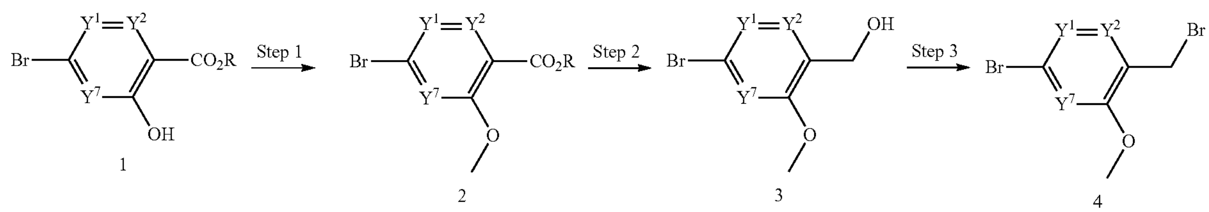

1 2 3 4

-continued

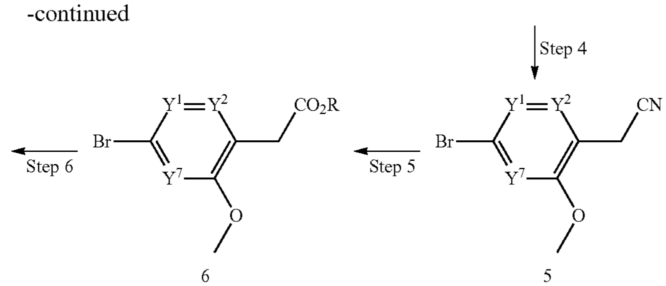

6

5

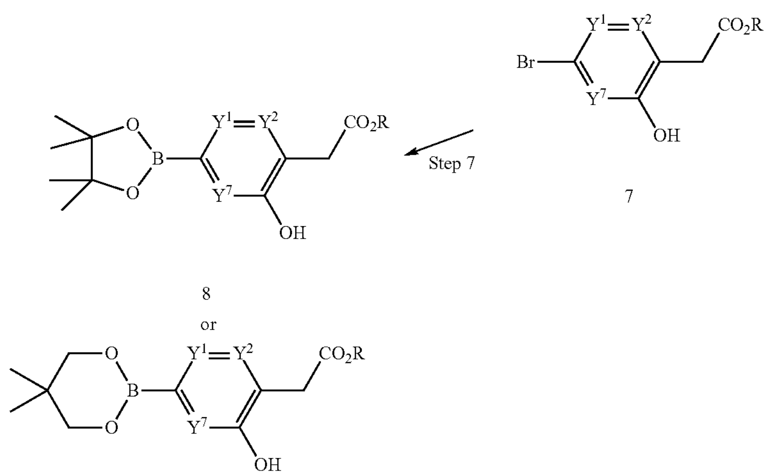

7

8 or

9

R = methyl, ethyl
$Y^1$, $Y^2$, and $Y^7$ are as defined in Formula IX

Scheme 1 shows the synthesis of intermediates 7, 8, and 9 which are used in the preparation of compounds of the present invention. In Step 1, the hydroxyl group of intermediate 1 is methylated with iodomethane and a carbonate base at elevated temperature to give methoxy intermediate 2. In Step 2, the ester group of intermediate 2 is then reduced to alcohol intermediate 3 using $NaBH_4$. The alcohol of intermediate 3 is converted to bromide intermediate 4 in Step 3 using $PBr_3$, which is then reacted with TMSCN and TBAF in Step 4 to give intermediate 5. The cyano group of intermediate 5 is treated with sulfuric acid in an alcohol solution at elevated temperature in Step 5 to give ester intermediate 6, then the methoxy group is demethylated with $BBr_3$ in Step 6 to give intermediate 7. Optionally, intermediate 7 can be converted to a boronate in Step 7 using KOAc, and Pd(dppf)$Cl_2$, and either bis(pinacolato)diboron or bis(neopentyl glycoloato)diboron at elevated temperature to give boronate 8 or 9, respectively.

Scheme 2

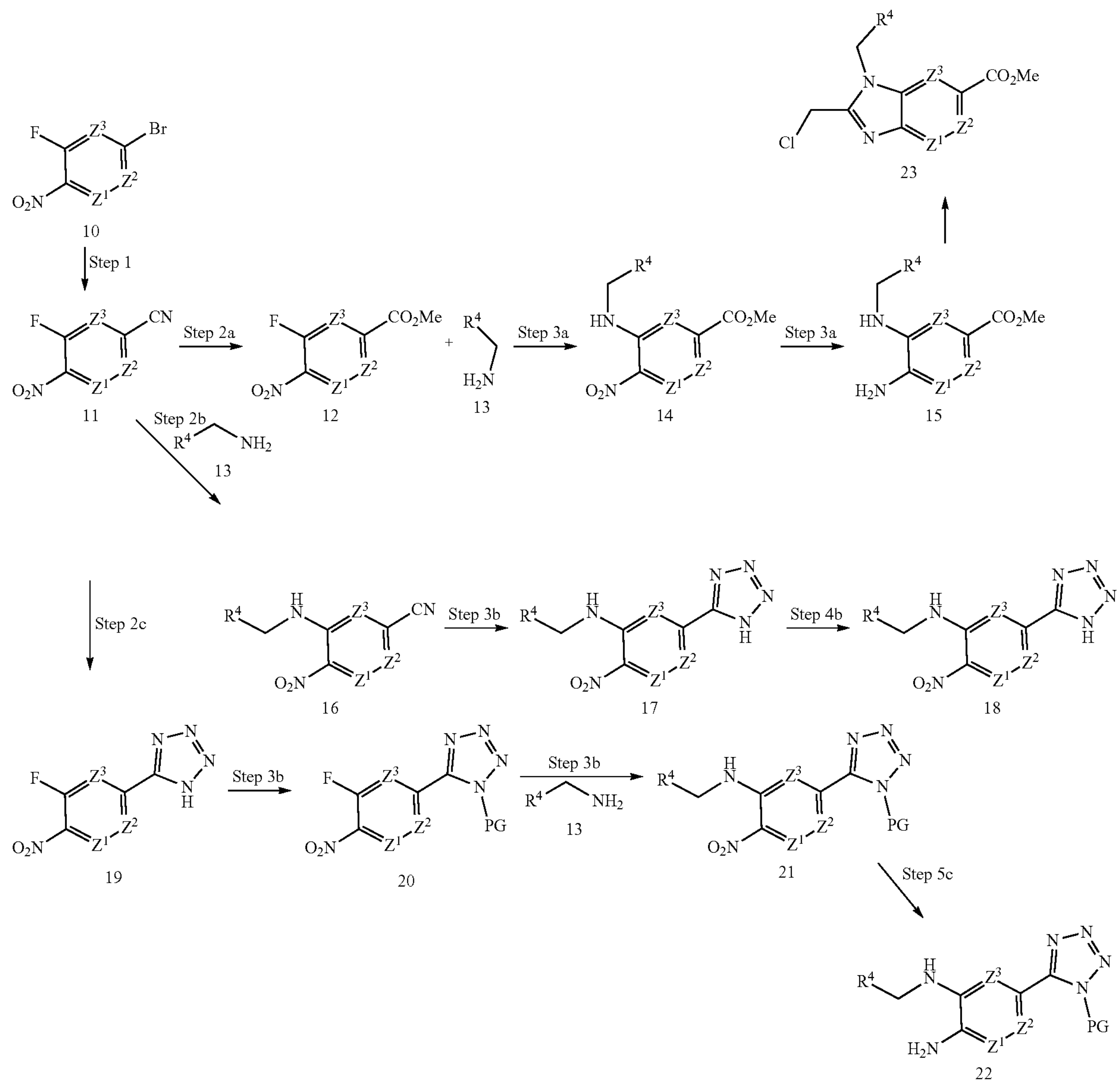

10 11 12 13 14 15 16 17 18 19 20 21 22 23

$Z^1$, $Z^2$, $Z^3$, and $R^4$ are as defined in Formula IX
PG = protecting group e.g. SEM (trimethylsilylethoxymethyl)

Scheme 2 shows the synthesis of intermediates 15, 18, 22, and 23 which are also used in the preparation of compounds of the present invention. Bromide 10 is converted to nitrile 11 in Step 1 using zinc cyanide and a palladium catalyst at elevated temperature. Nitrile intermediate 11 is converted to ester intermediate 12 in Step 2a using thionyl chloride in an alcohol solution at elevated temperature, then the fluorine is displaced in a $S_N$Ar reaction in Step 3a with amine 13 and a carbonate base at elevated temperature to give intermediate 14. The nitro group is then reduced in Step 4a under an atmosphere of hydrogen using Lindlar catalyst (5% Pd) in methanol to give intermediate 15. Intermediate 15 can be reacted with 2-chloroacetyl chloride using a tertiary amine base to give 2-chloromethylimidazole intermediate 23.

To access tetrazole intermediates, intermediate 11 undergoes $S_N$Ar reaction with amine 13 in Step 2b using an amine base to give intermediate 16, which then is converted to tetrazole intermediate 17 using tributyltin azide at elevated temperature in Step 3b. The nitro group is then reduced in Step 4b under hydrogen pressure (4 bar) using a palladium on carbon catalyst to give intermediate 18. Alternatively, intermediate 11 is reacted with tributyltin azide at elevated temperature in Step 2c to give tetrazole intermediate 19, which is then protected in Step 3c on the tetrazole nitrogen with a group such as SEM (trimethylsilylethoxymethyl) giving intermediate 20. The fluorine is displaced in a $S_N$Ar reaction in Step 4c with amine 13 and a tertiary amine base to give intermediate 21, then reduction of the nitro group in Step 5c using iron in acetic acid at elevated temperature gives protected tetrazole intermediate 22.

Scheme 3

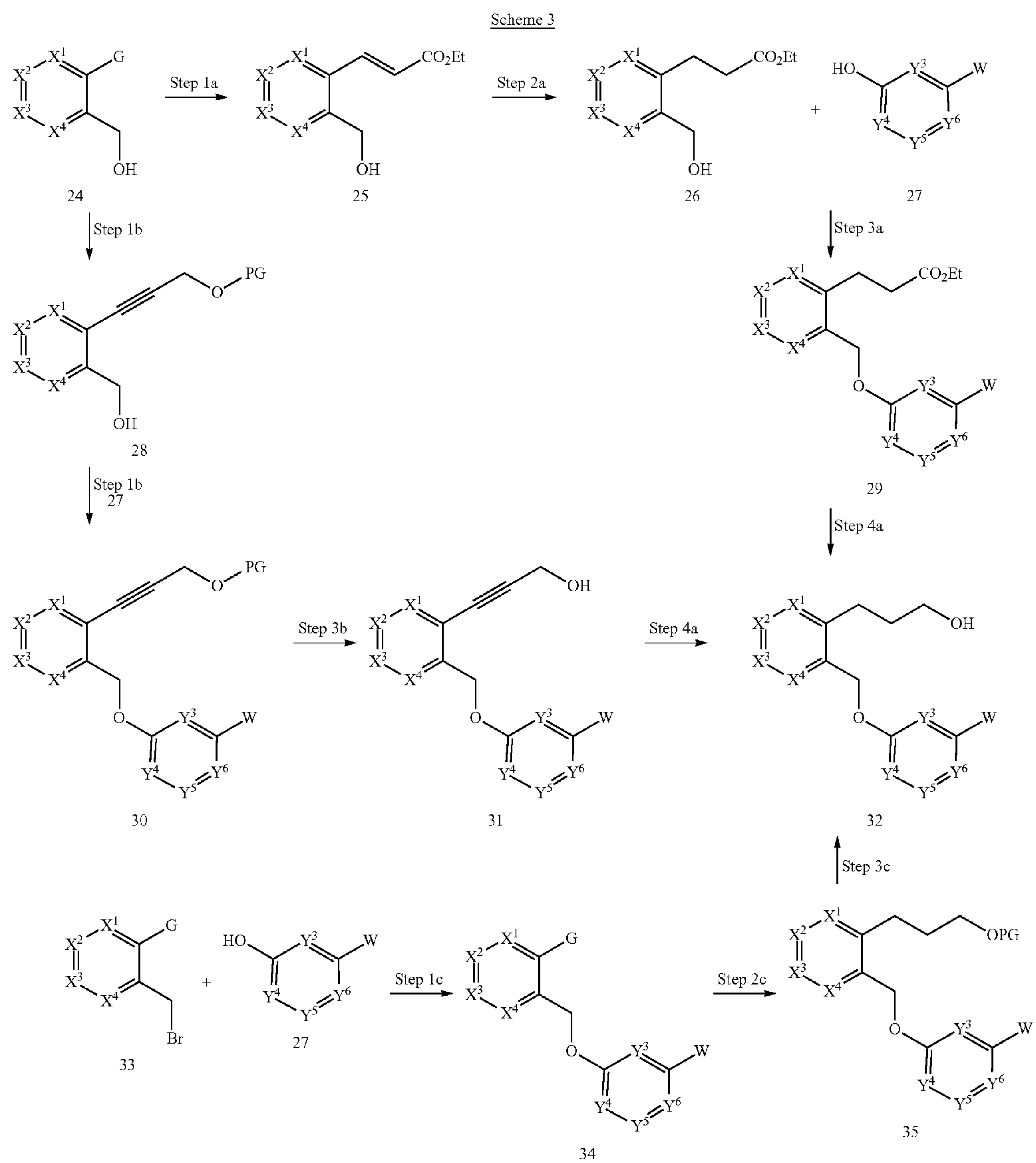

24 25 26 27 28 29 30 31 32 33 27 34 35

G = Br, I; W = Cl, Br $X^1$, $X^2$, $X^3$, $X^4$, $Y^3$, $Y^4$, $Y^5$, and $Y^6$ are as defined in Formula IX;

PG = protecting group e.g. TBS (tert-butyldimethylsilyl)

Scheme 3 shows three routes for synthesizing intermediate 32 which is used in the preparation of compounds of the present invention. In Step 1a in the first route, halide intermediate 24 undergoes a Heck coupling with ethyl acrylate using palladium acetate and a carbonate base at elevated temperature to give intermediate 25, which then undergoes olefin reduction under hydrogen (40 psi) in Step 2a to give intermediate 26. In Step 3a, the alcohol group of intermediate 26 is converted to the bromide using $PBr_3$, then reacted with intermediate 27 and $Ag_2CO_3$ at elevated temperature to give intermediate 29. Reduction of the ester group with $LiBH_4$ in Step 4a gives intermediate 32.

In the second route, intermediate 33 (which can be prepared from intermediate 24 using $PBr_3$) is first reacted in Step 1c with intermediate 27 using $Ag_2CO_3$ at elevated temperature to give intermediate 34, which then undergoes a Negishi coupling in Step 2c with bromo-[3-[tert-butyl (dimethyl)silyl]oxypropyl]zinc and a palladium catalyst at elevated temperature to give intermediate 35. Deprotection using TBAF in Step 3c then gives intermediate 32.

In the third route, intermediate 24 undergoes Sonogashira coupling with tert-butyildimethyl(2-propynyloxy)silane using a palladium catalyst and tertiary amine base in Step 1b to give intermediate 28, which then undergoes a Mitsunobu reaction with intermediate 27 to give intermediate 30. Deprotection using TBAF in Step 3b and then hydrogenation of the alkyne using platinum oxide under an atmosphere of hydrogen in Step 4b gives Intermediate 32.

Scheme 4

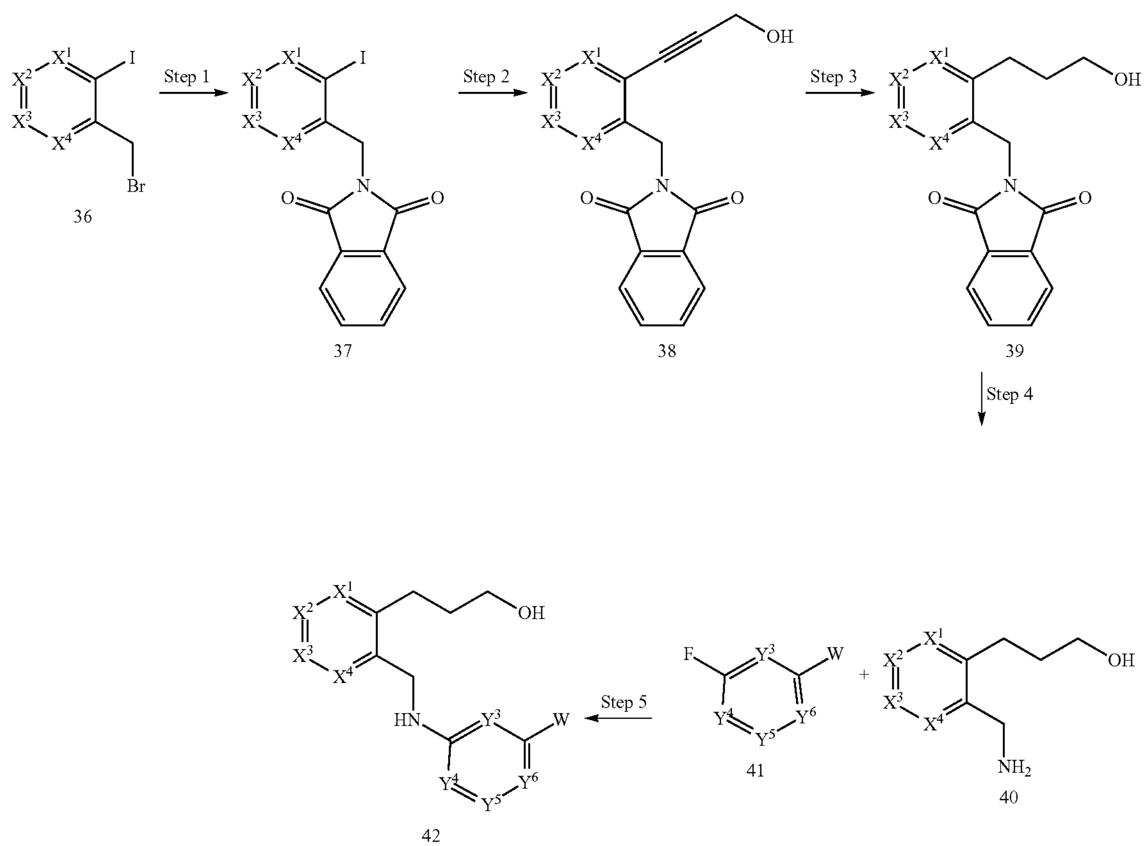

36 37 38 39 40 41 42

W = Cl, Br,
$X^1$, $X^2$, $X^3$, $X^4$, $Y^3$, $Y^4$, $Y^5$, ands $Y^6$ are as defined in Formula IX wherein at least one of $Y^3$ and $Y^4$ is N Scheme 4 shows the synthesis of intermediate 42 which is used in the preparation of compounds of the present invention. In Step 1, bromide intermediate 36 is reacted with potassium phthalimide at elevated temperature to give intermediate 37. In Step 2, a Sonogashira coupling with propargyl alcohol gives alkyne intermediate 38. In Step 3, the alkyne of intermediate 38 is reduced with a rhodium catalyst at elevated temperature under hydrogen pressure (90 psi) to give intermediate 39. The phthalimide group is reacted with hydrazine at elevated temperature to give amine 40 in Step 4, which then undergoes a $S_NAr$ reaction with intermediate 41 using DIPEA at elevated temperature in Step 5 to give intermediate 42.

Scheme 5

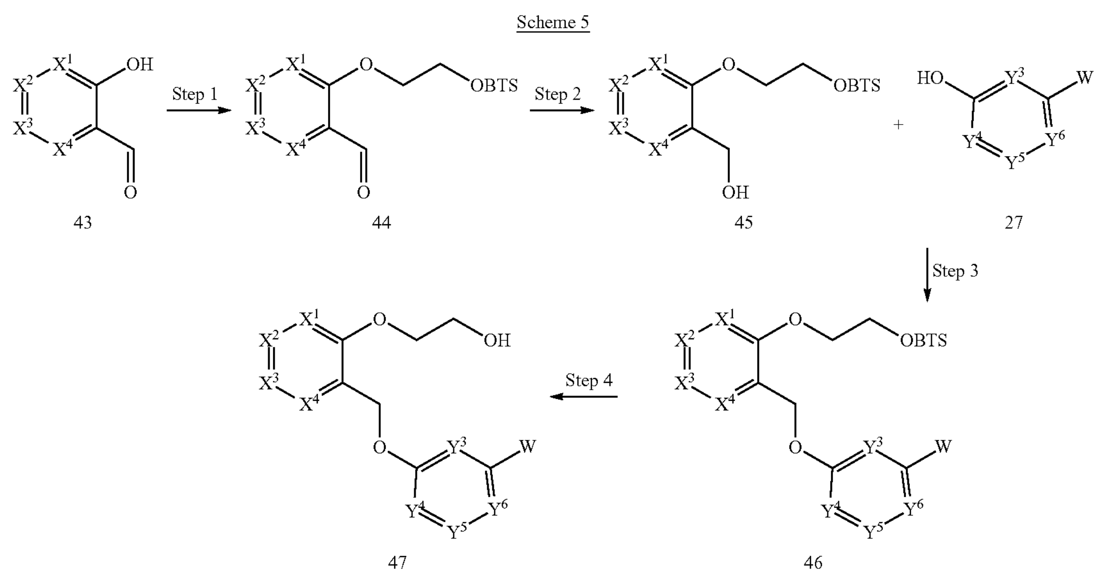

43 44 45 27 47 46

W = Cl, Br,
$X^1$, $X^2$, $X^3$, $X^4$, $Y^3$, $Y^4$, $Y^5$, $Y^6$, and $Y^7$ are defined as defined in Formula IX Scheme 5 shows the synthesis of intermediate 47 which is used in the preparation of compounds of the present invention. In Step 1, intermediate 43 is reacted with (2-bromoethoxy)-tert-butyldimethylsilane using a carbonate base at elevated temperature. The aldehyde of intermediate 44 is reduced in Step 2 using sodium borohydride to give alcohol 45, which then undergoes a Mitsunobu reaction with intermediate 27 in Step 3 to give intermediate 46. Removal of the tert-butyldimethylsilyl group in Step 4 with TBAF gives intermediate 47.

Scheme 6

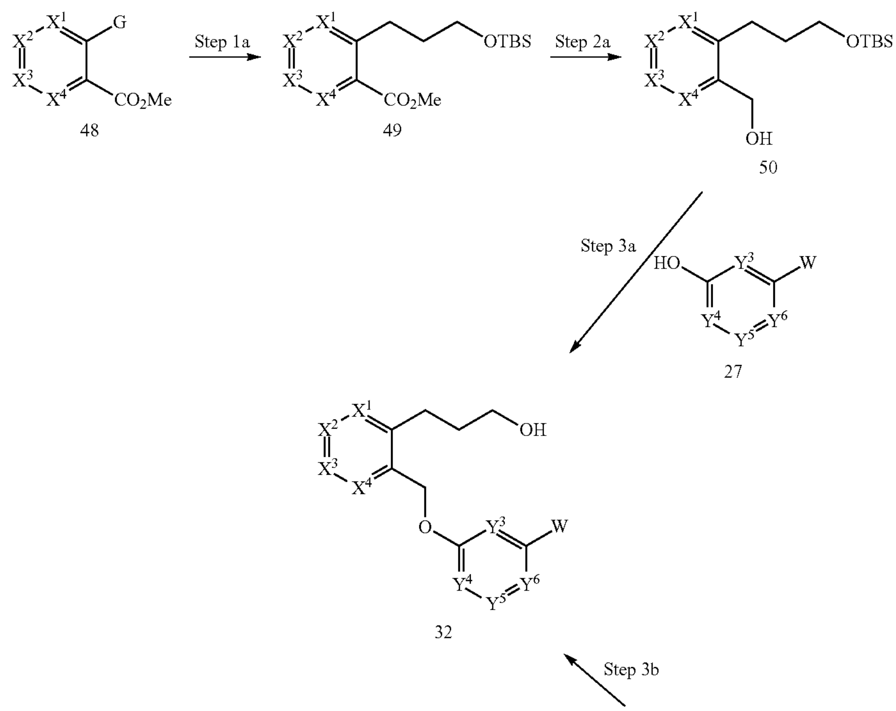

48 49 50 27 32

-continued

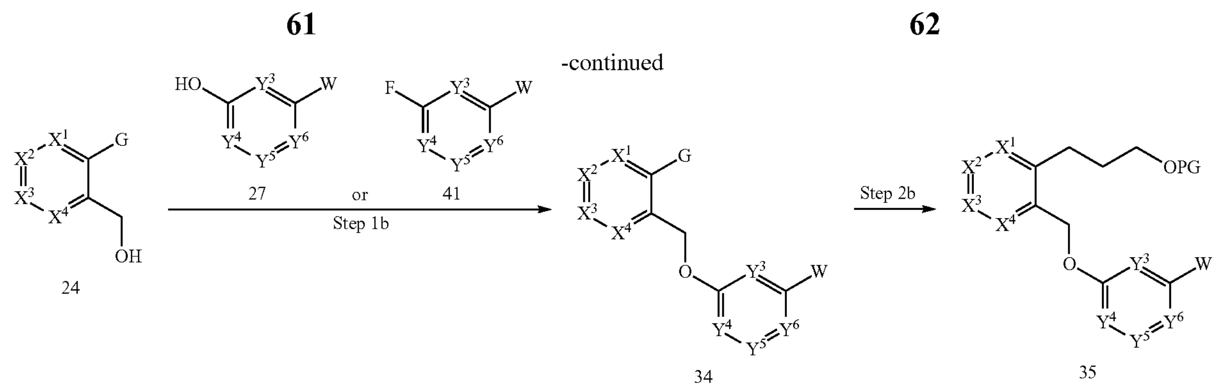

24
27
41
34
35

G = Br, I; W = Cl, Br;
$X^1$, $X^2$, $X^3$, $X^4$, $Y^1$, $Y^2$, $Y^3$, $Y^4$, $Y^5$, and $Y^6$ are as defined in Formula IX
PG = protecting group e.g. TBS (tert-butyldimethylsilyl)

Intermediate 32, as described in Scheme 3, can be prepared by the alternative routes shown in Scheme 6. In Step 1a, intermediate 48 undergoes a Negishi coupling with bromo-[3-[tert-butyl(dimethyl)silyl]oxypropyl]zinc and a palladium catalyst at elevated temperature to give intermediate 49, which is then reduced to alcohol intermediate 50 in Step 2a using lithium aluminum hydride. In Step 3a, intermediate 50 is reacted with intermediate 27 under Mitsunobu conditions to give intermediate 32.

Alternatively, intermediate 24 is reacted with either intermediate 27 under Mitsunobu conditions, or with potassium tert-butoxide and aryl fluoride intermediate 41 to give intermediate 34 in Step 1b. Steps 2b and 3b are as described in Scheme 3 (Negishi coupling with bromo-[3-[tert-butyl(dimethyl)silyl]oxypropyl]zinc, followed by deprotection to give intermediate 32).

Scheme 7

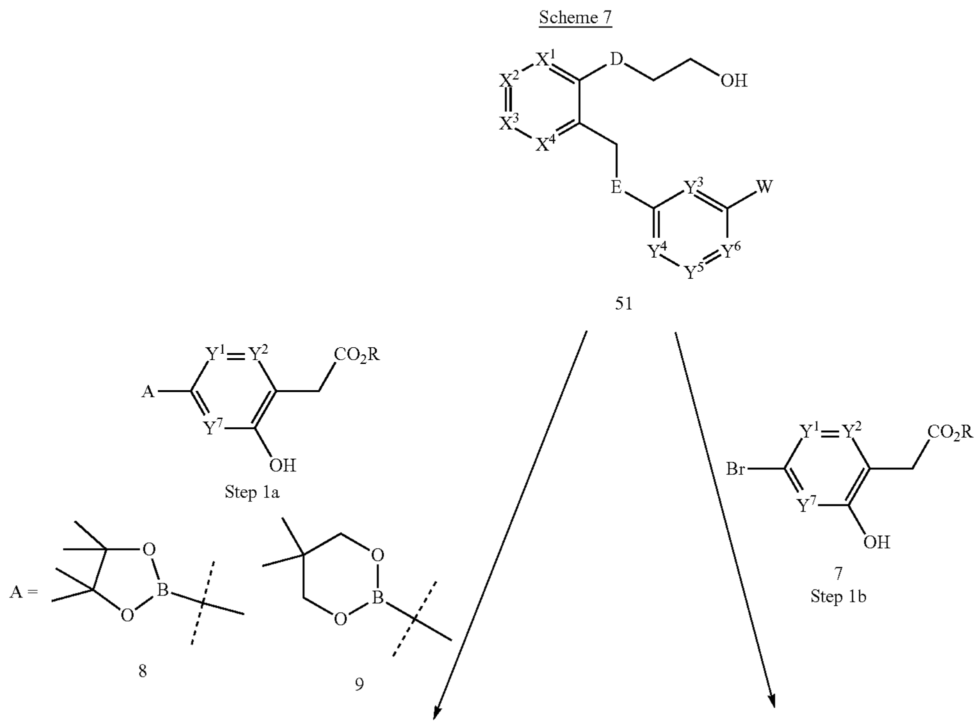

51
A =
8
9
7

-continued

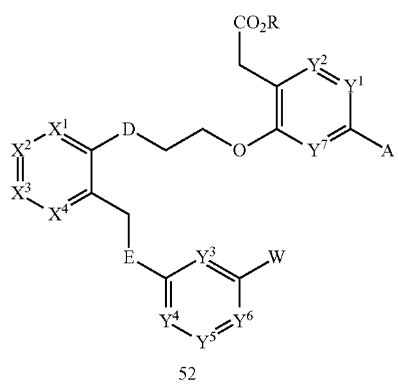

52

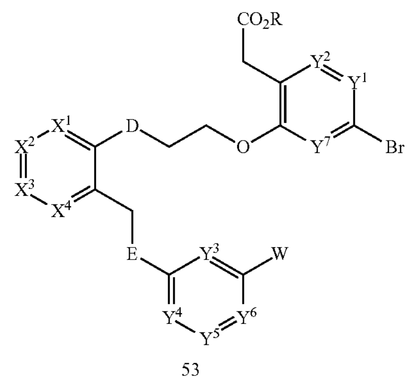

53

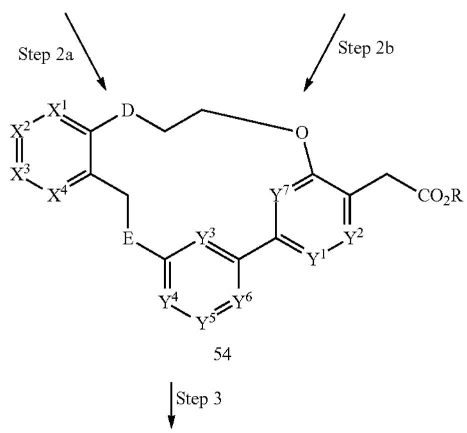

54

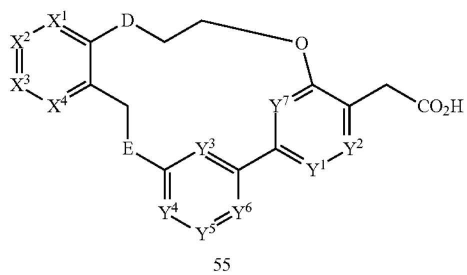

55

R = methyl, ethyl; D = $-CH_2-$, $-O-$, or is absent;
E = $-O-$, $-NH-$;
W = Br, Cl
$X^1$, $X^2$, $X^3$, $X^4$, $Y^1$, $Y^2$, $Y^3$, $Y^4$, $Y^5$, $Y^6$, and $Y^7$ are as defined in Formula IX Scheme 7 shows two routes for synthesizing intermediate 55, which is used in the preparation of compounds of the present invention. In the first route, intermediate 51 undergoes a Mitsunobu reaction with intermediate 8 or 9 to give intermediate 52 in Step 1a. In Step 2a, intermediate 52 then undergoes an intramolecular cross-coupling with a palladium catalyst to form macrocyclic intermediate 54. In the second route, intermediate 51 undergoes a Mitsunobu reaction with intermediate 7 to give intermediate 53 in Step 1b, then palladium-catalyzed intramolecular Stille coupling at elevated temperature in Step 2b gives intermediate 54. The ester group of intermediate 54 is hydrolyzed in Step 3 using either aqueous LiOH or a guanidine base in ACN/water to give intermediate 55.

Scheme 8
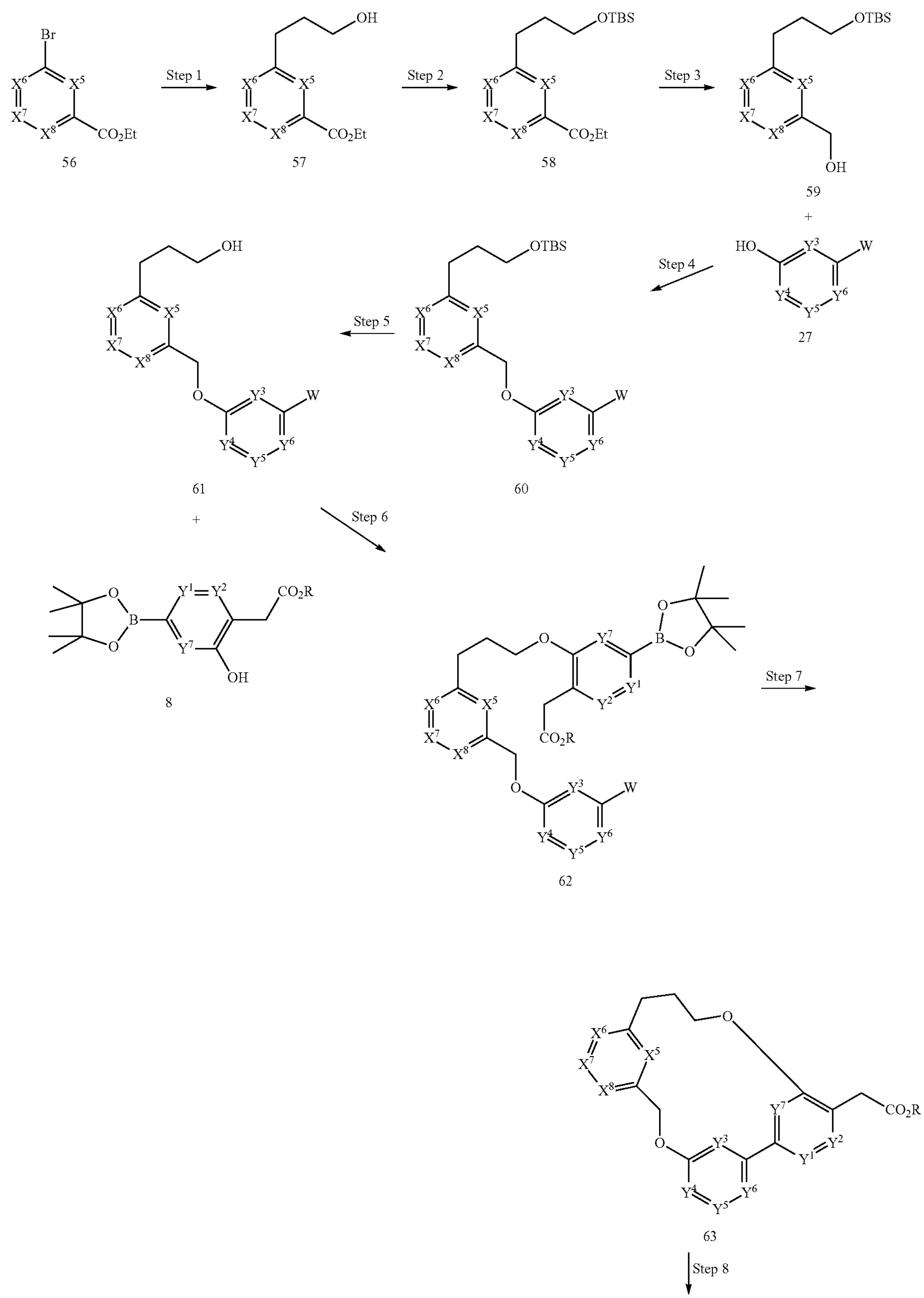
56 57 58 59 + 27 60 61 + 8 62 63

-continued

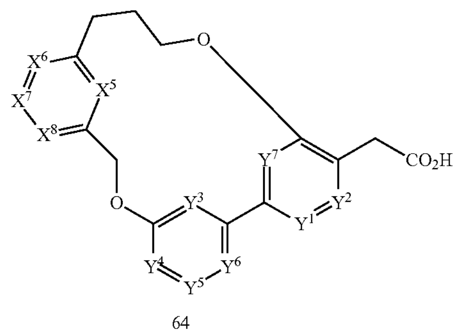

64

R = methyl, ethyl; W = Cl, Br
$X^5$, $X^6$, $X^7$, $X^8$, $Y^1$, $Y^2$, $Y^3$, $Y^4$, $Y^5$, $Y^6$, and $Y^7$ are as defined in Formula IX Scheme 8 shows the synthesis of intermediate 64 which is used in the preparation of compounds of the present invention. In Step 1, intermediate 56 undergoes a reductive coupling with 3-bromo-1-propanol at elevated temperature to give intermediate 57, which then is protected with a TBS group in Step 2 to give intermediate 58. Reduction of the ester with lithium borohydride then gives alcohol intermediate 59 in Step 3, which then undergoes a Mitsunobu reaction with intermediate 27 in Step 4 to give intermediate 60. Removal of the TBS protecting group with TBAF gives intermediate 61 in Step 5, which then undergoes a Mitsunobu reaction with intermediate 8 in Step 6 to give intermediate 62. In Step 7, intermediate 62 is cyclized using a palladium catalyst and potassium phosphate to give intermediate 63, which is then hydrolyzed in Step 8 using a using either aqueous LiOH or a guanidine base in ACN/water to give acid intermediate 64.

Scheme 9

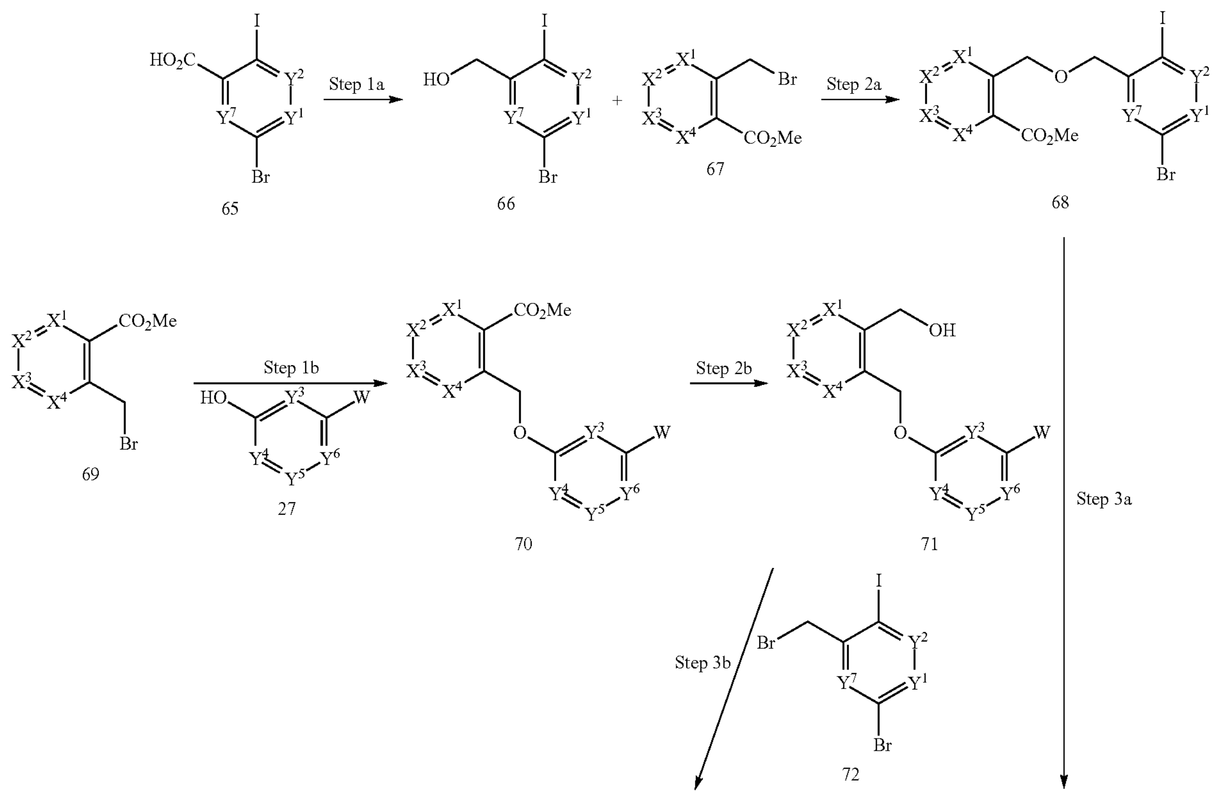

65 66 67 68 69 27 70 71 72

-continued

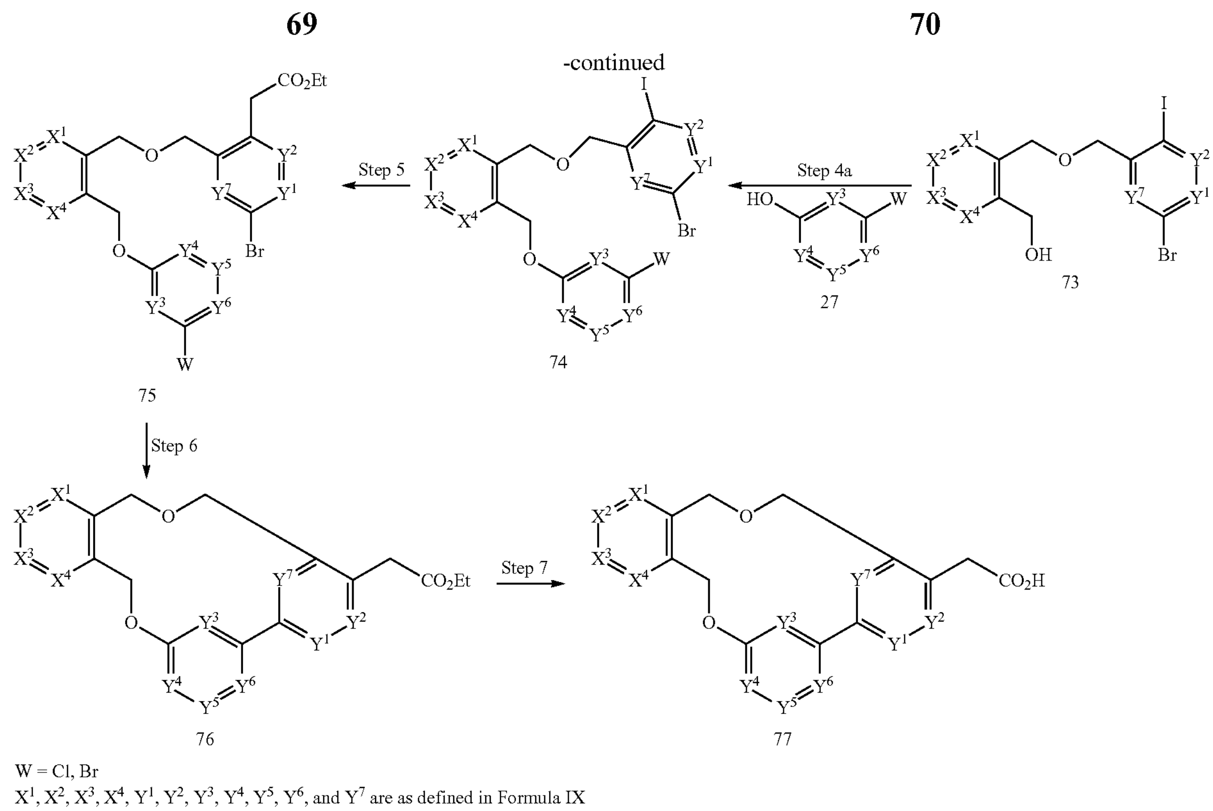

75 74 27 73 76 77

W = Cl, Br $X^1$, $X^2$, $X^3$, $X^4$, $Y^1$, $Y^2$, $Y^3$, $Y^4$, $Y^5$, $Y^6$, and $Y^7$ are as defined in Formula IX Scheme 9 shows the synthesis of intermediate 77 which is used in the preparation of compounds of the present invention, and two synthetic routes to the common intermediate 74 are shown.

In the first route to intermediate 74, in Step 1a, acid intermediate 65 is reduced using borane-dimethylsulfide complex to give alcohol intermediate 66, which then undergoes a reaction with sodium hydride and bromide intermediate 67 in Step 2a to give intermediate 68. In Step 3a, ester reduction with lithium borohydride gives intermediate 73, which then undergoes a Mitsunobu reaction with intermediate 27 to give intermediate 74 in Step 4a.

In the second route to intermediate 74, in Step 1b, alkyl bromide intermediate 69 is reacted with intermediate 27 using silver carbonate at elevated temperature to give intermediate 70. In Step 2b, the ester of intermediate 70 is reduced with lithium borohydride to give alcohol 71, which is then reacted with alkyl bromide 72 using potassium tert-butoxide to give intermediate 74 in Step 3b.

In Step 5, intermediate 74 is coupled with ethyl diazoacetate using a palladium catalyst at elevated temperature to give intermediate 75. In Step 6, an intramolecular Stille coupling with a palladium catalyst at elevated temperature gives intermediate 76. Alternatively, Step 6 is accomplished by one-pot coupling with bis(neopentyl glycolato)diboron using a palladium catalyst and potassium pivalate and intramolecular cross-coupling to give cyclic intermediate 76. Intermediate 76 is then hydrolyzed using either aqueous LiOH or a guanidine base in ACN/water in Step 7 to give acid intermediate 77.

Scheme 10

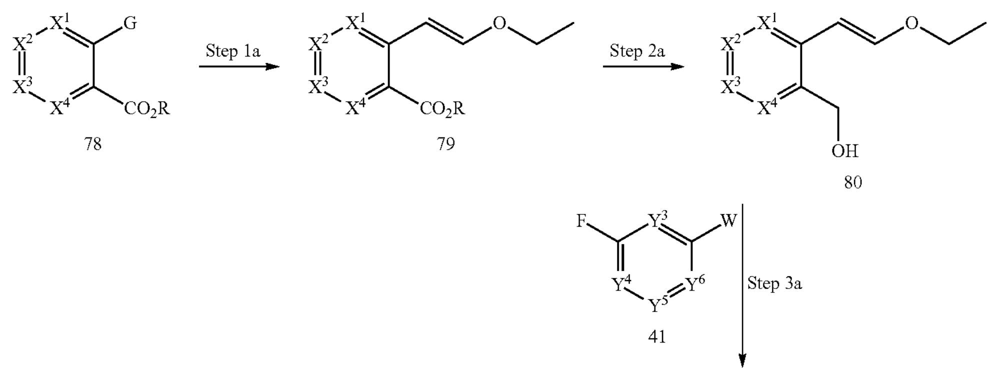

78 79 80 41

-continued

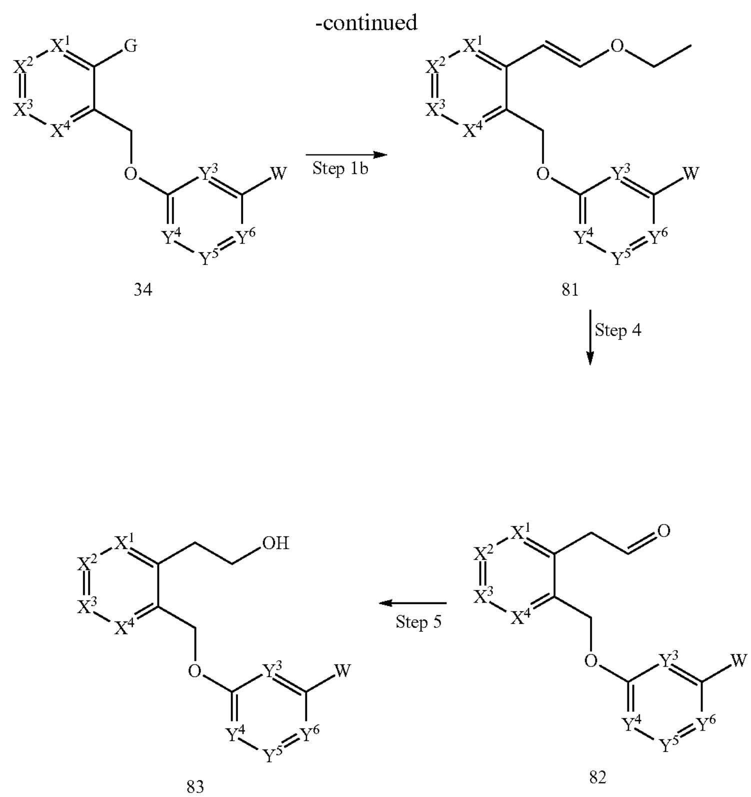

34 81 82 83

G = Cl, Br, I; W = Cl, Br
R = methyl, ethyl;
$X^1$, $X^2$, $X^3$, $X^4$, $Y^3$, $Y^4$, $Y^5$, and $Y^6$ are as defined in Formula IX Scheme 10 shows the preparation of intermediate 83, which is used in the preparation of compounds of the present invention. Two routes to common intermediate 81 are shown. In the first route, intermediate 78 is coupled with 2-[(E)-2-ethoxyvinyl]-4,4,5,5-tetramethyl-1,3,2-dioxaborolane using a palladium catalyst and carbonate base at elevated temperature in Step 1a to give intermediate 79. In Step 2a the ester is treated with a reducing agent such as diisobutylaluminum hydride to give alcohol 80, then reacted with aryl fluoride 41 using a strong organic base such as potassium tert-butoxide to give intermediate 81. In the second route, intermediate 34 (see Scheme 3) is first coupled with (E)-1-ethoxyethene-2-boronic acid pinacol ester using a palladium catalyst and an inorganic base at elevated temperature to give intermediate 81 in Step 1b.

In Step 4, intermediate 81 is treated with HCl in an organic solvent to give aldehyde 82, which is then reduced with $NaBH_4$ in Step 3 to give alcohol intermediate 83. Alternatively, intermediate 81 can be converted to intermediate 83 in one step using mercuric acetate and $NaBH_4$.

Scheme 11

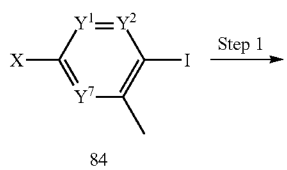

84

-continued

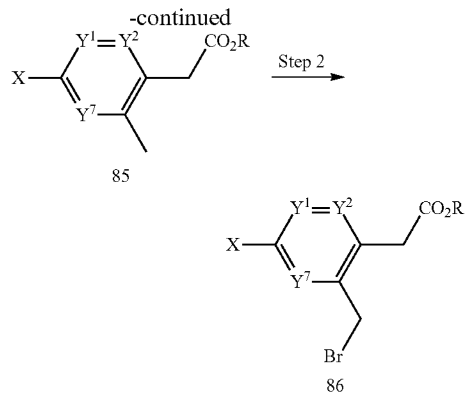

85 86

X = Br, I; R = methyl, ethyl;
$Y^1$, $Y^2$, and $Y^7$ are as defined in Formula IX Scheme 11 shows the preparation of intermediate 86, which is used in the preparation of compounds of the present invention. In Step 1, aryl iodide 84 undergoes Negishi coupling with (2-ethoxy-2-oxoethyl)zinc(II) bromide and a palladium catalyst at elevated temperature. In Step 2, intermediate 85 undergoes photochemical bromination with N-bromosuccinimide in a flow reactor to give bromide intermediate 86.

Scheme 12
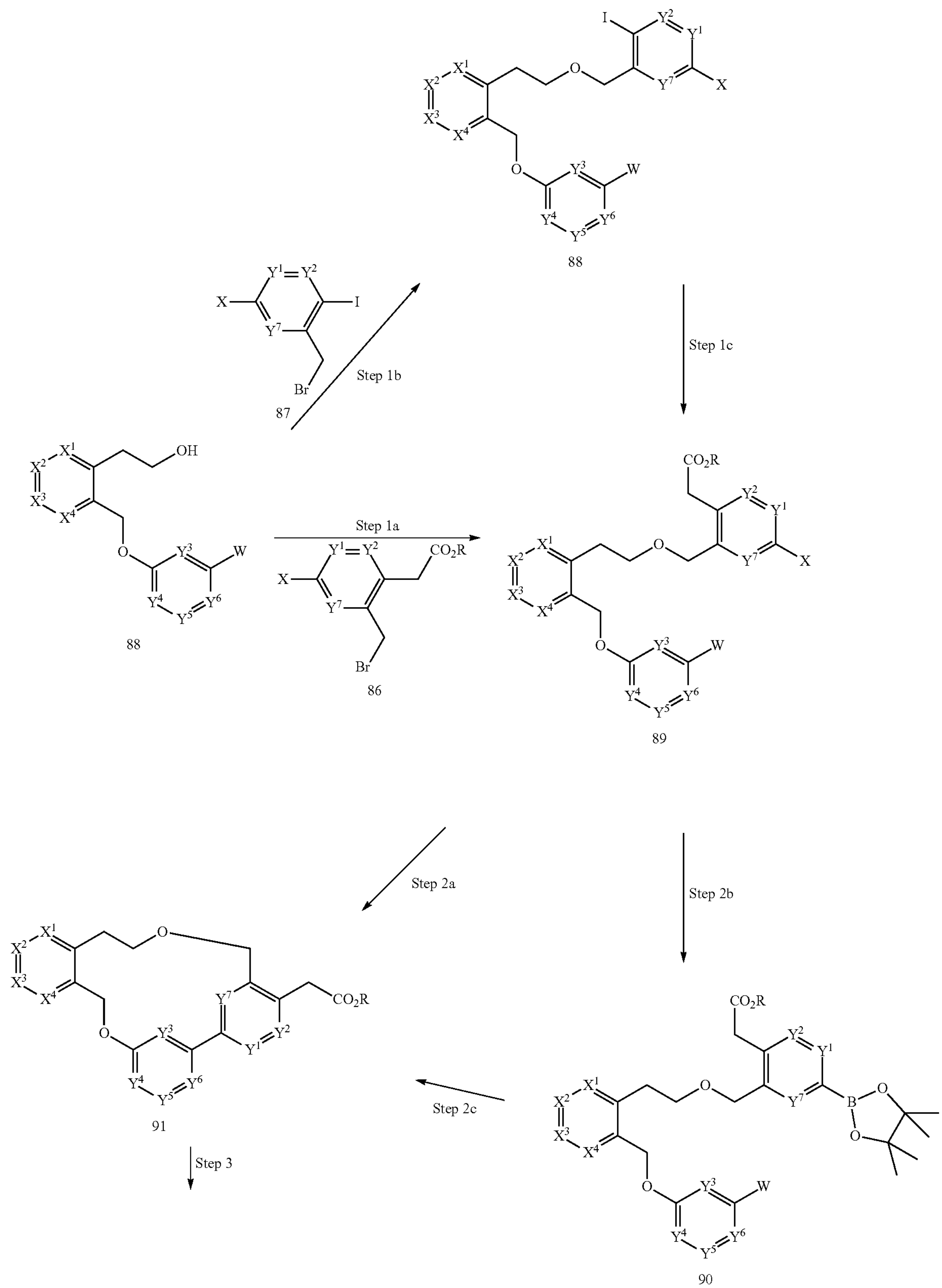
88, 87, 88, 86, 89, 91, 90

-continued

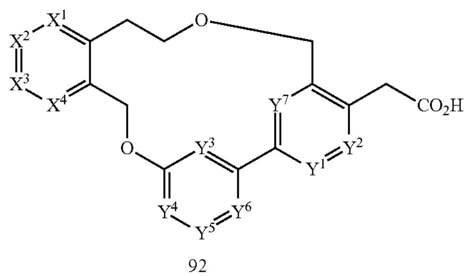

92

X = Br, I; W = Cl, Br

R = methyl, ethyl;

$X^1$, $X^2$, $X^3$, $X^4$, $Y^1$, $Y^2$, $Y^3$, $Y^4$, $Y^5$, $Y^6$, and $Y^7$ are as defined in Formula IX Scheme 12 shows multiple routes to the preparation of intermediate 92, which is used in the preparation of compounds of the present invention. In Step 1a, intermediate 83 is reacted with intermediate 86 using 2,6-di-tert-butylpyridine and silver trifluoromethanesulfonate to give intermediate 89. Alternatively, intermediate 83 can be first reacted in Step 1b with alkyl bromide 87 under similar conditions to Step 1a to give intermediate 88, which then undergoes Negishi coupling in Step 1c with (2-ethoxy-2-oxoethyl))zinc bromide and a palladium catalyst at elevated temperature to give intermediate 89. In Step 2a, intermediate 89 undergoes a palladium-catalyzed intramolecular Stille coupling at elevated temperature to give intermediate 91. Alternatively, in Step 2b, the bromide 89 is converted to the boronic ester intermediate 90 by cross-coupling with bis(pinacolato)diboron, Pd(dppf)$Cl_2$ and potassium acetate at elevated temperature, which then in Step 2c is cyclized via intramolecular cross-coupling with a palladium catalyst to form macrocyclic intermediate 91 (Steps 2b and 2c can be performed as a single reaction step). Finally in Step 3 the ester is hydrolyzed using either aqueous LiOH or a guanidine base in ACN/water to give acid intermediate 92.

Scheme 13

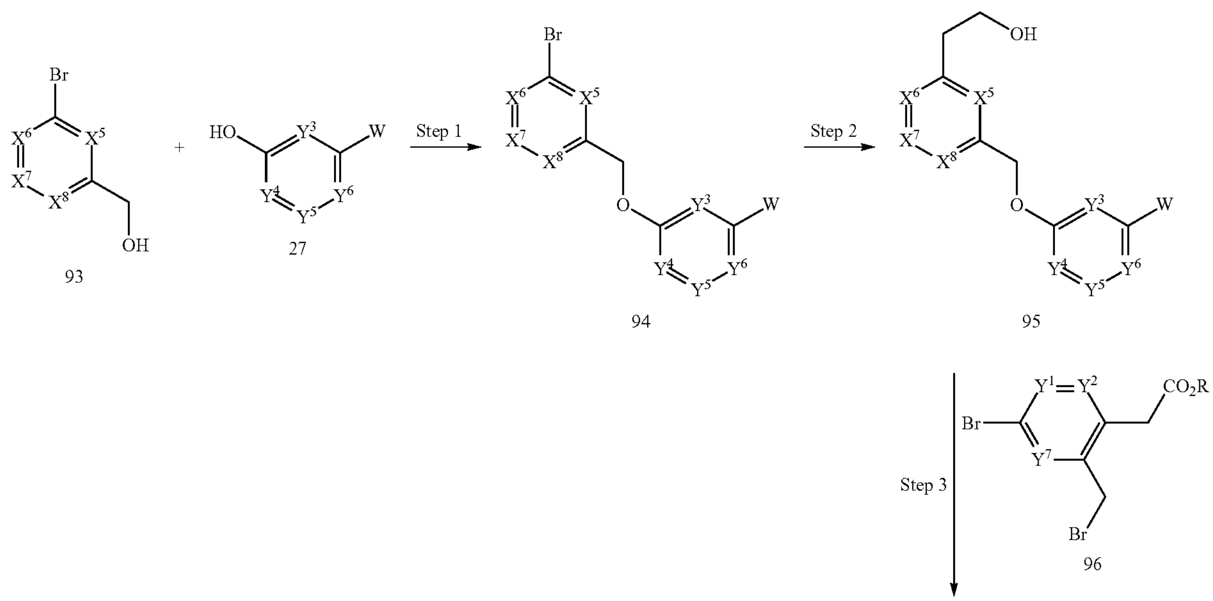

93 27 94 95 96

-continued

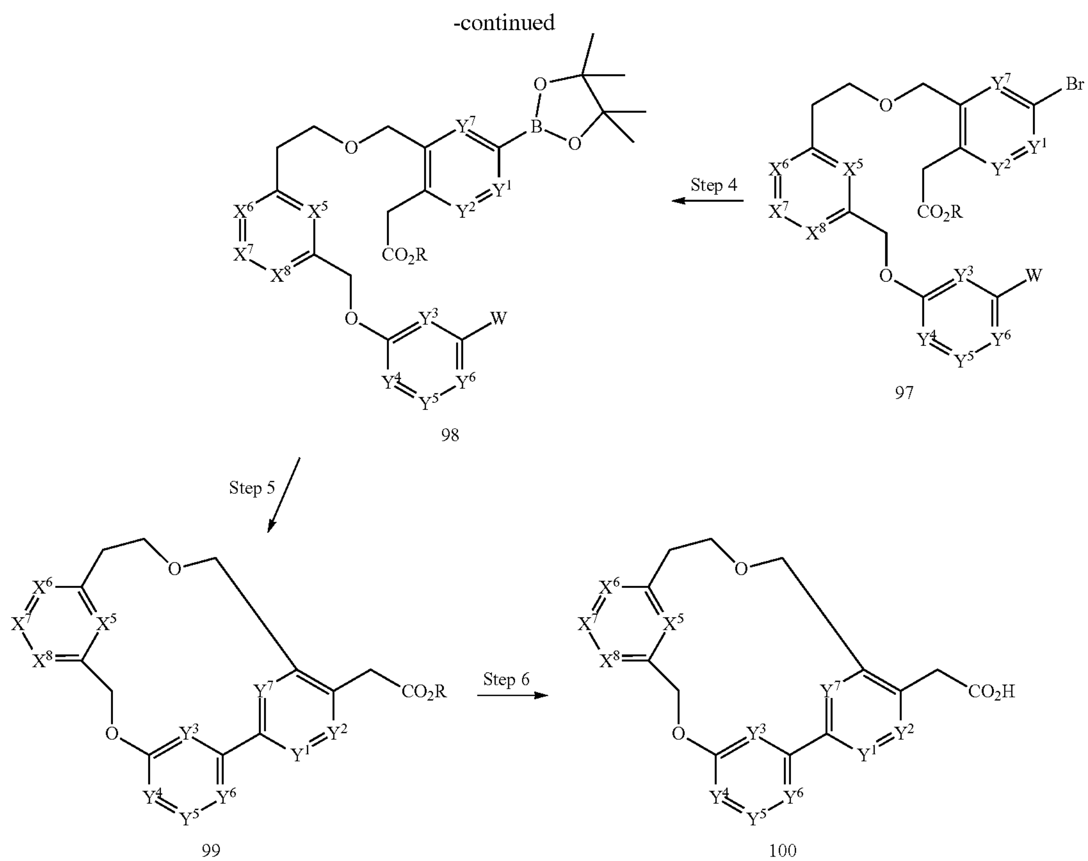

98

97

99

100

R = methyl, ethyl; W = Cl, Br;
$X^5$, $X^6$, $X^7$, $X^8$, $Y^1$, $Y^2$, $Y^3$, $Y^4$, $Y^5$, $Y^6$, and $Y^7$ are as defined in Formula IX Scheme 13 shows the preparation of intermediate 100, which is used in the preparation of compounds of the present invention. Intermediate 93 is first coupled to intermediate 27 using Mitsunobu conditions to give intermediate 94 in Step 1. In Step 2, intermediate 94 is coupled with bromoethanol using nickel and iridium catalysts and irradiating the reaction under blue light (456 nm) to give intermediate 95. Alternatively, intermediate 95 is prepared in a manner analogous to the synthetic routes shown in the preparation of intermediate 83 in Scheme 10, starting with intermediate 93 in place of intermediate 78. In Step 3, intermediate 95 is reacted with intermediate 96 using 2,6-di-tert-butylpyridine and silver trifluoromethanesulfonate to give intermediate 97.

In Step 4, bromide intermediate 97 is converted to the boronic ester intermediate 98 by cross-coupling with bis (pinacolato)diboron, $Pd(dppf)Cl_2$ and potassium acetate at elevated temperature. In Step 5, intermediate 98 then undergoes an intramolecular cross-coupling with a palladium catalyst to form macrocyclic intermediate 99. Alternatively, intermediate 97 is converted in one step to intermediate 99 via intramolecular Stille coupling using hexamethylditin and a palladium catalyst at elevated temperature. Intermediate 99 is then hydrolyzed using either aqueous LiOH or a guanidine base in ACN/water in Step 6 to give acid intermediate 100.

Scheme 14

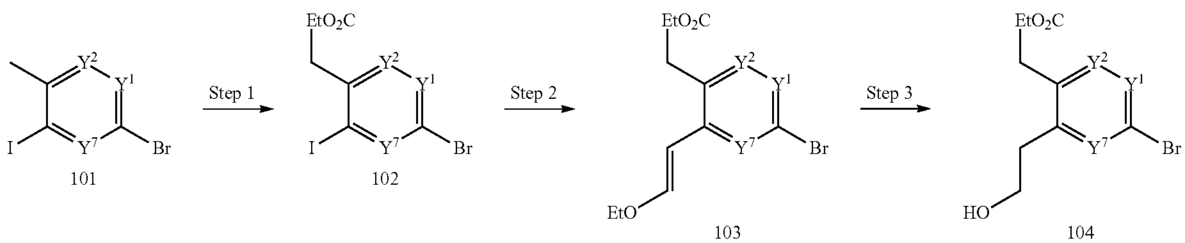

101 102 103 104

-continued

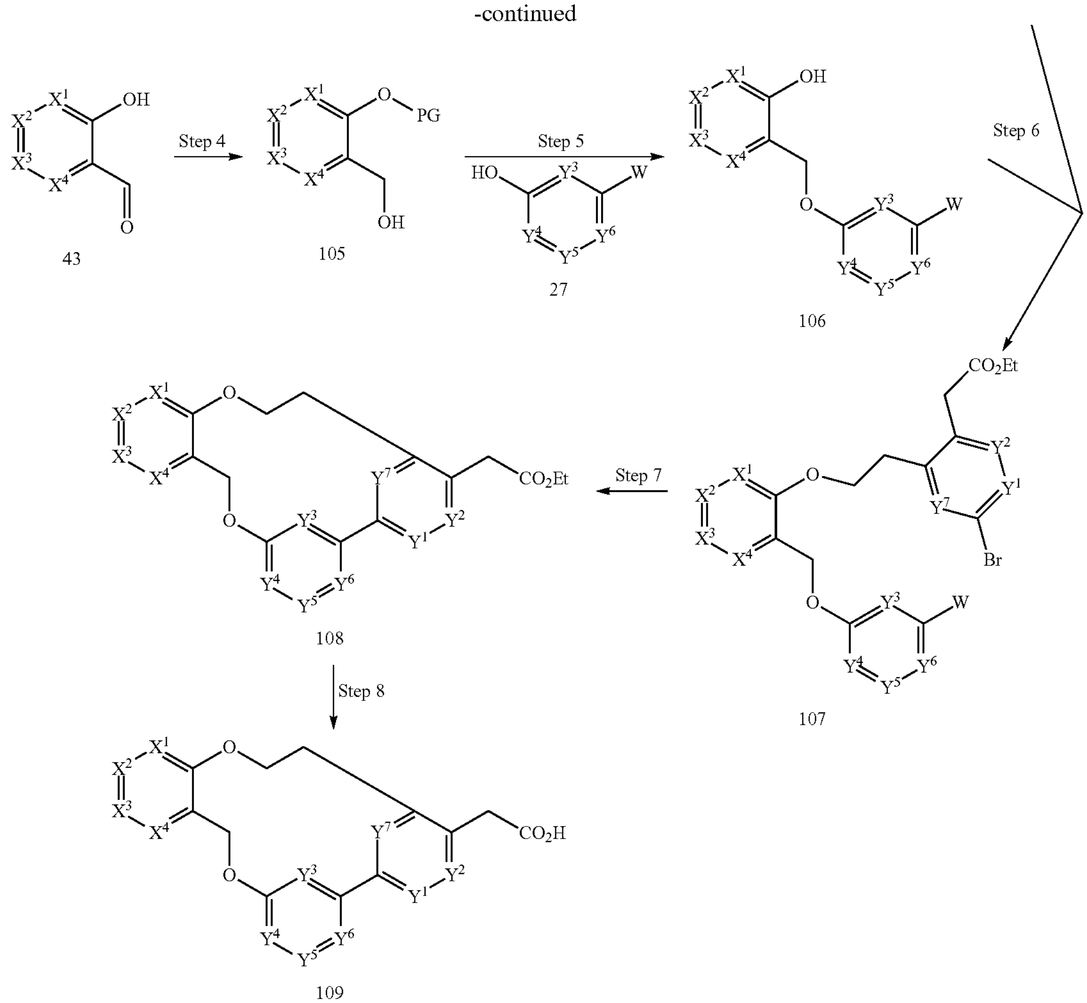

43 105 27 106 107 108 109

W = Cl, Br; PG = protecting group e.g. SEM (trimethylsilylethoxymethyl)
$X^1$, $X^2$, $X^3$, $X^4$, $Y^1$, $Y^2$, $Y^3$, $Y^4$, $Y^5$, $Y^6$, and $Y^7$ are as defined in Formula IX Scheme 14 shows the preparation of intermediate 109, which is used to prepare compounds of the present invention. In Step 1, intermediate 101 undergoes radical bromination with N-bromosuccinimide at elevated temperature, then reacted with trimethylsilyl cyanide and TBAF, then treated with sulfuric acid in aqueous EtOH at elevated temperature to give ester intermediate 102. In Step 2, intermediate 102 is coupled with (E)-1-ethoxyethene-2-boronic acid pinacol ester using a palladium catalyst and a carbonate base to give intermediate 103, which is then converted to alcohol 104 in Step 3 using mercuric acetate and sodium borohydride. Separately, aldehyde intermediate 43 is first protected e.g. with a SEM group and then reduced with sodium borohydride in Step 4 to give intermediate 105. In Step 5, intermediate 105 undergoes a Mitsunobu reaction with intermediate 27 to give intermediate 106. Intermediates 104 and 106 are coupled via Mitsunobu reaction to give intermediate 107, which then undergoes intramolecular cyclization in Step 7 in a manner analogous to Step 2a (one-pot Stille coupling) or Steps 2b and 2c (borylation followed by Pd-catalyzed cross-coupling) in Scheme 12 to give intermediate 108. Ester hydrolysis using either aqueous LiOH or a guanidine base in ACN/water in Step 8 then gives intermediate 109.

Scheme 15

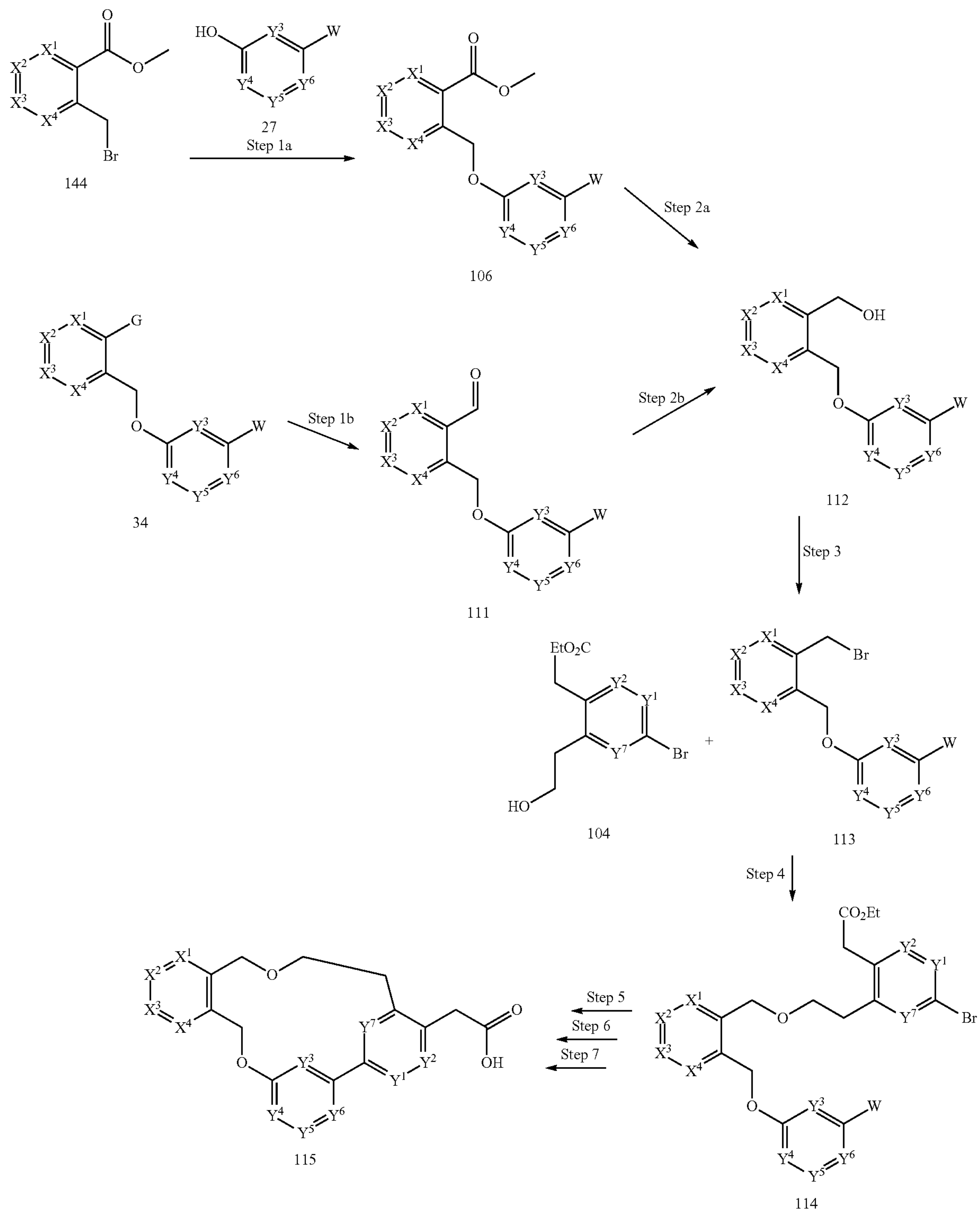

144, 27, 106, 34, 111, 112, 104, 113, 114, 115

G = Br, I; W = Cl, Br;

$X^1$, $X^2$, $X^3$, $X^4$, $Y^1$, $Y^2$, $Y^3$, $Y^4$, $Y^5$, $Y^6$, and $Y^7$ are as defined in Formula IX Scheme 15 shows the preparation of intermediate 115, which is used to prepare compounds of the present invention. In Step 1a, alkyl bromide intermediate 144 is reacted with intermediate 27 using silver carbonate at elevated temperature, followed by ester reduction using Red-Al® in Step 2a to give intermediate 112. Alternatively, intermediate 34 is carbonylated in Step 1b using potassium formate and a palladium catalyst to give intermediate 111, followed by reduction of the aldehyde in Step 2b using $NaBH_4$ to give intermediate 112. In Step 3, the alcohol of intermediate 112 is converted to the alkyl bromide using $CBr_4$ and triphenylphosphine to give intermediate 113. In Step 4, intermediates 113 and 104 are reacted with silver trifluoromethanesulfonate to give intermediate 114. Intermediate 114 then undergoes intramolecular cyclization in Step 5 in a manner analogous to Step 2a (one-pot Stille coupling) in Scheme 12, or in Steps 5 and 6 in a manner similar to Steps 2b and 2c (borylation followed by Pd-catalyzed cross-coupling) in Scheme 12. The resulting ester is hydrolyzed in Step 7 using either aqueous LiOH or a guanidine base in ACN/water to give intermediate 115.

Scheme 16

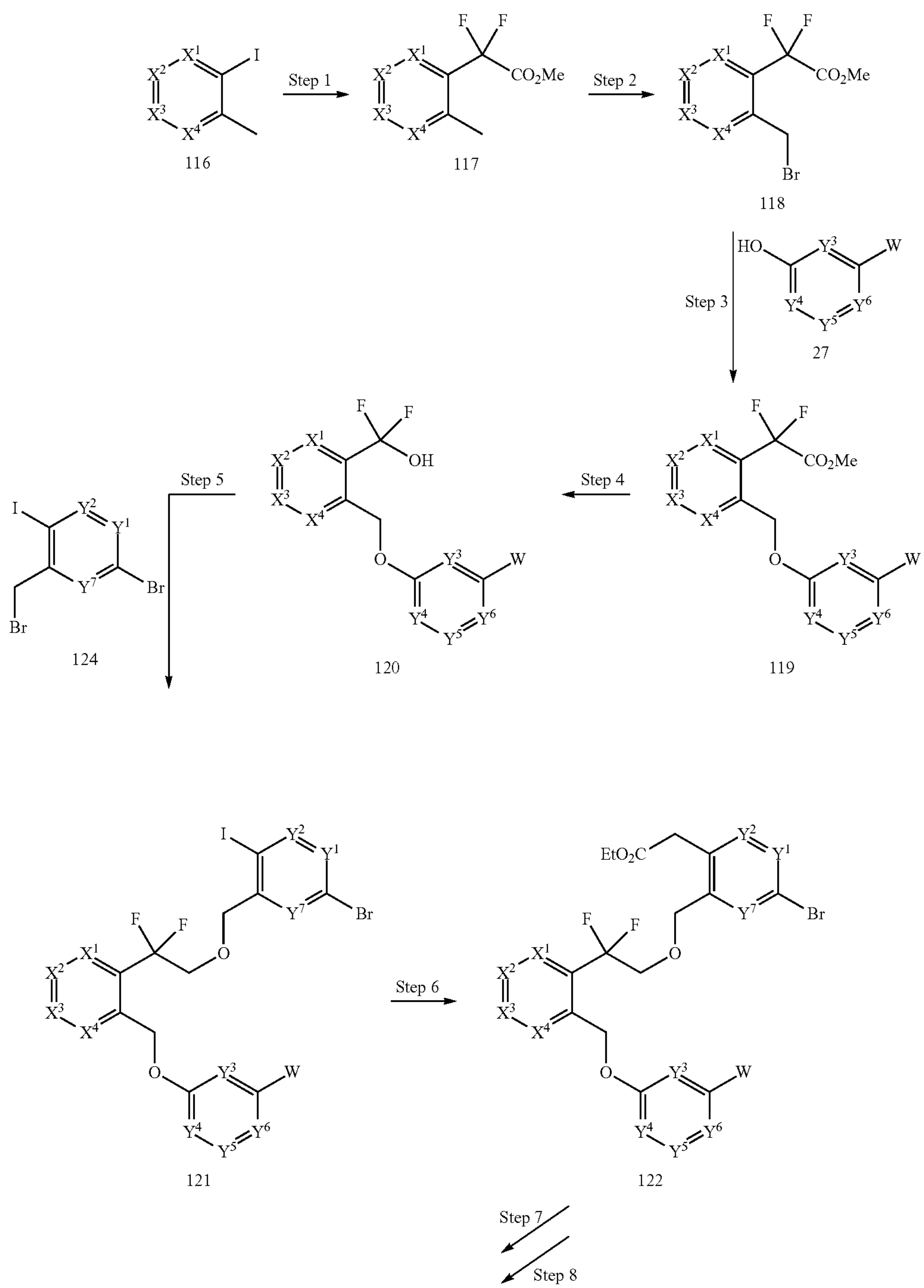

116 117 118 27 119 120 124 121 122

-continued

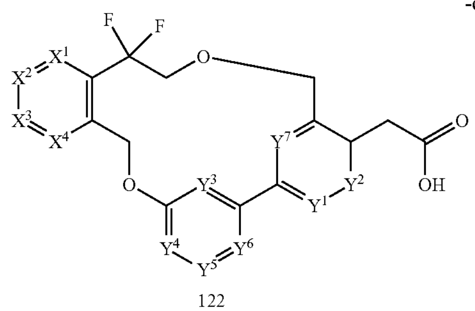

122

W = Cl, Br;

$X^1$, $X^2$, $X^3$, $X^4$, $Y^1$, $Y^2$, $Y^3$, $Y^4$, $Y^5$, $Y^6$, and $Y^7$ are as defined in Formula IX Scheme 16 shows the preparation of intermediate 123, which is used in the preparation of compounds of the present invention. In Step 1, intermediate 116 is reacted with methyl bromodifluoroacetate and copper to give intermediate 117, which is then brominated photochemically in Step 2 using N-bromosuccinimide in a flow reactor to give alkyl bromide intermediate 118. In Step 3, intermediate 118 is reacted with intermediate 27 using a phosphate base at elevated temperature to give intermediate 119, which then undergoes $LiBH_4$ reduction in Step 4 to give alcohol intermediate 120. In Step 5, intermediate 120 is treated with NaH and reacted with intermediate 124 to give intermediate 121. In Step 6, intermediate 121 undergoes Negishi coupling with (2-ethoxy-2-oxo-ethyl)zinc bromide and a palladium catalyst at elevated temperature to give intermediate 122. Intermediate 122 then undergoes intramolecular cyclization in Step 7 in a manner analogous to Step 2a (one-pot Stille coupling) or Steps 2b and 2c (borylation followed by Pd-catalyzed cross-coupling) in Scheme 12. Ester hydrolysis using either aqueous LiOH or a guanidine base in ACN/water in Step 8 then gives intermediate 123.

Scheme 17

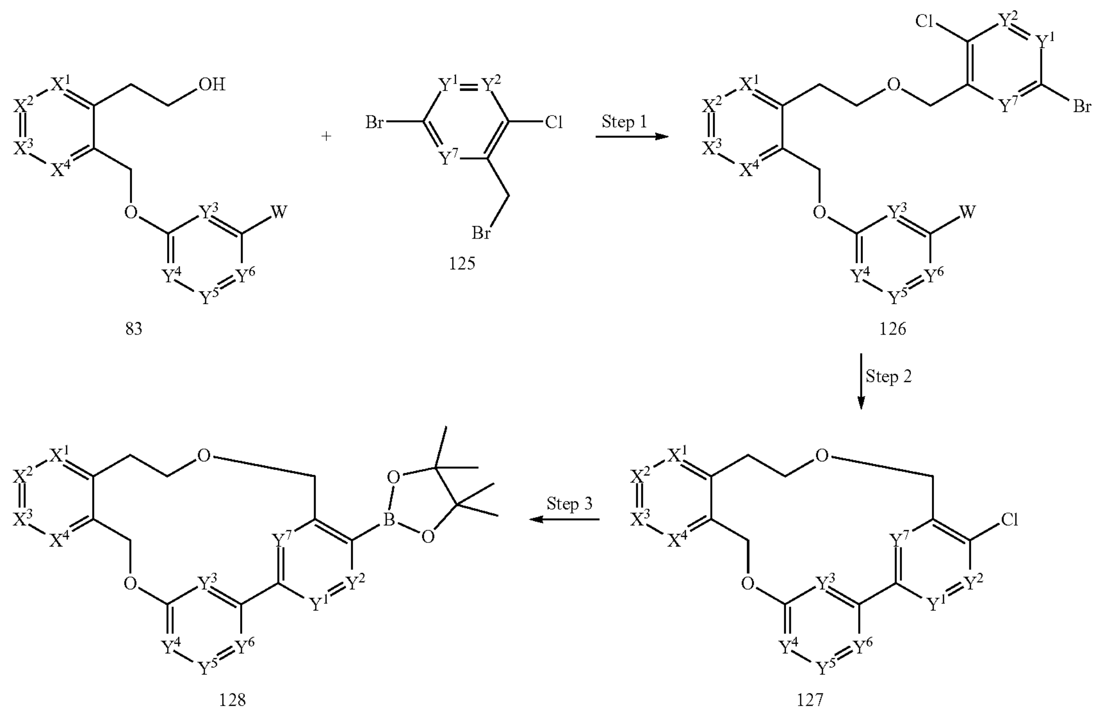

83 125 126 127 128

W = Cl, Br;

$X^1$, $X^2$, $X^3$, $X^4$, $Y^1$, $Y^2$, $Y^3$, $Y^4$, $Y^5$, $Y^6$, and $Y^7$ are as defined in Formula IX Scheme 17 shows the preparation of boronate intermediate 128, which is used in the preparation of compounds of the present invention. In Step 1, intermediate 83 is reacted with alkyl bromide intermediate 125 using silver trifluoromethanesulfonate to give intermediate 126, which then undergoes intramolecular cyclization in Step 2 in a manner analogous to Step 2a (one-pot Stille coupling) or Steps 2b and 2c (borylation followed by Pd-catalyzed cross-coupling) in Scheme 12. Finally, in Step 3 intermediate 127 is coupled with bis(pinacolato)diboron using a palladium catalyst and potassium acetate at elevated temperature to give boronate intermediate 128.

Scheme 18

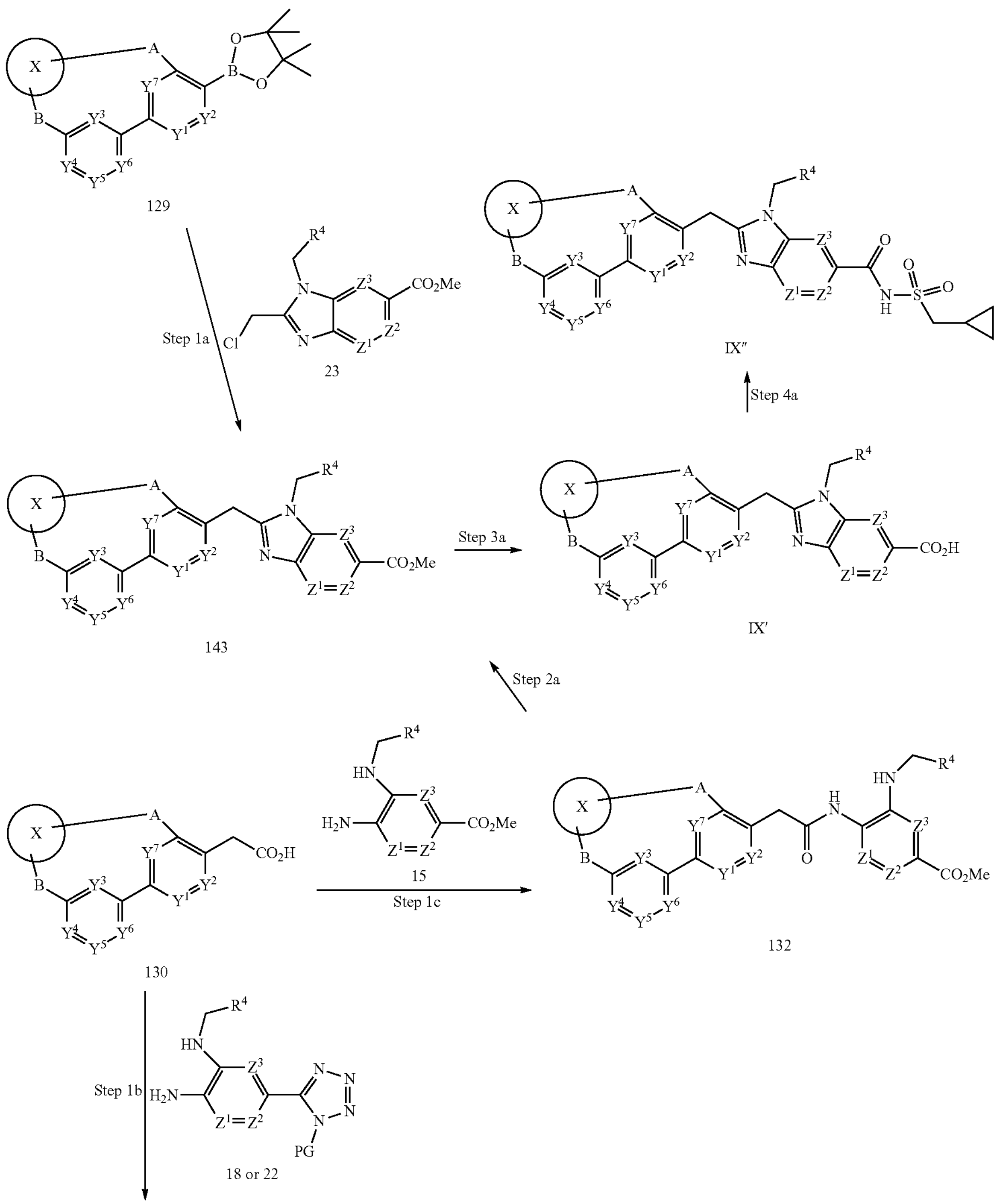

129, 23, IX″, 143, IX′, 15, 130, 132, 18 or 22

-continued

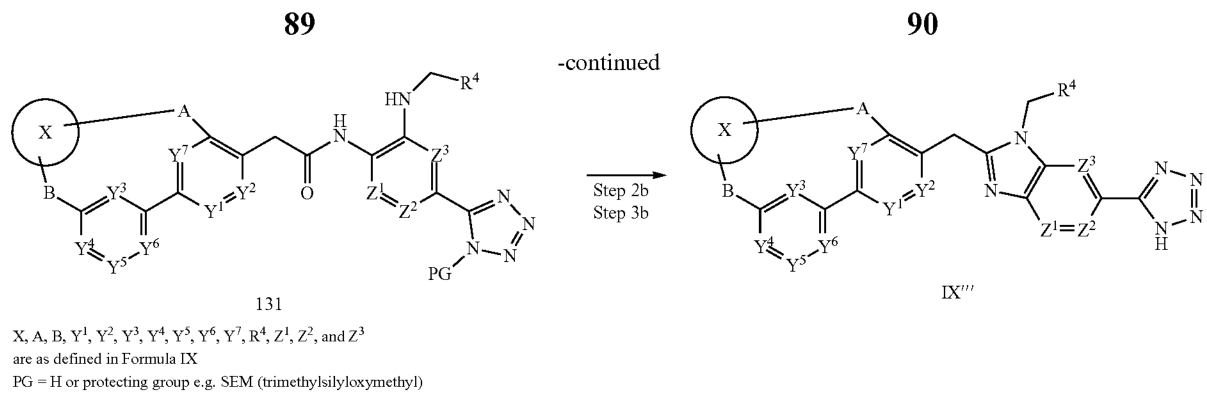

131

IX'''

X, A, B, $Y^1$, $Y^2$, $Y^3$, $Y^4$, $Y^5$, $Y^6$, $Y^7$, $R^4$, $Z^1$, $Z^2$, and $Z^3$ are as defined in Formula IX PG = H or protecting group e.g. SEM (trimethylsilyloxymethyl)

Scheme 18 shows the preparation of compounds of the present invention via a number of different routes from either intermediate 129 (a general formula which encompasses intermediate 128) or intermediate 130 (a general formula which encompasses intermediates 55, 64, 77, 92, 100, 109, 115 and 123).

To prepare acid compounds of Formula IX', intermediate 129 is coupled with chloromethylimidazole intermediate 23 in Step 1a using a palladium catalyst and a phosphate base at elevated temperature to give intermediate 143, then in Step 3a the ester is hydrolyzed using either aqueous LiOH or a guanidine base in ACN/water at elevated temperature to give acid of Formula IX'. Alternatively, acid intermediate 130 is coupled with intermediate 15 in Step 1c with an amide coupling reagent such as EDC or HATU to give intermediate 132. Intermediate 132 is then cyclized in Step 2a using acetic acid at elevated temperature to give intermediate 143, then the ester is hydrolyzed as described in Step 3a.

Compounds of the Formula IX" are prepared in Step 4a by coupling an acid of the Formula IX' with cyclopropylmethanesulfonamide using EDC and 4-dimethylaminopyridine.

Compounds of the Formula IX''' are prepared by coupling intermediate 130 with intermediate 18 (without a tetrazole nitrogen protecting group such as SEM) or 22 (with a tetrazole nitrogen protecting group) using HATU in Step 1b to give intermediate 131, then in Step 2b cyclization with acetic acid at elevated temperature (then if needed, Step 3b—tetrazole deprotection e.g. using TBAF to remove a SEM group) gives the tetrazole compound of Formula IX'''.

Scheme 19

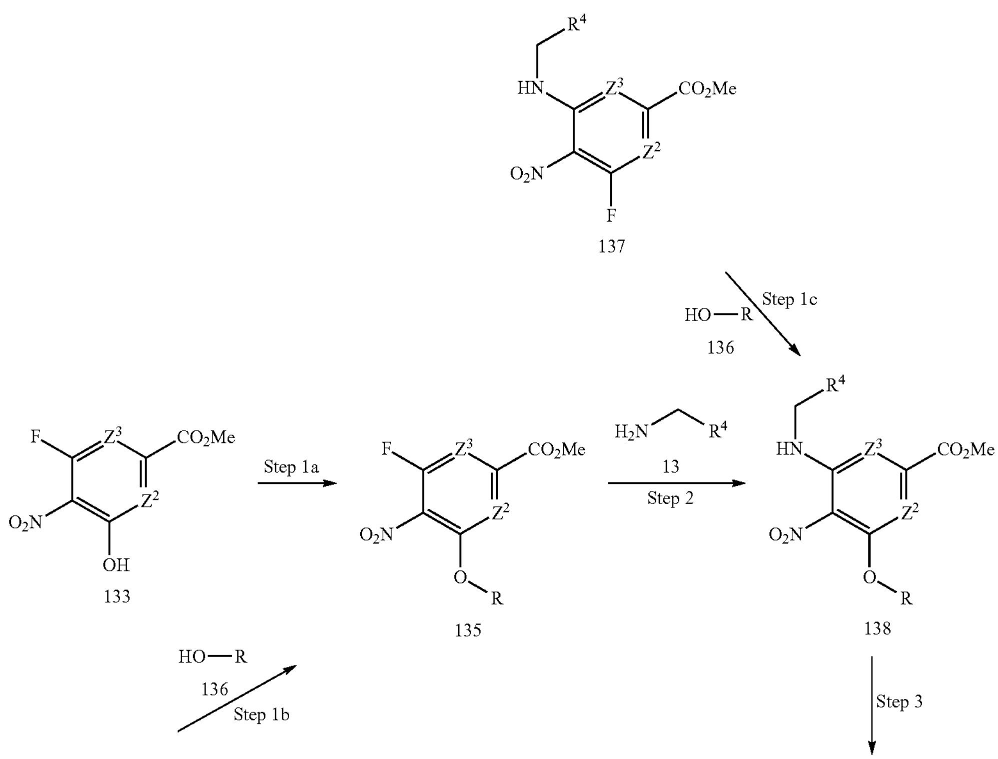

137

133

135

138

-continued

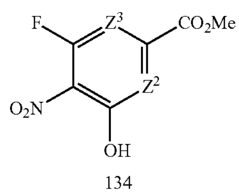

134

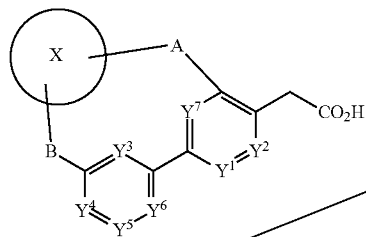

130

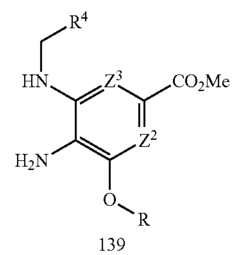

139

Steps 4, 5, and 6

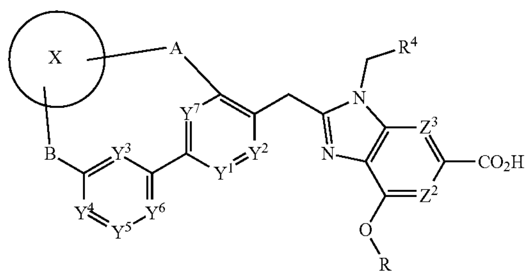

IX''''

X, A, B, $Y^1$, $Y^2$, $Y^3$, $Y^4$, $Y^5$, $Y^6$, $Y^7$, $R^4$, $Z^2$, and $Z^3$ are as defined in Formula IX —O—R is a subset of $R^3$ as defined in Formula IX Scheme 19 shows the preparation of compounds of the present invention of Formula IX''''. Intermediate 133 undergoes a Mitsunobu reaction in Step 1a with alcohol intermediate 136 to give 135, which then undergoes a $S_NAr$ reaction in Step 2 with amine 13 and a tertiary amine base at elevated temperature to give intermediate 138. Alternatively, difluoro aryl intermediate 134 first undergoes $S_NAr$ reaction in Step 1b with alcohol 136, which is first treated with NaH and then reacted with intermediate 134 at elevated temperature to give intermediate 135. A second alternative gives intermediate 138 in Step 1c by $S_NAr$ reaction with intermediate 137 and 136 in a manner similar to Step 1b. The nitro group of intermediate 138 is reduced e.g. with hydrogen gas and palladium on carbon to give aniline intermediate 139 in Step 3. Then, in a manner analogous to Steps 1c, 2a, and 3a in Scheme 18, compounds of Formula IX'''' are prepared in three steps from intermediates 139 and 130. If the "—O—R" group depicted in Scheme 19 bears a protecting group, e.g. a Boc group on a nitrogen or tert-butyldimethylsilyl group on an oxygen, that protecting group can be removed as a last step (e.g. using TFA to remove a Boc group or TBAF to remove a tert-butyldimethylsilyl group).

Scheme 20

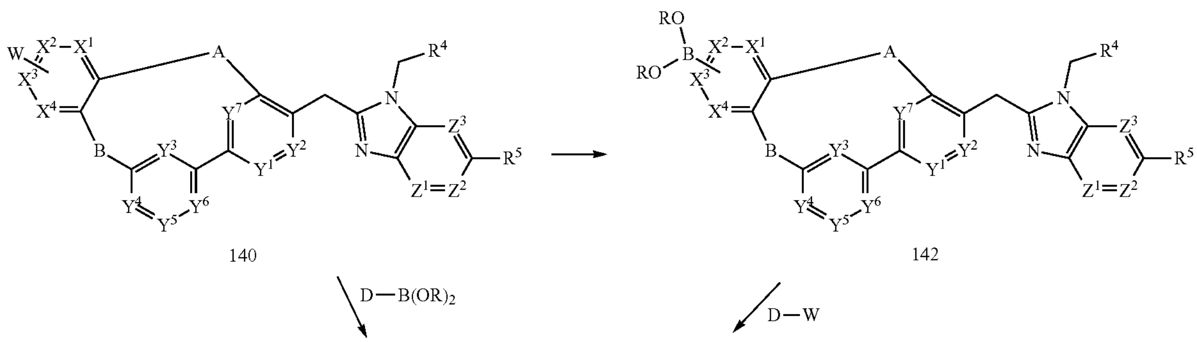

140

142

-continued

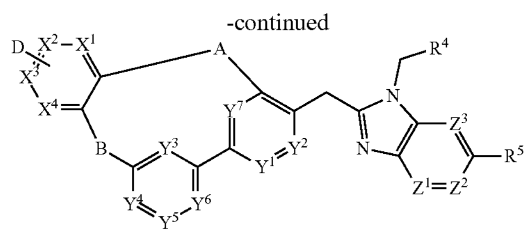

141

W = Cl, Br, or I
$X^1$, $X^2$, $X^3$, $X^4$, $Y^1$, $Y^2$, $Y^3$, $Y^4$, $Y^5$, $Y^6$, $Y^7$, $Z^1$, $Z^2$, $Z^3$, $R^4$, $R^5$, A, and B are defined as Formula IX
D = 5- or 6-membered optionally substitued aryl or heteroaryl group
R = H or alkyl groups joined to form a cyclic boronic ester Scheme 20 shows the preparation of compounds of the present invention from halide intermediate 140. Intermediate 140 undergoes a cross-coupling reaction (e.g. Suzuki) with an optionally substituted 5- or 6-membered aryl or heteroaryl boronic acid or boronic ester using a palladium catalyst and an inorganic base at elevated temperature to give 141. Alternatively, 140 can be converted to boronate 142, for example using tetrahydroxydiboron and a palladium catalyst at elevated temperature giving 142 as a boronic acid, which then undergoes a cross-coupling reaction (e.g. Suzuki) with an optionally substituted 5- or 6-membered aryl or heteroaryl halide to give 141. These steps can be carried out on either protected or unprotected versions of $R^5$, for example an ester can serve as a protected functional group which can be hydrolyzed to give $R^5$═—$CO_2H$.

PREPARATIONS AND EXAMPLES

LC-ES/MS is performed on an AGILENT® HP1200 liquid chromatography system. Electrospray mass spectrometry measurements (acquired in positive and/or negative mode) are performed on a Mass Selective Detector quadrupole mass spectrometer interfaced to an HPLC which may or may not have an ELSD. LC-ES/MS conditions (low pH): column: PHENOMENEX© GEMINI© NX C18 2.0×50 mm 3.0 μm, 110 Å; gradient: 5-95% B in 1.5 min, then 95% B for 0.5 min column temperature: 50° C.+/−10° C.; flow rate: 1.2 mL/min; 1 μL injection volume; Solvent A: deionized water with 0.1% HCOOH; Solvent B: ACN with 0.1% formic acid; wavelength 200-400 nm and 212-216 nm. If the HPLC is equipped with an ELSD the settings are 45° C. evaporator temperature, 40° C. nebulizer temperature, and 1.6 SLM gas flow rate. Alternate LC-MS conditions (high pH): column: Waters xBridge® C18 column 2.1×50 mm, 3.5 μm; gradient: 5-95% B in 1.5 min, then 95% B for 0.50 min; column temperature: 50° C.+/−10° C.; flow rate: 1.2 mL/min; 1 μL injection volume; Solvent A: 10 mM $NH_4HCO_3$ pH 9; Solvent B: ACN; wavelength: 200-400 nm and 212-216 nm; if had ELSD: 45° C. evaporator temp, 40° C. nebulizer temp, and 1.60 SLM gas flow rate.

Preparation 1

Methyl 4-bromo-5-fluoro-2-methoxy-benzoate

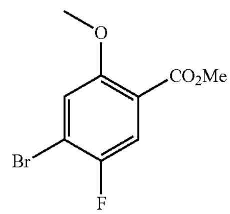

To a mixture of methyl 4-bromo-5-fluoro-2-hydroxy-benzoate (10.0 g, 40.1 mmol) and potassium carbonate (13.8 g, 100 mmol) in ACN (200 mL) add iodomethane (5.0 mL, 80.2 mmol). Stir the reaction at 60° C. for 15 h. Dilute the reaction mixture with water (150 mL) and extract with DCM (3×60 mL). Wash the combined organic layers with water (50 mL). Dry the organic phase over sodium sulfate, filter, and concentrate under reduced pressure to give 10.3 g of the title compound (98%), which is used in crude form in Preparation 2. $^1$H-NMR (400 MHz, $CDCl_3$) δ 7.60 (d, J=9 Hz, 1H), 7.15 (d, J=5 Hz, 1H), 3.90 (s, 6H).

Preparation 2

(4-Bromo-5-fluoro-2-methoxy-phenyl)methanol

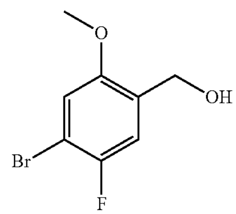

To a solution of methyl 4-bromo-5-fluoro-2-methoxy-benzoate (14 g, 53.2 mmol) and MeOH (30 mL) in THE (300 mL) add sodium borohydride (10.7 g, 272 mmol). Stir the reaction at 50° C. for 4 h. Concentrate the reaction mixture under reduced pressure. Dissolve the residue in EtOAc (300 mL) and wash with brine (2×100 mL). Dry the organic phase over sodium sulfate, filter, and concentrate under reduced pressure. Purify the residue via silica gel chromatography using a gradient of 0 to 20% EtOAc in hexanes to give 11.5 g of the title compound (92%). $^1$H-NMR (400 MHz, $CDCl_3$) δ 7.14 (d, J=8 Hz, 1H), 7.0 (d, J=6 Hz, 1H), 4.63 (s, 2H), 3.85 (s, 3H).

Preparation 3

1-Bromo-4-(bromomethyl)-2-fluoro-5-methoxy-benzene

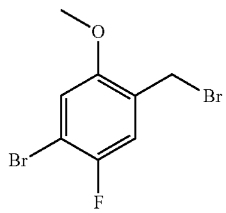

To a solution of (4-bromo-5-fluoro-2-methoxy-phenyl) methanol (11.5 g, 48.9 mmol) in DCM (200 mL) add phosphorus tribromide (5.6 mL, 59 mmol). Stir the reaction at RT for 1 h. Quench the reaction with addition of ice water (50 mL) and basify to pH 7 with saturated aqueous sodium bicarbonate solution. Wash the organic layer with water (100 mL). Dry the organic phase over sodium sulfate, filter, and concentrate under reduced pressure to give 12.5 g of the title compound (86%), which is used in crude form in Preparation 4. $^1$H-NMR (400 MHz, $CDCl_3$) δ 7.13 (d, J=8 Hz, 1H), 7.03 (d, J=6 Hz, 1H), 4.46 (s, 2H), 3.89 (s, 3H).

Preparation 4

2-(4-Bromo-5-fluoro-2-methoxy-phenyl)acetonitrile

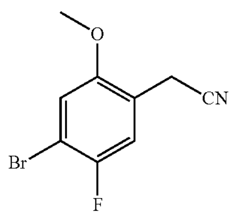

To a solution of 1-bromo-4-(bromomethyl)-2-fluoro-5-methoxy-benzene (12.5 g, 42.0 mmol) and TMSCN (6.8 mL, 50.5 mmol) in ACN (250 mL) add TBAF solution (1.0 M in THF, 50 mL, 50 mmol). Stir the reaction at RT for 4 h. Concentrate the reaction under reduced pressure. Dissolve the residue in EtOAc (200 mL) and wash with saturated aqueous sodium chloride (2×50 mL). Dry the organic phase over sodium sulfate, filter, and concentrate under reduced pressure. Purify the residue via silica gel chromatography using a gradient of 0 to 10% EtOAc in petroleum ether to give 8.0 g of the title compound (78%). $^1$H-NMR (400 MHz, $CDCl_3$) δ 7.19 (d, J=8 Hz, 1H), 7.04 (d, J=5 Hz, 1H), 3.86 (s, 3H), 3.64 (s, 2H).

Preparation 5

Ethyl 2-(4-bromo-5-fluoro-2-methoxy-phenyl)acetate

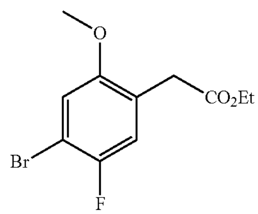 [SMILES: CCOC(=O)Cc1cc(F)c(Br)cc1OC]

To a solution of 2-(4-bromo-5-fluoro-2-methoxy-phenyl) acetonitrile (8.0 g, 32.8 mmol) in ethanol (100 mL) add concentrated sulfuric acid (25 mL). Stir the reaction at 80° C. for 18 h. Neutralize the reaction to pH 7 with saturated aqueous sodium bicarbonate solution. Extract the reaction mixture with DCM (2×100 mL). Dry the organic phase over sodium sulfate, filter, and concentrate under reduced pressure to give 9.3 g of the title compound (97%), which is used in crude form in Preparation 6. 1H-NMR (400 MHz, CDCl3) δ 7.02-6.99 (m, 2H), 4.16 (q, J=7 Hz, 2H), 3.80 (s, 3H), 3.56 (s, 2H), 1.26 (t, J=7 Hz, 3H).

Preparation 6

Ethyl 2-(4-bromo-5-fluoro-2-hydroxy-phenyl)acetate

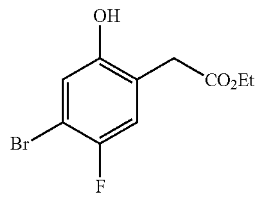 [SMILES: CCOC(=O)Cc1cc(F)c(Br)cc1O]

Cool a solution of ethyl 2-(4-bromo-5-fluoro-2-methoxy-phenyl)acetate (5.0 g, 17.2 mmol) in DCM (100 mL) to −78° C. Add boron tribromide (8.0 mL, 84.8 mmol) and stir the reaction at RT for 2 h. Cool the reaction mixture to 0° C. and quench the reaction with ice water (40 mL). Basify the solution to pH 7 with saturated aqueous sodium bicarbonate solution. Wash the organic layer with water (20 mL). Dry the organic phase over sodium sulfate, filter, and concentrate under reduced pressure to give 4.0 g of the title compound (84%), which is used in crude form in Preparations 10, 54 and 60. $^1$H-NMR (400 MHz, $CDCl_3$) δ 7.69 (s, 1H), 7.14 (d, J=6 Hz, 1H), 6.90 (d, J=4 Hz, 1H), 4.22 (q, J=7 Hz, 2H), 3.61 (s, 2H), 1.31 (t, J=8 Hz, 3H).

Preparation 7

Methyl 2-(4-bromo-2-hydroxy-5-methyl-phenyl)acetate

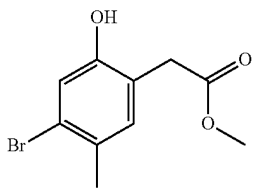

Prepare the title compound essentially as described in Preparation 6 using methyl 2-(4-bromo-2-methoxy-5-methyl-phenyl)acetate. ES-MS m/z 259 and 261 (M+H).

Preparation 8

Methyl 2-[2-hydroxy-4-(4,4,5,5-tetramethyl-1,3,2-dioxaborolan-2-yl)phenyl]acetate

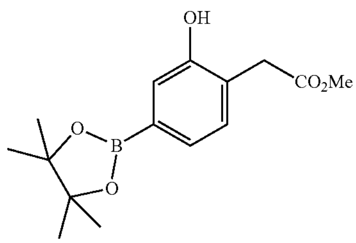 [SMILES: COC(=O)Cc1ccc(B2OC(C)(C)C(C)(C)O2)cc1O]

To a mixture of methyl 2-(4-bromo-2-hydroxy-phenyl) acetate (1.30 g, 5.30 mmol), bis(pinacolato)diboron (1.98 g, 7.72 mmol), KOAc (2.23 g, 22.5 mmol), and Pd(dppf)$Cl_2$ (420 mg, 0.57 mmol) add 1,4-dioxane (24 mL). Stir the reaction mixture under a nitrogen atmosphere at 80° C. for 60 h. Filter the mixture through a Celite® pad, and rinse with EtOAc. Concentrate the filtrate under reduced pressure. Dissolve the residue in DCM, adsorb onto silica, and purify via silica gel flash chromatography using a gradient of 0 to 55% EtOAc in hexanes to give 748 mg of the title compound (48%). ES-MS m/z 293 (M+H).

Preparation 9

Methyl 2-[2-hydroxy-5-methyl-4-(4,4,5,5-tetramethyl-1,3,2-dioxaborolan-2-yl)phenyl]acetate

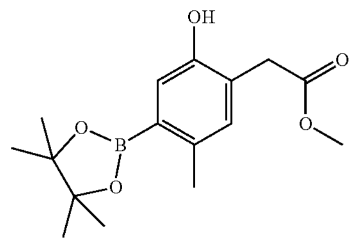

Prepare the title compound essentially as described in Preparation 8 using methyl 2-(4-bromo-2-hydroxy-5-methyl-phenyl)acetate. Purify via silica gel flash chromatography using a gradient of 5 to 80% EtOAc in hexanes. ES-MS m/z 304 (M−H).

Preparation 10

Ethyl 2-[4-(5,5-dimethyl-1,3,2-dioxaborinan-2-yl)-5-fluoro-2-hydroxyphenyl]acetate

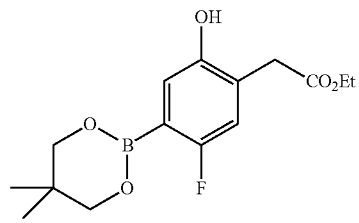 [SMILES: CCOC(=O)Cc1cc(F)c(B2OCC(C)(C)CO2)cc1O]

Purge a flask containing ethyl 2-(4-bromo-5-fluoro-2-hydroxy-phenyl)acetate (2.43 g, 8.16 mmol), bis(neopentyl glycoloato)diboron (2.82 g, 12.2 mmol) and KOAc (2.04 g, 20.4 mmol) with nitrogen. Add anhydrous 1,4-dioxane (33 mL) and sparge with nitrogen while stirring for 5 min. Add dichlorobis(tricyclohexylphosphine)palladium(II) (0.31 g, 0.41 mmol) and sparge with nitrogen while stirring for 5 min. Stir at 90° C. for 6 h, then wash down solids using 1,4-dioxane (15 mL) and stir overnight at RT. Add diatomaceous earth and dilute with MTBE (0.1 L). Stir for 30 min, filter through a pad of Celite® and rinse with MTBE (0.1 L). Concentrate the filtrate under reduced pressure at 50° C. Dissolve the residue in toluene (0.1 L) and concentrate again at 50° C. Purify the residue by eluting through a pad of silica gel using a 1:1 mixture of EtOAc and heptane. Concentrate fractions containing the title compound to a final volume of 30 mL and stir the resulting slurry for 1 h at ambient temperature. Collect the solid by filtration, wash with heptane (0.1 L) and dry under reduced pressure at 50° C. for 19 h to afford 1.77 g of the title compound (64%) as a pale orange solid. ES-MS m/z 243 (M+H for boronic acid). $^1$H-NMR (400 MHz, $CDCl_3$) δ 7.28 (s, 1H), 7.27 (d, J=5.2 Hz, 1H), 6.81 (d, J=9.2 Hz, 1H), 4.22 (q, J=7.2 Hz, 2H), 3.80 (s, 4H), 3.65 (s, 2H), 1.30 (t, J=7.2 Hz, 3H), 1.05 (s, 6H).

Preparation 11

Ethyl 2-[5-fluoro-2-hydroxy-4-(4,4,5,5-tetramethyl-1,3,2-dioxaborolan-2-yl)phenyl]acetate

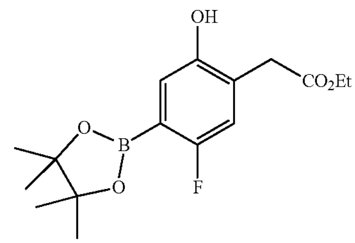 [SMILES: CCOC(=O)Cc1cc(F)c(B2OC(C)(C)C(C)(C)O2)cc1O]

Prepare the title compound essentially as described in Preparation 10 using bis(pinacolato)diboron, stirring the mixture at 90° C. for 2 h, then 100° C. for 18 h. Purify the title compound via silica gel flash chromatography using a gradient of 0 to 50% EtOAc in cyclohexane, then re-purify via silica gel flash chromatography using a gradient of 0 to 40% EtOAc in cyclohexane. ES-MS m/z 325 (M+H).

Preparation 12

(5-Bromo-4-fluoro-2-iodophenyl)methanol

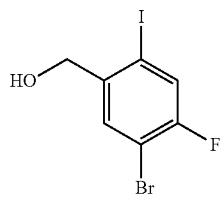 [SMILES: OCc1cc(Br)c(F)cc1I]

To a solution of 5-bromo-4-fluoro-2-iodo-benzoic acid (6.3 g, 18.2 mmol) in THE (55 mL) add borane dimethylsulfide complex (2 M in THF, 27 mL, 54 mmol). Stir the reaction mixture at RT for 21 h. Concentrate the reaction mixture and dissolve the residue in EtOAc. Wash the solution with saturated aqueous ammonium chloride. Dry the organic phase over magnesium sulfate, filter, and concentrate under reduced pressure. Purify the residue via silica gel flash chromatography using a gradient of 10 to 30% EtOAc in heptane to give 5.1 g of the title compound (85%). ES-MS m/z 313 and 315 ($M-H_2O$).

Preparation 13

Methyl 3,5-difluoro-4-nitro-benzoate

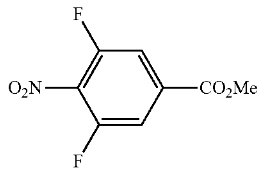 [SMILES: COC(=O)c1cc(F)c([N+](=O)[O-])c(F)c1]

Cool a solution of thionyl chloride (37 mL, 74 mmol) in MeOH (110 mL) to −10° C. and add 3,5-difluoro-4-nitrobenzonitrile (2.8 g, 15 mmol). Stir at RT for 3 h then gradually increase the temperature to 65° C. over 2 h. Filter the mixture and concentrate under reduced pressure. Dissolve the residue in EtOAc (150 mL). Wash with saturated aqueous sodium bicarbonate solution (50 mL) and brine (50 mL). Dry the organic phase over sodium sulfate, filter, and concentrate under reduced pressure. Purify the residue via silica gel chromatography using 10% EtOAc in petroleum ether to give 2.24 g of the title compound (66%). $^1$H-NMR (400 MHz, $CDCl_3$) δ 7.78 (d, 2H), 4.0 (s, 3H).

Preparation 14

Methyl 3-fluoro-4-nitro-5-[[(2S)-oxetan-2-ylmethyl]amino]benzoate

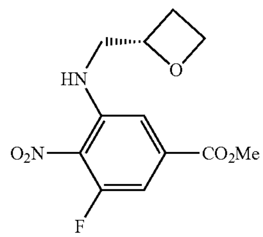 [SMILES: COC(=O)c1cc(F)c([N+](=O)[O-])c(NC[C@@H]2CCO2)c1]

Stir a mixture of [(2S)-oxetan-2-yl]methanamine (545 mg, 6.13 mmol, CAS 2091328-57-1), methyl 3,5-difluoro-4-nitro-benzoate (1.4 g, 6.1 mmol), and potassium carbonate (1.7 g, 12 mmol) in ACN (14 mL) at 70° C. for 16 h. Dilute the reaction mixture with water (14 mL) and extract with EtOAc (3×14 mL). Wash the combined organic layers with brine (14 mL). Dry the organic phase over sodium sulfate, filter, and concentrate under reduced pressure. Purify the residue via silica gel chromatography using a gradient of 0 to 30% EtOAc in petroleum ether to give 1.68 g of the title compound (79%). ES-MS m/z 285 (M+H).

Preparation 15

Methyl (S)-3-methoxy-4-nitro-5-((oxetan-2-ylmethyl)amino)benzoate

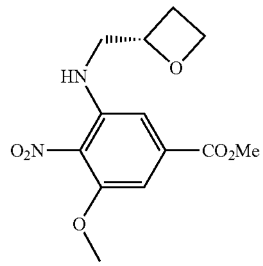 [SMILES: COC(=O)c1cc(NC[C@@H]2CCO2)c([N+](=O)[O-])c(OC)c1]

Prepare the title compound essentially as described in Preparation 14 using methyl 3-fluoro-5-methoxy-4-nitrobenzoate. Purify the residue via silica gel chromatography using a gradient of 5 to 30% EtOAc in DCM to give the title compound. ES-MS m/z 296 (M+H).

Preparation 16

Methyl 4-amino-3-fluoro-5-[[(2S)-oxetan-2-ylmethyl]amino]benzoate

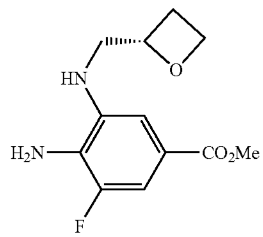

To a solution of methyl 3-fluoro-4-nitro-5-[[(2S)-oxetan-2-ylmethyl]amino]benzoate (1.68 g, 4.84 mmol) in MeOH (17 mL) add Lindlar catalyst containing 5% palladium (600 mg, 0.28 mmol). Stir at RT for 16 h under an atmosphere of hydrogen gas. Filter the reaction mixture and concentrate the filtrate under reduced pressure to give 1.4 g of the title compound (100%), which is used in crude form in Preparation 86 and 91. ES-MS m/z 255 (M+H).

Preparation 17

Methyl 4-amino-3-methoxy-5-[[(2S)-oxetan-2-yl]methylamino]benzoate

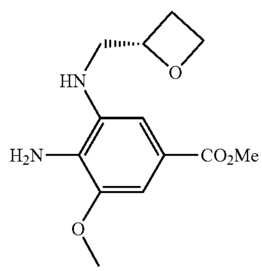

Prepare the title compound essentially as described in Preparation 16 using methyl (S)-3-methoxy-4-nitro-5-((oxetan-2-ylmethyl)amino)benzoate. The title compound is used in crude form in Preparations 89, 93, 99, and 100. ES-MS m/z 267 (M+H).

Preparation 18

Methyl 3-(((1-ethyl-1H-imidazol-5-yl)methyl)amino)-4-nitrobenzoate

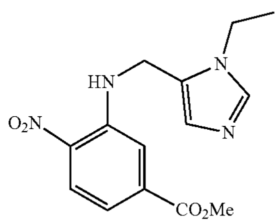 [SMILES: CCn1cncc1CNc1cc(C(=O)OC)ccc1N]

To a solution of methyl 3-fluoro-4-nitrobenzoate (300 mg, 1.5 mmol) and TEA (1.1 mL, 8.1 mmol) in THF (6 mL) and DMF (3 mL), add (1-ethyl-1H-imidazol-5-yl)methanamine dihydrochloride (339 mg, 1.6 mmol). Stir at 35° C. for 2 h, then 50° C. for 16 h. Dilute the crude reaction mixture with water and extract with EtOAc (3×15 mL). Wash the combined organic layers with water and saturated aqueous NaCl, dry the organic phase over magnesium sulfate, filter, and concentrate under reduced pressure. Purify the residue via silica gel flash chromatography using a gradient of 0 to 100% EtOAc in heptane followed by 5% MeOH in DCM to give 395 mg of the title compound (88%). ES-MS m/z 305 (M+H).

Preparation 19

Methyl 4-amino-3-(((1-ethyl-1H-imidazol-5-yl)methyl)amino)benzoate

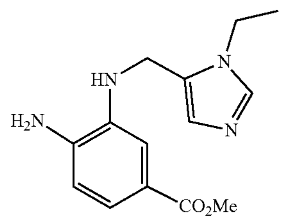

Stir a solution of iron (193 mg, 3.5 mmol), ammonium chloride (10 mg, 0.19 mmol), and acetic acid (46 mg, 0.77 mmol) in water (3 mL) at 50° C. for 15 min. Add a solution of methyl 3-(((1-ethyl-1H-imidazol-5-yl)methyl)amino)-4-nitrobenzoate (117 mg, 0.38 mmol) in DMF (1 mL). Stir at 50° C. for 15 min. Quench the reaction with aqueous sodium carbonate solution to pH 8 and filter through Celite®. Wash the residue with water (2×20 mL) and back extract the aqueous layer with EtOAc (2×20 mL). Dry the combined organic phase over magnesium sulfate, filter, and concentrate under reduced pressure to give 106 mg of the title compound (100%), which is used in crude form in Preparation 95. ES-MS m/z 275 (M+H).

Preparation 20

3-Fluoro-5-methoxy-4-nitrobenzonitrile

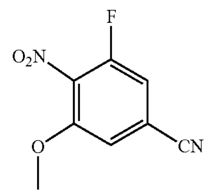

To a mixture of 5-bromo-1-fluoro-3-methoxy-2-nitrobenzene (700 mg, 2.7 mmol), zinc cyanide (226 mg, 1.9 mmol), and tetrakis(triphenylphosphine)palladium(0) (317 mg, 0.27 mmol), add DMF (17.8 mL). Stir at 100° C. for 1.5 h. Dilute the crude reaction mixture with water and extract with EtOAc. Dry the organic phase over magnesium sulfate, filter, and concentrate under reduced pressure. Purify the residue via silica gel flash chromatography using a gradient of 0 to 15% EtOAc in heptane to give 479 mg of the title compound (89%). ES-MS m/z 197 (M+H).

Preparation 21

(S)-3-Methoxy-4-nitro-5-((oxetan-2-ylmethyl)amino)benzonitrile

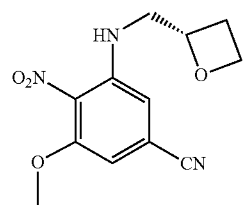 [SMILES: COc1cc(C#N)cc(NC[C@@H]2CCO2)c1[N+](=O)[O-]]

Add TEA (1.07 mL, 7.7 mmol) and (S)-oxetan-2-ylmethanamine (235 mg, 2.56 mmoL) to a solution of 3-fluoro-5-methoxy-4-nitrobenzonitrile (457 mg, 2.3 mmol) in DMF (7 mL). Stir at 35° C. overnight. Dilute the crude reaction mixture with water and extract with EtOAc. Dry the organic phase over magnesium sulfate, filter, and concentrate under reduced pressure. Purify the residue via silica gel flash chromatography using a gradient of 0 to 30% EtOAc in heptane to give 471 mg of the title compound (77%). ES-MS m/z 264 (M+H).

Preparation 22

(S)-3-Methoxy-2-nitro-N-(oxetan-2-ylmethyl)-5-(1H-tetrazol-5-yl)aniline

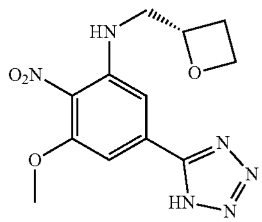 [SMILES: COc1cc(-c2nnn[nH]2)cc(NC[C@@H]2CCO2)c1[N+](=O)[O-]]

Add tributyltin azide (1.96 mL, 7.0 mmol) to a solution of (S)-3-methoxy-4-nitro-5-((oxetan-2-ylmethyl)amino)benzonitrile (217 mg, 0.82 mmol) in toluene (9.3 mL). Heat to 150° C. in a microwave with stirring for 2.5 h. Filter the crude reaction mixture through a plug of 10% w/w KF in silica. Concentrate and triturate the residue with DCM to give 194 mg of the title compound (62%). ES-MS m/z 307 (M+H).

Preparation 23

(S)-3-Methoxy-N1-(oxetan-2-ylmethyl)-5-(1H-tetrazol-5-yl)benzene-1,2-diamine

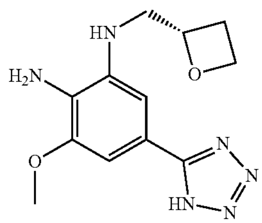

Add palladium on carbon (20 mg, 0.009 mmol) to a mixture of (S)-3-methoxy-2-nitro-N-(oxetan-2-ylmethyl)-5-(1H-tetrazol-5-yl)aniline (160 mg, 0.42 mmol) and MeOH (3 mL). Stir for 8 h at RT under 4 bar of hydrogen pressure. Filter the crude reaction mixture through Celite® and concentrate to give 120 mg of the title compound (52%), which is used in crude form in Preparation 96. ES-MS m/z 277 (M+H).

Preparation 24

4-[(6-Bromo-2-pyridyl)oxymethyl]-3-iodo-benzonitrile

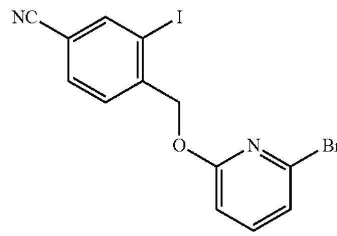

To a mixture of 4-(bromomethyl)-3-iodo-benzonitrile (2.88 g, 8.93 mmol), 6-bromopyridin-2-ol (1.10 g, 6.30 mmol), and silver carbonate (5.1 g, 18.0 mmol) add 1,4-dioxane (50 mL). Stir the reaction mixture at 60° C. for 15 h. Dilute the reaction with EtOAc (50 mL) and filter through celite. Wash the filtrate with water (2×50 mL) and saturated aqueous sodium chloride (50 mL). Dry the organic phase over magnesium sulfate, filter, and concentrate under reduced pressure. Purify the residue via silica gel flash chromatography eluting with a gradient of 5 to 30% EtOAc in hexanes to 2.8 g of the title compound (76%). ES-MS m/z 415 and 417 (M+H).

Preparation 25

Ethyl 4-cyano-3-(3-hydroxypropyl)benzoate

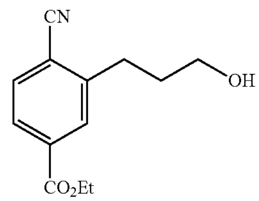 [SMILES: CCOC(=O)c1ccc(C#N)c(CCCO)c1]

Stir a mixture of nickel (II) bromide (167 mg, 0.76 mmol) and 4,4'-di-tert-butyl-2,2'-bipyridine (210 mg, 0.77) in anhydrous 1,4-dioxane (40 mL) while bubbling with nitrogen for 15 min at RT. Add ethyl 3-bromo-4-cyanobenzoate (2 g, 7.71 mmol), 3-bromo-1-propanol (1.7 mL, 18 mmol) and cobalt (II) phthalocyanine (441 mg, 0.77 mmol). Stir the mixture at RT for 5 min while bubbling with nitrogen. Add tetrakis(dimethylamino)ethylene (2.5 mL, 11 mmol) and continue stirring the mixture at RT for 5 min while bubbling with nitrogen. Seal the vessel and stir the mixture at 85° C. overnight. Cool the mixture to RT, filter through Celite® and concentrate under reduced pressure. Purify the residue via silica gel flash chromatography using a gradient of 20 to 50% EtOAc in cyclohexanes to give the title compound (863 mg, 46%) as a green solid. ES-MS m/z 251 ($M+NH_4$).

Preparation 26

Ethyl 3-[3-[tert-butyl(dimethyl)silyl]oxypropyl]-4-cyano-benzoate

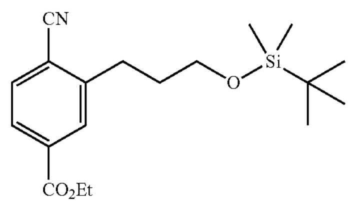 [SMILES: CCOC(=O)c1ccc(C#N)c(CCCO[Si](C)(C)C(C)(C)C)c1]

Add tert-butyldimethylchlorosilane (615 mg, 3.96 mmol) and imidazole (298 mg, 4.33 mmol) to a solution of ethyl 4-cyano-3-(3-hydroxypropyl)benzoate (863 mg, 3.59 mmol) in DCM (15 mL) at RT. Stir the mixture for 1 h and concentrate under reduced pressure. Purify the residue via silica gel flash chromatography using a gradient of 0% to 50% EtOAc in cyclohexanes to provide the title compound (1.24 g, 94%) as a colorless oil. ES-MS m/z 348 (M+H).

Preparation 27

2-[3-[tert-Butyl(dimethyl)silyl]oxypropyl]-4-(hydroxymethyl)benzonitrile

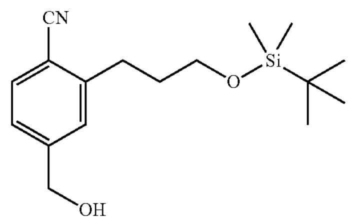 [SMILES: CC(C)(C)[Si](C)(C)OCCCc1cc(CO)ccc1C#N]

Add lithium borohydride in THE (2.0 M, 3.9 mL, 7.8 mmol) to a solution of ethyl 3-[3-[tert-butyl(dimethyl)silyl]oxypropyl]-4-cyano-benzoate (1.24 g, 3.39 mmol) in anhydrous THE (9 mL) at 0° C. under nitrogen atmosphere. Remove the cooling bath after 5 min and stir at RT overnight. Concentrate to remove most of the reaction solvent and add citric acid (5%) carefully at 0° C. Extract the aqueous layer with DCM, combine organic layers, dry over anhydrous sodium sulfate, filter and concentrate under reduced pressure. Purify the residue via silica gel flash chromatography using a gradient of 10% to 50% EtOAc in cyclohexanes to provide the title compound (935 mg, 90%) as a colorless waxy solid. ES-MS m/z 306 (M+H).

Preparation 28

4-[(6-Bromo-2-pyridyl)oxymethyl]-3-[3-[tert-butyl(dimethyl)silyl]oxypropyl]benzonitrile

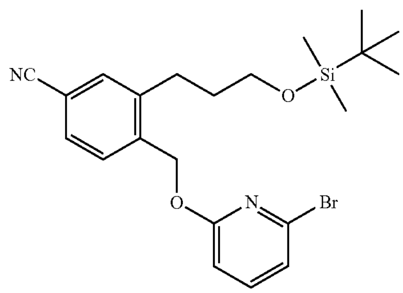 [SMILES: CC(C)(C)[Si](C)(C)OCCCc1cc(C#N)ccc1COc1cccc(Br)n1]

To a mixture of 4-[(6-bromo-2-pyridyl)oxymethyl]-3-iodo-benzonitrile (2.6 g, 6.3 mmol) and tetrakis(triphenylphosphine)palladium(0) (0.27 g, 0.23 mmol) in 1,4-dioxane (50 mL) add bromo-[3-[tert-butyl(dimethyl)silyl]oxypropyl]zinc (0.50 M in THF, 25 mL, 12.5 mmol). Stir at 60° C. for 1 h. Dilute the reaction mixture with EtOAc (100 mL), then wash with saturated aqueous ammonium chloride solution (100 mL) and brine (100 mL). Dry the organic phase over sodium sulfate, filter, and concentrate under reduced pressure. Purify the residue via silica gel flash chromatography eluting with a gradient of 5 to 50% EtOAc in hexanes to give 1.07 g of the title compound (37%). ES-MS m/z 461 and 463 (M+H).

Preparation 29

4-[(6-Bromo-2-pyridyl)oxymethyl]-3-(3-hydroxypropyl)benzonitrile

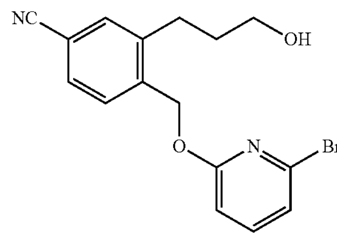

To a mixture of 4-[(6-bromo-2-pyridyl)oxymethyl]-3-[3-[tert-butyl(dimethyl)silyl]oxypropyl]benzonitrile (1.32 g, 2.86 mmol) in THE (50 mL) add TBAF solution (1.0 M in THF, 2.9 mL, 2.9 mmol). Stir the reaction mixture at RT for 1 h. Dilute with EtOAc (50 mL) and wash with saturated aqueous ammonium chloride solution (50 mL) and brine (50 mL). Dry the organic phase over sodium sulfate, filter, and concentrate under reduced pressure. Purify the residue via silica gel flash chromatography eluting with a gradient of 5 to 75% EtOAc in hexanes to give 0.90 g of the title compound (92%). ES-MS m/z 347 and 349 (M+H).

Preparation 30

4-[(6-Bromo-2-pyridyl)oxymethyl]-2-[3-[tert-butyl(dimethyl)silyl]oxypropyl]benzonitrile

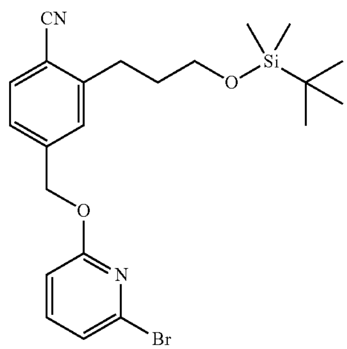 [SMILES: CC(C)(C)[Si](C)(C)OCCCc1cc(COc2cccc(Br)n2)ccc1C#N]

Add DIAD (915 μL, 4.5 mmol) slowly to a solution of triphenylphosphine (1.21 g, 4.61 mmol) in anhydrous THE (15 mL) at 0° C. under nitrogen atmosphere. Stir the mixture for 30 min and then add a solution of 2-[3-[tert-butyl(dimethyl)silyl]oxypropyl]-4-(hydroxymethyl)benzonitrile (925 mg, 3.03 mmol) in anhydrous THE (6 mL) and 2-bromo-6-hydroxypyridine (610 mg, 3.33 mmol). Remove the cooling bath, stir at RT for 2 h, and concentrate the mixture under reduced pressure. Purify the residue via silica gel flash chromatography using a gradient of 0 to 30% of EtOAc in cyclohexanes to provide 1.12 g of the title compound (78%). ES-MS m/z 461 and 463 (M+H).

Preparation 31

4-[(6-bromo-2-pyridyl)oxymethyl]-2-(3-hydroxypropyl)benzonitrile

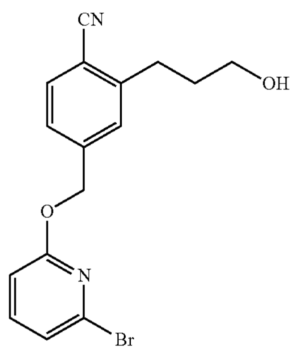 [SMILES: N#Cc1ccc(COc2cccc(Br)n2)cc1CCCO]

Add slowly TBAF solution (1.0 M in THF, 2.7 mL, 2.7 mmol) to a solution of 4-[(6-bromo-2-pyridyl)oxymethyl]-2-[3-[tert-butyl(dimethyl)silyl]oxypropyl]benzonitrile (1.12 g, 2.43 mmol) in THE (24 mL) at RT. Stir the mixture for 1 h. Concentrate the reaction mixture and dilute the residue with MTBE and water. Separate the organic layer and wash with water and saturated aqueous NaCl, dry over anhydrous $Na_2SO_4$, then filter and concentrate under reduced pressure. Purify the residue via silica gel flash chromatography using a gradient of 25 to 50% of EtOAc in cyclohexanes to provide the title compound (790 mg, 89%) as a white solid. ES-MS m/z 347 and 349 (M+H).

Preparation 32

3-(2-((tert-Butyldimethylsilyl)oxy)ethoxy)-4-formylbenzonitrile

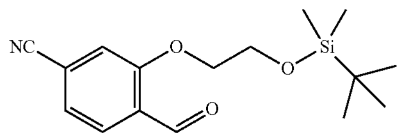 [SMILES: CC(C)(C)[Si](C)(C)OCCOc1cc(C#N)ccc1C=O]

To a solution of 4-formyl-3-hydroxybenzonitrile (3.0 g, 18.8 mmol) in DMF (56 mL), add sodium iodide (1.4 g, 9.3 mmol), potassium carbonate (3.8 g, 38 mmol), and (2-bromoethoxy)-tert-butyldimethylsilane (6.1 mL, 28 mmol). Stir the mixture at 70° C. for 24 h. Dilute the crude reaction mixture with water and EtOAc and extract the aqueous layer with EtOAc. Dry the organic phase over magnesium sulfate, filter, and concentrate under reduced pressure. Purify the residue via silica gel flash chromatography using a gradient of 0 to 30% EtOAc in heptane to give 5.68 g of the title compound (99%). ES-MS m/z 306 (M+H).

Preparation 33

3-(2-((tert-Butyldimethylsilyl)oxy)ethoxy)-4-(hydroxymethyl)benzonitrile

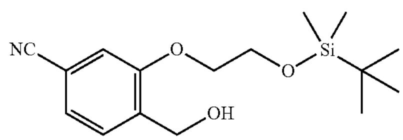 [SMILES: CC(C)(C)[Si](C)(C)OCCOc1cc(C#N)ccc1CO]

Cool a solution of 3-(2-((tert-butyldimethylsilyl)oxy)ethoxy)-4-formylbenzonitrile (450 mg, 1.47 mmol) in MeOH (4.6 mL) to 0° C. Add sodium borohydride (112 mg, 2.96 mmol) and stir the mixture at 0° C. for 15 min. Warm the mixture to RT and stir for 1 h.

Dilute the mixture with water and adjust to pH 7 with 1 M aqueous HCl solution, then extract with EtOAc. Dry the organic phase over magnesium sulfate, filter, and concentrate under reduced pressure. Pass the residue through a silica gel pad to give 350 mg of the title compound (77%). $^1$H-NMR (400 MHz, $CDCl_3$) δ 7.32 (d, J=7.7 Hz, 1H), 7.15 (d, J=7.7 Hz, 1H), 7.02 (d, J=1.0 Hz, 1H), 4.60 (s, 2H), 4.0 (m, 2H), 3.8 (m, 2H), 3.03 (s, 1H), 0.81 (s, 9H), 0.0 (s, 6H).

Preparation 34

4-(((6-Bromopyridin-2-yl)oxy)methyl)-3-(2-((tert-butyldimethylsilyl)oxy)ethoxy)benzonitrile

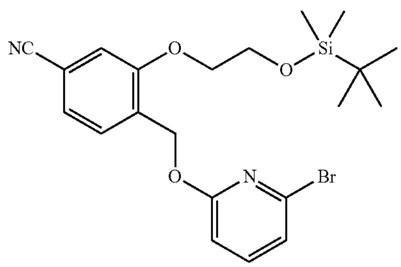 [SMILES: CC(C)(C)[Si](C)(C)OCCOc1cc(C#N)ccc1COc1cccc(Br)n1]

To a solution of 3-(2-((tert-butyldimethylsilyl)oxy)ethoxy)-4-(hydroxymethyl)benzonitrile (350 mg, 1.14 mmol), 6-bromopyridin-2-ol (1.4 g, 8.0 mmol), and triphenylphosphine (2.35 g, 8.96 mmol) in THE (50 mL) add DIAD (1.76 mL, 8.94 mmol). Stir the mixture at 50° C. for 4 h and then concentrate the crude reaction mixture. Dilute the residue with EtOAc, then wash with water (3×) and brine. Dry the organic phase over magnesium sulfate, filter, and concentrate under reduced pressure. Purify the residue via silica gel flash chromatography using a gradient of 0 to 20% EtOAc in heptane to give 247 mg of the title compound (47%). ES-MS m/z 463 and 465 (M+H).

Preparation 35

4-(((6-Bromopyridin-2-yl)oxy)methyl)-3-(2-hydroxyethoxy)benzonitrile

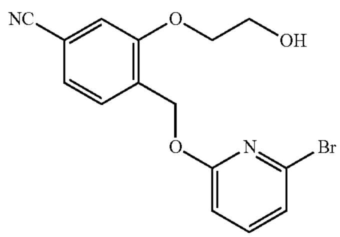

Prepare the title compound essentially as described in Preparation 31 using 4-(((6-bromopyridin-2-yl)oxy)methyl)-3-(2-((tert-butyldimethylsilyl)oxy)ethoxy)benzonitrile, stirring the reaction at RT for 2 h. Purify the title compound via silica gel flash chromatography using a gradient of 0 to 20% EtOAc in DCM. ES-MS m/z 349 and 351 (M+H).

Preparation 36

Ethyl (E)-3-[5-chloro-2-(hydroxymethyl)phenyl]prop-2-enoate

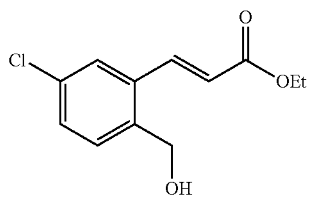 [SMILES: CCOC(=O)/C=C/c1cc(Cl)ccc1CO]

To a mixture of (2-bromo-4-chloro-phenyl)methanol (17.5 g, 79.0 mmol), tetrabutylammonium chloride (26.1 g, 93.9 mmol), potassium carbonate (16.7 g, 121 mmol), and palladium acetate (1.47 g, 6.55 mmol) in DMF (400 mL) add ethyl acrylate (10.3 mL, 94.8 mmol). Stir the reaction mixture under a nitrogen atmosphere at 90° C. for 6 h. Filter the reaction mixture through a Celite® pad, then rinse with EtOAc (200 mL). Dilute the filtrate with EtOAc (200 mL) and wash with water (800 mL). Back-extract the aqueous layer with EtOAc (250 mL). Dry the combined organic phase over magnesium sulfate, filter, and concentrate under reduced pressure. Dissolve the residue in DCM, adsorb onto silica, and purify via silica gel chromatography using a gradient of 15 to 40% EtOAc in hexanes to give 6.14 g of the title compound (32%). ES-MS m/z 258 ($M+NH_4^+$).

Preparation 37

Ethyl 3-[5-chloro-2-(hydroxymethyl)phenyl]propanoate

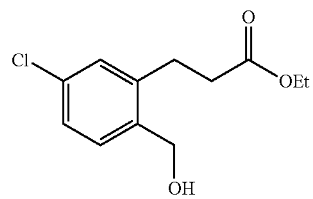 [SMILES: CCOC(=O)CCc1cc(Cl)ccc1CO]

To a mixture of sulfided platinum on carbon (5%, 220 mg, 0.056 mmol) in EtOAc (20 mL) add ethyl (E)-3-[5-chloro-2-(hydroxymethyl)phenyl]prop-2-enoate (2.21 g, 9.18 mmol) in EtOAc (30 mL). Shake in a Parr shaker at RT at 40 psi of hydrogen gas pressure for 1 h. Filter through a pad of Celite® and concentrate the filtrate under reduced pressure to provide 1.91 g of the title compound (86%), which is used in crude form in Preparation 38. ES-MS m/z 225 ($M-H_2O$).

Preparation 38

Ethyl 3-[2-(bromomethyl)-5-chloro-phenyl]propanoate

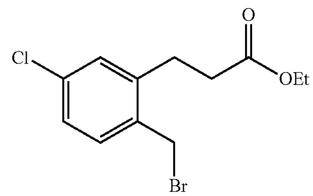 [SMILES: CCOC(=O)CCc1cc(Cl)ccc1CBr]

To a mixture of ethyl 3-[5-chloro-2-(hydroxymethyl)phenyl]propanoate (1.90 g, 7.80 mmol) in diethyl ether (40 mL) dropwise add phosphorus tribromide (0.80 mL, 8.5 mmol). Stir under a nitrogen atmosphere at RT for 1 h. Quench with slow, dropwise addition of saturated aqueous sodium bicarbonate solution (5 mL). Separate the layers and extract the aqueous layer with diethyl ether (5 mL). Dry the combined organic phase over magnesium sulfate, filter, and concentrate under reduced pressure to provide 2.40 g of the title compound (100%), which is used in crude form in Preparation 45. ES-MS m/z 322 and 324 ($M+NH_4^+$).

Preparation 39

4-[(1,3-Dioxoisoindolin-2-yl)methyl]-3-iodo-benzonitrile

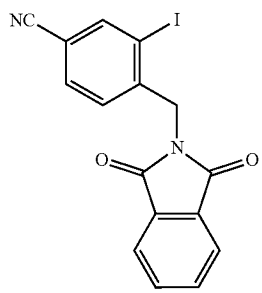 [SMILES: N#Cc1ccc(CN2C(=O)c3ccccc3C2=O)c(I)c1]

To a solution of 4-(bromomethyl)-3-iodobenzonitrile (10 g, 30.13 mmol) in DMF (100 mL), add potassium phthalimide (6.14 g, 33.14 mmol). Heat the reaction mixture at 80° C. for 2 h and then stir at RT for 16 h. Remove solvent and triturate the solid residue in 500 mL of water for 30 min. Filter the white solid, wash with water and dry the solid under vacuum at 45° C. for 20 h, to provide the title compound as a white solid (11.5 g, 88%). ES-MS m/z 405 ($M+OH^-$).

Preparation 40

4-[(1,3-Dioxoisoindolin-2-yl)methyl]-3-(3-hydroxy-prop-1-ynyl)benzonitrile

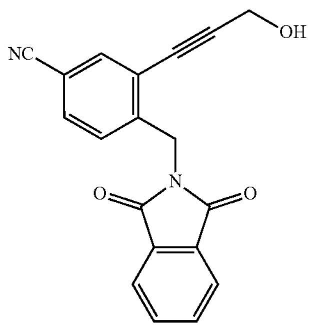 [SMILES: N#Cc1ccc(CN2C(=O)c3ccccc3C2=O)c(C#CCO)c1]

To a suspension of 4-[(1,3-dioxoisoindolin-2-yl)methyl]-3-iodo-benzonitrile (5.0 g, 11.7 mmol) in THE (50 mL) and TEA (50 mL), add bis(triphenylphosphine)palladium dichloride (0.33 g, 0.47 mmol), cuprous iodide (0.18 g, 0.94 mmol) and propargyl alcohol (2.05 mL, 35.2 mmol). Heat reaction mixture at 40° C. for 3 h. Cool to RT, dilute with EtOAc (50 mL) and water (50 mL) and filter the mixture through Celite®. Separate phases and extract aqueous phase with more EtOAc (2×50 mL). Combine organics, dry over magnesium sulfate, filter, and concentrate under reduced pressure. Purify the residue via silica gel chromatography using a gradient of 30% of EtOAc in cyclohexane to 100% EtOAc to give 3.2 g (79%) of the title compound as a cream solid. ES-MS m/z 315 (M−H).

Preparation 41

4-[(1,3-Dioxoisoindolin-2-yl)methyl]-3-(3-hydroxy-propyl)benzonitrile

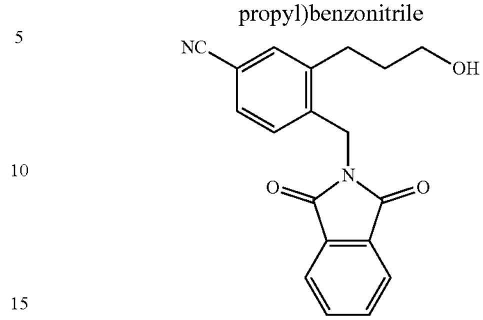

In a 250 mL Buchi® Miniclave reactor, to a suspension of 4-[(1,3-dioxoisoindolin-2-yl)methyl]-3-(3-hydroxyprop-1-ynyl)benzonitrile (3 g, 9.48 mmol) in MeOH (60 mL), add 1,1'-bis(di-i-propylphosphino)ferrocene(1,5-cyclooctadiene)rhodium(I) tetrafluoroborate (0.34 g, 0.47 mmol). Charge reactor with 90 psi of hydrogen and heat at 50° C. for 2 h. Cool reaction mixture to RT, evaporate solvents and purify the residue via silica plug using EtOAc as solvent, to provide 2.4 g (75%) of the title compound as a light cream solid. ES-MS m/z 321 (M+H).

Preparation 42

4-(Aminomethyl)-3-(3-hydroxypropyl)benzonitrile

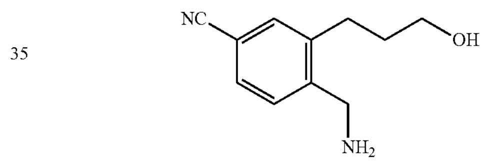

To a suspension of 4-[(1,3-dioxoisoindolin-2-yl)methyl]-3-(3-hydroxypropyl)benzonitrile (2.4 g, 7.49 mmol) in MeOH (45 mL), add hydrazine monohydrate (1.90 mL, 37.6 mmol) and stir at 60° C. for 20 h. Cool reaction mixture to RT and filter the solid. Evaporate filtrate liquids, dilute the residue with water (30 mL) and extract with DCM/MeOH 9:1 (3×20 mL). Combine organics, dry over magnesium sulfate, filter, and concentrate under reduce pressure to give the title compound as a reddish oil (880 mg, 49%). ES-MS m/z 191 (M+H).

Preparation 43

Methyl 2-(((5-bromo-4-fluoro-2-iodobenzyl)oxy)methyl)-4-cyanobenzoate

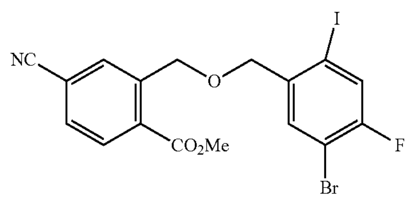 [SMILES: COC(=O)c1ccc(C#N)cc1COCc1cc(Br)c(F)cc1I]

To a solution of (5-bromo-4-fluoro-2-iodophenyl)methanol (1.5 g, 4.5 mmol) in THE (24 mL) at 0° C. add sodium hydride (60% in mineral oil, 362 mg, 9.1 mmol). Stir at 0° C. for 30 min. Add methyl 2-(bromomethyl)-4-cyano-benzoate (2.3 g, 9.1 mmol) and stir at RT for 1 h. Dilute the reaction with EtOAc and wash the organic layer with water and saturated aqueous NaCl. Back extract the aqueous layer with EtOAc. Dry the organic phase over magnesium sulfate, filter, and concentrate under reduced pressure. Purify the residue via silica gel flash chromatography using DCM to give 2.5 g of the title compound (67%) which is 61% pure, and used without further purification in Preparation 44. ES-MS m/z 504 and 506 (M+H).

Preparation 44

3-(((5-Bromo-4-fluoro-2-iodobenzyl)oxy)methyl)-4-(hydroxymethyl)benzonitrile

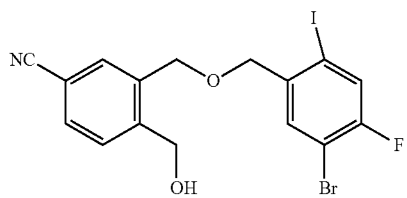 [SMILES: N#Cc1ccc(CO)c(COCc2cc(Br)c(F)cc2I)c1]

Prepare the title compound essentially as described in Preparation 27 using methyl 2-(((5-bromo-4-fluoro-2-iodobenzyl)oxy)methyl)-4-cyanobenzoate (Preparation 43) and a 10:1 mixture of THF:MeOH as reaction solvent. After stirring the reaction at RT for 20 h, add an additional portion of lithium borohydride (0.5 equivalents) and stir at RT for 2 h. Dilute the reaction mixture with EtOAc and wash the organic layer with water and saturated aqueous NaCl. Dry the organic phase over magnesium sulfate, filter, and concentrate under reduced pressure. Purify the residue via silica gel flash chromatography using a gradient of 0 to 50% EtOAc in heptane to give the title compound. ES-MS m/z 476 and 478 (M+H).

Preparation 45

Ethyl 3-[2-[(6-bromo-2-pyridyl)oxymethyl]-5-chloro-phenyl]propanoate

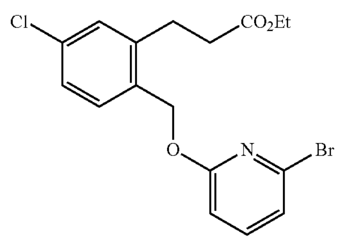 [SMILES: CCOC(=O)CCc1cc(Cl)ccc1COc1cccc(Br)n1]

To a mixture of ethyl 3-[2-(bromomethyl)-5-chloro-phenyl]propanoate (2.40 g, 7.85 mmol), 6-bromopyridin-2-ol (1.98 g, 11.4 mmol), and silver carbonate (4.34 g, 15.7 mmol) add 1,4-dioxane (40 mL). Stir the reaction mixture at 40° C. for 15 h. Filter through a pad of Celite® and concentrate the filtrate under reduced pressure. Dissolve the residue in DCM, adsorb onto silica, and purify via silica gel chromatography using a gradient of 0 to 40% EtOAc in hexanes to give 1.16 g of the title compound (37%). ES-MS m/z 398, 400 and 402 (M+H).

Preparation 46

3-[2-[(6-Bromo-2-pyridyl)oxymethyl]-5-chloro-phenyl]propan-1-ol

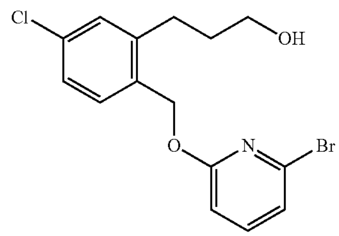 [SMILES: OCCCc1cc(Cl)ccc1COc1cccc(Br)n1]

To a mixture of ethyl 3-[2-[(6-bromo-2-pyridyl)oxymethyl]-5-chloro-phenyl]propanoate (1.16 g, 2.90 mmol) in THE (12 mL) dropwise add lithium borohydride (2.0 M in THF, 3.2 mL, 6.4 mmol). Stir the reaction mixture at RT for 6 h. Add an additional portion of lithium borohydride (2.0 M in THF, 2.0 mL, 4.0 mmol). Stir the reaction mixture at RT for an additional 17 h. Quench the reaction with dropwise addition of water. Dilute the mixture with EtOAc (50 mL) and wash with water (40 mL). Back extract the aqueous layer with EtOAc (25 mL). Dry the combined organic phase over magnesium sulfate, filter, and concentrate under reduced pressure. Dissolve the residue in DCM, adsorb onto silica, and purify via silica gel flash chromatography eluting with a gradient of 0 to 55% EtOAc in hexanes to give 461 mg of the title compound (35%). ES-MS m/z 356, 358 and 360 (M+H).

Preparation 47

4-[[(6-Bromo-2-pyridyl)amino]methyl]-3-(3-hydroxypropyl)benzonitrile

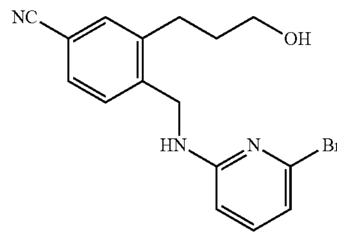 [SMILES: N#Cc1ccc(CNc2cccc(Br)n2)c(CCCO)c1]

To a solution of 4-(aminomethyl)-3-(3-hydroxypropyl) benzonitrile (800 mg, 3.36 mmol) in DMSO (16 mL), add 2-bromo-6-fluoropyridine (610 mg, 3.36 mmol) and DIPEA (1.17 mL, 6.72 mmol) and stir at 100° C. for 18 h. Cool reaction mixture to RT, dilute with water (40 mL), and extract with EtOAc (3×20 mL). Combine organics, dry over magnesium sulfate, filter, and concentrate under reduce pressure. Purify the residue via silica gel chromatography using a gradient of 30% of EtOAc in cyclohexanes to 100% EtOAc to provide the title compound as a thick brown oil (400 mg, 33%). ES-MS m/z 346 and 348 (M+H).

Preparation 48

4-[(3-Bromophenoxy)methyl]-3-iodo-benzonitrile

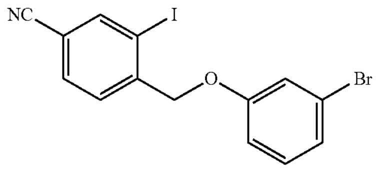 [SMILES: N#Cc1ccc(COc2cccc(Br)c2)c(I)c1]

To a mixture of 4-(bromomethyl)-3-iodo-benzonitrile (2.0 g, 6.2 mmol), 3-bromophenol (1.10 g, 6.4 mmol), and potassium carbonate (2.6 g, 19.0 mmol) add 1,4-dioxane (20 mL). Stir the reaction mixture at RT for 15 h. Dilute the reaction with EtOAc (100 mL) and filter through Celite®. Wash the filtrate with water (2×50 mL) and saturated aqueous NaCl (50 mL). Dry the organic phase over sodium sulfate, filter, and concentrate under reduced pressure. Purify the residue via silica gel flash chromatography eluting with a gradient of 0 to 30% EtOAc in hexanes to afford 2.4 g of the title compound (93%). $^1H$ NMR (400.13 MHz, $CDCl_3$) δ 8.16 (d, J=1.5 Hz, 1H), 7.71 (dd, J=1.5, 8.0 Hz, 1H), 7.64 (d, J=8.0 Hz, 1H), 7.23-7.17 (m, 3H), 6.92 (dt, J=7.5, 2.1 Hz, 1H), 5.05 (s, 2H).

Preparation 49

4-[(3-Bromophenoxy)methyl]-3-[3-[tert-butyl(dimethyl)silyl]oxypropyl]benzonitrile

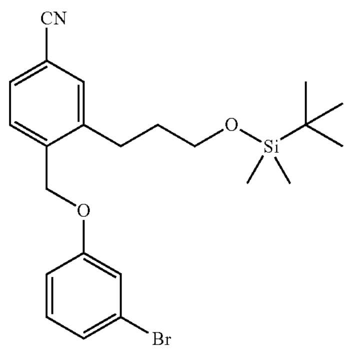 [SMILES: CC(C)(C)[Si](C)(C)OCCCc1cc(C#N)ccc1COc1cccc(Br)c1]

Prepare the title compound essentially as described in Preparation 28 using 4-[(3-bromophenoxy)methyl]-3-iodo-benzonitrile. ES-MS m/z 460 and 462 (M+H).

Preparation 50

4-[(3-Bromophenoxy)methyl]-3-(3-hydroxypropyl)benzonitrile

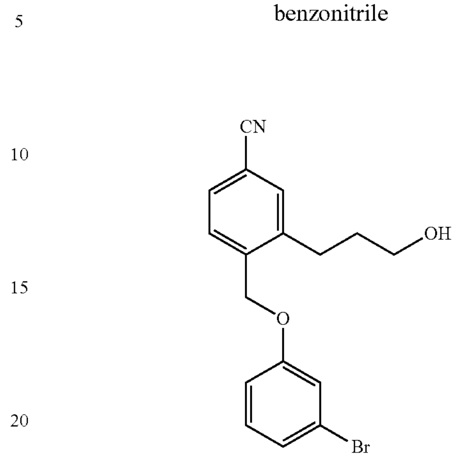

Prepare the title compound essentially as described in Preparation 29 using 4-[(3-bromophenoxy)methyl]-3-[3-[tert-butyl(dimethyl)silyl]oxypropyl]benzonitrile. ES-MS m/z 344 and 346 (M−H).

Preparation 51

2-Bromo-6-[[2-iodo-4-(trifluoromethyl)phenyl]methoxy]pyridine

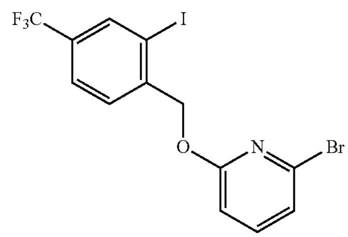 [SMILES: FC(F)(F)c1ccc(COc2cccc(Br)n2)c(I)c1]

To a mixture of [2-iodo-4-(trifluoromethyl)phenyl]methanol (2.0 g, 6.6 mmol), 2-bromo-6-fluoro-pyridine (1.2 g, 6.6 mmol), and 1,4-dioxane (25 mL) add potassium tert-butoxide (0.98 g, 8.6 mmol). Stir the reaction mixture at 50° C. for 2 h. Dilute the reaction with EtOAc (100 mL) and filter through Celite®. Wash the filtrate with water (2×50 mL) and saturated aqueous sodium chloride (50 mL). Dry the organic phase over sodium sulfate, filter, and concentrate under reduced pressure. Purify the residue via silica gel flash chromatography eluting with a gradient of 10 to 50% EtOAc in hexanes to 2.0 g of the title compound (66%). ES-MS m/z 458 and 460 (M+H).

Preparation 52

3-[2-[(6-Bromo-2-pyridyl)oxymethyl]-5-(trifluoromethyl)phenyl]propoxy-tert-butyl-dimethyl-silane

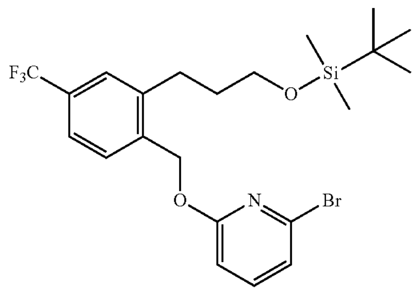 [SMILES: CC(C)(C)[Si](C)(C)OCCCc1cc(C(F)(F)F)ccc1COc1cccc(Br)n1]

Prepare the title compound essentially as described in Preparation 28 using 2-bromo-6-[[2-iodo-4-(trifluoromethyl)phenyl]methoxy]pyridine. Purify the title compound via silica gel flash chromatography eluting with a gradient of 0 to 10% EtOAc in hexanes. Use directly in Preparation 53 without further characterization.

Preparation 53

3-[2-[(6-Bromo-2-pyridyl)oxymethyl]-5-(trifluoromethyl)phenyl]propan-1-ol

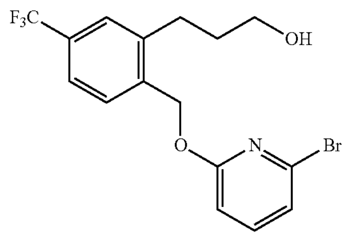 [SMILES: OCCCc1cc(C(F)(F)F)ccc1COc1cccc(Br)n1]

Prepare the title compound essentially as described in Preparation 29 using 3-[2-[(6-bromo-2-pyridyl)oxymethyl]-5-(trifluoromethyl)phenyl]propoxy-tert-butyl-dimethyl-silane. ES-MS m/z 390 and 392 (M+H).

Preparation 54

Ethyl 2-[4-bromo-2-[3-[2-[(6-bromo-2-pyridyl)oxymethyl]-5-cyano-phenyl]propoxy]-5-fluoro-phenyl]acetate

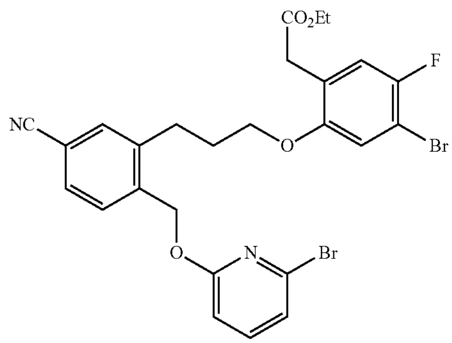

To a mixture of 4-[(6-bromo-2-pyridyl)oxymethyl]-3-(3-hydroxypropyl)benzonitrile (550 mg, 1.58 mmol) and ethyl 2-(4-bromo-5-fluoro-2-hydroxy-phenyl)acetate (0.40 g, 1.4 mmol) in THF (10 mL) add tri-n-butylphosphine (0.90 mL, 4.0 mmol). Dropwise add a solution of DEAD (40% solution in toluene, 1.1 mL, 2.8 mmol) in DCM (1.1 mL). Stir the reaction mixture at RT for 15 h. Quench the reaction with MeOH (5 mL) and concentrate under reduced pressure. Purify the residue via silica gel flash chromatography eluting with a gradient of 5 to 40% EtOAc in hexanes to give 1.1 g of the title compound (92%). ES-MS m/z 605, 607, and 609 (M+H).

Preparation 55

Methyl 2-[2-[3-[2-[(6-bromo-2-pyridyl)oxymethyl]-5-chloro-phenyl]propoxy]-4-(4,4,5,5-tetramethyl-1,3,2-dioxaborolan-2-yl)phenyl]acetate

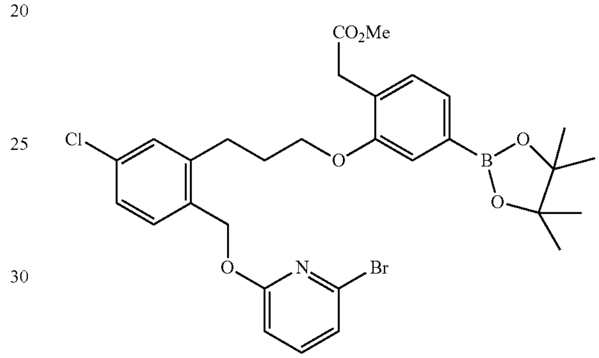

To a mixture of 3-[2-[(6-bromo-2-pyridyl)oxymethyl]-5-chloro-phenyl]propan-1-ol (420 mg, 1.18 mmol), methyl 2-[2-hydroxy-4-(4,4,5,5-tetramethyl-1,3,2-dioxaborolan-2-yl)phenyl]acetate (422 mg, 1.45 mmol), and triphenylphosphine (460 mg, 1.75 mmol) in THE (8 mL) dropwise add DIAD (0.35 mL, 1.80 mmol). Stir the reaction mixture at RT for 1.5 h. Adsorb the mixture onto silica and purify via silica gel flash chromatography eluting with a gradient of 0 to 30% EtOAc in hexanes to give 306 mg of the title compound (41%). ES-MS m/z 630 and 632 (M+H).

Preparation 56

Methyl 2-[2-[3-[2-[[(6-bromopyridin-2-yl)oxy]methyl]-5-cyanophenyl]propoxy]-4-(4,4,5,5-tetramethyl-1,3,2-dioxaborolan-2-yl)phenyl]acetate

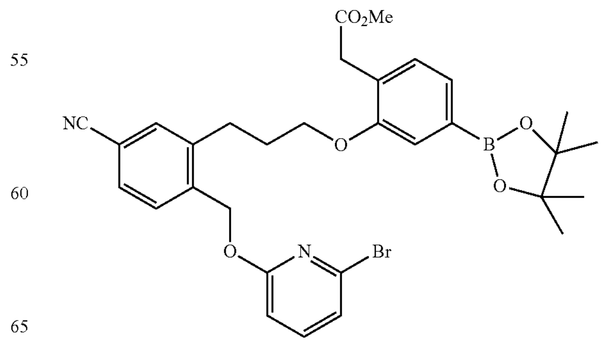

To a mixture of 4-[(6-bromo-2-pyridyl)oxymethyl]-3-(3-hydroxypropyl)benzonitrile (14.5 g, 41.9 mmol) and methyl 2-[2-hydroxy-4-(4,4,5,5-tetramethyl-1,3,2-dioxaborolan-2-yl)phenyl]acetate (18.7 g, 63.9 mmol) in THE (250 mL) add tri-n-butylphosphine (21 mL, 84 mmol). Cool the solution in an ice bath and dropwise add DIAD (17 mL, 86 mmol). Stir the reaction mixture at 45° C. for 14 h and then concentrate under reduced pressure. Suspend the residue in EtOAc (100 mL) and collect the solid by filtration. Wash the solid with EtOAc (3×25 mL) to give 19.7 g of the title compound (76%). ES-MS m/z 621, 623 (M+H).

Preparation 57

Ethyl 2-[2-[3-[2-[[(6-bromo-2-pyridyl)amino]methyl]-5-cyano-phenyl]propoxy]-4-(5,5-dimethyl-1,3,2-dioxaborinan-2-yl)-5-fluoro-phenyl]acetate

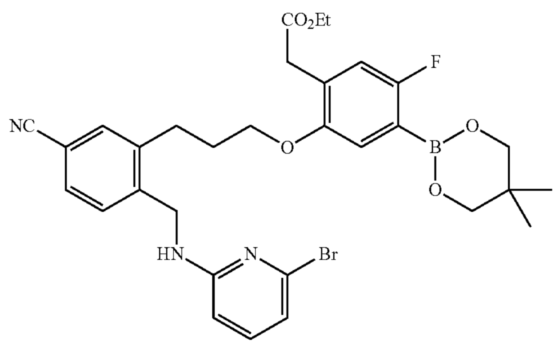 [SMILES: CCOC(=O)Cc1cc(F)c(B2OCC(C)(C)CO2)cc1OCCCc1cc(C#N)ccc1CNc1cccc(Br)n1]

To a solution of 4-[[(6-bromo-2-pyridyl)amino]methyl]-3-(3-hydroxypropyl)benzonitrile (380 mg, 1.04 mmol) and ethyl 2-[4-(5,5-dimethyl-1,3,2-dioxaborinan-2-yl)-5-fluoro-2-hydroxyphenyl]acetate (0.38 g, 1.15 mmol) in THE (5.2 mL) at 4° C., add triphenylphosphine (0.30 g, 1.15 mmol) and di-tertbutyl azodicarboxylate (0.27 g, 1.15 mmol). Stir at RT for 22 h, concentrate the reaction mixture and purify the residue via silica gel chromatography using a gradient of 10 to 70% EtOAc in cyclohexanes to get the title compound as a pale brown solid (500 mg, 60%). ES-MS m/z 570 and 572 (M+H for boronic acid).

Preparation 58

Methyl 2-[2-[3-[2-[(6-bromo-2-pyridyl)oxymethyl]-5-cyano-phenyl]propoxy]-5-methyl-4-(4,4,5,5-tetramethyl-1,3,2-dioxaborolan-2-yl)phenyl]acetate

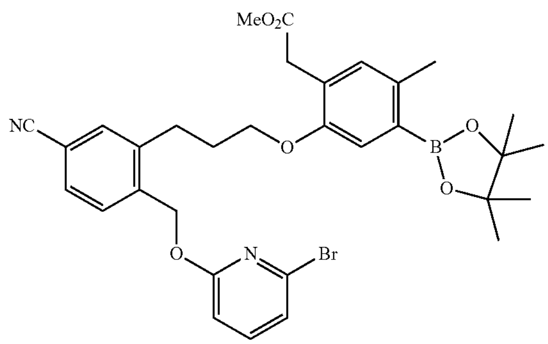 [SMILES: COC(=O)Cc1cc(C)c(B2OC(C)(C)C(C)(C)O2)cc1OCCCc1cc(C#N)ccc1COc1cccc(Br)n1]

Prepare the title compound essentially as described in Preparation 55 using 4-[(6-bromo-2-pyridyl)oxymethyl]-3-(3-hydroxypropyl)benzonitrile and methyl 2-[2-hydroxy-5-methyl-4-(4,4,5,5-tetramethyl-1,3,2-dioxaborolan-2-yl)phenyl]acetate. Use tri-n-butylphosphine instead of triphenylphosphine, DEAD instead of DIAD, and use dioxane as solvent instead of THF. Purify via silica gel flash chromatography using a gradient of 80-100% DCM in hexanes. ES-MS m/z 635 and 637 (M+H).

Preparation 59

Ethyl 2-[2-[3-[5-[(6-bromo-2-pyridyl)oxymethyl]-2-cyano-phenyl]propoxy]-5-fluoro-4-(4,4,5,5-tetramethyl-1,3,2-dioxaborolan-2-yl)phenyl]acetate

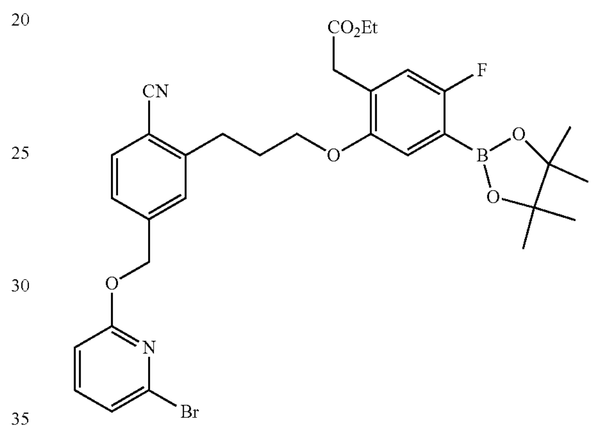

Add slowly a solution of di-tertbutyl azodicarboxylate (390 mg, 1.7 mmol) in anhydrous THE (2 mL) to a solution of triphenylphosphine (435 mg, 1.66 mmol), 4-[(6-bromo-2-pyridyl)oxymethyl]-2-(3-hydroxypropyl)benzonitrile (400 mg, 1.09 mmol) and ethyl 2-[5-fluoro-2-hydroxy-4-(4,4,5,5-tetramethyl-1,3,2-dioxaborolan-2-yl)phenyl]acetate (480 mg, purity 83%, 1.23 mmol) in anhydrous THF (8 mL) at RT. Stir the mixture at RT for 1 h. Add triphenylphosphine (170 mg, 0.65 mmol), and after 5 min add slowly a solution of di-tertbutyl azodicarboxylate (157 mg, 0.65 mmol) in anhydrous THE (2 ml). Concentrate the reaction mixture and purify the residue via silica gel flash chromatography using a gradient of 10 to 50% EtOAc in cyclohexanes to give the title compound as a brown waxy solid (689 mg, purity 90%, 86%). ES-MS m/z 653 and 655 (M+H).

Preparation 60

Ethyl 2-(4-bromo-2-(2-(2-(((6-bromopyridin-2-yl)oxy)methyl)-5-cyanophenoxy)ethoxy)-5-fluorophenyl)acetate

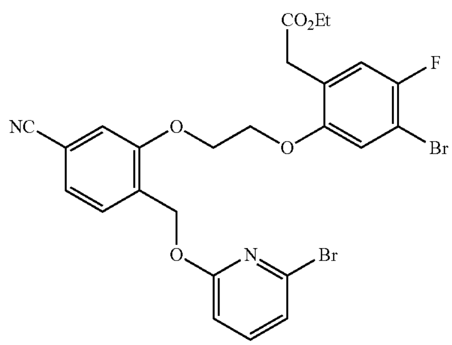 [SMILES: CCOC(=O)Cc1cc(F)c(Br)cc1OCCOc1cc(C#N)ccc1COc1cccc(Br)n1]

To a solution of 4-(((6-bromopyridin-2-yl)oxy)methyl)-3-(2-hydroxyethoxy)benzonitrile (640 mg, 1.83 mmol), ethyl 2-(4-bromo-5-fluoro-2-hydroxy-phenyl)acetate (506 mg, 1.83 mmoL), and TMAD (671 mg, 3.70 mmol) in THE (9 mL) add tri-N-butylphosphine (0.91 mL, 3.65 mmol). Stir at 35° C. for 2 h. Quench the reaction with MeOH and concentrate the crude mixture. Purify the residue via silica gel flash chromatography using a gradient of 0 to 30% EtOAc in heptane to give 876 mg of the title compound (79%). ES-MS m/z 607, 609, and 611 (M+H).

Preparation 61

3-(((5-Bromo-4-fluoro-2-iodobenzyl)oxy)methyl)-4-(((6-bromopyridin-2-yl)oxy)methyl)benzonitrile

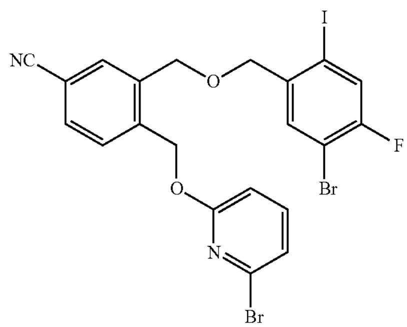 [SMILES: N#Cc1ccc(COc2cccc(Br)n2)c(COCc2cc(Br)c(F)cc2I)c1]

Prepare the title compound essentially as described in Preparation 34 using 3-(((5-bromo-4-fluoro-2-iodobenzyl)oxy)methyl)-4-(hydroxymethyl)benzonitrile. Purify the title compound via silica gel flash chromatography using a gradient of 0 to 10% EtOAc in heptane. ES-MS m/z 631, 633, and 635 (M+H).

Preparation 62

Ethyl 2-(4-bromo-2-(((2-(((6-bromopyridin-2-yl)oxy)methyl)-5-cyanobenzyl)oxy)methyl)-5-fluorophenyl)acetate

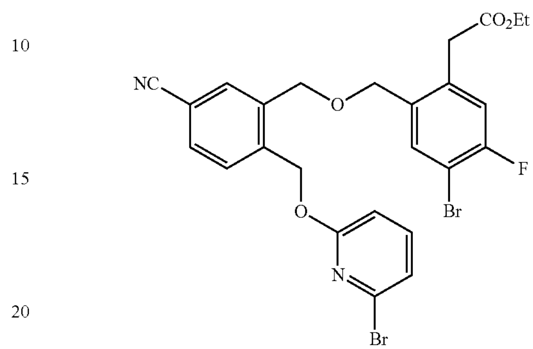

To a solution of 3-(((5-bromo-4-fluoro-2-iodobenzyl)oxy)methyl)-4-(((6-bromopyridin-2-yl)oxy)methyl)benzonitrile (2.69 mg, 4.3 mmol) in ACN (75 mL), add bis(triphenylphosphine)palladium (II) dichloride (305 mg, 0.43 mmol), TEA (1.48 mL, 10.6 mmol), and formic acid (0.24 mL, 6.4 mmol). Stir the reaction at 70° C. and add a solution of ethyl diazoacetate (2 M in DCM, 8.5 mL, 17 mmol) in ACN (25 mL) over 10 min. Stir at 70° C. for 2 h. Add second portions (half the amounts of initial addition) of all reagents and heat for a further 1.5 h. Dilute the reaction mixture with EtOAc and wash the organic layer with water. Dry the organic phase over magnesium sulfate, filter, and concentrate under reduced pressure. Purify the residue via silica gel flash chromatography using a gradient of 0 to 10% EtOAc in heptane to give 898 mg of the title compound (36%). ES-MS m/z 591, 593, and 595 (M+H).

Preparation 63

Methyl 2-[2-[3-[2-[(3-bromophenoxy)methyl]-5-cyano-phenyl]propoxy]-5-methyl-4-(4,4,5,5-tetramethyl-1,3,2-dioxaborolan-2-yl)phenyl]acetate

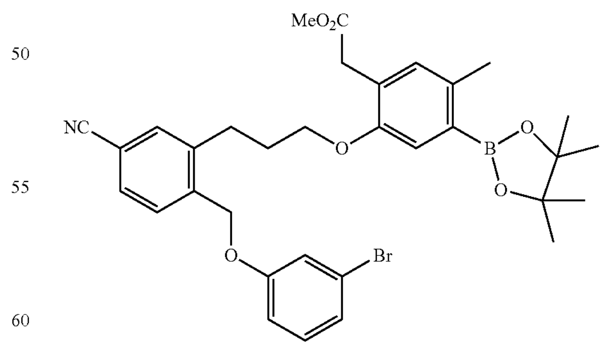

Prepare the title compound essentially as described in Preparation 54 using 4-[(3-bromophenoxy)methyl]-3-(3-hydroxypropyl)benzonitrile and methyl 2-[2-hydroxy-5-methyl-4-(4,4,5,5-tetramethyl-1,3,2-dioxaborolan-2-yl)phenyl]acetate, using 1,4-dioxane as reaction solvent and adding DEAD as a 40% solution in toluene. Purify the title compound via silica gel flash chromatography eluting with a gradient of 80 to 100% DCM in hexanes. ES-MS m/z 651 and 653 ($M+NH_4$).

Preparation 64

Methyl 2-[2-[3-[2-[(6-bromo-2-pyridyl)oxymethyl]-5-(trifluoromethyl)phenyl]propoxy]-5-methyl-4-(4,4,5,5-tetramethyl-1,3,2-dioxaborolan-2-yl)phenyl] acetate

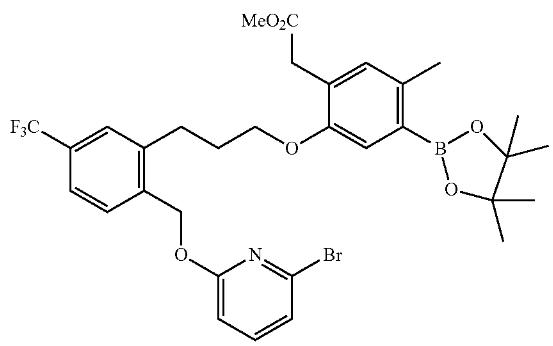 [SMILES: COC(=O)Cc1cc(C)c(B2OC(C)(C)C(C)(C)O2)cc1OCCCc1cc(C(F)(F)F)ccc1COc1cccc(Br)n1]

Prepare the title compound essentially as described in Preparation 54 using 3-[2-[(6-bromo-2-pyridyl)oxymethyl]-5-(trifluoromethyl)phenyl]propan-1-ol and methyl 2-[2-hydroxy-5-methyl-4-(4,4,5,5-tetramethyl-1,3,2-dioxaborolan-2-yl)phenyl]acetate, adding DEAD to the reaction as a 40% solution in toluene. Purify the title compound via silica gel flash chromatography eluting with a gradient of 85 to 100% DCM in hexanes. ES-MS m/z 678 and 680 (M+H).

Preparation 65

Ethyl 2-($5^4$-cyano-$1^6$-fluoro-3,9-dioxa-2(2,6)-pyridina-1(1,3),5(1,2)-dibenzenacyclononaphane-$1^4$-yl)acetate

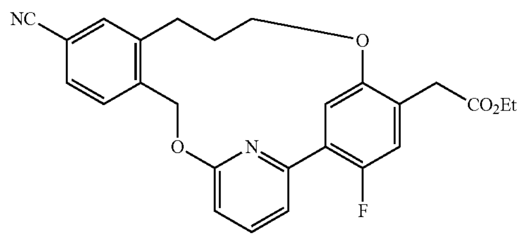 [SMILES: CCOC(=O)Cc1cc(F)c2cc1OCCCc1cc(C#N)ccc1COc1cccc-2n1]

To a solution of ethyl 2-[4-bromo-2-[3-[2-[(6-bromo-2-pyridyl)oxymethyl]-5-cyano-phenyl]propoxy]-5-fluoro-phenyl]acetate (1.1 g, 0.92 mmol) in 1,4-dioxane (40 mL) add hexamethylditin (0.71 g, 2.2 mmol). Add tetrakis(triphenylphosphine)palladium(0) (0.20 g, 0.20 mmol). Stir the reaction mixture at 90° C. for 60 h. Concentrate under reduced pressure and purify the residue via silica gel flash chromatography eluting with a gradient of 5 to 45% EtOAc in hexanes to give 303 mg of the title compound (47%). ES-MS m/z 447 (M+H).

Preparation 66

Methyl 2-($5^4$-chloro-3,9-dioxa-2(2,6)-pyridina-1(1,3),5(1,2)-dibenzenacyclononaphane-$1^4$-yl)acetate

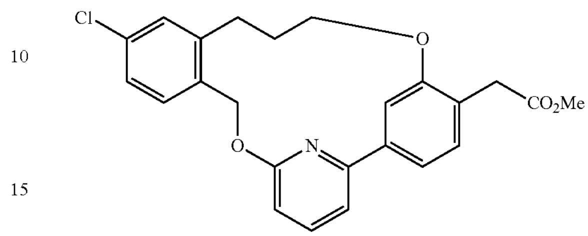

To a mixture of methyl 2-[2-[3-[2-[(6-bromo-2-pyridyl)oxymethyl]-5-chloro-phenyl]propoxy]-4-(4,4,5,5-tetramethyl-1,3,2-dioxaborolan-2-yl)phenyl]acetate (306 mg, 0.49 mmol), chloro(2-dicyclohexylphosphino-2',4',6'-triisopropyl-1,1'-biphenyl)(2'-amino-1,1'-biphenyl-2-yl) palladium (II) (XPhos Gen 2, 28.9 mg, 0.036 mmol), and potassium phosphate (420 mg, 1.94 mmol) add THE (48 mL) and water (5.4 mL). Stir the reaction mixture under a nitrogen atmosphere at 40° C. for 15 h. Concentrate the mixture under reduced pressure. Dissolve the residue in DCM, adsorb onto Celite®, and purify via silica gel flash chromatography eluting with a gradient of 0 to 40% EtOAc in hexanes to give 152 mg of the title compound (74%). ES-MS m/z 424 and 426 (M+H).

Preparation 67

Methyl 2-($5^4$-cyano-3,9-dioxa-2(2,6)-pyridina-1(1,3),5(1,2)-dibenzenacyclononaphane-$1^4$-yl)acetate

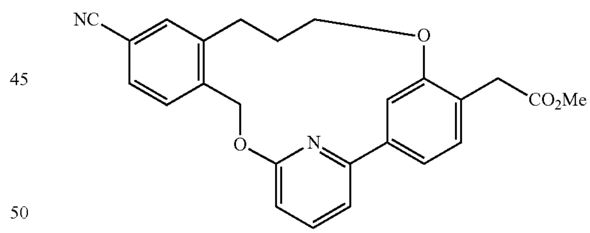

To a mixture of methyl 2-[2-[3-[2-[[(6-bromopyridin-2-yl)oxy]methyl]-5-cyanophenyl]propoxy]-4-(4,4,5,5-tetramethyl-1,3,2-dioxaborolan-2-yl)phenyl]acetate (19.7 g, 31.7 mmol), chloro(2-dicyclohexylphosphino-2',4',6'-triisopropyl-1,1'-biphenyl)(2'-amino-1,1'-biphenyl-2-yl) palladium (II) (XPhos Gen 2, 1.3 g, 1.6 mmol), and potassium phosphate (28.5 g, 132 mmol) add THE (500 mL) and water (52 mL). Stir the reaction mixture under a nitrogen atmosphere at 45° C. for 2 h 15 min. Dilute the reaction with EtOAc (200 mL) and wash with half-saturated brine (400 mL). Dry the organic phase over $MgSO_4$, filter, and concentrate under reduced pressure. Suspend the residue in EtOAc (100 mL) and collect the solid by filtration. Wash the solid with EtOAc (3×30 mL) to give 10.7 g of the title compound (82%). ES-MS m/z 415 (M+H).

Preparation 68

Ethyl 2-($5^4$-cyano-$1^6$-fluoro-9-oxa-3-aza-2(2,6)-pyridina-1(1,3),5(1,2)-dibenzenacyclononaphane-$1^4$-yl)acetate

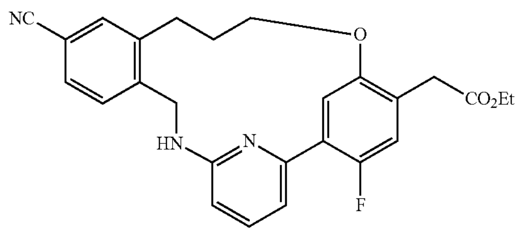 [SMILES: CCOC(=O)Cc1cc(F)c2cc1OCCCc1cc(C#N)ccc1CNc1cccc-2n1]

To a solution of ethyl 2-[2-[3-[2-[[(6-bromo-2-pyridyl)amino]methyl]-5-cyano-phenyl]propoxy]-4-(5,5-dimethyl-1,3,2-dioxaborinan-2-yl)-5-fluoro-phenyl]acetate (460 mg, 0.57 mmol) in 1,4-dioxane (11.5 mL), add $PdCl_2$(dtbpf) (77 mg, 0.11 mmol) and 1M aqueous potassium phosphate solution (1.73 mL, 1.73 mmol). Stir at 70° C. for 2 h, cool to RT and dilute the reaction mixture with saturated ammonium chloride solution (15 mL) and EtOAc (10 mL). Separate phases, extract aqueous phase with EtOAc (2×5 mL). Combine organics, dry over magnesium sulfate, filter, and concentrate under reduced pressure. Purify the residue via silica gel chromatography using 30% of EtOAc in cyclohexanes as eluent system to provide the title compound (125 mg, 49%) as a light-yellow solid. ES-MS m/z 446 (M+H).

Preparation 69

Methyl 2-($5^4$-cyano-$1^6$-methyl-3,9-dioxa-2(2,6)-pyridina-1(1,3),5(1,2)-dibenzenacyclononaphane-$1^4$-yl)acetate

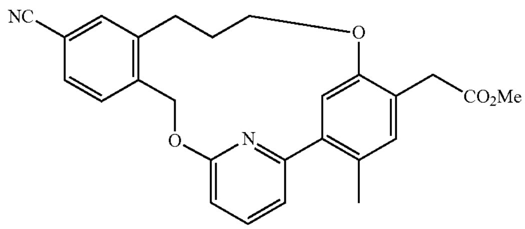 [SMILES: COC(=O)Cc1cc(C)c2cc1OCCCc1cc(C#N)ccc1COc1cccc-2n1]

Prepare the title compound essentially as described in Preparation 66 using methyl 2-[2-[3-[2-[(6-bromo-2-pyridyl)oxymethyl]-5-cyano-phenyl]propoxy]-5-methyl-4-(4,4,5,5-tetramethyl-1,3,2-dioxaborolan-2-yl)phenyl]acetate. Purify via silica gel flash chromatography using a gradient of 0 to 20% EtOAc in DCM. ES-MS m/z 429 (M+H).

Preparation 70

Ethyl 2-($5^4$-cyano-$1^6$-fluoro-3,9-dioxa-2(2,6)-pyridina-1,5(1,3)-dibenzenacyclononaphane-$1^4$-yl)acetate

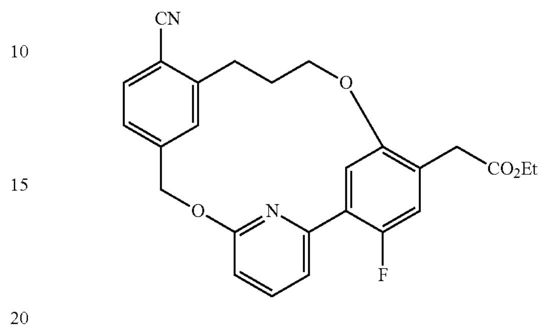

To a solution of ethyl 2-[2-[3-[5-[(6-bromo-2-pyridyl)oxymethyl]-2-cyano-phenyl]propoxy]-5-fluoro-4-(4,4,5,5-tetramethyl-1,3,2-dioxaborolan-2-yl)phenyl]acetate (650 mg, 90% purity, 0.89 mmol) in 1,4-dioxane (30 mL), add $PdCl_2$(dtbpf) (119 mg, 0.18 mmol) and 1M aqueous potassium phosphate solution (2.7 mL, 2.7 mmol). Stir the mixture at 50° C. for 15 min under nitrogen atmosphere, then cool to RT and dilute with DCM. Dry over anhydrous $Na_2SO_4$, filter, and concentrate under reduced pressure. Purify the residue via silica gel flash chromatography using a gradient of 10 to 30% EtOAc in cyclohexanes to provide the title compound (150 mg, 38%) as a very pale brown solid. ES-MS m/z 447 (M+H).

Preparation 71

Ethyl 2-($5^4$-cyano-$1^6$-fluoro-3,6,9-trioxa-2(2,6)-pyridina-1(1,3),5(1,2)-dibenzenacyclononaphane-$1^4$-yl)acetate

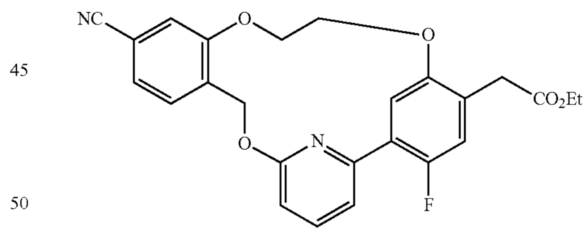

To a solution of ethyl 2-(4-bromo-2-(2-(2-(((6-bromopyridin-2-yl)oxy)methyl)-5-cyanophenoxy)ethoxy)-5-fluorophenyl)acetate (400 mg, 0.66 mmol), KOAc (0.2 g, 2.0 mmol), bis(pinacolato)diboron (187 mg, 0.72 mmol) in 1,4-dioxane (2.2 mL) add Pd(dppf)$Cl_2$-DCM complex (27 mg, 0.032 mmol). Stir the mixture at 85° C. for 1 h, then dilute the with water and extract three times with EtOAc. Dry the organic phase over magnesium sulfate, filter, and concentrate under reduced pressure. To the residue, add THE (66 mL), potassium phosphate tribasic (0.6 g, 3.0 mmol), water (7.3 mL), and a premade solution of palladium (II) chloride (6.0 mg, 0.033 mmol) and 2-dicyclohexylphosphine-2',4',6'-triisopropylbiphenyl (32 mg, 0.066 mmol) in THE (1 mL). Stir at 45° C. for 16 h. Dilute the crude mixture with water and extract three times with EtOAc (3×). Dry the organic phase over magnesium sulfate, filter, and concentrate under reduced pressure. Purify the residue via silica gel flash chromatography using a gradient of 0 to 30% EtOAc in heptane to give 94 mg of the title compound (32%). ES-MS m/z 449 (M+H).

Preparation 72

Ethyl 2-($5^4$-cyano-$1^6$-fluoro-3,7-dioxa-2(2,6)-pyridina-1(1,3),5(1,2)-dibenzenacyclooctaphane-$1^4$-yl)acetate

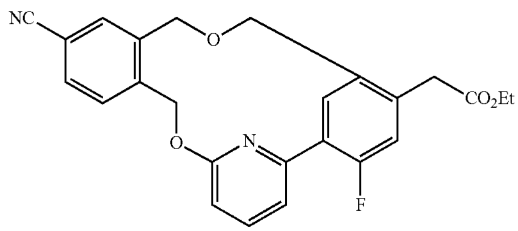 [SMILES: CCOC(=O)Cc1cc(F)c2cc1COCc1cc(C#N)ccc1COc1cccc-2n1]

Prepare the title compound essentially as described in Preparation 65 using ethyl 2-(4-bromo-2-(((2-(((6-bromopyridin-2-yl)oxy)methyl)-5-cyanobenzyl)oxy)methyl)-5-fluorophenyl)acetate, using 1.1 eq of hexamethylditin and with Pd(dppf)$Cl_2$-DCM as catalyst, and stirring the reaction at 100° C. for 3.5 h. Dilute the crude reaction mixture with water and extract with EtOAc. Dry the organic phase over magnesium sulfate, filter, and concentrate under reduced pressure. Purify the residue via silica gel flash chromatography using a gradient of 0 to 80% EtOAc in heptane to give the title compound. ES-MS m/z 433 (M+H).

Preparation 73

Methyl 2-($5^4$-cyano-$1^6$-methyl-3,9-dioxa-1,2(1,3),5(1,2)-tribenzenacyclononaphane-$1^4$-yl)acetate

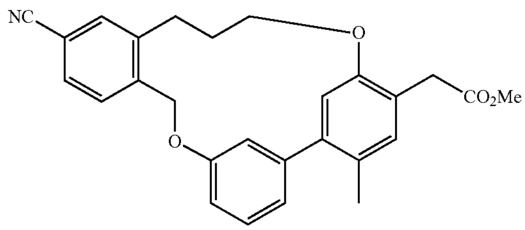 [SMILES: COC(=O)Cc1cc(C)c2cc1OCCCc1cc(C#N)ccc1COc1cccc-2c1]

Prepare the title compound essentially as described in Preparation 66 using methyl 2-[2-[3-[2-[(3-bromophenoxy)methyl]-5-cyano-phenyl]propoxy]-5-methyl-4-(4,4,5,5-tetramethyl-1,3,2-dioxaborolan-2-yl)phenyl]acetate, stirring the reaction mixture at 40° C. for 1 h. Purify the mixture via silica gel flash chromatography eluting with a gradient of 0 to 20% EtOAc in DCM to afford the title compound. ES-MS m/z 428 (M+H).

Preparation 74

Methyl 2-($1^6$-methyl-$5^4$-(trifluoromethyl)-3,9-dioxa-2(2,6)-pyridina-1(1,3),5(1,2)-dibenzenacyclononaphane-$1^4$-yl)acetate

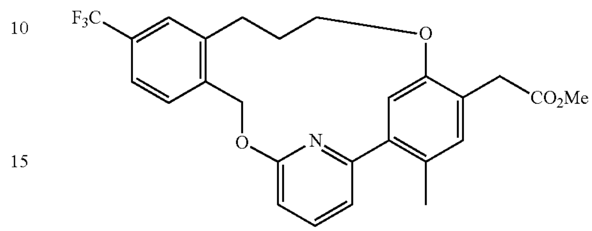

Prepare the title compound essentially as described in Preparation 66 using methyl 2-[2-[3-[2-[(6-bromo-2-pyridyl)oxymethyl]-5-(trifluoromethyl)phenyl]propoxy]-5-methyl-4-(4,4,5,5-tetramethyl-1,3,2-dioxaborolan-2-yl)phenyl]acetate, stirring the reaction at 40° C. for 1 h. Purify the title compound via silica gel flash chromatography eluting with a gradient of 0 to 20% EtOAc in DCM. ES-MS m/z 472 (M+H).

Preparation 75

2-($5^4$-Cyano-$1^6$-fluoro-3,9-dioxa-2(2,6)-pyridina-1(1,3),5(1,2)-dibenzenacyclononaphane-$1^4$-yl)acetic acid

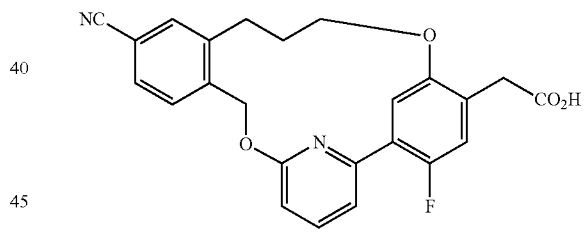

To a mixture of ethyl 2-($5^4$-cyano-$1^6$-fluoro-3,9-dioxa-2(2,6)-pyridina-1(1,3),5(1,2)-dibenzenacyclononaphane-$1^4$-yl)acetate (290 mg, 0.649 mmol) in ACN:water (5 mL:0.5 mL) add 1,3,4,6,7,8-hexahydro-2H-pyrimido[1,2-a]pyrimidine (0.30 g, 2.0 mmol). Stir the reaction mixture at RT for 15 h. Adjust the pH of the reaction mixture to pH 7 with 1.0 M aqueous citric acid solution and concentrate under reduced pressure to remove volatiles. Dilute the residue with EtOAc (100 mL) and wash with water (50 mL) and saturated aqueous NaCl (50 mL). Dry the organic phase over sodium sulfate, filter, and concentrate under reduced pressure to give 238 mg of the title compound (88%), which is used in crude form in Preparations 85 and 86. ES-MS m/z 419 (M+H).

Preparation 76

2-($5^4$-Chloro-3,9-dioxa-2(2,6)-pyridina-1(1,3),5(1,2)-dibenzenacyclononaphane-$1^4$-yl)acetic acid

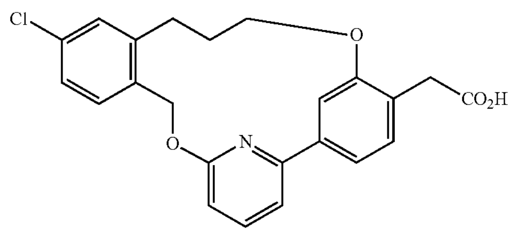 [SMILES: O=C(O)Cc1ccc2cc1OCCCc1cc(Cl)ccc1COc1cccc-2n1]

To a mixture of methyl 2-($5^4$-chloro-3,9-dioxa-2(2,6)-pyridina-1(1,3),5(1,2)-dibenzenacyclononaphane-$1^4$-yl)acetate (152 mg, 0.36 mmol) in ACN (3.6 mL) and THE (3 mL) add an aqueous solution of lithium hydroxide (1.0 M, 1.1 mL, 1.1 mmol). Stir the mixture at 40° C. for 2 h. Quench the reaction with aqueous citric acid solution (1.0 M, 2.2 mL) and then dilute with EtOAc. Remove the aqueous layer and extract with EtOAc (2×3 mL). Dry the combined organic phase over magnesium sulfate, filter, and concentrate under reduced pressure to give 150 mg of the title compound (100%), which is used in crude form in Preparation 87. ES-MS m/z 410 (M+H).

Preparation 77

2-($5^4$-Cyano-3,9-dioxa-2(2,6)-pyridina-1(1,3),5(1,2)-dibenzenacyclononaphane-$1^4$-yl)acetic acid

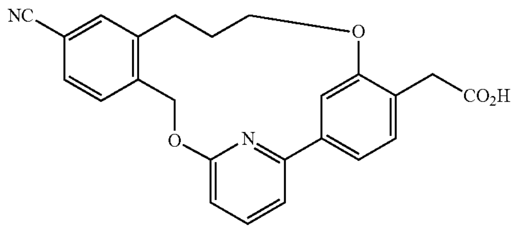 [SMILES: N#Cc1ccc2c(c1)CCCOc1cc(ccc1CC(=O)O)-c1cccc(n1)OC2]

Prepare the title compound essentially as described in Preparation 75 starting with methyl 2-(54 cyano-3,9-dioxa-2(2,6)-pyridina-1(1,3),5(1,2)-dibenzenacyclononaphane-$1^4$-yl)acetate. After the reaction is complete, cool to RT and neutralize with an aqueous solution of citric acid. Filter the resulting precipitate and dry the resulting filter cake under vacuum to give the title compound (100%). ES-MS m/z 401 (M+H)

Preparation 78

2-($5^4$-Cyano-$1^6$-fluoro-9-oxa-3-aza-2(2,6)-pyridina-1(1,3),5(1,2)-dibenzenacyclononaphane-$1^4$-yl)acetic acid

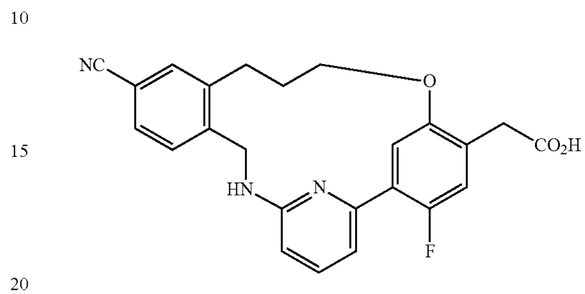

To a suspension of ethyl 2-($5^4$-cyano-$1^6$-fluoro-9-oxa-3-aza-2(2,6)-pyridina-1(1,3),5(1,2)-dibenzenacyclononaphane-$1^4$-yl)acetate (122 mg, 027 mmol) in ACN (3 mL), THE (1 mL) and water (1 mL), add 1,5,7-triazabicyclo[4.4.0]dec-5-ene (116 mg, 0.81 mmol). Stir at 45° C. for 2 h, cool to RT and quench with 1M citric acid solution (2 mL). Extract with EtOAc (3×3 mL). Combine organics, wash with water and brine, dry over magnesium sulfate, filter, and concentrate under reduce pressure, to give a waxy pale yellow solid (115 mg, 100%). ES-MS m/z 418 (M+H).

Preparation 79

2-($5^4$-Cyano-$1^6$-methyl-3,9-dioxa-2(2,6)-pyridina-1(1,3),5(1,2)-dibenzenacyclononaphane-$1^4$-yl)acetic acid

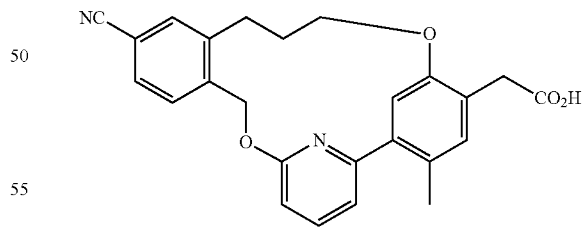

Prepare the title compound essentially as described in Preparation 75 using methyl 2-($5^4$-cyano-$1^6$-methyl-3,9-dioxa-2(2,6)-pyridina-1(1,3),5(1,2)-dibenzenacyclononaphane-$1^4$-yl)acetate. ES-MS m/z 415 (M+H).

Preparation 80

2-($5^4$-Cyano-$1^6$-fluoro-3,9-dioxa-2(2,6)-pyridina-1,5(1,3)-dibenzenacyclononaphane-$1^4$-yl)acetic acid

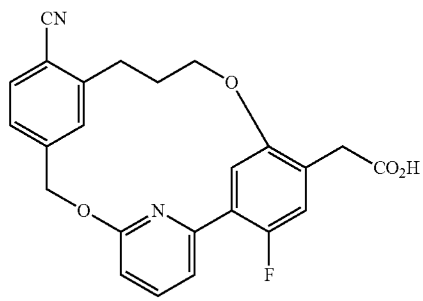 [SMILES: N#Cc1ccc2cc1CCCOc1cc(c(F)cc1CC(=O)O)-c1cccc(n1)OC2]

Prepare the title compound essentially as described in Preparation 78 using ethyl 2-($5^4$-cyano-$1^6$-fluoro-3,9-dioxa-2(2,6)-pyridina-1,5(1,3)-dibenzenacyclononaphane-$1^4$-yl) acetate. ES-MS m/z 419 (M+H).

Preparation 81

2-($5^4$-Cyano-$1^6$-fluoro-3,6,9-trioxa-2(2,6)-pyridina-1(1,3),5(1,2)-dibenzenacyclononaphane-$1^4$-yl)acetic acid

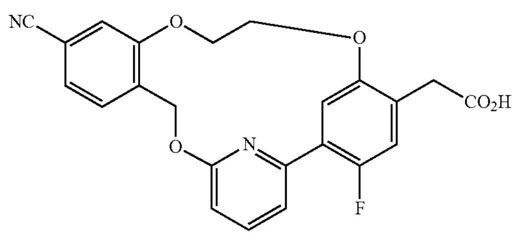 [SMILES: N#Cc1ccc2c(c1)OCCOc1cc(c(F)cc1CC(=O)O)-c1cccc(n1)OC2]

Prepare the title compound essentially as described in Preparation 75 using ethyl 2-($5^4$-cyano-$1^6$-fluoro-3,6,9-trioxa-2(2,6)-pyridina-1(1,3),5(1,2)-dibenzenacyclononaphane-$1^4$-yl)acetate, stirring the reaction at 45° C. for 3 h. Quench the reaction with formic acid to pH 7 and dilute with water. Extract three times with EtOAc and then three times with 3:1 chloroform:isopropanol. Dry the organic phase over magnesium sulfate, filter, and concentrate under reduced pressure. Purify the residue via silica gel flash chromatography using a gradient of 10 to 80% EtOAc in DCM to give the title compound. ES-MS m/z 421 (M+H).

Preparation 82

2-($5^4$-Cyano-$1^6$-fluoro-3,7-dioxa-2(2,6)-pyridina-1(1,3),5(1,2)-dibenzenacyclooctaphane-$1^4$-yl)acetic acid

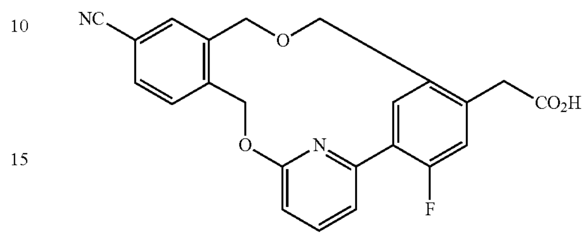

Prepare the title compound essentially as described in Preparation 75 using ethyl 2-($5^4$-cyano-$1^6$-fluoro-3,7-dioxa-2(2,6)-pyridina-1(1,3),5(1,2)-dibenzenacyclooctaphane-$1^4$-yl), stirring the reaction at 45° C. for 1 h. Quench the reaction to pH 6-7 with formic acid and extract with EtOAc, followed by 3:1 chloroform:2-propanol. Dry the organic phase over magnesium sulfate, filter, and concentrate under reduced pressure to give the title compound (95%), which is used in crude form in Preparation 98. ES-MS m/z 405 (M+H).

Preparation 83

2-($5^4$-Cyano-$1^6$-methyl-3,9-dioxa-1,2(1,3),5(1,2)-tribenzenacyclononaphane-$1^4$-yl)acetic acid

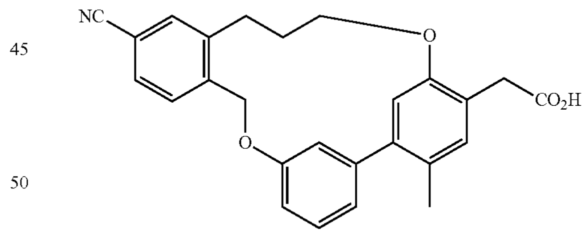

Prepare the title compound essentially as described in Preparation 75 using methyl 2-($5^4$-cyano-$1^6$-methyl-3,9-dioxa-1,2(1,3),5(1,2)-tribenzenacyclononaphane-$1^4$-yl)acetate, stirring the reaction mixture at 45° C. for 1 h. Use the title compound in crude form in Preparation 99. ES-MS m/z 412 (M−H).

Preparation 84

2-($1^6$-Methyl-$5^4$-(trifluoromethyl)-3,9-dioxa-2(2,6)-pyridina-1(1,3),5(1,2)-dibenzenacyclononaphane-$1^4$-yl)acetic acid

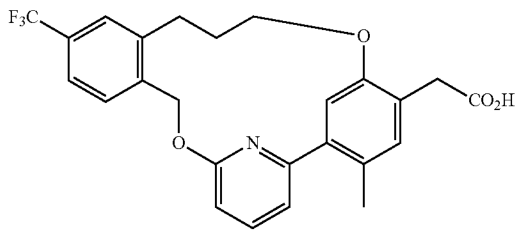 [SMILES: Cc1cc(CC(=O)O)c2cc1-c1cccc(n1)OCc1ccc(C(F)(F)F)cc1CCCO2]

Prepare the title compound essentially as described in Preparation 75 using methyl 2-($1^6$-methyl-$5^4$-(trifluoromethyl)-3,9-dioxa-2(2,6)-pyridina-1(1,3),5(1,2)-dibenzenacyclononaphane-$1^4$-yl)acetate, stirring the reaction at 50° C. for 1 h. Use the title compound in crude form in Preparation 100. ES-MS m/z 458 (M+H).

Preparation 85

Methyl (S)-4-(2-($5^4$-cyano-$1^6$-fluoro-3,9-dioxa-2(2,6)-pyridina-1(1,3),5(1,2)-dibenzenacyclononaphane-$1^4$-yl)acetamido)-3-((oxetan-2-ylmethyl)amino)benzoate

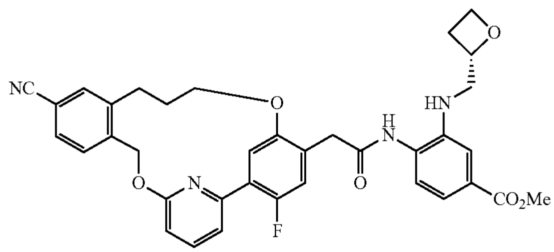 [SMILES: COC(=O)c1ccc(NC(=O)Cc2cc(F)c3cc2OCCCc2cc(C#N)ccc2COc2cccc-3n2)c(NC[C@@H]2CCO2)c1]

To a mixture of 2-($5^4$-cyano-$1^6$-fluoro-3,9-dioxa-2(2,6)-pyridina-1(1,3),5(1,2)-dibenzenacyclononaphane-$1^4$-yl)acetic acid, (crude, 0.170 g, 0.361 mmol) and methyl 4-amino-3-[[(2S)-oxetan-2-yl]methylamino]benzoate (prepared essentially as described in WO 2020/263695; 100 mg, 0.423 mmol) in pyridine (3 mL) add EDC (125 mg, 0.639 mmol). Stir the reaction mixture at RT for 15 h. Quench the reaction with saturated aqueous ammonium chloride to pH 6. Dilute the mixture with water (5 mL) and extract with EtOAc (3×10 mL). Wash the combined organics with saturated aqueous sodium chloride (10 mL). Dry the organic phase over sodium sulfate, filter, and concentrate under reduced pressure. Purify the residue via silica gel chromatography eluting with a gradient of 0 to 50% EtOAc in petroleum ether to give 225 mg of the title compound (71%). ES-MS m/z 637 (M+H).

Preparation 86

Methyl (S)-4-(2-($5^4$-cyano-$1^6$-fluoro-3,9-dioxa-2(2,6)-pyridina-1(1,3),5(1,2)-dibenzenacyclononaphane-$1^4$-yl)acetamido)-3-fluoro-5-((oxetan-2-ylmethyl)amino)benzoate

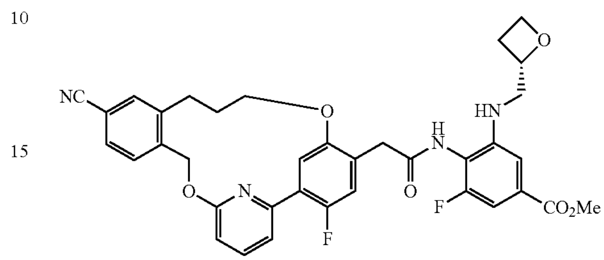

To a mixture of 2-($5^4$-cyano-$1^6$-fluoro-3,9-dioxa-2(2,6)-pyridina-1(1,3),5(1,2)-dibenzenacyclononaphane-$1^4$-yl)acetic acid (238 mg, 0.568 mmol) and methyl 4-amino-3-fluoro-5-[[(2S)-oxetan-2-ylmethyl]amino]benzoate (0.20 g, 0.79 mmol) in DMF (5 mL) add DIPEA (0.15 mL, 0.86 mmol). Add HATU (0.20 g, 0.53 mmol). Stir at RT for 4 h. Dilute the reaction with EtOAc (100 mL) and wash with water (50 mL) and saturated aqueous NaCl (50 mL). Dry the organic phase over sodium sulfate, filter, and concentrate under reduced pressure to give 0.46 g of the title compound (99%), which is used in crude form in Preparation 102. ES-MS m/z 655 (M+H).

Preparation 87

Methyl (S)-4-(2-($5^4$-chloro-3,9-dioxa-2(2,6)-pyridina-1(1,3),5(1,2)-dibenzenacyclononaphane-$1^4$-yl)acetamido)-3-((oxetan-2-ylmethyl)amino)benzoate

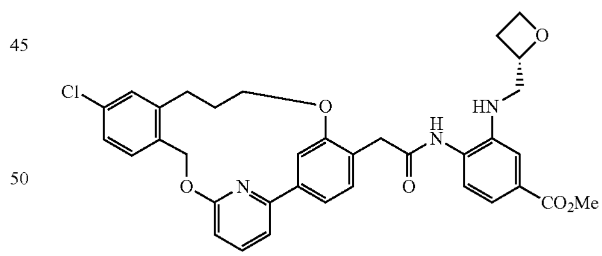

Prepare the title compound essentially as described in Preparation 86 using 2-($5^4$-chloro-3,9-dioxa-2(2,6)-pyridina-1(1,3),5(1,2)-dibenzenacyclononaphane-$1^4$-yl)acetic acid and methyl 4-amino-3-[[(2S)-oxetan-2-yl]methylamino]benzoate (prepared essentially as described in WO 2020/263695), stirring the reaction for 16 h before workup. The title compound is used in crude form in Preparation 104. ES-MS m/z 628 (M+H).

Preparation 88

Methyl (S)-4-(2-($5^4$-cyano-3,9-dioxa-2(2,6)-pyridina-1(1,3),5(1,2)-dibenzenacyclononaphane-$1^4$-yl)acetamido)-3-((oxetan-2-ylmethyl)amino)benzoate

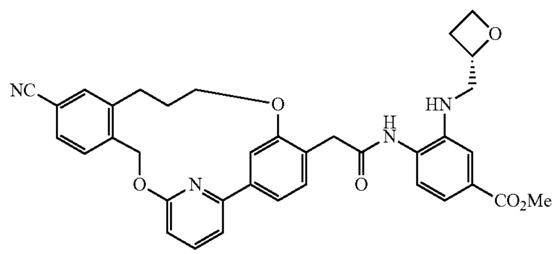 [SMILES: COC(=O)c1ccc(NC(=O)Cc2ccc3cc2OCCCc2cc(C#N)ccc2COc2cccc-3n2)c(NC[C@@H]2CCO2)c1]

Prepare the title compound essentially as described in Preparation 86 using 2-($5^4$-cyano-3,9-dioxa-2(2,6)-pyridina-1(1,3),5(1,2)-dibenzenacyclononaphane-$1^4$-yl)acetic acid and methyl 4-amino-3-[[(2S)-oxetan-2-yl]methylamino]benzoate (prepared essentially as described in WO 2020/263695). Obtain the crude title compound and use without purification in Preparation 105. ES-MS m/z 619 (M+H)

Preparation 89

Methyl (S)-4-(2-($5^4$-cyano-3,9-dioxa-2(2,6)-pyridina-1(1,3),5(1,2)-dibenzenacyclononaphane-$1^4$-yl)acetamido)-3-methoxy-5-((oxetan-2-ylmethyl)amino)benzoate

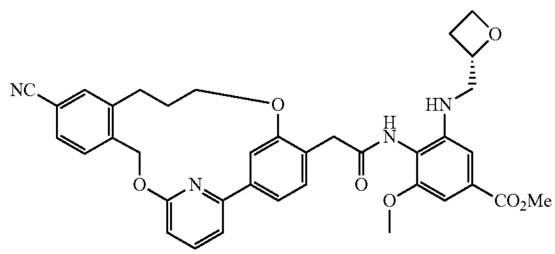 [SMILES: COC(=O)c1cc(NC[C@@H]2CCO2)c(NC(=O)Cc2ccc3cc2OCCCc2cc(C#N)ccc2COc2cccc-3n2)c(OC)c1]

Prepare the title compound essentially as described in Preparation 86 using 2-($5^4$-cyano-3,9-dioxa-2(2,6)-pyridina-1(1,3),5(1,2)-dibenzenacyclononaphane-$1^4$-yl)acetic acid and methyl 4-amino-3-methoxy-5-[[(2S)-oxetan-2-yl]methylamino]benzoate (Preparation 17). Purify the residue via silica gel chromatography using a gradient of 5 to 80% EtOAc in DCM to give the title compound. ES-MS m/z 649 (M+H).

Preparation 90

Methyl (S)-5-(2-($5^4$-cyano-3,9-dioxa-2(2,6)-pyridina-1(1,3),5(1,2)-dibenzenacyclononaphane-$1^4$-yl)acetamido)-6-((oxetan-2-ylmethyl)amino)picolinate

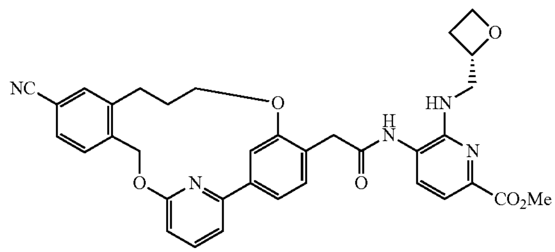

Prepare the title compound essentially as described in Preparation 86 using 2-($5^4$-cyano-3,9-dioxa-2(2,6)-pyridina-1(1,3),5(1,2)-dibenzenacyclononaphane-$1^4$-yl)acetic acid (0.3 g, 0.75 mmol) and methyl (S)-5-amino-6-((oxetan-2-ylmethyl)amino)picolinate. The title compound is used in the next step (Preparation 107) without purification. ES-MS m/z 620 (M+H)

Preparation 91

Methyl (S)-4-(2-($5^4$-cyano-3,9-dioxa-2(2,6)-pyridina-1(1,3),5(1,2)-dibenzenacyclononaphane-$1^4$-yl)acetamido)-3-fluoro-5-((oxetan-2-ylmethyl)amino)benzoate

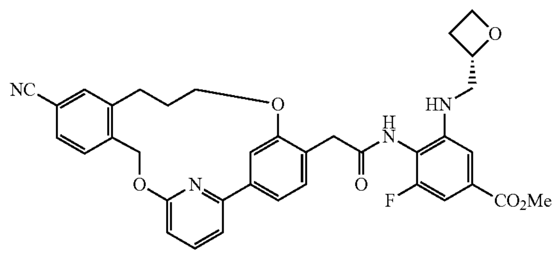

Prepare the title compound essentially as described in Preparation 86 using 2-($5^4$-cyano-3,9-dioxa-2(2,6)-pyridina-1(1,3),5(1,2)-dibenzenacyclononaphane-$1^4$-yl)acetic acid and methyl 4-amino-3-fluoro-5-[[(2S)-oxetan-2-yl-methyl]amino]benzoate. The title compound is used in the next step (Preparation 108) without purification. ES-MS m/z 637 (M+H)

Preparation 92

Methyl (S)-4-(2-($5^4$-cyano-$1^6$-fluoro-9-oxa-3-aza-2(2,6)-pyridina-1(1,3),5(1,2)-dibenzenacyclononaphane-$1^4$-yl)acetamido)-3-((oxetan-2-ylmethyl)amino)benzoate

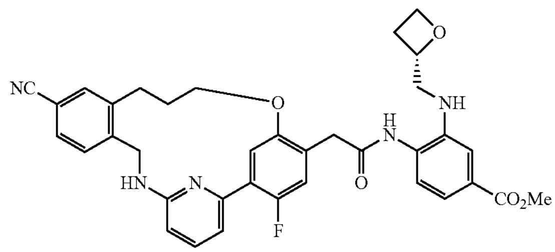 [SMILES: COC(=O)c1ccc(NC(=O)Cc2cc(F)c3cc2OCCCc2cc(C#N)ccc2CNc2cccc-3n2)c(NC[C@@H]2CCO2)c1]

To a solution of 2-($5^4$-cyano-$1^6$-fluoro-9-oxa-3-aza-2(2,6)-pyridina-1(1,3),5(1,2)-dibenzenacyclononaphane-$1^4$-yl)acetic acid (115 mg, 0.27 mmol) in DMF (3.0 mL), add methyl 4-amino-3-[[(2S)-oxetan-2-yl]methylamino]benzoate (prepared essentially as described in WO 2020/263695) (75 mg, 0.32 mmol), HATU (160 mg, 0.42 mmol) and DIPEA (0.15 mL, 0.86 mmol). Stir at RT for 2 h, dilute with water (10 mL) and extract with EtOAc (4×5 mL). Combine organics, wash with water and brine, dry over magnesium sulfate, filter, and concentrate under vacuum to give the title compound as a brown solid (160 mg, 79%). ES-MS m/z 636 (M+H).

Preparation 93

Methyl (S)-4-(2-($5^4$-cyano-$1^6$-methyl-3,9-dioxa-2(2,6)-pyridina-1(1,3),5(1,2)-dibenzenacyclononaphane-$1^4$-yl)acetamido)-3-methoxy-5-((oxetan-2-ylmethyl)amino)benzoate

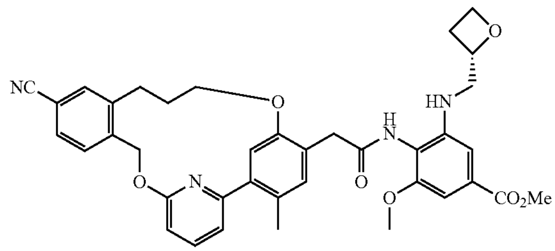 [SMILES: COC(=O)c1cc(NC[C@@H]2CCO2)c(NC(=O)Cc2cc(C)c3cc2OCCCc2cc(C#N)ccc2COc2cccc-3n2)c(OC)c1]

Prepare the title compound essentially as described in Preparation 86 using 2-($5^4$-cyano-$1^6$-methyl-3,9-dioxa-2(2,6)-pyridina-1(1,3),5(1,2)-dibenzenacyclononaphane-$1^4$-yl)acetic acid and methyl 4-amino-3-methoxy-5-[[(2S)-oxetan-2-yl]methylamino]benzoate (Preparation 17). Use the title compound as a crude product in the next step (Preparation 103) without purification. ES-MS m/z 663 (M+H).

Preparation 94

Methyl (S)-4-(2-($5^4$-cyano-$1^6$-fluoro-3,9-dioxa-2(2,6)-pyridina-1,5(1,3)-dibenzenacyclononaphane-$1^4$-yl)acetamido)-3-((oxetan-2-ylmethyl)amino)benzoate

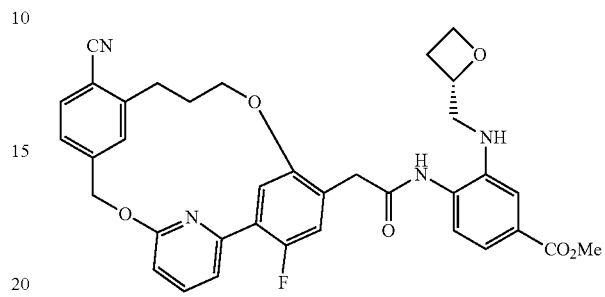

Prepare the title compound essentially as described in Preparation 86 using 2-($5^4$-cyano-$1^6$-fluoro-3,9-dioxa-2(2,6)-pyridina-1,5(1,3)-dibenzenacyclononaphane-$1^4$-yl)acetic acid and methyl 4-amino-3-[[(2S)-oxetan-2-yl]methylamino]benzoate (prepared essentially as described in WO 2020/263695). The title compound is used in its crude form without purification in Preparation 110. ES-MS m/z 637 (M+H).

Preparation 95

Methyl 4-(2-($5^4$-cyano-3,9-dioxa-2(2,6)-pyridina-1(1,3),5(1,2)-dibenzenacyclononaphane-$1^4$-yl)acetamido)-3-(((1-ethyl-1H-imidazol-5-yl)methyl)amino)benzoate

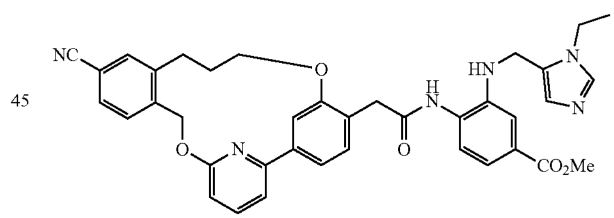

Prepare the title compound essentially as described in Preparation 86 using 2-($5^4$-cyano-3,9-dioxa-2(2,6)-pyridina-1(1,3),5(1,2)-dibenzenacyclononaphane-$1^4$-yl)acetic acid (100 mg, 0.25 mmol) and methyl 4-amino-3-(((1-ethyl-1H-imidazol-5-yl)methyl)amino)benzoate (Preparation 19). Stir the reaction at RT for 18 h, then dilute with water and EtOAc, then extract the aqueous layer four times with EtOAc. Dry the organic phase over magnesium sulfate, filter, and concentrate under reduced pressure to give the title compound which is used in crude form in Preparation 111. ES-MS m/z 657(M+H).

Preparation 96

(S)-2-($5^4$-Cyano-3,9-dioxa-2(2,6)-pyridina-1(1,3),5(1,2)-dibenzenacyclononaphane-$1^4$-yl)-N-(2-methoxy-6-((oxetan-2-ylmethyl)amino)-4-(1H-tetrazol-5-yl)phenyl)acetamide

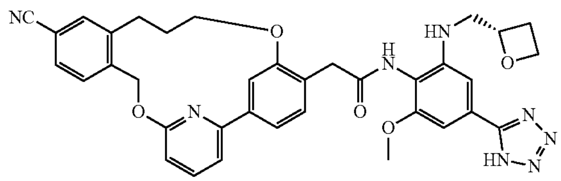 [SMILES: COc1cc(-c2nnn[nH]2)cc(NC[C@@H]2CCO2)c1NC(=O)Cc1ccc2cc1OCCCc1cc(C#N)ccc1COc1cccc-2n1]

Prepare the title compound essentially as described in Preparation 86 using 2-($5^4$-cyano-3,9-dioxa-2(2,6)-pyridina-1(1,3),5(1,2)-dibenzenacyclononaphane-$1^4$-yl)acetic acid and (S)-3-methoxy-N1-(oxetan-2-ylmethyl)-5-(1H-tetrazol-5-yl)benzene-1,2-diamine. Stir at RT for 67 h. Dilute the mixture with water and EtOAc and extract the aqueous layer with EtOAc. Dry the organic phase over magnesium sulfate, filter, and concentrate under reduced pressure. Purify the residue via silica gel flash chromatography using a gradient of 0 to 100% EtOAc in heptane followed by 0 to 10% MeOH in DCM. ES-MS m/z 659 (M+H).

Preparation 97

Methyl (S)-4-(2-($5^4$-cyano-$1^6$-fluoro-3,6,9-trioxa-2(2,6)-pyridina-1(1,3),5(1,2)-dibenzenacyclononaphane-$1^4$-yl)acetamido)-3-((oxetan-2-ylmethyl)amino)benzoate

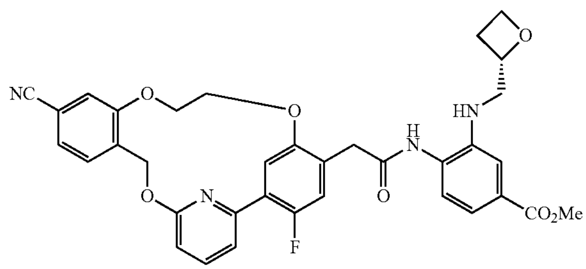 [SMILES: COC(=O)c1ccc(NC(=O)Cc2cc(F)c3cc2OCCOc2cc(C#N)ccc2COc2cccc-3n2)c(NC[C@@H]2CCO2)c1]

Prepare the title compound essentially as described in Preparation 86 using 2-($5^4$-cyano-$1^6$-fluoro-3,6,9-trioxa-2(2,6)-pyridina-1(1,3),5(1,2)-dibenzenacyclononaphane-$1^4$-yl)acetic acid and methyl 4-amino-3-[[(2S)-oxetan-2-yl]methylamino]benzoate (prepared essentially as described in WO 2020/263695), stirring the reaction at RT for 24 h. Dilute the crude reaction with water and extract three times with EtOAc. Dry the organic phase over magnesium sulfate, filter, and concentrate under reduced pressure to provide the title compound, which is used in crude form in Preparation 112. ES-MS m/z 639 (M+H).

Preparation 98

Methyl (S)-4-(2-($5^4$-cyano-$1^6$-fluoro-3,7-dioxa-2(2,6)-pyridina-1(1,3),5(1,2)-dibenzenacyclooctaphane-$1^4$-yl)acetamido)-3-((oxetan-2-ylmethyl)amino)benzoate

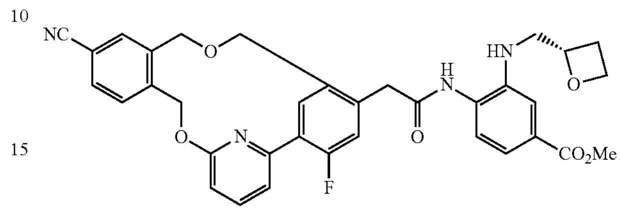

Prepare the title compound essentially as described in Preparation 86 using 2-($5^4$-cyano-$1^6$-fluoro-3,7-dioxa-2(2,6)-pyridina-1(1,3),5(1,2)-dibenzenacyclooctaphane-$1^4$-yl) acetic acid and methyl 4-amino-3-[[(2S)-oxetan-2-yl]methylamino]benzoate (prepared essentially as described in WO 2020/263695), stirring the reaction at RT for 2 h. Dilute reaction with water and EtOAc and extract the aqueous layer with EtOAc. Dry the organic phase over magnesium sulfate, filter, and concentrate under reduced pressure to give the title compound, which is used in crude form in Preparation 113. ES-MS m/z 623 (M+H).

Preparation 99

Methyl (S)-4-(2-($5^4$-cyano-$1^6$-methyl-3,9-dioxa-1,2(1,3),5(1,2)-tribenzenacyclononaphane-$1^4$-yl)acetamido)-3-methoxy-5-((oxetan-2-ylmethyl)amino)benzoate

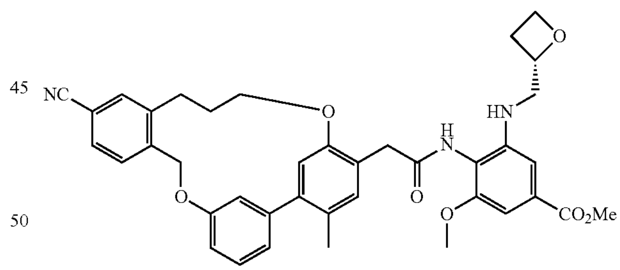

Prepare the title compound essentially as described in Preparation 85 using 2-($5^4$-cyano-$1^6$-methyl-3,9-dioxa-1,2(1,3),5(1,2)-tribenzenacyclononaphane-$1^4$-yl)acetic acid (Preparation 83) and methyl 4-amino-3-methoxy-5-[[(2S)-oxetan-2-yl]methylamino]benzoate (Preparation 17). Use the title compound without purification in Preparation 114. ES-MS m/z 662 (M+H).

Preparation 100

Methyl (S)-3-methoxy-4-(2-($1^6$-methyl-$5^4$-(trifluoromethyl)-3,9-dioxa-2(2,6)-pyridina-1(1,3),5(1,2)-dibenzenacyclononaphane-$1^4$-yl)acetamido)-5-((oxetan-2-ylmethyl)amino)benzoate

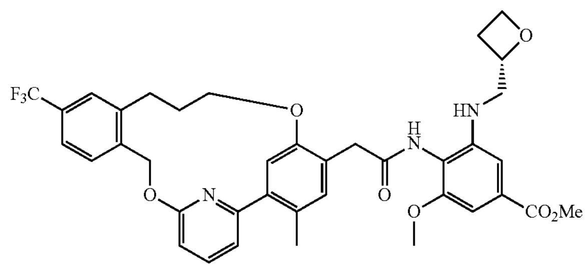 [SMILES: COC(=O)c1cc(NC[C@@H]2CCO2)c(NC(=O)Cc2cc(C)c3cc2OCCCc2cc(C(F)(F)F)ccc2COc2cccc-3n2)c(OC)c1]

Prepare the title compound essentially as described in Preparation 85 using 2-($1^6$-methyl-$5^4$-(trifluoromethyl)-3,9-dioxa-2(2,6)-pyridina-1(1,3),5(1,2)-dibenzenacyclononaphane-$1^4$-yl)acetic acid (Preparation 84) and methyl 4-amino-3-methoxy-5-[[(2S)-oxetan-2-yl]methylamino]benzoate (Preparation 17). Use the title compound as a crude product without purification in Preparation 115. ES-MS m/z 706 (M+H).

Preparation 101

Methyl (S)-2-(($5^4$-cyano-$1^6$-fluoro-3,9-dioxa-2(2,6)-pyridina-1(1,3),5(1,2)-dibenzenacyclononaphane-$1^4$-yl)methyl)-1-(oxetan-2-ylmethyl)-1H-benzo[d]imidazole-6-carboxylate

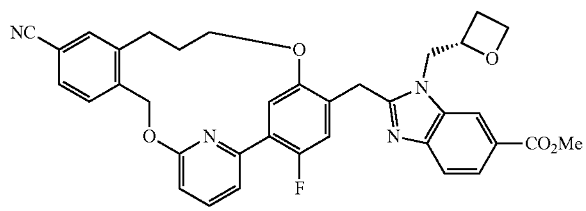 [SMILES: COC(=O)c1ccc2nc(Cc3cc(F)c4cc3OCCCc3cc(C#N)ccc3COc3cccc-4n3)n(C[C@@H]3CCO3)c2c1]

Stir a solution of methyl (S)-4-(2-($5^4$-cyano-$1^6$-fluoro-3,9-dioxa-2(2,6)-pyridina-1(1,3),5(1,2)-dibenzenacyclononaphane-$1^4$-yl)acetamido)-3-((oxetan-2-ylmethyl)amino)benzoate (220 mg, 0.295 mmol) in acetic acid (3.0 mL) at 80° C. for 2 h. Filter the reaction mixture and concentrate under reduced pressure to give 200 mg of the title compound (87%), which is used in crude form in Example 1. ES-MS m/z 619 (M+H).

Preparation 102

Methyl (S)-2-(($5^4$-cyano-$1^6$-fluoro-3,9-dioxa-2(2,6)-pyridina-1(1,3),5(1,2)-dibenzenacyclononaphane-$1^4$-yl)methyl)-4-fluoro-1-(oxetan-2-ylmethyl)-1H-benzo[d]imidazole-6-carboxylate

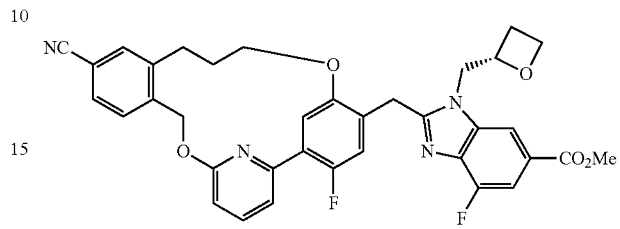

Stir methyl (S)-4-(2-($5^4$-cyano-$1^6$-fluoro-3,9-dioxa-2(2,6)-pyridina-1(1,3),5(1,2)-dibenzenacyclononaphane-$1^4$-yl)acetamido)-3-fluoro-5-((oxetan-2-ylmethyl)amino)benzoate (0.46 g, 0.56 mmol) in acetic acid (5.0 mL) at 55° C. for 15 h. Concentrate the reaction mixture and dissolve the residue in EtOAc (100 mL). Wash the organic phase with saturated aqueous sodium bicarbonate solution and brine. Dry the organic phase over sodium sulfate, filter, and concentrate under reduced pressure. Purify the residue via silica gel chromatography using a gradient of 5 to 60% EtOAc in hexanes to give 0.24 g of the title compound (67%). ES-MS m/z 637 (M+H).

Preparation 103

Methyl (S)-2-(($5^4$-cyano-$1^6$-methyl-3,9-dioxa-2(2,6)-pyridina-1(1,3),5(1,2)-dibenzenacyclononaphane-$1^4$-yl)methyl)-4-methoxy-1-(oxetan-2-ylmethyl)-1H-benzo[d]imidazole-6-carboxylate

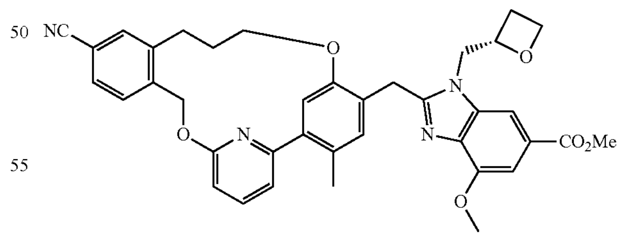

Prepare the title compound essentially as described in Preparation 102 using methyl (S)-4-(2-($5^4$-cyano-$1^6$-methyl-3,9-dioxa-2(2,6)-pyridina-1(1,3),5(1,2)-dibenzenacyclononaphane-$1^4$-yl)acetamido)-3-methoxy-5-((oxetan-2-ylmethyl)amino)benzoate (Preparation 93) and 1:1 DCM: acetic acid. Purify via silica gel flash chromatography using a gradient of 5 to 60% EtOAc in DCM. ES-MS m/z 645 (M+H).

Preparation 104

Methyl (S)-2-(($5^4$-chloro-3,9-dioxa-2(2,6)-pyridina-1(1,3),5(1,2)-dibenzenacyclononaphane-$1^4$-yl)methyl)-1-(oxetan-2-ylmethyl)-1H-benzo[d]imidazole-6-carboxylate

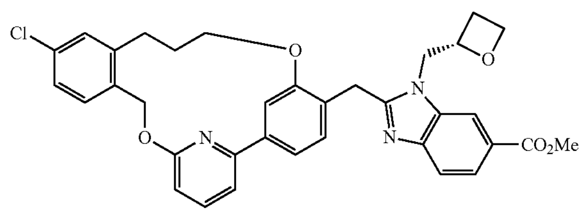 [SMILES: COC(=O)c1ccc2nc(Cc3ccc4cc3OCCCc3cc(Cl)ccc3COc3cccc-4n3)n(C[C@@H]3CCO3)c2c1]

Prepare the title compound essentially as described in Preparation 102 using methyl (S)-4-(2-($5^4$-chloro-3,9-dioxa-2(2,6)-pyridina-1(1,3),5(1,2)-dibenzenacyclononaphane-$1^4$-yl)acetamido)-3-((oxetan-2-ylmethyl)amino)benzoate, stirring the reaction mixture at 55° C. for 3.5 h and then 65° C. for 2 h. Concentrate the mixture under reduced pressure and azeotrope with ACN. Dissolve the residue in DCM, adsorb onto Celite®, and purify via silica gel chromatography eluting with a gradient of 0 to 100% EtOAc in hexanes. ES-MS m/z 610 (M+H).

Preparation 105

Methyl (S)-2-(($5^4$-cyano-3,9-dioxa-2(2,6)-pyridina-1(1,3),5(1,2)-dibenzenacyclononaphane-$1^4$-yl)methyl)-1-(oxetan-2-ylmethyl)-1H-benzo[d]imidazole-6-carboxylate

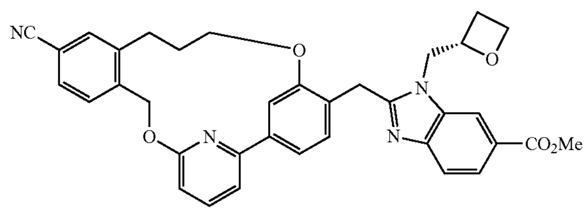 [SMILES: COC(=O)c1ccc2nc(Cc3ccc4cc3OCCCc3cc(C#N)ccc3COc3cccc-4n3)n(C[C@@H]3CCO3)c2c1]

Prepare the title compound essentially as described in Preparation 102 using methyl (S)-4-(2-($5^4$-cyano-3,9-dioxa-2(2,6)-pyridina-1(1,3),5(1,2)-dibenzenacyclononaphane-$1^4$-yl)acetamido)-3-((oxetan-2-ylmethyl)amino)benzoate (Preparation 88) in 1:1 dichloroethane:acetic acid. Purify the residue via silica gel chromatography using a gradient of 5 to 60% EtOAc in DCM to give the title compound. ES-MS m/z 601 (M+H).

Preparation 106

Methyl (S)-2-(($5^4$-cyano-3,9-dioxa-2(2,6)-pyridina-1(1,3),5(1,2)-dibenzenacyclononaphane-$1^4$-yl)methyl)-4-methoxy-1-(oxetan-2-ylmethyl)-1H-benzo[d]imidazole-6-carboxylate

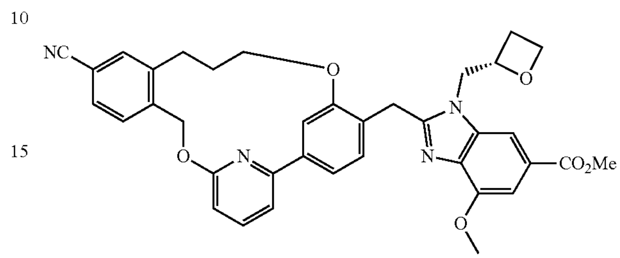

Prepare the title compound essentially as described in Preparation 102 using methyl (S)-4-(2-($5^4$-cyano-3,9-dioxa-2(2,6)-pyridina-1(1,3),5(1,2)-dibenzenacyclononaphane-$1^4$-yl)acetamido)-3-methoxy-5-((oxetan-2-ylmethyl)amino)benzoate in 1:1 dichloroethane:acetic acid. Purify the residue via silica gel chromatography using a gradient of 5 to 60% EtOAc in DCM to give the title compound. ES-MS m/z 631 (M+H).

Preparation 107

Methyl (S)-2-(($5^4$-cyano-3,9-dioxa-2(2,6)-pyridina-1(1,3),5(1,2)-dibenzenacyclononaphane-$1^4$-yl)methyl)-3-(oxetan-2-ylmethyl)-3H-imidazo[4,5-b]pyridine-5-carboxylate

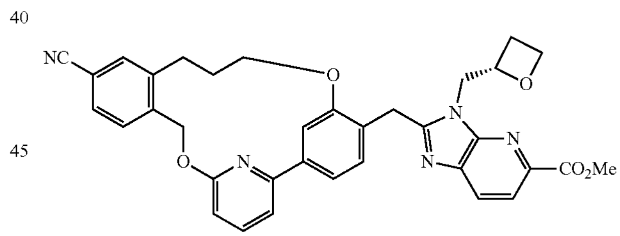

Prepare the title compound essentially as described in Preparation 102 using methyl (S)-5-(2-($5^4$-cyano-3,9-dioxa-2(2,6)-pyridina-1(1,3),5(1,2)-dibenzenacyclononaphane-$1^4$-yl)acetamido)-6-((oxetan-2-ylmethyl)amino)picolinate in 1:1 dichloroethane:acetic acid, increasing the reaction time to 48 h. Purify the residue via silica gel chromatography using a gradient of 5 to 60% EtOAc in DCM to give the title compound. ES-MS m/z 602 (M+H).

Preparation 108

Methyl (S)-2-(($5^4$-cyano-3,9-dioxa-2(2,6)-pyridina-1(1,3),5(1,2)-dibenzenacyclononaphane-$1^4$-yl)methyl)-4-fluoro-1-(oxetan-2-ylmethyl)-1H-benzo[d]imidazole-6-carboxylate

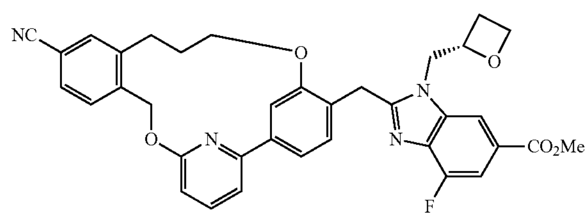 [SMILES: COC(=O)c1cc(F)c2nc(Cc3ccc4cc3OCCCc3cc(C#N)ccc3COc3cccc-4n3)n(C[C@@H]3CCO3)c2c1]

Prepare the title compound essentially as described in Preparation 102 using methyl (S)-4-(2-($5^4$-cyano-3,9-dioxa-2(2,6)-pyridina-1(1,3),5(1,2)-dibenzenacyclononaphane-$1^4$-yl)acetamido)-3-fluoro-5-((oxetan-2-ylmethyl)amino)benzoate (0.38 g, 0.48 mmol) in 1:1 dichloroethane and acetic acid. Purify the residue via silica gel chromatography using a gradient of 5 to 60% EtOAc in DCM to give 0.24 g of the title compound (67%). ES-MS m/z 619 (M+H).

Preparation 109

Methyl (S)-2-(($5^4$-cyano-$1^6$-fluoro-9-oxa-3-aza-2(2,6)-pyridina-1(1,3),5(1,2)-dibenzenacyclononaphane-$1^4$-yl)methyl)-1-(oxetan-2-ylmethyl)-1H-benzo[d]imidazole-6-carboxylate

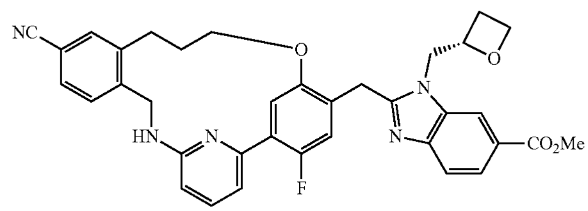 [SMILES: COC(=O)c1ccc2nc(Cc3cc(F)c4cc3OCCCc3cc(C#N)ccc3CNc3cccc-4n3)n(C[C@@H]3CCO3)c2c1]

Heat a solution of methyl (S)-4-(2-($5^4$-cyano-$1^6$-fluoro-9-oxa-3-aza-2(2,6)-pyridina-1(1,3),5(1,2)-dibenzenacyclononaphane-$1^4$-yl)acetamido)-3-((oxetan-2-ylmethyl)amino)benzoate (160 mg, 0.20 mmol) in 1,2-dichloroethane (1.5 mL) and acetic acid (1.25 mL) at 50° C. for 6 h. Cool reaction mixture to RT, concentrate solvents under reduce pressure, and purify the residue via silica gel chromatography using a gradient of 10 to 50% EtOAc in DCM to provide 70 mg (53%) of the title compound as a white solid. ES-MS m/z 618 (M+H).

Preparation 110

Methyl (S)-2-(($5^4$-cyano-$1^6$-fluoro-3,9-dioxa-2(2,6)-pyridina-1,5(1,3)-dibenzenacyclononaphane-$1^4$-yl)methyl)-1-(oxetan-2-ylmethyl)-1H-benzo[d]imidazole-6-carboxylate

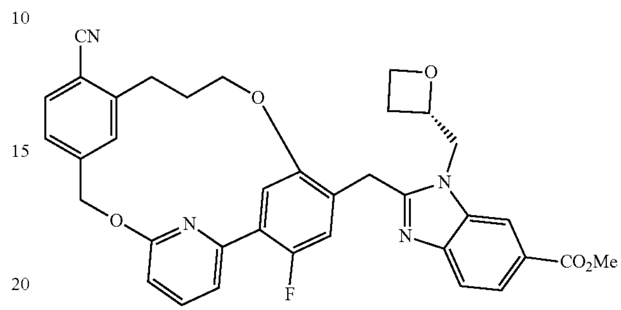

Prepare the title compound essentially as described in Preparation 109 using methyl (S)-4-(2-($5^4$-cyano-$1^6$-fluoro-3,9-dioxa-2(2,6)-pyridina-1,5(1,3)-dibenzenacyclononaphane-$1^4$-yl)acetamido)-3-((oxetan-2-ylmethyl)amino)benzoate, stirring the reaction mixture at 60° C. for 5.5 h. Cool the mixture to RT and concentrate under reduced pressure. Purify the residue via silica gel chromatography using a gradient of 10 to 30% EtOAc in DCM. ES-MS m/z 619 (M+H).

Preparation 111

Methyl 2-(($5^4$-cyano-3,9-dioxa-2(2,6)-pyridina-1(1,3),5(1,2)-dibenzenacyclononaphane-$1^4$-yl)methyl)-1-((1-ethyl-1H-imidazol-5-yl)methyl)-1H-benzo[d]imidazole-6-carboxylate

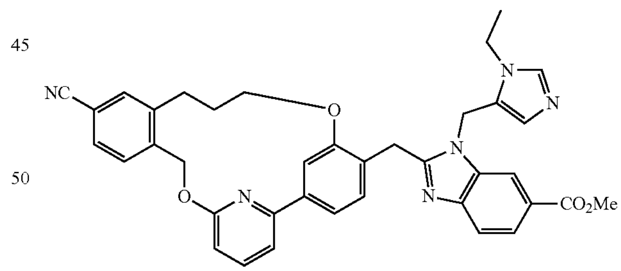

Prepare the title compound essentially as described in Preparation 101 using methyl 4-(2-($5^4$-cyano-3,9-dioxa-2(2,6)-pyridina-1(1,3),5(1,2)-dibenzenacyclononaphane-$1^4$-yl)acetamido)-3-(((1-ethyl-1H-imidazol-5-yl)methyl)amino)benzoate (Preparation 95), stirring the reaction at 65° C. for 5 h then 80° C. for 17 h. Concentrate the solution and azeotrope with ACN. Purify the residue via silica gel chromatography using a gradient of 0 to 100% EtOAc in heptane then a gradient of 0 to 10% MeOH in DCM. ES-MS m/z 639 (M+H).

Preparation 112

Methyl (S)-2-(($5^4$-cyano-$1^6$-fluoro-3,6,9-trioxa-2(2,6)-pyridina-1(1,3),5(1,2)-dibenzenacyclononaphane-$1^4$-yl)methyl)-1-(oxetan-2-ylmethyl)-1H-benzo[d]imidazole-6-carboxylate

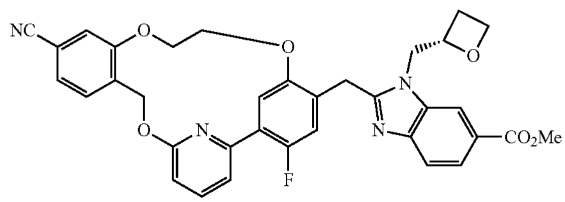 [SMILES: COC(=O)c1ccc2nc(Cc3cc(F)c4cc3OCCOc3cc(C#N)ccc3COc3cccc-4n3)n(C[C@@H]3CCO3)c2c1]

Prepare the title compound essentially as described in Preparation 101 using methyl (S)-4-(2-($5^4$-cyano-$1^6$-fluoro-3,6,9-trioxa-2(2,6)-pyridina-1(1,3),5(1,2)-dibenzenacyclononaphane-$1^4$-yl)acetamido)-3-((oxetan-2-ylmethyl)amino)benzoate, stirring the reaction at 65° C. for 3 h. Concentrate the reaction and azeotrope with ACN. Purify the residue via silica gel flash chromatography using a gradient of 0 to 100% EtOAc in heptane then a gradient of 0 to 2% MeOH in DCM to give the title compound. ES-MS m/z 621 (M+H).

Preparation 113

Methyl (S)-2-(($5^4$-cyano-$1^6$-fluoro-3,7-dioxa-2(2,6)-pyridina-1(1,3),5(1,2)-dibenzenacyclooctaphane-$1^4$-yl)methyl)-1-(oxetan-2-ylmethyl)-1H-benzo[d]imidazole-6-carboxylate

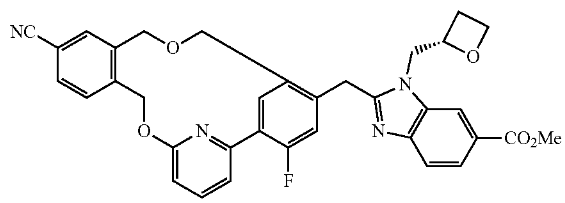 [SMILES: COC(=O)c1ccc2nc(Cc3cc(F)c4cc3COCc3cc(C#N)ccc3COc3cccc-4n3)n(C[C@@H]3CCO3)c2c1]

Prepare the title compound essentially as described in Preparation 101 using methyl (S)-4-(2-($5^4$-cyano-$1^6$-fluoro-3,7-dioxa-2(2,6)-pyridina-1(1,3),5(1,2)-dibenzenacyclooctaphane-$1^4$-yl)acetamido)-3-((oxetan-2-ylmethyl)amino)benzoate, stirring the reaction at 65° C. for 1.5 h. Concentrate the solution and azeotrope with ACN, then purify the residue via silica gel flash chromatography using a gradient of 0 to 60% EtOAc in heptane to give the title compound. ES-MS m/z 605 (M+H).

Preparation 114

Methyl (S)-2-(($5^4$-cyano-$1^6$-methyl-3,9-dioxa-1,2(1,3),5(1,2)-tribenzenacyclononaphane-$1^4$-yl)methyl)-4-methoxy-1-(oxetan-2-ylmethyl)-1H-benzo[d]imidazole-6-carboxylate

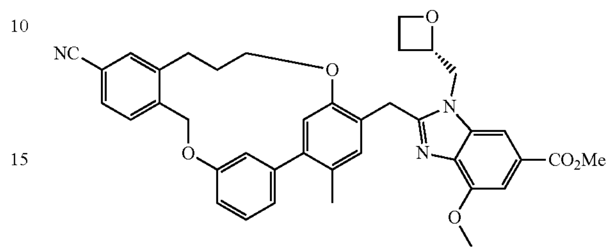

Prepare the title compound essentially as described in Preparation 102 using methyl (S)-4-(2-($5^4$-cyano-$1^6$-methyl-3,9-dioxa-1,2(1,3),5(1,2)-tribenzenacyclononaphane-$1^4$-yl)acetamido)-3-methoxy-5-((oxetan-2-ylmethyl)amino)benzoate (Preparation 99) in 1:1 dichloroethane:acetic acid. ES-MS m/z 645 (M+H).

Preparation 115

Methyl (S)-4-methoxy-2-(($1^6$-methyl-$5^4$-(trifluoromethyl)-3,9-dioxa-2(2,6)-pyridina-1(1,3),5(1,2)-dibenzenacyclononaphane-$1^4$-yl)methyl)-1-(oxetan-2-ylmethyl)-1H-benzo[d]imidazole-6-carboxylate

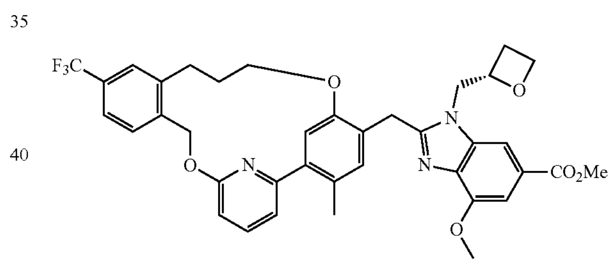

Prepare the title compound essentially as described in Preparation 102 using methyl (S)-3-methoxy-4-(2-($1^6$-methyl-$5^4$-(trifluoromethyl)-3,9-dioxa-2(2,6)-pyridina-1(1,3),5(1,2)-dibenzenacyclononaphane-$1^4$-yl)acetamido)-5-((oxetan-2-ylmethyl)amino)benzoate (Preparation 100) in 1:1 dichloroethane:acetic acid. Purify the title compound via silica gel chromatography using a gradient of 80 to 100% DCM in hexane. ES-MS m/z 688 (M+H).

Preparation 116

Methyl 2-(4-bromo-2-methylphenyl)acetate

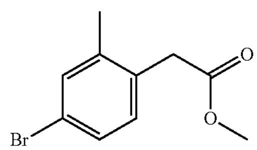

Add thionyl chloride (2.5 mL, 34.3 mmol) dropwise over 15 min to a 4° C. solution of 2-(4-bromo-2-methylphenyl) acetic acid (5 g, 20.74 mmol) in MeOH (42 mL). Stir the reaction for 3 h then evaporate solvents under reduced pressure. To the residue add water (50 mL) and saturated aqueous $NaHCO_3$ to bring the solution to pH=7-8, then extract with EtOAc (3×30 mL). Combine the organics, wash with water and saturated aqueous NaCl, dry over $MgSO_4$, then filter and concentrate under reduced pressure to give the title compound as an orange oil (5.06 g, 100%). The title compound does not ionize by LCMS and is used in Preparation 117 without further characterization.

Preparation 117

Methyl-4-bromo-2-(bromomethyl)phenyl acetate

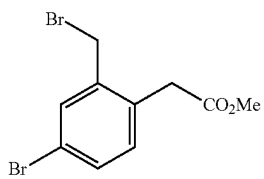 [SMILES: COC(=O)Cc1ccc(Br)cc1CBr]

Transfer a solution of methyl 2-(4-bromo-2-methylphenyl)acetate (4.03 g, 15.7 mmol) and N-bromosuccinimide (2.66 g, 14.9 mmol) in ACN (85 mL) through a photochemical flow reactor equipped with 4×370 nm lamps and 4×440 nm lamps, (reactor size=52 mL, residence time=1.3 mL/min, 40° C.). Collect the solution over 2 h, evaporate the solvent, then add water (20 mL) and MTBE (20 mL) to the residue. Separate the layers and extract aqueous phase with MTBE (2×20 mL). Combine the organics, wash with 20% aqueous $NaHSO_3$ solution, water, and saturated aqueous NaCl, dry over $MgSO_4$, filter and concentrate under reduced pressure. Purify the residue via silica gel chromatography using a gradient of 10 to 40% DCM in cyclohexanes to give the title compound as a white waxy solid (5.1 g, 85% purity, 75% yield). ES-MS m/z 338/340/342 ($M+NH_4^+$).

Preparation 118

Methyl 3-fluoro-5-methoxy-4-nitro-benzoate

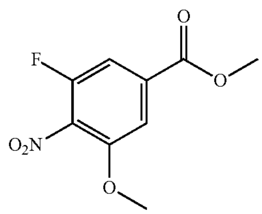 [SMILES: COC(=O)c1cc(F)c([N+](=O)[O-])c(OC)c1]

To a solution of methyl 3,5-difluoro-4-nitro-benzoate (0.3 g, 1.38 mmol) in MeOH (4 mL) add a solution of sodium methylate (25% by mass in MeOH, 0.33 mL, 1.44 mmol), and heat the reaction at 65° C. for 2.5 h. Cool the reaction mixture to RT, then add water and extract with EtOAc (3×5 mL). Combine the organics, wash with saturated aqueous NaCl, dry over $MgSO_4$, then filter and concentrate in vacuo. Purify the residue via silica gel chromatography using a gradient of EtOAc in heptane (0 to 10%) to give 245 mg (76%) of the title compound as a yellow oil. ES-MS m/z 230 (M+H).

Preparation 119

Ethyl 3-fluoro-5-methoxy-4-nitro-benzoate

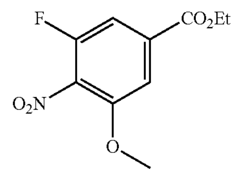 [SMILES: CCOC(=O)c1cc(F)c([N+](=O)[O-])c(OC)c1]

Add sulfuric acid (2 mL, 3.1 g, 31 mmol) to a solution of 3-fluoro-5-methoxy-4-nitro-benzoic acid (0.67 g, 3.1 mmol) in EtOH (10 mL) and heat the mixture to 80° C. for 1 h. Quench the reaction mixture with saturated aqueous $NaHCO_3$ and extract with DCM. Dry the organic layer over MgSO4, filter, and concentrate to give the title compound (0.73 g, 96%) which is used without further purification in Preparation 121. ES-MS m/z 244 (M+H).

Preparation 120

Methyl 3-fluoro-5-(2-methoxyethoxy)-4-nitro-benzoate

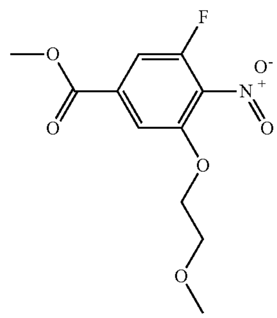

Suspend sodium hydride (92 mg, 2.30 mmol) in THF (10 ml), then add 2-methoxyethanol (0.18 mL, 2.31 mmol) and stir at RT for 30 min. Next, add methyl 3,5-difluoro-4-nitro-benzoate (0.5 g, 2.30 mmol) and stir the mixture at 60° C. for 16 h. Dilute the reaction with water (100 mL) and extract with EtOAc (3×50 mL). Dry the organics over $Na_2SO_4$, filter, and concentrate. Purify by silica gel chromatography using a gradient of 0 to 20% EtOAc in heptane to give the title compound (225 mg, 40%) as a yellow oil. ES-MS m/z 274 (M+H).

Preparation 121

Ethyl 3-methoxy-4-nitro-5-(oxazol-2-ylmethyl-amino)benzoate

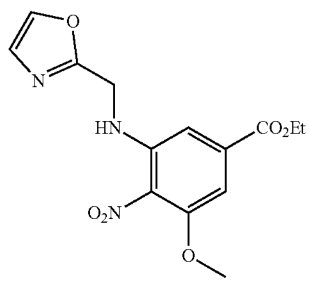

Prepare the title compound essentially as described in Preparation 14 using ethyl 3-fluoro-5-methoxy-4-nitro-benzoate (0.30 g, 1.0 mmol) and 1-(1,3-oxazol-2-yl)methanamine hydrochloride (0.20 g, 1.0 mmol). Purify the title compound via silica gel chromatography using a gradient of 0 to 50% EtOAc in heptane. ES-MS m/z 322 (M+H).

Preparation 122

Ethyl-4-amino-3-methoxy-5-(oxazol-2-ylmethyl-amino)benzoate

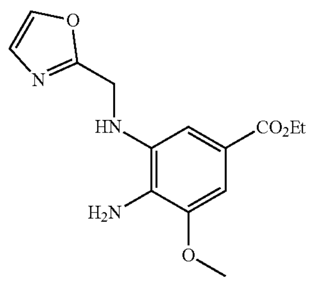 [SMILES: CCOC(=O)c1cc(NCc2ncco2)c(N)c(OC)c1]

Suspend iron powder (0.33 g, 5.8 mmol) and $NH_4Cl$ (0.015 g, 0.28 mmol) in water (4.4 mL) and add acetic acid (0.07 mL, 1.18 mmol). Stir at 50° C. for 15 min then add a solution of ethyl 3-methoxy-4-nitro-5-(oxazol-2-ylmethyl-amino)benzoate (0.165 g, 0.514 mmol) in DMF (1.45 mL). Stir the mixture at 50° C. for 20 min, cool to RT, filter the mixture through Celite® and rinse with EtOAc (100 mL). Wash the organics with saturated $NaHCO_3$ solution (100 mL) and dry over $MgSO_4$. Filter and concentrate to afford the title compound (0.11 g, 74%) as a yellow oil, which is used without purification in Preparation 169. ES-MS m/z 292 (M+H).

Preparation 123

Methyl 3-(2-methoxyethoxy)-4-nitro-5-[[(2S)-oxetan-2-yl]-methylamino]benzoate

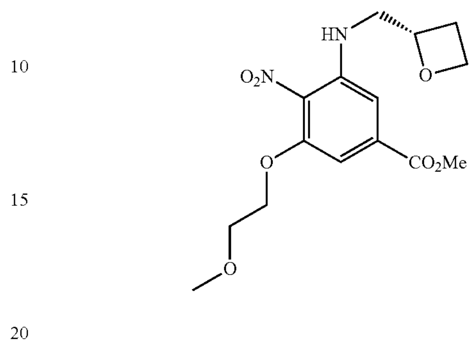

Prepare the title compound essentially as described in Preparation 14 using methyl 3-fluoro-5-(2-methoxyethoxy)-4-nitro-benzoate and [(2S)-oxetan-2-yl]methanamine. Purify the title compound via silica gel chromatography using a gradient of 0 to 30% EtOAc in heptane. ES-MS m/z 341 (M+H).

Preparation 124

Methyl 4-amino-3-(2-methoxyethoxy)-5-[[(2S)-oxetan-2-yl]methylamino]benzoate

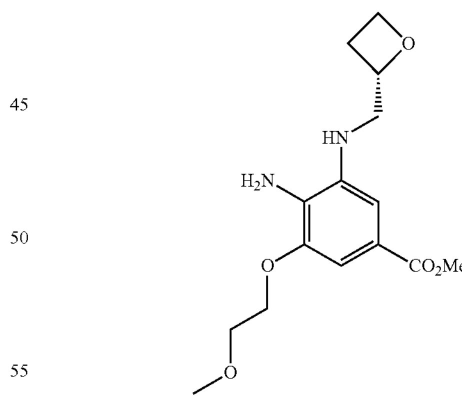

Prepare the title compound essentially as described in Preparation 122 using methyl 3-(2-methoxyethoxy)-4-nitro-5-(oxetan-2-yl-methylamino)benzoate. The product is used without further purification in Preparation 170. ES-MS m/z 311 (M+H).

Preparation 125

4-[(6-Bromo-2-pyridyl)oxymethyl]-3-[(E)-2-ethoxyvinyl]benzonitrile

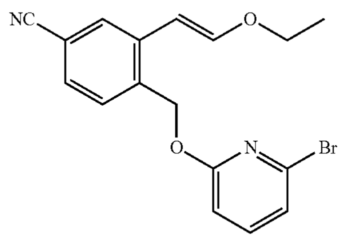 [SMILES: CCO/C=C/c1cc(C#N)ccc1COc1cccc(Br)n1]

To a solution of 4-[(6-bromo-2-pyridyl)oxymethyl]-3-iodo-benzonitrile (6 g, 14.45 mmol) in 1,4 dioxane (100 mL) under nitrogen bubbling, add $Cs_2CO_3$ (9.5 g, 29 mmol), tetrakis(triphenylphosphine)palladium(0) (835 mg, 0.72 mmol) and (E)-1-ethoxyethene-2-boronic acid pinacol ester (4.2 mL, 18.8 mmol). Heat reaction mixture under nitrogen at 90° C. for 1 day, then add more tetrakis(triphenylphosphine)palladium(0) (835 mg, 0.72 mmol) and (E)-1-ethoxyethene-2-boronic acid pinacol ester (1 mL, 4.48 mmol). Continue heating the mixture at 90° C. for 2 days. Cool the mixture, add water (100 mL) and extract with EtOAc (3×60 mL). Combine organics, dry over $MgSO_4$, filter, and concentrate under reduce pressure. Purify the residue via silica gel chromatography using a gradient of 0 to 10% EtOAc in cyclohexanes to give 3.6 g (60% yield) of the title compound as a pale yellow solid. ES-MS m/z 359/361 (M+H).

Preparation 126

4-[(6-Bromo-2-pyridyl)oxymethyl]-3-(2-oxoethyl)benzonitrile

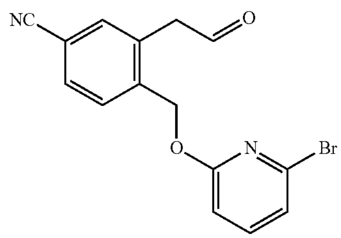 [SMILES: N#Cc1ccc(COc2cccc(Br)n2)c(CC=O)c1]

To a solution of 4-[(6-bromo-2-pyridyl)oxymethyl]-3-[(E)-2-ethoxyvinyl]benzonitrile (3.6 g, 8.5 mmol) in THF (54 mL) add 4M HCl in 1,4-dioxane (21 mL, 85 mmol). Stir the mixture for 20 h at RT. Concentrate the mixture, add water (50 mL) and 2M aqueous sodium carbonate until pH=8, and then extract with EtOAc (3×40 mL). Combine the organics, dry over $MgSO_4$, filter, and concentrate under reduce pressure to afford the title compound as a pale orange solid (3.9 g, 97%). ES-MS m/z 331/333 (M+H).

Preparation 127

4-[(6-Bromo-2-pyridyl)oxymethyl]-3-(2-hydroxyethyl)benzonitrile

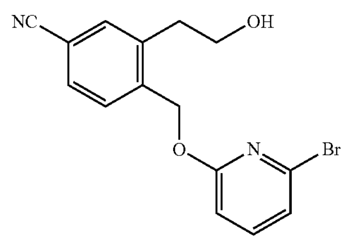 [SMILES: N#Cc1ccc(COc2cccc(Br)n2)c(CCO)c1]

To a solution of 4-[(6-bromo-2-pyridyl)oxymethyl]-3-(2-oxoethyl)benzonitrile (3.9 g, 8.24 mmol) in MeOH (60 mL), add sodium borohydride (550 mg, 14.53 mmoL) in batches. Stir the mixture for 1 h at RT, evaporate solvent, add DCM (30 mL) and 1M NaOH solution (10 mL) and stir for 10 min. Separate the phases and extract the aqueous phase with more DCM (2×5 mL). Combine the organics, wash with water and saturated aqueous NaCl, dry over $MgSO_4$, filter and concentrate under reduced pressure. Purify the residue via silica gel chromatography using a gradient of 10 to 40% EtOAc in cyclohexanes to give the title compound as a white waxy solid (1.71 g, 60%). ES-MS m/z 333/335 (M+H).

Preparation 128

2-bromo-4-(hydroxymethyl)benzonitrile

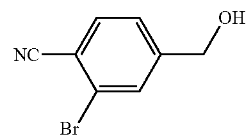 [SMILES: N#Cc1ccc(CO)cc1Br]

Add lithium borohydride in THE (7.7 mL, 15.4 mmol, 2.0 mol/L) to a solution of ethyl 3-bromo-4-cyanobenzoate (2 g, 7.71 mmol) in anhydrous THE (20 mL) at 0° C. under nitrogen atmosphere. Allow mixture to reach RT and stir overnight. Remove most of THE and add citric acid (5% aqueous) carefully at 0° C. Extract the aqueous layer with EtOAc, combine the organic layers, wash with water and saturated aqueous NaCl, dry over anhydrous $Na_2SO_4$, filter and concentrate under reduced pressure. Purify the residue via silica gel chromatography using a gradient of 30 to 100% EtOAc in cyclohexanes to provide the title compound (1.56 g, 92% purity, 88%) as a white solid. $^1H$ NMR (400 MHz, DMSO) δ 7.91 (d, J=7.9 Hz, 1H), 7.80 (s, 1H), 7.51 (d, J=7.5 Hz, 1H), 5.57 (t, J=5.8 Hz, 1H), 4.59 (d, J=5.9 Hz, 2H).

Preparation 129

2-Bromo-4-[(6-chloro-2-pyridyl)oxymethyl]benzonitrile

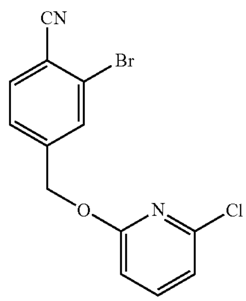 [SMILES: N#Cc1ccc(COc2cccc(Cl)n2)cc1Br]

Prepare the title compound essentially as described in Preparation 30 using 2-bromo-4-(hydroxymethyl)benzonitrile and 6-chloropyridin-2-ol. Purify the title compound via silica gel chromatography using a gradient of 10 to 30% EtOAc in cyclohexanes. ES-MS m/z 323, 325, 327 (M+H).

Preparation 130

4-[(6-Chloro-2-pyridyl)oxymethyl]-2-(2-hydroxyethyl)benzonitrile

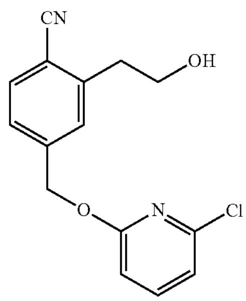 [SMILES: N#Cc1ccc(COc2cccc(Cl)n2)cc1CCO]

Charge a vial with nickel(II) chloride ethylene glycol dimethyl ether complex (34 mg, 0.15 mmol) and 4,4'-di-tert-butyl-2,2'-bipyridine (48 mg, 0.17 mmol). Purge the vial with nitrogen and add anhydrous 1,2-dimethoxyethane (3 mL). Stir mixture for 15 min.

Charge another vial with $Na_2CO_3$ (335 mg, 3.13 mmol), 2-bromo-4-[(6-chloro-2-pyridyl)oxymethyl]benzonitrile (502 mg, 1.55 mmol) and $(Ir[dF(CF_3)ppy]_2(dtbpy))PF_6$ (18 mg, 0.016 mmol). Purge the vial with nitrogen and add anhydrous 1,2-dimethoxyethane (12 mL), 2-bromoethanol (1.1 mL, 15 mmol), tris(trimethylsilyl)silane (740 µL, 2.33 mmol) and the previously prepared Ni catalyst. Bubble the mixture with nitrogen for 5 min and irradiate it in EvoluChem™ photoredox box with Kessil LED light 456 nm with fan overnight. Filter off the solid, wash it with DCM and concentrate the filtrate. Purify the residue via silica gel chromatography using a gradient of 0 to 10% of EtOAc in DCM as eluent system to provide the title compound (190 mg, 42%) as a yellow waxy solid. ES-MS m/z 289, 291 (M+H).

Preparation 131

2-Bromo-6-[(4-fluoro-2-iodo-phenyl)methoxy]pyridine

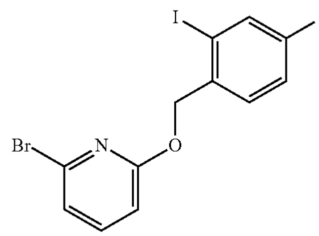

To a mixture of (4-fluoro-2-iodo-phenyl)methanol (2.0 g, 7.9 mmol), 2-bromo-6-fluoro-pyridine (1.4 g, 7.9 mmol), and 1,4-dioxane (25 mL) add potassium tert-butoxide (1.20 g, 10.0 mmol). Stir the reaction mixture at 60° C. for 16 h. Dilute the reaction with EtOAc (100 mL) and filter through Celite®. Wash the filtrate with water (2×50 mL) and saturated aqueous sodium chloride (50 mL). Dry the organic phase over $Na_2SO_4$, filter, and concentrate under reduced pressure. Purify the residue via silica gel flash chromatography eluting with a gradient of 5 to 50% DCM in hexanes to give 2.16 g of the title compound (67%). ES-MS m/z 408 and 410 (M+H).

Preparation 132

3-[2-[(6-Bromo-2-pyridyl)oxymethyl]-5-fluoro-phenyl]propoxy-tert-butyl-dimethyl-silane

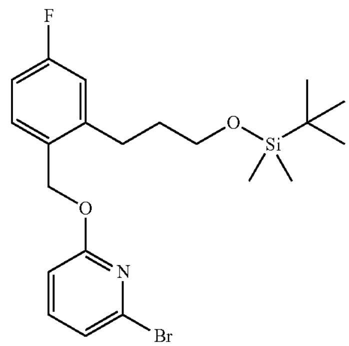 [SMILES: CC(C)(C)[Si](C)(C)OCCCc1cc(F)ccc1COc1cccc(Br)n1]

Prepare the title compound essentially as described in Preparation 28 using 2-bromo-6-[(4-fluoro-2-iodo-phenyl)methoxy]pyridine. Purify the title compound via silica gel flash chromatography eluting with a gradient of 0 to 10% EtOAc in hexanes to give an oil that does not ionize by ES-MS, which is used directly in Preparation 133 without further identification.

Preparation 133

3-[2-[(6-Bromo-2-pyridyl)oxymethyl]-5-fluoro-phenyl]propan-1-ol

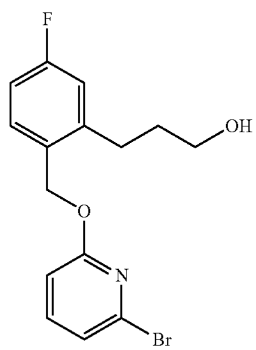 [SMILES: OCCCc1cc(F)ccc1COc1cccc(Br)n1]

Prepare the title compound essentially as described in Preparation 29 using 3-[2-[(6-bromo-2-pyridyl)oxymethyl]-5-fluoro-phenyl]propoxy-tert-butyl-dimethyl-silane (Preparation 132). ES-MS m/z 340 and 342 (M+H).

Preparation 134

Methyl 2-[3-[tert-butyl(dimethyl)silyl]oxypropyl]-6-(trifluoromethyl)pyridine-3-carboxylate

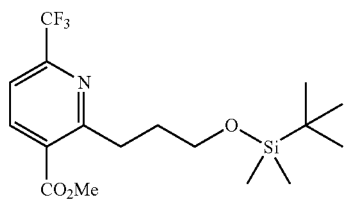 [SMILES: COC(=O)c1ccc(C(F)(F)F)nc1CCCO[Si](C)(C)C(C)(C)C]

Prepare the title compound essentially as described in Preparation 28 using methyl 2-bromo-6-(trifluoromethyl) pyridine-3-carboxylate. Purify the title compound via silica gel chromatography using a gradient of 0 to 10% EtOAc in DCM. ES-MS m/z 378 (M+H).

Preparation 135

[2-[3-[tert-Butyl(dimethyl)silyl]oxypropyl]-6-(trifluoromethyl)-3-pyridyl]methanol

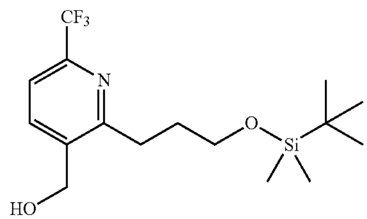 [SMILES: CC(C)(C)[Si](C)(C)OCCCc1nc(C(F)(F)F)ccc1CO]

Cool a mixture of methyl 2-[3-[tert-butyl(dimethyl)silyl] oxypropyl]-6-(trifluoromethyl) pyridine-3-carboxylate (2.0 g, 5.3 mmol) add THF (40 mL) to −10° C. in an ice/salt bath. To this mixture add lithium aluminum hydride (0.20 g, 5.3 mmol) and stir with cooling for 1 h. Quench the reaction by dropwise addition of water (1 mL) then dilute with EtOAc (50 mL). Filter the resulting mixture through Celite® and rinse with EtOAc (100 mL). Wash the filtrate with water (100 mL) and saturated aqueous NaCl (100 mL) then dry over $Na_2SO_4$. Filter and concentrate to give the title compound (1.66 g, 84%) as a tan oil, which is used in Preparation 136 without further purification. ES-MS m/z 350 (M+H).

Preparation 136

3-[3-[(6-Bromo-2-pyridyl)oxymethyl]-6-(trifluoromethyl)-2-pyridyl]propoxy-tert-butyl-dimethyl-silane

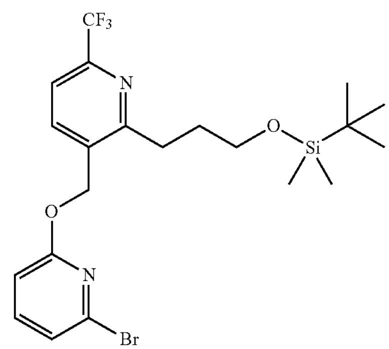 [SMILES: CC(C)(C)[Si](C)(C)OCCCc1nc(C(F)(F)F)ccc1COc1cccc(Br)n1]

Prepare the title compound essentially as described in Preparation 51 using [2-[3-[tert-butyl(dimethyl)silyl]oxypropyl]-6-(trifluoromethyl)-3-pyridyl]methanol and 2-bromo-6-fluoro-pyridine, stirring the reaction at 60° C. for 16 h. Purify the title compound via silica gel flash chromatography eluting with a gradient of 5 to 50% DCM in hexanes. ES-MS m/z 506 and 508 (M+H).

Preparation 137

3-[3-[(6-Bromo-2-pyridyl)oxymethyl]-6-(trifluoromethyl)-2-pyridyl]propan-1-ol

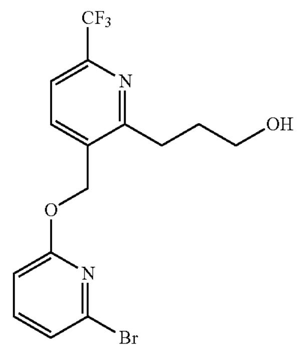 [SMILES: OCCCc1nc(C(F)(F)F)ccc1COc1cccc(Br)n1]

Prepare the title compound essentially as described in Preparation 29 using 3-[3-[(6-bromo-2-pyridyl)oxymethyl]-6-(trifluoromethyl)-2-pyridyl]propoxy-tert-butyl-dimethyl-silane. Purify the title compound via silica gel flash chromatography eluting with a gradient of 5 to 50% EtOAc in hexanes. ES-MS m/z 390 and 392 (M+H).

Preparation 138

(3-Iodo-4-pyridyl)methanol

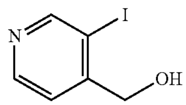

Cool a mixture of methyl 3-iodopyridine-4-carboxylate (5.0 g, 19 mmol) in THE (40 mL) and MeOH (10 mL) to −10° C. using an ice/salt bath, then add sodium borohydride (1.52 g, 40.2 mmol) and stir with cooling for 1 h. Quench the reaction by dropwise addition of water (1 mL) then dilute with EtOAc (50 mL). Filter the resulting mixture through Celite® and rinse w/EtOAc (100 mL). Wash the filtrate with water (100 mL) and saturated aqueous NaCl (100 mL) then dry over $Na_2SO_4$. Purify the residue via silica gel chromatography using a gradient of 5 to 50% (1:4 MeOH:EtOAc) in DCM to give the title compound (1.63 g, 36%) as a tan solid. ES-MS m/z 236 (M+H).

Preparation 139

2-Bromo-6-[(3-iodo-4-pyridyl)methoxy]pyridine

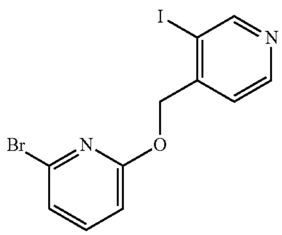 [SMILES: Brc1cccc(OCc2ccncc2I)n1]

Prepare the title compound essentially as described in Preparation 51 using (3-iodo-4-pyridyl)methanol and 2-bromo-6-fluoro-pyridine, stirring the reaction at 60° C. for 16 h. Purify the title compound via silica gel chromatography using a gradient of 5 to 50% EtOAc in DCM. ES-MS m/z 390 and 392 (M+H).

Preparation 140

3-[4-[(6-Bromo-2-pyridyl)oxymethyl]-3-pyridyl]propoxy-tert-butyl-dimethyl-silane

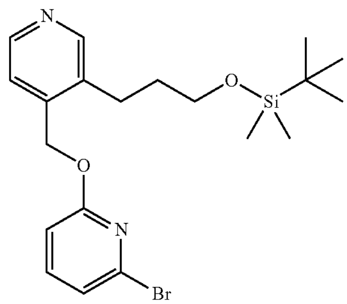 [SMILES: CC(C)(C)[Si](C)(C)OCCCc1cnccc1COc1cccc(Br)n1]

Prepare the title compound essentially as described in Preparation 28 using 2-bromo-6-[(3-iodo-4-pyridyl)methoxy]pyridine. Purify the title compound via silica gel chromatography using a gradient of 0 to 80% EtOAc in hexanes, and use it in Preparation 141 without further characterization.

Preparation 141

3-[4-[(6-Bromo-2-pyridyl)oxymethyl]-3-pyridyl]propan-1-ol

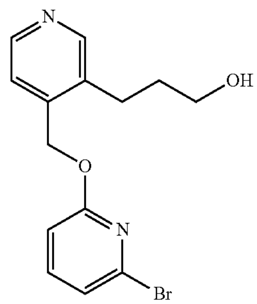 [SMILES: OCCCc1cnccc1COc1cccc(Br)n1]

Prepare the title compound essentially as described in Preparation 29 using 3-[4-[(6-bromo-2-pyridyl)oxymethyl]-3-pyridyl]propoxy-tert-butyl-dimethyl-silane (Preparation 140). Purify the title compound via silica gel chromatography eluting with a gradient of 5 to 75% (1:4 MeOH:EtOAc) in DCM. ES-MS m/z 322 and 324 (M+H).

Preparation 142

Methyl 2-[4-bromo-2-[2-[2-[(6-bromo-2-pyridyl)oxymethyl]-5-cyano-phenyl]ethoxymethyl]phenyl]acetate

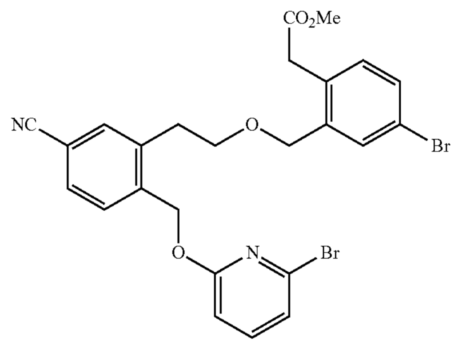 [SMILES: COC(=O)Cc1ccc(Br)cc1COCCc1cc(C#N)ccc1COc1cccc(Br)n1]

To a solution of 4-[(6-bromo-2-pyridyl)oxymethyl]-3-(2-hydroxyethyl)benzonitrile (1 g, 2.85 mmol) and methyl-4-bromo-2-(bromomethyl)phenyl acetate (1.65 g, 4.10 mmol) in DCM (15 mL) at 4° C. add 2,6-di-tert-butylpyridine (0.93 mL, 4.24 mmol) and silver trifluoromethanesulfonate (1.10 g, 4.24 mmol). Stir the mixture for 1 h at low temperature, then at RT. After 5 h, add more silver trifluoromethanesulfonate (220 mg, 0.85 mmol). After 20 h, filter the reaction mixture through Celite®, rinsing with DCM. Evaporate the filtrate liquids and purify by silica gel chromatography using a gradient of 10 to 100% DCM/cyclohexanes to give the title compound as a white solid (570 mg, 75% purity, 26% yield). ES-MS m/z 573/575/577 (M+H).

Preparation 143

Methyl 2-[2-[2-[2-[(6-bromo-2-pyridyl)oxymethyl]-5-cyano-phenyl]ethoxymethyl]-4-(4,4,5,5-tetramethyl-1,3,2-dioxaborolan-2-yl)phenyl]acetate

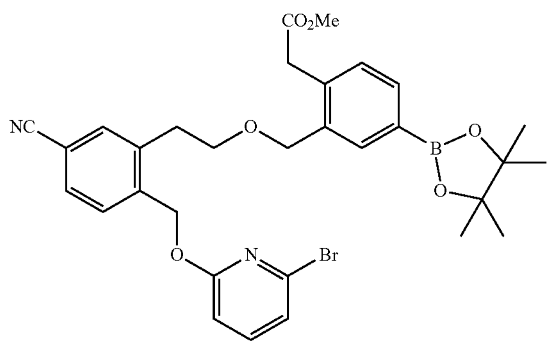 [SMILES: COC(=O)Cc1ccc(B2OC(C)(C)C(C)(C)O2)cc1COCCc1cc(C#N)ccc1COc1cccc(Br)n1]

To a solution of methyl 2-[4-bromo-2-[2-[2-[(6-bromo-2-pyridyl)oxymethyl]-5-cyano-phenyl]ethoxymethyl]phenyl] acetate (630 mg, 0.83 mmol, 75% purity) in anhydrous 1,4-dioxane (8.2 mL) under nitrogen, add bis(pinacolato) diboron (260 mg, 1 mmol), and KOAc (202 mg, 2.01 mmol). After 5 min, add Pd(dppf)$Cl_2$ DCM complex (40 mg, 0.048 mmol) and heat reaction mixture at 80° C. After 3 h, cool the reaction mixture to RT, then add water (10 mL) and EtOAc (10 mL). Separate the layers and extract the aqueous phase with EtOAc (2×5 mL). Combine the organics, wash with water and saturated aqueous NaCl, dry over $MgSO_4$, filter and concentrate under reduced pressure to afford the title compound as a brown oil (850 mg, 60% purity), which is used in Preparation 150 without further purification. ES-MS m/z 621/623 (M+H).

Preparation 144

Methyl 2-[4-bromo-2-[2-[5-[(6-chloro-2-pyridyl) oxymethyl]-2-cyano-phenyl]ethoxymethyl]phenyl] acetate

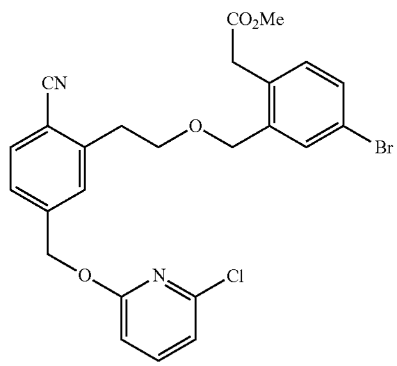 [SMILES: COC(=O)Cc1ccc(Br)cc1COCCc1cc(COc2cccc(Cl)n2)ccc1C#N]

Prepare the title compound essentially as described in Preparation 142 using 4-[(6-chloro-2-pyridyl)oxymethyl]-2-(2-hydroxyethyl)benzonitrile, with the addition of activated 3 Å molecular sieves to the reaction mixture. Purify the title compound via silica gel chromatography using a gradient of 50% to 100% DCM in cyclohexanes. ES-MS m/z 529, 531, 533 (M+H).

Preparation 145

Methyl 2-[2-[2-[5-[(6-chloro-2-pyridyl)oxymethyl]-2-cyano-phenyl]ethoxymethyl]-4-(4,4,5,5-tetramethyl-1,3,2-dioxaborolan-2-yl)phenyl]acetate

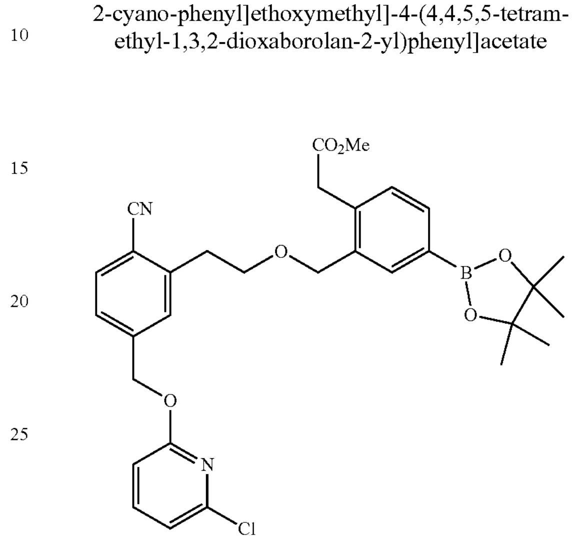

Prepare the title compound essentially as described in Preparation 143 using methyl 2-[4-bromo-2-[2-[5-[(6-chloro-2-pyridyl)oxymethyl]-2-cyano-phenyl]ethoxymethyl]phenyl]acetate. Upon completion of the reaction, cool to RT, add saturated $NaHCO_3$ and EtOAc and filter the mixture through Celite®. Separate aqueous layer and wash organic layer with water and saturated aqueous NaCl, dry over anhydrous $Na_2SO_4$, filter and remove solvent. Purify the residue via silica gel chromatography using a gradient of 0 to 2% EtOAc in DCM provide the title compound as a colorless waxy solid. ES-MS m/z 577 and 579 (M+H).

Preparation 146

Methyl 2-[2-[3-[2-[(6-bromo-2-pyridyl)oxymethyl]-5-fluoro-phenyl]propoxy]-5-methyl-4-(4,4,5,5-tetramethyl-1,3,2-dioxaborolan-2-yl)phenyl]acetate

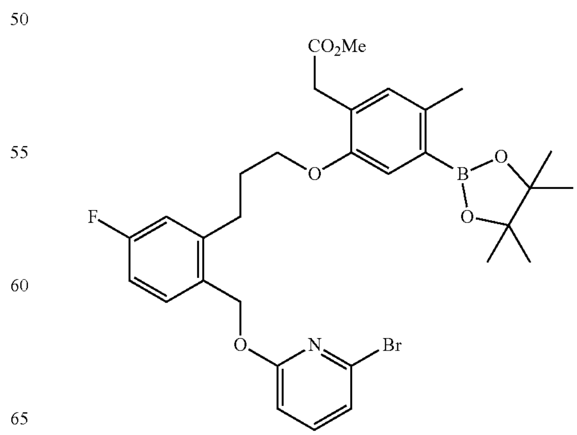

Prepare the title compound essentially as described in Preparation 54 using 3-[2-[(6-bromo-2-pyridyl)oxymethyl]-5-fluoro-phenyl]propan-1-ol and methyl 2-[2-hydroxy-5-methyl-4-(4,4,5,5-tetramethyl-1,3,2-dioxaborolan-2-yl)phenyl]acetate, and using a 40% solution of DEAD in toluene. Purify the title compound via silica gel flash chromatography eluting with a gradient of 85 to 100% DCM in hexanes. ES-MS m/z 628 and 630 (M+H).

Preparation 147

Methyl 2-[2-[3-[3-[(6-bromo-2-pyridyl)oxymethyl]-6-(trifluoromethyl)-2-pyridyl]propoxy]-5-methyl-4-(4,4,5,5-tetramethyl-1,3,2-dioxaborolan-2-yl)phenyl] acetate

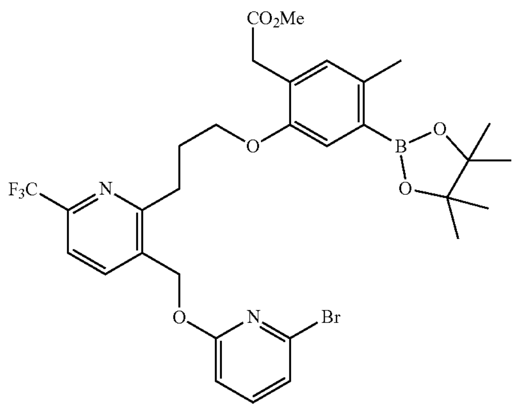 [SMILES: COC(=O)Cc1cc(C)c(B2OC(C)(C)C(C)(C)O2)cc1OCCCc1nc(C(F)(F)F)ccc1COc1cccc(Br)n1]

Prepare the title compound essentially as described in Preparation 55 using 3-[3-[(6-bromo-2-pyridyl)oxymethyl]-6-(trifluoromethyl)-2-pyridyl]propan-1-ol and methyl 2-[2-hydroxy-5-methyl-4-(4,4,5,5-tetramethyl-1,3,2-dioxaborolan-2-yl)phenyl]acetate in 1,4-dioxane as solvent. Stir the reaction mixture at RT for 15 h, then quench the reaction with MeOH and concentrate under reduced pressure. Purify the title compound via silica gel flash chromatography eluting with a gradient of 85 to 100% DCM in hexanes. ES-MS m/z 678 and 680 (M+H).

Preparation 148

Methyl 2-[2-[3-[4-[(6-bromo-2-pyridyl)oxymethyl]-3-pyridyl]propoxy]-5-methyl-4-(4,4,5,5-tetramethyl-1,3,2-dioxaborolan-2-yl)phenyl]acetate

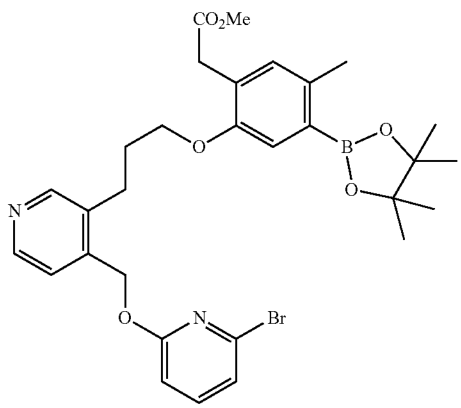 [SMILES: COC(=O)Cc1cc(C)c(B2OC(C)(C)C(C)(C)O2)cc1OCCCc1cnccc1COc1cccc(Br)n1]

Prepare the title compound essentially as described in Preparation 55 using 3-[4-[(6-bromo-2-pyridyl)oxymethyl]-3-pyridyl]propan-1-ol and methyl 2-[2-hydroxy-5-methyl-4-(4,4,5,5-tetramethyl-1,3,2-dioxaborolan-2-yl)phenyl]acetate in 1,4-dioxane as solvent and stirring the reaction at RT for 15 h. Quench the reaction with MeOH and concentrate under reduced pressure. Purify the residue via silica gel chromatography using a gradient of 85 to 100% DCM in hexanes to give the title compound. ES-MS m/z 611 and 613 (M+H).

Preparation 149

Methyl 2-($5^4$-(4,4,5,5-tetramethyl-1,3,2-dioxaborolan-2-yl)-3,9-dioxa-2(2,6)-pyridina-1(1,3),5(1,2)-dibenzenacyclononaphane-$1^4$-yl)acetate

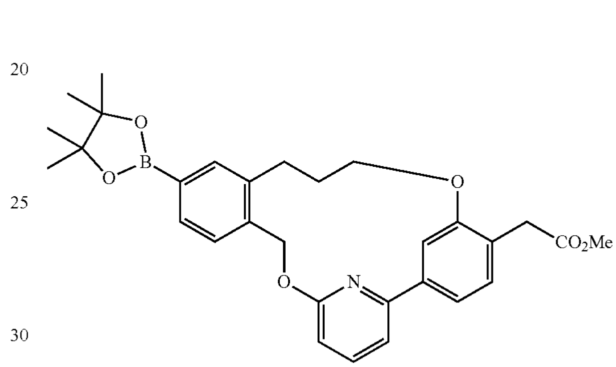

Add bis(pinacolato)diboron (3.93 g, 15.2 mmol) and KOAc (3.04 g, 30.4 mmol) to a slurry of methyl 2-($5^4$-chloro-3,9-dioxa-2(2,6)-pyridina-1(1,3),5(1,2)-dibenzenacyclononaphane-$1^4$-yl)acetate (4.33 g, 10.1 mmol) in 1,4-dioxane (0.2 L). Sparge the mixture with nitrogen for 5 min and then add [chloro(2-dicyclohexylphosphino-2',4',6'-tri-i-propyl-1,1'-biphenyl)(2'-amino-1,1'-biphenyl-2-yl) palladium(II)] (0.25 g, 0.31 mmol). Stir the mixture at 85° C. for 2.5 h under a positive pressure of nitrogen, then cool and concentrate under reduced pressure to remove most of the volatiles. Partition the residue between DCM (0.15 L) and water (0.15 L), separate the phases and extract the aqueous with further DCM (50 mL). Wash the combined organic phases with 2 M aqueous $K_2CO_3$ (50 mL) then brine (50 mL), then dry over $MgSO_4$ and filter. Concentrate the filtrate to 30 mL volume, add MeOH (0.2 L) and then concentrate to 60 mL volume. Stir the mixture at ambient temperature for 3 h, collect the solid by filtration and wash with MeOH (30 mL). Dry the filter cake under reduced pressure at 50° C. for 13 h to afford 4.95 g of the title compound (94%) as a grey solid. ES-MS m/z 515 and 516 (M+H).

Preparation 150

Methyl 2-($5^4$-cyano-3,8-dioxa-2(2,6)-pyridina-1(1,3),5(1,2)-dibenzenacyclononaphane-$1^4$-yl) acetate

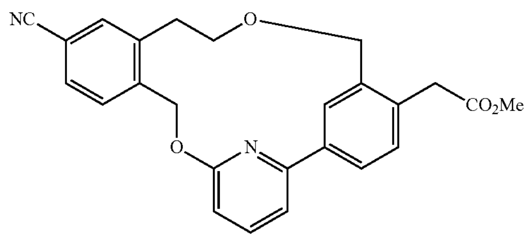 [SMILES: COC(=O)Cc1ccc2cc1COCCc1cc(C#N)ccc1COc1cccc-2n1]

Prepare the title compound essentially as described in Preparation 68 using methyl 2-[2-[2-[2-[(6-bromo-2-pyridyl)oxymethyl]-5-cyano-phenyl]ethoxymethyl]-4-(4,4,5,5-tetramethyl-1,3,2-dioxaborolan-2-yl)phenyl]acetate (Preparation 143). ES-MS m/z 415 (M+H).

Preparation 151

Ethyl 2-($5^4$-cyano-$1^6$-fluoro-3,8-dioxa-2(2,6)-pyridina-1(1,3),5(1,2)-dibenzenacyclooctaphane-$1^4$-yl)acetate

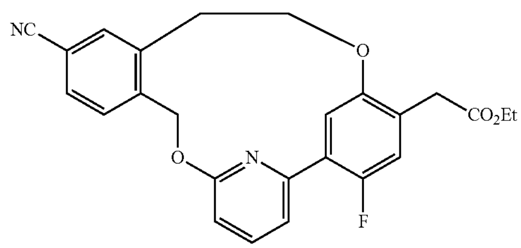 [SMILES: CCOC(=O)Cc1cc(F)c2cc1OCCc1cc(C#N)ccc1COc1cccc-2n1]

To a round bottom flask under nitrogen atmosphere add 4-[(6-bromo-2-pyridyl)oxymethyl]-3-(2-hydroxyethyl)benzonitrile (400 mg, 1.20 mmol), triphenylphosphine (473 mg 1.80 mmol), and a solution of ethyl 2-[5-fluoro-2-hydroxy-4-(4,4,5,5-tetramethyl-1,3,2-dioxaborolan-2-yl)phenyl]acetate (563 mg, 1.44 mmol) in anhydrous THE (10 mL). Stir the mixture until solids dissolve and cool down in an ice bath. Add to the mixture a solution of di-tert-butyl azodicarboxylate (423 mg, 1.80 mmol) in THE (1.6 mL). Remove the ice bath and leave the reaction at RT for 2 h. Add to the reaction THE (26 mL) and aqueous potassium phosphate (1 M, 7.2 mL) and stir the mixture for 5 min. Add $Pd(dtbpf)Cl_2$ (80 mg, 0.12 mmol) to the reaction, flush with nitrogen several times and heat the reaction to 80° C. for 3 h. Cool down the reaction to RT, dilute with EtOAc and add Celite®.

Stir the mixture for 10 min, filter the mixture through a pad of Celite®, and wash the Celite® pad with EtOAc. Dry the filtrate over $MgSO_4$, filter, and concentrate the filtrate under reduced pressure. Purify the residue via silica gel chromatography using a gradient from 0 to 100% of EtOAc in cyclohexane to give the title product as a white solid (150 mg, 28.9%). ES-MS m/z 433 (M+H).

Preparation 152

Methyl 2-($5^4$-cyano-3,8-dioxa-2(2,6)-pyridina-1,5(1,3)-dibenzenacyclononaphane-$1^4$-yl)acetate

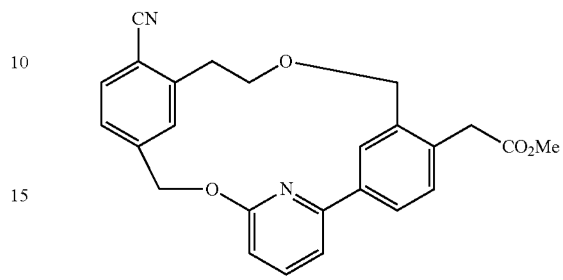

Bubble nitrogen for 5 min into a mixture of methyl 2-[2-[2-[5-[(6-chloro-2-pyridyl)oxymethyl]-2-cyano-phenyl]ethoxymethyl]-4-(4,4,5,5-tetramethyl-1,3,2-dioxaborolan-2-yl)phenyl]acetate (132 mg, 0.20 mmol, 88 mass %), THF (5 mL) and aqueous potassium phosphate tribasic (1.0 M, 1 mL, 1.0 mmol). Add XPhos Pd(crotyl)Cl (Pd-170 catalyst, CAS number 1798782-02-1, 6 mg, 0.009 mmol) and stir the mixture at 50° C. for 50 min. Cool the reaction mixture to RT and add water and EtOAc. Separate aqueous layer and wash organic layer with water and saturated aqueous NaCl, dry over anhydrous $Na_2SO_4$, filter and concentrate. Purify the residue via silica gel chromatography using DCM to provide the title compound (51 mg, 61%) as a white solid. ES-MS m/z 415 (M+H).

Preparation 153

Methyl 2-($5^4$-fluoro-$1^6$-methyl-3,9-dioxa-2(2,6)-pyridina-1(1,3),5(1,2)-dibenzenacyclononaphane-$1^4$-yl)acetate

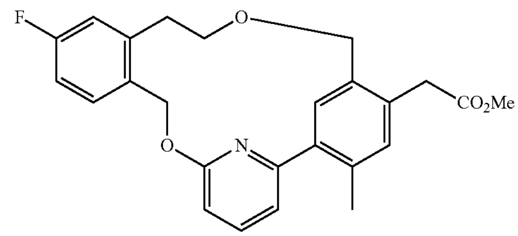 [SMILES: COC(=O)Cc1cc(C)c2cc1COCCc1cc(F)ccc1COc1cccc-2n1]

Prepare the title compound essentially as described in Preparation 66 using methyl 2-[2-[3-[2-[(6-bromo-2-pyridyl)oxymethyl]-5-fluoro-phenyl]propoxy]-5-methyl-4-(4,4,5,5-tetramethyl-1,3,2-dioxaborolan-2-yl)phenyl]acetate and stirring the reaction mixture under a nitrogen atmosphere at 40° C. for 1 h. Purify the title compound via silica gel flash chromatography eluting with a gradient of 0 to 20% EtOAc in DCM. ES-MS m/z 422 (M+H).

Preparation 154

Methyl 2-($1^6$-methyl-$5^6$-(trifluoromethyl)-3,9-dioxa-2(2,6),5(3,2)-dipyridina-1(1,3)-benzenacyclononaphane-$1^4$-yl)acetate

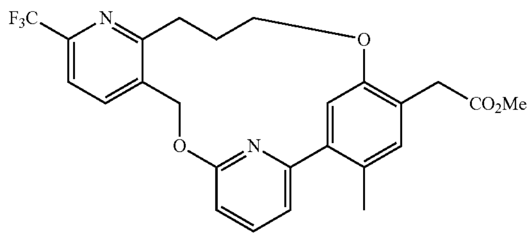 [SMILES: COC(=O)Cc1cc(C)c2cc1OCCCc1nc(C(F)(F)F)ccc1COc1cccc-2n1]

Prepare the title compound essentially as described in Preparation 66 using methyl 2-[2-[3-[3-[(6-bromo-2-pyridyl)oxymethyl]-6-(trifluoromethyl)-2-pyridyl]propoxy]-5-methyl-4-(4,4,5,5-tetramethyl-1,3,2-dioxaborolan-2-yl)phenyl]acetate, stirring the reaction at 40° C. for 1 h. Purify the title compound via silica gel chromatography using a gradient of 0 to 20% EtOAc in DCM. ES-MS m/z 473 (M+H).

Preparation 155

Methyl 2-($1^6$-methyl-3,9-dioxa-2(2,6),5(4,3)-dipyridina-1(1,3)-benzenacyclononaphane-$1^4$-yl) acetate

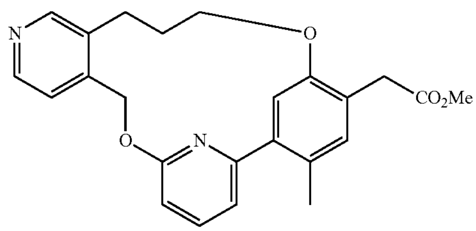 [SMILES: COC(=O)Cc1cc(C)c2cc1OCCCc1cnccc1COc1cccc-2n1]

Prepare the title compound essentially as described in Preparation 66 using methyl 2-[2-[3-[4-[(6-bromo-2-pyridyl)oxymethyl]-3-pyridyl]propoxy]-5-methyl-4-(4,4,5,5-tetramethyl-1,3,2-dioxaborolan-2-yl)phenyl]acetate and stirring the reaction at 40° C. for 1 h. Purify the title compound via silica gel chromatography using a gradient of 5 to 35% EtOAc in DCM. ES-MS m/z 405 (M+H).

Preparation 156

2-($5^4$-Bromo-3,9-dioxa-2(2,6)-pyridina-1(1,3),5(1,2)-dibenzenacyclononaphane-$1^4$-yl)acetic acid

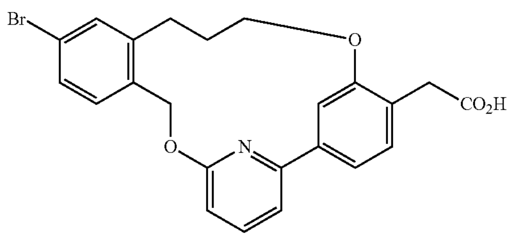 [SMILES: O=C(O)Cc1ccc2cc1OCCCc1cc(Br)ccc1COc1cccc-2n1]

Add MeOH (20 mL) and water (5 mL) to a mixture of methyl 2-($5^4$-(4,4,5,5-tetramethyl-1,3,2-dioxaborolan-2-yl)-3,9-dioxa-2(2,6)-pyridina-1(1,3),5(1,2)-dibenzenacyclononaphane-$1^4$-yl)acetate (4.45 g, 8.55 mmol) and cupric bromide (5.73 g, 25.7 mmol). Stir the mixture at 80° C. for 30 h. Cool the mixture to ambient temperature, add 30% aqueous $NH_4OH$ and dilute to a final volume of approx. 0.5 L with water. Stir the mixture for 0.5 h, collect the solid by filtration and wash with 10% aqueous $NH_4OH$ (0.1 L) then water (0.1 L). Add THE (0.14 L), MeOH (70 mL) and 1 M aqueous LiOH (35 mL) to the damp solid and stir at 60° C. for 3.5 h. Add 1 M aqueous $KH_2PO_4$ (0.1 L) to the mixture and then dilute to a final volume of approx. 1 L with water. Leave the mixture to cool naturally with stirring for 1 h, collect the solid by filtration and wash with 1:4 water:MeOH (0.2 L) and water (0.1 L). Dry the filter cake under reduced pressure at 50° C. for 16 h to afford 3.66 g of the title compound (92%) as an off-white solid. ES-MS m/z 454 and 456 (M+H).

Preparation 157

2-($5^4$-cyano-3,8-dioxa-2(2,6)-pyridina-1(1,3),5(1,2)-dibenzenacyclononaphane-$1^4$-yl) acetic acid

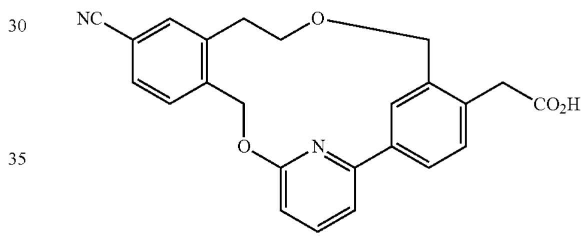

Prepare the title compound essentially as described in Preparation 78 using methyl 2-($5^4$-cyano-3,8-dioxa-2(2,6)-pyridina-1(1,3),5(1,2)-dibenzenacyclononaphane-$1^4$-yl) acetate. ES-MS m/z 401 (M+H).

Preparation 158

2-($5^4$-cyano-$1^6$-fluoro-3,8-dioxa-2(2,6)-pyridina-1(1,3),5(1,2)-dibenzenacyclooctaphane-$1^4$-yl)acetic acid

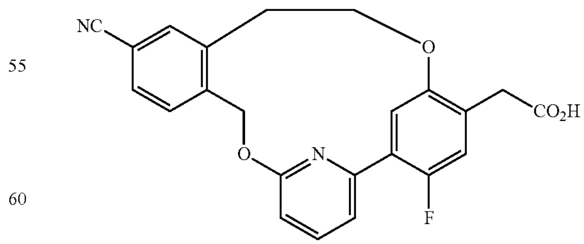

Prepare the title compound essentially as described in Preparation 78 using ethyl 2-($5^4$-cyano-$1^6$-fluoro-3,8-dioxa-2(2,6)-pyridina-1(1,3),5(1,2)-dibenzenacyclooctaphane-$1^4$-yl)acetate. ES-MS m/z 418 (M+H).

Preparation 159

2-($5^4$-Cyano-3,8-dioxa-2(2,6)-pyridina-1,5(1,3)-dibenzenacyclononaphane-$1^4$-yl)acetic acid

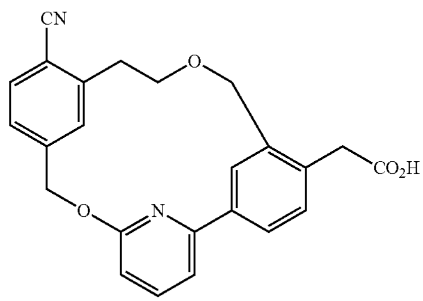 [SMILES: N#Cc1ccc2cc1CCOCc1cc(ccc1CC(=O)O)-c1cccc(n1)OC2]

Prepare the title compound essentially as described in Preparation 78 using methyl 2-($5^4$-cyano-3,8-dioxa-2(2,6)-pyridina-1,5(1,3)-dibenzenacyclononaphane-$1^4$-yl)acetate. ES-MS m/z 401 (M+H).

Preparation 160

2-($1^6$-Methyl-$5^4$-(fluoro)-3,9-dioxa-2(2,6)-pyridina-1(1,3),5(1,2)-dibenzenacyclononaphane-$1^4$-yl)acetic acid

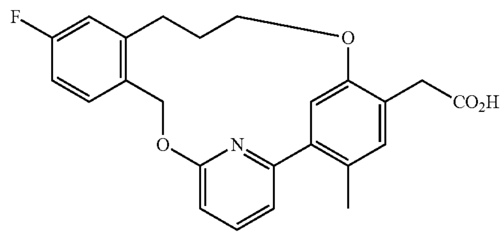 [SMILES: Cc1cc(CC(=O)O)c2cc1-c1cccc(n1)OCc1ccc(F)cc1CCCO2]

Prepare the title compound essentially as described in Preparation 75 using methyl 2-($1^6$-methyl-$5^4$-(fluoro)-3,9-dioxa-2(2,6)-pyridina-1(1,3),5(1,2)-dibenzenacyclononaphane-$1^4$-yl)acetate, stirring the reaction at 50° C. for 1 h. The title compound is used without purification in Preparation 168. ES-MS m/z 408 (M+H).

Preparation 161

Methyl 2-($1^6$-methyl-$5^6$-(trifluoromethyl)-3,9-dioxa-2(2,6),5(3,2)-dipyridina-1(1,3)-benzenacyclononaphane-$1^4$-yl)acetic acid

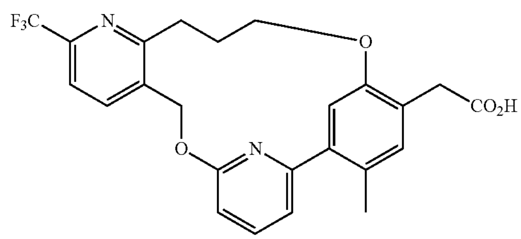 [SMILES: Cc1cc(CC(=O)O)c2cc1-c1cccc(n1)OCc1ccc(C(F)(F)F)nc1CCCO2]

Prepare the title compound essentially as described in Preparation 75 using methyl 2-($1^6$-methyl-$5^6$-(trifluoromethyl)-3,9-dioxa-2(2,6),5(3,2)-dipyridina-1(1,3)-benzenacyclononaphane-$1^4$-yl)acetate, stirring the reaction at 50° C. for 1 h. The title compound is used without further purification in Preparation 171. ES-MS m/z 459 (M+H).

Preparation 162

2-($1^6$-Methyl-3,9-dioxa-2(2,6),5(4,3)-dipyridina-1(1,3)-benzenacyclononaphane-$1^4$-yl)acetic acid

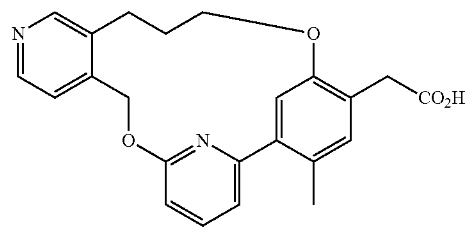 [SMILES: Cc1cc(CC(=O)O)c2cc1-c1cccc(n1)OCc1ccncc1CCCO2]

Prepare the title compound essentially as described in Preparation 75 using methyl 2-($1^6$-methyl-3,9-dioxa-2(2,6),5(4,3)-dipyridina-1(1,3)-benzenacyclononaphane-$1^4$-yl)acetate and stirring the reaction at 50° C. for 1 h. Use the title compound without further purification in Preparation 172. ES-MS m/z 391 (M+H).

Preparation 163

Methyl (S)-4-(2-($5^4$-cyano-$1^6$-fluoro-3,7-dioxa-2(2,6)-pyridina-1(1,3),5(1,2)-dibenzenacyclooctaphane-$1^4$-yl)acetamido)-3-methoxy-5-((oxetan-2-ylmethyl)amino)benzoate

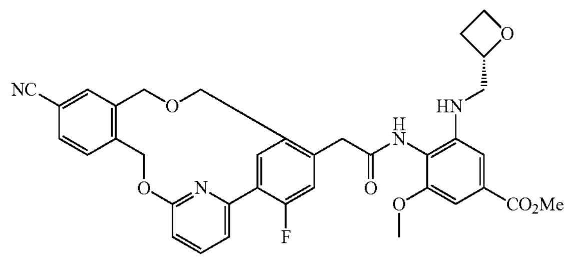 [SMILES: COC(=O)c1cc(NC[C@@H]2CCO2)c(NC(=O)Cc2cc(F)c3cc2COCc2cc(C#N)ccc2COc2cccc-3n2)c(OC)c1]

Prepare the title compound essentially as described in Preparation 86 using 2-($5^4$-cyano-$1^6$-fluoro-3,7-dioxa-2(2,6)-pyridina-1(1,3),5(1,2)-dibenzenacyclooctaphane-$1^4$-yl) acetic acid and methyl 4-amino-3-methoxy-5-[[(2S)-oxetan-2-yl]methylamino]benzoate stirring the reaction for 16 h. The title compound is used in the next step (Preparation 173) without purification. ES-MS m/z 653 (M+H).

Preparation 164

Methyl (S)-4-(2-($5^4$-bromo-3,9-dioxa-2(2,6)-pyridina-1(1,3),5(1,2)-dibenzenacyclononaphane-$1^4$-yl)acetamido)-3-((oxetan-2-ylmethyl)amino)benzoate

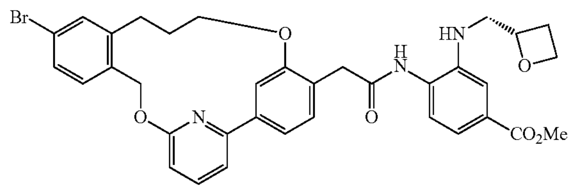

Add DMF (33 mL) and pyridine (6 mL) to a mixture of 2-($5^4$-bromo-3,9-dioxa-2(2,6)-pyridina-1(1,3),5(1,2)-dibenzenacyclononaphane-$1^4$-yl)acetic acid (3.10 g, 6.69 mmol) and methyl 4-amino-3-[[(2S)-oxetan-2-yl]methylamino]benzoate (prepared essentially as described in WO 2020/263695; 1.75 g, 7.41 mmol) and stir for 30 min. Add 2,4,6-tripropyl-1,3,5,2,4,6-trioxatriphosphorinane-2,4,6-trioxide (1.68 mol/L in EtOAc, 10 mL, 16.8 mmol) and stir the mixture for 50 min. Dilute the reaction mixture to a final volume of 0.2 L with water and stir for 20 min. Collect the solid by filtration and wash with water (0.1 L). Dry the filter cake under reduced pressure at 50° C. for 24 h to give 4.64 g of the title compound (99%) as a pale pink solid. ES-MS m/z 672 and 674 (M+H).

Preparation 165

Methyl (S)-4-(2-($5^4$-cyano-3,8-dioxa-2(2,6)-pyridina-1(1,3),5(1,2)-dibenzenacyclononaphane-$1^4$-yl)acetamido)-3-((oxetan-2-ylmethyl)amino)benzoate

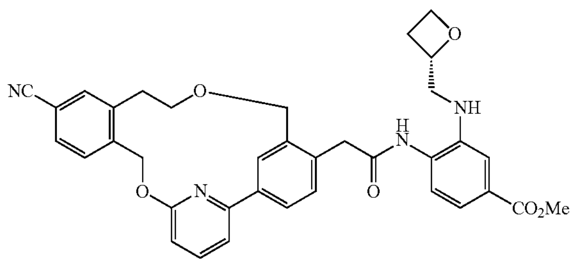 [SMILES: COC(=O)c1ccc(NC(=O)Cc2ccc3cc2COCCc2cc(C#N)ccc2COc2cccc-3n2)c(NC[C@@H]2CCO2)c1]

Prepare the title compound essentially as described in Preparation 86 using 2-($5^4$-cyano-3,8-dioxa-2(2,6)-pyridina-1(1,3),5(1,2)-dibenzenacyclononaphane-$1^4$-yl)acetic acid and methyl 4-amino-3-[[(2S)-oxetan-2-yl]methylamino]benzoate (prepared essentially as described in WO 2020/263695). The title compound is used in the next step (Preparation 175) without purification. ES-MS m/z 619 (M+H).

Preparation 166

Methyl (S)-4-(2-($5^4$-cyano-$1^6$-fluoro-3,8-dioxa-2(2,6)-pyridina-1(1,3),5(1,2)-dibenzenacyclooctaphane-$1^4$-yl)acetamido)-3-((oxetan-2-ylmethyl)amino)benzoate

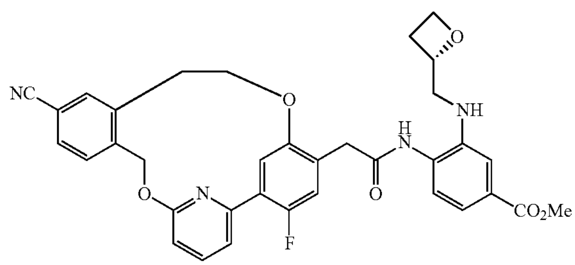 [SMILES: COC(=O)c1ccc(NC(=O)Cc2cc(F)c3cc2OCCc2cc(C#N)ccc2COc2cccc-3n2)c(NC[C@@H]2CCO2)c1]

Prepare the title compound essentially as described in Preparation 86 using 2-($5^4$-cyano-$1^6$-fluoro-3,8-dioxa-2(2,6)-pyridina-1(1,3),5(1,2)-dibenzenacyclooctaphane-$1^4$-yl)acetic acid and methyl 4-amino-3-[[(2S)-oxetan-2-yl]methylamino]benzoate (prepared essentially as described in WO 2020/263695). The title compound is used in crude form in Preparation 176. ES-MS m/z 623 (M+H).

Preparation 167

Methyl (S)-4-(2-($5^4$-cyano-3,8-dioxa-2(2,6)-pyridina-1,5(1,3)-dibenzenacyclononaphane-$1^4$-yl)acetamido)-3-((oxetan-2-ylmethyl)amino)benzoate

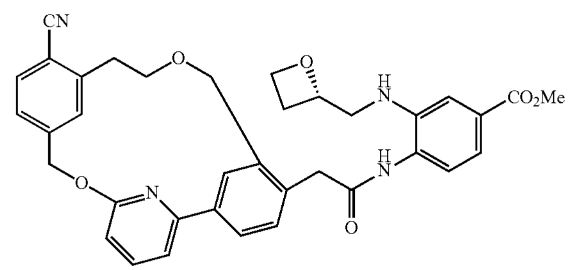 [SMILES: COC(=O)c1ccc(NC(=O)Cc2ccc3cc2COCCc2cc(ccc2C#N)COc2cccc-3n2)c(NC[C@@H]2CCO2)c1]

Prepare the title compound essentially as described in Preparation 86 using 2-($5^4$-cyano-3,8-dioxa-2(2,6)-pyridina-1,5(1,3)-dibenzenacyclononaphane-$1^4$-yl)acetic acid and methyl 4-amino-3-[[(2S)-oxetan-2-yl]methylamino]benzoate (prepared essentially as described in WO 2020/263695). The title compound is used in crude form in Preparation 177. ES-MS m/z 619 (M+H).

Preparation 168

Methyl (S)-3-methoxy-4-(2-($1^6$-methyl-$5^4$-(fluoro)-3,9-dioxa-2(2,6)-pyridina-1(1,3),5(1,2)-dibenzenacyclononaphane-$1^4$-yl)acetamido)-5-((oxetan-2-ylmethyl)amino)benzoate

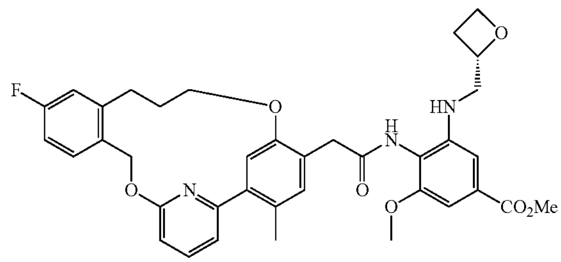 [SMILES: COC(=O)c1cc(NC[C@@H]2CCO2)c(NC(=O)Cc2cc(C)c3cc2OCCCc2cc(F)ccc2COc2cccc-3n2)c(OC)c1]

Prepare the title compound essentially as described in Preparation 86 using 2-($1^6$-methyl-$5^4$-(fluoro)-3,9-dioxa-2(2,6)-pyridina-1(1,3),5(1,2)-dibenzenacyclononaphane-$1^4$-yl)acetic acid (Preparation 160) and methyl 4-amino-3-methoxy-5-[[(2S)-oxetan-2-yl]methylamino]benzoate. The title compound is used without purification in Preparation 178. ES-MS m/z 656 (M+H).

Preparation 169 Ethyl 4-(2-($5^4$-cyano-3,9-dioxa-2(2,6)-pyridina-1(1,3),5(1,2)-dibenzenacyclononaphane-$1^4$-yl)acetamido)-3-methoxy-5-((oxazol-2-ylmethyl)amino)benzoate

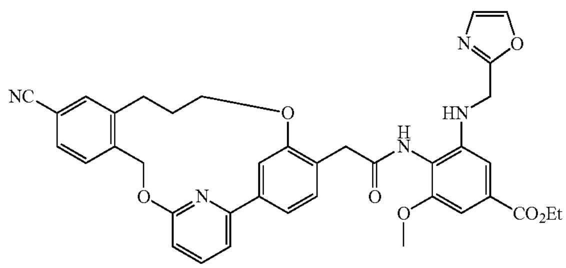 [SMILES: CCOC(=O)c1cc(NCc2ncco2)c(NC(=O)Cc2ccc3cc2OCCCc2cc(C#N)ccc2COc2cccc-3n2)c(OC)c1]

Prepare the title compound essentially as described in Preparation 85 using 2-($5^4$-cyano-3,9-dioxa-2(2,6)-pyridina-1(1,3),5(1,2)-dibenzenacyclononaphane-$1^4$-yl)acetic acid and ethyl-4-amino-3-methoxy-5-(oxazol-2-ylmethylamino)benzoate (Preparation 122). The title compound is used without purification in Preparation 179. ES-MS m/z 674 (M+H).

Preparation 170

Methyl (S)-4-(2-($5^4$-cyano-3,9-dioxa-2(2,6)-pyridina-1(1,3),5(1,2)-dibenzenacyclononaphane-$1^4$-yl)acetamido)-3-(2-methoxyethoxy)-5-((oxetan-2-ylmethyl)amino)benzoate

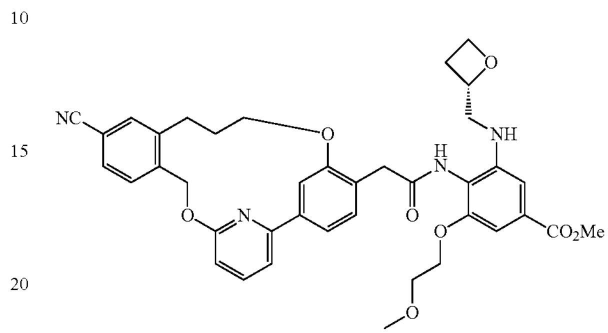

Prepare the title compound essentially as described in Preparation 85 using 2-($5^4$-cyano-3,9-dioxa-2(2,6)-pyridina-1(1,3),5(1,2)-dibenzenacyclononaphane-$1^4$-yl)acetic acid and methyl 4-amino-3-(2-methoxyethoxy)-5-[[(2S)-oxetan-2-yl]methylamino]benzoate (Preparation 124). The title compound is used without further purification in Preparation 180. ES-MS m/z 693 (M+H).

Preparation 171

Methyl (S)-3-methoxy-4-(2-($1^6$-methyl-$5^6$-(trifluoromethyl)-3,9-dioxa-2(2,6),5(3,2)-dipyridina-1(1,3)-benzenacyclononaphane-$1^4$-yl)acetamido)-5-((oxetan-2-ylmethyl)amino)benzoate

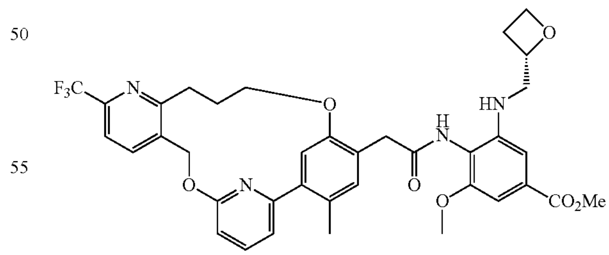

Prepare the title compound essentially as described in Preparation 86 using methyl 2-($1^6$-methyl-$5^6$-(trifluoromethyl)-3,9-dioxa-2(2,6),5(3,2)-dipyridina-1(1,3)-benzenacyclononaphane-$1^4$-yl)acetic acid (Preparation 161) and methyl 4-amino-3-methoxy-5-[[(2S)-oxetan-2-yl]methylamino]benzoate. Use the title compound in Preparation 183 without further purification. ES-MS m/z 707 (M+H).

Preparation 172

Methyl (S)-3-methoxy-4-(2-($1^6$-methyl-3,9-dioxa-2(2,6),5(4,3)-dipyridina-1(1,3)-benzenacyclononaphane-$1^4$-yl)acetamido)-5-((oxetan-2-ylmethyl)amino)benzoate

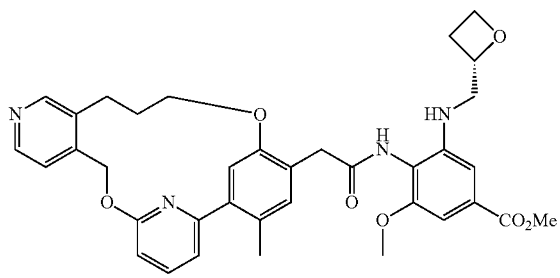 [SMILES: COC(=O)c1cc(NC[C@@H]2CCO2)c(NC(=O)Cc2cc(C)c3cc2OCCCc2cnccc2COc2cccc-3n2)c(OC)c1]

Prepare the title compound essentially as described in Preparation 86 using 2-($1^6$-methyl-3,9-dioxa-2(2,6),5(4,3)-dipyridina-1(1,3)-benzenacyclononaphane-$1^4$-yl)acetic acid (Preparation 162) and methyl 4-amino-3-methoxy-5-[[(2S)-oxetan-2-yl]methylamino]benzoate. Use the title compound in the next step (Preparation 184) without further purification. ES-MS m/z 639 (M+H).

Preparation 173

Methyl (S)-2-(($5^4$-cyano-$1^6$-fluoro-3,7-dioxa-2(2,6)-pyridina-1(1,3),5(1,2)-dibenzenacyclooctaphane-$1^4$-yl)methyl)-4-methoxy-1-(oxetan-2-ylmethyl)-1H-benzo[d]imidazole-6-carboxylate

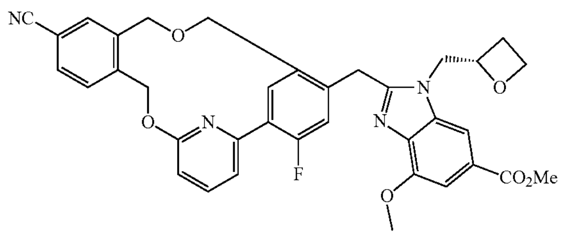 [SMILES: COC(=O)c1cc(OC)c2nc(Cc3cc(F)c4cc3COCc3cc(C#N)ccc3COc3cccc-4n3)n(C[C@@H]3CCO3)c2c1]

Prepare the title compound essentially as described in Preparation 102 using methyl (S)-4-(2-($5^4$-cyano-$1^6$-fluoro-3,7-dioxa-2(2,6)-pyridina-1(1,3),5(1,2)-dibenzenacyclooctaphane-$1^4$-yl)acetamido)-3-methoxy-5-((oxetan-2-ylmethyl)amino)benzoate (from Preparation 163), heating the reaction at 65° C. for 9 h. Cool the mixture to RT and evaporate the solvent under reduced pressure, adding ACN to help remove the acetic acid. Purify the residue via silica gel chromatography using a gradient of 0 to 40% EtOAc in DCM and then 10% MeOH in DCM to give the title compound as a pale orange solid. ES-MS m/z 635 (M+H).

Preparation 174

Methyl (S)-2-(($5^4$-bromo-3,9-dioxa-2(2,6)-pyridina-1(1,3),5(1,2)-dibenzenacyclononaphane-$1^4$-yl)methyl)-1-(oxetan-2-ylmethyl)-1H-benzo[d]imidazole-6-carboxylate

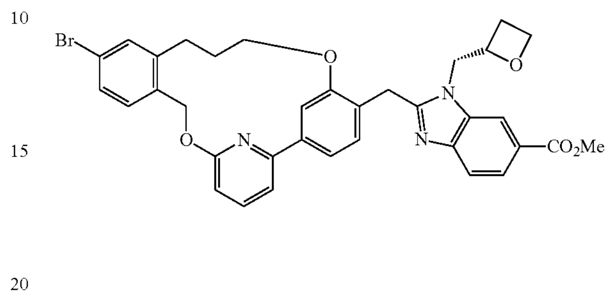

Prepare the title compound essentially as described in Preparation 102 using methyl (S)-4-(2-($5^4$-bromo-3,9-dioxa-2(2,6)-pyridina-1(1,3),5(1,2)-dibenzenacyclononaphane-$1^4$-yl)acetamido)-3-((oxetan-2-ylmethyl)amino)benzoate and using 1:1 acetic acid:2-chlorotoluene as solvent. Stir the reaction at 60° C. for 32 h under a positive pressure of nitrogen. Concentrate the reaction mixture under reduced pressure. Dissolve the residue in DCM, concentrate onto diatomaceous earth and purify by silica gel chromatography using a gradient of 0-50% EtOAc in DCM to give the title compound as a white solid. ES-MS m/z 654 and 656 (M+H).

Preparation 175

Methyl (S)-2-(($5^4$-cyano-3,8-dioxa-2(2,6)-pyridina-1(1,3),5(1,2)-dibenzenacyclononaphane-$1^4$-yl)methyl)-1-(oxetan-2-ylmethyl)-1H-benzo[d]imidazole-6-carboxylate

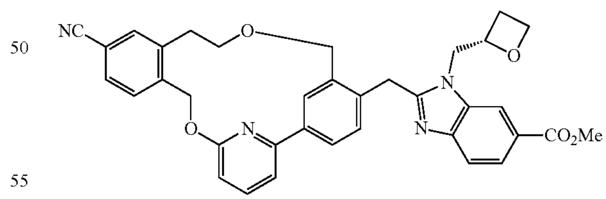

Prepare the title compound essentially as described in Preparation 102 using methyl (S)-4-(2-($5^4$-cyano-3,8-dioxa-2(2,6)-pyridina-1(1,3),5(1,2)-dibenzenacyclononaphane-$1^4$-yl)acetamido)-3-((oxetan-2-ylmethyl)amino)benzoate in 1:1 1,2-dichloroethane:acetic acid as solvent, heating the reaction at 50° C. for 5 h. Cool reaction mixture to RT, concentrate solvents under reduce pressure, and purify the residue via silica gel chromatography using a gradient of 10 to 50% EtOAc in DCM to give the title compound as a white solid. ES-MS m/z 601 (M+H).

Preparation 176

Methyl (S)-2-(($5^4$-cyano-$1^6$-fluoro-3,8-dioxa-2(2,6)-pyridina-1(1,3),5(1,2)-dibenzenacyclooctaphane-$1^4$-yl)methyl)-1-(oxetan-2-ylmethyl)-1H-benzo[d]imidazole-6-carboxylate

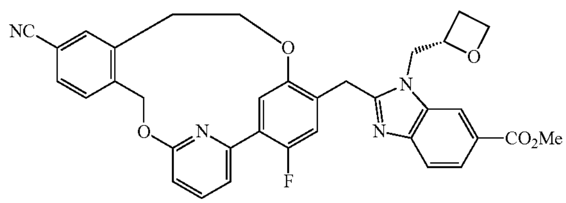 [SMILES: COC(=O)c1ccc2nc(Cc3cc(F)c4cc3OCCc3cc(C#N)ccc3COc3cccc-4n3)n(C[C@@H]3CCO3)c2c1]

Prepare the title compound essentially as described in Preparation 102 using methyl (S)-4-(2-($5^4$-cyano-$1^6$-fluoro-3,8-dioxa-2(2,6)-pyridina-1(1,3),5(1,2)-dibenzenacyclooctaphane-$1^4$-yl)acetamido)-3-((oxetan-2-ylmethyl)amino) benzoate in 1:1 1,2-dichloroethane:acetic acid as solvent, heating to 52° C. for 4 h. Cool down the reaction to RT and remove the solvent under reduced pressure. Purify the residue via silica gel chromatography using a gradient from 0 to 100% of EtOAc in DCM to give the title compound as a yellow solid. ES-MS m/z 605 (M+H).

Preparation 177

Methyl (S)-2-(($5^4$-cyano-3,8-dioxa-2(2,6)-pyridina-1,5(1,3)-dibenzenacyclononaphane-$1^4$-yl)methyl)-1-(oxetan-2-ylmethyl)-1H-benzo[d]imidazole-6-carboxylate

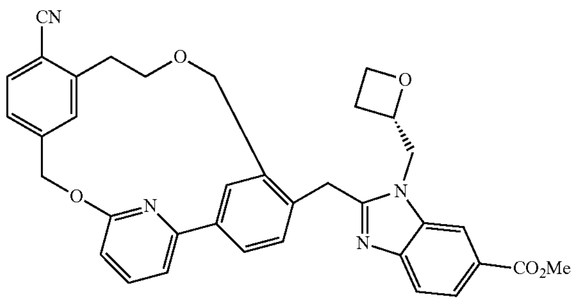 [SMILES: COC(=O)c1ccc2nc(Cc3ccc4cc3COCCc3cc(ccc3C#N)COc3cccc-4n3)n(C[C@@H]3CCO3)c2c1]

Prepare the title compound essentially as described in Preparation 102 using methyl (S)-4-(2-($5^4$-cyano-3,8-dioxa-2(2,6)-pyridina-1,5(1,3)-dibenzenacyclononaphane-$1^4$-yl) acetamido)-3-((oxetan-2-ylmethyl)amino)benzoate in 1:1 1,2-dichloroethane:acetic acid as solvent, heating the reaction at 60° C. for 5 h. Cool reaction mixture to RT, concentrate solvents under reduce pressure, and purify the residue via silica gel chromatography using a gradient of 25 to 50% EtOAc in DCM to give the title compound as a white solid. ES-MS m/z 601 (M+H).

Preparation 178

Methyl (S)-4-methoxy-2-(($1^6$-methyl-$5^4$-(fluoro)-3,9-dioxa-2(2,6)-pyridina-1(1,3),5(1,2)-dibenzenacyclononaphane-$1^4$-yl)methyl)-1-(oxetan-2-ylmethyl)-1H-benzo[d]imidazole-6-carboxylate

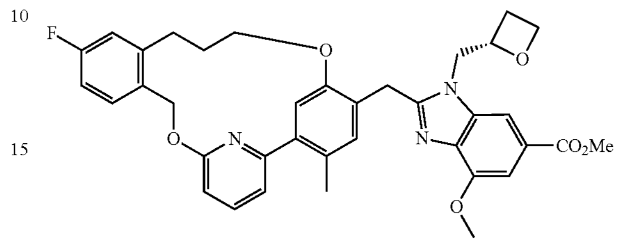

Prepare the title compound essentially as described in Preparation 102 using methyl (S)-3-methoxy-4-(2-($1^6$-methyl-$5^4$-(fluoro)-3,9-dioxa-2(2,6)-pyridina-1(1,3),5(1,2)-dibenzenacyclononaphane-$1^4$-yl)acetamido)-5-((oxetan-2-ylmethyl)amino)benzoate in 1:1 dichloroethane:acetic acid. Purify the title compound via silica gel chromatography using a gradient of 80 to 100% DCM in Hexane. ES-MS m/z 638 (M+H).

Preparation 179

Ethyl 2-(($5^4$-cyano-3,9-dioxa-2(2,6)-pyridina-1(1,3),5(1,2)-dibenzenacyclononaphane-$1^4$-yl)methyl)-4-methoxy-1-(oxazol-2-ylmethyl)-1H-benzo[d]imidazole-6-carboxylate

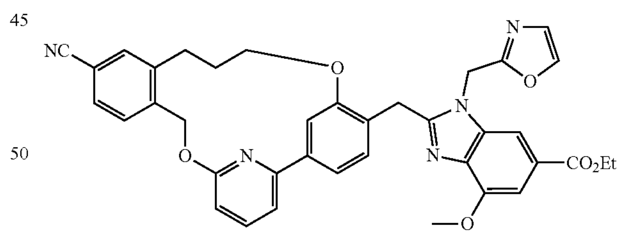

Prepare the title compound essentially as described in Preparation 101 using ethyl 4-(2-($5^4$-cyano-3,9-dioxa-2(2,6)-pyridina-1(1,3),5(1,2)-dibenzenacyclononaphane-$1^4$-yl) acetamido)-3-methoxy-5-((oxazol-2-ylmethyl)amino)benzoate in acetic acid. Concentrate the reaction mixture and precipitate the title compound from heptane, which is used in Example 23 without further purification. ES-MS m/z 656 (M+H).

Preparation 180

Methyl (S)-2-(($5^4$-cyano-3,9-dioxa-2(2,6)-pyridina-1(1,3),5(1,2)-dibenzenacyclononaphane-$1^4$-yl)methyl)-4-(2-methoxyethoxy)-1-(oxetan-2-ylmethyl)-1H-benzo[d]imidazole-6-carboxylate

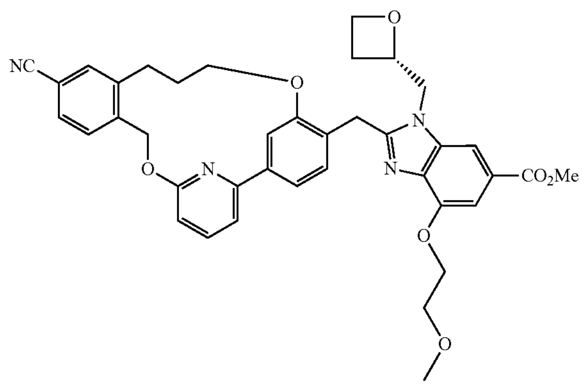 [SMILES: COCCOc1cc(C(=O)OC)cc2c1nc(Cc1ccc3cc1OCCCc1cc(C#N)ccc1COc1cccc-3n1)n2C[C@@H]1CCO1]

Prepare the title compound essentially as described in Preparation 101 using methyl (S)-4-(2-($5^4$-cyano-3,9-dioxa-2(2,6)-pyridina-1(1,3),5(1,2)-dibenzenacyclononaphane-$1^4$-yl)acetamido)-3-(2-methoxyethoxy)-5-((oxetan-2-ylmethyl)amino)benzoate in acetic acid. Purify the title compound via silica gel chromatography using a gradient of 0 to 80% EtOAc in heptane. ES-MS m/z 675 (M+H).

Preparation 181

Methyl (S)-2-(($5^4$-formyl-3,9-dioxa-2(2,6)-pyridina-1(1,3),5(1,2)-dibenzenacyclononaphane-$1^4$-yl)methyl)-1-(oxetan-2-ylmethyl)-1H-benzo[d]imidazole-6-carboxylate

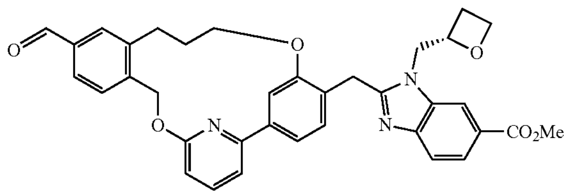 [SMILES: COC(=O)c1ccc2nc(Cc3ccc4cc3OCCCc3cc(C=O)ccc3COc3cccc-4n3)n(C[C@@H]3CCO3)c2c1]

Charge a Schlenk tube with bis(acetonitrile)dichloropalladium(II) (11 mg, 0.042 mmol) and butyldi-1-adamantylphosphine (48 mg, 0.13 mmol). Purge the tube with nitrogen (3× vacuum/nitrogen cycles), and add 4-methylmorpholine (3 mL, 27.24 mmol). Purge the tube again with nitrogen while stirring (5× vacuum/nitrogen cycles). Close tube and stir at ambient temperature for 1 h. Charge a glass pressure vessel with methyl (S)-2-(($5^4$-bromo-3,9-dioxa-2(2,6)-pyridina-1(1,3),5(1,2)-dibenzenacyclononaphane-$1^4$-yl)methyl)-1-(oxetan-2-ylmethyl)-1H-benzo[d]imidazole-6-carboxylate (290 mg, 0.42 mmol), and 4-methylmorpholine (9 mL, 81.73 mmol, 100 mass %). Cap with a septum and bubble the mixture with nitrogen while stirring. After 30 min, transfer the catalyst suspension to the pressure vessel and purge it three times with synthesis gas to 80 psi, then refill to 80 psi with synthesis gas. Stir and heat the mixture overnight at 105° C. Cool the reaction mixture to RT and remove the solvent. Partition the residue between DCM (20 mL) and 2 M aqueous $K_2CO_3$ (20 mL). Separate the organic layer and extract the aqueous layer with DCM (10 mL). Combine the organic layers, wash with saturated aqueous NaCl (10 mL), filter and concentrate to afford 320 mg orange residue. Purify the residue via silica gel chromatography using a gradient of 0 to 50% EtOAc in DCM to give the title compound (250 mg, 89%) as a white solid. ES-MS m/z 604 (M+H).

Preparation 182

(S)-2-(($5^4$-Formyl-3,9-dioxa-2(2,6)-pyridina-1(1,3),5(1,2)-dibenzenacyclononaphane-$1^4$-yl)methyl)-1-(oxetan-2-ylmethyl)-1H-benzo[d]imidazole-6-carboxylic acid

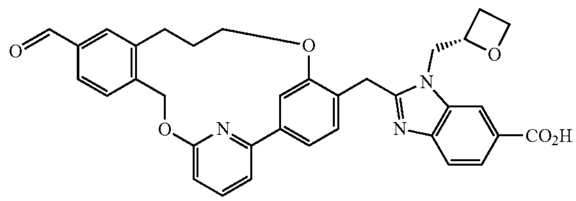 [SMILES: O=Cc1ccc2c(c1)CCCOc1cc(ccc1Cc1nc3ccc(C(=O)O)cc3n1C[C@@H]1CCO1)-c1cccc(n1)OC2]

Add 1 M aqueous LiOH (1.25 mL, 1.25 mmol) to a stirred suspension of methyl (S)-2-(($5^4$-formyl-3,9-dioxa-2(2,6)-pyridina-1(1,3),5(1,2)-dibenzenacyclononaphane-$1^4$-yl)methyl)-1-(oxetan-2-ylmethyl)-1H-benzo[d]imidazole-6-carboxylate (0.25 g, 0.37 mmol, 90 mass %) in THE (5 mL), and MeOH (2.5 mL). Seal the reaction vessel and stir at 60° C. for 2 h. Quench reaction with 1 M aqueous $K_2HIPO_4$ (5 mL), dilute to a volume of 60 mL with water and stir the mixture overnight at ambient temperature. Adjust the reaction pH to 4 by the addition of 5% aqueous citric acid, dilute with saturated aqueous NaCl (50 mL), and extract with DCM (50 mL) then three times with 1:4 isopropanol DCM (50 mL, 25 mL, 25 mL). Combine and concentrate the organic extracts under reduced pressure at 50° C. Dissolve the residue in 1:1 DCM:MeOH, concentrate onto diatomaceous earth and then purify by silica gel chromatography using a gradient of 0 to 20% MeOH in DCM. Concentrate the appropriate fractions under reduced pressure at 50° C. to afford a white residue, then stir the residue in EtOAc (5 mL) for 0.5 h. Collect the solid by filtration and wash with EtOAc (5 mL). Dry the solid at 45° C. under reduced pressure for 21 h to afford the title compound (125 mg, 51%) as a white solid. ES-MS m/z 590 (M+H).

Preparation 183

Methyl (S)-4-methoxy-2-(($1^6$-methyl-$5^6$-(trifluoromethyl)-3,9-dioxa-2(2,6),5(3,2)-dipyridina-1(1,3)-benzenacyclononaphane-$1^4$-yl)methyl)-1-(oxetan-2-ylmethyl)-1H-benzo[d]imidazole-6-carboxylate

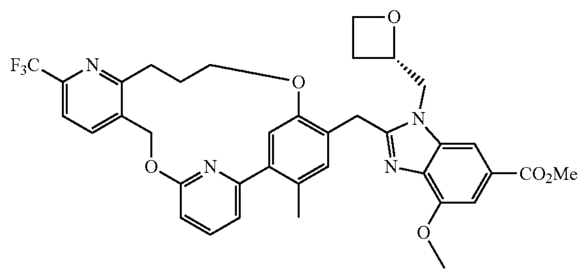 [SMILES: COC(=O)c1cc(OC)c2nc(Cc3cc(C)c4cc3OCCCc3nc(C(F)(F)F)ccc3COc3cccc-4n3)n(C[C@@H]3CCO3)c2c1]

Prepare the title compound essentially as described in Preparation 102 using methyl (S)-3-methoxy-4-(2-($1^6$-methyl-$5^6$-(trifluoromethyl)-3,9-dioxa-2(2,6),5(3,2)-dipyridina-1(1,3)-benzenacyclononaphane-$1^4$-yl)acetamido)-5-((oxetan-2-ylmethyl)amino)benzoate in 1:1 DCM: acetic acid as solvent. Purify the title compound via silica gel chromatography using a gradient of 80 to 100% DCM in hexanes. ES-MS m/z 689 (M+H).

Preparation 184

Methyl (S)-4-methoxy-2-(($1^6$-methyl-3,9-dioxa-2(2,6),5(4,3)-dipyridina-1(1,3)-benzenacyclononaphane-$1^4$-yl)methyl)-1-(oxetan-2-ylmethyl)-1H-benzo[d]imidazole-6-carboxylate

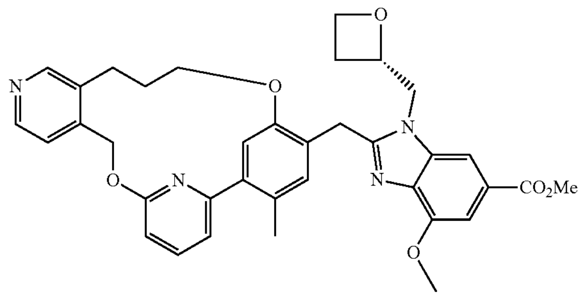 [SMILES: COC(=O)c1cc(OC)c2nc(Cc3cc(C)c4cc3OCCCc3cnccc3COc3cccc-4n3)n(C[C@@H]3CCO3)c2c1]

Prepare the title compound essentially as described in Preparation 102 using methyl (S)-3-methoxy-4-(2-($1^6$-methyl-3,9-dioxa-2(2,6),5(4,3)-dipyridina-1(1,3)-benzenacyclononaphane-$1^4$-yl)acetamido)-5-((oxetan-2-ylmethyl)amino)benzoate (Preparation 172) in 1:1 dichloroethane: acetic acid as solvent. Purify the title compound via silica gel chromatography using a gradient of 80 to 100% EtOAc in DCM. ES-MS m/z 621 (M+H).

Preparation 185

5-(3-Fluoro-4-nitro-phenyl)-1H-tetrazole

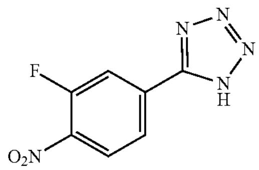 [SMILES: O=[N+]([O-])c1ccc(-c2nnn[nH]2)cc1F]

To a solution of 3-fluoro-4-nitro-benzonitrile (470 mg, 2.8 mmol) and TMSCN (4.5 mL, 33 mmol) in toluene (9 mL) add tributyltin azide (2 mL, 7 mmol), then heat in a microwave reactor at 150° C. for 2 h. Quench the reaction with saturated aqueous $NaHCO_3$ and extract with EtOAc. Dry the organic phase over $MgSO_4$, filter, and concentrate under reduced pressure. Purify the residue via silica gel chromatography using a mixture of DCM/MeOH/formic acid (9:1:0.1) to give 586 mg of the title compound (99%). ES-MS m/z 210 (M+H).

Preparation 186

2-[[5-(3-Fluoro-4-nitro-phenyl)tetrazol-1-yl]methoxy]ethyl-trimethyl-silane

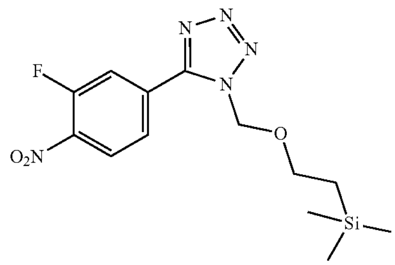 [SMILES: C[Si](C)(C)CCOCn1nnnc1-c1ccc([N+](=O)[O-])c(F)c1]

To a solution of 5-(3-fluoro-4-nitro-phenyl)-1H-tetrazole (860 mg, 4.1 mmol) in THE (12 mL) add sodium hydride (60% in mineral oil, 180 mg, 4.5 mmol) at 0° C. Add 2-(chloromethoxy)ethyl-trimethyl-silane (0.79 mL, 4.5 mmol) to the mixture and stir at RT for 16 h. Quench the reaction with water and extract with EtOAc. Dry the organic phase over $MgSO_4$, filter, and concentrate under reduced pressure. Purify the residue via silica gel chromatography eluting with heptane:EtOAc (8:2) to give 240 mg of the title compound (17%). ES-MS m/z 377 (M+H).

Preparation 187

Fumaric acid; [(2S)-oxetan-2-yl]methanamine

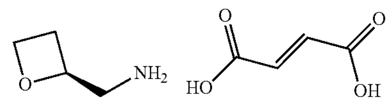 [SMILES: NC[C@@H]1CCO1 ; O=C(O)/C=C/C(=O)O]

Mix [(2S)-oxetan-2-yl]methanamine (3.6 wt % in EtOH, 1500 g, 620 mmol) and fumaric acid (72 g, 620 mmol) at 25° C. under nitrogen for 36 h. Filter off the solid and dry the solid under reduced pressure to give the title compound (65 g, 52%) as a white solid. $^1H$ NMR (400.21 MHz, MeOH-$d_4$) δ 6.72 (s, 2H), 5.02 (ddd, J=14.8, 7.0, 3.7 Hz, 1H), 4.77-4.70 (m, 1H), 4.61 (dt, J=9.0, 6.1 Hz, 1H), 3.27 (dd, J=7.1, 13.4 Hz, 1H), 3.16 (dd, J=3.7, 13.4 Hz, 1H), 2.87-2.81 (m, 1H), 2.60-2.54 (m, 1H).

Preparation 188

2-Nitro-N-[[(2R)-oxetan-2-yl]methyl]-5-[1-(2-trimethylsilylethoxymethyl)tetrazol-5-yl]aniline

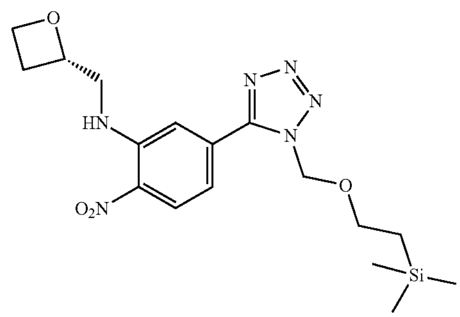 [SMILES: C[Si](C)(C)CCOCn1nnnc1-c1ccc([N+](=O)[O-])c(NC[C@@H]2CCO2)c1]

Stir a solution of fumaric acid; [(2S)-oxetan-2-yl]methanamine (160 mg, 0.79 mmol) and TEA (0.39 mL, 2.8 mmol) in N,N-dimethylacetamide (2 mL) at RT for 1 h. Add 2-[[5-(3-fluoro-4-nitro-phenyl)tetrazol-1-yl]methoxy]ethyl-trimethyl-silane (240 mg, 0.7 mmol) and stir the mixture at 35° C. for 16 h. Quench the reaction with water and extract with EtOAc. Dry the organic phase over $MgSO_4$, filter, and concentrate under reduced pressure. Purify the residue via silica gel chromatography eluting with heptane:EtOAc (1:1) to give 200 mg of the title compound (70%). ES-MS m/z 429 (M+Na).

Preparation 189

N2-[[(2R)-Oxetan-2-yl]methyl]-4-[1-(2-trimethylsilylethoxymethyl)tetrazol-5-yl]benzene-1,2-diamine

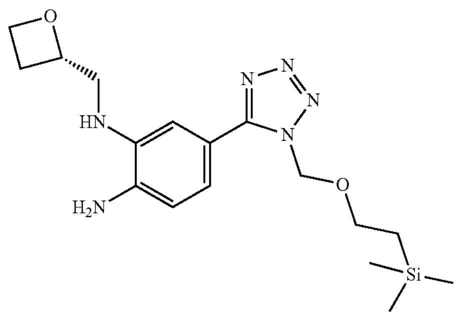

Vigorously stir a mixture of iron (100 mg, 2 mmol), ammonium chloride (7 mg, 0.1 mmol) and acetic acid (30 µL, 0.5 mmol) in water (3 mL) at 50° C. for 15 min. Add 2-nitro-N-[[(2R)-oxetan-2-yl]methyl]-5-[1-(2-trimethylsilylethoxymethyl)tetrazol-5-yl]aniline (100 mg, 0.2 mmol) in DMF (1 mL) and stir the mixture at 50° C. for 1 h. Filter the reaction mixture through Celite® pad, then quench with water and extract with EtOAc. Dry the organic phase over $MgSO_4$, filter, and concentrate under reduced pressure to give 98 mg of the title compound (99%). ES-MS m/z 377 (M+H).

Preparation 190

(S)-2-($5^4$-Cyano-3,9-dioxa-2(2,6)-pyridina-1(1,3),5(1,2)-dibenzenacyclononaphane-$1^4$-yl)-N-(2-((oxetan-2-ylmethyl)amino)-4-(1-((2-(trimethylsilyl)ethoxy)methyl)-1H-tetrazol-5-yl)phenyl)acetamide

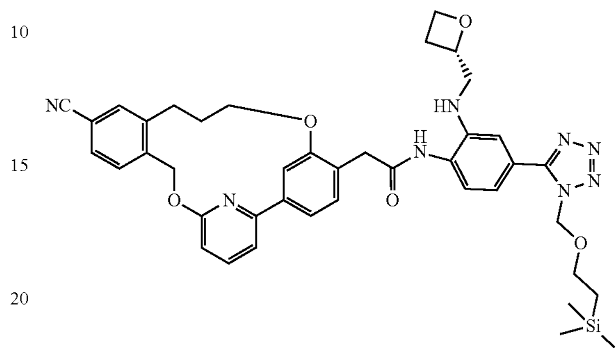

To a solution of 2-($5^4$-cyano-3,9-dioxa-2(2,6)-pyridina-1(1,3),5(1,2)-dibenzenacyclononaphane-$1^4$-yl)acetic acid (100 mg, 0.25 mmol), N2-[[(2R)-oxetan-2-yl]methyl]-4-[1-(2-trimethylsilylethoxymethyl)tetrazol-5-yl]benzene-1,2-diamine (98 mg, 0.26 mmol) and TEA (104 µL, 0.75 mmol) in DMF (2 mL), add HATU (142 mg, 0.37 mmol). Stir the mixture at RT for 1 h. Quench the reaction with water and extract with EtOAc. Dry the organic phase over $MgSO_4$, filter, and concentrate under reduced pressure to give 190 mg of the title compound (99%). LC-MS retention time=2.17 min.

Preparation 191

(S)-$1^4$-((1-(Oxetan-2-ylmethyl)-6-(1-((2-(trimethylsilyl)ethoxy)methyl)-1H-tetrazol-5-yl)-1H-benzo[d]imidazol-2-yl)methyl)-3,9-dioxa-2(2,6)-pyridina-1(1,3),5(1,2)-dibenzenacyclononaphane-$5^4$-carbonitrile

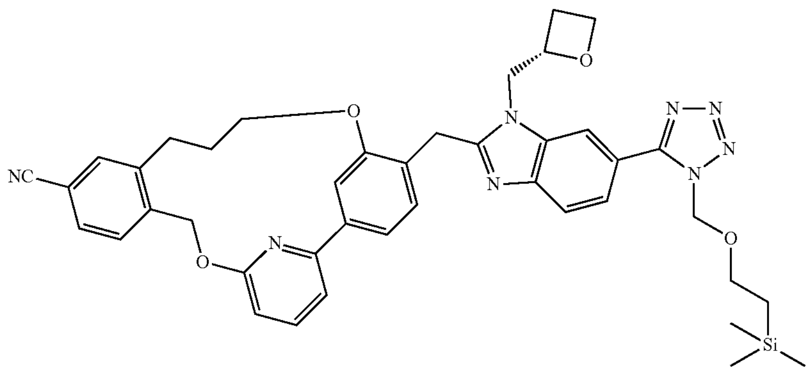 [SMILES: C[Si](C)(C)CCOCn1nnnc1-c1ccc2nc(Cc3ccc4cc3OCCCc3cc(C#N)ccc3COc3cccc-4n3)n(C[C@@H]3CCO3)c2c1]

Prepare the title compound essentially as described in Preparation 102 using (S)-2-($5^4$-cyano-3,9-dioxa-2(2,6)-pyridina-1(1,3),5(1,2)-dibenzenacyclononaphane-$1^4$-yl)-N-(2-((oxetan-2-ylmethyl)amino)-4-(1-((2-(trimethylsilyl)ethoxy)methyl)-1H-tetrazol-5-yl)phenyl)acetamide in 1:1 1,2-dichloroethane:acetic acid as solvent, heating the reaction at 85° C. for 16 h. Concentrate the mixture under reduced pressure. Purify the residue via silica gel chromatography using a gradient of 0 to 100% EtOAc in heptane to give the title compound. ES-MS m/z 741 (M+H).

Preparation 192

1-Bromo-4-(bromomethyl)-2-fluoro-5-iodo-benzene

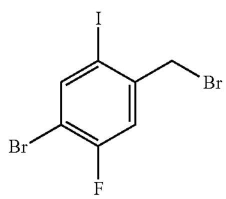 [SMILES: Fc1cc(CBr)c(I)cc1Br]

Add N-bromosuccinimide (26.84 g, 150.8 mmol) to a solution of 4-bromo-5-fluoro-2-iodotoluene (25 g, 75.4 mmol) in chloroform (30 mL); then, add 2,2'-azobis(2-methylpropionitrile) (1.26 g, 7.54 mmol) and heat the reaction at 80° C. for 5 h. Cool to RT, add saturated solution of $NaHCO_3$ (300 mL) and extract with DCM (200 mL). Combine the organics, dry over $MgSO_4$, filter, and concentrate under reduced pressure. Purify the residue via silica gel chromatography using heptane as eluent to give 16.04 g (54% yield) of the title compound. $^1H$ NMR (400.13 MHz, $CDCl_3$) δ 8.05 (d, J=6.8 Hz, 1H), 7.29 (d, J=9.00, 1H), 4.51 (s, 2H).

Preparation 193

2-(4-Bromo-5-fluoro-2-iodo-phenyl)acetonitrile

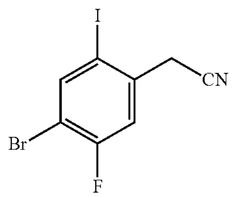 [SMILES: N#CCc1cc(F)c(Br)cc1I]

To a solution of 1-bromo-4-(bromomethyl)-2-fluoro-5-iodo-benzene (16.04 g, 40.74 mmol) and TMSCN (7.24 mL, 53 mmol) in ACN (110 mL), add slowly TBAF (1 M in THF, 53 mL, 53 mmol). Heat the reaction at 40° C. for 3 h. Evaporate the solvents under reduced pressure, dissolve the residue in EtOAc (150 mL) and wash the organics with saturated aqueous NaCl (3×50 mL). Dry the organics over $MgSO_4$, filter, and concentrate under reduced pressure. Purify the residue via silica gel chromatography using a gradient of EtOAc in heptane from 0 to 15% to afford the title compound as an orange oil (10.34 g, 69%). ES-MS m/z 340/342 (M+H).

Preparation 194

Ethyl 2-(4-bromo-5-fluoro-2-iodo-phenyl)acetate

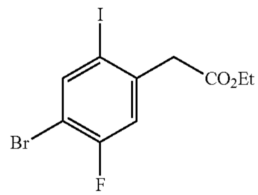 [SMILES: CCOC(=O)Cc1cc(F)c(Br)cc1I]

To a solution of 2-(4-bromo-5-fluoro-2-iodo-phenyl)acetonitrile (10.34 g, 30.43 mmol) in 8 M EtOH in water (92 mL), add sulfuric acid (24 mL) at RT. Heat the reaction mixture at 80° C. for 18 h. Cool the mixture to RT, basify the reaction by addition of saturated aqueous $NaHCO_3$ up to pH >7, and extract with DCM (3×50 mL). Combine the organics, wash with water and saturated aqueous NaCl, dry over $MgSO_4$, filter, and concentrate under reduced pressure. Purify the residue via silica gel chromatography using a gradient of EtOAc in heptane from 0 to 10% to give 8.88 g (75%) of the title compound as a white solid. ES-MS m/z 387/389 (M+H).

Preparation 195

Ethyl 2-[4-bromo-2-[2-ethoxyvinyl]-5-fluoro-phenyl]acetate

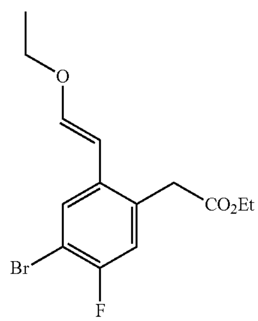 [SMILES: CCO/C=C/c1cc(Br)c(F)cc1CC(=O)OCC]

Add tetrakis(triphenylphosphine)palladium(0) (1.3 g, 1.1 mmol), $Cs_2CO_3$ (7.4 g, 23 mmol) and 2-(2-ethoxyvinyl)-4,4,5,5-tetramethyl-1,3,2-dioxaborolane (3.3 mL, 15 mmol) to a solution of ethyl 2-(4-bromo-5-fluoro-2-iodo-phenyl)acetate (4.37 g, 11.31 mmol) in 1,4-dioxane (80 mL) under nitrogen. Heat the mixture at 90° C. for 5 h. Dilute the mixture with water (100 mL) and extract with EtOAc (100 mL). Combine the organics, dry over $MgSO_4$, filter, and concentrate under reduced pressure. Purify the residue via silica gel chromatography using a gradient of EtOAc in heptane from 0 to 10% to give 2.51 g (67%) of the title compound as a yellow oil. ES-MS m/z 331/333 (M+H).

Preparation 196

Ethyl 2-[4-bromo-5-fluoro-2-(2-hydroxyethyl)phenyl]acetate

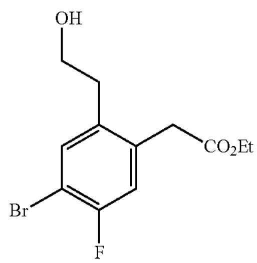 [SMILES: CCOC(=O)Cc1cc(F)c(Br)cc1CCO]

To a solution of ethyl 2-[4-bromo-2-[2-ethoxyvinyl]-5-fluoro-phenyl]acetate (2.51 g, 7.59 mmol) in THE (45 mL) at 0° C., add mercuric acetate (6.3 g, 19 mmol) and stir for 2 h at 0° C. Meanwhile, add sodium borohydride (520 mg, 13.75 mmol) to a solution of $K_2CO_3$ (60 g) in water (56 mL), and add this mixture to the previous reaction with the starting material. Stir the reaction at RT for 40 min, then dilute with water (50 mL) and extract with EtOAc (3×50 mL). Combine the organics, dry over $MgSO_4$, filter, and concentrate under reduced pressure. Purify the residue via silica gel chromatography using a gradient of EtOAc in heptane from 0 to 25% to afford the title compound as a colorless oil (1.31 g, 40% yield). ES-MS m/z 305/307 (M+H).

Preparation 197

4-Formyl-3-hydroxy-benzonitrile

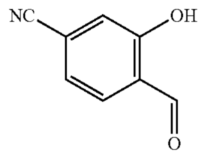 [SMILES: N#Cc1ccc(C=O)c(O)c1]

To a solution of 4-cyano-2-methoxybenzaldehyde (13 g, 79.86 mmol) in DCM (480 mL), add boron tribromide (100 g, 399.16 mmol) at −10° C. in batches. Stir the reaction at RT for 3 days, cool to 0° C., and slowly add water (21 mL). Dilute the reaction with water (100 mL) and extract with DCM (3×100 mL). Combine the organics, dry over $MgSO_4$, filter, and concentrate under reduced pressure. Purify the residue via silica gel chromatography using a gradient of 0 to 20% EtOAc in heptane to give 7.61 g (65%) of the title compound. ES-MS m/z 148 (M+H).

Preparation 198

4-Formyl-3-(2-trimethylsilylethoxymethoxy)benzonitrile

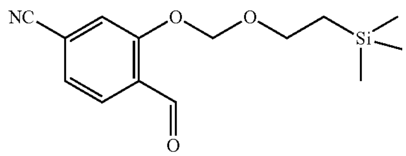 [SMILES: C[Si](C)(C)CCOCOc1cc(C#N)ccc1C=O]

Add DIPEA (9.5 mL, 54 mmol) and 2-(trimethylsilyl)ethoxymethyl chloride (5.3 mL, 30 mmol) to a solution of 4-formyl-3-hydroxy-benzonitrile (4 g, 27.18 mmol) in DCM (68 mL) and diethyl ether (30 mL). Stir the reaction mixture for 3 h at RT. Dilute the reaction with saturated aqueous $NH_4Cl$ and extract with DCM (3×50 mL). Combine the organics, wash with water and saturated aqueous NaCl, dry over $MgSO_4$, filter, and concentrate under reduced pressure. Purify the residue via silica gel chromatography using a gradient of 0 to 20% EtOAc in heptane to afford the title compound (5.67 g, 75%). ES-MS m/z 278 (M+H).

Preparation 199

4-(Hydroxymethyl)-3-(2-trimethylsilylethoxymethoxy)benzonitrile

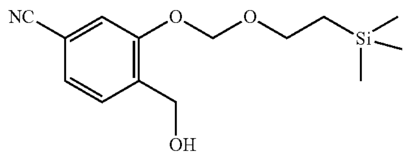 [SMILES: C[Si](C)(C)CCOCOc1cc(C#N)ccc1CO]

To a solution of 4-formyl-3-(2-trimethylsilylethoxymethoxy)benzonitrile (5.67 g, 20.4 mmol) in THE (30 mL) and MeOH (30 mL) at 0° C., add sodium borohydride (1.6 g, 42 mmol) in batches. Stir the reaction mixture for 1 h, then add water (50 mL) and extract with EtOAc (3×50 mL). Combine the organics, wash with water and saturated aqueous NaCl, dry over $MgSO_4$, filter, and concentrate under reduced pressure to give 5.55 g (97%) of the title compound. ES-MS m/z 280 (M+H).

Preparation 200

4-[(6-Bromo-2-pyridyl)oxymethyl]-3-(2-trimethylsilylethoxymethoxy)benzonitrile

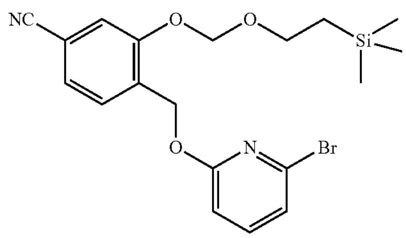 [SMILES: C[Si](C)(C)CCOCOc1cc(C#N)ccc1COc1cccc(Br)n1]

Add sodium hydride (60% in mineral oil, 500 mg, 12.5 mmol) to a solution of 4-(hydroxymethyl)-3-(2-trimethylsilylethoxymethoxy)benzonitrile (2.65 g, 9.48 mmol) in THE (60 mL) at RT. Stir the mixture for 30 min, then add 2-bromo-6-fluoropyridine (1.7 g, 9.5 mmol) and heat the reaction at 60° C. for 3 h. Cool the reaction to ambient temperature, dilute with water (50 mL) and extract with EtOAc (3×50 mL). Combine the organics, wash with water and saturated aqueous NaCl, dry over $MgSO_4$, filter, and concentrate under reduced pressure. Purify the residue via silica gel chromatography using a gradient of 0 to 10% EtOAc in heptane to give 3.18 g (77%) of the title compound. $^1H$ NMR (400.13 MHz, $CDCl_3$) δ 7.57 (d, J=7.6 Hz, 1H), 7.46 (m, 2H), 7.32 (d, J=8 Hz, 1H), 7.11 (d, J=7.2 Hz, 1H), 6.77 (d, J=8 Hz, 1H), 5.44 (s, 2H), 5.31 (s, 2H); 3.78 (t, J=8.4 Hz, 2H), 0.98 (t, J=8.4 Hz, 2H). 0.02 (s, 9H).

Preparation 201

4-[(6-Bromo-2-pyridyl)oxymethyl]-3-hydroxy-benzonitrile

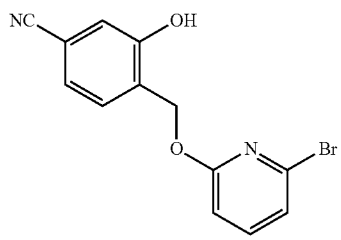 [SMILES: N#Cc1ccc(COc2cccc(Br)n2)c(O)c1]

Add carbon tetrabromide (364 mg, 1.1 mmol) to a solution of 4-[(6-bromo-2-pyridyl)oxymethyl]-3-(2-trimethylsilylethoxymethoxy)benzonitrile (3.18 g, 7.31 mmol) in 2-propanol (75 mL). Heat the reaction mixture at 80° C. for 10 h, then concentrate solvents under reduced pressure and purify the residue via silica gel chromatography using a gradient of 0 to 20% EtOAc in heptane to afford the title compound as a white solid (1.72 g, 57%). ES-MS m/z 305/307 (M+H).

Preparation 202

Ethyl 2-[4-bromo-2-[2-[2-[(6-bromo-2-pyridyl)oxymethyl]-5-cyano-phenoxy]ethyl]-5-fluoro-phenyl]acetate

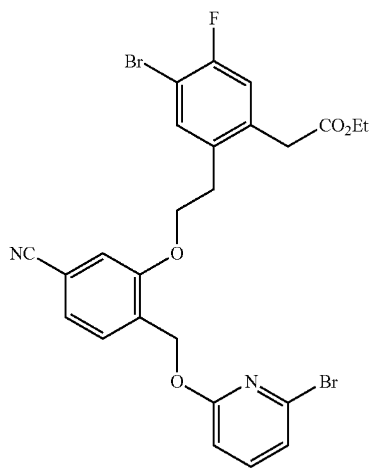 [SMILES: CCOC(=O)Cc1cc(F)c(Br)cc1CCOc1cc(C#N)ccc1COc1cccc(Br)n1]

To a solution of ethyl 2-[4-bromo-5-fluoro-2-(2-hydroxyethyl)phenyl]acetate (519 mg, 1.70 mmol), 4-[(6-bromo-2-pyridyl)oxymethyl]-3-hydroxy-benzonitrile (500 mg, 1.64 mmol) and triphenylphosphine (645 mg, 2.46 mmol) in THE (17 mL), add at 0° C. DEAD (40% in toluene, 0.97 mL, 2.46 mmol) diluted in THE (1 mL). Stir the reaction mixture at RT overnight. After 14 h, add more DEAD (40% in toluene, 0.53 mL, 1.36 mmol) diluted in THE (1 mL) at 0° C. After 20 h at RT, dilute the reaction mixture with water (25 mL) and extract with EtOAc (3×10 mL). Combine the organics, filter, and concentrate under reduced pressure. Purify the residue via silica gel chromatography using a gradient of 10 to 30% EtOAc in heptane to give 444 mg (44%) of the title compound as a white solid. ES-MS m/z 591/593/595 (M+H).

Preparation 203

Ethyl 2-($5^4$-cyano-$1^6$-fluoro-3,6-dioxa-2(2,6)-pyridina-1(1,3),5(1,2)-dibenzenacyclooctaphane-$1^4$-yl)acetate

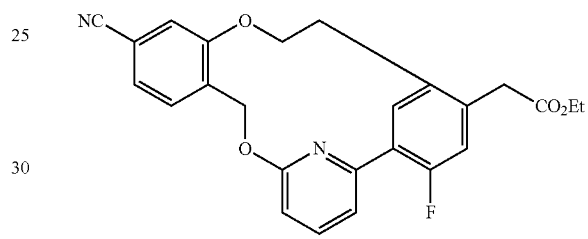

In two different batches, bubble nitrogen through a solution of ethyl 2-[4-bromo-2-[2-[2-[(6-bromo-2-pyridyl)oxymethyl]-5-cyano-phenoxy]ethyl]-5-fluoro-phenyl]acetate (299 mg, 0.50 mmol) in 1,4-dioxane (10 mL) then add hexamethylditin (0.16 mL, 0.76 mmol) and $Pd(dppf)Cl_2$ DCM complex (100 mg, 0.12 mmol). Heat the reaction mixture batches at 100° C. for 3 h. Cool both batches to RT and combine them. Dilute with water and extract three times with EtOAc. Combine the organics, wash with water and saturated aqueous NaCl, dry over MgSO4, filter, and concentrate under reduced pressure. Purify the residue via silica gel chromatography using a gradient of 10 to 20% EtOAc in heptane to afford the title compound as a white solid (90 mg, 41%). ES-MS m/z 433 (M+H).

Preparation 204

2-($5^4$-Cyano-$1^6$-fluoro-3,6-dioxa-2(2,6)-pyridina-1(1,3),5(1,2)-dibenzenacyclooctaphane-$1^4$-yl)acetic acid

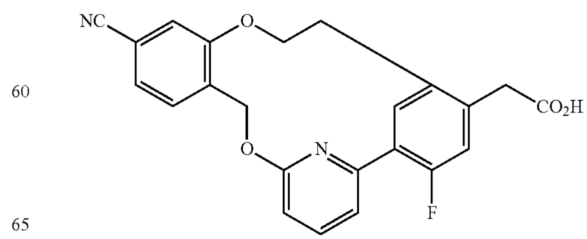

Prepare the title compound essentially as described in Preparation 75 using ethyl 2-($5^4$-cyano-$1^6$-fluoro-3,6-dioxa-2(2,6)-pyridina-1(1,3),5(1,2)-dibenzenacyclooctaphane-$1^4$-yl)acetate, heating the reaction at 45° C. for 3 h. Add formic acid to the mixture until pH=5-6, dilute with water, and extract three times with 3:1 DCM:isopropanol. Combine the organics, wash with water and saturated aqueous NaCl, dry over MgSO4, filter, and concentrate under reduce pressure to afford the title compound as a white solid. ES-MS m/z 405 (M+H).

Preparation 205

Methyl (S)-4-(2-($5^4$-cyano-$1^6$-fluoro-3,6-dioxa-2(2,6)-pyridina-1(1,3),5(1,2)-dibenzenacyclooctaphane-$1^4$-yl)acetamido)-3-((oxetan-2-ylmethyl)amino)benzoate

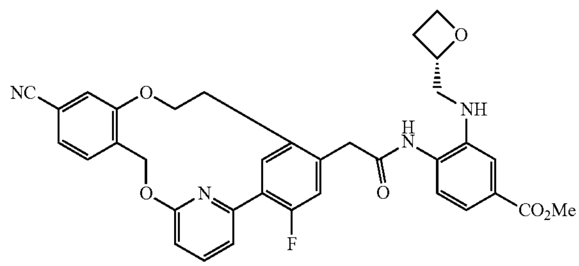 [SMILES: COC(=O)c1ccc(NC(=O)Cc2cc(F)c3cc2CCOc2cc(C#N)ccc2COc2cccc-3n2)c(NC[C@@H]2CCO2)c1]

To a solution of 2-($5^4$-cyano-$1^6$-fluoro-3,6-dioxa-2(2,6)-pyridina-1(1,3),5(1,2)-dibenzenacyclooctaphane-$1^4$-yl)acetic acid (82 mg, 0.20 mmol) and methyl 4-amino-3-[[(2S)-oxetan-2-yl]methylamino]benzoate (48 mg, 0.20 mmol) in DMF (2 mL), add DIPEA (0.10 mL, 0.58 mmol) and HATU (115 mg, 0.30 mmol). After 24 h stirring at RT, add more DIPEA (0.055 mL, 0.31 mmol) and HATU (60 mg, 0.15 mmol). After 30 h, add water and EtOAc, and extract the mixture three times with EtOAc. Combine the organics, wash with water and saturated aqueous NaCl, dry over $MgSO_4$, filter, and concentrate under reduced pressure to give the title compound (200 mg, >100%) which is used without further purification in Preparation 206. ES-MS m/z 623 (M+H).

Preparation 206

Methyl (S)-2-(($5^4$-cyano-$1^6$-fluoro-3,6-dioxa-2(2,6)-pyridina-1(1,3),5(1,2)-dibenzenacyclooctaphane-$1^4$-yl)methyl)-1-(oxetan-2-ylmethyl)-1H-benzo[d]imidazole-6-carboxylate

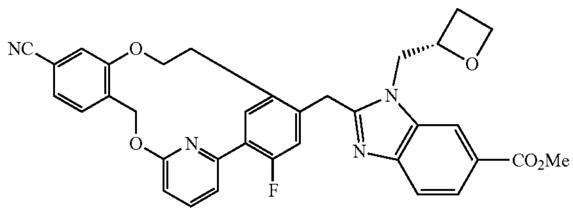 [SMILES: COC(=O)c1ccc2nc(Cc3cc(F)c4cc3CCOc3cc(C#N)ccc3COc3cccc-4n3)n(C[C@@H]3CCO3)c2c1]

Add acetic acid (6 mL) to methyl (S)-4-(2-($5^4$-cyano-$1^6$-fluoro-3,6-dioxa-2(2,6)-pyridina-1(1,3),5(1,2)-dibenzenacyclooctaphane-$1^4$-yl)acetamido)-3-((oxetan-2-ylmethyl)amino)benzoate (Preparation 205, 200 mg, 0.32 mmol), and stir at 65° C. for 2 h. Cool the mixture to RT, evaporate the solvent under reduced pressure and purify the residue via silica gel chromatography using a gradient of 0 to 20% EtOAc in DCM to give 92 mg (47%) of the title compound. ES-MS m/z 605 (M+H).

Preparation 207

Ethyl 3-amino-5-bromo-pyridine-2-carboxylate

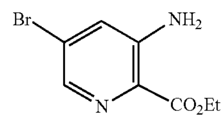

Slowly add sulfuric acid (52 mL, 927 mmol) to a solution of 3-amino-5-bromopyridine-2-carboxylic acid (15 g, 65.66 mmol) in 8M ethanol in water (197 mL). Heat the reaction at 80° C. for 18 h. Cool the mixture to RT, then slowly add NaOH (2 M aqueous) until pH=8, and extract with EtOAc (3×100 mL). Combine the organics, dry over $MgSO_4$, filter, and concentrate under reduced pressure to give the title compound as a pale-yellow solid (13.93 g, 86%). ES-MS m/z 245/247 (M+H).

Preparation 208

(3-Amino-5-bromo-2-pyridyl)methanol

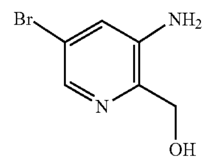

To a solution of ethyl 3-amino-5-bromo-pyridine-2-carboxylate (13.93 g, 56.84 mmol) in THE (230 mL) and MeOH (23 mL) at 0° C., add portion wise lithium borohydride (3.75 g, 172 mmol). Stir the reaction at RT for 1 h. Add saturated solution of $NaHCO_3$ and extract with EtOAc (5×100 mL). Combine the organics, dry over magnesium sulfate, filter, and concentrate under reduced pressure. Add ACN to the residue and filter the resulting slurry, washing the solid with ACN, then dry the solid under vacuum to afford 9.87 g (81%) of the title compound as a beige solid. ES-MS m/z 203/205 (M+H).

Preparation 209

(5-Bromo-3-iodo-2-pyridyl)methanol

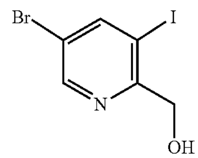

Add 4-methylbenzenesulfonic acid, hydrate (27.81 g, 146.2 mmol) to a suspension of (3-amino-5-bromo-2-pyridyl)methanol (9.87 g, 48.63 mmol) in ACN (170 mL). Stir the mixture for 10 min, then cool to 0° C. Add sodium nitrite (6.72 g, 97.4 mmol) in water (20 mL) to the mixture, then add potassium iodide (20.48 g, 123.4 mmol) in water (20 mL). Stir the reaction at 0° C. for 10 min, then 2 h at RT. Add a saturated aqueous solution of $NaHCO_3$ to the mixture and extract with EtOAc (3×100 mL). Combine the organics, wash with 5% aqueous sodium bisulfite, water, and saturated aqueous NaCl, dry over $MgSO_4$, then filter and concentrate under reduced pressure. Triturate the resulting solid with ACN, then filter and dry the solid under vacuum to give the title compound as a brownish solid (10.31 g, 61%). ES-MS m/z 314/316 (M+H).

Preparation 210

[5-Bromo-3-[3-[tert-butyl(dimethyl)silyl]oxyprop-1-ynyl]-2-pyridyl]methanol

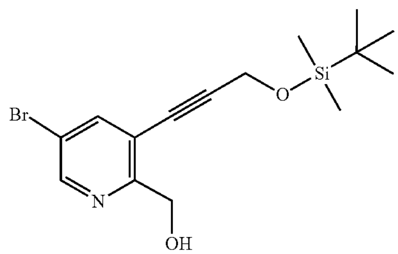 [SMILES: CC(C)(C)[Si](C)(C)OCC#Cc1cc(Br)cnc1CO]

Add bis(triphenylphosphine)palladium (II) dichloride (2.64 g, 3.73 mmol), cuprous iodide (0.71 g, 3.76 mmol) and TEA (31 mL, 225 mmol) to a solution of (5-bromo-3-iodo-2-pyridyl)methanol (11.78 g, 37.53 mmol) under nitrogen at RT. Add tert-butyildimethyl(2-propynyloxy)silane (10 mL, 48 mmol) then heat the reaction at 40° C. for 20 h. Cool the reaction to RT, add water and brine, then extract the mixture three times with EtOAc. Combine the organics, dry over $MgSO_4$, filter, and concentrate under reduced pressure. Purify the residue via silica gel chromatography using a gradient of 0 to 20% EtOAc in heptane to give 9.03 g (67%) of the title compound as a brown oil. ES-MS m/z 356/358 (M+H).

Preparation 211

5-[3-[tert-Butyl(dimethyl)silyl]oxyprop-1-ynyl]-6-(hydroxymethyl)pyridine-3-carbonitrile

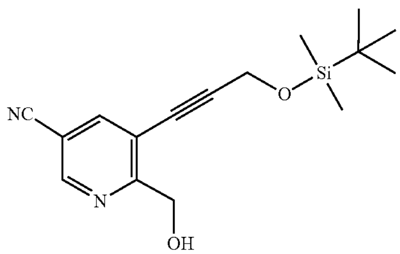 [SMILES: CC(C)(C)[Si](C)(C)OCC#Cc1cc(C#N)cnc1CO]

Add zinc cyanide (2.09 g, 17.85 mmol) to a solution of [5-bromo-3-[3-[tert-butyl(dimethyl)silyl]oxyprop-1-ynyl]-2-pyridyl]methanol (9.03 g, 25.26 mmol) in DMF (180 mL) under nitrogen, then add tetrakis(triphenylphosphine)palladium(0) (2.93 g, 2.54 mmol). Heat the reaction at 100° C. for 2 h. Cool the mixture to RT, add water and saturated aqueous NaCl and extract the mixture three times with EtOAc. Combine the organics, dry over $MgSO_4$, filter, and concentrate under reduced pressure. Purify the residue via silica gel chromatography using a gradient of 0 to 25% EtOAc in heptane to afford 4.6 g (60%) of the title compound as a brown oil. ES-MS m/z 303 (M+H).

Preparation 212

6-[(6-Bromo-2-pyridyl)oxymethyl]-5-[3-[tert-butyl(dimethyl)silyl]oxyprop-1-ynyl]pyridine-3-carbonitrile

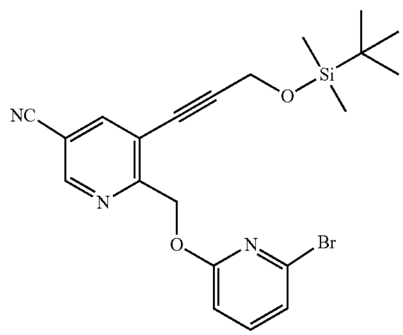 [SMILES: CC(C)(C)[Si](C)(C)OCC#Cc1cc(C#N)cnc1COc1cccc(Br)n1]

Prepare the title compound essentially as described in Preparation 34 using 5-[3-[tert-butyl(dimethyl)silyl]oxyprop-1-ynyl]-6-(hydroxymethyl)pyridine-3-carbonitrile. Upon completion, cool the reaction to RT, evaporate the solvent under reduced pressure and purify the residue via silica gel chromatography using a gradient of 0 to 15% EtOAc in heptane to give the title compound as a pale yellow solid. ES-MS m/z 458/460 (M+H).

Preparation 213

6-[(6-Bromo-2-pyridyl)oxymethyl]-5-(3-hydroxyprop-1-ynyl)pyridine-3-carbonitrile

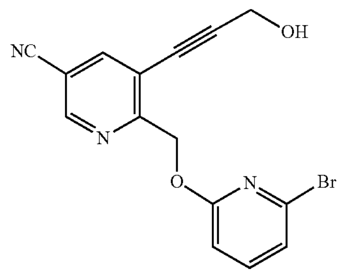 [SMILES: N#Cc1cnc(COc2cccc(Br)n2)c(C#CCO)c1]

Add 1M TBAF in THE (16.1 mL, 16.1 mmol) to a solution of 6-[(6-bromo-2-pyridyl)oxymethyl]-5-[3-[tert-butyl(dimethyl)silyl]oxyprop-1-ynyl]pyridine-3-carbonitrile (6.15 g, 13.42 mmol) in THE (40 mL). Stir the mixture at RT for 7 h. Add saturated aqueous solution of $NaHCO_3$ and extract the mixture three times with EtOAc. Combine the organics, wash with water and saturated aqueous NaCl, dry over $MgSO_4$, filter, and concentrate under reduced pressure. Purify the residue via silica gel chromatography using a gradient of 0 to 50% EtOAc in heptane to afford 3.04 g (66%) of the title compound as a colorless oil. ES-MS m/z 344/346 (M+H).

Preparation 214

6-[(6-Bromo-2-pyridyl)oxymethyl]-5-(3-hydroxy-propyl)pyridine-3-carbonitrile

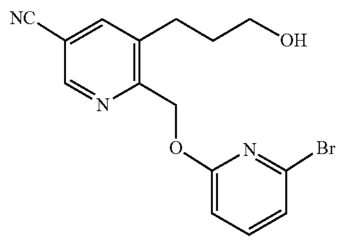 [SMILES: N#Cc1cnc(COc2cccc(Br)n2)c(CCCO)c1]

Add platinum oxide (0.06 g, 0.26 mmol) to a solution of 6-[(6-bromo-2-pyridyl)oxymethyl]-5-(3-hydroxyprop-1-ynyl)pyridine-3-carbonitrile (0.65 g, 1.88 mmol) in MeOH (18 mL) and two drops of acetic acid. Charge the reaction vessel with an atmosphere of hydrogen (15 psi) and stir the mixture at RT for 5 h. Filter the reaction through a pad of Celite® washing with MeOH and EtOAc. Evaporate the filtrate under vacuum and purify the residue via silica gel chromatography using a gradient of 0 to 30% EtOAc in heptane to give the title compound (0.33 g, 51%). ES-MS m/z 348/350 (M+H).

Preparation 215

Ethyl 2-[4-bromo-2-[3-[2-[(6-bromo-2-pyridyl)oxymethyl]-5-cyano-3-pyridyl]propoxy]-5-fluoro-phenyl]acetate

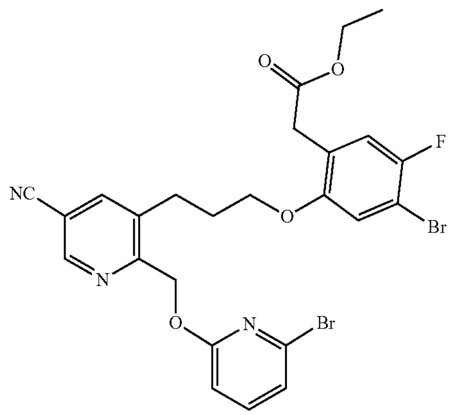 [SMILES: CCOC(=O)Cc1cc(F)c(Br)cc1OCCCc1cc(C#N)cnc1COc1cccc(Br)n1]

Prepare the title compound essentially as described in Preparation 60 using 6-[(6-bromo-2-pyridyl)oxymethyl]-5-(3-hydroxypropyl)pyridine-3-carbonitrile (1.01 g, 2.9 mmol), eliminating the MeOH quench step, giving the title compound as a white solid. ES-MS m/z 606/608 (M+H).

Preparation 216

Ethyl 2-($5^5$-cyano-$1^6$-fluoro-3,9-dioxa-2(2,6),5(2,3)-dipyridina-1(1,3)-benzenacyclononaphane-$1^4$-yl)acetate

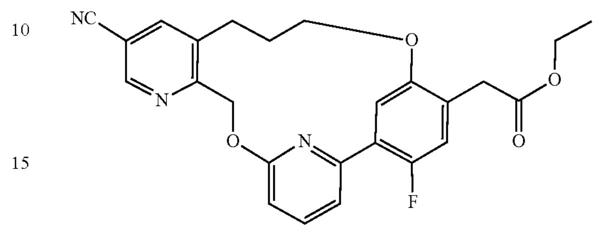

To a mixture of ethyl 2-[4-bromo-2-[3-[2-[(6-bromo-2-pyridyl)oxymethyl]-5-cyano-3-pyridyl]propoxy]-5-fluoro-phenyl]acetate (0.75 g, 1.23 mmol), cesium fluoride (203 mg, 1.33 mmol), and hexamethylditin (321 mg, 0.98 mmol) in 1,4-dioxane (55 mL) under nitrogen, add chloro(2-dicyclohexylphosphino-2',4',6'-triisopropyl-1,1'-biphenyl)[2-(2'-amino-1,1'-biphenyl)]palladium(II) (XPhos Pd G2, 75.2 mg, 0.094 mmol). Heat the reaction mixture at 100° C. for 18 h. Cool the mixture to RT, filter through a pad of Celite®, wash with EtOAc (2×100 mL) and MeOH (2×100 mL). Evaporate the filtrate and purify the residue via silica gel chromatography using a gradient of 0 to 50% EtOAc in heptane to afford 0.27 g (49%) of the title compound as a light-yellow solid. ES-MS m/z 448 (M+H).

Preparation 217

2-($5^5$-Cyano-$1^6$-fluoro-3,9-dioxa-2(2,6),5(2,3)-dipyridina-1(1,3)-benzenacyclononaphane-$1^4$-yl)acetic acid

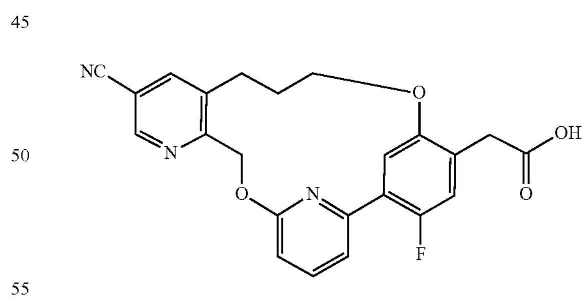

To a mixture of ethyl 2-($5^5$-cyano-$1^6$-fluoro-3,9-dioxa-2(2,6),5(2,3)-dipyridina-1(1,3)-benzenacyclononaphane-$1^4$-yl)acetate (0.12 g, 0.27 mmol) in ACN (3.2 mL), THE (0.8 mL) and water (0.5 mL), add 1,3,4,6,7,8-hexahydro-2H-pyrimido[1,2-a]pyrimidine (0.075 g, 0.54 mmol). Heat the suspension at 45° C. for 2 h. Cool the mixture to RT, add formic acid until pH=4, and extract with EtOAc (3×5 mL). Combine the organics, wash with water and saturated aqueous NaCl, dry over $MgSO_4$, filter, and concentrate under reduced pressure to give the title compound as a white solid (0.11 g, 98%). ES-MS m/z 420 (M+H).

Preparation 218

Methyl (S)-4-(2-($5^5$-cyano-$1^6$-fluoro-3,9-dioxa-2(2,6),5(2,3)-dipyridina-1(1,3)-benzenacyclononaphane-$1^4$-yl)acetamido)-3-methoxy-5-((oxetan-2-ylmethyl)amino)benzoate

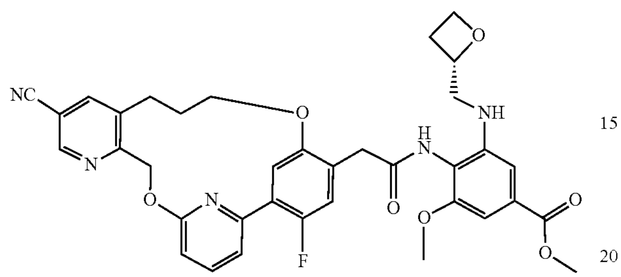

To a solution of 2-($5^5$-cyano-$1^6$-fluoro-3,9-dioxa-2(2,6),5(2,3)-dipyridina-1(1,3)-benzenacyclononaphane-$1^4$-yl) acetic acid (0.11 g, 0.26 mmol) and methyl 4-amino-3-methoxy-5-[[(2S)-oxetan-2-yl]methylamino]benzoate (0.077 g, 0.29 mmol) in DMF (1.3 mL), add DIPEA (0.13 mL, 0.74 mmol) and HATU (0.16 g, 0.40 mmol). Stir the reaction at RT for 16 h. Add saturated aqueous $NaHCO_3$ solution and extract with EtOAc (2×40 mL). Combine the organics, dry over $MgSO_4$, filter, and concentrate under reduced pressure to give the title compound as a beige solid (0.22 g), which is used in Preparation 219 without further purification. ES-MS m/z 668 (M+H).

Preparation 219

Methyl (S)-2-(($5^5$-cyano-$1^6$-fluoro-3,9-dioxa-2(2,6),5(2,3)-dipyridina-1(1,3)-benzenacyclononaphane-$1^4$-yl)methyl)-4-methoxy-1-(oxetan-2-ylmethyl)-1H-benzo[d]imidazole-6-carboxylate

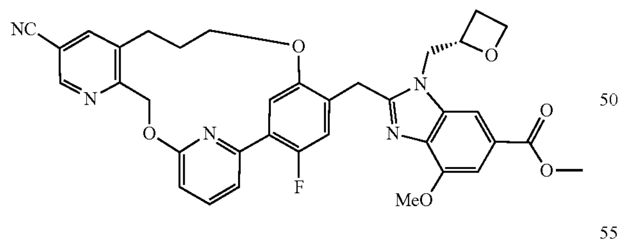

Prepare the title compound essentially as described in Preparation 102 using methyl (S)-4-(2-($5^5$-cyano-$1^6$-fluoro-3,9-dioxa-2(2,6),5(2,3)-dipyridina-1(1,3)-benzenacyclononaphane-$1^4$-yl)acetamido)-3-methoxy-5-((oxetan-2-ylmethyl)amino)benzoate (Preparation 218) heating the reaction at 100° C. for 2 h. Upon completion, cool the reaction to RT, add ACN and evaporate. Repeat this operation three times to ensure acetic acid removal. Purify the residue via silica gel chromatography using a gradient of 0 to 100% EtOAc in heptane to give the title compound as a light brown solid. ES-MS m/z 650 (M+H).

Preparation 220

4-[(6-Chloro-2-pyridyl)oxymethyl]-3-iodo-benzonitrile

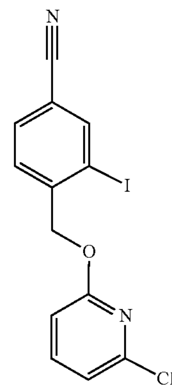

Stir a mixture of 4-(bromomethyl)-3-iodo-benzonitrile (20.0 g, 62.1 mmol), 6-chloropyridin-2-ol (8.45 g, 65.2 mmol) and silver carbonate (17.1 g, 62.0 mmol) in 1,4-dioxane (400 mL) for 20 h at 70° C. Add more 6-chloropyridin-2-ol (1.61 g, 12.4 mmol) and silver carbonate (3.5 g, 13 mmol) and stir the mixture for 5 h at 70° C. Cool the mixture to RT and filter through a silica gel plug using DCM as eluent to yield the title compound as a pale yellow solid (24.6 g, 107%). ES-MS m/z 371.0/373.0 (M+H).

Preparation 221

4-[(6-Chloro-2-pyridyl)oxymethyl]-3-formyl-benzonitrile

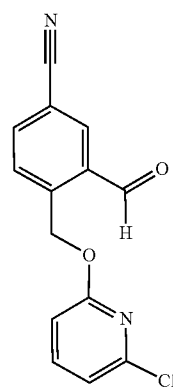

To a mixture of 4-[(6-chloro-2-pyridyl)oxymethyl]-3-iodo-benzonitrile (15.0 g, 40.5 mmol), 1,4-diazabicyclo[2.2.2]octane (460 mg, 4.06 mmol) and potassium formate (6.90 g, 81.2 mmol) in DMF (180 mL) add tert-butyl isocyanide (5.52 mL, 48.6 mmol), methanesulfonato(tri-t-butylphosphino)(2'-methylamino-1,1'-biphenyl-2-yl)palladium(II) [P(t-Bu)3 Pd G4, 775 mg, 1.29 mmol] and tri-tert-butylphosphonium tetrafluoroborate (360 mg, 1.22 mmol). Stir the mixture for 23 h at 75° C. Cool the mixture to RT and filter through a silica gel plug using DMF as eluent. Cool the filtrate to 0° C., add 1N HCl (120 mL) and stir for 15 min at 0° C. Dilute the reaction mixture with water (200 mL) and stir for 30 min at RT. Filter the resulting solid to yield the title compound as pale green solid (5.4 g, 77% purity, 37% yield). ES-MS m/z 273.0/275.0 (M+H).

Preparation 222

4-[(6-Chloro-2-pyridyl)oxymethyl]-3-(hydroxymethyl)benzonitrile

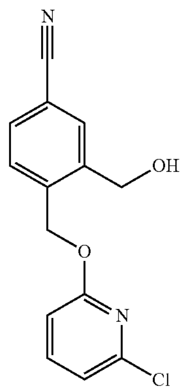 [SMILES: N#Cc1ccc(COc2cccc(Cl)n2)c(CO)c1]

Cool a solution of 4-[(6-chloro-2-pyridyl)oxymethyl]-3-formyl-benzonitrile (1.0 g, 3.67 mmol) in MeOH (20 mL) to at 0° C. and add sodium borohydride (290 mg, 7.26 mmol) portionwise. Stir the mixture for 30 min at RT then cool to 0° C. Add to the mixture:water (25 mL), then 5% aqueous citric acid solution up to pH=5, then more water (50 mL). Stir the reaction mixture for 30 min at RT. Filter the resulting solid to yield the title compound as white solid (901 mg, 89%). ES-MS m/z 275.0/277.0 (M+H).

Preparation 223

3-(Bromomethyl)-4-[(6-chloro-2-pyridyl)oxymethyl]benzonitrile

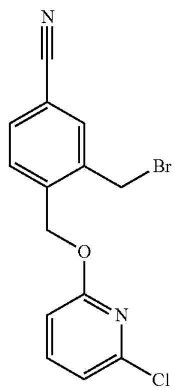 [SMILES: N#Cc1ccc(COc2cccc(Cl)n2)c(CBr)c1]

Cool a solution of 4-[(6-chloro-2-pyridyl)oxymethyl]-3-(hydroxymethyl)benzonitrile (870 mg, 3.17 mmol) and triphenylphosphine (932 mg, 3.52 mmol) in DCM (20 mL) at 0° C. Add carbon tetrabromide (920 mg, 2.77 mmol) and stir the reaction mixture for 30 min at RT. Filter the reaction mixture through a silica plug using DCM as eluent to yield the compound as a pale brown solid (1.25 g; 116% yield). ES-MS m/z 337.0/339.0/341.0 (M+H).

Preparation 224

Ethyl 2-[4-bromo-2-[2-[[2-[(6-chloro-2-pyridyl)oxymethyl]-5-cyano-phenyl]methoxy]ethyl]-5-fluoro-phenyl]acetate

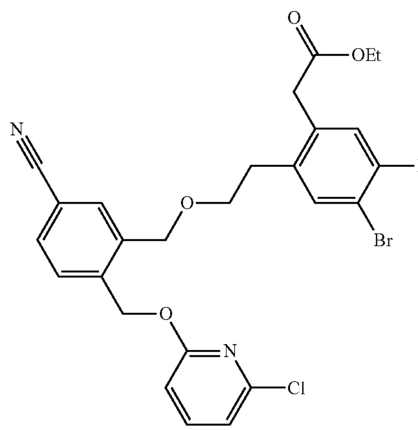

Stir a solution of ethyl 2-[4-bromo-5-fluoro-2-(2-hydroxyethyl)phenyl]acetate (750 mg, 2.46 mmol), 3-(bromomethyl)-4-[(6-chloro-2-pyridyl)oxymethyl]benzonitrile (1.24 g, 3.67 mmol) and 2,6-di-tert-butylpyridine (2.3 mL, 9.9 mmol) in DCM (13.0 mL) at RT. Add silver trifluoromethanesulfonate (2.60 g, 10.0 mmol) portionwise and stir the reaction mixture at RT for 2 h. Filter the mixture and wash the solid with DCM (50 mL). Concentrate the filtrate solvents under reduced pressure. Purify the residue via silica gel chromatography using a gradient of 0 to 100% EtOAc in DCM to give the title compound as a yellow solid (480 mg, 34%). ES-MS m/z 561/563 (M+H).

Preparation 225

Ethyl 2-[2-[2-[[2-[(6-chloro-2-pyridyl)oxymethyl]-5-cyano-phenyl]methoxy]ethyl]-5-fluoro-4-(4,4,5,5-tetramethyl-1,3,2-dioxaborolan-2-yl)phenyl]acetate

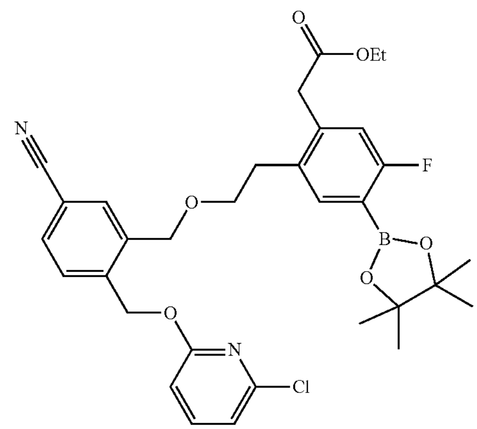 [SMILES: CCOC(=O)Cc1cc(F)c(B2OC(C)(C)C(C)(C)O2)cc1CCOCc1cc(C#N)ccc1COc1cccc(Cl)n1]

To a mixture of ethyl 2-[4-bromo-2-[2-[[2-[(6-chloro-2-pyridyl)oxymethyl]-5-cyano-phenyl]methoxy]ethyl]-5-fluoro-phenyl]acetate (150 mg, 0.27 mmol), bis(pinacolato) diboron (60 mg, 0.23 mmol) and KOAc (54 mg, 0.54 mmol) in 1,4-dioxane (2.5 mL) under nitrogen bubbling, add dichlorobis(tricyclohexylphosphine)palladium(II) (30 mg, 0.04 mmol) and stir reaction mixture at 90° C. for 30 min. Cool the reaction mixture to RT, concentrate under reduced pressure and purify the residue via filtration through a plug of silica gel using a gradient of 0 to 100% EtOAc in DCM as eluent to give the title compound as a pale white solid (101 mg, 65%). ES-MS m/z 609/611(M+H).

Preparation 226

Ethyl 2-($5^4$-cyano-$1^6$-fluoro-3,7-dioxa-2(2,6)-pyridina-1(1,3),5(1,2)-dibenzenacyclononaphane-$1^4$-yl)acetate

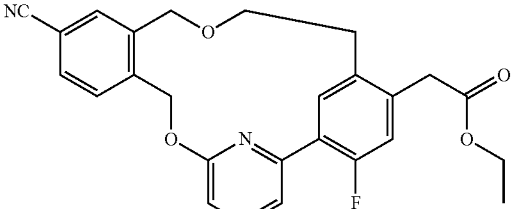

To a mixture of ethyl 2-[2-[2-[[2-[(6-chloro-2-pyridyl)oxymethyl]-5-cyano-phenyl]methoxy]ethyl]-5-fluoro-4-(4,4,5,5-tetramethyl-1,3,2-dioxaborolan-2-yl)phenyl]acetate (160 mg, 0.26 mmol) in THF (9.0 mL) with nitrogen bubbling through the mixture, add 1N potassium phosphate tribasic in water (1.30 mL, 1.30 mmol) and chloro(2-dicyclohexylphosphino-2',4',6'-triisopropyl-1,1'-biphenyl)[2-(2'-amino-1,1'-biphenyl)]palladium(II) (XPhos Pd G2, 21 mg, 0.03 mmol) and stir the reaction for 30 min at 70° C. Cool the reaction mixture to RT, then add MTBE (25 mL) and water (25 mL). Separate the phases and extract the aqueous phase with MTBE (3×20 mL). Combine organics, wash with water and saturated aqueous NaCl, dry over sodium sulfate, filter and concentrate under reduced pressure. Purify the residue by silica gel chromatography using a gradient of 0 to 100% EtOAc in DCM as eluent to give the title compound (45 mg, 34%) as a white solid. ES-MS m/z 447.0 (M+H).

Preparation 227

2-($5^4$-Cyano-$1^6$-fluoro-3,7-dioxa-2(2,6)-pyridina-1(1,3),5(1,2)-dibenzenacyclononaphane-$1^4$-yl)acetic acid

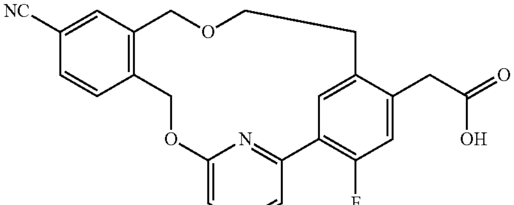

To a mixture of ethyl 2-($5^4$-cyano-$1^6$-fluoro-3,7-dioxa-2(2,6)-pyridina-1(1,3),5(1,2)-dibenzenacyclononaphane-$1^4$-yl)acetate (91 mg, 0.24 mmol) in ACN (2.7 mL), THE (0.90 mL) and water (0.90 mL) under nitrogen bubbling, add 1,5,7-triazabicyclo[4.4.0]dec-5-ene (96 mg, 0.67 mmol) portionwise and stir the reaction for 1 h at 45° C. Cool the reaction mixture to RT, add water (5 mL), 5% aqueous citric acid solution up to pH=5 and stir the mixture for 15 min at RT. Filter the resulting solid to yield the title compound as white solid (72 mg, 85%). ES-MS m/z 419.0 (M+H).

Preparation 228

Methyl (S)-4-(2-($5^4$-cyano-$1^6$-fluoro-3,7-dioxa-2(2,6)-pyridina-1(1,3),5(1,2)-dibenzenacyclononaphane-$1^4$-yl)acetamido)-2-methoxy-5-((oxetan-2-ylmethyl)amino)benzoate

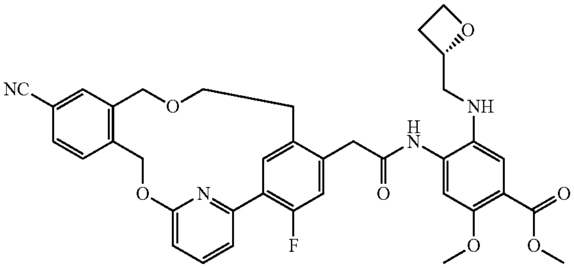 [SMILES: COC(=O)c1cc(NC[C@@H]2CCO2)c(NC(=O)Cc2cc(F)c3cc2CCOCc2cc(C#N)ccc2COc2cccc-3n2)cc1OC]

To a solution of 2-($5^4$-cyano-$1^6$-fluoro-3,7-dioxa-2(2,6)-pyridina-1(1,3),5(1,2)-dibenzenacyclononaphane-$1^4$-yl)acetic acid (70 mg, 0.167 mmol) in DMF (2.5 mL), add methyl 4-amino-3-methoxy-5-[[(2S)-oxetan-2-yl]methylamino]benzoate (50 mg, 0.19 mmol), HATU (96 mg, 0.25 mmol) and DIPEA (0.1 mL, 0.60 mmol). Stir the mixture at RT for 2 h, then add water (10 mL) and EtOAc (10 mL). Separate the phases and extract the aqueous phase with EtOAc (3×10 mL). Combine the organics, wash with 2 M aqueous $Na_2CO_3$, water, and saturated aqueous NaCl, dry over $Na_2SO_4$, filter and concentrate under reduced pressure to give the title compound as a brown solid (193 mg, 48% purity, 83% yield), which is used without further purification in Preparation 229. ES-MS m/z 667.2 (M+H).

Preparation 229

Methyl (S)-2-(($5^4$-cyano-$1^6$-fluoro-3,7-dioxa-2(2,6)-pyridina-1(1,3),5(1,2)-dibenzenacyclononaphane-$1^4$-yl)methyl)-4-methoxy-1-(oxetan-2-ylmethyl)-1H-benzo[d]imidazole-6-carboxylate

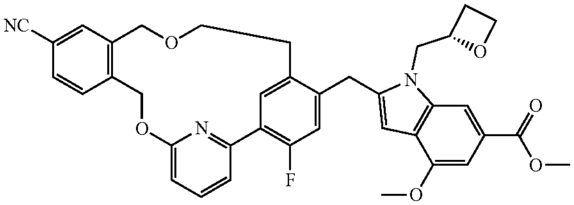 [SMILES: COC(=O)c1cc(OC)c2cc(Cc3cc(F)c4cc3CCOCc3cc(C#N)ccc3COc3cccc-4n3)n(C[C@@H]3CCO3)c2c1]

Heat a solution of methyl (S)-4-(2-($5^4$-cyano-$1^6$-fluoro-3,7-dioxa-2(2,6)-pyridina-1(1,3),5(1,2)-dibenzenacyclononaphane-1[4]-yl)acetamido)-2-methoxy-5-((oxetan-2-ylmethyl)amino)benzoate (Preparation 228, 190 mg, 0.28 mmol) in 1,2-dichloroethane (3.0 mL) and acetic acid (1.5 mL) at 60° C. for 6 h. Cool the reaction mixture to RT, concentrate the solvents under reduced pressure, and purify the residue via silica gel chromatography using a gradient of 0 to 100% EtOAc in DCM to give the title compound (58 mg, 31%) as a white solid. ES-MS m/z 649.2/650.2 (M+H).

Preparation 230

2-Bromo-4-chloro-6-fluoro-benzaldehyde

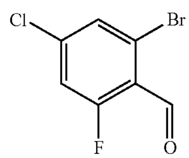

To a solution of 1,2-dibromo-5-chloro-3-fluorobenzene (50 g, 170 mmol) in heptane (130 mL) and THE (210 mL) at −45° C. add dropwise isopropylmagnesium chloride (2 M solution in THF, 94 mL, 188 mmol) keeping the internal reaction temperature between −40° C. and −45° C. Stir at −40° C. for 30 min, then add dropwise DMF (66 mL, 853 mmol) and stir at −20° C. for 1 h. Warm the reaction mixture up to 0° C., add 1 N HCl until pH=7 and extract with EtOAc (3×300 mL). Combine the organics, wash with water and saturated aqueous NaCl, dry over $Na_2SO_4$, filter, and concentrate under reduced pressure. Purify the residue via silica gel chromatography using a gradient of 0 to 12% EtOAc in petroleum ether to give the title compound (22.70 g, 52%) as a yellow solid. ES-MS m/z 238 (M+H).

Preparation 231

(2-Bromo-4-chloro-6-fluoro-phenyl)methanol

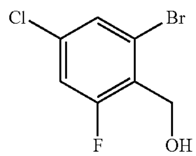 [SMILES: OCc1c(F)cc(Cl)cc1Br]

Add sodium borohydride (5.16 g, 134 mmol) to a solution of 2-bromo-4-chloro-6-fluoro-benzaldehyde (22.70 g, 89.88 mmol) in MeOH (240 mL) at 0° C. Stir at RT for 2 h. Cool to 0° C. and add 1N HCl until pH=7, concentrate most of the solvent and extract the mixture with EtOAc (3×150 mL). Combine the organics, wash with water and saturated aqueous NaCl, dry over $Na_2SO_4$, filter, and concentrate under reduced pressure to afford the title compound as an orange solid (22.3 g, 88%). ES-MS m/z 263 (M+Na).

Preparation 232

1-Bromo-2-(bromomethyl)-5-chloro-3-fluoro-benzene

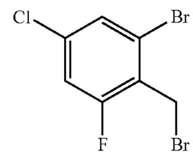 [SMILES: Fc1cc(Cl)cc(Br)c1CBr]

To a solution of (2-bromo-4-chloro-6-fluoro-phenyl) methanol (22.3 g, 79.2 mmol) in DCM (220 mL) at 0° C., add dropwise phosphorous tribromide (7.51 mL, 79.2 mmol). Bring the reaction mixture to RT and stir for 2 h. Concentrate solvents under reduced pressure and purify the residue via silica gel chromatography using a gradient of 0 to 2% EtOAc in petroleum ether to give the tile compound (26.83 g, 95%) as a colorless oil. $^1$H-NMR (400 MHz, DMSO-$d_6$) δ 7.75 (t, J=2 Hz, 1H), 7.63 (dd, J=9.5, 2 Hz, 1H), 4.70 (d, J=2 Hz, 2H).

Preparation 233

2-[(2-Bromo-4-chloro-6-fluoro-phenyl)methoxy]-6-chloro-pyridine

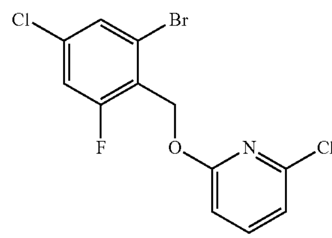 [SMILES: Fc1cc(Cl)cc(Br)c1COc1cccc(Cl)n1]

To a solution of 1-bromo-2-(bromomethyl)-5-chloro-3-fluoro-benzene (34.1 g, 107 mmol) and 2-chloro-6-hydroxypyridine (57 g, 431 mmol) in ACN (1000 mL), add silver carbonate (180 g, 653 mmol). Stir the reaction mixture at 40° C. for 36 h. Cool the mixture to RT, then filter and concentrate the filtrate under reduced pressure. Purify the residue via silica gel chromatography using a gradient of 0 to 5% EtOAc in petroleum ether to afford the title compound as a white solid (22.8 g, 52%). ES-MS m/z 350/352 (M+H).

Preparation 234

2-Chloro-6-[[4-chloro-2-[(E)-2-ethoxyvinyl]-6-fluoro-phenyl]methoxy]pyridine

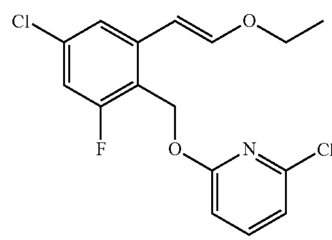 [SMILES: CCO/C=C/c1cc(Cl)cc(F)c1COc1cccc(Cl)n1]

To a mixture of 2-[(2-bromo-4-chloro-6-fluoro-phenyl) methoxy]-6-chloro-pyridine (20.8 g, 50.4 mmol) and cesium carbonate (33 g, 101 mmol) in 1,4-dioxane (200 mL), add 2-[(E)-2-ethoxyvinyl]-4,4,5,5-tetramethyl-1,3,2-dioxaborolane (11.8 mL, 55.4 mmol) under nitrogen, then add tetrakis (triphenylphosphine)palladium(0) (6.13 g, 5.0 mmol). Heat the reaction at 90° C. for 12 h, then add more 2-[(E)-2-ethoxyvinyl]-4,4,5,5-tetramethyl-1,3,2-dioxaborolane (5.4 mL, 25 mmol) and tetrakis(triphenylphosphine)palladium (0) (3.1 g, 2.5 mmol). Stir the mixture at 90° C. for 4 h more. Cool the mixture to RT and concentrate under reduced pressure, then add water (150 mL) and extract with EtOAc (3×150 mL). Combine the organics, dry over $Na_2SO_4$, filter, and evaporate under reduced pressure. Purify the residue via silica gel chromatography using a gradient of 0 to 20% DCM in petroleum ether to give the title compound (13.71 g, 70%) as a white solid. ES-MS m/z 342 (M+H).

Preparation 235

2-[5-Chloro-2-[(6-chloro-2-pyridyl)oxymethyl]-3-fluoro-phenyl]ethanol

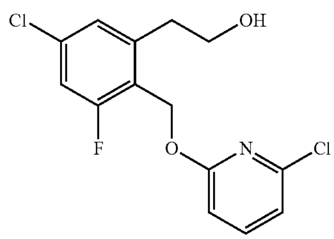 [SMILES: OCCc1cc(Cl)cc(F)c1COc1cccc(Cl)n1]

To a solution of 2-chloro-6-[[4-chloro-2-[(E)-2-ethoxyvinyl]-6-fluoro-phenyl]methoxy]pyridine (12.7 g, 35.3 mmol) in THE (280 mL) and water (280 mL) at 0° C., add mercuric acetate (37.53 g, 117.8 mmol) and stir at 0° C. for 3 h. Add 50% aqueous $K_2CO_3$ (190 mL) and sodium borohydride (6 g, 158.59 mmol) to the mixture at 0° C., then stir at 0° C. for 3 h. Add water (200 mL) to the mixture and extract with EtOAc (3×500 mL). Combine the organics, dry over $Na_2SO_4$, filter, and concentrate under reduced pressure. Purify the residue via silica gel chromatography using a gradient of 0 to 25% EtOAc in petroleum ether to give the title compound as a colorless oil (9.46 g, 78%). ES-MS m/z 316 (M+H).

Preparation 236

1-Bromo-5-(bromomethyl)-2-fluoro-4-iodobenzene

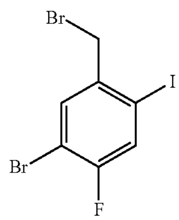 [SMILES: Fc1cc(I)c(CBr)cc1Br]

Prepare a solution of 5-bromo-4-fluoro-2-iodotoluene (50.2 g, 156 mmol) and N-bromosuccinimide (29.2 g, 164 mmol) in ACN (0.8 L). Pump through a photochemical reactor consisting of a coiled PFA reaction tube (⅛" o.d., 52 mL volume) maintained at 40° C. and surrounded by an array of four Kessil PR160-370 nm (40 W) and four Evoluchem 450 nm (30 W) lamps at a flowrate of between 2 mL/min and 3 mL/min. Once complete, pump ACN (60 mL) through the reactor at the same rate. Stir the reactor output and add 20% aqueous sodium bisulfite (0.2 L) and then water to a final volume of 2 L. Stir the resulting slurry for 30 min at ambient temperature. Collect the solid by filtration and wash with water (0.5 L). Dissolve the filter cake in a mixture of EtOAc (0.1 L) and heptane (0.4 L) and wash the organic layer with 50 mL portions of water, saturated aqueous $NaHCO_3$ and saturated aqueous NaCl, then dry over $MgSO_4$ and filter. Concentrate the filtrate under reduced pressure at 50° C. to afford 35.19 g of the title compound (53%, 93% purity) as a cream solid. $^1$H-NMR (400 MHz, $CDCl_3$) δ 7.65 (d, J=6.8 Hz, 1H), 7.60 (J=7.6 Hz, 1H), 4.51 (s, 2H). $^{19}$F{1H}-NMR (386.5 MHz, CDCl3) −105.55 (s).

Preparation 237

2-[[2-[2-[(5-Bromo-4-fluoro-2-iodo-phenyl) methoxy]ethyl]-4-chloro-6-fluoro-phenyl]methoxy]-6-chloro-pyridine

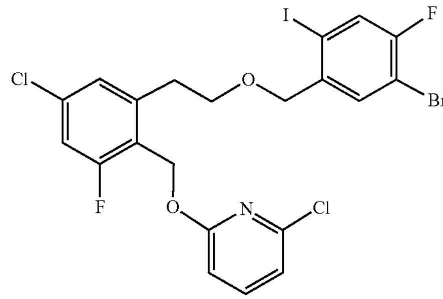 [SMILES: Fc1cc(I)c(COCCc2cc(Cl)cc(F)c2COc2cccc(Cl)n2)cc1Br]

Add silver trifluoromethanesulfonate (8.30 g, 32 mmol) to a solution of 2-[5-chloro-2-[(6-chloro-2-pyridyl)oxymethyl]-3-fluoro-phenyl]ethanol (5.5 g, 16.0 mmol), 1-bromo-5-(bromomethyl)-2-fluoro-4-iodobenzene (10.85 g, 24.80 mmol) and 2,6-ditertbutyl-4-methylpyridine (5 g, 24 mmol) in DCM (30 mL). Stir the reaction at RT for 5 h. Filter the reaction mixture through Celite®, dilute with water (100 mL) and extract with EtOAc (3×100 mL). Combine the organics, dry over $Na_2SO_4$, filter, and concentrate under reduced pressure. Purify the residue via silica gel chromatography using a gradient of 0 to 6% EtOAc in petroleum ether to give the title compound as a colorless oil (8.51 g, 76%). ES-MS m/z 628/630 (M+H).

Preparation 238

Ethyl 2-[4-bromo-2-[2-[5-chloro-2-[(6-chloro-2-pyridyl)oxymethyl]-3-fluoro-phenyl]ethoxymethyl]-5-fluoro-phenyl]acetate

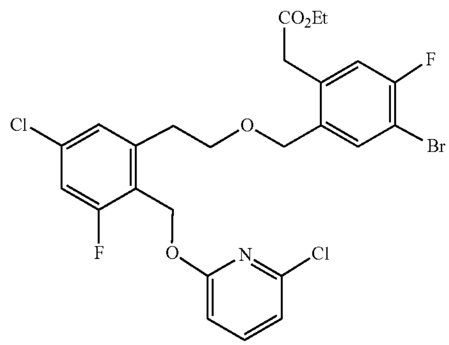 [SMILES: CCOC(=O)Cc1cc(F)c(Br)cc1COCCc1cc(Cl)cc(F)c1COc1cccc(Cl)n1]

To a mixture of 2-[[2-[2-[(5-bromo-4-fluoro-2-iodo-phenyl)methoxy]ethyl]-4-chloro-6-fluoro-phenyl]methoxy]-6-chloro-pyridine (1.49 g, 1.94 mmol) and chloro[(4,5-bis(diphenylphosphino)-9,9-dimethylxanthene)-2-(2'-amino-1,1'-biphenyl)]palladium(II) (Xantphos-Pd-G2, 0.2 g, 0.2 mmol) in THE (7 mL) under nitrogen, add (2-ethoxy-2-oxoethyl))zinc bromide (0.5 M in THF, 8 mL, 4 mmol). Heat the mixture at 65° C. for 2 h in a microwave reactor. Cool the mixture to RT, add saturated aqueous $NH_4Cl$ solution (30 mL), then dilute with water (30 mL) and extract with EtOAc (3×50 mL). Combine the organics, dry over $Na_2SO_4$, filter, and concentrate under reduced pressure. Purify the residue via silica gel chromatography using a gradient of 0 to 15% EtOAc in petroleum ether to afford 0.57 g (45%) of the title compound as a colorless oil. ES-MS m/z 588/590 (M+H).

Preparation 239

Ethyl 2-($5^4$-chloro-$1^6$,$5^6$-difluoro-3,8-dioxa-2(2,6)-pyridina-1(1,3),5(1,2)-dibenzenacyclononaphane-$1^4$-yl)acetate

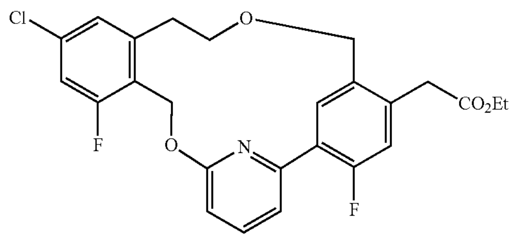 [SMILES: CCOC(=O)Cc1cc(F)c2cc1COCCc1cc(Cl)cc(F)c1COc1cccc-2n1]

To a solution of ethyl 2-[4-bromo-2-[2-[5-chloro-2-[(6-chloro-2-pyridyl)oxymethyl]-3-fluoro-phenyl]ethoxymethyl]-5-fluoro-phenyl]acetate (1.43 g, 2.19 mmol), potassium 2,2-dimethylpropanoate (0.78 g, 5.49 mmol) and bis(pinacolato)diboron (0.8 g, 3 mmol) in THE (85 mL) under nitrogen, add chloro(2-dicyclohexylphosphino-2',4',6'-triisopropyl-1,1'-biphenyl)[2-(2'-amino-1,1'-biphenyl)]palladium(II) (XPhos Pd G2, 176 mg, 0.21 mmol). Heat the reaction at 55° C. for 4 h. Add potassium phosphate tribasic (1.42 g, 6.57 mmol) in water (6.57 mL) to the reaction and heat at 55° C. for 2 h. Cool the mixture to RT, add water (30 mL), and extract with EtOAc (3×100 mL). Combine the organics, dry over $Na_2SO_4$, filter, and concentrate under reduced pressure. Purify the residue via silica gel chromatography using a gradient of 0 to 15% EtOAc in petroleum ether to give the title compound as a beige solid (308 mg, 27%). ES-MS m/z 474 (M+H).

Preparation 240

2-($5^4$-Chloro-$1^6$,$5^6$-difluoro-3,8-dioxa-2(2,6)-pyridina-1(1,3),5(1,2)-dibenzenacyclononaphane-$1^4$-yl)acetic acid

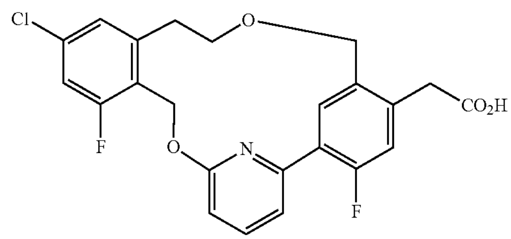 [SMILES: O=C(O)Cc1cc(F)c2cc1COCCc1cc(Cl)cc(F)c1COc1cccc-2n1]

Prepare the title compound essentially as described in Preparation 227 using ethyl 2-($5^4$-chloro-$1^6$,$5^6$-difluoro-3,8-dioxa-2(2,6)-pyridina-1(1,3),5(1,2)-dibenzenacyclononaphane-$1^4$-yl)acetate. ES-MS m/z 446 (M+H).

Preparation 241

Methyl (S)-4-(2-($5^4$-chloro-$1^6$,$5^6$-difluoro-3,8-dioxa-2(2,6)-pyridina-1(1,3),5(1,2)-dibenzenacyclononaphane-$1^4$-yl)acetamido)-3-(2-methoxyethoxy)-5-((oxetan-2-ylmethyl)amino)benzoate

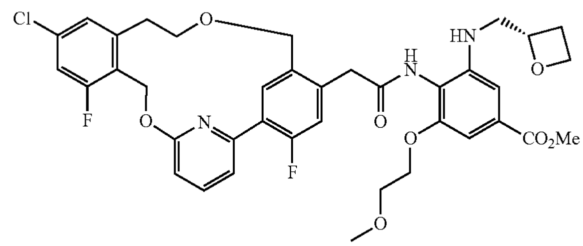 [SMILES: COCCOc1cc(C(=O)OC)cc(NC[C@@H]2CCO2)c1NC(=O)Cc1cc(F)c2cc1COCCc1cc(Cl)cc(F)c1COc1cccc-2n1]

To a solution of 2-($5^4$-chloro-$1^6$,$5^6$-difluoro-3,8-dioxa-2(2,6)-pyridina-1(1,3),5(1,2)-dibenzenacyclononaphane-$1^4$-yl)acetic acid (245 mg, 0.54 mmol) and HATU (356 mg, 0.91 mmol) in DMF (5.4 mL) under nitrogen add methyl 4-amino-3-(2-methoxyethoxy)-5-[[(2S)-oxetan-2-yl]methylamino]benzoate (242 mg, 0.70 mmol) and DIPEA (0.28 mL, 1.62 mmol). Stir the mixture at RT for 2 h, then add water (10 mL) and extract with EtOAc (3×25 mL). Combine the organics, wash with water and saturated aqueous NaCl, dry over $Na_2SO_4$, filter, and concentrate under reduced pressure to afford the title compound as a white solid (594 mg, 34% purity), which is used without further purification in Preparation 242. ES-MS m/z 738 (M+H).

Preparation 242

Methyl (S)-2-((5[4]-chloro-1[6],5[6]-difluoro-3,8-dioxa-2(2,6)-pyridina-1(1,3),5(1,2)-dibenzenacyclononaphane-1[4]-yl)methyl)-4-(2-methoxyethoxy)-1-(oxetan-2-ylmethyl)-1H-benzo[d]imidazole-6-carboxylate

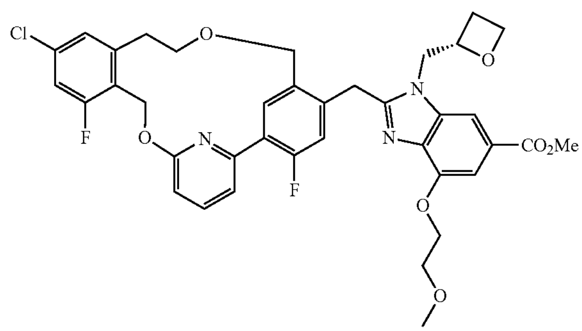 [SMILES: COCCOc1cc(C(=O)OC)cc2c1nc(Cc1cc(F)c3cc1COCCc1cc(Cl)cc(F)c1COc1cccc-3n1)n2C[C@@H]1CCO1]

Prepare the title compound essentially as described in Preparation 102 using methyl (S)-4-(2-(5[4]-chloro-1[6],5[6]-difluoro-3,8-dioxa-2(2,6)-pyridina-1(1,3),5(1,2)-dibenzenacyclononaphane-1[4]-yl)acetamido)-3-(2-methoxyethoxy)-5-((oxetan-2-ylmethyl)amino)benzoate in 1:1 1,2-dichloroethane:acetic acid as solvent, heating the reaction at 60° C. for 6 h. Cool the reaction mixture to RT, evaporate solvents under reduced pressure, adding EtOAc/toluene (1:1) to help removal of acetic acid in the concentration. Purify the residue via silica gel chromatography using a gradient of 0 to 5% MeOH in DCM to give the title compound as a light-yellow solid (64% purity). ES-MS m/z 720 (M+H).

Preparation 243

2-Bromo-6-(bromomethyl)nicotinonitrile

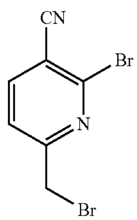 [SMILES: N#Cc1ccc(CBr)nc1Br]

Transfer a solution of 2-bromo-6-methylnicotinonitrile (23 g, 113.2 mmol) and N-bromosuccinimide (30.8 g, 170 mmol) in ACN (560 mL) through a photochemical flow reactor equipped with a 440-460 nM, 200 W lamp, (reactor size=15 m, 15 mL, flow rate=1 mL/min, 25° C.). Evaporate the reaction solvent and partition the residue between water and DCM. Separate the organic layer, wash with saturated aqueous NaCl, dry over anhydrous $Na_2SO_4$, filter and remove solvent. Dissolve the residue in THF (400 mL), add diethyl phosphite (8.63 mL, 65.8 mmol) and DIPEA (17.8 mL, 99.0 mmol) under $N_2$ at 0° C. for 0.5 h. Warm the reaction mixture to RT and stir overnight to give a black solution.

Partition the reaction mixture between water and EtOAc. Separate the organic layer, wash with saturated aqueous NaCl, dry over anhydrous $Na_2SO_4$, filter and concentrate under reduced pressure. Purify the residue by silica gel chromatography using a gradient of 0 to 25% EtOAc in petroleum ether to provide the title compound (28.45 g, 84%) as a white solid. ES-MS m/z 275, 277, 279 (M+H).

Preparation 244

2-Bromo-6-[(6-chloro-2-pyridyl)oxymethyl]pyridine-3-carbonitrile

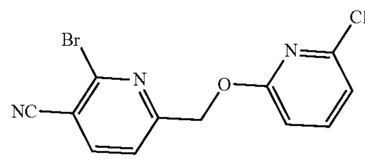 [SMILES: N#Cc1ccc(COc2cccc(Cl)n2)nc1Br]

Add silver carbonate (10.5 g, 37.3 mmol) to a solution of 2-bromo-6-(bromomethyl)nicotinonitrile (1.84 g, 6.33 mmol) and 2-chloro-6-hydroxypyridine (3.35 g, 25.3 mmol) in ACN (150 mL) at RT. Stir the mixture at 60° C. for 48 h. Filter off the solid and concentrate filtrate under reduced pressure. Purify the residue by silica gel chromatography using a gradient of 0 to 23% EtOAc in petroleum ether to provide the title compound (957 mg, 91 wt % pure, 42%) as a white solid. ES-MS m/z 324, 326, 328 (M+H).

Preparation 245

6-[(6-Chloro-2-pyridyl)oxymethyl]-2-[(E)-2-ethoxyvinyl]pyridine-3-carbonitrile

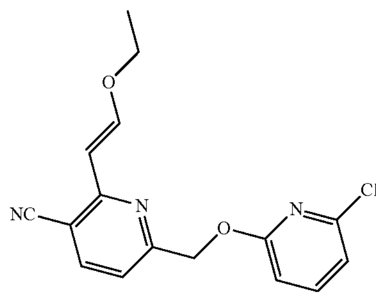 [SMILES: CCO/C=C/c1nc(COc2cccc(Cl)n2)ccc1C#N]

Add 2-[(E)-2-ethoxyvinyl]-4,4,5,5-tetramethyl-1,3,2-dioxaborolane (13.5 mL, 63.4 mmol) and 1,1'-bis(diphenylphosphino)ferrocene-palladium(II)dichloride DCM complex (4.7 g, 5.65 mmol) to a mixture of 2-bromo-6-[(6-chloro-2-pyridyl)oxymethyl]pyridine-3-carbonitrile (20.4 g, 56.6 mmol, 91 wt % pure) and potassium phosphate tribasic (24.5 g, 113 mmol) in 1,4-dioxane (200 mL) and water (60 mL). Purge the mixture with nitrogen and stir at 90° C. for 4 h. Cool the mixture to RT, dilute with water (250 mL) and extract with EtOAc (250 mL×4). Combine the organic layers, dry over anhydrous $Na_2SO_4$, filter and remove solvent. Purify the residue by silica gel chromatography using a gradient of 0 to 20% EtOAc in petroleum ether to provide the title compound (15.7 g, 83 wt % purity, 73%) as a yellow solid. ES-MS m/z 316, 318 (M+H).

Preparation 246

6-[(6-Chloro-2-pyridyl)oxymethyl]-2-(2-hydroxyethyl)pyridine-3-carbonitrile

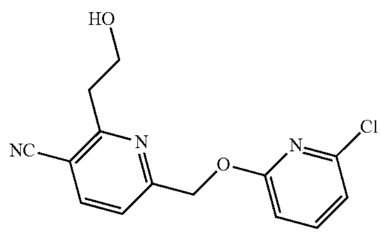 [SMILES: N#Cc1ccc(COc2cccc(Cl)n2)nc1CCO]

Prepare the title compound essentially as described in Preparation 235 using 6-[(6-chloro-2-pyridyl)oxymethyl]-2-[(E)-2-ethoxyvinyl]pyridine-3-carbonitrile. Upon completion of the reaction, filter off a solid and wash with EtOAc. From the filtrate, separate the organic layer and extract the aqueous layer with EtOAc three times. Combine the organic layers, dry over anhydrous $Na_2SO_4$, then filter and concentrate under reduced pressure. Purify the residue by silica gel chromatography using a gradient of 0 to 45% EtOAc in petroleum ether to provide title the compound as a light-yellow solid. ES-MS m/z 290, 292 (M+H)

Preparation 247

Methyl 2-[4-bromo-2-[2-[6-[(6-chloro-2-pyridyl)oxymethyl]-3-cyano-2-pyridyl]ethoxymethyl]phenyl]acetate

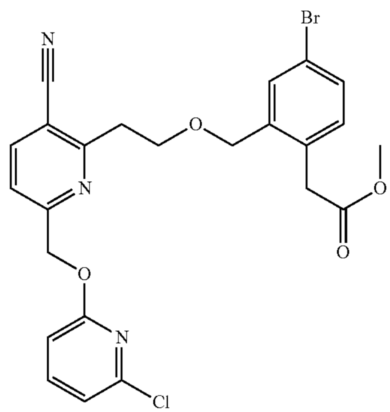 [SMILES: COC(=O)Cc1ccc(Br)cc1COCCc1nc(COc2cccc(Cl)n2)ccc1C#N]

Prepare the title compound essentially as described in Preparation 224 using 6-[(6-chloro-2-pyridyl)oxymethyl]-2-(2-hydroxyethyl)pyridine-3-carbonitrile and methyl 2-[4-bromo-2-(bromomethyl)phenyl]acetate, stirring the reaction at 40° C. overnight. Upon completion of the reaction, remove ACN under reduced pressure, dilute the residue with water and extract with EtOAc. Dry the organics over anhydrous $Na_2SO_4$, filter and concentrate. Purify the residue by preparative HPLC [column: Phenomenex Luna C18 250×50 mm, 10 μm; mobile phase: 40 to 85% ACN in aqueous formic acid (0.225%)] to provide the title compound as light yellow waxy solid. ES-MS m/z 530, 532, 534 (M+H).

Preparation 248

Methyl 2-($5^5$-cyano-3,8-dioxa-2,5(2,6)-dipyridina-1(1,3)-benzenacyclononaphane-$1^4$-yl)acetate

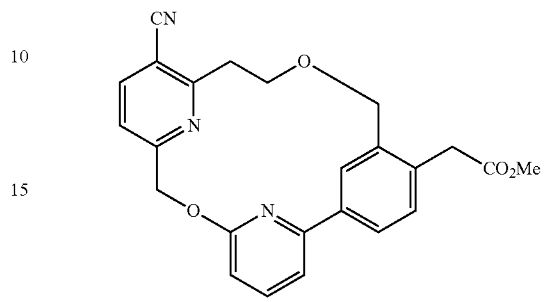

Prepare the title compound essentially as described in Preparation 216 using methyl 2-[4-bromo-2-[2-[6-[(6-chloro-2-pyridyl)oxymethyl]-3-cyano-2-pyridyl]ethoxymethyl]phenyl]acetate as starting material and (2-dicyclohexylphosphino-2',4',6'-triisopropyl-1,1'-biphenyl)[2-(2'-amino-1,1'-biphenyl)]palladium(II) methanesulfonate (XPhos Pd G3) as catalyst, heating the reaction to 110° C. overnight. When the reaction is complete, concentrate the reaction mixture, add water, and extract three times with EtOAc. Dry the combined organics over $Na_2SO_4$, filter, and concentrate. Purify the residue by HPLC [column: Welch Xtimate C18 150×40 mm, 10 μm; mobile phase: 40 to 80% ACN in aqueous formic acid (0.225%)] to provide the title compound as a white solid. ES-MS m/z 416 (M+H).

Preparation 249

2-($5^5$-Cyano-3,8-dioxa-2,5(2,6)-dipyridina-1(1,3)-benzenacyclononaphane-$1^4$-yl)acetic acid

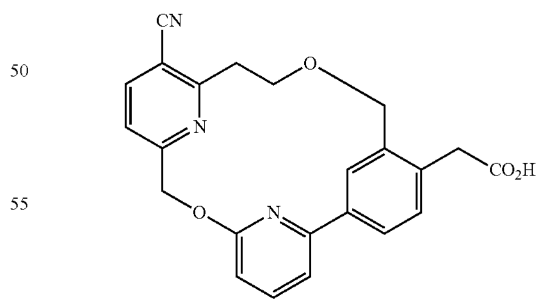

Prepare the title compound essentially as described in Preparation 78 using methyl 2-($5^5$-cyano-3,8-dioxa-2,5(2,6)-dipyridina-1(1,3)-benzenacyclononaphane-$1^4$-yl)acetate. When the reaction is complete, remove the organic solvents and water and aqueous citric acid (1 M) to bring the pH to 5-6. Filter the resulting solid and wash with water to provide the title compound as a white solid. ES-MS m/z 402 (M+H).

Preparation 250

Methyl (S)-4-(2-($5^5$-cyano-3,8-dioxa-2,5(2,6)-dipyridina-1(1,3)-benzenacyclononaphane-$1^4$-yl)acetamido)-3-(2-methoxyethoxy)-5-((oxetan-2-ylmethyl)amino)benzoate

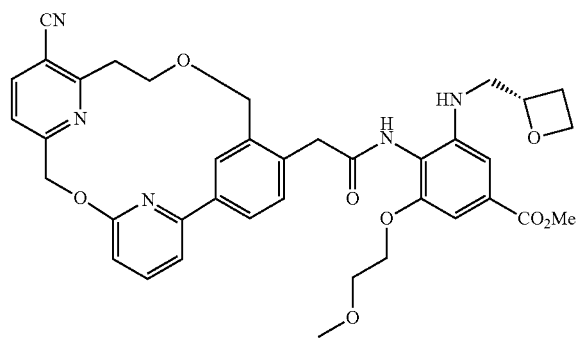 [SMILES: COCCOc1cc(C(=O)OC)cc(NC[C@@H]2CCO2)c1NC(=O)Cc1ccc2cc1COCCc1nc(ccc1C#N)COc1cccc-2n1]

Prepare the title compound essentially as described in Preparation 86 using 2-(55-cyano-3,8-dioxa-2,5(2,6)-dipyridina-1(1,3)-benzenacyclononaphane-$1^4$-yl)acetic acid and methyl 4-amino-3-(2-methoxyethoxy)-5-[[(2S)-oxetan-2-yl]methylamino]benzoate, stirring the reaction at RT overnight. Dilute the reaction mixture with water and extract three times with EtOAc. Combine organic layers, wash with water and saturated aqueous NaCl, dry over $Na_2SO_4$, filter, and concentrate under vacuum to give the title compound as an orange waxy solid which is 54 wt % pure. ES-MS m/z 694 (M+H).

Preparation 251

Methyl (S)-2-(($5^5$-cyano-3,8-dioxa-2,5(2,6)-dipyridina-1(1,3)-benzenacyclononaphane-$1^4$-yl)methyl)-4-(2-methoxyethoxy)-1-(oxetan-2-ylmethyl)-1H-benzo[d]imidazole-6-carboxylate

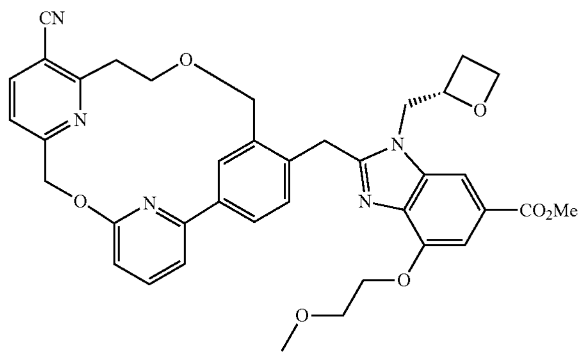 [SMILES: COCCOc1cc(C(=O)OC)cc2c1nc(Cc1ccc3cc1COCCc1nc(ccc1C#N)COc1cccc-3n1)n2C[C@@H]1CCO1]

Prepare the title compound essentially as described in Preparation 109 using methyl (S)-4-(2-($5^5$-cyano-3,8-dioxa-2,5(2,6)-dipyridina-1(1,3)-benzenacyclononaphane-$1^4$-yl)acetamido)-3-(2-methoxyethoxy)-5-((oxetan-2-ylmethyl)amino)benzoate (54 wt % pure), stirring under nitrogen atmosphere at 60° C. for 6 h. Purify by silica gel chromatography using a gradient of 0 to 6% MeOH in DCM providing the title compound as an orange waxy solid which is 63 wt % pure. ES-MS m/z 676 (M+H).

Preparation 252

Methyl 2-chloro-5-(((6-chloropyridin-2-yl)oxy)methyl)benzoate

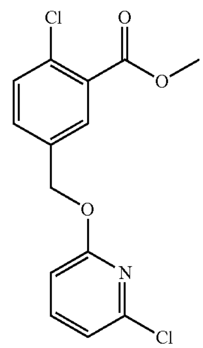 [SMILES: COC(=O)c1cc(COc2cccc(Cl)n2)ccc1Cl]

To a solution of methyl 5-(bromomethyl)-2-chlorobenzoate (25 g, 95 mmol) in 1,4-dioxane (600 mL), add 6-chloropyridin-2-ol (14.2 g, 110 mmol) and silver carbonate (53.2 g, 193 mmol). Stir the mixture at 60° C. for 23 h. Filter the reaction suspension through Celite® and rinse with EtOAc. Concentrate the filtrate under reduced pressure to give 29.4 g of the title compound (99%), which is used without further purification in Preparation 253. ES-MS m/z 312, 314 (M+H).

Preparation 253

(2-Chloro-5-(((6-chloropyridin-2-yl)oxy)methyl)phenyl)methanol

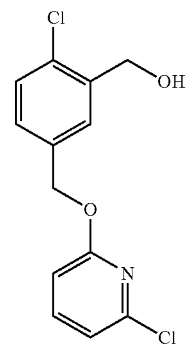 [SMILES: OCc1cc(COc2cccc(Cl)n2)ccc1Cl]

Cool a solution of methyl 2-chloro-5-(((6-chloropyridin-2-yl)oxy)methyl)benzoate (from Preparation 252, 22 g, 71 mmol) in THE (200 mL) to 0° C., then add Red-Al® (60 wt % in toluene, 30 mL, 92 mL) dropwise. Stir the mixture at 0° C. for 10 min then quench the reaction with EtOAc (10 mL). Stir the mixture at RT for 2 h, then dilute the reaction with water (200 mL) and EtOAc (200 mL). Extract the aqueous layer with EtOAc (2×100 mL). Dry the combined organic phases over $MgSO_4$, filter, and concentrate under reduced pressure to give 20.7 g of the title compound (100%), which is used without further purification in Preparation 254. ES-MS m/z 284, 286 (M+H).

Preparation 254

2-((3-(Bromomethyl)-4-chlorobenzyl)oxy)-6-chloropyridine

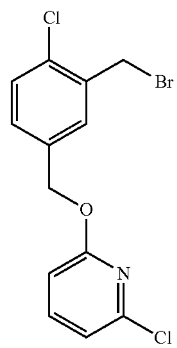 [SMILES: Clc1cccc(OCc2ccc(Cl)c(CBr)c2)n1]

Cool a solution of (2-chloro-5-(((6-chloropyridin-2-yl)oxy)methyl)phenyl)methanol (from Preparation 253, 1.5 g, 5.3 mmoL) and triphenylphosphine (2.0 g, 7.5 mmoL) in DCM (35 mL) to 0° C. Add carbon tetrabromide (1.9 g, 5.7 mmoL), stir the reaction mixture at 0° C. for 10 min then at RT for 30 min. Filter the reaction solution through a pad of silica gel and rinse with DCM. Concentrate the filtrate under reduced pressure to give 1.8 g of the title compound (100%), which is used without further purification in Preparation 255. ES-MS m/z 345/347/349 (M+H).

Preparation 255

Ethyl 2-(4-bromo-2-(2-((2-chloro-5-(((6-chloropyridin-2-yl)oxy)methyl)benzyl)oxy)ethyl)-5-fluorophenyl)acetate

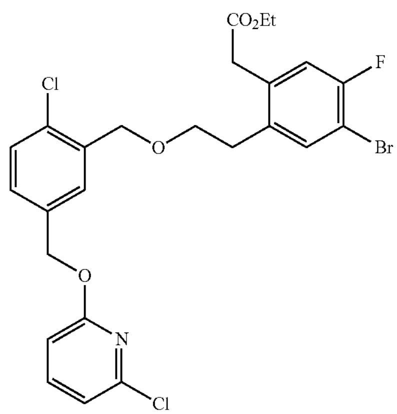 [SMILES: CCOC(=O)Cc1cc(F)c(Br)cc1CCOCc1cc(COc2cccc(Cl)n2)ccc1Cl]

Prepare the title compound essentially as described in Preparation 224 using 2-((3-(bromomethyl)-4-chlorobenzyl)oxy)-6-chloropyridine (from Preparation 254) and ethyl 2-[4-bromo-5-fluoro-2-(2-hydroxyethyl)phenyl]acetate, stirring the reaction at RT for 1 h 15 min. Filter and concentrate the reaction mixture under reduced pressure, then purify via silica gel chromatography using a gradient of 0 to 20% EtOAc in hexanes to give the title compound. ES-MS m/z 570/572/574 (M+H).

Preparation 256

Ethyl 2-(2-(2-((2-chloro-5-(((6-chloropyridin-2-yl)oxy)methyl)benzyl)oxy)ethyl)-5-fluoro-4-(4,4,5,5-tetramethyl-1,3,2-dioxaborolan-2-yl)phenyl)acetate

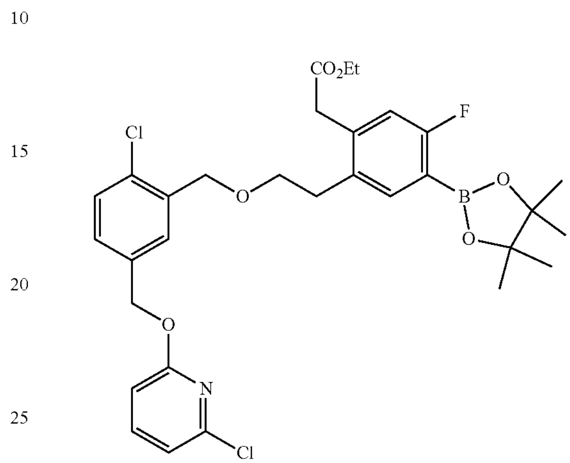

To a mixture of ethyl 2-(4-bromo-2-(2-((2-chloro-5-(((6-chloropyridin-2-yl)oxy)methyl)benzyl)oxy)ethyl)-5-fluorophenyl)acetate (855 mg, 1.5 mmoL), bis(pinacolato)diboron (480 mg, 1.87 mmoL), KOAc (450 mg, 4.5 mmoL), and dichlorobis(tricyclohexylphosphine)palladium (II) (225 mg, 0.30 mmoL) add 1,4-dioxane (15 mL). Stir the mixture at 90° C. for 5 h, then add Pd(dppf)$Cl_2$ (125 mg, 0.17 mmoL) and stir the mixture at 90° C. for 15 h. Filter the crude mixture through a pad of silica gel and rinse with EtOAc. Concentrate the filtrate under reduced pressure to give the title compound, which is used without further purification in Preparation 257. ES-MS m/z 536 (M+H for boronic acid).

Preparation 257

Ethyl 2-($5^4$-chloro-$1^6$-fluoro-3,7-dioxa-2(2,6)-pyridina-1,5(1,3)-dibenzenacyclononaphane-$1^4$-yl)acetate

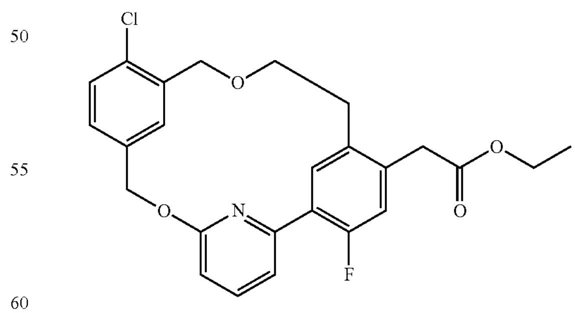

To a solution of ethyl 2-(2-(2-((2-chloro-5-(((6-chloropyridin-2-yl)oxy)methyl)benzyl)oxy)ethyl)-5-fluoro-4-(4,4,5,5-tetramethyl-1,3,2-dioxaborolan-2-yl)phenyl)acetate (from Preparation 256, 925 mg, 1.5 mmoL) and XPhos Pd G2 (145 mg, 0.18 mmoL) in THE (50 mL), add a solution of potassium phosphate (1.6 g, 7.4 mmoL) in water (5 mL).

Stir the reaction mixture at 60° C. for 1.5 h. Dilute the crude reaction mixture with EtOAc (50 mL) and 1:1 water:saturated aqueous NaCl (50 mL), and extract the aqueous layer with EtOAc (50 mL). Dry the combined organic phases over $MgSO_4$, filter, and concentrate under reduced pressure. Purify the residue via silica gel chromatography using a gradient of 0 to 40% EtOAc in hexanes to give 140 mg of the title compound (20%). ES-MS m/z 456 (M+H).

Preparation 258

2-($5^4$-Chloro-$1^6$-fluoro-3,7-dioxa-2(2,6)-pyridina-1,5(1,3)-dibenzenacyclononaphane-$1^4$-yl)acetic acid

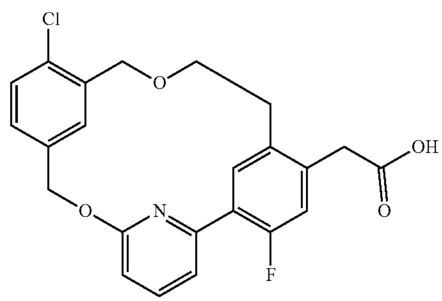 [SMILES: O=C(O)Cc1cc(F)c2cc1CCOCc1cc(ccc1Cl)COc1cccc-2n1]

Prepare the title compound essentially as described in Preparation 75 using ethyl 2-($5^4$-chloro-$1^6$-fluoro-3,7-dioxa-2(2,6)-pyridina-1,5(1,3)-dibenzenacyclononaphane-$1^4$-yl)acetate, using 3:3:1 ACN:1,4-dioxane:water as solvent and heating the reaction at 50° C. for 1 h 20 min. Dilute the reaction with water and quench with 1 M aqueous citric acid solution. Collect the precipitated material by filtration and rinse with water to give the title compound. ES-MS m/z 428 (M+H).

Preparation 259

Methyl (S)-4-(2-($5^4$-chloro-$1^6$-fluoro-3,7-dioxa-2(2,6)-pyridina-1,5(1,3)-dibenzenacyclononaphane-$1^4$-yl)acetamido)-3-(2-methoxyethoxy)-5-((oxetan-2-ylmethyl)amino)benzoate

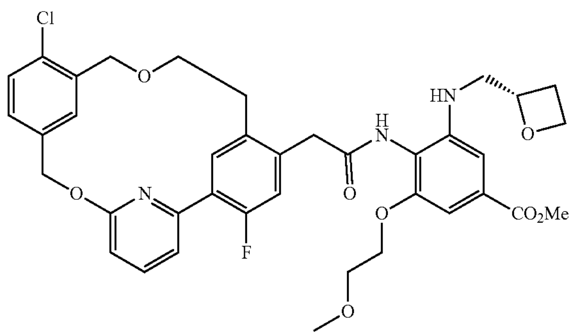 [SMILES: COCCOc1cc(C(=O)OC)cc(NC[C@@H]2CCO2)c1NC(=O)Cc1cc(F)c2cc1CCOCc1cc(ccc1Cl)COc1cccc-2n1]

Prepare the title compound essentially as described in Preparation 86 using 2-($5^4$-chloro-$1^6$-fluoro-3,7-dioxa-2(2,6)-pyridina-1,5(1,3)-dibenzenacyclononaphane-$1^4$-yl)acetic acid and methyl 4-amino-3-(2-methoxyethoxy)-5-[[(2S)-oxetan-2-yl]methylamino]benzoate, stirring the reaction at RT for 17 h. Dilute the reaction with EtOAc and water, wash the organic layer with water and back-extract the aqueous layer twice with EtOAc. Dry the combined organic phases over $MgSO_4$, filter, and concentrate under reduced pressure to provide the title compound, which is used without further purification in Preparation 260. ES-MS m/z 720 (M+H).

Preparation 260

Methyl (S)-2-(($5^4$-chloro-$1^6$-fluoro-3,7-dioxa-2(2,6)-pyridina-1,5(1,3)-dibenzenacyclononaphane-$1^4$-yl)methyl)-4-(2-methoxyethoxy)-1-(oxetan-2-ylmethyl)-1H-benzo[d]imidazole-6-carboxylate

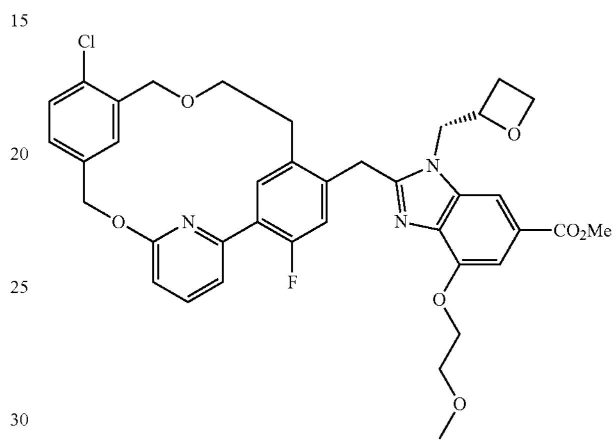

Prepare the title compound essentially as described in Preparation 109 using methyl (S)-4-(2-($5^4$-chloro-$1^6$-fluoro-3,7-dioxa-2(2,6)-pyridina-1,5(1,3)-dibenzenacyclononaphane-$1^4$-yl)acetamido)-3-(2-methoxyethoxy)-5-((oxetan-2-ylmethyl)amino)benzoate (from Preparation 259). Purify via silica gel chromatography using a gradient of 0 to 100% EtOAc in hexanes to give the title compound. ES-MS m/z 702 (M+H).

Preparation 261

4-[(6-Bromo-5-fluoro-2-pyridyl)oxymethyl]-3-iodo-benzonitrile

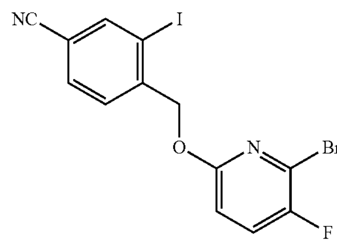 [SMILES: N#Cc1ccc(COc2ccc(F)c(Br)n2)c(I)c1]

Prepare two batches on equal scale as follows: add $Na_2CO_3$ to a solution of 4-(bromomethyl)-3-iodo-benzonitrile (22.4 g, 62.6 mmol) in acetone (340 mL) and water (340 mL). Stir both batches at 80° C. overnight, then combine the two batches. Concentrate the mixture to remove the acetone, then filter off the solid and wash with water. Dry the solid under vacuum, then stir it for 30 min in DCM (70 mL). Filter the solid, rinse with DCM, and dry under vacuum to give 4-(hydroxymethyl)-3-iodo-benzonitrile (23.6 g, 72%) as a white solid. $^1$H-NMR (400 MHz, DMSO-$d_6$) δ 8.28 (d, J=1.6 Hz, 1H), 7.88 (dd, J=8.0, 1.6 Hz, 1H), 7.62 (d, J=8.0 Hz, 1H), 5.71 (t, J=5.6 Hz, 1H), 4.44 (d, J=5.2 Hz, 2H).

To a solution of 4-(hydroxymethyl)-3-iodo-benzonitrile (11.5 g, 43.5 mmol), 2-bromo-3,6-difluoro-pyridine (7.08 g, 35.8 mmol) in 1,4-dioxane (80 mL) at 0° C. under nitrogen, add potassium tert-butoxide (1 M in THF, 43 mL, 43 mmol). Stir the reaction at 0° C. for 1 h, then stir the reaction for 7 h at RT. Dilute the reaction with a saturated aqueous solution of $NH_4Cl$ (50 mL), then add water (100 mL) and extract with EtOAc (250 mL×3). Combine the organic layers, wash with saturated aqueous NaCl (60 mL), dry over $Na_2SO_4$, filter and concentrate under reduced pressure. Purify the residue by silica gel chromatography over using a gradient of 0 to 45% DCM in petroleum ether to give the title compound as a white solid (14.28 g, 88%). ES-MS m/z 432 (M+H).

Preparation 262

4-[(6-Bromo-5-fluoro-2-pyridyl)oxymethyl]-3-[(E)-2-ethoxyvinyl]benzonitrile

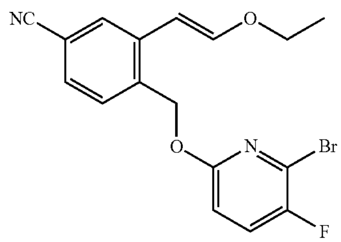 [SMILES: CCO/C=C/c1cc(C#N)ccc1COc1ccc(F)c(Br)n1]

Prepare the title compound essentially as described in Preparation 245 using 4-[(6-bromo-5-fluoro-2-pyridyl) oxymethyl]-3-iodo-benzonitrile as starting material and $K_2CO_3$ as the base, heating the reaction at 90° C. for 1.5 h. Upon completion, concentrate the reaction mixture under reduced pressure, then add water and extract with three times with EtOAc. Combine the organic layers, wash with saturated aqueous NaCl, dry over $Na_2SO_4$, filter and concentrate under reduced pressure. Purify by silica gel chromatography using a gradient of 0 to 60% EtOAc in petroleum ether to give the title compound as a white solid. ES-MS m/z 377 (M+H).

Preparation 263

4-[(6-Bromo-5-fluoro-2-pyridyl)oxymethyl]-3-(2-oxoethyl)benzonitrile

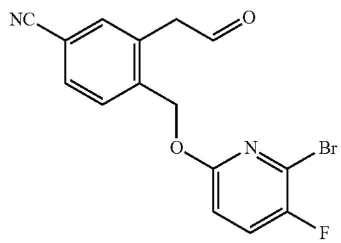 [SMILES: N#Cc1ccc(COc2ccc(F)c(Br)n2)c(CC=O)c1]

Prepare the title compound essentially as described in Preparation 126 using 4-[(6-bromo-5-fluoro-2-pyridyl) oxymethyl]-3-[(E)-2-ethoxyvinyl]benzonitrile, stirring the reaction at RT for 20 h. Upon completion, dilute the reaction with water and extract three times with EtOAc. Combine the organic layers, wash with saturated aqueous NaCl, dry over $Na_2SO_4$, filter and concentrate under reduced pressure to give the title compound as a light-yellow solid which is used in Preparation 264 without further purification. ES-MS m/z 349, 351 (M+H).

Preparation 264

4-[(6-Bromo-5-fluoro-2-pyridyl)oxymethyl]-3-(2-hydroxyethyl)benzonitrile

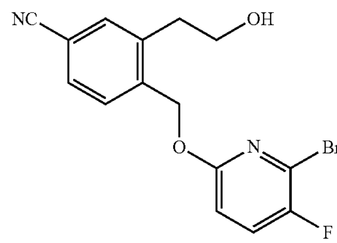 [SMILES: N#Cc1ccc(COc2ccc(F)c(Br)n2)c(CCO)c1]

To solution of 4-[(6-bromo-5-fluoro-2-pyridyl)oxymethyl]-3-(2-oxoethyl)benzonitrile (from Preparation 263, 8.54 g, 22.0 mmol) in MeOH (80 mL) at 0° C., add sodium borohydride (3.59 g, 93.9 mmol) and stir the reaction at RT for 4 h. Quench the reaction with saturated aqueous solution of $NH_4Cl$ and stir for 20 min at RT. Concentrate the reaction mixture under reduced pressure to remove the solvent. Dilute the residue with water (50 mL) and extract with EtOAc (200 mL×3). Combine the organic layers, wash with saturated aqueous NaCl (60 mL), dry over $Na_2SO_4$, filter and concentrate under reduced pressure. Purify the residue by silica gel chromatography using a gradient of 0 to 30% EtOAc in petroleum ether to give the title compound as a yellow oil (7.1 g, 87%). ES-MS m/z 351/353 (M+H).

Preparation 265

Methyl 2-(4-bromo-2-((2-(((6-bromo-5-fluoropyridin-2-yl)oxy)methyl)-5-cyanophenethoxy)methyl) phenyl)acetate

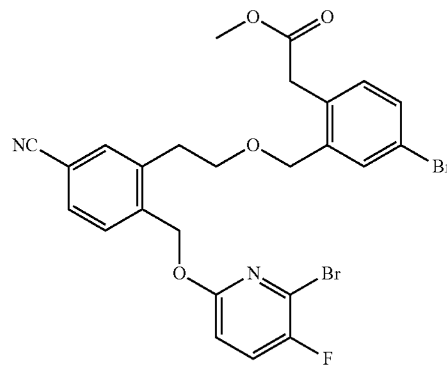 [SMILES: COC(=O)Cc1ccc(Br)cc1COCCc1cc(C#N)ccc1COc1ccc(F)c(Br)n1]

Prepare the title compound essentially as described in Preparation 224 using 4-[(6-bromo-5-fluoro-2-pyridyl) oxymethyl]-3-(2-hydroxyethyl)benzonitrile and methyl 2-[4-bromo-2-(bromomethyl)phenyl]acetate as starting materials, using 2,6-di-tert-butyl-4-methylpyridine in place of 2,6-di-tert-butylpyridine, and stirring the reaction at RT overnight. Upon completion, concentrate the reaction mixture, then add water and extract three times with EtOAc. Combine the organic layers, wash with saturated aqueous NaCl, dry over $Na_2SO_4$, filter and concentrate. Purify by silica gel chromatography using a gradient of 0 to 100% DCM in petroleum ether to give the title compound as a pale-yellow oil. ES-MS m/z 592 (M+H).

Preparation 266

Methyl 2-($5^4$-cyano-$2^3$-fluoro-3,8-dioxa-2(2,6)-pyridina-1(1,3),5(1,2)-dibenzenacyclononaphane-$1^4$-yl)acetate

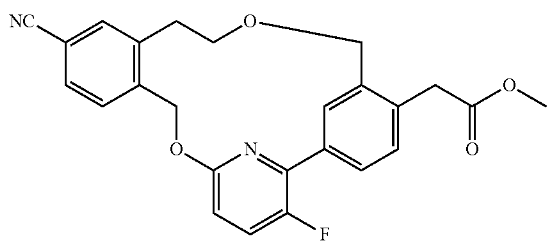 [SMILES: COC(=O)Cc1ccc2cc1COCCc1cc(C#N)ccc1COc1ccc(F)c-2n1]

Prepare the title compound essentially as described in Preparation 216 using methyl 2-(4-bromo-2-((2-(((6-bromo-5-fluoropyridin-2-yl)oxy)methyl)-5-cyanophenethoxy) methyl)phenyl)acetate as starting material, using (2-Dicyclohexylphosphino-2',4',6'-triisopropyl-1,1'-biphenyl)[2-(2'-amino-1,1'-biphenyl)]palladium(II) methanesulfonate (XPhos Pd G3) as catalyst, and protecting the reaction mixture from light during heating. Upon completion, concentrate the reaction mixture under reduced pressure to remove the solvent. Dilute the residue with water and extract three times with EtOAc. Combine the organic layers, wash with saturated aqueous NaCl, dry over $Na_2SO_4$, filter and concentrate under reduced pressure. Purify by silica gel chromatography using a gradient of 0 to 33% EtOAc in petroleum ether to give the title compound as a brown solid. ES-MS m/z 433 (M+H).

Preparation 267

2-($5^4$-Cyano-$2^3$-fluoro-3,8-dioxa-2(2,6)-pyridina-1(1,3),5(1,2)-dibenzenacyclononaphane-$1^4$-yl)acetic acid

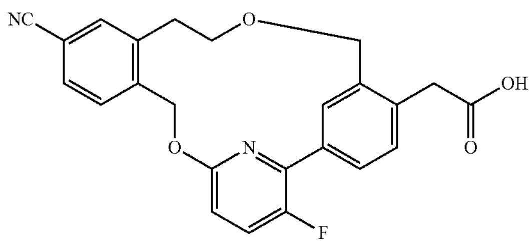 [SMILES: N#Cc1ccc2c(c1)CCOCc1cc(ccc1CC(=O)O)-c1nc(ccc1F)OC2]

Prepare the title compound essentially as described in Preparation 78 using methyl 2-($5^4$-cyano-$2^3$-fluoro-3,8-dioxa-2(2,6)-pyridina-1(1,3),5(1,2)-dibenzenacyclononaphane-$1^4$-yl)acetate. Upon completion, quench the reaction with 1 M aqueous citric acid solution until pH=4.5. Filter the crashed solid, wash it with water, collect it and dry it under reduced pressure to give the titled compound as a white solid, which is used in Preparation 268 without further purification. ES-MS m/z 419 (M+H).

Preparation 268

Methyl (S)-4-(2-($5^4$-cyano-$2^3$-fluoro-3,8-dioxa-2(2,6)-pyridina-1(1,3),5(1,2)-dibenzenacyclononaphane-$1^4$-yl)acetamido)-3-(2-methoxyethoxy)-5-((oxetan-2-ylmethyl)amino)benzoate

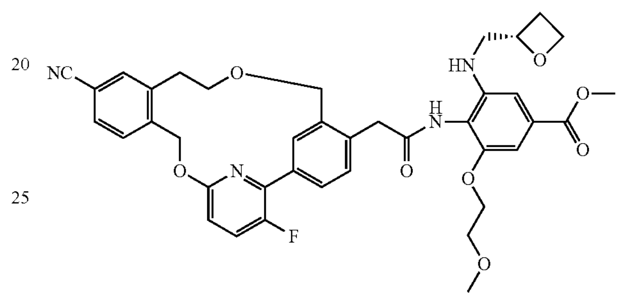

Prepare the title compound essentially as described in Preparation 86 using 2-($5^4$-cyano-$2^3$-fluoro-3,8-dioxa-2(2,6)-pyridina-1(1,3),5(1,2)-dibenzenacyclononaphane-$1^4$-yl) acetic acid (Preparation 267) and methyl 4-amino-3-(2-methoxyethoxy)-5-[[(2S)-oxetan-2-yl]methylamino] benzoate, stirring the reaction at RT overnight. Upon completion, dilute the reaction with water and extract three times with EtOAc. Combine the organic layers, wash with saturated aqueous NaCl, dry over $Na_2SO_4$, filter and concentrate under reduced pressure to give the title compound as a pale-brown oil which is used in Preparation 269 without further purification. ES-MS m/z 711 (M+H).

Preparation 269

Methyl (S)-2-(($5^4$-cyano-$2^3$-fluoro-3,8-dioxa-2(2,6)-pyridina-1(1,3),5(1,2)-dibenzenacyclononaphane-$1^4$-yl)methyl)-4-(2-methoxyethoxy)-1-(oxetan-2-ylmethyl)-1H-benzo[d]imidazole-6-carboxylate

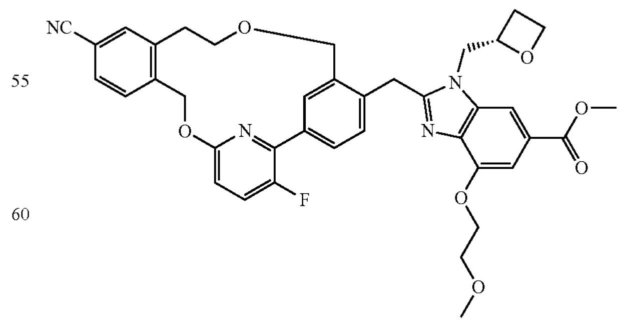

Prepare the title compound essentially as described in Preparation 102 using methyl (S)-4-(2-($5^4$-cyano-$2^3$-fluoro- 3,8-dioxa-2(2,6)-pyridina-1(1,3),5(1,2)-dibenzenacyclononaphane-$1^4$-yl)acetamido)-3-(2-methoxyethoxy)-5-((oxetan-2-ylmethyl)amino)benzoate (Preparation 268) and 1:1 1,2-dichloroethane:acetic acid, heating the reaction at 55° C. for 5 h. Upon completion of the reaction, remove the solvent under reduced pressure, then add 1:1 EtOAc:toluene to the residue and concentrate in vacuo. Purify by silica gel chromatography using a gradient of 0 to 6% MeOH in DCM to give the title compound as an orange oil. ES-MS m/z 693 (M+H).

Preparation 270

Methyl 2-(5-cyano-2-methyl-phenyl)-2,2-difluoro-acetate

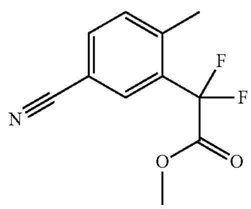 [SMILES: COC(=O)C(F)(F)c1cc(C#N)ccc1C]

Stir 3-iodo-4-methylbenzonitrile (5 g, 19.96 mmol) and copper (12 g, 179.4 mmol) in THE (30 mL) and DMSO (80 mL). To this slurry, add methyl bromodifluoroacetate (6 mL, 51.9 mmol) and continue to stir this mixture at 30° C. under nitrogen for 18 h. After this time, add 100 mL of saturated aqueous $NaHCO_3$ solution followed by 100 mL of EtOAc. Filter this mixture and wash the solids with EtOAc (3×50 mL). The filtrate is then separated, and the organic layer washed with saturated aqueous $NH_4Cl$ solution. Dry the organics over $MgSO_4$, filter, and concentrate. Purify this residue via silica gel chromatography (0-25% EtOAc in hexanes) to give the product as a clear crystalline solid (3.3 g, 73%). $^1$H NMR (DMSO-$d_6$) δ 2.41 (s, 3H), 3.33 (s, 3H), 7.61 (d, J=8.0 Hz, 1H), 7.99 (d, J=7.9 Hz, 1H), 8.04 (d, J=1.2 Hz, 1H).

Preparation 271

Methyl 2-[2-(bromomethyl)-5-cyano-phenyl]-2,2-difluoro-acetate

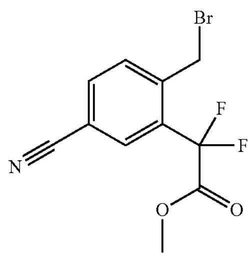 [SMILES: COC(=O)C(F)(F)c1cc(C#N)ccc1CBr]

Dissolve methyl 2-(5-cyano-2-methyl-phenyl)-2,2-difluoro-acetate (4.4 g, 20 mmol) and N-bromosuccinimide (4 g, 22.47 mmol) in ACN (100 mL). Subject this solution to a 4100K white lightbulb via flow conditions (1.0 mL/min; 72 feet of ⅛" outer diameter reaction tubing, wrapped around a beaker; maintained at 30° C.) twice. After this processing, concentrate the reaction liquid to dryness and then purify this residue via silica gel chromatography (0-10% EtOAc in hexanes) to give the product as a clear, thick oil (3.7 g, 62%). $^1$H NMR (DMSO-$d_6$) δ 3.41 (s, 3H), 3.89 (s, 2H), 7.61 (d, J=7.9 Hz, 1H), 7.99 (d, J=8.0 Hz, 1H), 8.03 (s, 1H).

Preparation 272

2-[2-[(6-Bromo-2-pyridyl)oxymethyl]-5-cyano-phenyl]-2,2-difluoro-acetic acid

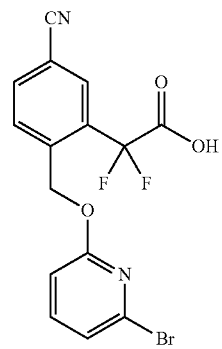 [SMILES: N#Cc1ccc(COc2cccc(Br)n2)c(C(F)(F)C(=O)O)c1]

Dissolve methyl 2-[2-(bromomethyl)-5-cyano-phenyl]-2,2-difluoro-acetate (6.2 g, 20 mmol) and 2-bromo-6-hydroxypyridine (4.5 g, 2 5 mmol) in DMSO (50 mL). Add potassium phosphate tribasic (6.6 g, 30 mmol) to this solution and heat to 60° C. for 2 h. After this time, quench the reaction with 1N HCl (to pH ~6) and extract with EtOAc. Dry the combined organics over $MgSO_4$, filter, and concentrate to give the product as a thick brown oil (7.8 g, 100%). ES-MS m/z ($^{79}$Br/$^{81}$Br) 382.8/384.8 $[M+H]^+$.

Preparation 273

Methyl 2-[2-[(6-bromo-2-pyridyl)oxymethyl]-5-cyano-phenyl]-2,2-difluoro-acetate

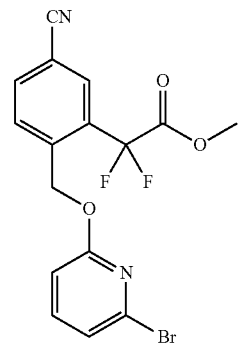 [SMILES: COC(=O)C(F)(F)c1cc(C#N)ccc1COc1cccc(Br)n1]

Stir 2-[2-[(6-bromo-2-pyridyl)oxymethyl]-5-cyano-phenyl]-2,2-difluoro-acetic acid (7.8 g, 20 mmol) in MeOH (100 mL). Add concentrated sulfuric acid (0.1 mL, 2 mmol) and heat to reflux for 30 h. Concentrate the reaction mixture to dryness and then purify the residue via silica gel chromatography (0-100% EtOAc in hexanes) to give the product as a white crystalline solid (8 g, 99%). ES-MS m/z ($^{79}$Br/$^{81}$Br) 396.8/398.8 [M+H]$^+$.

Preparation 274

4-[(6-Bromo-2-pyridyl)oxymethyl]-3-(1,1-difluoro-2-hydroxy-ethyl)benzonitrile

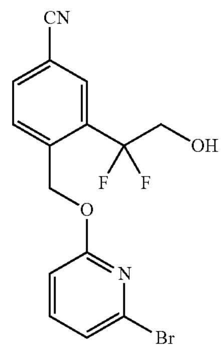 [SMILES: N#Cc1ccc(COc2cccc(Br)n2)c(C(F)(F)CO)c1]

Dissolve methyl 2-[2-[(6-bromo-2-pyridyl)oxymethyl]-5-cyano-phenyl]-2,2-difluoro-acetate (8 g, 20.14 mmol) in THE (100 mL). To this solution add lithium borohydride (0.88 g, 40.4 mmol) and stir at ambient temperature under nitrogen for 2 h. After this time, quench the reaction with saturated $NH_4Cl$ solution, and extract with EtOAc. Dry the organics over $MgSO_4$, filter, and concentrate. Purify this residue via silica gel chromatography (0-50% EtOAc in hexanes) to give the product as a thick, clear oil (4.7 g, 63%). ES-MS m/z ($^{79}$Br/$^{81}$Br) 368.8/370.8 [M+H]$^+$.

Preparation 275

3-[2-[(5-Bromo-2-iodo-phenyl)methoxy]-1,1-difluoro-ethyl]-4-[(6-bromo-2-pyridyl)oxymethyl]benzonitrile

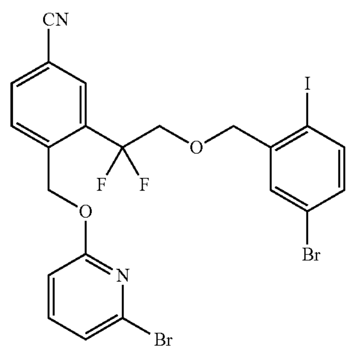 [SMILES: N#Cc1ccc(COc2cccc(Br)n2)c(C(F)(F)COCc2cc(Br)ccc2I)c1]

Dissolve 4-[(6-bromo-2-pyridyl)oxymethyl]-3-(1,1-difluoro-2-hydroxy-ethyl)benzonitrile (4.5 g, 12 mmol) in THE (60 mL) and DMF (10 mL). To this solution add sodium hydride (0.6 g, 15 mmol; 60% mass in mineral oil) and stir at ambient temperature under nitrogen for 5 min. Then add 4-bromo-2-(chloromethyl)-1-iodobenzene (4.8 g, 14 mmol) and continue stirring at ambient temperature under nitrogen for 18 h. After this time, quench the reaction with saturated aqueous $NH_4Cl$ solution, and extract with EtOAc. Dry the organics over $MgSO_4$, filter, and concentrate. Purify this residue via silica gel chromatography (0-30% EtOAc in hexanes) to give the product as a thick clear oil (3.9 g, 48%). ES-MS m/z ($^{79}$Br/$^{81}$Br) 663.0/665.0 [M+H]$^+$.

Preparation 276

Ethyl 2-[4-bromo-2-[[2-[2-[(6-bromo-2-pyridyl)oxymethyl]-5-cyano-phenyl]-2,2-difluoro-ethoxy]methyl]phenyl]acetate

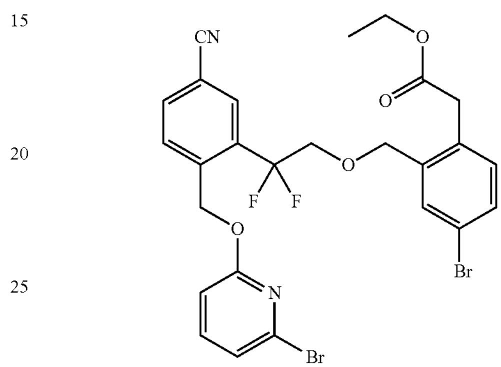

Dissolve 3-[2-[(5-bromo-2-iodo-phenyl)methoxy]-1,1-difluoro-ethyl]-4-[(6-bromo-2-pyridyl)oxymethyl]benzonitrile (3.9 g, 5.9 mmol) and [(4,5-bis(diphenylphosphino)-9,9-dimethylxanthene)-2-(2'-amino-1,1'-biphenyl)]palladium (II) methanesulfonate (XantPhos Pd G3, 0.6 g, 0.6 mmol) in THE (30 mL). To this solution add (2-ethoxy-2-oxo-ethyl)zinc bromide (0.5 M in ether) (18 mL, 9.0 mmol) and heat this mixture to 60° C. under nitrogen for 18 h. After this time, cool the reaction to ambient temperature, quench the reaction with saturated aqueous $NaHCO_3$ solution, and extract with EtOAc. Dry the organics over $MgSO_4$, filter, and concentrate. Purify this residue via silica gel chromatography (0-30% EtOAc in hexanes) to give the product as a thick, light brown oil (1.6 g, 44%). ES-MS m/z ($^{79}$Br/$^{81}$Br) 623.2/625.2 [M+H]$^+$.

Preparation 277

Ethyl 2-($5^4$-cyano-6,6-difluoro-3,8-dioxa-2(2,6)-pyridina-1(1,3),5(1,2)-dibenzeneacyclonaphane-$1^4$-yl)acetate

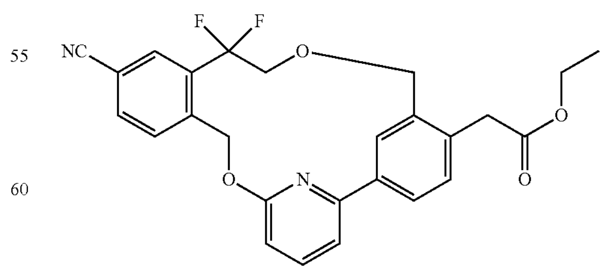

Dissolve ethyl 2-[4-bromo-2-[[2-[2-[(6-bromo-2-pyridyl)oxymethyl]-5-cyano-phenyl]-2,2-difluoro-ethoxy]methyl]phenyl]acetate (1.6 g, 2.9 mmol) in 1,4-dioxane (30 mL). To this solution add KOAc (0.64 g, 6.39 mmol) and bis(pinacolato)diboron (0.8 g, 3.09 mmol) and bubble nitrogen through this for 10 min. After this time add 1,1'-bis(diphenylphosphino)ferrocene-palladium(II)dichloride DCM complex (0.11 g, 0.132 mmol) and heat this mixture to 80° C. under nitrogen for 18 h. After this time, cool the reaction to ambient temperature, dilute with saturated aqueous NaCl solution, and extract with EtOAc. Dry the organics over $MgSO_4$, filter, and concentrate. Dissolve this residue in 1,4-dioxane (50 mL) and water (3 mL) and add potassium phosphate tribasic (1.4 g, 6.5 mmol) followed by chloro(2-dicyclohexylphosphino-2',4',6'-triisopropyl-1,1'-biphenyl)[2-(2'-amino-1,1'-biphenyl)]palladium(II) (XPhos Pd G2, 0.1 g, 0.125 mmol). Heat this mixture to 60° C. for 2 h. After this time, cool the reaction to ambient temperature, quench the reaction with saturated aqueous $NH_4Cl$ solution, and extract with EtOAc. Dry the organics over $MgSO_4$, filter, and concentrate. Purify this residue via silica gel chromatography (0-50% EtOAc in hexanes) to give the product as a white solid (249 mg, 21%). ES-MS (m z) 465.2 (M+H).

Preparation 278

Methyl (S)-2-(($5^4$-cyano-6,6-difluoro-3.8-dioxa-2(2,6)-pyridina-1(1,3),5(1,2)-dibenzenacyclonaphane-$1^4$-yl)methyl)-4-(2-methoxyethoxy)-1-(oxatan-2-ylmethyl)-1H-benzo[d]imidazole-6-carboxylate

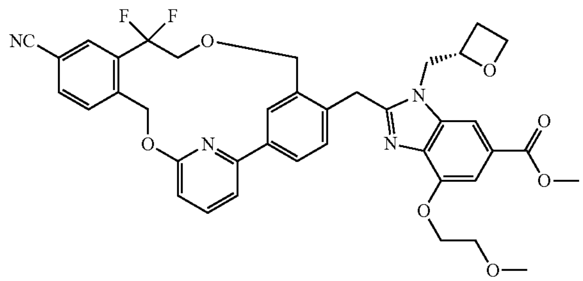 [SMILES: COCCOc1cc(C(=O)OC)cc2c1nc(Cc1ccc3cc1COCC(F)(F)c1cc(C#N)ccc1COc1cccc-3n1)n2C[C@@H]1CCO1]

Dissolve ethyl 2-($5^4$-cyano-6,6-difluoro-3,8-dioxa-2(2,6)-pyridina-1(1,3),5(1,2)-dibenzeneacyclonaphane-$1^4$-yl) acetate (249 mg, 0.54 mmol) in ACN (5 mL), THE (1.8 mL) and water (1.8 mL). To this solution add 1,5,7-triazabicyclo[4.4.0]dec-5-ene (0.23 g, 1.62 mmol) and stir this mixture at ambient temperature for 2 h. After this time, quench the reaction with saturated aqueous $NH_4Cl$ solution and extract with EtOAc. Dry the organics over $MgSO_4$, filter, and concentrate. Dissolve this residue in DMF (2 mL) and add methyl 4-amino-3-(2-methoxyethoxy)-5-[[(2S)-oxetan-2-yl]methylamino]benzoate (0.055 g, 0.18 mmol), DMF (0.09 mL, 0.5 mmol) and HATU (0.09 g, 0.24 mmol) and stir at ambient temperature for 18 h. After this time, quench the reaction with saturated aqueous $NH_4Cl$ solution, and extract with EtOAc. Dry the organics over $MgSO_4$, filter, and concentrate. Dissolve this residue in 1,2-dichloroethane (1 mL), add acetic acid (1 mL), and heat this mixture to 50° C. for 18 h. Concentrate the mixture to dryness and purify the residue via silica gel chromatography (0-100% EtOAc in hexanes) to give the title compound as an off-white solid (61 mg, 52.5%). ES-MS (m z) 711.4 (M+H).

Preparation 279

4-[(2-Chloropyrimidin-4-yl)oxymethyl]-3-iodo-benzonitrile

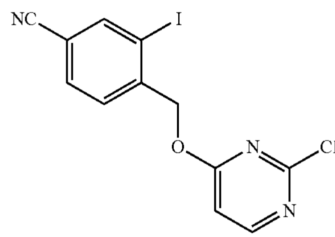 [SMILES: N#Cc1ccc(COc2ccnc(Cl)n2)c(I)c1]

To a solution of 2-chloropyrimidin-4-ol (8.50 g, 65.1 mmol) in DMF (150 mL), add $Cs_2CO_3$ (42.5 g, 130 mmol), and 4-(bromomethyl)-3-iodo-benzonitrile (21.04 g, 65.35 mmol). Stir the reaction mixture at ambient temperature for 16 h. Pour the crude reaction into water and collect the precipitate via filtration. Dissolve the solid material into DCM and wash twice with water. Dry the organic phase over $MgSO_4$, filter, and concentrate under reduced pressure to give the title compound (20.3 g, 84%) as a light orange solid, which is used in Preparation 280 without further purification. ES/MS m/z 372 (M+H).

Preparation 280

4-[(2-Chloropyrimidin-4-yl)oxymethyl]-3-[(E)-2-ethoxyvinyl]benzonitrile

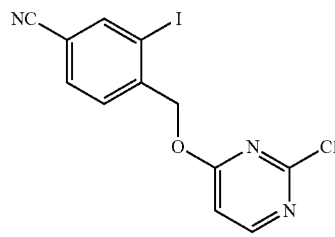 [SMILES: N#Cc1ccc(COc2ccnc(Cl)n2)c(I)c1]

To a solution of 4-[(2-chloropyrimidin-4-yl)oxymethyl]-3-iodo-benzonitrile (10.1 g, 27.2 mmol) in THE (150 mL), add tribasic potassium phosphate (40 mL, 80 mmol, 2 M solution in water), 2-[(E)-2-ethoxyvinyl]-4,4,5,5-tetramethyl-1,3,2-dioxaborolane (7.5 mL, 35 mmol), and bis(triphenylphosphine)palladium(II) dichloride (953 mg, 1.36 mmol). Sparge the solution with nitrogen for 15 min, then stir at 55° C. for 4 h. Dilute the reaction mixture with water and extract with EtOAc. Dry the organic phase with $MgSO_4$, filter, and concentrate under reduced pressure. Dissolve the residue in EtOAc and wash with water to remove pinacol. Dry the organic phase with $MgSO_4$, filter, and concentrate under reduced pressure. Purify the residue via silica gel chromatography using a gradient of 0 to 30% EtOAc in hexanes to give the title compound (5.97 g, 70%). ES/MS m/z ($^{35}Cl/^{37}Cl$) 315/317 $[M+H]^+$.

Preparation 281

4-[(2-Chloropyrimidin-4-yl)oxymethyl]-3-(2-hydroxyethyl)benzonitrile

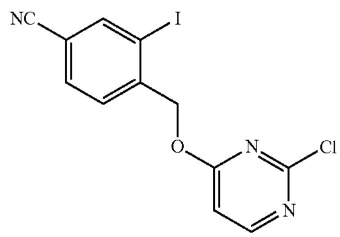 [SMILES: N#Cc1ccc(COc2ccnc(Cl)n2)c(I)c1]

To a solution of 4-[(2-chloropyrimidin-4-yl)oxymethyl]-3-[(E)-2-ethoxyvinyl]benzonitrile (5.75 g, 18.2 mmol) in THF (85 mL), add hydrochloric acid (46 mL, 184 mmol, 4M solution in dioxane). Stir at ambient temperature for 2.5 h. Concentrate the reaction under reduced pressure, then dilute the residue with DCM. Adjust the mixture to pH=8 using saturated aqueous $NaHCO_3$ solution, then extract with DCM. Dry the organic phase with $MgSO_4$, filter, and concentrate under reduced pressure. Dissolve the residue in MeOH (100 mL), cool to 0° C. in an ice bath, then gradually add sodium borohydride (1.28 g, 33.7 mmol). Stir the mixture at 0° C. for 30 min. Quench the reaction mixture with 1 M aqueous NaOH, then further dilute the solution with water and DCM, and extract with DCM. Dry the organic phase over $MgSO_4$, filter, and concentrate under reduced pressure. Purify the residue via silica gel chromatography using a gradient of 0 to 50% EtOAc in hexanes give the title compound (2.86 g, 44%). ES/MS m/z ($^{35}$Cl/$^{37}$Cl) 289/291 $[M+H]^+$.

Preparation 282

Methyl 2-[4-bromo-2-[2-[2-[(2-chloropyrimidin-4-yl)oxymethyl]-5-cyano-phenyl]ethoxymethyl]phenyl]acetate

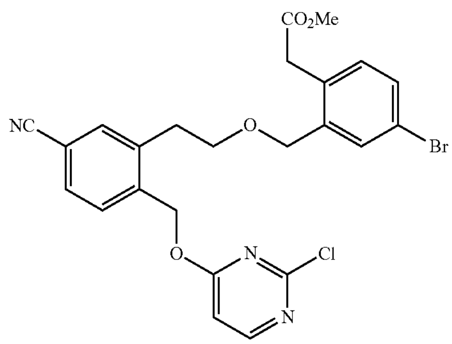 [SMILES: COC(=O)Cc1ccc(Br)cc1COCCc1cc(C#N)ccc1COc1ccnc(Cl)n1]

Cool a solution of 4-[(2-chloropyrimidin-4-yl)oxymethyl]-3-(2-hydroxyethyl)benzonitrile (200 mg, 0.69 mmol) in anhydrous DCM (4.6 mL) to 0° C. in an ice bath, add methyl 2-[4-bromo-2-(bromomethyl)phenyl]acetate (556 mg, 1.73 mmol), then add 2,6-di-tert-butylpyridine (0.31 mL, 1.38 mmol) and silver trifluoromethanesulfonate (354 mg, 1.38 mmol). Stir the mixture for 1 h at 0° C., then allow to stir for 16 h at ambient temperature. Filter the reaction mixture through a pad of diatomaceous earth and rinse the pad with DCM. Concentrate the filtrate under reduced pressure and purify the residue via silica gel chromatography using a gradient of 0 to 40% EtOAc in hexanes to give the title compound (128 mg, 35%). ES/MS m/z ($^{79}$Br/$^{81}$Br) 529/531 $[M+H]^+$.

Preparation 283

Methyl 2-[2-[2-[2-[(2-chloropyrimidin-4-yl)oxymethyl]-5-cyano-phenyl]ethoxymethyl]-4-(4,4,5,5-tetramethyl-1,3,2-dioxaborolan-2-yl)phenyl]acetate

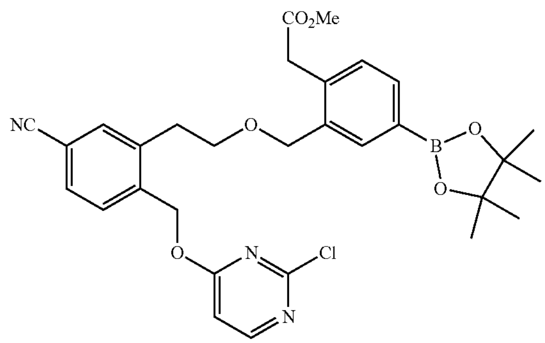 [SMILES: COC(=O)Cc1ccc(B2OC(C)(C)C(C)(C)O2)cc1COCCc1cc(C#N)ccc1COc1ccnc(Cl)n1]

To a solution of methyl 2-[4-bromo-2-[2-[2-[(2-chloropyrimidin-4-yl)oxymethyl]-5-cyano-phenyl]ethoxymethyl]phenyl]acetate (566 mg, 0.715 mmol) in 1,4-dioxane (7.5 mL), add bis(pinacolato)diboron (222 mg, 0.86 mmol), KOAc (177 mg, 1.80 mmol), and 1,1'-bis(diphenylphosphino)ferrocene palladium(II) dichloride dichloromethane complex (30 mg, 0.036 mmol). Sparge the solution with nitrogen for 10 min, then heat to 80° C. Stir for 19 h. Cool the reaction to ambient temperature and filter through a plug of silica gel, washing the silica gel plug with DCM. Concentrate the filtrate under reduced pressure to obtain the title compound, which is used in Preparation 284 without further purification. ES/MS m/z ($^{35}$Cl/$^{37}$Cl) 496/498 $[M+H]^+$ (as boronic acid).

Preparation 284

Methyl 2-($5^4$-cyano-3,8-dioxa-2(2,4)-pyrimidina-1(1,3),5(1,2)-dibenzenacyclononaphane-$1^4$-yl)acetate

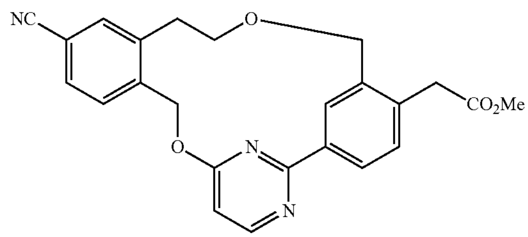 [SMILES: COC(=O)Cc1ccc2cc1COCCc1cc(C#N)ccc1COc1ccnc-2n1]

To a solution of methyl 2-[2-[2-[2-[(2-chloropyrimidin-4-yl)oxymethyl]-5-cyano-phenyl]ethoxymethyl]-4-(4,4,5,5-tetramethyl-1,3,2-dioxaborolan-2-yl)phenyl]acetate (Preparation 283, 130 mg, 0.225 mmol) in THE (5.6 mL), add tribasic potassium phosphate (0.68 mL, 0.68 mmol, 1 M aqueous solution). Sparge the solution with nitrogen for 10 min, then add chloro(2-dicyclohexylphosphino-2',4',6'-triisopropyl-1,1'-biphenyl)[2-(2'-amino-1,1'-biphenyl)]palladium(II) (XPhos Pd G2, 8.9 mg, 0.011 mmol) and resume sparging for a further 5 min. Heat the solution at 50° C. for 6 h. Cool the reaction to ambient temperature, then add water and extract with EtOAc. Dry the combined organic phases over $MgSO_4$, filter, and concentrate under reduced pressure. Purify the crude residue via silica gel chromatography using a 0 to 40% gradient of EtOAc in hexanes to give the title compound (21 mg, 22%). ES/MS m/z 416 (M+H).

Preparation 285

2-($5^4$-Cyano-3,8-dioxa-2(2,4)-pyrimidina-1(1,3),5(1,2)-dibenzenacyclononaphane-$1^4$-yl)acetic acid

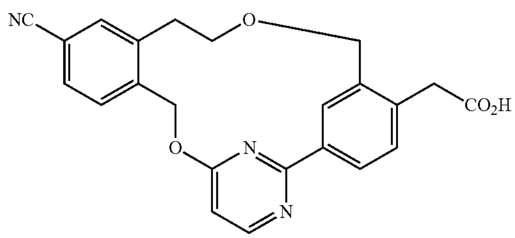 [SMILES: N#Cc1ccc2c(c1)CCOCc1cc(ccc1CC(=O)O)-c1nccc(n1)OC2]

Prepare the title compound essentially as described in Preparation 217 using methyl 2-($5^4$-cyano-3,8-dioxa-2(2,4)-pyrimidina-1(1,3),5(1,2)-dibenzenacyclononaphane-$1^4$-yl) acetate, stirring the reaction at ambient temperature for 2 h. Upon completion, quench the reaction with 5% aqueous citric acid bringing the pH to 4, then dilute mixture with EtOAc. Separate the layers and extract the aqueous layer with EtOAc. Wash the combined organic phases with saturated aqueous NaCl solution. Dry the organic phase over $MgSO_4$, filter, and concentrate under vacuum. Triturate the resulting solid with water to give the title compound. ES/MS m/z 402 (M+H).

Preparation 286

Methyl (S)-4-(2-($5^4$-cyano-3,8-dioxa-2(2,4)-pyrimidina-1(1,3),5(1,2)-dibenzenacyclononaphane-$1^4$-yl) acetamido)-3-methoxy-5-((oxetan-2-ylmethyl) amino)benzoate

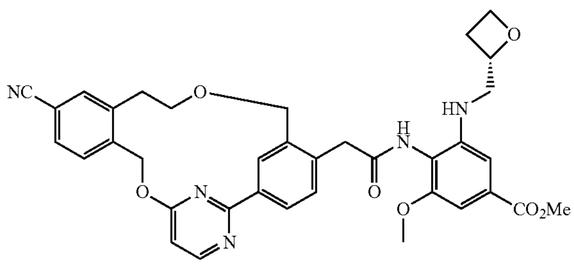 [SMILES: COC(=O)c1cc(NC[C@@H]2CCO2)c(NC(=O)Cc2ccc3cc2COCCc2cc(C#N)ccc2COc2ccnc-3n2)c(OC)c1]

Prepare the title compound essentially as described in Preparation 164 using 2-($5^4$-cyano-3,8-dioxa-2(2,4)-pyrimidina-1(1,3),5(1,2)-dibenzenacyclononaphane-$1^4$-yl)acetic acid and methyl 4-amino-3-methoxy-5-[[(2S)-oxetan-2-yl] methylamino]benzoate as starting materials, adding 2,4,6-tripropyl-1,3,5,2,4,6-trioxatriphosphorinane-2,4,6-trioxide as a 50% solution in DMFm and heating the solution to 42° C. for 24 h. Cool reaction to ambient temperature and then add water. Extract the aqueous layer with EtOAc, then wash the organics with saturated aqueous $NaHCO_3$ solution. Dry the organics over $MgSO_4$, filter, and concentrate under reduced pressure to give the title compound which is used in Preparation 287 without further purification (23.6 mg, 83%). ES/MS m/z 650 (M+H).

Preparation 287

Methyl (S)-2-(($5^4$-cyano-3,8-dioxa-2(2,4)-pyrimidina-1(1,3),5(1,2)-dibenzenacyclononaphane-$1^4$-yl) methyl)-4-methoxy-1-(oxetan-2-ylmethyl)-1H-benzo [d]imidazole-6-carboxylate

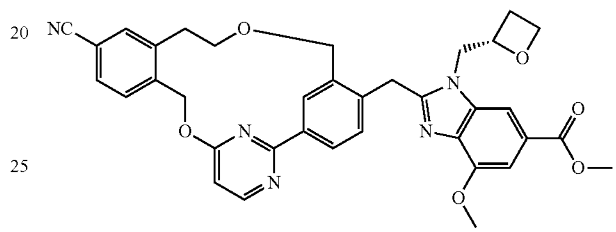

Prepare the title compound essentially as described in Preparation 102 using methyl (S)-4-(2-($5^4$-cyano-3,8-dioxa-2(2,4)-pyrimidina-1(1,3),5(1,2)-dibenzenacyclononaphane-$1^4$-yl)acetamido)-3-methoxy-5-((oxetan-2-ylmethyl)amino) benzoate (Preparation 286) and using a 5:1 mixture of 1,2-dichloroethane:acetic acid as solvent, heating the reaction to 53° C. for 22 h. Upon completion, cool the reaction mixture to ambient temperature, dilute with DCM, and concentrate under reduced pressure. Dissolve the residue in EtOAc and concentrate under reduced pressure twice. Purify the residue via silica gel chromatography using a gradient of 0 to 5% MeOH in DCM to give the title compound. ES/MS m/z 632 (M+H).

Preparation 288

Ethyl 4-[(E)-2-ethoxyvinyl]-6-(trifluoromethyl)pyridine-3-carboxylate

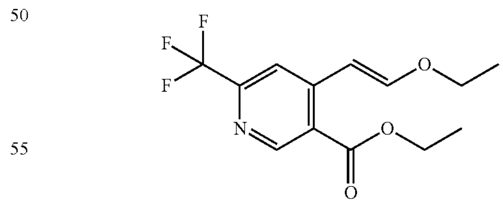

To a solution of ethyl 4-chloro-6-(trifluoromethyl)nicotinate (15 g, 57.4 mmol) and $Cs_2CO_3$ (37 g, 112.4 mmol) in 1,4-dioxane (130 mL) and water (45 mL), add 2-[(E)-2-ethoxyvinyl]-4,4,5,5-tetramethyl-1,3,2-dioxaborolane (13.4 mL, 62.9 mmol), then add tetrakis(triphenylphosphine)palladium(0) (7 g, 5.75 mmol). Sparge the solution with nitrogen, then heat the mixture to 90° C. and stir for 16 h. Concentrate the reaction mixture under reduced pressure, then dilute with water. Extract aqueous layer with EtOAc, dry the combined organics over $Na_2SO_4$, filter, and concentrate under reduced pressure. Purify the residue silica gel chromatography eluting with a gradient of 0 to 23% EtOAc in petroleum ether to give the title compound (14.5 g, 84%). ES/MS m/z 290 (M+H).

Preparation 289

[4-[(E)-2-Ethoxyvinyl]-6-(trifluoromethyl)-3-pyridyl]methanol

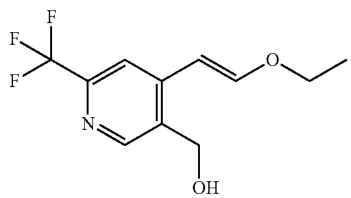 [SMILES: CCO/C=C/c1cc(C(F)(F)F)ncc1CO]

To a solution of ethyl 4-[(E)-2-ethoxyvinyl]-6-(trifluoromethyl)pyridine-3-carboxylate (14.5 g, 48.1 mmol) in THE (100 mL) at −78° C. under an inert atmosphere, add diisobutylaluminum hydride (150 mL, 150 mmol, 1M solution in toluene). Remove the reaction vessel from the cooling bath and allow to stir at ambient temperature for 5 h. Quench the reaction by adding a saturated aqueous solution of potassium sodium tartrate (200 mL) at 0° C., then add DCM (100 mL). Extract the mixture with DCM, then wash the combined organic phases with saturated aqueous NaCl solution. Dry the organic phase over $MgSO_4$, filter, and concentrate under reduced pressure. Purify the residue via silica gel chromatography eluting with a gradient of 0 to 30% EtOAc in petroleum ether to give the title compound (11 g, 90%). ES/MS m/z 247 ($M^+$).

Preparation 290

5-[(6-Bromo-2-pyridyl)oxymethyl]-4-[(E)-2-ethoxyvinyl]-2-(trifluoromethyl)pyridine

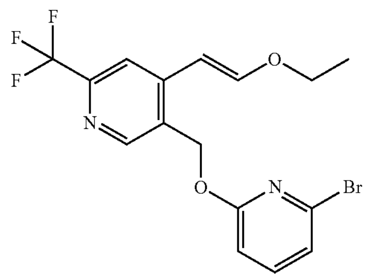 [SMILES: CCO/C=C/c1cc(C(F)(F)F)ncc1COc1cccc(Br)n1]

To a solution of [4-[(E)-2-ethoxyvinyl]-6-(trifluoromethyl)-3-pyridyl]methanol (10.5 g, 40.4 mmol) and 2-bromo-6-fluoropyridine (5.4 mL, 51 mmol) in 1,4-dioxane (100 mL), add potassium tert-butoxide (52 mL, 52 mmol, 1M solution in THF) at 0° C. Stir the reaction at 0° C. for 30 min, then at ambient temperature for 2 h. Quench the reaction with saturated aqueous $NH_4Cl$ solution (100 mL), then extract with EtOAc. Dry the organics over $MgSO_4$, filter, and concentrate under reduced pressure. Purify the residue via silica gel chromatography using a gradient of 0 to 30% EtOAc in petroleum ether to give the title compound (17 g, 96%). ES/MS m/z ($^{79}Br/^{81}Br$) 402/404 $[M+H]^+$.

Preparation 291

2-[5-[(6-Bromo-2-pyridyl)oxymethyl]-2-(trifluoromethyl)-4-pyridyl]ethanol

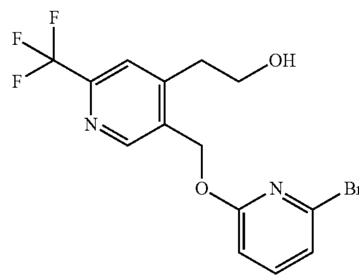 [SMILES: OCCc1cc(C(F)(F)F)ncc1COc1cccc(Br)n1]

To a solution of 5-[(6-bromo-2-pyridyl)oxymethyl]-4-[(E)-2-ethoxyvinyl]-2-(trifluoromethyl)pyridine (16.5 g, 39.3 mmol) in THF (300 mL) and water (500 mL) add mercuric acetate (14.45 g, 44.89 mmol) at 0° C. Stir the mixture for 30 min at 0° C., then add 50% aqueous $K_2CO_3$ solution (210 mL) and sodium borohydride (6.31 g, 165 mmol). Stir the mixture at 0° C. for 2.5 h. Filter the reaction mixture, washing the filter with EtOAc. Transfer the filtrate to a separatory funnel and extract with EtOAc. Dry the combined organic phases with $Na_2SO_4$, filter, and concentrate under reduced pressure. Purify the residue via silica gel chromatography using a gradient of 0 to 25% EtOAc in petroleum ether to give the title compound (12.1 g, 81%). ES/MS m/z ($^{79}Br/^{81}Br$) 376/378 $[M+H]^+$.

Preparation 292

4-[2-[(5-Bromo-2-chloro-phenyl)methoxy]ethyl]-5-[(6-bromo-2-pyridyl)oxymethyl]-2-(trifluoromethyl)pyridine

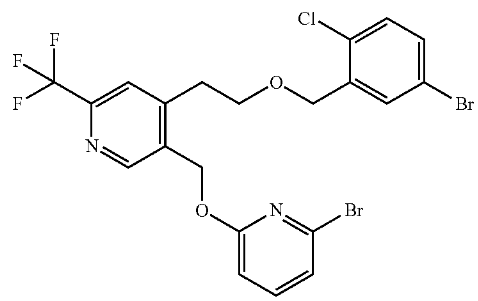 [SMILES: FC(F)(F)c1cc(CCOCc2cc(Br)ccc2Cl)c(COc2cccc(Br)n2)cn1]

To a solution 2-[5-[(6-bromo-2-pyridyl)oxymethyl]-2-(trifluoromethyl)-4-pyridyl]ethanol (5.46 g, 14.3 mmol), 4-bromo-1-chloro-2-(chloromethyl)benzene (5.19 g, 21.4 mmol), and 2,6-di-tert-butyl-4-methylpyridine (6 g, 28.64 mmol) in 1,2-dichloroethane (100 mL), add silver trifluoromethanesulfonate (12 g, 46.24 mmol) at ambient temperature under an inert atmosphere. Heat the reaction to 70° C. and stir for 18 h. Concentrate the crude reaction under reduced pressure, then dilute the resultant residue with water. Extract from the aqueous with EtOAc, then wash the combined organic phases with saturated aqueous NaCl solution. Dry the organic phase over $Na_2SO_4$, filter, and concentrate under reduced pressure. Purify the residue via silica gel chromatography eluting with a gradient of 0 to 20% EtOAc in petroleum ether to give the title compound (3.3 g, 37%). ES/MS m/z 580 (M+H).

Preparation 293

$1^4$-Chloro-$5^6$-(trifluoromethyl)-3,8-dioxa-2(2,6),5(3,4)-dipyridina-1(1,3)-benzenacyclononaphane

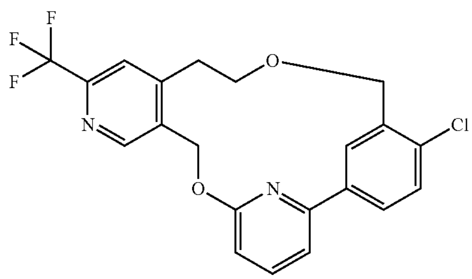 [SMILES: FC(F)(F)c1cc2c(cn1)COc1cccc(n1)-c1ccc(Cl)c(c1)COCC2]

Prepare the title compound essentially as described in Preparation 216 using 4-[2-[(5-bromo-2-chloro-phenyl)methoxy]ethyl]-5-[(6-bromo-2-pyridyl)oxymethyl]-2-(trifluoromethyl)pyridine as starting material and using (2-dicyclohexylphosphino-2',4',6'-triisopropyl-1,1'-biphenyl)[2-(2'-amino-1,1'-biphenyl)]palladium(II) methanesulfonate (XPhos Pd G3) as catalyst, heating the reaction at 110° C. for 15 h. Concentrate the crude reaction under reduced pressure, then dilute the residue with water. Extract from the aqueous with EtOAc, then wash the combined organic phases with saturated aqueous sodium chloride solution. Dry the organic phase over $Na_2SO_4$, filter, and concentrate under reduced pressure. Purify the residue via reverse phase HPLC chromatography using a gradient of 30-100% ACN in aqueous formic acid to give the title compound (403 mg, 14%) as a white solid. ES/MS m/z 421 (M+H).

Preparation 294

$1^4$-(4,4,5,5-Tetramethyl-1,3,2-dioxaborolan-2-yl)-$5^6$-(trifluoromethyl)-3,8-dioxa-2(2,6),5(3,4)-dipyridina-1(1,3)-benzenacyclononaphane

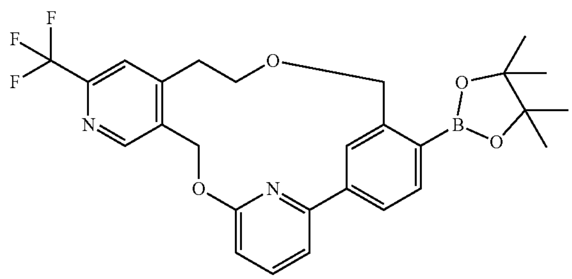 [SMILES: CC1(C)OB(c2ccc3cc2COCCc2cc(C(F)(F)F)ncc2COc2cccc-3n2)OC1(C)C]

To a solution of $1^4$-chloro-$5^6$-(trifluoromethyl)-3,8-dioxa-2(2,6),5(3,4)-dipyridina-1(1,3)-benzenacyclononaphane (275 mg, 0.62 mmol), KOAc (155 mg, 1.56 mmol), and bis(pinacolato)diboron (321 mg, 1.24 mmol) in 1,4-dioxane (6.5 mL), add chloro(2-dicyclohexylphosphino-2',4',6'-triisopropyl-1,1'-biphenyl)[2-(2'-amino-1,1'-biphenyl)]palladium(II) (XPhos Pd G2, 50 mg, 0.06 mmol). Sparge the solution with nitrogen, then heat to 80° C. and stir for 18 h. Concentrate the reaction mixture under reduced pressure, then dilute the residue with water. Extract from the aqueous with EtOAc, then wash the combined organic phases with saturated aqueous NaCl solution. Dry the organic phase over $Na_2SO_4$, filter, and concentrate under reduced pressure. Purify the residue via silica gel chromatography eluting with a gradient of 0 to 30% EtOAc in petroleum ether to give the title compound (274 mg, 70%). ES/MS m/z 513 (M+H).

Preparation 295

Methyl 2-(chloromethyl)-7-(2-methoxyethoxy)-3-[[(2S)-oxetan-2-yl]methyl]benzimidazole-5-carboxylate

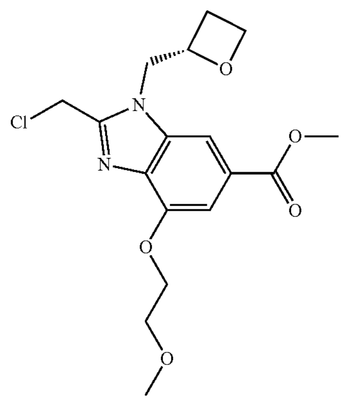 [SMILES: COCCOc1cc(C(=O)OC)cc2c1nc(CCl)n2C[C@@H]1CCO1]

To a solution of methyl 4-amino-3-(2-methoxyethoxy)-5-[[(2S)-oxetan-2-yl]methylamino]benzoate (310 mg, 0.93 mmol) in EtOH (6 mL), add 2-chloro-1,1,1-trimethoxyethane (710 mg, 4.50 mmol) at ambient temperature. Heat the mixture to 90° C. for 2 h, then concentrate the reaction under reduced pressure. Purify the residue via silica gel chromatography eluting with a gradient of 0 to 5% MeOH in DCM to give the title compound (360 mg, 94%). ES/MS m/z 369 (M+H).

Preparation 296

Methyl (S)-4-(2-methoxyethoxy)-1-(oxetan-2-ylmethyl)-2-(($5^6$-(trifluoromethyl)-3,8-dioxa-2(2,6),5(3,4)-dipyridina-1(1,3)-benzenacyclononaphane-$1^4$-yl)methyl)-1H-benzo[d]imidazole-6-carboxylate

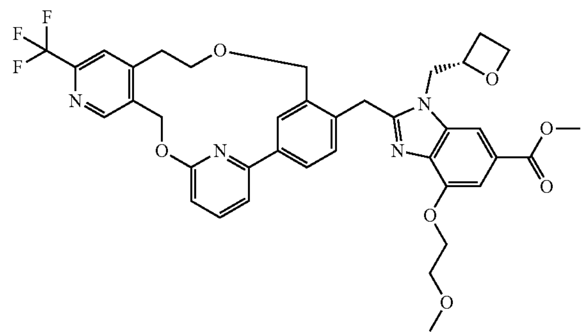 [SMILES: COCCOc1cc(C(=O)OC)cc2c1nc(Cc1ccc3cc1COCCc1cc(C(F)(F)F)ncc1COc1cccc-3n1)n2C[C@@H]1CCO1]

To a solution of $1^4$-(4,4,5,5-tetramethyl-1,3,2-dioxaborolan-2-yl)-$5^6$-(trifluoromethyl)-3,8-dioxa-2(2,6),5(3,4)-dipyridina-1(1,3)-benzenacyclononaphane (160 mg, 0.25 mmol, 81 wt %), methyl 2-(chloromethyl)-7-(2-methoxyethoxy)-3-[[(2S)-oxetan-2-yl]methyl]benzimidazole-5-carboxylate (256 mg, 0.62 mmol, 89 mass %), and tribasic potassium phosphate (172 mg, 0.79 mmol) in 2-methyltetrahydrofuran (1.6 mL) and water (0.32 mL), add chloro(2-dicyclohexylphosphino-2',4',6'-triisopropyl-1,1'-biphenyl)[2-(2'-amino-1,1'-biphenyl)]palladium(II) (XPhos Pd G2, 26 mg, 0.03 mmol). Sparge the solution with nitrogen, then heat the reaction to 80° C. for 18 h. Concentrate the reaction mixture under reduced pressure, then dilute the residue with water. Extract the mixture with EtOAc, then wash the combined organic phases with saturated aqueous NaCl solution. Dry the organic phase over $Na_2SO_4$, filter, and concentrate under reduced pressure. Purify the residue via silica gel chromatography eluting with a gradient of 0 to 60% EtOAc in petroleum ether to obtain the title compound (100 mg, 53%). ES/MS m/z 719 (M+H).

Preparation 297

Ethyl 2-(2-methyloxazol-4-yl)acetate

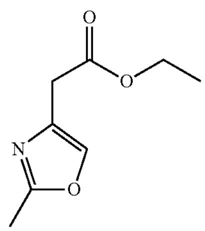

Add ethyl 4-chloro-3-oxo-butanoate (40 g, 243 mmol) to a solution of acetamide (15 g, 254 mmol) in toluene (80 mL) at RT. Heat to 130° C. and stir for 12 h. Filter the reaction mixture and concentrate the filtrate under reduced pressure. Purify the residue via silica gel chromatography eluting with a gradient of 10 to 15% EtOAc in petroleum ether to give the title compound as a yellow oil with 30% purity (19 g, 13%). ES/MS m/z 170 (M+H).

Preparation 298

2-(2-Methyloxazol-4-yl)ethanol

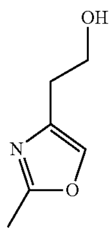

Add calcium chloride (26 g, 234 mmol) to a solution of ethyl 2-(2-methyloxazol-4-yl)acetate (20 g, 35.5 mmol) in EtOH (400 mL). Stir the mixture for 20 min, cool to 0° C., and then add sodium borohydride (10 g, 265 mmol). Stir the reaction mixture at RT for 12 h and then adjust the pH to 7 with 1 M aqueous HCl. Extract the mixture with DCM (3×200 mL), dry the combined organics over $Na_2SO_4$, filter, and concentrate. Purify the reside via silica gel chromatography eluting with a gradient of 50 to 100% EtOAc in petroleum ether, followed by a gradient of 0 to 15% MeOH in DCM to give the title compound as a yellow oil with 70% purity (5 g, 78%). ES/MS m/z 128 (M+H).

Preparation 299

Methyl 3-fluoro-5-hydroxy-4-nitro-benzoate

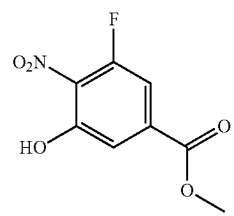

At −40° C., add boron tribromide (2 M solution in DCM, 65.4 mL, 131 mmol) dropwise to a solution of methyl 3-fluoro-5-methoxy-4-nitro-benzoate (30 g, 131 mmol) in DCM (500 mL). Stir the mixture at −40° C. for 30 min and then at ambient temperature for 16 h. Pour the mixture into ice water (2 L) and extract with DCM (3×800 mL). Wash the combined organic layers with saturated aqueous NaCl solution (2×300 mL), dry over $Na_2SO_4$, filter, and concentrate. Purify the residue via silica gel chromatography eluting with a gradient of 0 to 30% EtOAc in petroleum ether to give the title compound as a yellow solid (16.5 g, 59%). $^1H$ NMR ($CDCl_3$) δ 10.31 (s, 1H), 7.63 (s, 1H), 7.41 (d, 1H, J=11), 3.98 (s, 3H). $^{19}F$ NMR ($CDCl_3$) δ −113.37 (s).

Preparation 300

Methyl 3-fluoro-5-[2-(2-methyloxazol-4-yl)ethoxy]-4-nitro-benzoate

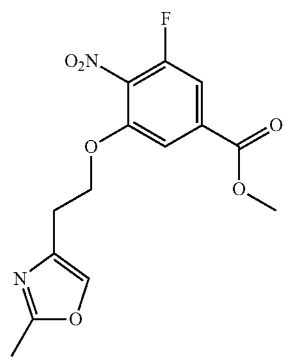

At 0° C., add diispropylazodicarboxylate (5.6 g, 28 mmol) to a solution of methyl 3-fluoro-5-hydroxy-4-nitro-benzoate (3 g, 13.9 mmol) and 2-(2-methyloxazol-4-yl)ethanol (3 g, 16.5 mmol) in THE (30 mL). Allow the mixture to warm to ambient temperature and stir for 12 h. Dilute the mixture with water (30 mL) and extract with EtOAc (3×50 mL). Wash the combined organics with saturated aqueous NaCl (100 mL), dry over $Na_2SO_4$, filter, and concentrate. Purify the residue via silica gel chromatography eluting with a gradient of 0 to 50% EtOAc in petroleum ether to give the title compound as a light yellow solid with 17% purity (6 g, 23%). ES/MS m/z 325 (M+H).

Preparation 301

Methyl 3-[2-(2-methyloxazol-4-yl)ethoxy]-4-nitro-5-[[(2S)-oxetan-2-yl]methylamino]benzoate

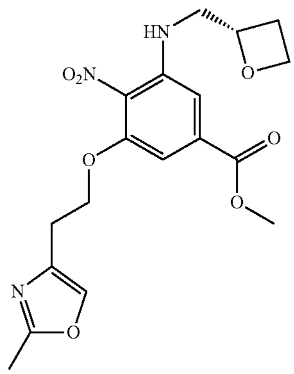 [SMILES: COC(=O)c1cc(NC[C@@H]2CCO2)c([N+](=O)[O-])c(OCCc2coc(C)n2)c1]

Add (S)-oxetan-2-ylmethanamine (15 g, 6.29 mmol) and TEA (1 mL, 7.17 mmol) to a solution of methyl 3-fluoro-5-[2-(2-methyloxazol-4-yl)ethoxy]-4-nitro-benzoate (6 g, 3.15 mmol) in DMSO (150 mL). Stir the mixture at 80° C. for 12 h, cool to ambient temperature, dilute with water (300 mL), and extract with EtOAc (3×400 mL). Wash the combined organic layers with saturated aqueous NaCl solution (3×500 mL), dry over $Na_2SO_4$, filter, and concentrate. Purify the residue via silica gel chromatography eluting with a gradient of 0 to 60% EtOAc in petroleum ether to afford the title compound as a yellow oil with 24% purity (2 g, 39%). ES/MS m/z 392 (M+H).

Preparation 302

Methyl 4-amino-3-[2-(2-methyloxazol-4-yl)ethoxy]-5-[[(2S)-oxetan-2-yl]methylamino]benzoate

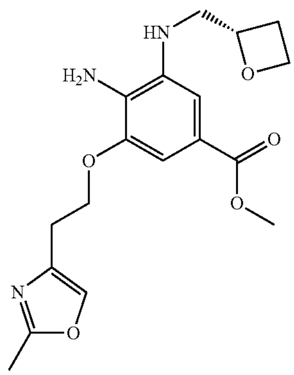 [SMILES: COC(=O)c1cc(NC[C@@H]2CCO2)c(N)c(OCCc2coc(C)n2)c1]

Add palladium on carbon (1 g, 10 wt % Pd) to a solution of methyl 3-[2-(2-methyloxazol-4-yl)ethoxy]-4-nitro-5-[[(2S)-oxetan-2-yl]methylamino]benzoate (2 g, 1.23 mmol) in EtOAc (150 mL). Purge the reaction vessel with hydrogen gas and evacuate three times. Attach a balloon of hydrogen gas to the vessel and stir for 2 h. Filter the mixture and concentrate under reduced pressure. Purify the residue by silica gel chromatography eluting with a gradient of 0 to 100% EtOAc in petroleum ether, and then purify further by preparative HPLC [column: Phenomenex C18 75×40 mm, 3 μm; mobile phase: 18 to 48% ACN in aqueous $NH_4HCO_3$ (10 mM)] to give the title compound as a white solid (88 mg, 19%). ES/MS m/z 362 (M+H).

Preparation 303

Methyl (S)-4-(2-($5^4$-cyano-3,9-dioxa-2(2,6)-pyridina-1(1,3),5(1,2)-dibenzenacyclononaphane-$1^4$-yl)acetamido)-3-(2-(2-methyloxazol-4-yl)ethoxy)-5-((oxetan-2-ylmethyl)amino)benzoate

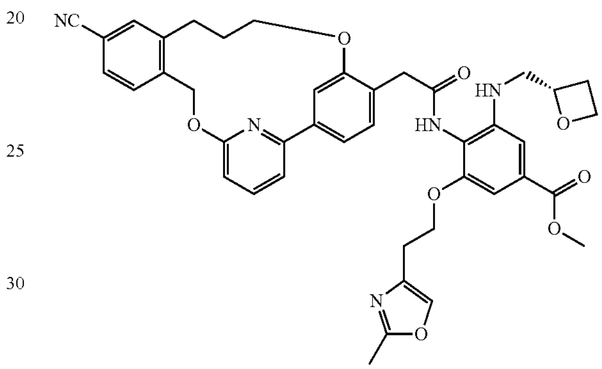

Prepare the title compound essentially as described in Preparation 86 using methyl 4-amino-3-[2-(2-methyloxazol-4-yl)ethoxy]-5-[[(2S)-oxetan-2-yl]methylamino]benzoate (80 mg, 0.215 mmol) and 2-($5^4$-cyano-3,9-dioxa-2(2,6)-pyridina-1(1,3),5(1,2)-dibenzenacyclononaphane-$1^4$-yl)acetic acid, and the product is used without further purification in Preparation 304. ES/MS m/z 744 (M+H).

Preparation 304

Methyl (S)-2-(($5^4$-cyano-3,9-dioxa-2(2,6)-pyridina-1(1,3),5(1,2)-dibenzenacyclononaphane-$1^4$-yl)methyl)-4-(2-(2-methyloxazol-4-yl)ethoxy)-1-(oxetan-2-ylmethyl)-1H-benzo[d]imidazole-6-carboxylate

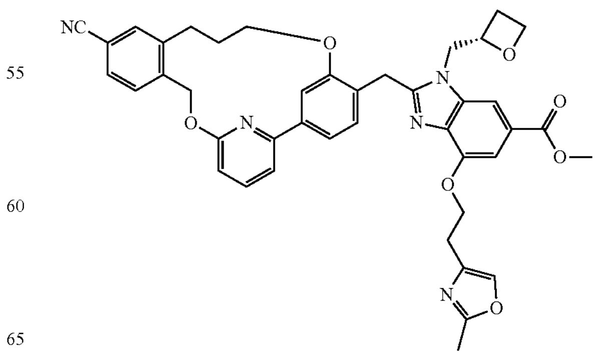

Prepare the title compound essentially as described in Preparation 102 using methyl (S)-4-(2-($5^4$-cyano-3,9-dioxa-2(2,6)-pyridina-1(1,3),5(1,2)-dibenzenacyclononaphane-$1^4$-yl)acetamido)-3-(2-(2-methyloxazol-4-yl)ethoxy)-5-((oxetan-2-ylmethyl)amino)benzoate (Preparation 303) and using a 1:1 mixture of 1,2-dichloroethane:acetic acid. Upon completion, cool the reaction to ambient temperature and remove volatiles under vacuum. Add 1:1 EtOAc/toluene and concentrate three times to remove residual acetic acid. Purify the residue via silica gel chromatography eluting with a gradient of 0 to 6% MeOH in DCM to give the title compound as an orange solid. ES/MS m/z 726 (M+H).

Preparation 305 tert-Butyl N-(2-hydroxyethyl)-N-(2,2,2-trifluoroethyl)carbamate

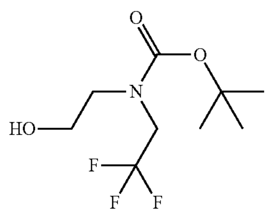 [SMILES: CC(C)(C)OC(=O)N(CCO)CC(F)(F)F]

A mixture of 2-bromoethanol (5 g, 38.8 mmol) and 2,2,2-trifluoroethylamine (9.66 g, 97.0 mmol) in ethanol (50 mL) was heated at 60° C. for 3 h in a sealed tube in a microwave reactor, then the reaction mixture was concentrated. To the residue was added TEA (5.2 mL, 3.7 g, 37 mmol) and di-tert-butyl pyrocarbonate (5.6 mL, 5.3 g, 24 mmol) and the mixture was stirred overnight at 55° C. under $N_2$. The reaction mixture was partitioned between EtOAc and water, and the organic phase was concentrated under reduced pressure. The residue was purified by silica gel chromatography using a gradient of 0 to 38% EtOAc in petroleum ether to give the title compound (2.5 g, 50%) as a yellow oil. $^1H$ NMR (400 MHz, DMSO) δ 4.76 (m, 1H), 4.06 (q, J=9.5 Hz, 2H), 3.67 (m, 2H), 3.30 (q, J=6 Hz, 2H), 1.41 (s, 9H).

Preparation 306

Methyl 3-[2-[tert-butoxycarbonyl(2,2,2-trifluoroethyl)amino]ethoxy]-5-fluoro-4-nitro-benzoate

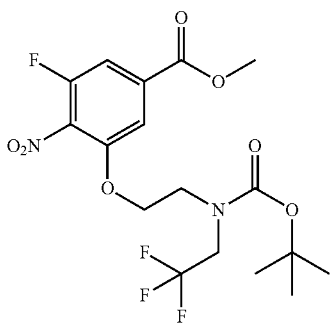 [SMILES: COC(=O)c1cc(F)c([N+](=O)[O-])c(OCCN(CC(F)(F)F)C(=O)OC(C)(C)C)c1]

To a solution of methyl 3-fluoro-5-hydroxy-4-nitro-benzoate (1.5 g, 6.6 mmol), tert-butyl N-(2-hydroxyethyl)-N-(2,2,2-trifluoroethyl)carbamate (2.1 g, 7.8 mmol) and triphenylphosphine (3.5 g, 13 mmol) in THF (10 mL), add DIAD (2.8 mL, 13 mmol) at 0° C. After the addition, stir the mixture at 20° C. for 18 h. Dilute mixture with water (50 mL) and extract with EtOAc (3×50 mL). Dry the combined organic layers over $Na_2SO_4$, filter, and concentrate under reduced pressure. Purify by silica gel chromatography eluting with a gradient of 0 to 20% EtOAc/petroleum ether to give the title compound as a yellow oil (3.2 g, 93%). ES/MS m/z 340.9 (M-Boc+H).

Preparation 307

Methyl 3-[2-[tert-butoxycarbonyl(2,2,2-trifluoroethyl)amino]ethoxy]-4-nitro-5-[[(2S)-oxetan-2-yl]methylamino]benzoate

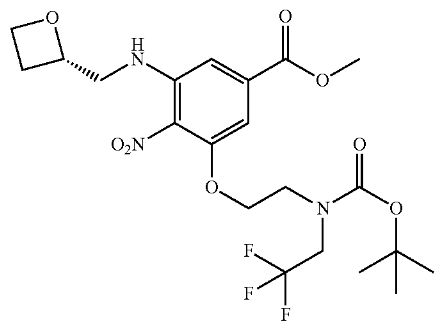 [SMILES: COC(=O)c1cc(NC[C@@H]2CCO2)c([N+](=O)[O-])c(OCCN(CC(F)(F)F)C(=O)OC(C)(C)C)c1]

Prepare the title compound essentially as described in Preparation 301 using methyl 3-[2-[tert-butoxycarbonyl(2,2,2-trifluoroethyl)amino]ethoxy]-5-fluoro-4-nitro-benzoate and fumaric acid; (S)-oxetane-2-ylmethanamine, heating the reaction at 100° C. for 3 h in a microwave reactor. ES/MS m/z 508.1 (M+H).

Preparation 308

Methyl 4-amino-3-[2-[tert-butoxycarbonyl(2,2,2-trifluoroethyl)amino]ethoxy]-5-[[(2S)-oxetan-2-yl]methylamino]benzoate

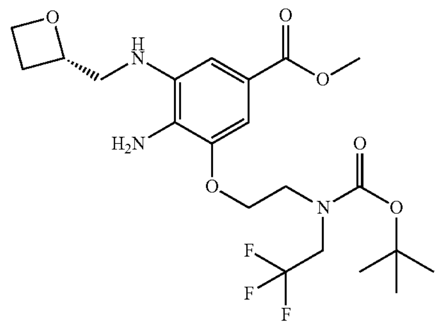

To a solution of methyl 3-[2-[tert-butoxycarbonyl(2,2,2-trifluoroethyl)amino]ethoxy]-4-nitro-5-[[(2S)-oxetan-2-yl]methylamino]benzoate (1.1 g, 1.8 mmol) in MeOH (10 mL), add Pd/C (810 mg, 10 mass %). Stir the mixture under hydrogen (15 psi) for 2 h at ambient temperature. Add diatomaceous earth, filter, and concentrate the filtrate under reduced pressure. Purify the residue by silica gel chromatography eluting with a gradient of 0 to 9% MeOH in DCM to give the title compound (940 mg, >99%). ES/MS m/z 478.1 (M+H).

Preparation 309

Methyl (S)-4-(2-($5^4$-cyano-3,9-dioxa-2(2,6)-pyridina-1(1,3),5(1,2)-dibenzenacyclononaphane-$1^4$-yl)acetamido)-3-[2-[tert-butoxycarbonyl(2,2,2-trifluoroethyl)amino]ethoxy]-5-[[(2S)-oxetan-2-yl]methylamino]benzoate

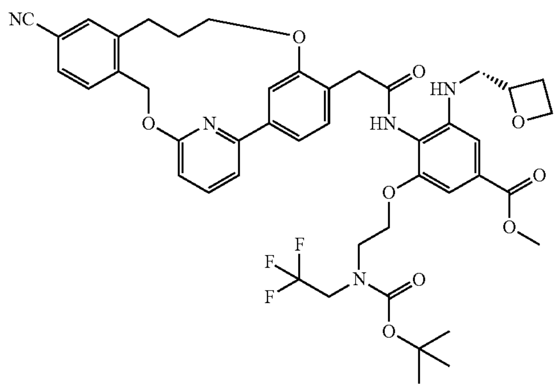

Prepare the title compound essentially as described in Preparation 86 using 2-($5^4$-cyano-3,9-dioxa-2(2,6)-pyridina-1(1,3),5(1,2)-dibenzenacyclononaphane-$1^4$-yl)acetic acid and methyl 4-amino-3-[2-[tert-butoxycarbonyl(2,2,2-trifluoroethyl)amino]ethoxy]-5-[[(2S)-oxetan-2-yl]methylamino]benzoate. ES/MS m/z 860.2 (M+H).

Preparation 310

Methyl (S)-4-(2-((tert-butoxycarbonyl)(2,2,2-trifluoroethyl)amino)ethoxy)-2-(($5^4$-cyano-3,9-dioxa-2(2,6)-pyridina-1(1,3),5(1,2)-dibenzenacyclononaphane-$1^4$-yl)methyl)-1-(oxetan-2-ylmethyl)-1H-benzo[d]imidazole-6-carboxylate

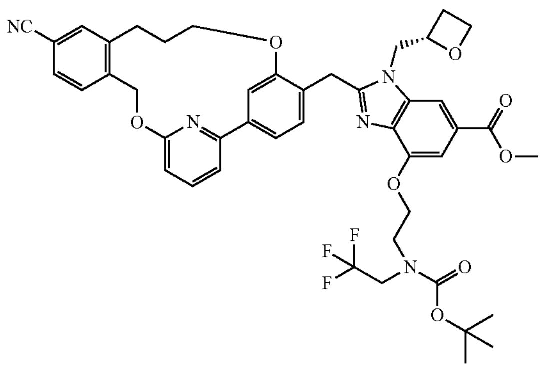 [SMILES: COC(=O)c1cc(OCCN(CC(F)(F)F)C(=O)OC(C)(C)C)c2nc(Cc3ccc4cc3OCCCc3cc(C#N)ccc3COc3cccc-4n3)n(C[C@@H]3CCO3)c2c1]

Prepare the title compound essentially as described in Preparation 102 using methyl (S)-4-(2-($5^4$-cyano-3,9-dioxa-2(2,6)-pyridina-1(1,3),5(1,2)-dibenzenacyclononaphane-$1^4$-yl)acetamido)-3-[2-[tert-butoxycarbonyl(2,2,2-trifluoroethyl)amino]ethoxy]-5-[[(2S)-oxetan-2-yl]methylamino]benzoate and a mixture of 1:1 DCM:acetic acid as solvent, heating the reaction at 55° C. for 18 h. Upon completion, cool the reaction to ambient temperature, dilute with toluene, and concentrate under reduced pressure. Purify the residue by silica gel chromatography eluting with a gradient of 0 to 14% MeOH in DCM to give the title compound as a brown oil. ES/MS m/z 842.2 (M+H).

Preparation 311

(S)-4-(2-((tert-Butoxycarbonyl)(2,2,2-trifluoroethyl)amino)ethoxy)-2-(($5^4$-cyano-3,9-dioxa-2(2,6)-pyridina-1(1,3),5(1,2)-dibenzenacyclononaphane-$1^4$-yl)methyl)-1-(oxetan-2-ylmethyl)-1H-benzo[d]imidazole-6-carboxylic acid

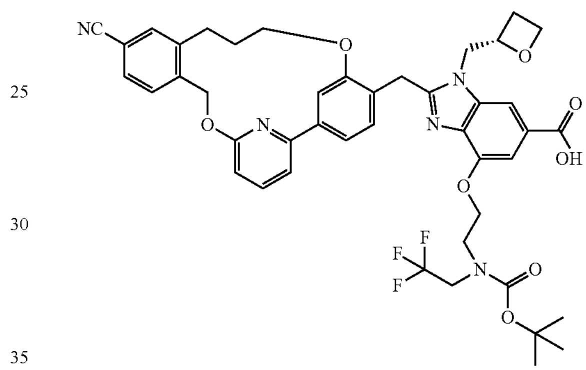

Prepare the title compound essentially as described in Example 5 using methyl (S)-4-(2-((tert-butoxycarbonyl)(2,2,2-trifluoroethyl)amino)ethoxy)-2-(($5^4$-cyano-3,9-dioxa-2(2,6)-pyridina-1(1,3),5(1,2)-dibenzenacyclononaphane-$1^4$-yl)methyl)-1-(oxetan-2-ylmethyl)-1H-benzo[d]imidazole-6-carboxylate 1,5,7-triazabicyclo[4.4.0]dec-5-ene in a mixture of 3:1:1 ACN:THF:water, heating the reaction at 55° C. for 2 h. Upon completion, cool the reaction to ambient temperature and quench with 1 M aqueous formic acid to give a precipitate. Filter and collect the precipitate to give the title compound, which is used without further purification in Example 54. ES/MS m/z 828.2 (M+H).

Preparation 312

2-Chloro-6-[(4-chloro-2-iodo-phenyl)methoxy]pyridine

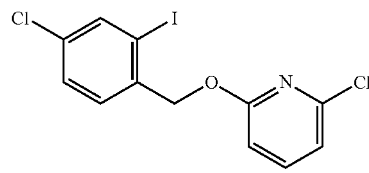 [SMILES: Clc1ccc(COc2cccc(Cl)n2)c(I)c1]

Prepare a solution of 4-chloro-2-iodo-1-methyl-benzene (40 g, 158 mmol) and N-bromosuccinimide (27.3 g, 153 mmol) in ACN (500 mL). Pump through a photochemical reactor consisting of a coiled PFA reaction tube (⅛" outer diameter, 53 mL volume) around a 4100K white lightbulb (42 W, 150 W equivalent), with a flowrate of 1.3 mL/min and maintaining the system temperature between 30 and 40° C. Once complete, pump ACN (100 mL) through the reactor at the same rate. Drip the output into a flask containing a suspension of 6-chloropyridin-2-ol (21.8 g, 168 mmol) and $K_2CO_3$ (44.1 g, 319 mmol) in ACN (400 mL). After full addition of the brominated material, stir at RT for 1 h. Filter the crude reaction mixture and concentrate under reduced pressure. Purify the residue via silica gel chromatography using 0 to 10% EtOAc in hexanes to give 45.8 g of the title compound (76%). ES-MS m/z 380 and 382 (M+H).

Preparation 313

2-Chloro-6-[[4-chloro-2-[2-ethoxyvinyl]phenyl]methoxy]pyridine

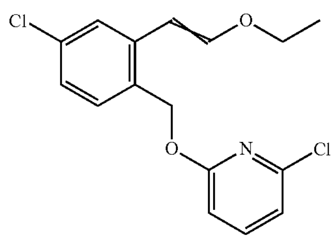 [SMILES: CCOC=Cc1cc(Cl)ccc1COc1cccc(Cl)n1]

To a solution of 2-chloro-6-[(4-chloro-2-iodo-phenyl)methoxy]pyridine (5.0 g, 13 mmol) in THE (70 mL) under $N_2$ add aqueous potassium phosphate (2 M, 150 mL, 300 mmol) and 1-ethoxyethene-2-boronic acid pinacol ester (1/1.3 isomeric mixture, 3.81 mL, 17.1 mmol) and stir the mixture for 5 min. Add bis(triphenylphosphine)palladium (II) dichloride (470 mg, 0.663 mmol) and heat the mixture to 65° C. for 21 h. Cool the mixture to RT and add water (100 mL) and EtOAc (100 mL). Stir the mixture for 5 min at RT, separate the organic layer and extract the aqueous layer with EtOAc (2×100 mL). Combined the organic layers and wash with water (100 mL), saturated aqueous NaCl (100 mL). Concentrate the organics and purify the residue by filtration through a plug of silica gel using DCM eluant to give the title compound as a brown solid (4.37 g, 100%). ES/MS m/z 324 (M+H).

Preparation 314

2-[5-Chloro-2-[(6-chloro-2-pyridyl)oxymethyl]phenyl]acetaldehyde

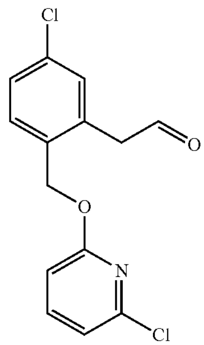 [SMILES: O=CCc1cc(Cl)ccc1COc1cccc(Cl)n1]

To a solution of 2-chloro-6-[[4-chloro-2-[2-ethoxyvinyl]phenyl]methoxy]pyridine (54.2 g, 161.1 mmol) in acetone (525 mL) and water (175 mL) add hydrochloric acid (35 mL, 407 mmol, 36.5% in water) and heat to 65° C. for one hour. Cool the reaction to RT and dilute with water (250 mL) and MTBE (250 mL). Separate the organic phase and extract the aqueous with MTBE (3×250 mL). Wash the combined organic layers with 2M aqueous $Na_2CO_3$ (250 mL), water (250 mL), saturated aqueous NaCl (250 mL), dry over $Na_2SO_4$ and remove the solvents in vacuo to give 44.5 g of the title compound (93%) which is used in Preparation 315 without further purification. ES-MS m/z 296.0, 298.0 (M+H).

Preparation 315

2-[5-Chloro-2-[(6-chloro-2-pyridyl)oxymethyl]phenyl]ethanol

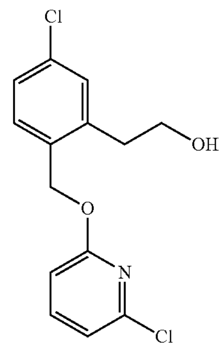 [SMILES: OCCc1cc(Cl)ccc1COc1cccc(Cl)n1]

To a solution of 2-[5-chloro-2-[(6-chloro-2-pyridyl)oxymethyl]phenyl]acetaldehyde (Preparation 314, 44.5 g, 150.3 mmol) in EtOH (400 mL) at 5° C. add sodium borohydride (11.85 g, 300.7 mmol) portionwise and stir at RT for one hour. Cool the reaction to 0° C. and quench with water (250 mL) and adjust the pH to 6 with 5% aqueous citric acid. Add MTBE (400 mL), separate the organic phase and extract the aqueous phase with MTBE (3×250 mL). Combine the organic layers and wash with water (250 mL), saturated aqueous NaCl (250 mL), dry over $Na_2SO_4$ and the remove the solvents in vacuo. Purify the crude material by silica gel chromatography using a gradient of 20 to 40% EtOAc in cyclohexane to give 31.95 g of the title compound (71%) which crystallizes upon standing. ES-MS m/z 298.0, 300.0 (M+H).

Preparation 316

2-[[2-[2-[(5-Bromo-2-iodo-phenyl)methoxy]ethyl]-4-chloro-phenyl]methoxy]-6-chloro-pyridine

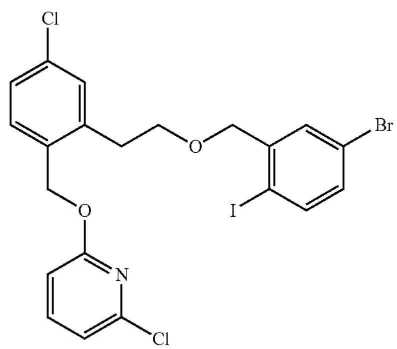 [SMILES: Clc1ccc(COc2cccc(Cl)n2)c(CCOCc2cc(Br)ccc2I)c1]

To a solution of 2-[5-chloro-2-[(6-chloro-2-pyridyl)oxymethyl]phenyl]ethanol (31.80 g, 106.6 mmol) in THE (360 mL) at 0° C. add sodium hydride (60 wt % in mineral oil, 8.14 g, 203 mmol) and stir for 20 min. To this add 4-bromo-2-(bromomethyl)-1-iodo-benzene (49.4 g, 131 mmol) portionwise and allow the mixture to warm to RT and stirred for 18 h. To this add more sodium hydride (60 wt % in mineral oil, 1.25 g, 31.3 mmol) followed by more 4-bromo-2-(bromomethyl)-1-iodo-benzene (4.9 g, 13 mmol) and stir the mixture at RT for another 5 h. Cool the reaction to 0° C. and quench with 5% aqueous citric acid (250 mL) and add MTBE (200 mL). Separate the organic phase and extract the aqueous with MTBE (3×250 mL). Combine the organic layers and wash with water (200 mL), saturated aqueous NaCl (200 mL), dry over $Na_2SO_4$ and remove the solvents in vacuo. Purify the residue by silica gel chromatography using a gradient of 40 to 100% DCM in cyclohexane to give 45.05 g of the title compound (71%) as a yellow oil. ES-MS m/z 593.8 (M+H).

Preparation 317

Ethyl 2-[4-bromo-2-[2-[5-chloro-2-[(6-chloro-2-pyridyl)oxymethyl]phenyl]ethoxymethyl]phenyl]acetate

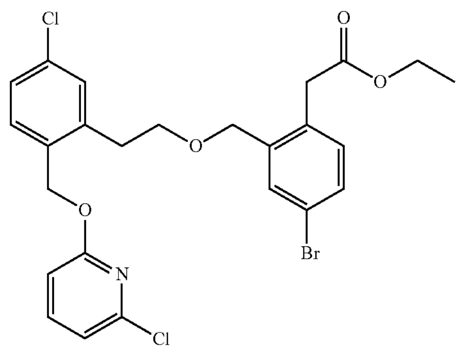 [SMILES: CCOC(=O)Cc1ccc(Br)cc1COCCc1cc(Cl)ccc1COc1cccc(Cl)n1]

Stir a solution of 2-[[2-[2-[(5-bromo-2-iodo-phenyl)methoxy]ethyl]-4-chloro-phenyl]methoxy]-6-chloro-pyridine (13.11 g, 22.1 mmol), and chloro[(4,5-bis(diphenylphosphino)-9,9-dimethylxanthene)-2-(2'-amino-1,1'-biphenyl)]palladium(II)](XantPhos Pd G2, 1.100 g, 1.107 mmol) in THE (50 mL) at RT under $N_2$. To this mixture add bromo-(2-ethoxy-2-oxo-ethyl)zinc (0.4 M in THF, 103 mL, 40 mmol) dropwise and heat the mixture to 65° C. for 3 h. Cool the reaction mixture to 0° C. and quench with 5% aqueous citric acid (200 mL) and add MTBE (200 mL). Separate the organic phase and extract the aqueous phase with MTBE (3×100 mL). Wash the combined organic layers with water (200 mL), saturated aqueous NaCl (200 mL), dry over $Na_2SO_4$ and remove the solvents under vacuum. Purify the residue by silica gel chromatography using a gradient of 20 to 100% DCM in cyclohexane to give 9.15 g of the title compound (75%) as a dark brown oil. ES-MS m/z 552.0, 554.0 (M+H).

Preparation 318

Ethyl 2-[2-[2-[5-chloro-2-[(6-chloro-2-pyridyl)oxymethyl]phenyl]ethoxymethyl]-4-(4,4,5,5-tetramethyl-1,3,2-dioxaborolan-2-yl)phenyl]acetate

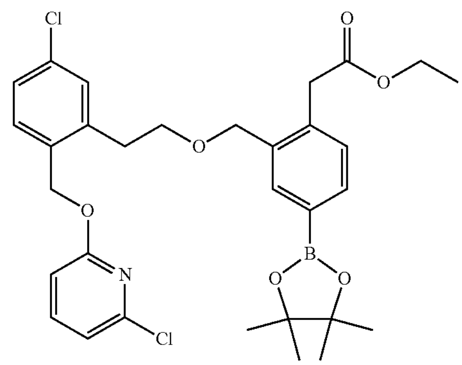 [SMILES: CCOC(=O)Cc1ccc(B2OC(C)(C)C(C)(C)O2)cc1COCCc1cc(Cl)ccc1COc1cccc(Cl)n1]

Bubble $N_2$ gas through a solution of ethyl 2-[4-bromo-2-[2-[5-chloro-2-[(6-chloro-2-pyridyl)oxymethyl]phenyl]ethoxymethyl]phenyl]acetate (7.50 g, 13.6 mmol), bis(pinacolato)diboron (4.39 g, 16.9 mmol), and KOAc (4.1 g, 41 mmol) in dioxane (270 mL) for 15 min. To this mixture add dichlorobis(tricyclohexylphosphine)palladium (II) (1.02 g, 1.35 mmol) and heat to 90° C. for 20 h. To this mixture add additional bis(pinacolato)diboron (0.439 g, 1.69 mmol), dichlorobis(tricyclohexylphosphine)palladium (II) (0.10 g, 0.13 mmol), and KOAc (0.410 g, 4.1 mmol). Heat the mixture to 90° C. for 4 h. Cool the mixture to RT and filter through a plug of silica gel eluting with DCM to give 9.11 g of the title compound as a crude dark brown oil (112%), which is used in Preparation 319 without further purification. ES-MS m/z 600.2, 602.2 (M+H).

Preparation 319

Ethyl 2-($5^4$-chloro-3,8-dioxa-2(2,6)-pyridina-1(1,3),5(1,2)-dibenzenacyclononaphane-$1^4$-yl)acetate

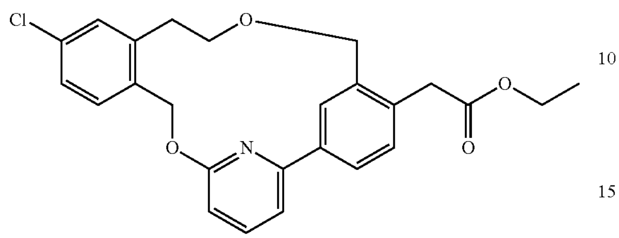

Bubble $N_2$ gas through a solution of ethyl 2-[2-[2-[5-chloro-2-[(6-chloro-2-pyridyl)oxymethyl]phenyl]ethoxymethyl]-4-(4,4,5,5-tetramethyl-1,3,2-dioxaborolan-2-yl)phenyl]acetate (9.10 g, 15.2 mmol) and aqueous potassium phosphate tribasic (1 M, 91 mL, 91 mmol) in THE (610 mL) for 15 min. To this mixture add [chloro(2-dicyclohexylphosphino-2',4',6'-tri-i-propyl-1,1'-biphenyl)(2'-amino-1,1'-biphenyl-2-yl) palladium(II)] (XPhos-Pd-G2, 1.22 g, 1.52 mmol) and heat to 65° C. for one hour. Cool the reaction to RT, dilute with water (300 mL) and extract with MTBE (3×250 mL).

Wash the combined organics with water (250 mL), saturated aqueous NaCl (250 mL), dry over $MgSO_4$, filter, and concentrate in vacuo. Purify the residue by silica gel chromatography using a gradient of 80 to 100% DCM in cyclohexane to give 1.6 g of the title compound (24.1%) as a white solid. ES-MS m/z 438.2 (M+H).

Preparation 320

2-($5^4$-Chloro-3,8-dioxa-2(2,6)-pyridina-1(1,3),5(1,2)-dibenzenacyclononaphane-$1^4$-yl)acetic acid

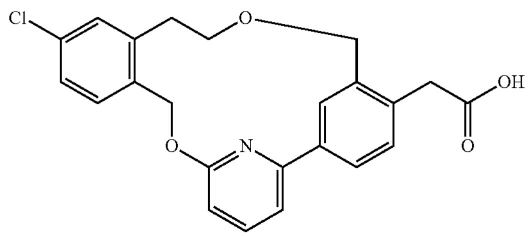 [SMILES: O=C(O)Cc1ccc2cc1COCCc1cc(Cl)ccc1COc1cccc-2n1]

To a solution of ethyl 2-($5^4$-chloro-3,8-dioxa-2(2,6)-pyridina-1(1,3),5(1,2)-dibenzenacyclononaphane-$1^4$-yl)acetate (900 mg, 2.06 mmol) in ACN (5 mL), 1,4-dioxane (5 mL), and water (5 mL) add 1,3,4,6,7,8-hexahydro-2H-pyrimido[1,2-a]pyrimidine (500 mg, 3.52 mmol) and heat to 50° C. for 3 h. Cool the reaction to RT, quench with 1N HCl (2 mL), dilute with water and extract with EtOAc (2×250 mL). Combine the organics, wash with saturated aqueous NaCl, dry over $MgSO_4$, filter and concentrate in vacuo to give 835 mg of the title compound (99%) as a light yellow solid. ES-MS m/z 410.9 (M+H).

Preparation 321

Methyl 3-[2-[tert-butyl(dimethyl)silyl]oxyethoxy]-5-fluoro-4-nitro-benzoate

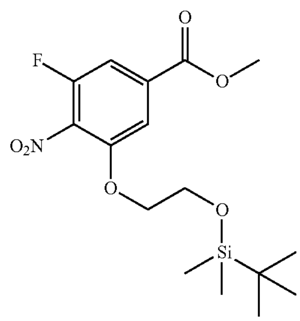 [SMILES: COC(=O)c1cc(F)c([N+](=O)[O-])c(OCCO[Si](C)(C)C(C)(C)C)c1]

To a 0° C. solution of methyl 3-fluoro-5-hydroxy-4-nitrobenzoate (2 g, 9.3 mmol), 2-((tert-butyldimethylsilyl)oxy) ethanol (2.6 g, 14 mmol) and triphenylphenylphosphine (3.5 g, 13 mmol) in THF (30 mL), add DIAD (3.8 g, 19 mmol). Allow to warm to 20° C. and stir for 12 h. Dilute with water (50 mL) and extract with EtOAc (3×80 mL). Wash the combined organic layers with saturated aqueous sodium chloride solution (100 mL), dry over $Na_2SO_4$, filter, and concentrate under reduced pressure. Purify the residue by silica gel chromatography eluting with 0-20% EtOAc/petroleum ether to give the title compound as colorless oil (4 g, 92%). $^1H$ NMR ($CDCl_3$) δ 7.59 (s, 1H), 7.51 (d, J=24 Hz, 1H), 4.25 (t, J=5 Hz, 2H), 3.98 (t, J=5 Hz, 2H), 3.97 (s, 3H), 0.88 (s, 9H), 0.07 (s, 6H).

Preparation 322

Methyl 3-(2-hydroxyethoxy)-4-nitro-5-[[(2S)-oxetan-2-yl]methylamino]benzoate

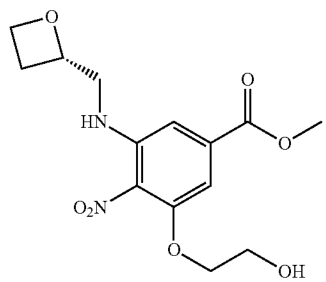 [SMILES: COC(=O)c1cc(NC[C@@H]2CCO2)c([N+](=O)[O-])c(OCCO)c1]

To a solution of methyl 3-[2-[tert-butyl(dimethyl)silyl] oxyethoxy]-5-fluoro-4-nitro-benzoate (2 g, 4.32 mmol) in DMSO (200 mL), add TEA (2.5 mL, 18 mmol) and (S)-oxetane-2-ylmethanamine (21 g, 8.7 mmol). Stir at 80° C. for 12 h. Dilute with water (200 mL) and extract with EtOAc (3×300 mL). Wash the combined organic layers with saturated aqueous sodium chloride solution (400 mL), dry over $Na_2SO_4$, filter, and concentrate in vacuo. Purify the residue by silica gel chromatography eluting with 0-50% EtOAc/petroleum ether to give the title compound (320 mg, 18%). $^1H$ NMR ($CDCl_3$) δ 7.16 (s, 1H), 6.93 (s, 1H), 6.39 (s, 1H), 5.11 (m, 1H), 4.72 (m, 1H), 4.59 (m, 1H), 4.24 (t, j=4 Hz, 2H), 3.97-3.93 (m, 5H), 3.50 (t, j=4 Hz, 2H), 2.73 (m, 1H), 2.58 (m, 1H).

Preparation 323

Methyl 3-[2-[tert-butyl(dimethyl)silyl]oxyethoxy]-4-nitro-5-[[(2S)-oxetan-2-yl]methylamino]benzoate

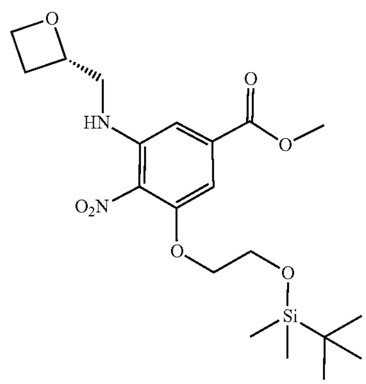 [SMILES: COC(=O)c1cc(NC[C@@H]2CCO2)c([N+](=O)[O-])c(OCCO[Si](C)(C)C(C)(C)C)c1]

To a solution of methyl 3-(2-hydroxyethoxy)-4-nitro-5-[[(2S)-oxetan-2-yl]methylamino]benzoate (320 mg, 0.78 mmol) in DCM (10 mL), add tert-butyldimethylchlorosilane (200 mg, 1.29 mmol) and imidazole (130 mg, 1.90 mmol). Stir the mixture at 20° C. for 2 h. Dilute with water (20 mL) and extract with DCM (3×30 mL). Wash the combined organic layers with saturated aqueous sodium chloride solution (50 mL), dry over $Na_2SO_4$, filter, and concentrate under reduced pressure. Purify the residue by silica gel chromatography eluting with 0-20% EtOAc/petroleum ether to give the title compound (400 mg, 93%). ES/MS (m z): 441.1 (M+H).

Preparation 324

Methyl 4-amino-3-[2-[tert-butyl(dimethyl)silyl]oxyethoxy]-5-[[(2S)-oxetan-2-yl]methylamino]benzoate

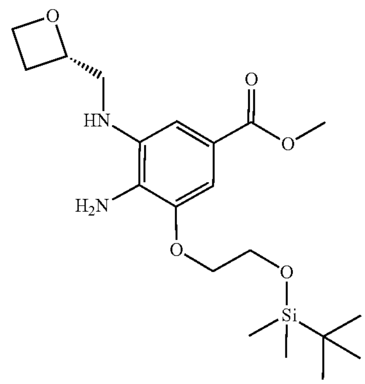 [SMILES: COC(=O)c1cc(NC[C@@H]2CCO2)c(N)c(OCCO[Si](C)(C)C(C)(C)C)c1]

To a solution of methyl 3-[2-[tert-butyl(dimethyl)silyl]oxyethoxy]-4-nitro-5-[[(2S)-oxetan-2-yl]methylamino]benzoate (670 mg, 1.22 mmol) in EtOAc (100 mL), add Pd/C (300 mg, 10 mass %). Purge with hydrogen gas three times and stir at 20° C. for one hour under a balloon filled with hydrogen. Filter the mixture and concentrate the filtrate under reduced pressure. Purify the residue by silica gel chromatography eluting with 0-10% MeOH/DCM to give the title compound (475 mg, 95%). ES/MS (m z): 411.4 (M+H).

Preparation 325

Methyl (S)-3-[2-[tert-butyl(dimethyl)silyl]oxy-ethoxy]-4-(2-($5^4$-chloro-3,8-dioxa-2(2,6)-pyridina-1(1,3),5(1,2)-dibenzenacyclononaphane-$1^4$-yl)acet-amido)-5-((oxetan-2-ylmethyl)amino)benzoate

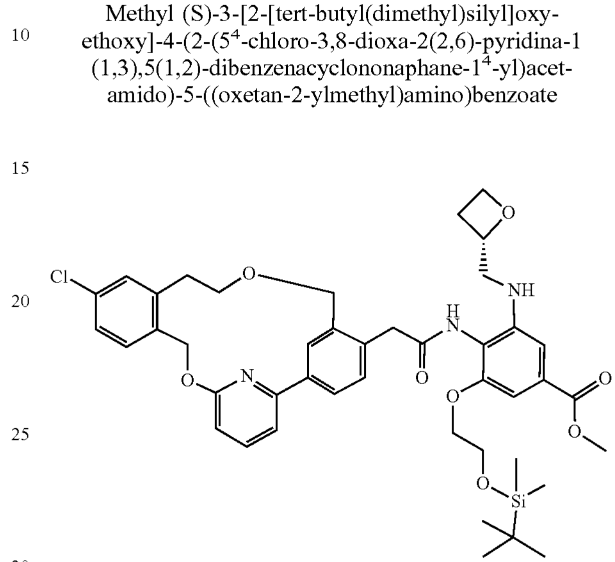

To a solution of 2-($5^4$-chloro-3,8-dioxa-2(2,6)-pyridina-1(1,3),5(1,2)-dibenzenacyclononaphane-$1^4$-yl)acetic acid (80 mg, 0.20 mmol) and methyl 4-amino-3-[2-[tert-butyl(dimethyl)silyl]oxyethoxy]-5-[[(2S)-oxetan-2-yl]methylamino]benzoate (87 mg, 0.21 mmol) in DMF (3 mL), add DIEA (0.07 mL, 0.4 mmol) followed by HATU (124 mg, 0.32 mmol). Stir the mixture at 20° C. for 2 h, then dilute with water (20 mL) to form a solid. Filter off the solid and dry under vacuum to give the title compound (132 mg, 84%). ES/MS m/z ($^{35}Cl/^{37}Cl$) 802.4/804.4 [M+H].

Preparation 326

Methyl (S)-4-[2-[tert-butyl(dimethyl)silyl]oxy-ethoxy]-2-(($5^4$-chloro-3,8-dioxa-2(2,6)-pyridina-1(1,3),5(1,2)-dibenzenacyclononaphane-$1^4$-yl)methyl)-1-(oxetan-2-ylmethyl)-1H-benzo[d]imidazole-6-carboxylate

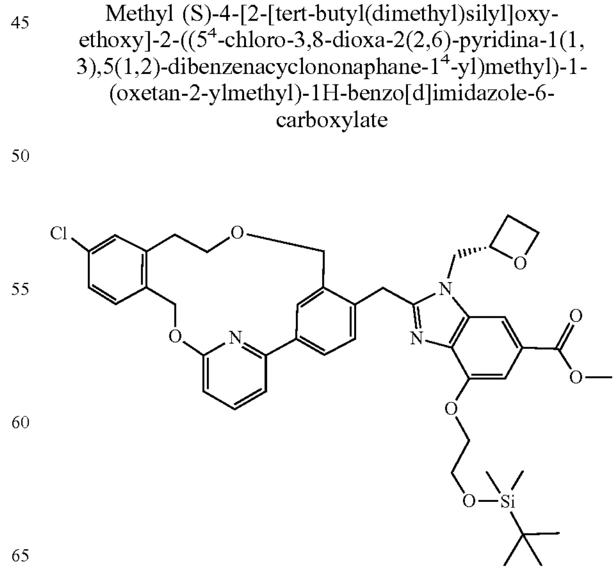

Heat a solution of methyl (S)-3-[2-[tert-butyl(dimethyl) silyl]oxyethoxy]-4-(2-($5^4$-chloro-3,8-dioxa-2(2,6)-pyridina-1(1,3),5(1,2)-dibenzenacyclononaphane-$1^4$-yl)acetamido)-5-((oxetan-2-ylmethyl)amino)benzoate (132 mg, 0.165 mmol) in acetic acid (3 mL) to 80° C. for 1.5 h, then cool to ambient temperature and concentrate under reduced pressure. Purify the residue by silica gel chromatography eluting with a gradient of 50 to 100% EtOAc/toluene followed by 2 to 5% MeOH/EtOAc to give the title compound (62 mg, 48%). The product elutes at 1.8 min by LC-ES/MS but does not ionize. Conditions for LCMS analysis: 2×50 Xbridge C18 3.5 μm at 50° C., 5-95% ACN in 10 mM aqueous $NH_4HCO_3$ (pH 9) over 1.5 minutes, then 95% ACN for 0.5 min.

Preparation 327

Methyl 3-[2-(dimethylamino)ethoxy]-5-fluoro-4-nitro-benzoate

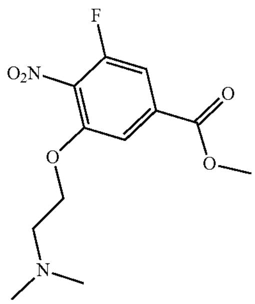

To a solution of methyl 3-fluoro-5-hydroxy-4-nitro-benzoate (2 g, 9.30 mmol) in THE (20 mL), add N,N-dimethylethanolamine (994 mg, 11.15 mmol), triphenylphosphine (2.92 g, 11.15 mmol) and DIAD (2.25 g, 11.15 mmol). Stir reaction at ambient temperature for 18 h. Filter the reaction mixture and concentrate the filtrate liquids under reduced pressure. Purify the residue via silica gel flash chromatography eluting with a gradient of 0 to 10% MeOH in DCM to give the title compound as a yellow oil (690 mg, 26%). ES/MS m/z 287 (M+H).

Preparation 328

Methyl 3-[2-(dimethylamino)ethoxy]-4-nitro-5-[[(2S)-oxetan-2-yl]methylamino]benzoate

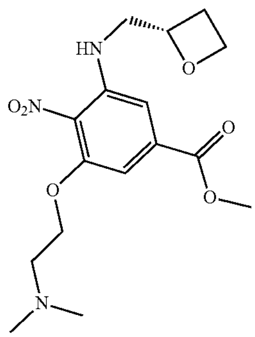

To a solution of methyl 3-[2-(dimethylamino)ethoxy]-5-fluoro-4-nitro-benzoate (690 mg, 2.41 mmol) in DMSO (8 mL), add (2S)-oxetan-2-yl-methanamine (420 mg, 4.8 mmol) and TEA (1.46 g, 14.4 mmol). Stir the reaction mixture at 80° C. for 18 h. Cool the mixture to ambient temperature, dilute with water (50 mL) and extract with EtOAc (2×50 mL). Combine the organics, wash with water and saturated aqueous NaCl solution (2×50 mL), dry over $Na_2SO_4$, filter and evaporate under reduced pressure. Purify the residue via silica gel flash chromatography eluting with a gradient of 0 to 20% MeOH in DCM to give the title compound as a colorless oil (1.03 g, 72%). ES/MS m/z 354 (M+H).

Preparation 329

Methyl 4-amino-3-[2-(dimethylamino)ethoxy]-5-[[(2S)-oxetan-2-yl]methylamino]benzoate

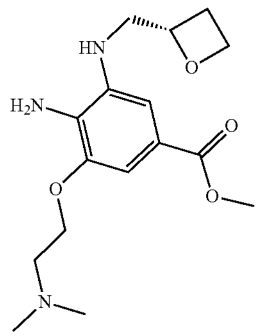

To a solution of methyl 3-[2-(dimethylamino)ethoxy]-4-nitro-5-[[(2S)-oxetan-2-yl]methylamino]benzoate (1.03 g, 1.75 mmol) in EtOAc (100 mL), add 10% Pd/C (200 mg, 0.18 mmol). Stir the mixture under hydrogen gas (14.5 psi) at ambient temperature for 2 h, then filter through diatomaceous earth and concentrate the filtrate under reduced pressure. Purify the residue by preparative HPLC to give the title compound as a white solid (102 mg, 17%). [column:Welch Xtimate C18 75×40 mm, 3 μm; Mobile phase A: $H_2O$ with $NH_3H_2O$+$NH_4HCO_3$; Mobile phase B: ACN; Gradient: B from 22% to 52%). ES/MS m/z 324 (M+H).

Preparation 330

Methyl (S)-4-(2-($5^4$-chloro-3,8-dioxa-2(2,6)-pyridina-1(1,3),5(1,2)-dibenzenacyclononaphane-$1^4$-yl)acetamido)-3-(2-(dimethylamino)ethoxy)-5-((oxetan-2-ylmethyl)amino)benzoate

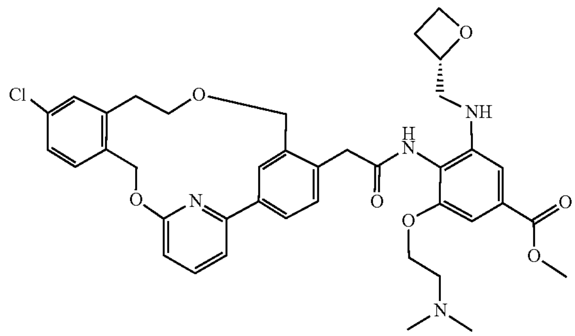 [SMILES: COC(=O)c1cc(NC[C@@H]2CCO2)c(NC(=O)Cc2ccc3cc2COCCc2cc(Cl)ccc2COc2cccc-3n2)c(OCCN(C)C)c1]

To a solution of 2-($5^4$-chloro-3,8-dioxa-2(2,6)-pyridina-1(1,3),5(1,2)-dibenzenacyclononaphane-$1^4$-yl)acetic acid (75 mg, 0.18 mmol) and methyl 4-amino-3-[2-(dimethylamino)ethoxy]-5-[[(2S)-oxetan-2-yl]methylamino]benzoate (60 mg, 0.18 mmol) in DMF (2 mL), add HATU (115 mg, 0.3 mmol) and DIPEA (0.10 mL, 0.5 mmol). Stir the mixture at ambient temperature for 17 h. Quench the reaction with water and filter the white solid that precipitates. Concentrate the filtrate liquids and extract with EtOAc. Combine the organic layers, dry the organics over $MgSO_4$, filter, and concentrate to give a solid residue. Combine the first white solid with the residue to give the title compound as a white solid (173 mg, 132%). ES/MS m/z 715 (M+H).

Preparation 331

Methyl (S)-2-(($5^4$-chloro-3,8-dioxa-2(2,6)-pyridina-1(1,3),5(1,2)-dibenzenacyclononaphane-$1^4$-yl)methyl)-4-(2-(dimethylamino)ethoxy)-1-(oxetan-2-ylmethyl)-1H-benzo[d]imidazole-6-carboxylate

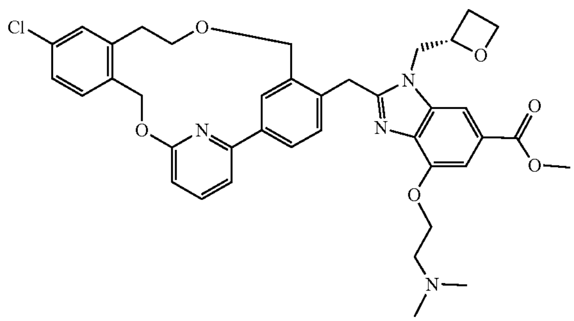 [SMILES: COC(=O)c1cc(OCCN(C)C)c2nc(Cc3ccc4cc3COCCc3cc(Cl)ccc3COc3cccc-4n3)n(C[C@@H]3CCO3)c2c1]

Heat a mixture of methyl (S)-4-(2-($5^4$-chloro-3,8-dioxa-2(2,6)-pyridina-1(1,3),5(1,2)-dibenzenacyclononaphane-$1^4$-yl)acetamido)-3-(2-(dimethylamino)ethoxy)-5-((oxetan-2-ylmethyl)amino)benzoate (130 mg; 0.18 mmol) in acetic acid (2 mL) and 1,2-dichloroethane (1.5 mL) at 55° C. for 21 h. Cool the mixture to ambient temperature and concentrate under reduced pressure. Purify the residue via silica gel flash chromatography eluting with a gradient of 0 to 10% MeOH in DCM to give the title compound as a white solid (89 mg, 70%). ES/MS m/z 697 (M+H).

Preparation 332

Methyl 3-[2-[tert-butoxycarbonyl(methyl)amino]ethoxy]-5-fluoro-4-nitro-benzoate

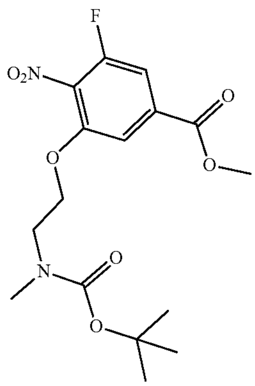

To a solution of methyl 3-fluoro-5-hydroxy-4-nitro-benzoate (2 g, 9.30 mmol) and tert-butyl-(2-hydroxyethyl)methyl carbamate (3.43 g, 18.6 mmol) in THE (20 mL), add triphenylphosphine (3.7 g, 14 mmol) and DIAD (2.82 g, 13.9 mmol). Stir reaction at ambient temperature for 12 h. Concentrate the mixture under reduced pressure and purify the residue via silica gel chromatography eluting with a gradient of 0 to 20% EtOAc in petroleum ether to give the title compound as a yellow oil (2.3 g, 66%). ES/MS (m z): 373 (M+H).

Preparation 333

Methyl 3-[2-[tert-butoxycarbonyl(methyl)amino]ethoxy]-4-nitro-5-[[(2S)-oxetan-2-yl]methylamino]benzoate

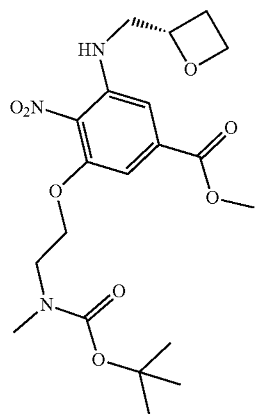

To a solution of methyl 3-[2-[tert-butoxycarbonyl(methyl)amino]ethoxy]-5-fluoro-4-nitro-benzoate (1 g, 2.68 mmol) in DMSO (60 mL), add a 3.6% w/w solution of (2S)-oxetan-2-yl-methanmine in EtOH (13.0 g, 5.4 mmol) and TEA (1.6 g, 16 mmol). Stir the reaction mixture at 80° C. for 12 h. Cool the mixture to ambient temperature, dilute with water (100 mL) and extract with EtOAc (3×100 mL). Combine the organics, wash with water and saturated aqueous NaCl solution (3×100 mL), dry over $Na_2SO_4$, filter, and concentrate under reduced pressure. Purify the residue via silica gel chromatography eluting with a gradient of 0 to 20% EtOAc in petroleum ether to give the title compound as a yellow oil (750 mg, 62%). ES/MS (m z): 440 (M+H-Boc).

Preparation 334

Methyl 4-amino-3-[2-[tert-butoxycarbonyl(methyl) amino]ethoxy]-5-[[(2S)-oxetan-2-yl]methylamino] benzoate

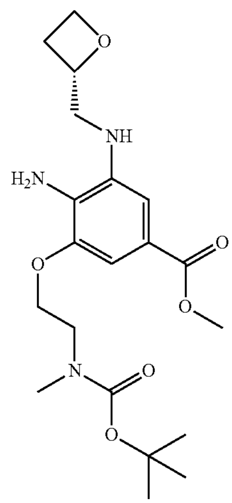 [SMILES: COC(=O)c1cc(NC[C@@H]2CCO2)c(N)c(OCCN(C)C(=O)OC(C)(C)C)c1]

To a solution of methyl 3-[2-[tert-butoxycarbonyl (methyl)amino]ethoxy]-4-nitro-5-[[(2S)-oxetan-2-yl]methylamino]benzoate (700 mg, 1.59 mmol) in EtOAc (50 mL), add 10% Pd/C (200 mg, 0.18 mmol). Stir the mixture under hydrogen gas (15 psi) at ambient temperature for 2 h. Filter the reaction mixture through diatomaceous earth and concentrate the filtrate under reduced pressure to give the title compound (536 mg, 82%). ES/MS (m z): 410 (M+H).

Preparation 335

Methyl (S)-3-(2-((tert-butoxycarbonyl)(methyl) amino)ethoxy)-4-(2-($5^4$-chloro-3,8-dioxa-2(2,6)-pyridina-1(1,3),5(1,2)-dibenzenacyclononaphane-$1^4$-yl)acetamido)-5-((oxetan-2-ylmethyl)amino) benzoate

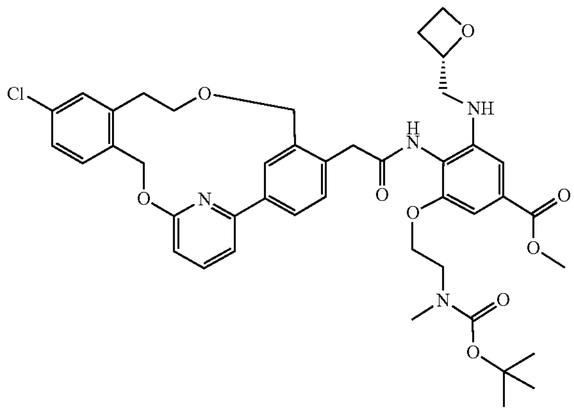 [SMILES: COC(=O)c1cc(NC[C@@H]2CCO2)c(NC(=O)Cc2ccc3cc2COCCc2cc(Cl)ccc2COc2cccc-3n2)c(OCCN(C)C(=O)OC(C)(C)C)c1]

To a solution of 2-($5^4$-chloro-3,8-dioxa-2(2,6)-pyridina-1(1,3),5(1,2)-dibenzenacyclononaphane-$1^4$-yl)acetic acid (80 mg, 0.19 mmol) and methyl 4-amino-3-[2-[tert-butoxycarbonyl(methyl)amino]ethoxy]-5-[[(2S)-oxetan-2-yl]methylamino]benzoate (82 mg, 0.19 mmol) in DMF (2 mL), add HATU (130 mg, 0.33 mmol) and DIEA (0.11 mL, 0.62 mmol). Stir the mixture at ambient temperature for 15 h, then quench with water and extract with EtOAc. Dry the organics over $MgSO_4$, filter, and concentrate under reduced pressure to give the title compound as a solid (155 mg, 80%), which is used in Preparation 336 without further purification. ES/MS (m z): 801 (M+H).

Preparation 336

Methyl (S)-4-(2-((tert-butoxycarbonyl)(methyl) amino)ethoxy)-2-(($5^4$-chloro-3,8-dioxa-2(2,6)-pyridina-1(1,3),5(1,2)-dibenzenacyclononaphane-$1^4$-yl)methyl)-1-(oxetan-2-ylmethyl)-1H-benzo[d] imidazole-6-carboxylate

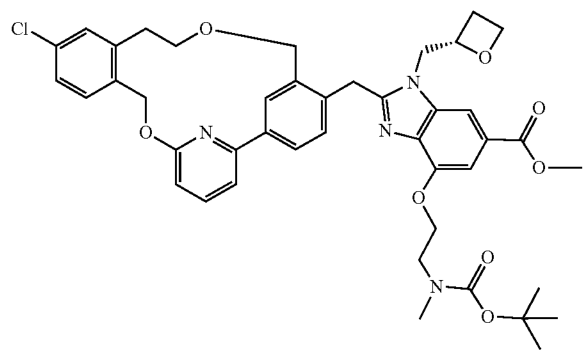 [SMILES: COC(=O)c1cc(OCCN(C)C(=O)OC(C)(C)C)c2nc(Cc3ccc4cc3COCCc3cc(Cl)ccc3COc3cccc-4n3)n(C[C@@H]3CCO3)c2c1]

Heat a mixture of methyl (S)-3-(2-((tert-butoxycarbonyl) (methyl)amino)ethoxy)-4-(2-($5^4$-chloro-3,8-dioxa-2(2,6)-pyridina-1(1,3),5(1,2)-dibenzenacyclononaphane-$1^4$-yl)acetamido)-5-((oxetan-2-ylmethyl)amino)benzoate (Preparation 335, 155 mg, 0.19 mmol) in acetic acid (1.5 mL) and 1,2-dichloroethane (1.5 mL) at 55° C. for 18 h. Cool the reaction to ambient temperature and concentrate under reduced pressure. Purify the residue via silica gel chromatography eluting with a gradient of 0 to 10% MeOH in DCM to give the title compound as a white solid (150 mg, 99%). ES/MS (m z): 783 (M+H).

Preparation 337

(S)-4-(2-((tert-Butoxycarbonyl)(methyl)amino) ethoxy)-2-(($5^4$-chloro-3,8-dioxa-2(2,6)-pyridina-1(1,3),5(1,2)-dibenzenacyclononaphane-$1^4$-yl)methyl)-1-(oxetan-2-ylmethyl)-1H-benzo[d]imidazole-6-carboxylic acid

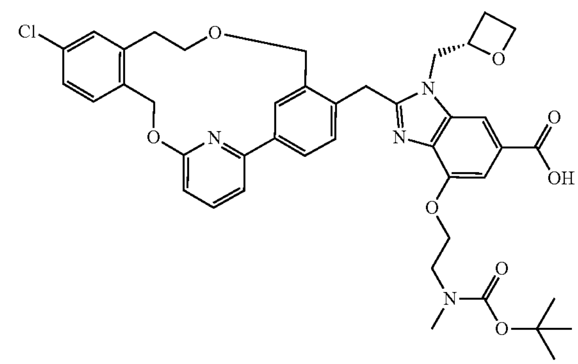 [SMILES: CN(CCOc1cc(C(=O)O)cc2c1nc(Cc1ccc3cc1COCCc1cc(Cl)ccc1COc1cccc-3n1)n2C[C@@H]1CCO1)C(=O)OC(C)(C)C]

To a nitrogen degassed mixture of methyl (S)-4-(2-((tert-butoxycarbonyl)(methyl)amino)ethoxy)-2-(($5^4$-chloro-3,8-dioxa-2(2,6)-pyridina-1(1,3),5(1,2)-dibenzenacyclononaphane-$1^4$-yl)methyl)-1-(oxetan-2-ylmethyl)-1H-benzo[d]imidazole-6-carboxylate (150 mg, 0.19 mmol) in ACN (2 mL), 1,4-dioxane (2 mL), and water (0.4 mL), add 1,5,7-triazabicyclo[4.4.0]dec-5-ene (86 mg, 0.60 mmol) and heat the mixture to 55° C. for 36 h. Cool the reaction mixture to ambient temperature, concentrate under reduced pressure, and purify the residue via reverse-phase chromatography using a gradient of 10 to 90% ACN in water (0.1% formic acid added to both solvents) to give the title compound as a white solid (64 mg, 43%). ES/MS (m z): 769 (M+H).

Preparation 338

Ethyl 2-(4-bromo-5-fluoro-2-methyl-phenyl)acetate

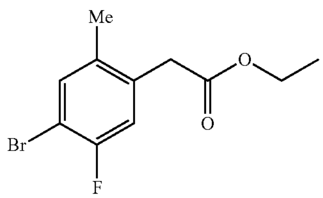

To solution of 1-bromo-2-fluoro-4-iodo-5-methyl-benzene (11 g, 34 mmol) and chloro[(4,5-bis(diphenylphosphino)-9,9-dimethylxanthene)-2-(2'-amino-1,1'-biphenyl)]palladium(II) (XantPhos-Pd-G2, 3.5 mg, 3.4 mmol) in THE (45 mL), add (2-ethoxy-2-oxoethyl)zinc(II) bromide (0.50 M in THF, 110 mL, 60 mmol) at RT and stir the mixture at 65° C. overnight under $N_2$. Quench the reaction by addition of 1N HCl (100 mL), then extract the mixture with EtOAc (3×100 mL). Combine the organic layers and wash with aqueous $K_2CO_3$ (100 mL), dry over $Na_2SO_4$ and concentrate in vacuo. Purify the residue by silica gel chromatography using a gradient of 0 to 20% EtOAc in petroleum ether to give the title compound (9.73 g, 98%) as a pale-yellow oil. ES/MS m/z 274.8 (M+H)

Preparation 339

Ethyl 2-[4-bromo-2-(bromomethyl)-5-fluoro-phenyl]acetate

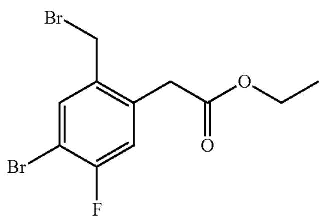 [SMILES: CCOC(=O)Cc1cc(F)c(Br)cc1CBr]

Prepare a solution of ethyl 2-(4-bromo-5-fluoro-2-methyl-phenyl)acetate (5.9 g, 21 mmol) and N-bromosuccinimide (3.6 g, 20 mmol) in ACN (110 mL). Pump the solution through a photochemical reactor consisting of a coiled PFA reaction tube (⅛" outer diameter, 53 mL volume) around a 4100K white lightbulb (42 W, 150 W equivalent), with a flowrate of 1.3 mL/min and maintaining the system temperature between 30 and 40° C. Once complete, pump ACN (100 mL) through the reactor at the same rate. Dilute the output mixture with water (500 mL) and heptane (200 mL). Extract the aqueous layer with heptane (200 mL) and wash the combined organic layers with saturated aqueous sodium thiosulfate solution (2×100 mL). Dry the organic layer over $MgSO_4$, filter, and concentrate under vacuum. Purify the residue via silica gel chromatography using a gradient of 0 to 10% EtOAc in hexanes to give 7.0 g of the title compound (92% yield, 90% pure). $^1$H-NMR (400 MHz, $CDCl_3$) δ 7.59 (d, J=7 Hz, 1H), 7.09 (d, J=9 Hz, 1H), 4.50 (s, 2H), 4.20 (q, J=7.5 Hz, 2H), 3.75 (s, 2H), 1.29 (t, J=7.5 Hz, 3H).

Preparation 340

Ethyl 2-[4-bromo-2-[2-[5-[(6-chloro-2-pyridyl)oxymethyl]-2-cyano-phenyl]ethoxymethyl]-5-fluoro-phenyl]acetate

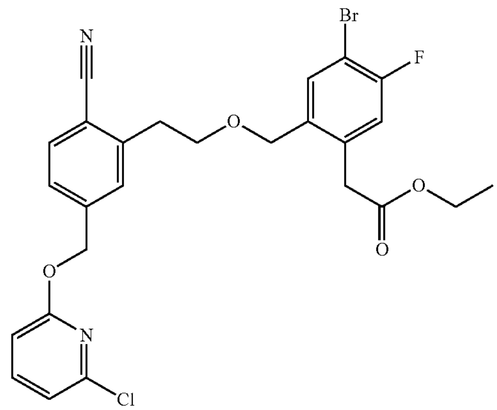 [SMILES: CCOC(=O)Cc1cc(F)c(Br)cc1COCCc1cc(COc2cccc(Cl)n2)ccc1C#N]

Charge a reaction vessel with 4-[(6-chloro-2-pyridyl)oxymethyl]-2-(2-hydroxyethyl)benzonitrile (700 mg, 2.4 mmol), ethyl 2-[4-bromo-2-(bromomethyl)-5-fluoro-phenyl]acetate (1.3 g, 3.2 mmol, 88 mass %), anhydrous DCM (20 mL) and 2,6-di-tert-butylpyridine (835 μL, 3.61 mmol). Cool the mixture to 0° C. under nitrogen atmosphere and add silver trifluoromethanesulfonate (878 mg, 3.38 mmol). Allow the mixture to reach RT and stir overnight. Filter the reaction mixture through Celite®, concentrate the filtrate and purify the residue by silica gel chromatography using a gradient of 20 to 100% DCM in cyclohexane to give the title compound (369 mg, 67 wt % pure, 18%) as a colorless waxy solid. ES-MS m/z 561, 563, 565 (M+H).

Preparation 341

Ethyl 2-[2-[2-[5-[(6-chloro-2-pyridyl)oxymethyl]-2-cyano-phenyl]ethoxymethyl]-5-fluoro-4-(4,4,5,5-tetramethyl-1,3,2-dioxaborolan-2-yl)phenyl]acetate

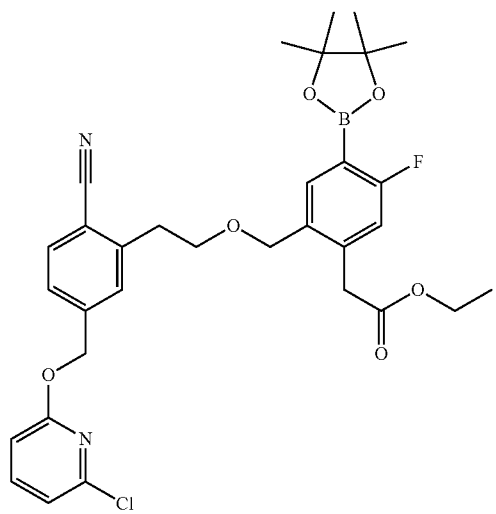 [SMILES: CCOC(=O)Cc1cc(F)c(B2OC(C)(C)C(C)(C)O2)cc1COCCc1cc(COc2cccc(Cl)n2)ccc1C#N]

Charge a reaction vessel with ethyl 2-[4-bromo-2-[2-[5-[(6-chloro-2-pyridyl)oxymethyl]-2-cyano-phenyl]ethoxymethyl]-5-fluoro-phenyl]acetate (340 mg, 0.41 mmol, 67 wt % pure), KOAc (140 mg, 1.40 mmol), bis(pinacolato)diboron (190 mg, 0.73 mmol) and anhydrous 1,4-dioxane (4 mL). Bubble the mixture with nitrogen, add dichlorobis(tricyclohexylphosphine)palladium(II) (61 mg, 0.081 mmol) and stir at 90° C. in a preheated bath for 5 h. Cool the reaction mixture to RT, add saturated aqueous $NaHCO_3$ and EtOAc and filter the mixture through Celite®. Separate aqueous layer and wash the organic layer with water and saturated aqueous NaCl, dry over $Na_2SO_4$, filter and concentrate. Purify the residue via silica gel chromatography using a gradient of 0 to 100% EtOAc in DCM to give the title compound (275 mg, 75 wt % pure, 84%) as a yellow waxy solid. ES-MS m/z 609 and 611 (M+H).

Preparation 342

Ethyl 2-($5^4$-cyano-$1^6$-fluoro-3,8-dioxa-2(2,6)-pyridina-1,5(1,3)-dibenzenacyclononaphane-$1^4$-yl)acetate

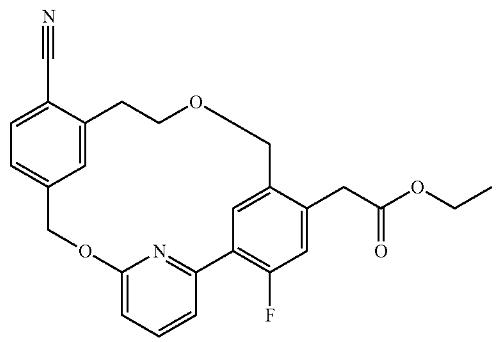 [SMILES: CCOC(=O)Cc1cc(F)c2cc1COCCc1cc(ccc1C#N)COc1cccc-2n1]

Charge a reaction vessel with ethyl 2-[2-[2-[5-[(6-chloro-2-pyridyl)oxymethyl]-2-cyano-phenyl]ethoxymethyl]-5-fluoro-4-(4,4,5,5-tetramethyl-1,3,2-dioxaborolan-2-yl)phenyl]acetate (190 mg, 0.23 mmol, 75 wt % pure) and THE (7.8 mL). Bubble the mixture with nitrogen, then add potassium phosphate tribasic (1.0 M in water, 1.2 mL, 1.2 mmol) and chloro(2-dicyclohexylphosphino-2',4',6'-triisopropyl-1,1'-biphenyl)[2-(2'-amino-1,1'-biphenyl)]palladium (II) (XPhos Pd G2, 20 mg, 0.025 mmol). Stir the mixture at 70° C. in a preheated bath for 30 min. Cool the reaction mixture to RT and add water and EtOAc. Separate the aqueous layer and wash the organic layer with water and saturated aqueous NaCl, dry over $Na_2SO_4$, filter and remove solvent. Purify the residue via silica gel chromatography using a gradient of 0 to 5% EtOAc in DCM to provide the title compound (49 mg, 90 wt % pure, 42%) as a pale brown solid. ES-MS m/z 447 (M+H).

Preparation 343

2-($5^4$-Cyano-$1^6$-fluoro-3,8-dioxa-2(2,6)-pyridina-1,5(1,3)-dibenzenacyclononaphane-$1^4$-yl)acetic acid

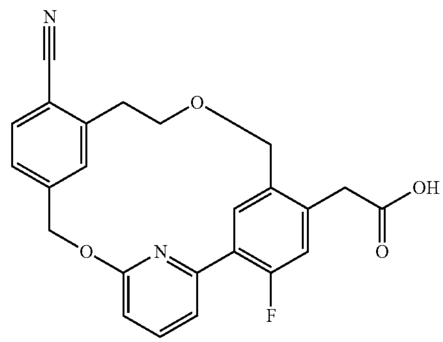 [SMILES: N#Cc1ccc2cc1CCOCc1cc(c(F)cc1CC(=O)O)-c1cccc(n1)OC2]

Add 1,5,7-triazabicyclo[4.4.0]dec-5-ene (62 mg, 0.44 mmol) to a suspension of ethyl 2-($5^4$-cyano-$1^6$-fluoro-3,8-dioxa-2(2,6)-pyridina-1,5(1,3)-dibenzenacyclononaphane-$1^4$-yl)acetate (72 mg, 0.145 mmol, 90 mass %) in a mixture of ACN (1.5 mL), THE (500 μL) and water (500 μL). Purge the mixture with $N_2$ and stir at 50° C. for 15 min. Remove the organic solvents with a nitrogen stream. Add EtOAc and aqueous citric acid (5%). Separate the aqueous layer and wash the organic layer with water and saturated aqueous NaCl, dry over $Na_2SO_4$, filter and remove the solvent to provide the title compound (65 mg, 97%, 91 mass %) as a white solid. ES-MS m/z 419 (M+H).

Preparation 344

Methyl (S)-2-(($5^4$-cyano-$1^6$-fluoro-3,8-dioxa-2(2,6)-pyridina-1,5(1,3)-dibenzenacyclononaphane-$1^4$-yl)methyl)-4-(2-methoxyethoxy)-1-(oxetan-2-ylmethyl)-1H-benzo[d]imidazole-6-carboxylate

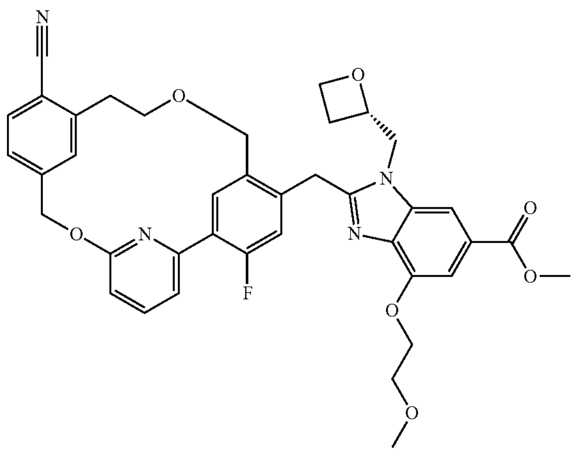 [SMILES: COCCOc1cc(C(=O)OC)cc2c1nc(Cc1cc(F)c3cc1COCCc1cc(ccc1C#N)COc1cccc-3n1)n2C[C@@H]1CCO1]

To a solution of 2-($5^4$-cyano-$1^6$-fluoro-3,8-dioxa-2(2,6)-pyridina-1,5(1,3)-dibenzenacyclononaphane-$1^4$-yl)acetic acid (65 mg, 0.14 mmol, 91 mass %) and methyl 4-amino-3-(2-methoxyethoxy)-5-[[(2S)-oxetan-2-yl]methylamino]benzoate (45 mg, 0.145 mmol) in anhydrous DMF (1.4 mL) under nitrogen atmosphere, add HATU (70 mg, 0.18 mmol) and DIPEA (74 µL, 0.42 mmol). Stir the mixture at RT for 3 h and dilute with water and EtOAc. Separate the aqueous layer and wash the organic layer with water and saturated aqueous NaCl, dry over $Na_2SO_4$, filter and remove solvent. Dissolve the residue in 1,2-dichloroethane (0.9 mL) and acetic acid (0.9 mL) and heat the mixture at 60° C. under $N_2$ for 8 h. Cool the reaction mixture to RT, concentrate solvents under reduced pressure, dry under vacuum at 35-40° C. and purify the residue via silica gel chromatography using a gradient of 25 to 100% EtOAc in DCM to provide the title compound (50 mg, 49%) as a white solid. ES-MS m/z 693 (M+H).

Preparation 345

Methyl 3-fluoro-5-((1-methylpyrrolidin-3-yl)oxy)-4-nitrobenzoate

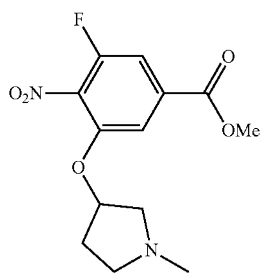 [SMILES: COC(=O)c1cc(F)c([N+](=O)[O-])c(OC2CCN(C)C2)c1]

Stir a solution of methyl 3-fluoro-5-hydroxy-4-nitrobenzoate (2.0 g, 9.3 mmol), 1-methylpyrrolidin-3-ol (1.13 g, 11.2 mmol), triphenylphosphine (2.93 g, 11.2 mmol), and DIAD (2.26 g, 11.2 mmol) in THF (80 mL) at RT for 12 h. Filter and concentrate the reaction mixture and purify the residue via silica gel chromatography using a gradient of 0 to 10% MeOH in DCM to give 1.03 g of the title compound (37%). ES-MS m/z 299 (M+H).

Preparation 346

Methyl 3-((1-methylpyrrolidin-3-yl)oxy)-4-nitro-5-((((S)-oxetan-2-yl)methyl)amino)benzoate

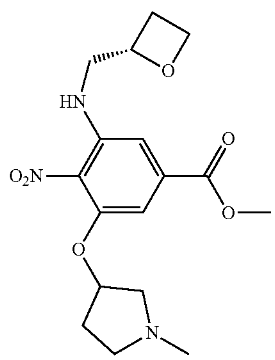

Stir a solution of methyl 3-fluoro-5-(1-methylpyrrolidin-3-yl)oxy)-4-nitrobenzoate (1.03 g, 3.45 mmol), [(2S)-oxetan-2-yl]methanamine (20 g, 8.3 mmol), and TEA (2.1 g, 21 mmol) in DMSO (150 mL) at 80° C. for 12 h. Dilute the reaction with water (50 mL) and extract with EtOAc (2×200 mL). Wash the combined organic layers with saturated aqueous NaCl (5×40 mL). Dry the organic layer over $MgSO_4$, filter, and concentrate. Purify the residue via silica gel chromatography using a gradient of 0 to 20% MeOH in DCM followed by purification via reversed phase chromatography using a gradient of 30 to 60% MeCN in aqueous ammonium hydroxide (0.05%) to give 520 mg of the title compound (41%) as a yellow oil. ES-MS m/z 366 (M+H).

Preparation 347

Methyl 4-amino-3-((1-methylpyrrolidin-3-yl)oxy)-5-((((S)-oxetan-2-yl)methyl)amino)benzoate

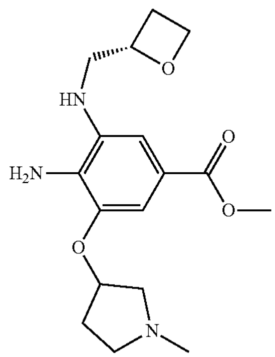 [SMILES: COC(=O)c1cc(NC[C@@H]2CCO2)c([N+](=O)[O-])c(OC2CCN(C)C2)c1]

Stir a solution of methyl 3-((1-methylpyrrolidin-3-yl)oxy)-4-nitro-5-((((S)-oxetan-2-yl)methyl)amino)benzoate (500 mg, 1.37 mmol) and palladium on carbon (10%, 200 mg, 0.19 mmol) in EtOAc (100 mL) at RT under an atmosphere of hydrogen gas for 2 h. Filter and concentrate the reaction mixture to give 358 mg of the title compound (78%) as a light yellow solid. ES-MS m/z 336 (M+H).

Preparation 348

Methyl 4-(2-($5^4$-cyano-3,9-dioxa-2(2,6)-pyridina-1(1,3),5(1,2)-dibenzenacyclononaphane-$1^4$-yl)acetamido)-3-((1-methylpyrrolidin-3-yl)oxy)-5-((((S)-oxetan-2-yl)methyl)amino)benzoate

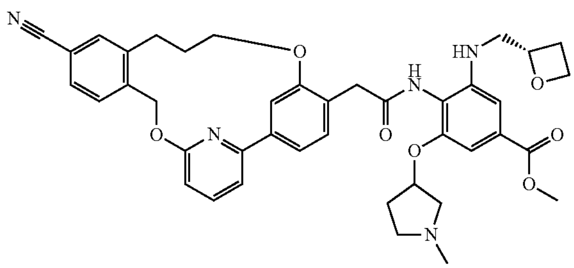 [SMILES: COC(=O)c1cc(NC[C@@H]2CCO2)c(NC(=O)Cc2ccc3cc2OCCCc2cc(C#N)ccc2COc2cccc-3n2)c(OC2CCN(C)C2)c1]

To a solution of 2-($5^4$-cyano-3,9-dioxa-2(2,6)-pyridina-1(1,3),5(1,2)-dibenzenacyclononaphane-$1^4$-yl)acetic acid (75 mg, 0.18 mmol) and HATU (100 mg, 0.26 mmol) in DMF (1.8 mL), add methyl 4-amino-3-((1-methylpyrrolidin-3-yl)oxy)-5-((((S)-oxetan-2-yl)methyl)amino)benzoate (67 mg, 0.20 mmol) and DIPEA (0.08 mL, 0.45 mmol). Stir at 20° C. for 2 h. Dilute the mixture with water (10 mL) and extract with EtOAc (2×10 mL). Wash the combined organic layers with saturated aqueous NaCl (10 mL), dry over $Na_2SO_4$, filter, and concentrate to give 425 mg of the title compound, which is used without further purification in Preparation 349. ES-MS m/z 718 (M+H).

Preparation 349

Methyl 2-(($5^4$-cyano-3,9-dioxa-2(2,6)-pyridina-1(1,3),5(1,2)-dibenzenacyclononaphane-$1^4$-yl)methyl)-4-((1-methylpyrrolidin-3-yl)oxy)-1-(((S)-oxetan-2-yl)methyl)-1H-benzo[d]imidazole-6-carboxylate

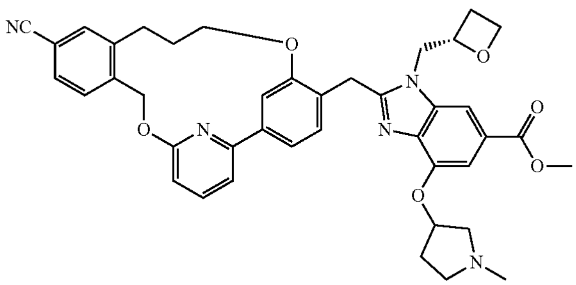 [SMILES: COC(=O)c1cc(OC2CCN(C)C2)c2nc(Cc3ccc4cc3OCCCc3cc(C#N)ccc3COc3cccc-4n3)n(C[C@@H]3CCO3)c2c1]

Stir a solution of methyl 4-(2-($5^4$-cyano-3,9-dioxa-2(2,6)-pyridina-1(1,3),5(1,2)-dibenzenacyclononaphane-$1^4$-yl)acetamido)-3-((1-methylpyrrolidin-3-yl)oxy)-5-((((S)-oxetan-2-yl)methyl)amino)benzoate (Preparation 348, 425 mg, 0.528 mmol) in 1,2-dichloroethane (4 mL) and acetic acid (4 mL) at 55° C. for 12 h. Dilute with 1:1 toluene:ACN (10 mL) and concentrate the solution. Purify the residue via silica gel chromatography using a gradient of 0 to 10% MeOH in DCM to give 100 mg of the title compound (27%) as a white solid. ES-MS m/z 700 (M+H).

Preparation 350

Ethyl 2-(4-bromo-2-((2-(((6-bromo-5-fluoropyridin-2-yl)oxy)methyl)-5-cyanophenethoxy)methyl)-5-fluorophenyl)acetate

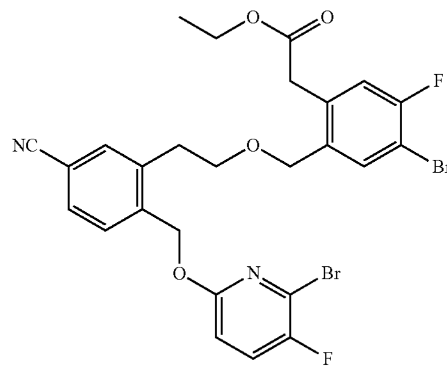 [SMILES: CCOC(=O)Cc1cc(F)c(Br)cc1COCCc1cc(C#N)ccc1COc1ccc(F)c(Br)n1]

To a solution of 4-[(6-bromo-5-fluoro-2-pyridyl)oxymethyl]-3-(2-hydroxyethyl)benzonitrile (4 g, 10.59 mmol), ethyl 2-[4-bromo-2-(bromomethyl)-5-fluoro-phenyl]acetate (8.3 g, 21 mmol) and 2,6-di-tert-butyl-4-methylpyridine (4.45 g, 21.2 mmol) in DCM (60 mL) add silver trifluoromethanesulfonate (8.3 g, 32 mmol) at 20° C. Stir the reaction at RT overnight, then concentrate the reaction mixture under reduced pressure to remove the solvent. Dilute the residue with water (100 mL) and extract with EtOAc (100 mL×2). Combine the organic layers, wash with saturated aqueous NaCl (60 mL), dry over $Na_2SO_4$, filter and concentrate under reduced pressure. Purify the residue by silica gel chromatography using a gradient of 0% to 100% DCM in petroleum ether to give the title compound as a pale-yellow solid (2.15 g, 25%) ES-MS m/z 625 (M+H).

Preparation 351

Ethyl 2-($5^4$-cyano-$1^6$,$2^3$-difluoro-3,8-dioxa-2(2,6)-pyridina-1(1,3),5(1,2)-dibenzenacyclononaphane-$1^4$-yl)acetate

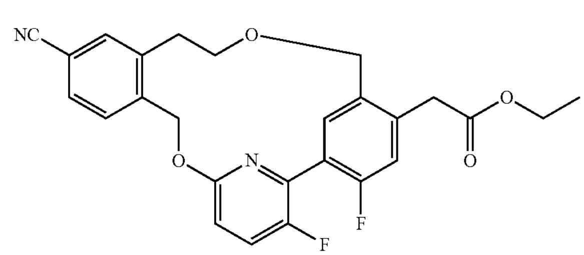 [SMILES: CCOC(=O)Cc1cc(F)c2cc1COCCc1cc(C#N)ccc1COc1ccc(F)c-2n1]

To a mixture of ethyl 2-(4-bromo-2-((2-(((6-bromo-5-fluoropyridin-2-yl)oxy)methyl)-5-cyanophenethoxy)methyl)-5-fluorophenyl)acetate (2.15 g, 2.63 mmol) and cesium fluoride (795 mg, 5.18 mmol) in 1,4-dioxane (230 mL) under nitrogen at RT, add (2-dicyclohexylphosphino-2',4',6'-triisopropyl-1,1'-biphenyl)[2-(2'-amino-1,1'-biphenyl)]palladium(II) methanesulfonate (XPhos Pd G3, 450 mg, 0.521 mmol) and hexamethylditin (1.34 g, 4.05 mmol). Protect the reaction from light heat the reaction to 110° C. and stir for 15 h, then concentrate the reaction mixture under reduced pressure to remove the solvent. Dilute the residue with water (100 mL) and extract with EtOAc (100 mL×3). Combine the organic layers, wash with saturated aqueous NaCl (60 mL), dry over $Na_2SO_4$, filter and concentrate under reduced pressure. Purify the crude residue by preparative HPLC [column: Xtimate C18 150×40 mm, 10 µm; mobile phase: gradient of 50 to 90% ACN in water (with $NH_3H_2O+NH_4HCO_3$)] to give the title compound as a white solid. (360.1 mg, 29%) ES-MS m/z 465 (M+H).

Preparation 352

2-($5^4$-Cyano-$1^6$,$2^3$-difluoro-3,8-dioxa-2(2,6)-pyridina-1(1,3),5(1,2)-dibenzenacyclononaphane-$1^4$-yl)acetic acid

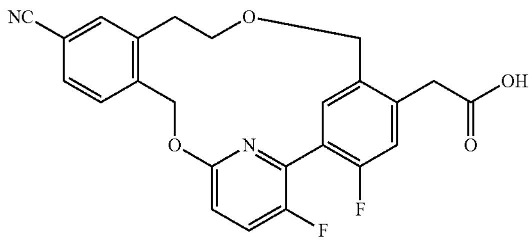

Purge gently with nitrogen a solution of ethyl 2-($5^4$-cyano-$1^6$,$2^3$-difluoro-3,8-dioxa-2(2,6)-pyridina-1(1,3),5(1,2)-dibenzenacyclononaphane-$1^4$-yl)acetate (345 mg, 0.74 mmol) in THE (2.47 mL), water (2.47 mL) and ACN (7.41 mL) and add 1,5,7-triazabicyclo[4.4.0]dec-5-ene (320 mg, 2.25 mmol). Seal the reaction vessel and purge with nitrogen. Heat the reaction mixture to 45° C. and stir at this temperature for 2 h then concentrate the reaction under reduced pressure to give the title compound as a white solid (385 mg, 100%) which is used in Preparation 353 without further purification. ES-MS m/z 437 (M+H).

Preparation 353

Methyl (S)-4-(2-($5^4$-cyano-$1^6$,$2^3$-difluoro-3,8-dioxa-2(2,6)-pyridina-1(1,3),5(1,2)-dibenzenacyclononaphane-$1^4$-yl)acetamido)-3-(2-methoxyethoxy)-5-((oxetan-2-ylmethyl)amino)benzoate

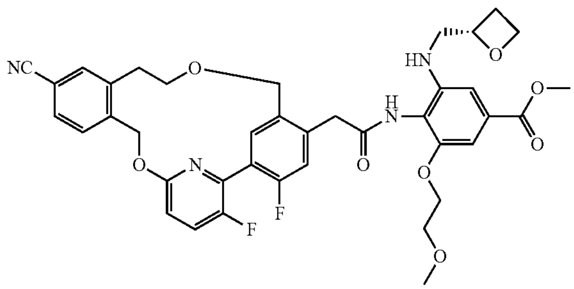

To a solution of 2-($5^4$-cyano-$1^6$,$2^3$-difluoro-3,8-dioxa-2(2,6)-pyridina-1(1,3),5(1,2)-dibenzenacyclononaphane-$1^4$-yl)acetic acid (Preparation 352, 250 mg, 0.48 mmol) and HATU (378 mg, 0.97 mmol) in DMF (6 mL), add methyl 4-amino-3-(2-methoxyethoxy)-5-[[(2S)-oxetan-2-yl]methylamino]benzoate (260 mg, 0.75 mmol), then add DIPEA (300 µL, 1.72 mmol) to the mixture and stir at 20° C. under $N_2$ overnight. Dilute the reaction with water (20 mL) and extract with EtOAc (20 mL×2). Combine the organic layers, wash with saturated aqueous NaCl (20 mL), dry over $Na_2SO_4$, filter and concentrate under reduced pressure to give the titled compound as pale-yellow solid (1.2 g, 100%) which is used in Preparation 354 without further purification. ES-MS m/z 729 (M+H).

Preparation 354

Methyl (S)-2-(($5^4$-cyano-$1^6$,$2^3$-difluoro-3,8-dioxa-2(2,6)-pyridina-1(1,3),5(1,2)-dibenzenacyclononaphane-$1^4$-yl)methyl)-4-(2-methoxyethoxy)-1-(oxetan-2-ylmethyl)-1H-benzo[d]imidazole-6-carboxylate

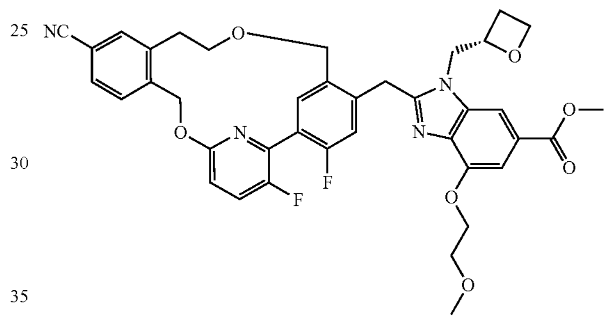

To a solution of methyl (S)-4-(2-($5^4$-cyano-$1^6$,$2^3$-difluoro-3,8-dioxa-2(2,6)-pyridina-1(1,3),5(1,2)-dibenzenacyclononaphane-$1^4$-yl)acetamido)-3-(2-methoxyethoxy)-5-((oxetan-2-ylmethyl)amino)benzoate (Preparation 353, 1.2 g, 0.49 mmol) in 1,2-dichloroethane (5 mL) at RT under $N_2$ add acetic acid (5 mL). Heat the reaction at 55° C. and stir overnight. Dilute the reaction with toluene/ACN 1:1 (5 mL), remove the solvent under reduced pressure and purify the residue by silica gel chromatography using a gradient of 0 to 5% MeOH in DCM to give the title product as a white solid (270 mg, 35%). ES-MS m/z 711 (M+H).

Preparation 355

Methyl (S)-2-(chloromethyl)-4-fluoro-1-(oxetan-2-ylmethyl)-1H-benzo[d]imidazole-6-carboxylate

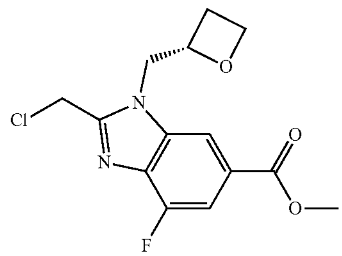 [SMILES: COC(=O)c1cc(F)c2nc(CCl)n(C[C@@H]3CCO3)c2c1]

Cool a solution of methyl 4-amino-3-fluoro-5-[[(2S)-oxetan-2-ylmethyl]amino]benzoate (2.0 g, 7.9 mmol) and TEA (1.1 mL, 7.9 mmol) in 1,2-dichloroethane (22 mL) to 0° C. and add 2-chloroacetyl chloride (0.63 mL, 7.9 mL). Stir the mixture at RT for 2 h. Dilute the reaction mixture with DCM and wash with water. Dry the organic layer over $MgSO_4$, filter, and concentrate. Dissolve the resulting residue in acetic acid (40 mL) and stir at 70° C. for 2 h. Concentrate the crude reaction and purify the residue via silica gel chromatography using a gradient of 0 to 4% MeOH in DCM to give 1.76 g of the title compound (72%) as a yellow oil. ES-MS m/z 313 (M+H).

Preparation 356

3-(2-((5-Bromo-2-chlorobenzyl)oxy)ethyl)-4-(((6-bromopyridin-2-yl)oxy)methyl)benzonitrile

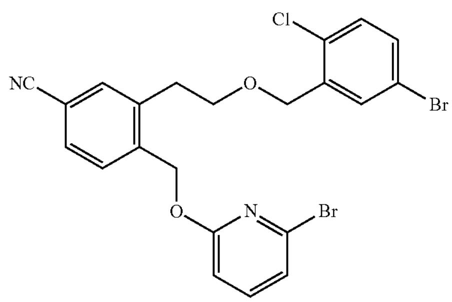 [SMILES: N#Cc1ccc(COc2cccc(Br)n2)c(CCOCc2cc(Br)ccc2Cl)c1]

Cool a solution of 4-[(6-bromo-2-pyridyl)oxymethyl]-3-(2-hydroxyethyl)benzonitrile (2.3 g, 6.8 mmol), 4-bromo-2-(bromomethyl)-1-chloro-benzene (2.7 g, 9.5 mmol), and 2,6-di-tert-butylpyridine (2.2 mL, 9.7 mmol) in DCM (36 mL) to 0° C. Add silver trifluoromethanesulfonate (3.0 g, 11.8 mmol) to the reaction mixture and stir at 0° C. for 15 min before stirring at RT for 18 h. Add additional silver trifluoromethanesulfonate (0.53 g, 2.1 mmol) to the reaction mixture and stir at RT for 22 h. Filter the crude reaction mixture through Celite®, concentrate, and purify the residue via silica gel chromatography using a gradient of 0 to 100% DCM in heptane to give 2.3 g of the title compound (62%) as a colorless sticky solid. ES-MS m/z 535/537/539 (M+H).

Preparation 357

$1^4$-Chloro-3,8-dioxa-2(2,6)-pyridina-1(1,3),5(1,2)-dibenzenacyclononaphane-$5^4$-carbonitrile

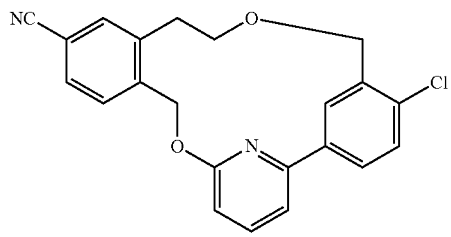 [SMILES: N#Cc1ccc2c(c1)CCOCc1cc(ccc1Cl)-c1cccc(n1)OC2]

Prepare the title compound essentially as described in Preparation 216 using 3-(2-((5-bromo-2-chlorobenzyl)oxy)ethyl)-4-(((6-bromopyridin-2-yl)oxy)methyl)benzonitrile, purify the title compound via silica gel chromatography using a gradient of 0 to 25% EtOAc in heptane to give the title compound as beige solid. ES-MS m/z 377 (M+H).

Preparation 358

$1^4$-(4,4,5,5-Tetramethyl-1,3,2-dioxaborolan-2-yl)-3,8-dioxa-2(2,6)-pyridina-1(1,3),5(1,2)-dibenzenacyclononaphane-$5^4$-carbonitrile

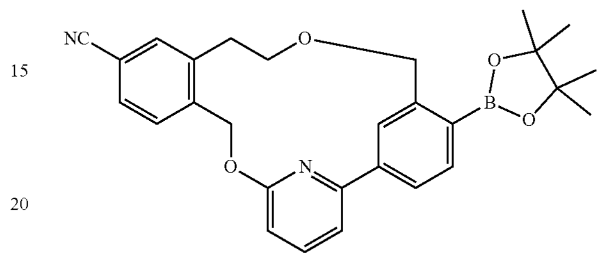

Stir a solution of $1^4$-chloro-3,8-dioxa-2(2,6)-pyridina-1(1,3),5(1,2)-dibenzenacyclononaphane-$5^4$-carbonitrile (170 mg, 0.45 mmol), (S)-1,2-propanediol (0.2 mL, 3 mmol), 2-dicyclohexylphosphino-2',4',6'-triisopropylbiphenyl (XPhos, 44 mg, 0.09 mmol), chloro(2-dicyclohexylphosphino-2',4',6'-triisopropyl-1,1'-biphenyl)[2-(2'-amino-1,1'-biphenyl)]palladium(II) (XPhos Pd Gen 2, 35 mg, 0.045 mmol), bis(pinacolato)diboron (0.34 g, 1.3 mmol), and KOAc (0.13 g, 1.3 mmol), in 2-methyltetrahydrofuran (14 mL) at 80° C. for 3 h. Filter and concentrate the reaction solution. Dissolve the residue in EtOAc and wash with water. Dry the organic layer over $MgSO_4$, filter, and concentrate to give 210 mg of the title compound (99%), which is used in Preparation 359 without further purification. ES-MS m/z 469 (M+H).

Preparation 359

Methyl (S)-2-(($5^4$-cyano-3,8-dioxa-2(2,6)-pyridina-1(1,3),5(1,2)-dibenzenacyclononaphane-$1^4$-yl)methyl)-4-fluoro-1-(oxetan-2-ylmethyl)-1H-benzo[d]imidazole-6-carboxylate

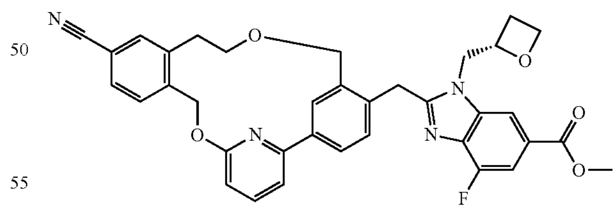

Stir a solution of $1^4$-(4,4,5,5-tetramethyl-1,3,2-dioxaborolan-2-yl)-3,8-dioxa-2(2,6)-pyridina-1(1,3),5(1,2)-dibenzenacyclononaphane-$5^4$-carbonitrile (0.12 g, 0.26 mmol), methyl (S)-2-(chloromethyl)-4-fluoro-1-(oxetan-2-ylmethyl)-1H-benzo[d]imidazole-6-carboxylate (0.12 g, 0.38 mmol), 2-dicyclohexylphosphino-2',4',6'-triisopropylbiphenyl (XPhos, 25 mg, 0.05 mmol), chloro(2-dicyclohexylphosphino-2',4',6'-triisopropyl-1,1'-biphenyl)[2-(2'-amino-1,1'-biphenyl)]palladium(II) (XPhos Pd Gen 2 20 mg, 0.025 mmol), and potassium phosphate tribasic (67 mg, 0.31 mmoL) in 2-methyltetrahydrofuran (3 mL) and water (0.3 mL) at 90° C. for 7 h. Filter the reaction solution and dilute with EtOAc, wash with water, dry the organic layer over $MgSO_4$, filter, and concentrate. Purify the residue via silica gel chromatography using a gradient of 0 to 50% EtOAc in DCM to give 20 mg of the title compound (10%) as a yellow solid. ES-MS m/z 619 (M+H).

Preparation 360

Methyl (S)-3-(2-(dimethylamino)-2-oxoethoxy)-4-nitro-5-((oxetan-2-ylmethyl)amino)benzoate

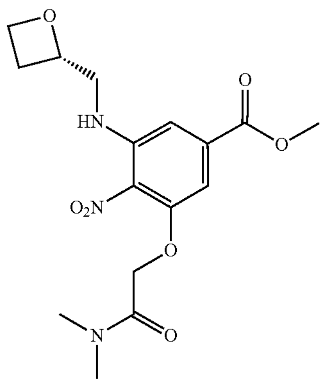 [SMILES: COC(=O)c1cc(NC[C@@H]2CCO2)c([N+](=O)[O-])c(OCC(=O)N(C)C)c1]

Add sodium hydride in mineral oil (60 wt %, 211 mg, 5.28 mmol) to a solution of 2-hydroxy-N,N-dimethylacetamide (730 mg, 7.08 mmol) in THE (10 mL) at 0° C., then remove the cooling bath and stir the mixture for 1 h. Re-cool the mixture to 0° C. and add methyl 3-fluoro-4-nitro-5-[[(2S)-oxetan-2-ylmethyl]amino]benzoate (1 g, 3.52 mmol). Remove the cooling bath and stir the mixture for 48 h. Quench the reaction with saturated $NH_4Cl$ solution (30 mL) and extract with EtOAc (3×50 mL). Separate the organic layer, dry over Na2SO4, filter and concentrate. Purify the residue by silica gel chromatography using a gradient of 0 to 60% EtOAc in petroleum ether to afford the title compound as a yellow oil (800 mg, 61%). ES-MS m/z 368 (M+H).

Preparation 361

Methyl (S)-4-amino-3-(2-(dimethylamino)-2-oxo-ethoxy)-5-((oxetan-2-ylmethyl)amino)benzoate

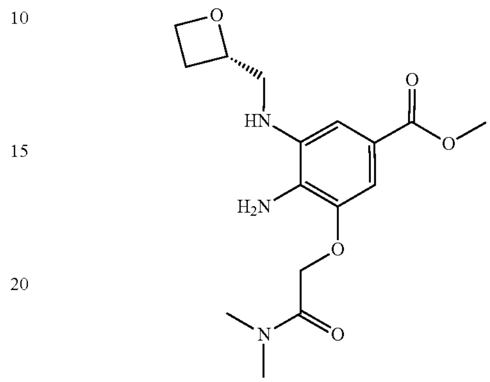

Purge a vessel containing methyl (S)-3-(2-(dimethylamino)-2-oxoethoxy)-4-nitro-5-((oxetan-2-ylmethyl)amino) benzoate (800 mg, 2.13 mmol), Pd/C (200 mg, 10 wt %), and EtOAc (60 mL) with hydrogen gas three times. Stir the mixture under one atmosphere of $H_2$ for 4 h at ambient temperature. Filter the mixture and concentrate under reduced pressure. Purify the product by silica gel chromatography using a gradient of 0 to 100% EtOAc in petroleum ether to afford the title compound as a yellow oil (636.4 mg, 88%). ES-MS m/z 338 (M+H).

Preparation 362

Methyl (S)-4-(2-($5^4$-cyano-3,9-dioxa-2(2,6)-pyridina-1(1,3),5(1,2)-dibenzenacyclononaphane-$1^4$-yl)acetamido)-3-(2-(dimethylamino)-2-oxoethoxy)-5-((oxetan-2-ylmethyl)amino)benzoate

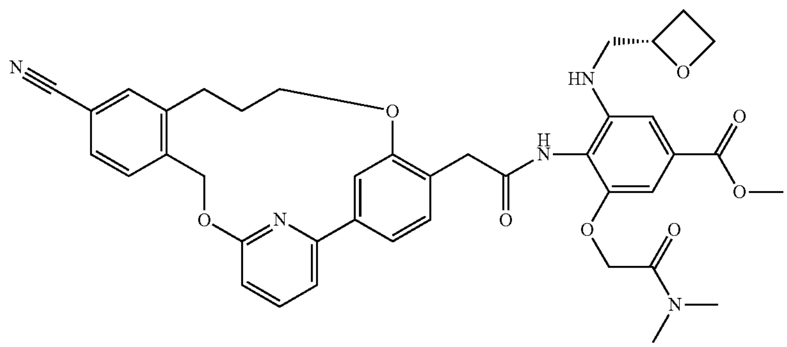 [SMILES: COC(=O)c1cc(NC[C@@H]2CCO2)c(NC(=O)Cc2ccc3cc2OCCCc2cc(C#N)ccc2COc2cccc-3n2)c(OCC(=O)N(C)C)c1]

At ambient temperature, add 1-propanephosphonic anhydride (50 wt % solution in DCM, 225 μL, 0.378 mmol) to a solution of 2-($5^4$-cyano-3,9-dioxa-2(2,6)-pyridina-1(1,3),5(1,2)-dibenzenacyclononaphane-$1^4$-yl)acetic acid (75 mg, 0.187 mmol) and methyl (S)-4-amino-3-(2-(dimethylamino)-2-oxoethoxy)-5-((oxetan-2-ylmethyl)amino)benzoate (69 mg, 0.20 mmol) in DMF (1 mL) and pyridine (150 μL, 1.85 mmol). Stir for 20 h and then add additional 1-propanephosphonic anhydride (225 μL, 0.378 mmol). After stirring another 23 h, quench the reaction by adding water (2 mL). Stir the mixture for 10 min, filter and collect the solid, then dry the solid at 60° C. under vacuum for 2 h to give the title compound as a beige solid (75.1 mg, 56%). ES-MS m/z 720 (M+H).

Preparation 363

Methyl (S)-2-(($5^4$-cyano-3,9-dioxa-2(2,6)-pyridina-1(1,3),5(1,2)-dibenzenacyclononaphane-$1^4$-yl)methyl)-4-(2-(dimethylamino)-2-oxoethoxy)-1-(oxetan-2-ylmethyl)-1H-benzo[d]imidazole-6-carboxylate

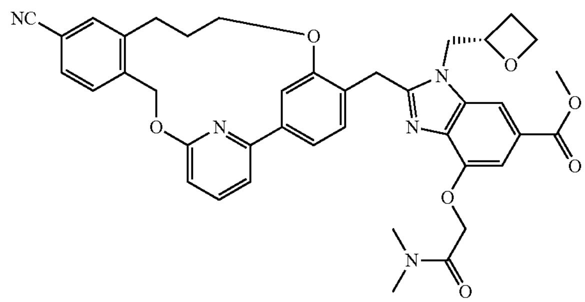 [SMILES: COC(=O)c1cc(OCC(=O)N(C)C)c2nc(Cc3ccc4cc3OCCCc3cc(C#N)ccc3COc3cccc-4n3)n(C[C@@H]3CCO3)c2c1]

Stir a solution of methyl (S)-4-(2-($5^4$-cyano-3,9-dioxa-2(2,6)-pyridina-1(1,3),5(1,2)-dibenzenacyclononaphane-$1^4$-yl)acetamido)-3-(2-(dimethylamino)-2-oxoethoxy)-5-((oxetan-2-ylmethyl)amino)benzoate (75 mg, 0.104 mmol) in acetic acid (3 mL) at 60° C. for 20 h. Remove the acetic acid under vacuum and purify the residue via silica gel chromatography using a gradient of 0 to 20% isopropanol in chloroform to give 70 mg of the title compound (70% purity, 72%). ES-MS m/z 703 (M+H).

Preparation 364

Methyl 3-[(3-ethylimidazol-4-yl)methylamino]-5-methoxy-4-nitro-benzoate

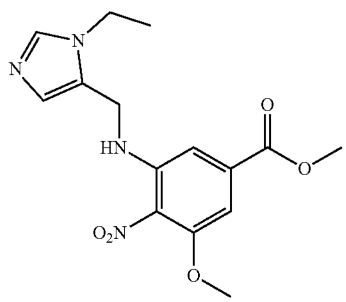 [SMILES: CCn1cncc1CNc1cc(C(=O)OC)cc(OC)c1[N+](=O)[O-]]

Add TEA (2.2 mL, 16 mmol) to a stirred solution of methyl 3-fluoro-5-methoxy-4-nitro-benzoate (900 mg, 3.93 mmol) and (1-ethyl-1H-imidazol-5-yl)methylamine dihydrochloride (900 mg, 4.32 mmol) in DMF (20 mL). Stir the mixture at 60° C. for 16 h. Allow the mixture to cool to ambient temperature and pour into saturated aqueous $NH_4Cl$ (100 mL). Extract the mixture with DCM (3×100 mL) and wash with saturated aqueous NaCl (3×50 mL). Dry the organics over $Na_2SO_4$, filter, and concentrate under reduced pressure. Purify the residue by flash chromatography using a gradient of 0 to 10% MeOH in EtOAc to give the title compound (800 mg, 61%) as a yellow oil. ES-MS m/z 335 (M+H).

Preparation 365

Methyl 4-amino-3-(((1-ethyl-1H-imidazol-5-yl)methyl)amino)-5-methoxybenzoate

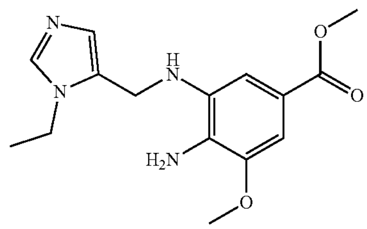 [SMILES: CCn1cncc1CNc1cc(C(=O)OC)cc(OC)c1N]

Add iron (801 mg, 14.34 mmol) and $NH_4Cl$ (768 mg, 14.4 mmol) to a solution of methyl 3-[(3-ethylimidazol-4-yl)methylamino]-5-methoxy-4-nitro-benzoate (960 mg, 2.87 mmol) in MeOH (30 mL) and water (10 mL). Stir at 80° C. for 2 h, cool to ambient temperature, then filter over a pad of Celite® and wash the pad with MeOH (30 mL). Concentrate the filtrate under reduced pressure to and purify by flash chromatography using a gradient of 0 to 15% MeOH in EtOAc. Re-purify by silica gel chromatography using a gradient of 0 to 10% MeOH in EtOAc to give the title compound as a brown solid (504 mg, 55%). ES-MS m/z 305 (M+H).

Preparation 366

Methyl 4-(2-($5^4$-cyano-3,9-dioxa-2(2,6)-pyridina-1(1,3),5(1,2)-dibenzenacyclononaphane-$1^4$-yl)acetamido)-3-(((1-ethyl-1H-imidazol-5-yl)methyl)amino)-5-methoxybenzoate

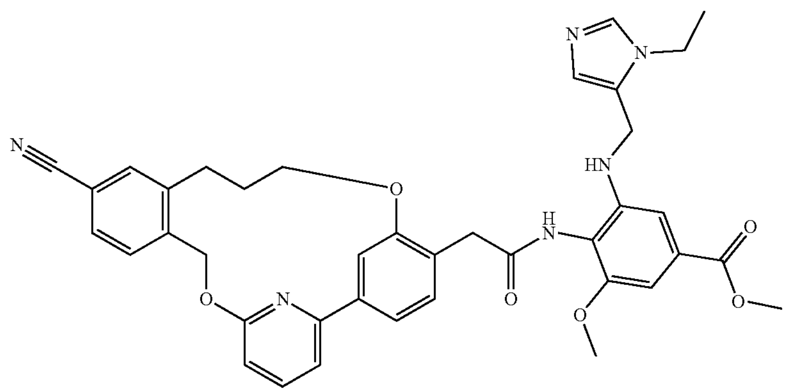 [SMILES: CCn1cncc1CNc1cc(C(=O)OC)cc(OC)c1NC(=O)Cc1ccc2cc1OCCCc1cc(C#N)ccc1COc1cccc-2n1]

At ambient temperature, add 1-propanephosphonic anhydride (50 wt % solution in DMF, 170 μL, 0.28 mmol) to a solution of 2-($5^4$-cyano-3,9-dioxa-2(2,6)-pyridina-1(1,3),5(1,2)-dibenzenacyclononaphane-$1^4$-yl)acetic acid (76 mg, 0.1898 mmol) and methyl 4-amino-3-(((1-ethyl-1H-imidazol-5-yl)methyl)amino)-5-methoxybenzoate (63 mg, 0.207 mmol) in DMF (600 μL) and pyridine (400 μL, 5 mmol). Stir the reaction at RT for 72 h, then dilute with EtOAc (100 mL), wash the organics with saturated $NaHCO_3$ (100 mL), filter over Celite®, and extract the filtrate three times with additional EtOAc. Combined the organics, wash twice with saturated aqueous NaCl, dry over $MgSO_4$, filter, and concentrate under reduced pressure to afford the title product (136 mg) which is used in Preparation 367 without further purification. ES-MS m/z 688 (M+H).

Preparation 367

Methyl 2-(($5^4$-cyano-3,9-dioxa-2(2,6)-pyridina-1(1,3),5(1,2)-dibenzenacyclononaphane-$1^4$-yl)methyl)-1-((1-ethyl-1H-imidazol-5-yl)methyl)-4-methoxy-1H-benzo[d]imidazole-6-carboxylate

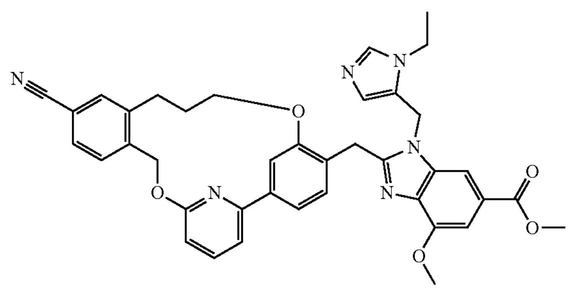 [SMILES: CCn1cncc1Cn1c(Cc2ccc3cc2OCCCc2cc(C#N)ccc2COc2cccc-3n2)nc2c(OC)cc(C(=O)OC)cc21]

Prepare the title compound essentially as described in Preparation 102 using methyl 4-(2-($5^4$-cyano-3,9-dioxa-2(2,6)-pyridina-1(1,3),5(1,2)-dibenzenacyclononaphane-$1^4$-yl)acetamido)-3-(((1-ethyl-1H-imidazol-5-yl)methyl)amino)-5-methoxybenzoate (Preparation 366) in a mixture of 1:1 acetic acid:1,2-dichloroethane as solvent, heating the reaction at 70° C. for 16 h. Cool the mixture to RT and concentrate under vacuum. Add 1:1 EtOAc/toluene and concentrate to remove residual acetic acid (twice). Dry the resulting yellow solid under vacuum for 2 h. Purify the solid by silica gel chromatography using a gradient of 90 to 100% EtOAc in DCM, followed by MeOH, to give the title compound as an off-white solid which is used in Example 63 without further purification. ES-MS m/z 670 (M+H).

Preparation 368

Methyl (S)-4-(2-($5^4$-cyano-3,8-dioxa-2(2,6)-pyridina-1(1,3),5(1,2)-dibenzenacyclononaphane-$1^4$-yl)acetamido)-3-(2-methoxyethoxy)-5-((oxetan-2-ylmethyl)amino)benzoate

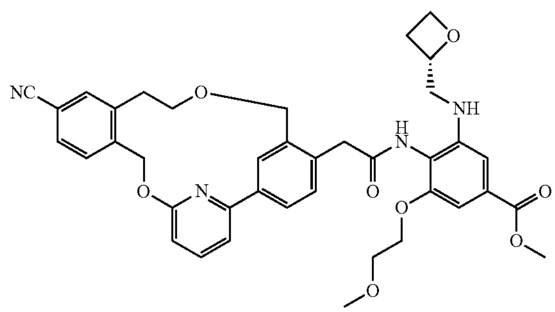 [SMILES: COCCOc1cc(C(=O)OC)cc(NC[C@@H]2CCO2)c1NC(=O)Cc1ccc2cc1COCCc1cc(C#N)ccc1COc1cccc-2n1]

To a solution of 2-($5^4$-cyano-3,8-dioxa-2(2,6)-pyridina-1(1,3),5(1,2)-dibenzenacyclononaphane-$1^4$-yl) acetic acid (44 mg, 0.103 mmol) in DMF (1.2 mL), add methyl 4-amino-3-(2-methoxyethoxy)-5-[[(2S)-oxetan-2-yl]methylamino]benzoate (32 mg, 0.103 mmol), HATU (59 mg, 0.155 mmol) and DIPEA (0.055 mL, 0.32 mmol). Stir the mixture at RT for 2 h, then dilute with water (10 mL) and extract with EtOAc (4×5 mL). Combine the organics, wash with water and saturated aqueous NaCl, dry over $MgSO_4$, filter, and concentrate under vacuum to give the title compound as a light brown solid (80 mg, 80% purity, 88% yield). ES-MS m/z 693 (M+H).

Preparation 369

Methyl (S)-2-((5$^4$-cyano-3,8-dioxa-2(2,6)-pyridina-1(1,3),5(1,2)-dibenzenacyclononaphane-1$^4$-yl)methyl)-4-(2-methoxyethoxy)-1-(oxetan-2-ylmethyl)-1H-benzo[d]imidazole-6-carboxylate

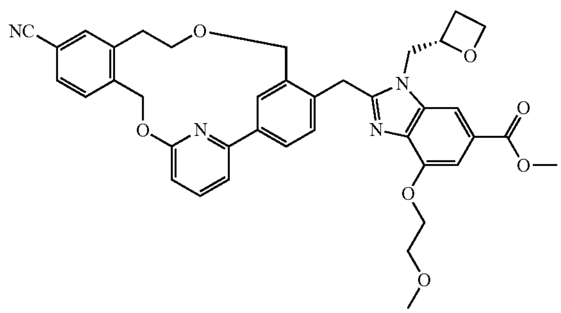 [SMILES: COCCOc1cc(C(=O)OC)cc2c1nc(Cc1ccc3cc1COCCc1cc(C#N)ccc1COc1cccc-3n1)n2C[C@@H]1CCO1]

Heat a solution of methyl (S)-4-(2-(5$^4$-cyano-3,8-dioxa-2(2,6)-pyridina-1(1,3),5(1,2)-dibenzenacyclononaphane-1$^4$-yl)acetamido)-3-(2-methoxyethoxy)-5-((oxetan-2-ylmethyl)amino)benzoate (80 mg, 80% purity, 0.092 mmol) in 1,2-dichloroethane (0.7 mL) and acetic acid (0.7 mL) at 58° C. for 6 h. Cool reaction mixture to RT, concentrate under reduce pressure, and purify the residue via silica gel chromatography using a gradient of 30 to 100% EtOAc in DCM to provide 25 mg (40%) of the title compound as a white solid. ES-MS m/z 675 (M+H).

Preparation 370

Methyl (S)-2-((5$^4$-cyano-3,8-dioxa-2(2,6)-pyridina-1,5(1,3)-dibenzenacyclononaphane-1$^4$-yl)methyl)-4-(2-methoxyethoxy)-1-(oxetan-2-ylmethyl)-1H-benzo[d]imidazole-6-carboxylate

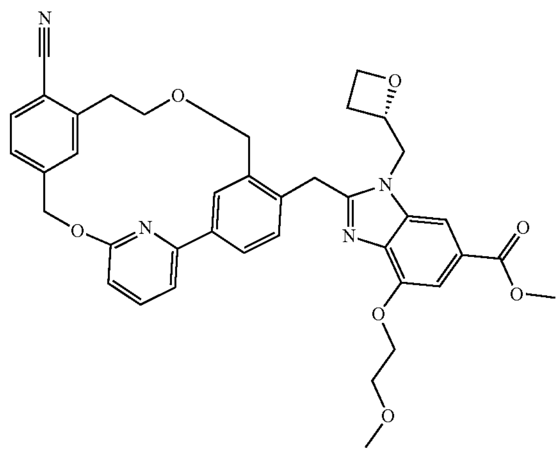 [SMILES: COCCOc1cc(C(=O)OC)cc2c1nc(Cc1ccc3cc1COCCc1cc(ccc1C#N)COc1cccc-3n1)n2C[C@@H]1CCO1]

To a solution of 2-(5$^4$-cyano-3,8-dioxa-2(2,6)-pyridina-1,5(1,3)-dibenzenacyclononaphane-1$^4$-yl)acetic acid (60 mg, 0.15 mmol) and methyl 4-amino-3-(2-methoxyethoxy)-5-[[(2S)-oxetan-2-yl]methylamino]benzoate (47 mg, 0.15) in anhydrous DMF (1.5 mL) under nitrogen atmosphere, add HATU (74 mg, 0.19 mmol) and DIPEA (0.08 mL, 0.45 mmol). Stir the mixture at RT for 2.5 h, then add water and EtOAc. Separate the aqueous layer and wash the organic layer with water and saturated aqueous NaCl, dry over $Na_2SO_4$, filter and concentrate. Heat a solution of the residue in 1,2-dichloroethane (0.9 mL) and acetic acid (0.9 mL) under nitrogen atmosphere at 60° C. for 8 h. Cool reaction mixture to RT, concentrate the solvents under reduced pressure, dry under vacuum at 35-40° C. and purify the residue via silica gel chromatography using a gradient of 25 to 100% of EtOAc in DCM as eluent system to provide the title compound (72 mg, 71%) as a white solid. ES-MS m/z 675 (M+H).

Preparation 371

(S)-(1$^4$-((6-(Methoxycarbonyl)-1-(oxetan-2-ylmethyl)-1H-benzo[d]imidazol-2-yl)methyl)-3,9-dioxa-2(2,6)-pyridina-1(1,3),5(1,2)-dibenzenacyclononaphane-5$^4$-yl)boronic acid

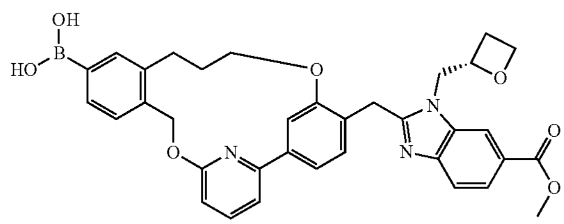 [SMILES: COC(=O)c1ccc2nc(Cc3ccc4cc3OCCCc3cc(B(O)O)ccc3COc3cccc-4n3)n(C[C@@H]3CCO3)c2c1]

Charge a reaction vessel with methyl (S)-2-((5$^4$-bromo-3,9-dioxa-2(2,6)-pyridina-1(1,3),5(1,2)-dibenzenacyclononaphane-1$^4$-yl)methyl)-1-(oxetan-2-ylmethyl)-1H-benzo[d]imidazole-6-carboxylate (500 mg, 0.72 mmol), anhydrous THE (5 mL) and MeOH (10 mL). Bubble the mixture with $N_2$ for 10 min, add anhydrous ethylene glycol (610 μL, 10.9 mmol) and DIPEA (315 μL, 1.82 mmol). Bubble the mixture with $N_2$ for 5 min, add tetrahydroxydiboron (139 mg, 1.47 mmol), tricyclohexylphosphine (5 mg, 0.018 mmol) and [(tricyclohexylphosphine)-2-(2'-aminobiphenyl)]palladium(II) methanesulfonate [P(Cy3) Pd G3, 26 mg, 0.039 mmol), seal the vessel and stir at 50° C. in a preheated bath for 2.5 h. Concentrate the reaction mixture, then add saturated aqueous $NaHCO_3$ and stir for 5 min. Filter off the solid, then wash the solid with water, ACN and MeOH to provide the title compound (500 mg, 90 wt % pure, 100%) as a gray solid. ES-MS m/z 620 (M+H).

Preparation 372

Methyl (S)-2-((5⁴-(4-fluoro-1H-imidazol-1-yl)-3,9-dioxa-2(2,6)-pyridina-1(1,3),5(1,2)-dibenzenacyclononaphane-1⁴-yl)methyl)-1-(oxetan-2-ylmethyl)-1H-benzo[d]imidazole-6-carboxylate

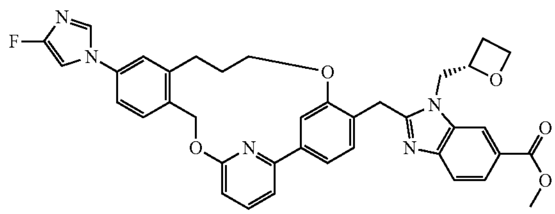 [SMILES: COC(=O)c1ccc2nc(Cc3ccc4cc3OCCCc3cc(-n5cnc(F)c5)ccc3COc3cccc-4n3)n(C[C@@H]3CCO3)c2c1]

Charge a reaction vessel with (S)-(1⁴-((6-(methoxycarbonyl)-1-(oxetan-2-ylmethyl)-1H-benzo[d]imidazol-2-yl)methyl)-3,9-dioxa-2(2,6)-pyridina-1(1,3),5(1,2)-dibenzenacyclononaphane-5⁴-yl)boronic acid (21 mg, 0.03 mmol, 90 wt % pure), 4-fluoro-1H-imidazole (14 mg, 0.15 mmol), copper(II) acetate (5.8 mg, 0.032 mmol), MeOH (245 µL) and pyridine (6 µL, 0.07 mmol). Seal the reaction vessel and stir the suspension at 60° C. for 10 h. Add EtOAc and aqueous ammonia (28%), separate the organic layer and wash with aqueous ammonia (28%), water and saturated aqueous NaCl, dry over $Na_2SO_4$, filter and concentrate. Purify the residue via silica gel chromatography using a gradient of 20 to 100% of EtOAc in DCM as eluent system to provide the title compound (8 mg, 10%) as a white solid. ES-MS m/z 660 (M+H).

Preparation 373

Methyl 2-(bromomethyl)-5-chlorobenzoate

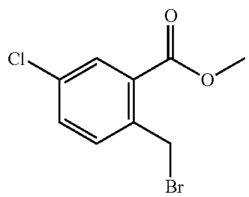

Prepare the title compound essentially as described in Preparation 236 using methyl 5-chloro-2-methylbenzoate. Stir the reactor output with water and aqueous sodium bisulfite, separate the layers, then extract the aqueous phase twice with heptane. Combine the organics, wash with water (3×), saturated aqueous $NaHCO_3$ and then saturated aqueous NaCl. Dry the organics over $MgSO_4$, filter and concentrate to give the title compound (67.99 g, 87%) as a yellow oil. $^1H$ NMR (400.21 MHz, $CDCl_3$) δ 7.98 (d, J=2.2 Hz, 1H), 7.49 (dd, J=2.3, 8.3 Hz, 1H), 7.43 (d, J=8.3 Hz, 1H), 4.94 (s, 2H), 3.97 (s, 3H).

Preparation 374

Methyl 5-chloro-2-[(6-chloro-2-pyridyl)oxymethyl]benzoate

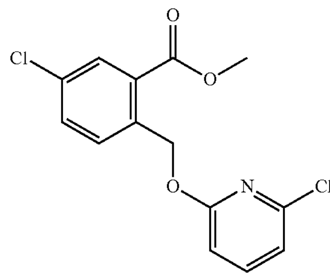 [SMILES: COC(=O)c1cc(Cl)ccc1COc1cccc(Cl)n1]

Add a solution of methyl 2-(bromomethyl)-5-chloro-benzoate (20.0 g, 67.5 mmol) in toluene (200 mL) to a mixture of 6-chloropyridin-2-ol (10.9 g, 84.1 mmol) and silver carbonate (14.9 g, 54.0 mmol). Heat the mixture under $N_2$ to 65° C. for 48 h, protecting the reaction vessel from light using aluminum foil and adding additional toluene (100 mL). Add DCM (200 mL) to the reaction and filter through a pad of Celite®, rinse the pad with DCM (100 mL). Concentrate the filtrate to a volume of 100 mL, filter off a first crop of solid material. Wash the solid with 1:1 toluene/heptane (50 mL) and heptane (2×50 mL). Add 100 mL heptane to the filtrate and then filter off a second crop of solid material, wash as before with 1:1 toluene/heptane (50 mL) and heptane (2×50 mL). Concentrate the filtrate and slurry the residue in heptane (200 mL) at 50° C. for 30 min, then stir at ambient temperature overnight. Filter off a third crop of solid and wash the solid with heptane (2×50 mL). Combine the first, second, and third crops of solid materials and dry under reduced pressure at 50° C. for 5.5 h to give the title compound (18.85 g, 89%) as a white solid. ES/MS m/z 312, 314 (M+H).

Preparation 375

[5-Chloro-2-[(6-chloro-2-pyridyl)oxymethyl]phenyl]methanol

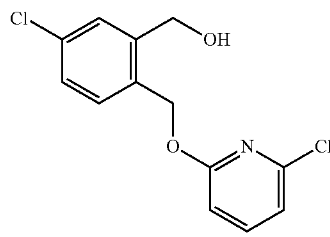 [SMILES: OCc1cc(Cl)ccc1COc1cccc(Cl)n1]

To a mixture of methyl 5-chloro-2-[(6-chloro-2-pyridyl)oxymethyl]benzoate (14.78 g, 46.87 mmol) in THE (75 mL) under $N_2$ add $LiBH_4$ (2 M in THF, 35 mL, 70 mmol). Stir the reaction mixture for 5 min at ambient temperature, then add MeOH (2.9 mL, 72 mmol) portionwise over 1 h. Add EtOAc (5 mL), water (10 mL), HCl (1 M aqueous, 100 mL), and MTBE (300 mL) to the mixture and separate the layers. Separate the layers, wash the organics with water (50 mL), aqueous $K_2CO_3$ (2 M, 50 mL), and saturated aqueous NaCl (50 mL). Dry the organics over $MgSO_4$, filter and concentrate the filtrate to give the title compound (13.54 g, 97%) as a waxy solid. ES/MS m/z 284, 286 (M+H).

Preparation 376

2-[[2-[(5-Bromo-4-fluoro-2-iodo-phenyl)methoxymethyl]-4-chloro-phenyl]methoxy]-6-chloro-pyridine

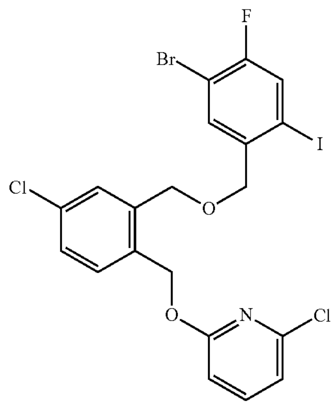 [SMILES: Fc1cc(I)c(COCc2cc(Cl)ccc2COc2cccc(Cl)n2)cc1Br]

Add THE (7.5 mL) to a mixture of [5-chloro-2-[(6-chloro-2-pyridyl)oxymethyl]phenyl]methanol (0.50 g, 1.7 mmol) and 1-bromo-5-(bromomethyl)-2-fluoro-4-iodobenzene (0.89 g, 2.1 mmol) under $N_2$, then add potassium tert-butoxide (1 M solution in tert-butanol, 2.2 mL, 2.2 mmol) portionwise. Stir the mixture at RT for 30 min, then add water (30 mL) and stir the mixture at RT overnight, resulting in a mixture with a sticky lower phase. Decant off the supernatant, add water and decant off the water. Dissolve the remainder in MeOH (55 mL) with heating at 60° C. and add SiliaMetS Triamine (1 g) and continue heating at 60° C. for 3.5 h. Filter the reaction while hot through a pad of Celite®, rinse the pad with hot MeOH (15 mL), and concentrate the filtrate. Dissolve the residue in MTBE (20 mL), filter, and concentrate. Purify the reside by silica gel chromatography using a gradient of 0 to 20% EtOAc in cyclohexane to give the title compound (0.75 g, 68%) as a colorless oil. ES/MS m/z 595, 597, 599(M+H).

Preparation 377

Ethyl 2-[4-bromo-2-[[5-chloro-2-[(6-chloro-2-pyridyl)oxymethyl]phenyl]methoxymethyl]-5-fluoro-phenyl]acetate

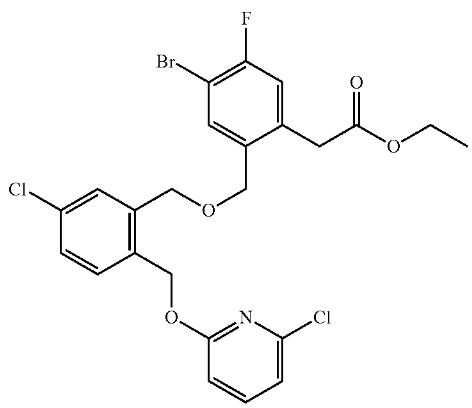 [SMILES: CCOC(=O)Cc1cc(F)c(Br)cc1COCc1cc(Cl)ccc1COc1cccc(Cl)n1]

Under $N_2$, add bromo-(2-ethoxy-2-oxo-ethyl)zinc (0.4 M in THF, 3.4 mL, 1.4 mmol) to a mixture of 2-[[2-[(5-bromo-4-fluoro-2-iodo-phenyl)methoxymethyl]-4-chloro-phenyl]methoxy]-6-chloro-pyridine (0.58 g, 0.91 mmol) and chloro[(4,5-bis(diphenylphosphino)-9,9-dimethylxanthene)-2-(2'-amino-1,1'-biphenyl)]palladium(II) (Pd-179, Xantphos Pd G2, 45 mg, 0.045 mmol) in THF (1 mL). Heat the reaction mixture to 60° C. for 10 h. Partition the reaction mixture between water (15 mL), aqueous citric acid (5%, 5 mL), and MTBE. Wash the organic phase with 5 mL portions of water, aqueous $K_2CO_3$ (2 M), and saturated aqueous NaCl. Concentrate the organics onto Celite® and purify by silica gel chromatography using a gradient of 5 to 40% EtOAc in cyclohexane to give the title compound (311 mg, 58%) as a colorless oil. $^1H$ NMR (400.13 MHz, $CDCl_3$) δ 7.56-7.52 (m, 2H), 7.46-7.44 (m, 2H), 7.32 (dd, J=2.2, 8.1 Hz, 1H), 7.07 (d, J=9.0 Hz, 1H), 6.94 (d, J=6.8 Hz, 1H), 6.66 (d, J=7.6 Hz, 1H), 5.36 (s, 2H), 4.66 (s, 2H), 4.57 (s, 2H), 4.11 (q, J=7.1 Hz, 2H), 3.68 (s, 2H), 1.22 (t, J=7.1 Hz, 3H).

Preparation 378

Ethyl 2-($5^4$-chloro-$1^6$-fluoro-3,7-dioxa-2(2,6)-pyridina-1(1,3),5(1,2)-dibenzenacyclooctaphane-$1^4$-yl)acetate

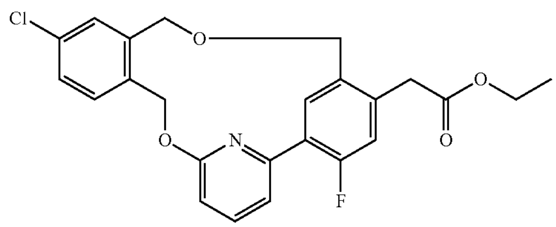 [SMILES: CCOC(=O)Cc1cc(F)c2cc1COCc1cc(Cl)ccc1COc1cccc-2n1]

Sparge $N_2$ for 10 min into a mixture of ethyl 2-[4-bromo-2-[[5-chloro-2-[(6-chloro-2-pyridyl)oxymethyl]phenyl]methoxymethyl]-5-fluoro-phenyl]acetate (0.59 g, 1.0 mmol), bis(neopentyl glycolato)diboron (0.28 g, 1.2 mmol) and potassium pivalate (0.36 g, 2.5 mmol) in anhydrous THE (40 mL), then add chloro(2-dicyclohexylphosphino-2',4',6'-tri-i-propyl-1,1'-biphenyl)(2'-amino-1,1'-biphenyl-2-yl) palladium(II) (X-Phos-Pd-G2, 42 mg, 0.052 mmol). Heat the reaction mixture at 45° C. for 1.5 h, then 55° C. for 1 h then add more bis(neopentyl glycolato)diboron (46 mg, 0.20 mmol) and continue heating at 55° C. for 45 min. Add potassium phosphate tribasic (1.0 M solution in water, 3 mL, 3.0 mmol) and continue heating at 55° C. for 2 h. Partition the reaction mixture between aqueous $K_2CO_3$ (2 M, 25 mL) and DCM (100 mL) and separate the layers. Extract the aqueous layer with DCM (25 mL), combine the organics and filter through Celite®. Concentrate the filtrate and purify the residue by silica gel chromatography using DCM. Triturate the product with a mixture of DCM (5 mL) and heptane (20 mL) and dry the solid under vacuum at 40° C. to give the title compound (144 mg, 32%) as a white solid. ES/MS m/z 442, 444 (M+H).

Preparation 379

2-($5^4$-Chloro-$1^6$-fluoro-3,7-dioxa-2(2,6)-pyridina-1(1,3),5(1,2)-dibenzenacyclooctaphane-$1^4$-yl)acetic acid

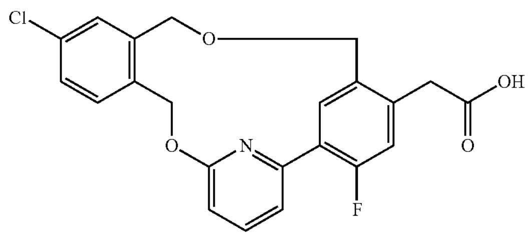 [SMILES: O=C(O)Cc1cc(F)c2cc1COCc1cc(Cl)ccc1COc1cccc-2n1]

Add LiOH (1M aqueous, 2.1 mL, 2.1 mmol) to a suspension of ethyl 2-($5^4$-chloro-$1^6$-fluoro-3,7-dioxa-2(2,6)-pyridina-1(1,3),5(1,2)-dibenzenacyclooctaphane-$1^4$-yl)acetate (227 mg, 0.51 mmol) in a mixture of THF (7 mL) and MeOH (3.4 mL). Heat the mixture at 60° C. for 1 h. Concentrate the reaction mixture and add aqueous citric acid (5%). Filter off the solid, wash it with water and dry it under vacuum at 40° C. to obtain the title compound (246 mg, 90 mass %, 100%) as a white solid. ES-MS m/z 414, 416 (M+H).

Preparation 380

Methyl (S)-2-(($5^4$-chloro-$1^6$-fluoro-3,7-dioxa-2(2,6)-pyridina-1(1,3),5(1,2)-dibenzenacyclooctaphane-$1^4$-yl)methyl)-4-(2-methoxyethoxy)-1-(oxetan-2-ylmethyl)-1H-benzo[d]imidazole-6-carboxylate

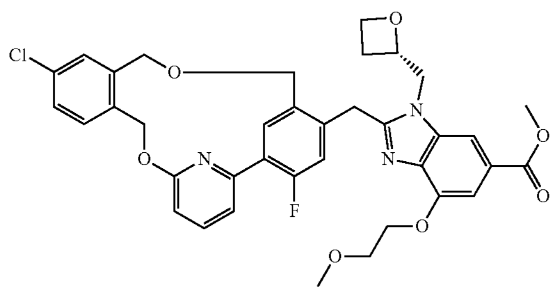 [SMILES: COCCOc1cc(C(=O)OC)cc2c1nc(Cc1cc(F)c3cc1COCc1cc(Cl)ccc1COc1cccc-3n1)n2C[C@@H]1CCO1]

To a solution of 2-($5^4$-chloro-$1^6$-fluoro-3,7-dioxa-2(2,6)-pyridina-1(1,3),5(1,2)-dibenzenacyclooctaphane-$1^4$-yl)acetic acid (246 mg, 0.535 mmol, 90 mass %) and methyl 4-amino-3-(2-methoxyethoxy)-5-[[(2S)-oxetan-2-yl]methylamino]benzoate (183 mg, 0.59 mmol) in anhydrous DMF (6 mL) under nitrogen atmosphere, add pyridine (492 µL, 6.08 mmol) and 2,4,6-tripropyl-1,3,5,2,4,6-trioxatriphosphorinane-2,4,6-trioxide (1.68 M in EtoAc, 800 µL, 1.34 mmol). Stir the mixture at RT for 30 min, then add water. Filter off the solid, wash with water, and dry at 40° C. overnight. Heat a suspension of the solid in 1,2-dichloroethane (6.4 mL) and acetic acid (6.4 mL) under $N_2$ atmosphere at 60° C. overnight. Cool the reaction mixture, dilute with EtOAc and water and filter off the solid. Separate the organic layer, dry over $Na_2SO_4$, filter and concentrate the organics under reduce pressure. Purify the residue via silica gel chromatography using a gradient of 0 to 50% EtOAc in DCM to provide the title compound (291 mg, 75%) as a white solid. ES-MS m/z 688, 690 (M+H).

Example 1

(S)-2-(($5^4$-Cyano-$1^6$-fluoro-3,9-dioxa-2(2,6)-pyridina-1(1,3),5(1,2)-dibenzenacyclononaphane-$1^4$-yl)methyl)-1-(oxetan-2-ylmethyl)-1H-benzo[d]imidazole-6-carboxylic acid

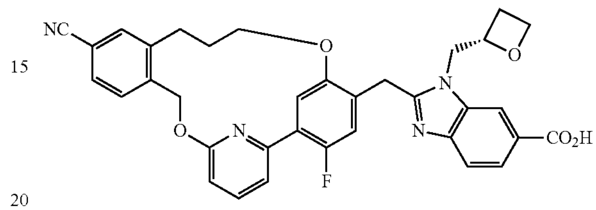

Stir a mixture of methyl (S)-2-(($5^4$-cyano-$1^6$-fluoro-3,9-dioxa-2(2,6)-pyridina-1(1,3),5(1,2)-dibenzenacyclononaphane-$1^4$-yl)methyl)-1-(oxetan-2-ylmethyl)-1H-benzo[d]imidazole-6-carboxylate, (200 mg, 0.257 mmol) and 1,5,7-triazabicyclo[4.4.0]dec-5-ene (300 mg, 2.11 mmol) in ACN:water (4.0 mL:1.0 mL) at 60° C. for 5 h. Adjust the mixture to pH 6 with 1.0 M aqueous hydrochloric acid solution. Purify the reaction mixture in its entirety via C18 reversed phase chromatography eluting with a gradient of 40 to 70% ACN in 0.225% aqueous formic acid to give 33 mg of the title compound (21%). ES-MS m/z 605 (M+H).

Example 2

(S)-2-(($5^4$-Cyano-$1^6$-fluoro-3,9-dioxa-2(2,6)-pyridina-1(1,3),5(1,2)-dibenzenacyclononaphane-$1^4$-yl)methyl)-4-fluoro-1-(oxetan-2-ylmethyl)-1H-benzo[d]imidazole-6-carboxylic acid

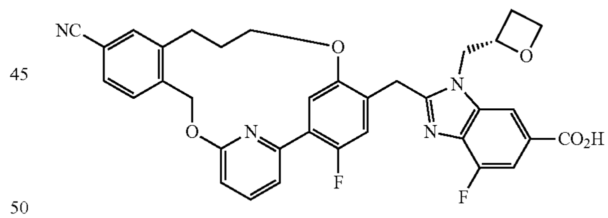

To a solution of methyl (S)-2-(($5^4$-cyano-$1^6$-fluoro-3,9-dioxa-2(2,6)-pyridina-1(1,3),5(1,2)-dibenzenacyclononaphane-$1^4$-yl)methyl)-4-fluoro-1-(oxetan-2-ylmethyl)-1H-benzo[d]imidazole-6-carboxylate (0.24 g, 0.38 mmol) in ACN:water (5.0 mL:1.0 mL) add 1,3,4,6,7,8-hexahydro-2 h-pyrimido[1,2-a]pyrimidine (50 mg, 0.40 mmol). Stir at RT for 15 h then at 60° C. for 4 h. Concentrate the reaction mixture to half volume and neutralize to pH 7 with 1 M aqueous citric acid solution. Dilute the mixture with water (100 mL) and extract with DCM (3×50 mL). Wash the combined organic layers with saturated aqueous sodium chloride (50 mL). Dry the organic phase over sodium sulfate, filter, and concentrate under reduced pressure. Purify the residue via silica gel chromatography using a gradient of 5 to 100% solvent B in solvent A, where solvent B is 20% MeOH in EtOAc and solvent B is DCM. Further purify the product via C18 reversed phase chromatography using a gradient of 25 to 40% ACN in 10 mM aqueous ammonium bicarbonate containing 5% MeOH to give 40 mg of the title compound (17%). ES-MS m/z 623 (M+H).

Example 3

(S)-2-(($5^4$-Chloro-3,9-dioxa-2(2,6)-pyridina-1(1,3),5(1,2)-dibenzenacyclononaphane-$1^4$-yl)methyl)-1-(oxetan-2-ylmethyl)-1H-benzo[d]imidazole-6-carboxylic acid

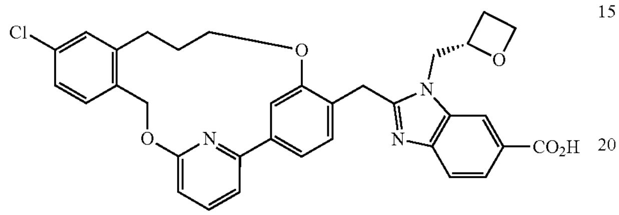

To a mixture of methyl (S)-2-(($5^4$-chloro-3,9-dioxa-2(2,6)-pyridina-1(1,3),5(1,2)-dibenzenacyclononaphane-$1^4$-yl)methyl)-1-(oxetan-2-ylmethyl)-1H-benzo[d]imidazole-6-carboxylate (45 mg, 0.074 mmol) in ACN:THF:MeOH (0.80 mL:0.50 mL:0.50 mL) add aqueous lithium hydroxide solution (1.0 M, 0.75 mL). Stir the mixture at 40° C. for 6 h and 55° C. for 30 min. Adsorb the mixture onto Celite® and purify via C18 reversed phase chromatography eluting with a gradient of 0 to 100% ACN in 10 mM aqueous ammonium bicarbonate with 5% MeOH to give 22 mg of the title compound (49%). ES-MS m/z 596 (M+H).

Example 4

(S)-2-(($5^4$-Cyano-3,9-dioxa-2(2,6)-pyridina-1(1,3),5(1,2)-dibenzenacyclononaphane-$1^4$-yl)methyl)-1-(oxetan-2-ylmethyl)-1H-benzo[d]imidazole-6-carboxylic acid

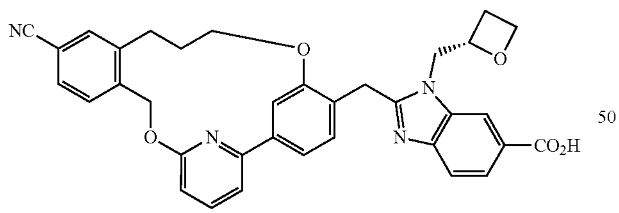

Stir a mixture of methyl (S)-2-(($5^4$-cyano-3,9-dioxa-2(2,6)-pyridina-1(1,3),5(1,2)-dibenzenacyclononaphane-$1^4$-yl)methyl)-1-(oxetan-2-ylmethyl)-1H-benzo[d]imidazole-6-carboxylate, (240 mg, 0.40 mmol) and 1,5,7-triazabicyclo[4.4.0]dec-5-ene (170 mg, 1.20 mmol) in 1,4-dioxane:ACN:water (5:5:1, 11 mL) at 60° C. for 3 h, 25° C. for 16 h, then 50° C. for 72 h. Concentrate the mixture to one-quarter volume and purify via C18 reversed phase chromatography eluting with a gradient for 10 to 80% ACN in 10 mM aqueous ammonium bicarbonate containing 5% MeOH to give 160 mg of the title compound (68%). ES-MS m/z 587 (M+H).

Example 5

(S)-2-(($5^4$-Cyano-3,9-dioxa-2(2,6)-pyridina-1(1,3),5(1,2)-dibenzenacyclononaphane-$1^4$-yl)methyl)-4-methoxy-1-(oxetan-2-ylmethyl)-1H-benzo[d]imidazole-6-carboxylic acid

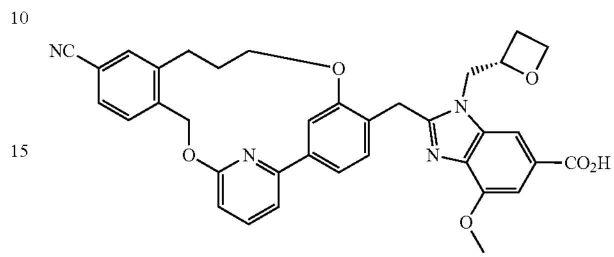

Stir a mixture of methyl (S)-2-(($5^4$-cyano-3,9-dioxa-2(2,6)-pyridina-1(1,3),5(1,2)-dibenzenacyclononaphane-$1^4$-yl)methyl)-4-methoxy-1-(oxetan-2-ylmethyl)-1H-benzo[d]imidazole-6-carboxylate, (230 mg, 0.28 mmol) and 1,5,7-triazabicyclo[4.4.0]dec-5-ene (170 mg, 1.20 mmol) in 1,4-dioxane:ACN:water (5:5:1, 11 mL) at 50° C. for 16 h, 65° C. for 4 h, then 50° C. for 72 h. Concentrate the mixture to one-quarter volume and purify via C18 reversed-phase chromatography eluting with a gradient of 10 to 80% ACN in 10 mM aqueous ammonium bicarbonate containing 5% MeOH to give the title compound (170 mg, 72%). ES-MS m/z 617 (M+H).

Example 6

(S)-2-(($5^4$-Cyano-3,9-dioxa-2(2,6)-pyridina-1(1,3),5(1,2)-dibenzenacyclononaphane-$1^4$-yl)methyl)-3-(oxetan-2-ylmethyl)-3H-imidazo[4,5-b]pyridine-5-carboxylic acid

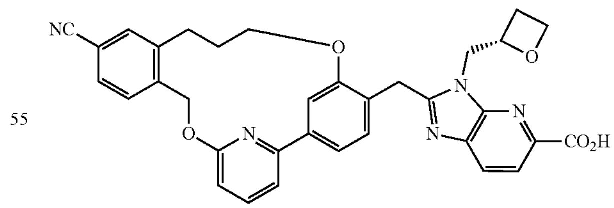

Prepare the title compound essentially as described in Example 5 using methyl (S)-2-(($5^4$-cyano-3,9-dioxa-2(2,6)-pyridina-1(1,3),5(1,2)-dibenzenacyclononaphane-$1^4$-yl)methyl)-3-(oxetan-2-ylmethyl)-3H-imidazo[4,5-b]pyridine-5-carboxylate. ES-MS m/z 588 (M+H).

Example 7

(S)-2-((5$^4$-cyano-3,9-dioxa-2(2,6)-pyridina-1(1,3),5(1,2)-dibenzenacyclononaphane-1$^4$-yl)methyl)-4-fluoro-1-(oxetan-2-ylmethyl)-1H-benzo[d]imidazole-6-carboxylic acid

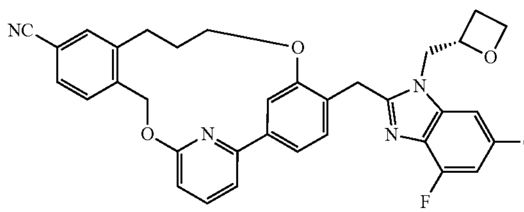

Prepare the title compound essentially as described in Example 5 using methyl (S)-2-((5$^4$-cyano-3,9-dioxa-2(2,6)-pyridina-1(1,3),5(1,2)-dibenzenacyclononaphane-1$^4$-yl)methyl)-4-fluoro-1-(oxetan-2-ylmethyl)-1H-benzo[d]imidazole-6-carboxylate. ES-MS m/z 605 (M+H).

Example 8

(S)-2-((5$^4$-Cyano-1$^6$-fluoro-9-oxa-3-aza-2(2,6)-pyridina-1(1,3),5(1,2)-dibenzenacyclononaphane-1$^4$-yl)methyl)-1-(oxetan-2-ylmethyl)-1H-benzo[d]imidazole-6-carboxylic acid

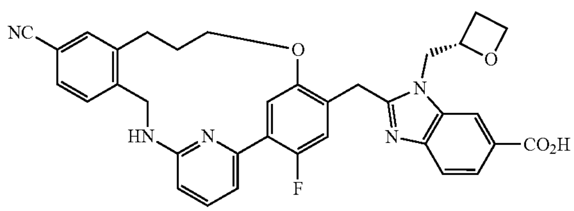 [SMILES: N#Cc1ccc2c(c1)CCCOc1cc(c(F)cc1Cc1nc3ccc(C(=O)O)cc3n1C[C@@H]1CCO1)-c1cccc(n1)NC2]

Prepare the title compound essentially as described in Example 5 using methyl (S)-2-((5$^4$-cyano-1$^6$-fluoro-9-oxa-3-aza-2(2,6)-pyridina-1(1,3),5(1,2)-dibenzenacyclononaphane-1$^4$-yl)methyl)-1-(oxetan-2-ylmethyl)-1H-benzo[d]imidazole-6-carboxylate in ACN:THF:water (1:1:0.4). Heat the mixture at 50° C. for 4 h, cool to RT and quench with 1M citric acid solution. Extract the mixture three times with EtOAc. Combine the organics, wash with water and brine, dry over magnesium sulfate, filter, and concentrate under reduced pressure. Purify the residue by C18 reverse phase chromatography using a gradient of 35 to 70% ACN in 20 mM aqueous ammonium bicarbonate to give the title compound as a white solid. ES-MS m/z 604 (M+H).

Example 9

(S)-2-((5$^4$-Cyano-16-methyl-3,9-dioxa-2(2,6)-pyridina-1(1,3),5(1,2)-dibenzenacyclononaphane-1$^4$-yl)methyl)-4-methoxy-1-(oxetan-2-ylmethyl)-1H-benzo[d]imidazole-6-carboxylic acid

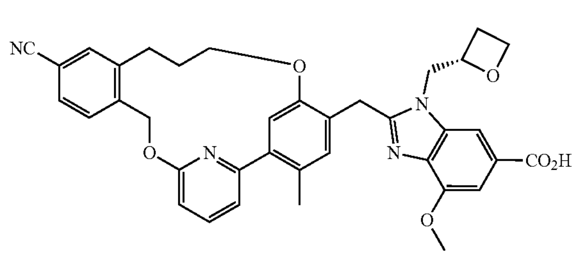 [SMILES: COc1cc(C(=O)O)cc2c1nc(Cc1cc(C)c3cc1OCCCc1cc(C#N)ccc1COc1cccc-3n1)n2C[C@@H]1CCO1]

Prepare the title compound essentially as described in Example 5 using methyl (S)-2-((5$^4$-cyano-1$^6$-methyl-3,9-dioxa-2(2,6)-pyridina-1(1,3),5(1,2)-dibenzenacyclononaphane-1$^4$-yl)methyl)-4-methoxy-1-(oxetan-2-ylmethyl)-1H-benzo[d]imidazole-6-carboxylate. ES-MS m/z 631 (M+H).

Example 10

(S)-2-((5$^4$-Cyano-1$^6$-fluoro-3,9-dioxa-2(2,6)-pyridina-1,5(1,3)-dibenzenacyclononaphane-1$^4$-yl)methyl)-1-(oxetan-2-ylmethyl)-1H-benzo[d]imidazole-6-carboxylic acid

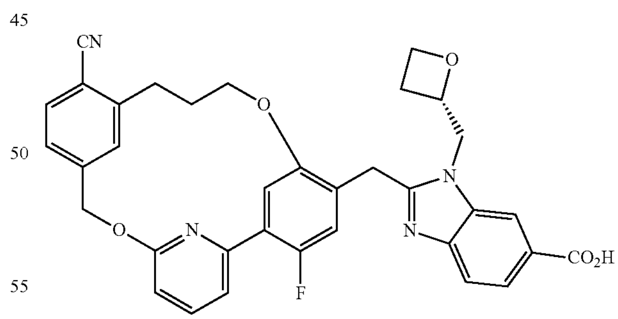

Prepare the title compound essentially as described in Example 5 using methyl (S)-2-((5$^4$-cyano-1$^6$-fluoro-3,9-dioxa-2(2,6)-pyridina-1,5(1,3)-dibenzenacyclononaphane-1$^4$-yl)methyl)-1-(oxetan-2-ylmethyl)-1H-benzo[d]imidazole-6-carboxylate. Heat the mixture at 60° C. under nitrogen atmosphere for 2 h, then cool to RT and quench with citric acid (5% aqueous). Filter the solid, then wash with water and ACN to give the title compound as a white solid. ES-MS m/z 605 (M+H).

Example 11

2-((5$^4$-cyano-3,9-dioxa-2(2,6)-pyridina-1(1,3),5(1,2)-dibenzenacyclononaphane-1$^4$-yl)methyl)-1-((1-ethyl-1H-imidazol-5-yl)methyl)-1H-benzo[d]imidazole-6-carboxylic acid

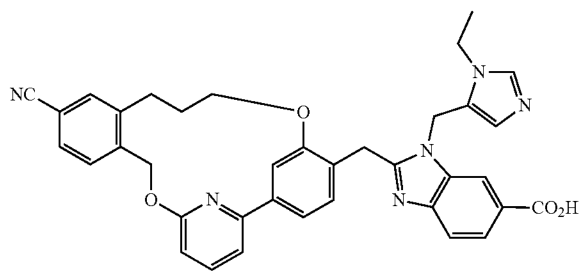 [SMILES: CCn1cncc1Cn1c(Cc2ccc3cc2OCCCc2cc(C#N)ccc2COc2cccc-3n2)nc2ccc(C(=O)O)cc21]

To a solution of methyl 2-((5$^4$-cyano-3,9-dioxa-2(2,6)-pyridina-1(1,3),5(1,2)-dibenzenacyclononaphane-1$^4$-yl)methyl)-1-((1-ethyl-1H-imidazol-5-yl)methyl)-1H-benzo[d]imidazole-6-carboxylate (39.7 mg, 0.06 mmol) in ACN (0.75 mL), THF (0.19 mL), and water (0.12 mL) add 1,3,4,6,7,8-hexahydro-2 h-pyrimido[1,2-a]pyrimidine (35 mg, 0.25 mmol). Stir the mixture at 45° C. for 3 h. Add additional 1,3,4,6,7,8-hexahydro-2 h-pyrimido[1,2-a]pyrimidine (7.5 mg, 0.05 mmol) and stir the reaction at 50° C. for 1 h. Quench the reaction to pH 6-7 with formic acid and extract with EtOAc. Dilute with water and extract with EtOAc. Dry the organic phase over magnesium sulfate, filter, and concentrate under reduced pressure. Purify the residue by C18 reversed phase chromatography using a gradient of 28 to 64% (1:1 ACN:MeOH) in (65 mM aqueous ammonium acetate:ACN 90:10 solution) to give 11.8 mg of the title compound (30%). ES-MS m/z 625 (M+H).

Example 12

(S)-1$^4$-((4-Methoxy-1-(oxetan-2-ylmethyl)-6-(1H-tetrazol-5-yl)-1H-benzo[d]imidazol-2-yl)methyl)-3,9-dioxa-2(2,6)-pyridina-1(1,3),5(1,2)-dibenzenacyclononaphane-5$^4$-carbonitrile

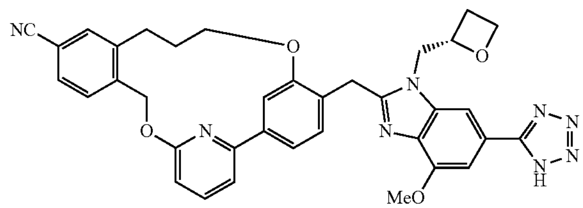 [SMILES: COc1cc(-c2nnn[nH]2)cc2c1nc(Cc1ccc3cc1OCCCc1cc(C#N)ccc1COc1cccc-3n1)n2C[C@@H]1CCO1]

Stir (S)-2-(5$^4$-cyano-3,9-dioxa-2(2,6)-pyridina-1(1,3),5(1,2)-dibenzenacyclononaphane-1$^4$-yl)-N-(2-methoxy-6-((oxetan-2-ylmethyl)amino)-4-(1H-tetrazol-5-yl)phenyl)acetamide (56 mg, 0.05 mmol) in acetic acid (1.0 mL) at 65° C. for 12 h. Concentrate the solution and azeotrope with ACN. Purify the residue by C18 reversed phase chromatography using a gradient of 41 to 83% 1:1 ACN:MeOH in 25 mM aqueous ammonium carbonate solution to give 9.4 mg of the title compound (28%). ES-MS m/z 641 (M+H).

Example 13

(S)-2-((5$^4$-Cyano-1$^6$-fluoro-3,6,9-trioxa-2(2,6)-pyridina-1(1,3),5(1,2)-dibenzenacyclononaphane-1$^4$-yl)methyl)-1-(oxetan-2-ylmethyl)-1H-benzo[d]imidazole-6-carboxylic acid

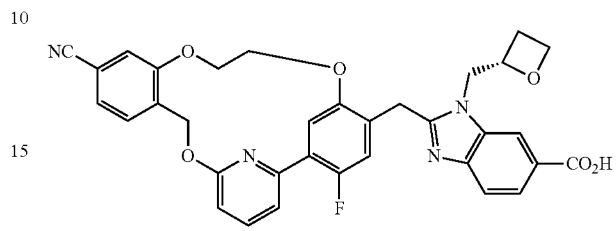

Prepare the title compound essentially as described in Example 1 using methyl (S)-2-((5$^4$-cyano-1$^6$-fluoro-3,6,9-trioxa-2(2,6)-pyridina-1(1,3),5(1,2)-dibenzenacyclononaphane-1$^4$-yl)methyl)-1-(oxetan-2-ylmethyl)-1H-benzo[d]imidazole-6-carboxylate, stirring the reaction at 45° C. for 2 h. When complete, quench the reaction with formic acid to pH 7 and dilute the crude mixture with water. Extract the mixture three times with EtOAc. Dry the organic phase over magnesium sulfate, filter, and concentrate under reduced pressure. Purify the residue via silica gel flash chromatography using a gradient of 0 to 40% 9:1 DCM:MeOH containing 1% formic acid in DCM to give the title compound. ES-MS m/z 607 (M+H).

Example 14

(S)-2-((5$^4$-Cyano-1$^6$-fluoro-3,7-dioxa-2(2,6)-pyridina-1(1,3),5(1,2)-dibenzenacyclooctaphane-1$^4$-yl)methyl)-1-(oxetan-2-ylmethyl)-1H-benzo[d]imidazole-6-carboxylic acid

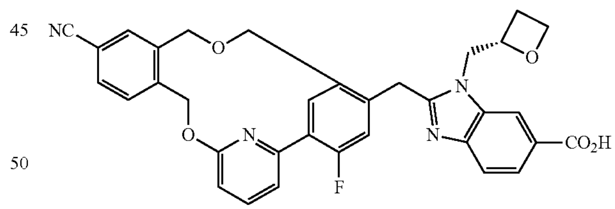

Prepare the title compound essentially as described for Example 2 using methyl (S)-2-((5$^4$-cyano-1$^6$-fluoro-3,7-dioxa-2(2,6)-pyridina-1(1,3),5(1,2)-dibenzenacyclooctaphane-1$^4$-yl)methyl)-1-(oxetan-2-ylmethyl)-1H-benzo[d]imidazole-6-carboxylate, stirring the reaction at 45° C. for 19 h, then add 1,4-dioxane and stir at 45° C. for 23 h. Quench the reaction to pH 6-7 with formic acid and extract with EtOAc, followed by 3:1 chloroform:2-propanol. Dry the organic phase over magnesium sulfate, filter, and concentrate under reduced pressure. Purify the residue by C18 reversed phase chromatography using a gradient of 30 to 73% 1:1 ACN:MeOH in 25 mM aqueous ammonium carbonate solution to give the title compound. ES-MS m/z 591 (M+H).

Example 15

(S)-2-(($5^4$-Cyano-$1^6$-methyl-3,9-dioxa-1,2(1,3),5(1,2)-tribenzenacyclononaphane-$1^4$-yl)methyl)-4-methoxy-1-(oxetan-2-ylmethyl)-1H-benzo[d]imidazole-6-carboxylic acid

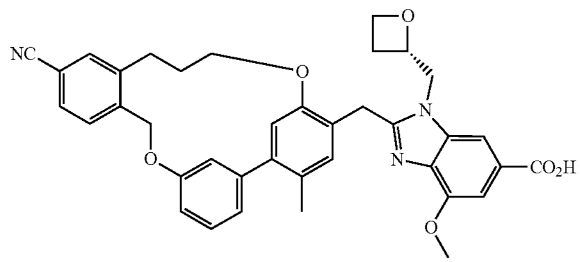 [SMILES: COc1cc(C(=O)O)cc2c1nc(Cc1cc(C)c3cc1OCCCc1cc(C#N)ccc1COc1cccc-3c1)n2C[C@@H]1CCO1]

Prepare the title compound essentially as described in Example 4 using methyl (S)-2-(($5^4$-cyano-$1^6$-methyl-3,9-dioxa-1,2(1,3),5(1,2)-tribenzenacyclononaphane-$1^4$-yl)methyl)-4-methoxy-1-(oxetan-2-ylmethyl)-1H-benzo[d]imidazole-6-carboxylate. Upon completion, concentrate the reaction mixture to one quarter volume, neutralize with citric acid solution and purify via C18 reversed phase chromatography eluting with a gradient for 10 to 80% ACN in 10 mM aqueous ammonium bicarbonate containing 5% MeOH to give the title compound. ES-MS m/z 630 (M+H).

Example 16

(S)-4-Methoxy-2-(($1^6$-methyl-$5^4$-(trifluoromethyl)-3,9-dioxa-2(2,6)-pyridina-1(1,3),5(1,2)-dibenzenacyclononaphane-$1^4$-yl)methyl)-1-(oxetan-2-ylmethyl)-1H-benzo[d]imidazole-6-carboxylic acid

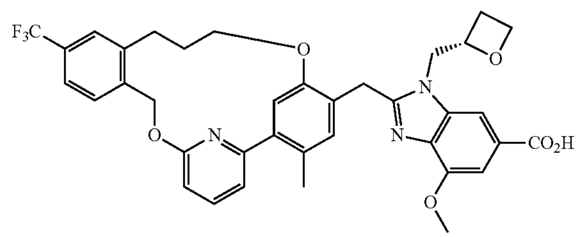 [SMILES: COc1cc(C(=O)O)cc2c1nc(Cc1cc(C)c3cc1OCCCc1cc(C(F)(F)F)ccc1COc1cccc-3n1)n2C[C@@H]1CCO1]

Prepare the title compound essentially as described in Example 1 using methyl (S)-4-methoxy-2-(($1^6$-methyl-$5^4$-(trifluoromethyl)-3,9-dioxa-2(2,6)-pyridina-1(1,3),5(1,2)-dibenzenacyclononaphane-$1^4$-yl)methyl)-1-(oxetan-2-ylmethyl)-1H-benzo[d]imidazole-6-carboxylate, using dioxane:ACN:water (6:6:1) as solvent, and stirring the reaction at 50° C. for 2 h. When complete, neutralize with citric acid and concentrate the reaction mixture. Dilute the residue with EtOAc and wash with water and saturated aqueous NaCl. Dry the organic phase over sodium sulfate, filter, and concentrate. Purify the residue via silica gel chromatography using a gradient of 10 to 80% (20% MeOH in EtOAc) in DCM to give the title compound. ES-MS m/z 674 (M+H).

Example 17

(S)-2-(($5^4$-cyano-$1^6$-fluoro-3,7-dioxa-2(2,6)-pyridina-1(1,3),5(1,2)-dibenzenacyclooctaphane-$1^4$-yl)methyl)-4-methoxy-1-(oxetan-2-ylmethyl)-1H-benzo[d]imidazole-6-carboxylic acid

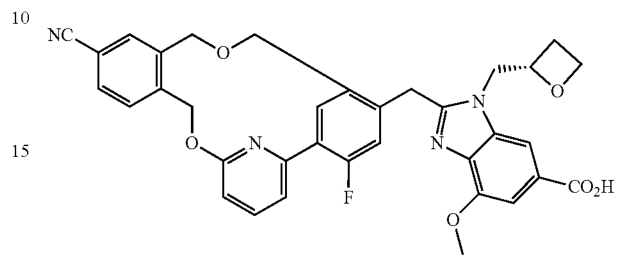

Prepare the title compound essentially as described in Example 2 using methyl (S)-2-(($5^4$-cyano-$1^6$-fluoro-3,7-dioxa-2(2,6)-pyridina-1(1,3),5(1,2)-dibenzenacyclooctaphane-$1^4$-yl)methyl)-4-methoxy-1-(oxetan-2-ylmethyl)-1H-benzo[d]imidazole-6-carboxylate. Stir the reaction at 45° C. for 4 h. Cool the mixture to RT, filter, and evaporate the filtrate. Purify the residue by reversed phase chromatography using a gradient of 30 to 73% solvent B in solvent A (solvent A=[65 mM NH4OAc+ACN (90:10)]; solvent B=ACN]) to give the title compound as a white solid. ES-MS m/z 621 (M+H).

Example 18

(S)-2-(($5^4$-Bromo-3,9-dioxa-2(2,6)-pyridina-1(1,3),5(1,2)-dibenzenacyclononaphane-$1^4$-yl)methyl)-1-(oxetan-2-ylmethyl)-1H-benzo[d]imidazole-6-carboxylic acid

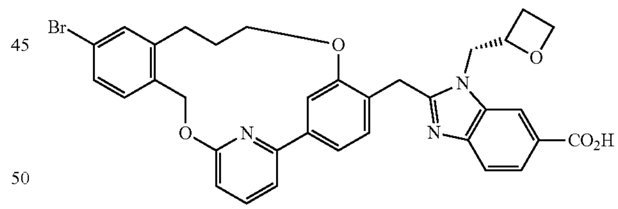

Prepare the title compound essentially as described in Example 3 using methyl (S)-2-(($5^4$-bromo-3,9-dioxa-2(2,6)-pyridina-1(1,3),5(1,2)-dibenzenacyclononaphane-$1^4$-yl)methyl)-1-(oxetan-2-ylmethyl)-1H-benzo[d]imidazole-6-carboxylate and using 2:1 THF:MeOH as solvent. Stir at 65° C. for 1.5 h and add 1 M aqueous $KH_2PO_4$. Dilute the reaction 2.5-fold with water and leave to cool with stirring for 45 min. Collect the solid by filtration and wash with 1:3 MeOH:water followed by water. Dry the filter cake under reduced pressure at 50° C. for 20 h to afford the title compound as a white solid. ES-MS m/z 640 and 642 (M+H).

Example 19

(S)-2-(($5^4$-Cyano-3,8-dioxa-2(2,6)-pyridina-1(1,3),5(1,2)-dibenzenacyclononaphane-$1^4$-yl)methyl)-1-(oxetan-2-ylmethyl)-1H-benzo[d]imidazole-6-carboxylic acid

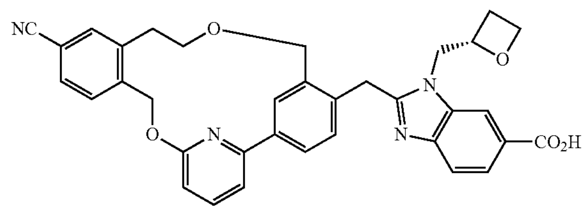 [SMILES: N#Cc1ccc2c(c1)CCOCc1cc(ccc1Cc1nc3ccc(C(=O)O)cc3n1C[C@@H]1CCO1)-c1cccc(n1)OC2]

Prepare the title compound essentially as described in Example 1 using methyl (S)-2-(($5^4$-cyano-3,8-dioxa-2(2,6)-pyridina-1(1,3),5(1,2)-dibenzenacyclononaphane-$1^4$-yl)methyl)-1-(oxetan-2-ylmethyl)-1H-benzo[d]imidazole-6-carboxylate in 3:1:1 ACN:THF:water. Heat the mixture at 55° C. for 3 h, cool to RT and quench with 5% aqueous citric acid up to pH=4-5 to precipitate a white solid. Filter the solid, wash with water (3 times) and ACN, and dry under vacuum at 45° C. overnight to give the title compound as a white solid. ES-MS m/z 587 (M+H).

Example 20

(S)-2-(($5^4$-Cyano-$1^6$-fluoro-3,8-dioxa-2(2,6)-pyridina-1(1,3),5(1,2)-dibenzenacyclooctaphane-$1^4$-yl)methyl)-1-(oxetan-2-ylmethyl)-1H-benzo[d]imidazole-6-carboxylic acid

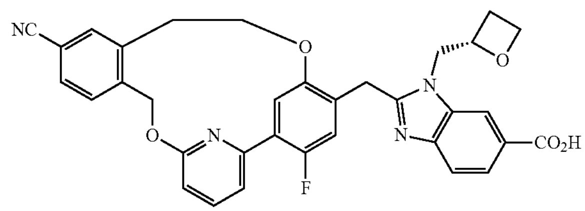 [SMILES: N#Cc1ccc2c(c1)CCOc1cc(c(F)cc1Cc1nc3ccc(C(=O)O)cc3n1C[C@@H]1CCO1)-c1cccc(n1)OC2]

Prepare the title compound essentially as described in Example 1 using methyl (S)-2-(($5^4$-cyano-$1^6$-fluoro-3,8-dioxa-2(2,6)-pyridina-1(1,3),5(1,2)-dibenzenacyclooctaphane-$1^4$-yl)methyl)-1-(oxetan-2-ylmethyl)-1H-benzo[d]imidazole-6-carboxylate in 3:1:1 ACN:1,4-dioxane:water as solvent. Heat the reaction to 60° C. for 3 h, then cool to RT and quench with a solution of citric acid (5% in water). Dilute with EtOAc, separate the phases and extract the aqueous phase twice with EtOAc. Combine the organic phases, wash with water and saturated aqueous NaCl, dry over $Na_2SO_4$, filter and concentrate under reduced pressure. Purify the residue by SFC [column: Chiralpak 20×250 mm, 5 μm; isocratic mobile phase: 35% $CO_2$ in (MeOH+0.5% dimethylethylamine) at 100 bar, flow rate 65 mL/min] to give the title compound as a white solid. ES-MS m/z 591 (M+H).

Example 21

(S)-2-(($5^4$-Cyano-3,8-dioxa-2(2,6)-pyridina-1,5(1,3)-dibenzenacyclononaphane-$1^4$-yl)methyl)-1-(oxetan-2-ylmethyl)-1H-benzo[d]imidazole-6-carboxylic acid

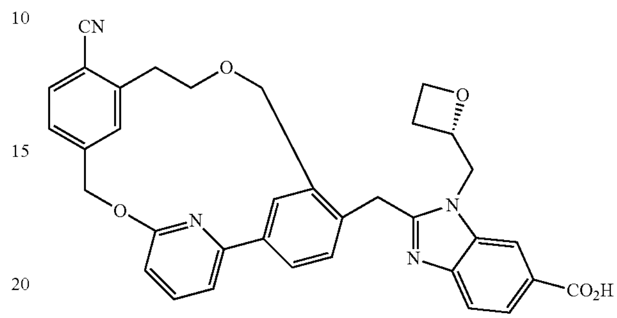

Prepare the title compound essentially as described in Example 1 using methyl (S)-2-(($5^4$-cyano-3,8-dioxa-2(2,6)-pyridina-1,5(1,3)-dibenzenacyclononaphane-$1^4$-yl)methyl)-1-(oxetan-2-ylmethyl)-1H-benzo[d]imidazole-6-carboxylate (90 mg, 0.14 mmol) in 3:1:1 ACN:1,4-dioxane:water as solvent. Heat the reaction to 60° C. for 1 h, cool to RT and quench with aqueous citric acid (5%). Filter the solid and wash with water and then ACN to provide the title compound as a white solid. ES-MS m/z 587 (M+H).

Example 22

(S)-4-Methoxy-2-(($1^6$-methyl-$5^4$-(fluoro)-3,9-dioxa-2(2,6)-pyridina-1(1,3),5(1,2)-dibenzenacyclononaphane-$1^4$-yl)methyl)-1-(oxetan-2-ylmethyl)-1H-benzo[d]imidazole-6-carboxylic acid

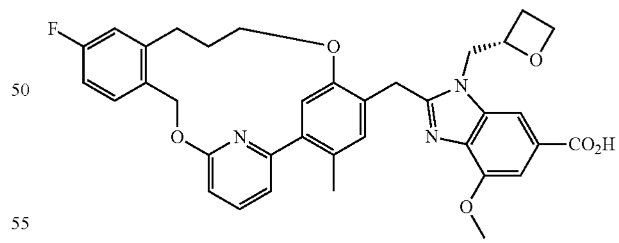

Prepare the title compound essentially as described in Example 4 using methyl (S)-4-methoxy-2-(($1^6$-methyl-$5^4$-(fluoro)-3,9-dioxa-2(2,6)-pyridina-1(1,3),5(1,2)-dibenzenacyclononaphane-$1^4$-yl)methyl)-1-(oxetan-2-ylmethyl)-1H-benzo[d]imidazole-6-carboxylate, stirring the reaction at 50° C. for 2 h. Concentrate the reaction, neutralize with aqueous citric acid and purify via C18 reversed phase chromatography using a gradient of 10 to 80% ACN in 10 mM aqueous $NH_4HCO_3$ containing 5% MeOH. ES-MS m/z 624 (M+H).

Example 23

2-((5$^4$-Cyano-3,9-dioxa-2(2,6)-pyridina-1(1,3),5(1,2)-dibenzenacyclononaphane-1$^4$-yl)methyl)-4-methoxy-1-(oxazol-2-ylmethyl)-1H-benzo[d]imidazole-6-carboxylic acid

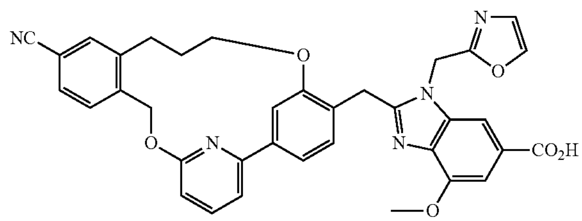 [SMILES: COc1cc(C(=O)O)cc2c1nc(Cc1ccc3cc1OCCCc1cc(C#N)ccc1COc1cccc-3n1)n2Cc1ncco1]

Prepare the title compound essentially as described in Example 1 using ethyl 2-((5$^4$-cyano-3,9-dioxa-2(2,6)-pyridina-1(1,3),5(1,2)-dibenzenacyclononaphane-1$^4$-yl)methyl)-4-methoxy-1-(oxazol-2-ylmethyl)-1H-benzo[d]imidazole-6-carboxylate, stirring the reaction at 65° C. for 72 h. Concentrate the mixture to one-quarter volume and adjust to pH=5 using formic acid. Collect the resulting precipitate and purify via C18 reversed phase chromatography eluting with a gradient for 10 to 80% ACN in 10 mM aqueous $NH_4HCO_3$ containing 5% MeOH to give the title compound as a colorless solid. ES-MS m/z 628 (M+H).

Example 24

(S)-2-((5$^4$-Cyano-3,9-dioxa-2(2,6)-pyridina-1(1,3),5(1,2)-dibenzenacyclononaphane-1$^4$-yl)methyl)-4-(2-methoxyethoxy)-1-(oxetan-2-ylmethyl)-1H-benzo[d]imidazole-6-carboxylic acid

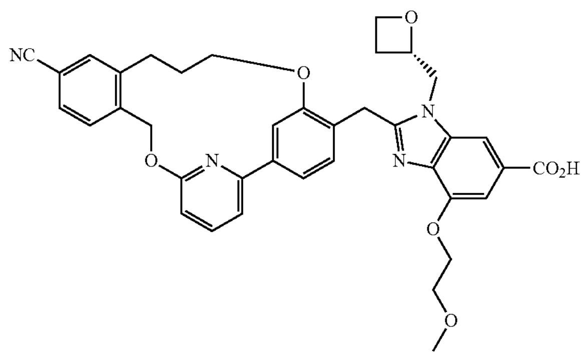 [SMILES: COCCOc1cc(C(=O)O)cc2c1nc(Cc1ccc3cc1OCCCc1cc(C#N)ccc1COc1cccc-3n1)n2C[C@@H]1CCO1]

Prepare the title compound essentially as described in Example 1 using methyl (S)-2-((5$^4$-cyano-3,9-dioxa-2(2,6)-pyridina-1(1,3),5(1,2)-dibenzenacyclononaphane-1$^4$-yl)methyl)-4-(2-methoxyethoxy)-1-(oxetan-2-ylmethyl)-1H-benzo[d]imidazole-6-carboxylate using 5:5:1 1,4-dioxane:ACN:water as solvent and stirring the reaction at 45° C. for 16 h. Concentrate the mixture to one-quarter volume and adjust to pH=5 using formic acid. Dilute the mixture with water and extract the organics with chloroform/isopropanol (3:1). Dry the organics over $MgSO_4$, filterer and concentrate. Purify the title compound via flash chromatography eluting with a gradient of 0 to 40% (10% formic acid in MeOH) in DCM. ES-MS m/z 661 (M+H).

Example 25

(S)-2-((5$^4$-(Hydroxymethyl)-3,9-dioxa-2(2,6)-pyridina-1(1,3),5(1,2)-dibenzenacyclononaphane-1$^4$-yl)methyl)-1-(oxetan-2-ylmethyl)-1H-benzo[d]imidazole-6-carboxylic acid

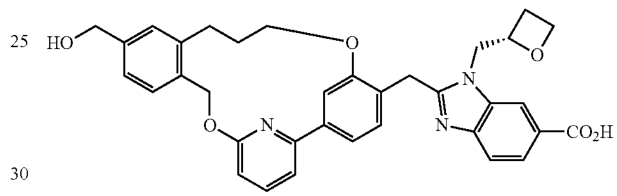

Add sodium borohydride (5.3 mg, 0.14 mmol) to a slurry of (S)-2-((5$^4$-formyl-3,9-dioxa-2(2,6)-pyridina-1(1,3),5(1,2)-dibenzenacyclononaphane-1$^4$-yl)methyl)-1-(oxetan-2-ylmethyl)-1H-benzo[d]imidazole-6-carboxylic acid (30 mg, 0.051 mmol) in a mixture of MeOH (460 μL) and THE (1 mL) at 0° C. Stir mixture for 5 min and then warm up to RT. Stir reaction for 20 min and then remove volatiles with a nitrogen stream at RT. Add aqueous citric acid (5%), stir for 5 min, filter the solid and wash with water and MeOH. Purify the solid via silica gel chromatography using 10% of MeOH in DCM to provide the title compound (8 mg, 25%) as a white solid. ES-MS m/z 592 (M+H).

Example 26

(S)-4-Methoxy-2-((1$^6$-methyl-5$^6$-(trifluoromethyl)-3,9-dioxa-2(2,6),5(3,2)-dipyridina-1(1,3)-benzenacyclononaphane-1$^4$-yl)methyl)-1-(oxetan-2-ylmethyl)-1H-benzo[d]imidazole-6-carboxylic acid; 1,3,4,6,7,8-hexahydro-2H-pyrimido[1,2-a]pyrimidine

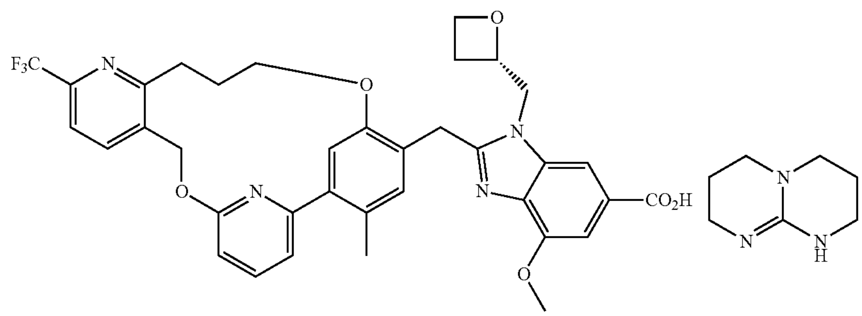 [SMILES: COc1cc(C(=O)O)cc2c1nc(Cc1cc(C)c3cc1OCCCc1nc(C(F)(F)F)ccc1COc1cccc-3n1)n2C[C@@H]1CCO1 ; C1CN=C2NCCCN2C1]

Prepare the title compound essentially as described in Example 4 using methyl (S)-4-methoxy-2-((1$^6$-methyl-5$^6$-(trifluoromethyl)-3,9-dioxa-2(2,6),5(3,2)-dipyridina-1(1,3)-benzenacyclononaphane-1$^4$-yl)methyl)-1-(oxetan-2-ylmethyl)-1H-benzo[d]imidazole-6-carboxylate, stirring the reaction at 45° C. for 16 h. Neutralize the reaction with aqueous citric acid, concentrate the mixture, and purify via C18 reversed phase chromatography using a gradient of 10 to 80% ACN in 10 mM aqueous $NH_4HCO_3$ containing 5% MeOH. ES-MS m/z 675 (M+H).

Example 27

(S)-4-Methoxy-2-((1$^6$-methyl-3,9-dioxa-2(2,6),5(4,3)-dipyridina-1(1,3)-benzenacyclononaphane-1$^4$-yl)methyl)-1-(oxetan-2-ylmethyl)-1H-benzo[d]imidazole-6-carboxylic acid

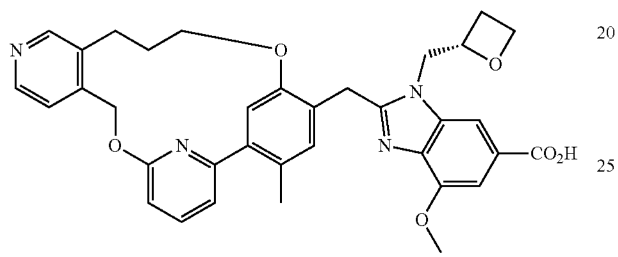

Prepare the title compound essentially as described in Example 4, using methyl (S)-4-methoxy-2-((1$^6$-methyl-3,9-dioxa-2(2,6),5(4,3)-dipyridina-1(1,3)-benzenacyclononaphane-1$^4$-yl)methyl)-1-(oxetan-2-ylmethyl)-1H-benzo[d]imidazole-6-carboxylate, stirring the reaction at 50° C. for 2 h. Concentrate the reaction, neutralize with aqueous citric acid and purify via C18 reversed phase chromatography using a gradient of 10 to 80% ACN in 10 mM aqueous $NH_4HCO_3$ containing 5% MeOH. Redissolve the purified product in DCM and neutralize with aqueous citric acid. Wash the organics with water and saturated aqueous NaCl. Dry over $Na_2SO_4$, filter and concentrate to give the title compound. ES-MS m/z 607 (M+H).

Example 28

(S)-1-(Oxetan-2-ylmethyl)-2-((5$^4$-(1-(oxetan-3-ylmethyl)-1H-pyrazol-4-yl)-3,9-dioxa-2(2,6)-pyridina-1(1,3),5(1,2)-dibenzenacyclononaphane-1$^4$-yl)methyl)-1H-benzo[d]imidazole-6-carboxylic acid

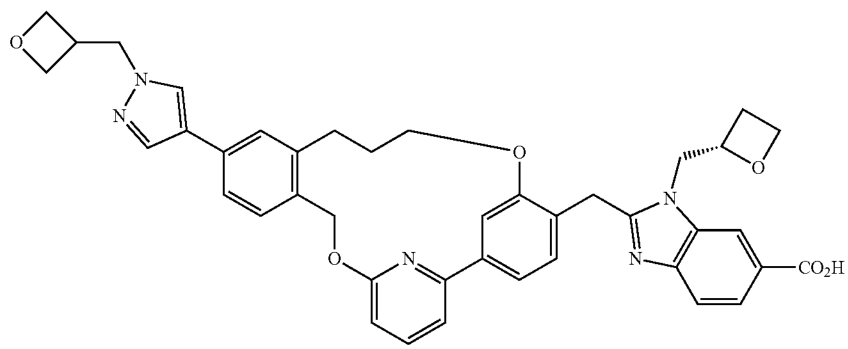 [SMILES: O=C(O)c1ccc2nc(Cc3ccc4cc3OCCCc3cc(-c5cnn(CC6COC6)c5)ccc3COc3cccc-4n3)n(C[C@@H]3CCO3)c2c1]

Add DMF (0.43 mL) and tripotassium phosphate (1 M aqueous solution, 0.13 mL, 0.13 mmol) to a vessel containing (S)-2-((5$^4$-bromo-3,9-dioxa-2(2,6)-pyridina-1(1,3),5(1,2)-dibenzenacyclononaphane-1$^4$-yl)methyl)-1-(oxetan-2-ylmethyl)-1H-benzo[d]imidazole-6-carboxylic acid (30 mg, 0.0436 mmol), 1-(oxetan-3-ylmethyl)-4-(tetramethyl-1,3,2-dioxaborolan-2-yl)-1H-pyrazole (19 mg, 0.0698 mmol) and 1,1'-bis(di-tert-butylphosphino)ferrocene palladium dichloride (1.4 mg, 0.0021 mmol). Purge the vessel with nitrogen, seal the vessel, and stir the mixture at 60° C. for 2 h. Cool to ambient temperature, and then purify the mixture directly via C18 reversed phase chromatography using ACN/10 mM aqueous $NH_4HCO_3$ as eluent.

Combine with material from a second analogous reaction, suspend the resulting solid 1:1 DCM:EtOAc, and partially concentrate under reduced pressure to remove DCM. Stir the suspension for 10 min at ambient temperature, then collect the solid by filtration and wash with EtOAc. Dry under reduced pressure at 50° C. for 16 h to afford 28 mg of the title compound (average 41% for each of two reactions) as a white solid. ES-MS m/z 698.

Example 29

(S)-2-((5[4]-(6-Methoxypyridin-3-yl)-3,9-dioxa-2(2,6)-pyridina-1(1,3),5(1,2)-dibenzenacyclononaphane-1[4]-yl)methyl)-1-(oxetan-2-ylmethyl)-1H-benzo[d]imidazole-6-carboxylic acid

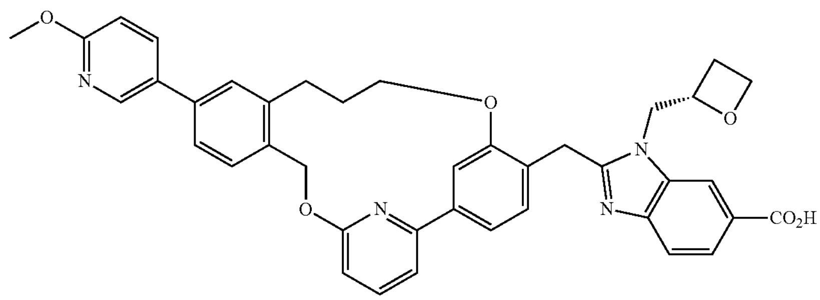 [SMILES: COc1ccc(-c2ccc3c(c2)CCCOc2cc(ccc2Cc2nc4ccc(C(=O)O)cc4n2C[C@@H]2CCO2)-c2cccc(n2)OC3)cn1]

Add (S)-2-((5[4]-bromo-3,9-dioxa-2(2,6)-pyridina-1(1,3),5(1,2)-dibenzenacyclononaphane-1[4]-yl)methyl)-1-(oxetan-2-ylmethyl)-1H-benzo[d]imidazole-6-carboxylic acid (30 mg, 0.0436 mmol), 2-methoxy-5-(4,4,5,5-tetramethyl-1,3,2-dioxaborolan-2-yl)pyridine (22 mg, 0.094 mmol) and 1,1'-bis(di-tert-butylphosphino)ferrocene palladium dichloride (3 mg, 0.0045 mmol) into a glass tube with stir bar. Purge the tube with nitrogen and add tripotassium phosphate (1 M aqueous solution, 0.13 mL, 0.13 mmol) and DMF (0.5 mL). Stir the mixture at 60° C. for 16 h. Add further 1,1'-bis(di-tert-butylphosphino)ferrocene palladium dichloride (3 mg, 0.0045 mmol) to the reaction and heat for 3 h at 60° C., then for 16 h at 90° C. Cool the mixture to ambient temperature, and then purify the reaction mixture directly using C18 reversed phase chromatography using ACN/10 mM aqueous $NH_4HCO_3$ as eluent to give the title compound (4.7 mg, 140%) as a solid. ES-MS m/z 669.

The following examples are prepared essentially as described in Example 29 using the appropriate boronic acid or boronate ester.

| Example | Name | Structure | Characterization |
| --- | --- | --- | --- |
| 30 | (S)-2-((5[4]-(1H-Pyrazol-4-yl)-3,9-dioxa-2(2,6)-pyridina-1(1,3),5(1,2)-dibenzenacyclononaphane-1[4]-yl)methyl)-1-(oxetan-2-ylmethyl)-1H-benzo[d]imidazole-6-carboxylic acid | 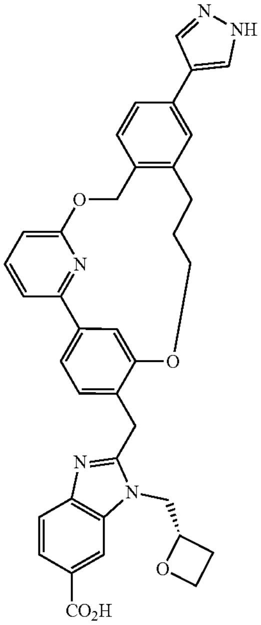 [SMILES: O=C(O)c1ccc2nc(Cc3ccc4cc3OCCCc3cc(-c5cn[nH]c5)ccc3COc3cccc-4n3)n(C[C@@H]3CCO3)c2c1] | ES-MS m/z 628 |

-continued
| Example | Name | Structure | Characterization |
|---|---|---|---|
| 31 | (S)-2-((5$^4$-(1-Methyl-1H-pyrazol-5-yl)-3,9-dioxa-2(2,6)-pyridina-1(1,3),5(1,2)-dibenzenacyclononaphane-1$^4$-yl)methyl)-1-(oxetan-2-ylmethyl)-1H-benzo[d]imidazole-6-carboxylic acid | 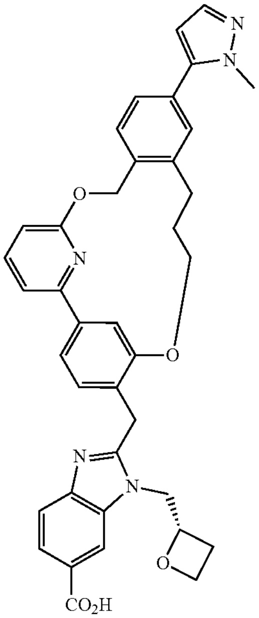 [SMILES: Cn1nccc1-c1ccc2c(c1)CCCOc1cc(ccc1Cc1nc3ccc(C(=O)O)cc3n1C[C@@H]1CCO1)-c1cccc(n1)OC2] | ES-MS m/z 642 |
| 32 | (S)-2-((5$^4$-(2-Methyl-2H-1,2,3-triazol-4-yl)-3,9-dioxa-2(2,6)-pyridina-1(1,3),5(1,2)-dibenzenacyclononaphane-1$^4$-yl)methyl)-1-(oxetan-2-ylmethyl)-1H-benzo[d]imidazole-6-carboxylic acid | 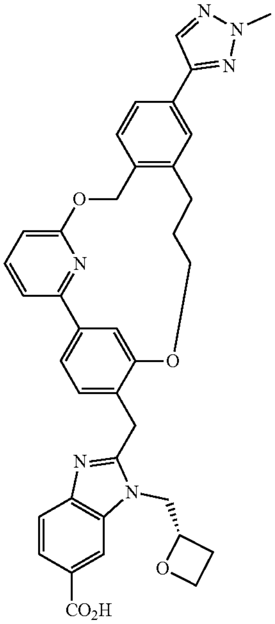 [SMILES: Cn1ncc(-c2ccc3c(c2)CCCOc2cc(ccc2Cc2nc4ccc(C(=O)O)cc4n2C[C@@H]2CCO2)-c2cccc(n2)OC3)n1] | ES-MS m/z 643 |

-continued
| Example | Name | Structure | Characterization |
|---|---|---|---|
| 33 | (S)-2-((5$^4$-(4-(Methylsulfonyl)phenyl)-3,9-dioxa-2(2,6)-pyridina-1(1,3),5(1,2)-dibenzenacyclononaphane-1$^4$-yl)methyl)-1-(oxetan-2-ylmethyl)-1H-benzo[d]imidazole-6-carboxylic acid | 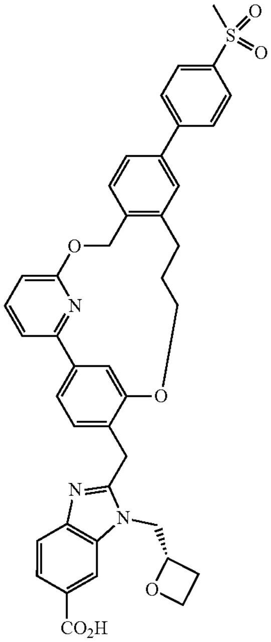 [SMILES: CS(=O)(=O)c1ccc(-c2ccc3c(c2)CCCOc2cc(ccc2Cc2nc4ccc(C(=O)O)cc4n2C[C@@H]2CCO2)-c2cccc(n2)OC3)cc1] | ES-MS m/z 716 |
| 34 | (S)-2-((5$^4$-(2-Methoxypyridin-4-yl)-3,9-dioxa-2(2,6)-pyridina-1(1,3),5(1,2)-dibenzenacyclononaphane-1$^4$-yl)methyl)-1-(oxetan-2-ylmethyl)-1H-benzo[d]imidazole-6-carboxylic acid | 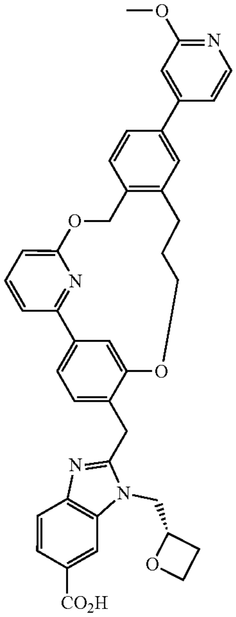 [SMILES: COc1cc(-c2ccc3c(c2)CCCOc2cc(ccc2Cc2nc4ccc(C(=O)O)cc4n2C[C@@H]2CCO2)-c2cccc(n2)OC3)ccn1] | ES-MS m/z 669 |

-continued
| Example | Name | Structure | Characterization |
|---|---|---|---|
| 35 | (S)-2-((5$^4$-(1-Cyclopropyl-1H-pyrazol-4-yl)-3,9-dioxa-2(2,6)-pyridina-1(1,3),5(1,2)-dibenzenacyclononaphane-1$^4$-yl)methyl)-1-(oxetan-2-ylmethyl)-1H-benzo[d]imidazole-6-carboxylic acid | 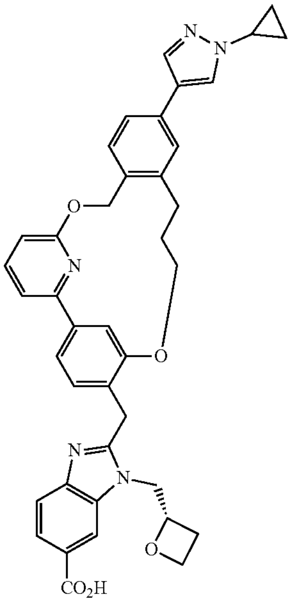 [SMILES: O=C(O)c1ccc2nc(Cc3ccc4cc3OCCCc3cc(-c5cnn(C6CC6)c5)ccc3COc3cccc-4n3)n(C[C@@H]3CCO3)c2c1] | ES-MS m/z 668 |
| 36 | (S)-2-((5$^4$-(1-Methyl-6-oxo-1,6-dihydropyridin-3-yl)-3,9-dioxa-2(2,6)-pyridina-1(1,3),5(1,2)-dibenzenacyclononaphane-1$^4$-yl)methyl)-1-(oxetan-2-ylmethyl)-1H-benzo[d]imidazole-6-carboxylic acid | 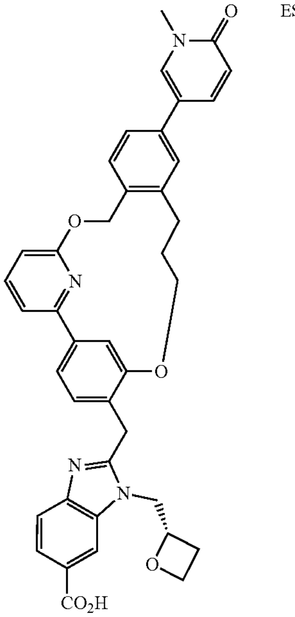 | ES-MS m/z 669 |

-continued
| Example | Name | Structure | Characterization |
|---|---|---|---|
| 37 | (S)-1-(Oxetan-2-ylmethyl)-2-((5$^4$-(pyridin-3-yl)-3,9-dioxa-2(2,6)-pyridina-1(1,3),5(1,2)-dibenzenacyclononaphane-1$^4$-yl)methyl)-1H-benzo[d]imidazole-6-carboxylic acid | 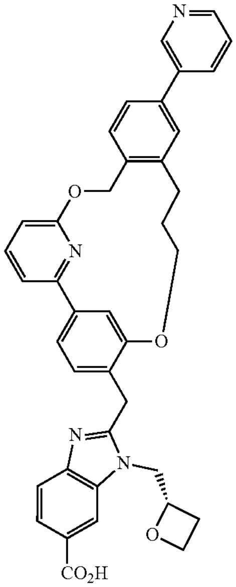 [SMILES: O=C(O)c1ccc2nc(Cc3ccc4cc3OCCCc3cc(-c5cccnc5)ccc3COc3cccc-4n3)n(C[C@@H]3CCO3)c2c1] | ES-MS m/z 639 |
| 38 | (S)-2-((5$^4$-(4-(Methylcarbamoyl)phenyl)-3,9-dioxa-2(2,6)-pyridina-1(1,3),5(1,2)-dibenzenacyclononaphane-1$^4$-yl)methyl)-1-(oxetan-2-ylmethyl)-1H-benzo[d]imidazole-6-carboxylic acid | 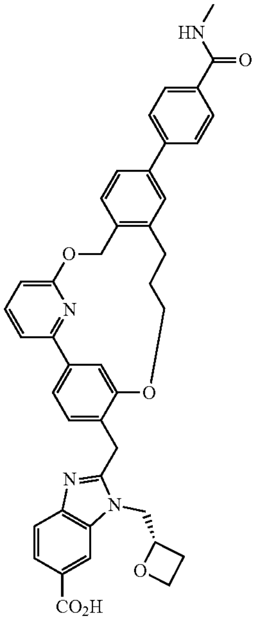 [SMILES: CNC(=O)c1ccc(-c2ccc3c(c2)CCCOc2cc(ccc2Cc2nc4ccc(C(=O)O)cc4n2C[C@@H]2CCO2)-c2cccc(n2)OC3)cc1] | ES-MS m/z 695 |

-continued
| Example | Name | Structure | Characterization |
|---|---|---|---|
| 39 | (S)-2-((5$^4$-(4-(Hydroxymethyl)phenyl)-3,9-dioxa-2(2,6)-pyridina-1(1,3),5(1,2)-dibenzenacyclononaphane-1$^4$-yl)methyl)-1-(oxetan-2-ylmethyl)-1H-benzo[d]imidazole-6-carboxylic acid | 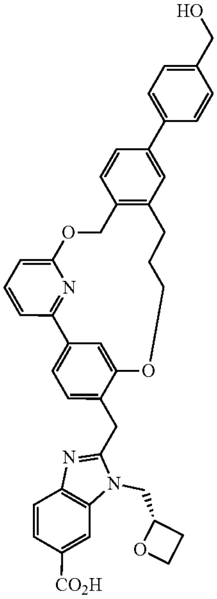 [SMILES: O=C(O)c1ccc2nc(Cc3ccc4cc3OCCCc3cc(-c5ccc(CO)cc5)ccc3COc3cccc-4n3)n(C[C@@H]3CCO3)c2c1] | ES-MS m/z 668 |
| 76 | (S)-1-(Oxetan-2-ylmethyl)-2-((5$^4$-(1-(oxetan-3-yl)-1H-pyrazol-4-yl)-3,9-dioxa-2(2,6)-pyridina-1(1,3),5(1,2)-dibenzenacyclononaphane-1$^4$-yl)methyl)-1H-benzo[d]imidazole-6-carboxylic acid | 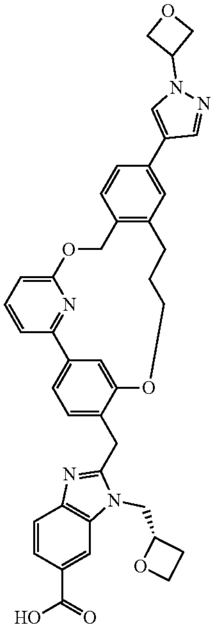 [SMILES: O=C(O)c1ccc2nc(Cc3ccc4cc3OCCCc3cc(-c5cnn(C6COC6)c5)ccc3COc3cccc-4n3)n(C[C@@H]3CCO3)c2c1] | ES/MS m/z 684 (M + H) |

-continued
| Example | Name | Structure | Characterization |
|---|---|---|---|
| 77 | (S)-2-((5⁴-(4-(Dimethylcarbamoyl)phenyl)-3,9-dioxa-2(2,6)-pyridina-1(1,3),5(1,2)-dibenzenacyclononaphane-1⁴-yl)methyl)-1-(oxetan-2-ylmethyl)-1H-benzo[d]imidazole-6-carboxylic acid | 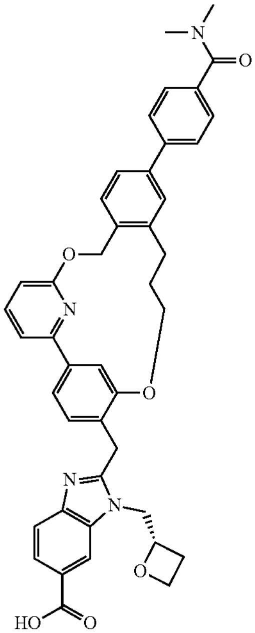 [SMILES: CN(C)C(=O)c1ccc(-c2ccc3c(c2)CCCOc2cc(ccc2Cc2nc4ccc(C(=O)O)cc4n2C[C@@H]2CCO2)-c2cccc(n2)OC3)cc1] | ES/MS m/z 709 (M + H) |
| 78 | (S)-2-((5⁴-(2-Aminopyridin-4-yl)-3,9-dioxa-2(2,6)-pyridina-1(1,3),5(1,2)-dibenzenacyclononaphane-1⁴-yl)methyl)-1-(oxetan-2-ylmethyl)-1H-benzo[d]imidazole-6-carboxylic acid | 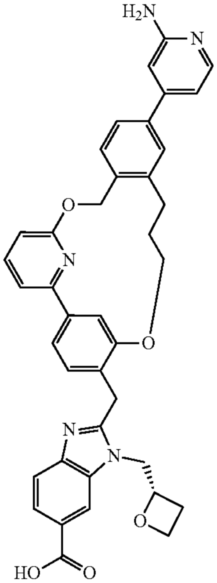 [SMILES: Nc1cc(-c2ccc3c(c2)CCCOc2cc(ccc2Cc2nc4ccc(C(=O)O)cc4n2C[C@@H]2CCO2)-c2cccc(n2)OC3)ccn1] | ES/MS m/z 654 (M + H) |

-continued
| Example | Name | Structure | Characterization |
|---|---|---|---|
| 79 | (S)-2-((5⁴-(1-Methyl-2-oxo-1,2-dihydropyridin-4-yl)-3,9-dioxa-2(2,6)-pyridina-1(1,3),5(1,2)-dibenzenacyclononaphane-1⁴-yl)methyl)-1-(oxetan-2-ylmethyl)-1H-benzo[d]imidazole-6-carboxylic acid | 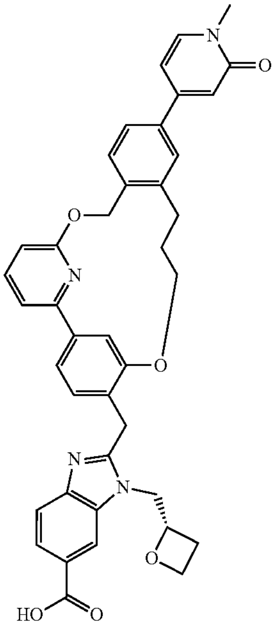 [SMILES: Cn1ccc(-c2ccc3c(c2)CCCOc2cc(ccc2Cc2nc4ccc(C(=O)O)cc4n2C[C@@H]2CCO2)-c2cccc(n2)OC3)cc1=O] | ES/MS m/z 669 (M + H) |
| 80 | (S)-1-(Oxetan-2-ylmethyl)-2-((5⁴-(6-oxo-1,6-dihydropyridin-3-yl)-3,9-dioxa-2(2,6)-pyridina-1(1,3),5(1,2)-dibenzenacyclononaphane-1⁴-yl)methyl)-1H-benzo[d]imidazole-6-carboxylic acid | 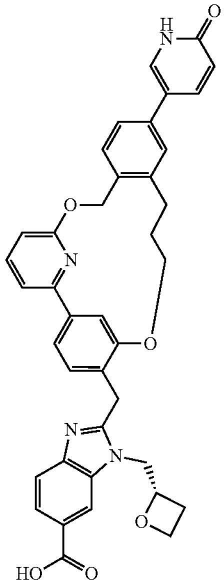 [SMILES: O=C(O)c1ccc2nc(Cc3ccc4cc3OCCCc3cc(-c5ccc(=O)[nH]c5)ccc3COc3cccc-4n3)n(C[C@@H]3CCO3)c2c1] | ES/MS m/z 655 (M + H) |

Example 40

(S)-2-((5[4]-(1-Methyl-1H-pyrazol-4-yl)-3,9-dioxa-2(2,6)-pyridina-1(1,3),5(1,2)-dibenzenacyclononaphane-1[4]-yl)methyl)-1-(oxetan-2-ylmethyl)-1H-benzo[d]imidazole-6-carboxylic acid

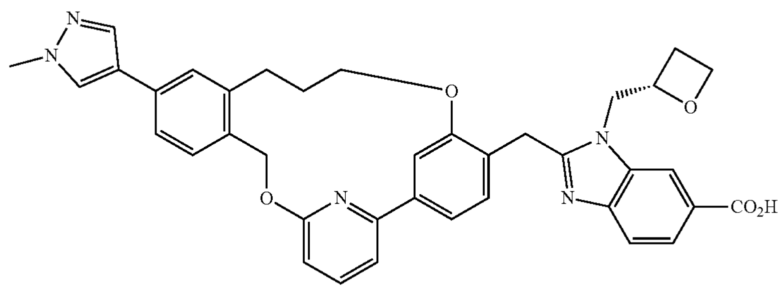 [SMILES: Cn1cc(-c2ccc3c(c2)CCCOc2cc(ccc2Cc2nc4ccc(C(=O)O)cc4n2C[C@@H]2CCO2)-c2cccc(n2)OC3)cn1]

Prepare the title compound essentially as described in Example 29 using 1-methyl-4-(4,4,5,5-tetramethyl-1,3,2-dioxaborolan-2-yl)pyrazole, stirring the reaction at 60° C. for 2 h and omitting the second addition of catalyst. Load the crude reaction mixture onto hydrophobic lipophilic balance (HLB) resin and elute with 10 mM aqueous $NH_4HCO_3$ buffer then with 1:1 DCM:MeOH. Concentrate fractions containing the title compound and then further purify using C18 reversed phase chromatography using a gradient of ACN in 10 mM aqueous $NH_4HCO_3$. ES-MS m/z 642.

Example 41

(S)-1[4]-((1-(Oxetan-2-ylmethyl)-6-(1H-tetrazol-5-yl)-1H-benzo[d]imidazol-2-yl)methyl)-3,9-dioxa-2(2,6)-pyridina-1(1,3),5(1,2)-dibenzenacyclononaphane-5[4]-carbonitrile

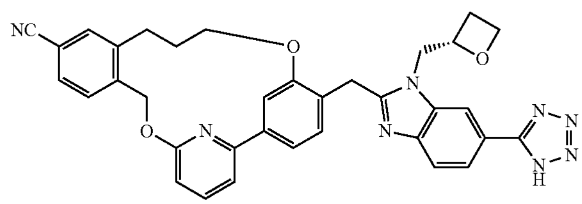 [SMILES: N#Cc1ccc2c(c1)CCCOc1cc(ccc1Cc1nc3ccc(-c4nnn[nH]4)cc3n1C[C@@H]1CCO1)-c1cccc(n1)OC2]

To a solution of (S)-1[4]-((1-(oxetan-2-ylmethyl)-6-(1-((2-(trimethylsilyl)ethoxy)methyl)-1H-tetrazol-5-yl)-1H-benzo[d]imidazol-2-yl)methyl)-3,9-dioxa-2(2,6)-pyridina-1(1,3),5(1,2)-dibenzenacyclononaphane-5[4]-carbonitrile (100 mg, 0.1 mmol) in THF (2 mL) and add TBAF (1 M in THF, 0.3 mL, 0.3 mmol). Stir the mixture at 60° C. for 16 h. Quench the reaction with water and dilute with EtOAc. Dry the organic phase over $MgSO_4$, filter, and concentrate under reduced pressure. Suspend the residue in an aqueous ammonia solution and stir at 50° C. for 6 h. Concentrate under reduced pressure and purify the solid by C18 reversed phase chromatography using a gradient of 30 to 70% ACN in aqueous ammonium acetate solution to give 93 mg of the title compound (10%). ES-MS m/z 611 (M+H).

Example 42

(S)-2-((5[4]-Cyano-1[6]-fluoro-3,6-dioxa-2(2,6)-pyridina-1(1,3),5(1,2)-dibenzenacyclooctaphane-1[4]-yl)methyl)-1-(oxetan-2-ylmethyl)-1H-benzo[d]imidazole-6-carboxylic acid

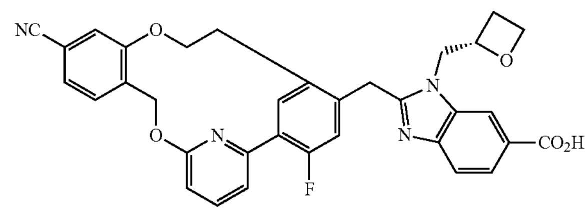 [SMILES: N#Cc1ccc2c(c1)OCCc1cc(c(F)cc1Cc1nc3ccc(C(=O)O)cc3n1C[C@@H]1CCO1)-c1cccc(n1)OC2]

To a solution of methyl (S)-2-((5[4]-cyano-1[6]-fluoro-3,6-dioxa-2(2,6)-pyridina-1(1,3),5(1,2)-dibenzenacyclooctaphane-1[4]-yl)methyl)-1-(oxetan-2-ylmethyl)-1H-benzo[d]imidazole-6-carboxylate (92 mg, 0.15 mmol) in ACN (8.4 mL) and water (4.8 mL), add 1,3,4,6,7,8-hexahydro-2H-pyrimido[1,2-a]pyrimidine (87 mg, 0.61 mmol). Stir at 45° C. overnight. Cool the mixture to RT, dilute with water and extract three times with 3:1 DCM:isopropanol. Combine the organics, wash with water and saturated aqueous NaCl, dry over $MgSO_4$, filter, and concentrate under reduced pressure. Purify the residue via silica gel chromatography using 30% EtOAc in DCM and then a gradient of 0 to 5% (10:1 MeOH:formic acid) in DCM. Repurify by reverse phase chromatography using 41 to 83% [1:1 ACN:MeOH] in 0.1% aqueous formic acid (pH3) to give the title compound (12 mg, 13%) as a white solid. ES-MS m/z 591 (M+H).

Example 43

(S)-2-(($5^5$-Cyano-$1^6$-fluoro-3,9-dioxa-2(2,6),5(2,3)-dipyridina-1(1,3)-benzenacyclononaphane-$1^4$-yl)methyl)-4-methoxy-1-(oxetan-2-ylmethyl)-1H-benzo[d]imidazole-6-carboxylic acid diformate salt

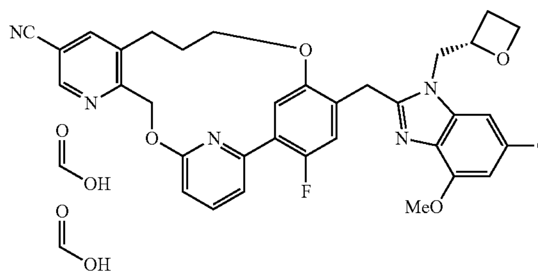

To a suspension of methyl (S)-2-(($5^5$-cyano-$1^6$-fluoro-3,9-dioxa-2(2,6),5(2,3)-dipyridina-1(1,3)-benzenacyclononaphane-$1^4$-yl)methyl)-4-methoxy-1-(oxetan-2-ylmethyl)-1H-benzo[d]imidazole-6-carboxylate (66 mg, 0.10 mmol) in ACN (1.2 mL), THE (0.3 mL) and water (0.2 mL), add 1,3,4,6,7,8-hexahydro-2H-pyrimido [1,2-a]pyrimidine (0.032 g, 0.23 mmol). Stir the suspension at 45° C. for 6 h. Cool the mixture to RT, add formic acid until pH=4, and extract with EtOAc (3×5 mL). Combine the organics, dry over $MgSO_4$, filter, and concentrate under reduce pressure. Purify the residue via silica gel chromatography using a gradient of 0 to 50% solvent B in solvent A, wherein solvent B=(DCM/MeOH/formic acid 9:0.9:0.1) and solvent A=DCM to give the title compound as a beige solid (15 mg, 24%). ES-MS m/z 636 (M+H-formate salt).

Example 44

(S)-2-(($5^4$-Cyano-$1^6$-fluoro-3,7-dioxa-2(2,6)-pyridina-1(1,3),5(1,2)-dibenzenacyclononaphane-$1^4$-yl)methyl)-4-methoxy-1-(oxetan-2-ylmethyl)-1H-benzo[d]imidazole-6-carboxylic acid

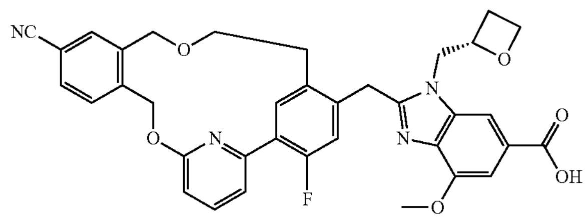 [SMILES: COc1cc(C(=O)O)cc2c1nc(Cc1cc(F)c3cc1CCOCc1cc(C#N)ccc1COc1cccc-3n1)n2C[C@@H]1CCO1]

To a suspension of methyl (S)-2-(($5^4$-cyano-$1^6$-fluoro-3,7-dioxa-2(2,6)-pyridina-1(1,3),5(1,2)-dibenzenacyclononaphane-$1^4$-yl)methyl)-4-methoxy-1-(oxetan-2-ylmethyl)-1H-benzo[d]imidazole-6-carboxylate (57 mg, 0.09 mmol) in degassed ACN (0.9 mL), 1,4-dioxane (0.3 mL) and water (0.3 mL), add 1,5,7-triazabicyclo[4.4.0]dec-5-ene (38 mg, 0.27 mmol). Heat the reaction mixture at 60° C. for 2 h, cool to RT, add 5% aqueous citric acid solution up to pH=5, then add water (2.0 mL) and stir the mixture at RT for 15 min. Filter the resulting solid, wash with water (5 mL) and dry under vacuum at 45° C. overnight. Suspend the solid in MeOH (1.0 mL) and stir the mixture for 15 min at RT. Filter the resulting solid, wash with MeOH (0.5 mL), EtOAc (1.5 mL) and dry under vacuum at 45° C. overnight to give the title compound as a pale brown solid (19 mg, 34%). ES-MS m/z 635.2/636.2 (M+H).

Example 45

(S)-2-(($5^4$-Chloro-$1^6$,$5^6$-difluoro-3,8-dioxa-2(2,6)-pyridina-1(1,3),5(1,2)-dibenzenacyclononaphane-$1^4$-yl)methyl)-4-(2-methoxyethoxy)-1-(oxetan-2-ylmethyl)-1H-benzo[d]imidazole-6-carboxylic acid

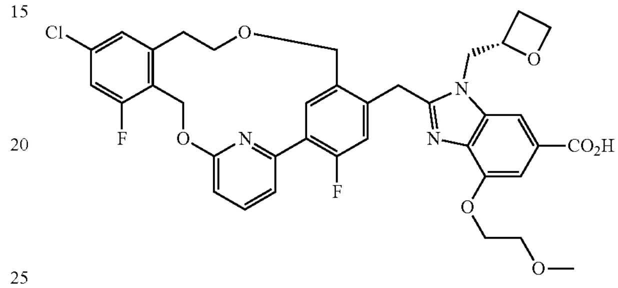

To a solution of methyl (S)-2-(($5^4$-chloro-$1^6$,$5^6$-difluoro-3,8-dioxa-2(2,6)-pyridina-1(1,3),5(1,2)-dibenzenacyclononaphane-$1^4$-yl)methyl)-4-(2-methoxyethoxy)-1-(oxetan-2-ylmethyl)-1H-benzo[d]imidazole-6-carboxylate (245 mg, 64% purity, 0.21 mmol) in ACN (2.4 mL), water (0.8 mL) and THE (0.8 mL) at 55° C., add 1,5,7-triazabicyclo [4.4.0]dec-5-ene (210 mg, 1.47 mmol). Stir the mixture at 55° C. for 2 h, cool to RT, add 5% aqueous citric acid until pH=4-5, then filter the white solid which precipitates. Dissolve the solid in ACN/MeOH and purify by preparative HPLC [column: Welch Xtimate C18 150×30 mm×5 µm; mobile phase: 30 to 70% ACN in aqueous formic acid (0.225%)] to afford the title compound as a white solid (31 mg, 20%). ES-MS m/z 706 (M+H).

Example 46

(S)-2-(($5^5$-Cyano-3,8-dioxa-2,5(2,6)-dipyridina-1(1,3)-benzenacyclononaphane-$1^4$-yl)methyl)-4-(2-methoxyethoxy)-1-(oxetan-2-ylmethyl)-1H-benzo[d]imidazole-6-carboxylic acid

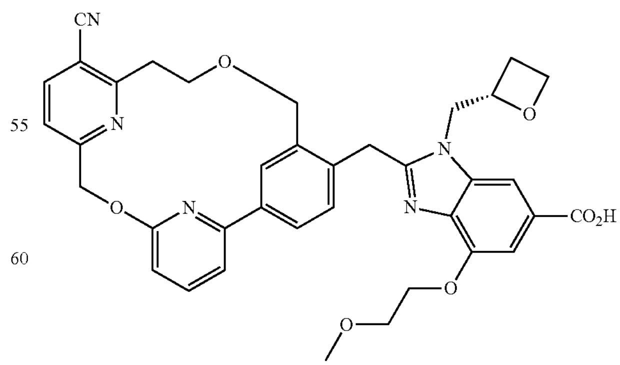

Prepare the title compound essentially as described in Example 5 using methyl (S)-2-(($5^5$-cyano-3,8-dioxa-2,5(2, 6)-dipyridina-1(1,3)-benzenacyclononaphane-$1^4$-yl)methyl)-4-(2-methoxyethoxy)-1-(oxetan-2-ylmethyl)-1H-benzo[d]imidazole-6-carboxylate (63 wt % pure) in a mixture of ACN:THF:water (3:1:1), heating the reaction at 55° C. under nitrogen atmosphere for 2 h. Cool the reaction mixture to RT and quench with aqueous citric acid (5%), then filter the solid and wash with water. Purify by preparative HPLC [column: Welch Xtimate C18 150×30 mm, 5 μm; mobile phase: 25 to 65% ACN in aqueous formic acid (0.225%)] to give title compound as a white solid. ES-MS m/z 662 (M+H).

Example 47

(S)-2-(($5^4$-Chloro-$1^6$-fluoro-3,7-dioxa-2(2,6)-pyridina-1,5(1,3)-dibenzenacyclononaphane-$1^4$-yl)methyl)-4-(2-methoxyethoxy)-1-(oxetan-2-ylmethyl)-1H-benzo[d]imidazole-6-carboxylic acid

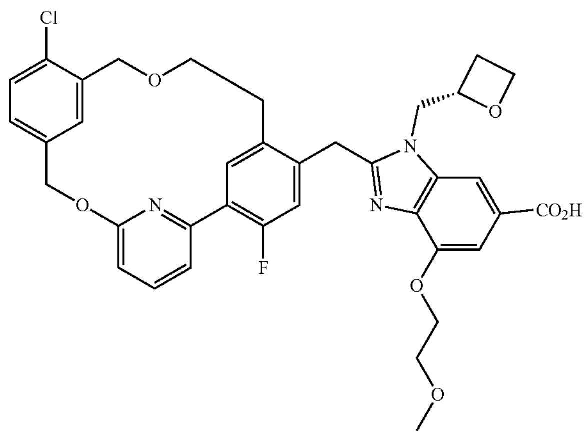 [SMILES: COCCOc1cc(C(=O)O)cc2c1nc(Cc1cc(F)c3cc1CCOCc1cc(ccc1Cl)COc1cccc-3n1)n2C[C@@H]1CCO1]

Prepare the title compound essentially as described in Example 2 using methyl (S)-2-(($5^4$-chloro-$1^6$-fluoro-3,7-dioxa-2(2,6)-pyridina-1,5(1,3)-dibenzenacyclononaphane-$1^4$-yl)methyl)-4-(2-methoxyethoxy)-1-(oxetan-2-ylmethyl)-1H-benzo[d]imidazole-6-carboxylate in 10:5:3 ACN:1,4-dioxane:water as solvent, stirring the reaction mixture at 55° C. for 6 h 30 min. Concentrate the crude reaction mixture onto Celite® and purify by C18 reversed phase chromatography using a gradient of 10 to 73% ACN in aqueous $NH_4HCO_3$ (10 mM plus 5% MeOH) to give the title compound. ES-MS m/z 688 (M+H).

Example 48

(S)-2-(($5^4$-Cyano-$1^6$-fluoro-3,7-dioxa-2(2,6)-pyridina-1,5(1,3)-dibenzenacyclononaphane-$1^4$-yl)methyl)-4-(2-methoxyethoxy)-1-(oxetan-2-ylmethyl)-1H-benzo[d]imidazole-6-carboxylic acid

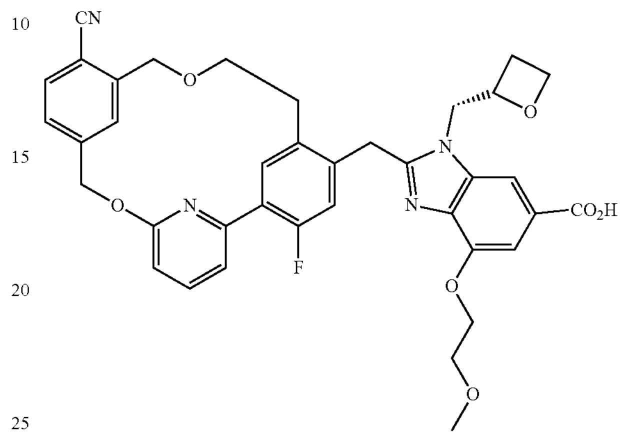

To a mixture of (S)-2-(($5^4$-chloro-$1^6$-fluoro-3,7-dioxa-2(2,6)-pyridina-1,5(1,3)-dibenzenacyclononaphane-$1^4$-yl)methyl)-4-(2-methoxyethoxy)-1-(oxetan-2-ylmethyl)-1H-benzo[d]imidazole-6-carboxylic acid (15 mg, 0.022 mmoL), potassium ferrocyanide trihydrate (14.5 mg, 0.039 mmoL), XPhos Pd(crotyl)Cl (Pd-170, 5.5 mg, 0.008 mmoL), and KOAc (5.6 mg, 0.056 mmoL) add 1,4-dioxane (1.0 mL) and water (0.4 mL). Stir the mixture at 90° C. for 4 h. Concentrate the reaction mixture onto Celite® and purify by C18 reversed phase chromatography using a gradient of 10 to 73% ACN in aqueous $NH_4HCO_3$ (10 mM plus 5% MeOH) to give 8.2 mg of the title compound (55%). ES-MS m/z 679 (M+H).

Example 49

(S)-2-(($5^4$-Cyano-$2^3$-fluoro-3,8-dioxa-2(2,6)-pyridina-1(1,3),5(1,2)-dibenzenacyclononaphane-$1^4$-yl)methyl)-4-(2-methoxyethoxy)-1-(oxetan-2-ylmethyl)-1H-benzo[d]imidazole-6-carboxylic acid

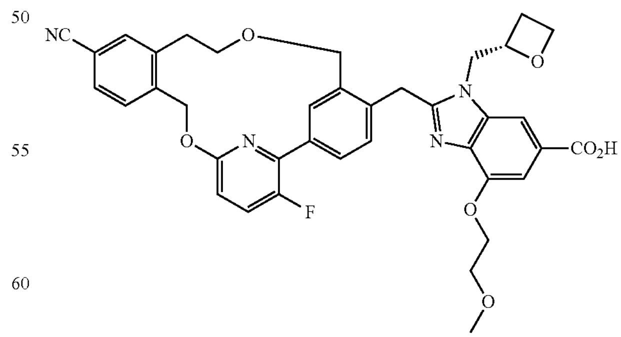

Prepare the title compound essentially as described in Example 45 using methyl (S)-2-(($5^4$-cyano-$2^3$-fluoro-3,8-dioxa-2(2,6)-pyridina-1(1,3),5(1,2)-dibenzenacyclononaphane-$1^4$-yl)methyl)-4-(2-methoxyethoxy)-1-(oxetan-2-ylmethyl)-1H-benzo[d]imidazole-6-carboxylate. Purify by preparative HPLC [column: Welch Xtimate C18 150×25 mm, 5 μm; mobile phase: 25 to 70% ACN in aqueous TFA (0.1%)]. Remove the organic solvent under reduced pressure and lyophilize the residual aqueous solution to get the titled product as a white solid. ES-MS m/z 679 (M+H).

Example 50

(S)-2-(($5^4$-cyano-6,6-difluoro-3.8-dioxa-2(2,6)-pyridina-1(1,3),5(1,2)-dibenzenacyclonaphane-$1^4$-yl)methyl)-4-(2-methoxyethoxy)-1-(oxatan-2-ylmethyl)-1H-benzo[d]imidazole-6-carboxylic acid

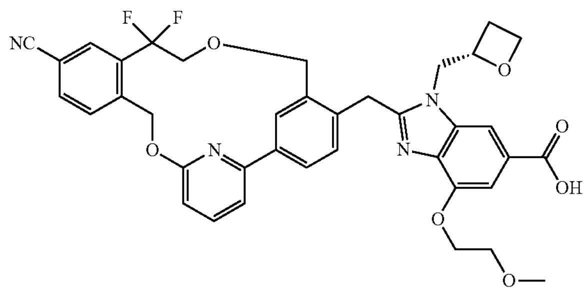 [SMILES: COCCOc1cc(C(=O)O)cc2c1nc(Cc1ccc3cc1COCC(F)(F)c1cc(C#N)ccc1COc1cccc-3n1)n2C[C@@H]1CCO1]

Dissolve methyl (S)-2-(($5^4$-cyano-6,6-difluoro-3.8-dioxa-2(2,6)-pyridina-1(1,3),5(1,2)-dibenzenacyclonaphane-$1^4$-yl)methyl)-4-(2-methoxyethoxy)-1-(oxatan-2-ylmethyl)-1H-benzo[d]imidazole-6-carboxylate (61 mg, 0.086 mmol) in ACN (1 mL), 1,4-dioxane (0.3 mL), and water (0.3 mL). To this solution add 1,5,7-triazabicyclo[4.4.0]dec-5-ene (0.04 g, 0.28 mmol) and stir this mixture at ambient temperature for 18 h. After this time, quench the reaction with 1N HCl (to pH 5), and extract with EtOAc. Dry the organics over $MgSO_4$, filter, and concentrate. Purify this material with reverse phase HPLC [column: Phenomenex Kinetex EVO C18 100×30 mm, 5 μm; mobile phase: 23 to 58% ACN in aqueous $NH_4HCO_3$ (10 mM plus 5% MeOH)] to give the title compound as a white solid (14.5 mg, 24.1%). ES-MS (m z) 697.4 (M+H).

Example 51

(S)-2-(($5^4$-Cyano-3,8-dioxa-2(2,4)-pyrimidina-1(1,3),5(1,2)-dibenzenacyclononaphane-$1^4$-yl)methyl)-4-methoxy-1-(oxetan-2-ylmethyl)-1H-benzo[d]imidazole-6-carboxylic acid

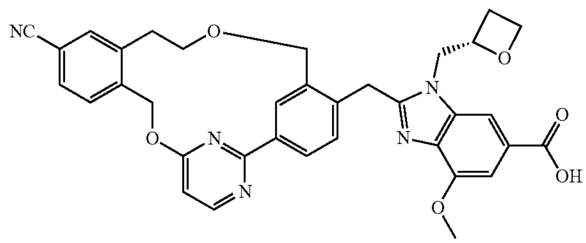 [SMILES: COc1cc(C(=O)O)cc2c1nc(Cc1ccc3cc1COCCc1cc(C#N)ccc1COc1ccnc-3n1)n2C[C@@H]1CCO1]

Prepare the title compound essentially as described in Example 2 using methyl (S)-2-(($5^4$-cyano-3,8-dioxa-2(2,4)-pyrimidina-1(1,3),5(1,2)-dibenzenacyclononaphane-$1^4$-yl)methyl)-4-methoxy-1-(oxetan-2-ylmethyl)-1H-benzo[d]imidazole-6-carboxylate as starting material, using 5:2:1 ACN:1,4-dioxane:water as solvent, heating the reaction to 40° C. for 21 h. Upon completion, cool the reaction to ambient temperature and quench with 5% aqueous citric acid bringing the pH to 4. Filter the resulting precipitate and wash the solid with water. Dry the collected solid under reduced pressure to give the title compound. ES/MS m/z 618 (M+H).

Example 52

(S)-4-(2-Methoxyethoxy)-1-(oxetan-2-ylmethyl)-2-(($5^6$-(trifluoromethyl)-3,8-dioxa-2(2,6),5(3,4)-dipyridina-1(1,3)-benzenacyclononaphane-$1^4$-yl)methyl)-1H-benzo[d]imidazole-6-carboxylic acid

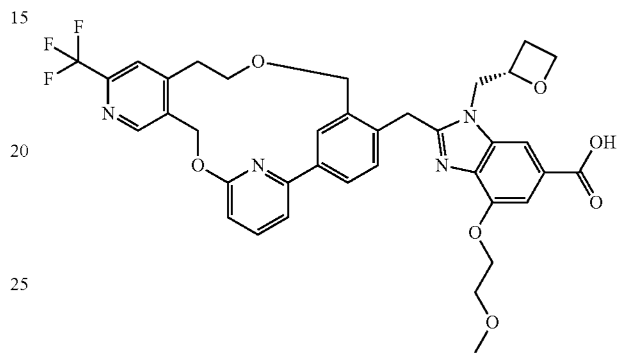

Prepare the title compound essentially as described in Example 2 using methyl (S)-4-(2-methoxyethoxy)-1-(oxetan-2-ylmethyl)-2-(($5^6$-(trifluoromethyl)-3,8-dioxa-2(2,6),5(3,4)-dipyridina-1(1,3)-benzenacyclononaphane-$1^4$-yl)methyl)-1H-benzo[d]imidazole-6-carboxylate and 2.8:1:1 ACN:THF:water as solvent, heating the reaction at 45° C. for 2 h. Quench the reaction with 1 M aqueous citric acid bringing the pH to 4.5. Filter the resultant colorless solid and dry under vacuum. Purify via reverse phase chromatography on a C18 column using a gradient of 42% to 75% ACN in aqueous formic acid (0.225%) to give the title compound. ES/MS m/z 705 (M+H).

Example 53

(S)-2-(($5^4$-Cyano-3,9-dioxa-2(2,6)-pyridina-1(1,3),5(1,2)-dibenzenacyclononaphane-$1^4$-yl)methyl)-4-(2-(2-methyloxazol-4-yl)ethoxy)-1-(oxetan-2-ylmethyl)-1H-benzo[d]imidazole-6-carboxylic acid

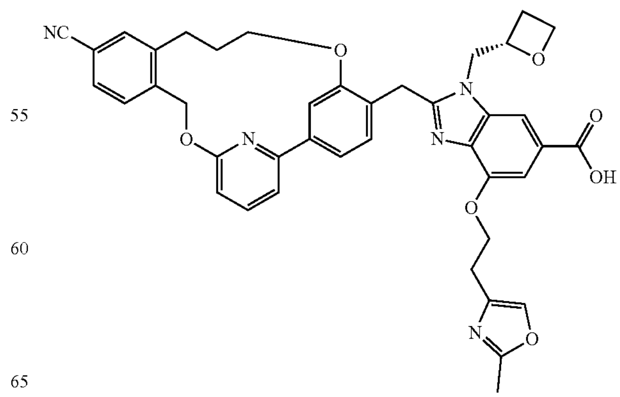

Prepare the title compound essentially as described in Example 5 using methyl (S)-2-((5$^4$-cyano-3,9-dioxa-2(2,6)-pyridina-1(1,3),5(1,2)-dibenzenacyclononaphane-1$^4$-yl)methyl)-4-(2-(2-methyloxazol-4-yl)ethoxy)-1-(oxetan-2-ylmethyl)-1H-benzo[d]imidazole-6-carboxylate and using mixture of 3:1:1 ACN:THF:water as solvent, stirring the reaction at 35° C. for 6 h. Upon completion, concentrate the mixture and dissolve the residue in a minimum of DMSO. Filter the DMSO solution and purify the filtrate by preparative HPLC [column: Welch Xtimate C18 150×30 mm, 5 μm; mobile phase: gradient of 10 to 45% ACN in aqueous $NH_4HCO_3$ (10 mM) to give the title compound as a white solid. ES/MS m/z 712 (M+H).

Example 54

(S)-2-((5$^4$-Cyano-3,9-dioxa-2(2,6)-pyridina-1(1,3),5(1,2)-dibenzenacyclononaphane-1$^4$-yl)methyl)-1-(oxetan-2-ylmethyl)-4-(2-((2,2,2-trifluoroethyl)amino)ethoxy)-1H-benzo[d]imidazole-6-carboxylic acid

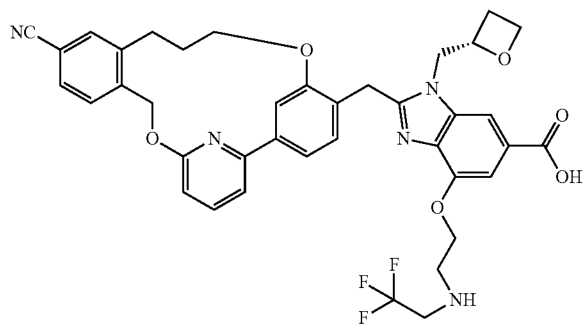 [SMILES: N#Cc1ccc2c(c1)CCCOc1cc(ccc1Cc1nc3c(OCCNCC(F)(F)F)cc(C(=O)O)cc3n1C[C@@H]1CCO1)-c1cccc(n1)OC2]

To a solution of (S)-4-(2-((tert-butoxycarbonyl)(2,2,2-trifluoroethyl)amino)ethoxy)-2-((5$^4$-cyano-3,9-dioxa-2(2,6)-pyridina-1(1,3),5(1,2)-dibenzenacyclononaphane-1$^4$-yl)methyl)-1-(oxetan-2-ylmethyl)-1H-benzo[d]imidazole-6-carboxylic acid (Preparation 311, 75 mg, 0.058 mmol) in toluene (7 mL), add silica gel (750 mg), and heat the mixture to 120° C. for 18 h. Cool the mixture to ambient temperature, filter, and concentrate in vacuo. Purify the residue via preparative HPLC [column: Xtimate C18 100×30 mm, 10 μm; mobile phase: gradient of 35 to 65% ACN in aqueous formic acid (0.2%)] to give the title compound as a colorless solid (2.5 mg, 5.7%). ES/MS m/z 728.6 (M+H).

Example 55

(S)-4-[2-Hydroxyethoxy]-2-((5$^4$-chloro-3,8-dioxa-2(2,6)-pyridina-1(1,3),5(1,2)-dibenzenacyclononaphane-1$^4$-yl)methyl)-1-(oxetan-2-ylmethyl)-1H-benzo[d]imidazole-6-carboxylic acid

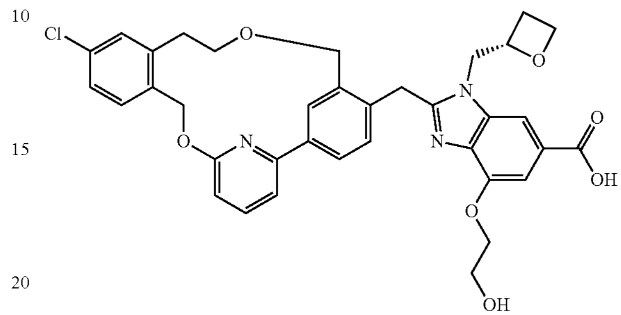

To a solution of methyl (S)-4-[2-[tert-butyl(dimethyl)silyl]oxyethoxy]-2-((5$^4$-chloro-3,8-dioxa-2(2,6)-pyridina-1(1,3),5(1,2)-dibenzenacyclononaphane-1$^4$-yl)methyl)-1-(oxetan-2-ylmethyl)-1H-benzo[d]imidazole-6-carboxylate (62 mg, 0.079 mmol) in THE (5 mL) and MeOH (2 mL), add LiOH (10 mg, 0.42 mmol) dissolved in water (2 mL) and heat to 45° C. for 1.5 h. Add more LiOH (12 mg, 0.050 mmol) dissolved in water (1 mL) and heat for another hour at 45° C., cool to ambient temperature, and concentrate under reduced pressure. Suspend the crude material in water (20 mL) and adjust the pH to 5 with 1N HCl. Filter the solid, collect, and dry under reduced pressure. Purify via C18 reversed phase chromatography eluting with 30-60% ACN in 10 mM aqueous ammonium bicarbonate containing 5% MeOH to give the title compound (7.5 mg, 14%). ES/MS (m z): 656.4 (M+H).

Example 56

(S)-2-((5$^4$-Chloro-3,8-dioxa-2(2,6)-pyridina-1(1,3),5(1,2)-dibenzenacyclononaphane-1$^4$-yl)methyl)-4-(2-(dimethylamino)ethoxy)-1-(oxetan-2-ylmethyl)-1H-benzo[d]imidazole-6-carboxylic acid

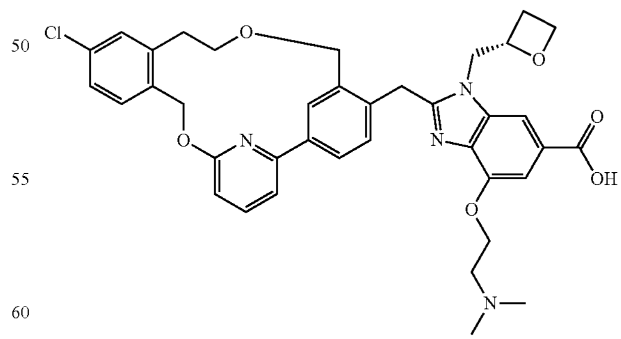

To a nitrogen-sparged mixture of methyl (S)-2-((5$^4$-chloro-3,8-dioxa-2(2,6)-pyridina-1(1,3),5(1,2)-dibenzenacyclononaphane-1$^4$-yl)methyl)-4-(2-(dimethylamino)ethoxy)-1-(oxetan-2-ylmethyl)-1H-benzo[d]imidazole-6-carboxylate (89 mg, 0.12 mmol) in ACN (2 mL), 1,4- dioxane (1 mL) and water (0.22 mL), add 1,5,7-triazabicyclo[4.4.0]dec-5-ene (60 mg, 0.42 mmol). Heat reaction mixture at 60° C. for 16 h. Cool the mixture to ambient temperature, concentrate under reduced pressure, and purify the residue via reverse-phase chromatography using a gradient of 10 to 80% ACN in water (0.1% formic acid added to both the ACN and water) to give the title compound as a colorless solid (42 mg, 48%). ES/MS m/z 683 (M+H).

Example 57

(S)-2-(($5^4$-Chloro-3,8-dioxa-2(2,6)-pyridina-1(1,3),5(1,2)-dibenzenacyclononaphane-$1^4$-yl)methyl)-4-(2-(methylamino)ethoxy)-1-(oxetan-2-ylmethyl)-1H-benzo[d]imidazole-6-carboxylic acid

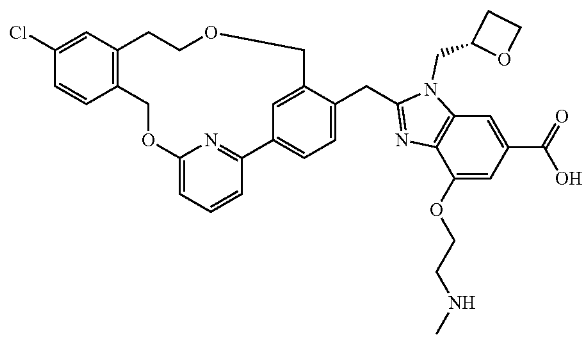 [SMILES: CNCCOc1cc(C(=O)O)cc2c1nc(Cc1ccc3cc1COCCc1cc(Cl)ccc1COc1cccc-3n1)n2C[C@@H]1CCO1]

To (S)-4-(2-((tert-butoxycarbonyl)(methyl)amino)ethoxy)-2-(($5^4$-chloro-3,8-dioxa-2(2,6)-pyridina-1(1,3),5(1,2)-dibenzenacyclononaphane-$1^4$-yl)methyl)-1-(oxetan-2-ylmethyl)-1H-benzo[d]imidazole-6-carboxylic acid (12.3 mg, 0.016 mmol) in DCM (2 mL), add TFA (0.1 mL, 1 mmol). Stir the mixture at ambient temperature for 15 min, then concentrate the reaction under reduced pressure and purify residue by reverse-phase chromatography using a gradient of 10 to 90% ACN in water (0.1% formic acid added to both solvents) to give the title compound (2.2 mg, 21%). ES/MS (m z): 669 (M+H).

Example 58

(S)-2-(($5^4$-Cyano-$1^6$-fluoro-3,8-dioxa-2(2,6)-pyridina-1,5(1,3)-dibenzenacyclononaphane-$1^4$-yl)methyl)-4-(2-methoxyethoxy)-1-(oxetan-2-ylmethyl)-1H-benzo[d]imidazole-6-carboxylic acid

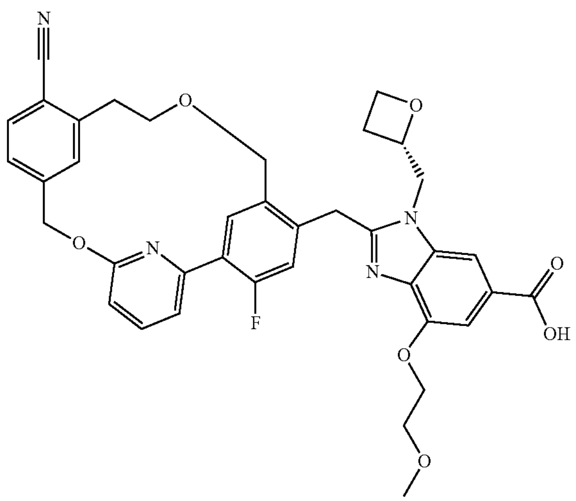 [SMILES: COCCOc1cc(C(=O)O)cc2c1nc(Cc1cc(F)c3cc1COCCc1cc(ccc1C#N)COc1cccc-3n1)n2C[C@@H]1CCO1]

Add 1,5,7-triazabicyclo[4.4.0]dec-5-ene (29 mg, 0.20 mmol) to a degassed suspension of methyl (S)-2-(($5^4$-cyano-$1^6$-fluoro-3,8-dioxa-2(2,6)-pyridina-1,5(1,3)-dibenzenacyclononaphane-$1^4$-yl)methyl)-4-(2-methoxyethoxy)-1-(oxetan-2-ylmethyl)-1H-benzo[d]imidazole-6-carboxylate (50 mg, 0.069 mmol) in a mixture of ACN (1.4 mL), 1,4-dioxane (0.5 mL) and water (0.5 mL). Heat the mixture at 60° C. under $N_2$ for 1.5 h, cool to RT and quench with aqueous citric acid (5%). Filter the solid and wash with water and then ACN to provide the title compound (34 mg, 70%) as a colorless solid. ES-MS m/z 679 (M+H).

Example 59

2-(($5^4$-Cyano-3,9-dioxa-2(2,6)-pyridina-1(1,3),5(1,2)-dibenzenacyclononaphane-$1^4$-yl)methyl)-4-((1-methylpyrrolidin-3-yl)oxy)-1-(((S)-oxetan-2-yl)methyl)-1H-benzo[d]imidazole-6-carboxylic acid

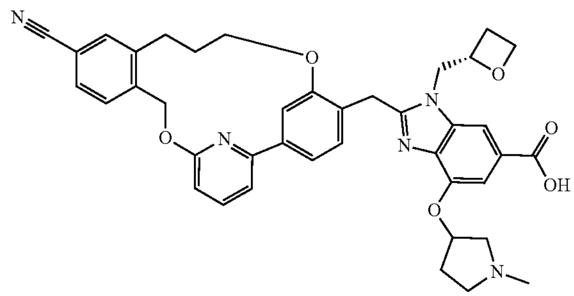 [SMILES: CN1CCC(Oc2cc(C(=O)O)cc3c2nc(Cc2ccc4cc2OCCCc2cc(C#N)ccc2COc2cccc-4n2)n3C[C@@H]2CCO2)C1]

Stir a solution of methyl 2-(($5^4$-cyano-3,9-dioxa-2(2,6)-pyridina-1(1,3),5(1,2)-dibenzenacyclononaphane-$1^4$-yl)methyl)-4-((1-methylpyrrolidin-3-yl)oxy)-1-(((S)-oxetan-2-yl)methyl)-1H-benzo[d]imidazole-6-carboxylate (90 mg, 0.12 mmol) and 1,5,7-triazabicyclo[4.4.0]dec-5-ene (55 mg, 0.39 mmol) in a nitrogen-sparged mixture of 1,4-dioxane (0.4 mL), water (0.4 mL), and ACN (0.4 mL) at 25° C. for 6 h. Adjust the mixture to pH 7 with formic acid and concentrate. Purify the residue via reversed phase chromatography using a gradient of 6 to 46% MeCN in aqueous ammonium hydroxide (0.04%) plus $NH_4HCO_3$ (10 mM) to give 30.5 mg of the title compound (35%). ES-MS m/z 686 (M+H).

Example 60

(S)-2-(($5^4$-Cyano-$1^6$,$2^3$-difluoro-3,8-dioxa-2(2,6)-pyridina-1(1,3),5(1,2)-dibenzenacyclononaphane-$1^4$-yl)methyl)-4-(2-methoxyethoxy)-1-(oxetan-2-ylmethyl)-1H-benzo[d]imidazole-6-carboxylic acid

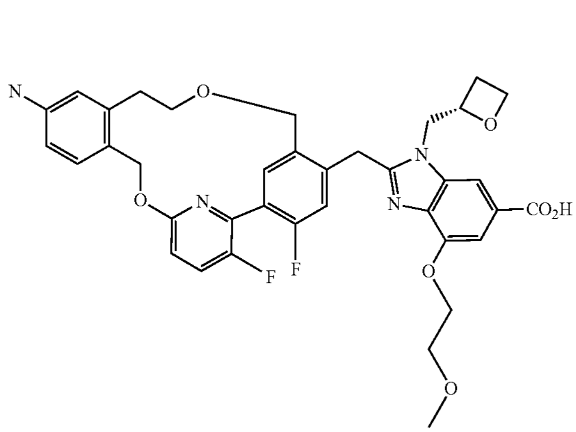 [SMILES: COCCOc1cc(C(=O)O)cc2c1nc(Cc1cc(F)c3cc1COCCc1cc(N)ccc1COc1ccc(F)c-3n1)n2C[C@@H]1CCO1]

To a degassed solution of methyl (S)-2-((5$^4$-cyano-1$^6$,2$^3$-difluoro-3,8-dioxa-2(2,6)-pyridina-1(1,3),5(1,2)-dibenzenacyclononaphane-1$^4$-yl)methyl)-4-(2-methoxyethoxy)-1-(oxetan-2-ylmethyl)-1H-benzo[d]imidazole-6-carboxylate (250 mg, 0.16 mmol) in THE (1.17 mL), water (1.17 mL) and ACN (3.51 mL) add 1,5,7-triazabicyclo[4.4.0]dec-5-ene (150 mg, 1.06 mmol). Seal the reaction vessel and purge with nitrogen. Heat the reaction mixture to 45° C. and stir at this temperature for 2 h. Quench the reaction with 1 M aqueous citric acid until pH=4.5, then filter the colorless solid and dry under reduced pressure. Purify the solid by preparative HPLC (column: Welch Xtimate C18 150×25 mm, 5 μm); mobile phase: gradient of 25 to 60% ACN in aqueous formic acid) to give the title compound as a colorless solid (53.9 mg, 49%) ES-MS m/z 697 (M+H).

Example 61

(S)-2-((5$^4$-cyano-3,8-dioxa-2(2,6)-pyridina-1(1,3),5(1,2)-dibenzenacyclononaphane-1$^4$-yl)methyl)-4-fluoro-1-(oxetan-2-ylmethyl)-1H-benzo[d]imidazole-6-carboxylic acid

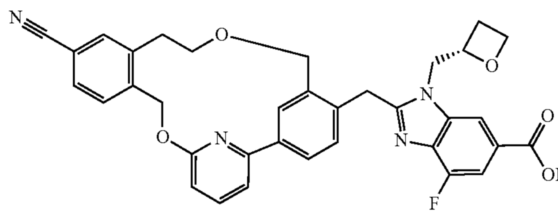

Stir a solution of methyl (S)-2-((5$^4$-cyano-3,8-dioxa-2(2,6)-pyridina-1(1,3),5(1,2)-dibenzenacyclononaphane-1$^4$-yl)methyl)-4-fluoro-1-(oxetan-2-ylmethyl)-1H-benzo[d]imidazole-6-carboxylate (20 mg, 0.03 mmol) and 1,3,4,6,7,8-hexahydro-2H-pyrimido[1,2-A]pyrimidine (20 mg, 0.1 mmol) in ACN (6 mL) and water (4 mL) at 45° C. for 7 h. Adjust to pH 6 with formic acid and extract with 3:1 chloroform:isopropanol. Dry the organic layer over magnesium sulfate, filter, and concentrate. Purify the residue via silica gel chromatography using a gradient of 0 to 10% (MeOH+10% formic acid) in DCM to give 4 mg of the title compound (20%). ES-MS m/z 605 (M+H).

Example 62

(S)-2-((5$^4$-Cyano-3,9-dioxa-2(2,6)-pyridina-1(1,3),5(1,2)-dibenzenacyclononaphane-1$^4$-yl)methyl)-4-(2-(dimethylamino)-2-oxoethoxy)-1-(oxetan-2-ylmethyl)-1H-benzo[d]imidazole-6-carboxylic acid

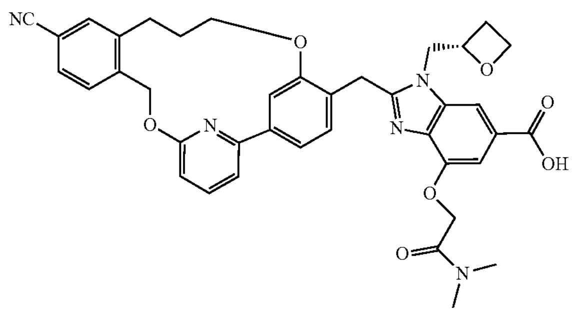 [SMILES: CN(C)C(=O)COc1cc(C(=O)O)cc2c1nc(Cc1ccc3cc1OCCCc1cc(C#N)ccc1COc1cccc-3n1)n2C[C@@H]1CCO1]

Stir a solution of methyl (S)-2-((5$^4$-cyano-3,9-dioxa-2(2,6)-pyridina-1(1,3),5(1,2)-dibenzenacyclononaphane-1$^4$-yl)methyl)-4-(2-(dimethylamino)-2-oxoethoxy)-1-(oxetan-2-ylmethyl)-1H-benzo[d]imidazole-6-carboxylate (50 mg, 0.0356 mmol) with trimethyltin hydroxide (34 mg, 0.178630 mmol) in 1,2-dichloroethane (1 mL) at 80° C. for 16 h. Increase the temperature to 90° C. for 7 h, and then to 100° C. for 72 h. Add additional trimethyltin hydroxide (34 mg, 0.179 mmol) and heat to 105° C. for 18 h. Allow the reaction mixture too cool to ambient temperature and concentrate under vacuum. Add 15% aqueous citric acid (1 mL) to form a gum that is filtered slowly over a fritted funnel. Wash the gum with water (2 mL) and dry at 60° C. in a vacuum oven. Purify the crude product by preparative HPLC [column: Phenomenex Kinetex EVO C18 250×30 mm, 5 μm; mobile phase: gradient of 0 to 100% ACN in aqueous $NH_4HCO_3$ (10 mM+5% MeOH)] to give the title compound as a colorless solid (12.5 mg, 51%). ES-MS m/z 688 (M+H).

Example 63

2-((5$^4$-Cyano-3,9-dioxa-2(2,6)-pyridina-1(1,3),5(1,2)-dibenzenacyclononaphane-1$^4$-yl)methyl)-1-((1-ethyl-1H-imidazol-5-yl)methyl)-4-methoxy-1H-benzo[d]imidazole-6-carboxylic acid

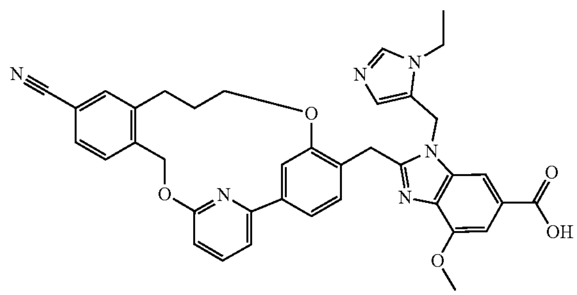 [SMILES: CCn1cncc1Cn1c(Cc2ccc3cc2OCCCc2cc(C#N)ccc2COc2cccc-3n2)nc2c(OC)cc(C(=O)O)cc21]

Use nitrogen to sparge a solution of 1,5,7-triazabicyclo[4.4.0]dec-5-ene (28 mg, 0.197 mmol) in a mixture of ACN (0.4 mL), 1,4-dioxane (0.4 mL), and water (0.15 mL) for 10 min. Add the oxygen-free solution to a reaction vessel methyl 2-((5$^4$-cyano-3,9-dioxa-2(2,6)-pyridina-1(1,3),5(1,2)-dibenzenacyclononaphane-1$^4$-yl)methyl)-1-((1-ethyl-1H-imidazol-5-yl)methyl)-4-methoxy-1H-benzo[d]imidazole-6-carboxylate (44 mg, 0.065 mmol). Stir the mixture at ambient temperature for 24 h. Partition the reaction mixture between EtOAc and 0.1 M aqueous HCl. Separate the organic layer and wash with saturated aqueous NaCl, dry over $MgSO_4$, filter, and concentrate under reduced pressure. Purify by the residue by preparative HPLC [column: Phenomenex Kinetex® EVO C18 100×30 mm, 5 μm; mobile phase: gradient of 14 to 48% ACN in aqueous formic acid (0.1%)] to afford the title compound (8.2 mg, 19%). ES-MS m/z 655 (M+H).

Example 64

(S)-2-(($5^4$-Cyano-3,8-dioxa-2(2,6)-pyridina-1(1,3),5(1,2)-dibenzenacyclononaphane-$1^4$-yl)methyl)-4-(2-methoxyethoxy)-1-(oxetan-2-ylmethyl)-1H-benzo[d]imidazole-6-carboxylic acid

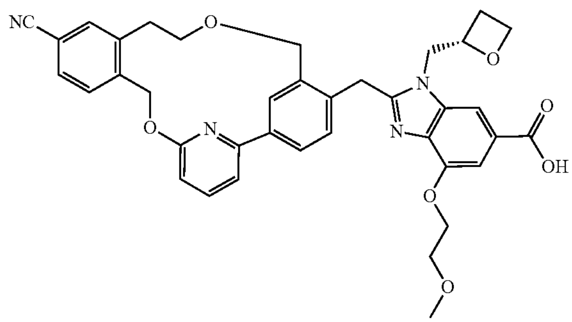 [SMILES: COCCOc1cc(C(=O)O)cc2c1nc(Cc1ccc3cc1COCCc1cc(C#N)ccc1COc1cccc-3n1)n2C[C@@H]1CCO1]

To a suspension of methyl (S)-2-(($5^4$-cyano-3,8-dioxa-2(2,6)-pyridina-1(1,3),5(1,2)-dibenzenacyclononaphane-$1^4$-yl)methyl)-4-(2-methoxyethoxy)-1-(oxetan-2-ylmethyl)-1H-benzo[d]imidazole-6-carboxylate (23 mg, 0.033 mmol) in degassed ACN (0.5 mL), THE (0.2 mL) and water (0.2 mL), add 1,5,7-triazabicyclo[4.4.0]dec-5-ene (15 mg, 0.11 mmol). Heat the mixture to 55° C. for 3 h, then cool to RT and add 5% aqueous citric acid to bring pH=4-5. Filter the resulting solid, wash the solid with water (3 times) and ACN, then dry under vacuum at 45° C. overnight to give the title compound as a beige solid (15 mg, 63%). ES-MS m/z 661 (M+H).

Example 65

(S)-2-(($5^4$-Cyano-3,8-dioxa-2(2,6)-pyridina-1,5(1,3)-dibenzenacyclononaphane-$1^4$-yl)methyl)-4-(2-methoxyethoxy)-1-(oxetan-2-ylmethyl)-1H-benzo[d]imidazole-6-carboxylic acid

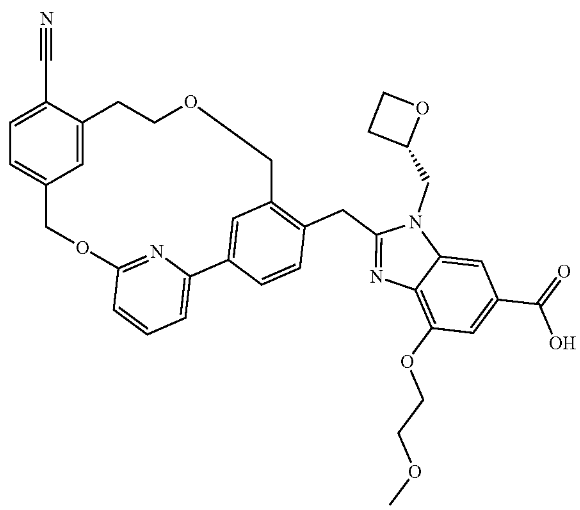 [SMILES: COCCOc1cc(C(=O)O)cc2c1nc(Cc1ccc3cc1COCCc1cc(ccc1C#N)COc1cccc-3n1)n2C[C@@H]1CCO1]

Add 1,5,7-triazabicyclo[4.4.0]dec-5-ene (26 mg, 0.18 mmol) to a degassed suspension of methyl (S)-2-(($5^4$-cyano-3,8-dioxa-2(2,6)-pyridina-1,5(1,3)-dibenzenacyclononaphane-$1^4$-yl)methyl)-4-(2-methoxyethoxy)-1-(oxetan-2-ylmethyl)-1H-benzo[d]imidazole-6-carboxylate (45 mg, 0.067 mmol) in a mixture of ACN (1.4 mL), 1,4-dioxane (0.5 mL) and water (0.5 mL). Heat the mixture at 60° C. under $N_2$ for 1.5 h, cool to RT and quench with aqueous citric acid (5%). Filter the solid and wash with water and then ACN to provide the title compound (26 mg, 59%) as a white solid. ES-MS m/z 661 (M+H).

Example 66

(S)-2-(($5^4$-(4-Fluoro-1H-imidazol-1-yl)-3,9-dioxa-2(2,6)-pyridina-1(1,3),5(1,2)-dibenzenacyclononaphane-$1^4$-yl)methyl)-1-(oxetan-2-ylmethyl)-1H-benzo[d]imidazole-6-carboxylic acid

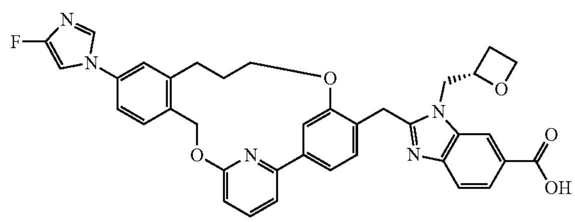 [SMILES: O=C(O)c1ccc2nc(Cc3ccc4cc3OCCCc3cc(-n5cnc(F)c5)ccc3COc3cccc-4n3)n(C[C@@H]3CCO3)c2c1]

Add aqueous LiOH (1M, 120 μL, 0.12 mmol) to a suspension of methyl (S)-2-(($5^4$-(4-fluoro-1H-imidazol-1-yl)-3,9-dioxa-2(2,6)-pyridina-1(1,3),5(1,2)-dibenzenacyclononaphane-$1^4$-yl)methyl)-1-(oxetan-2-ylmethyl)-1H-benzo[d]imidazole-6-carboxylate (30 mg, 0.045 mmol) in a mixture of MeOH (300 μL) and THE (600 μL) and stir at 60° C. for 12 h. Concentrate the reaction mixture and add aqueous citric acid (5%). Filter off the solid, wash with water, ACN and MeOH to provide the title compound (11 mg, 47%) as a pale brown solid. ES-MS m/z 646 (M+H).

Example 67

(S)-2-(($5^4$-Chloro-$1^6$-fluoro-3,7-dioxa-2(2,6)-pyridina-1(1,3),5(1,2)-dibenzenacyclooctaphane-$1^4$-yl)methyl)-4-(2-methoxyethoxy)-1-(oxetan-2-ylmethyl)-1H-benzo[d]imidazole-6-carboxylic acid

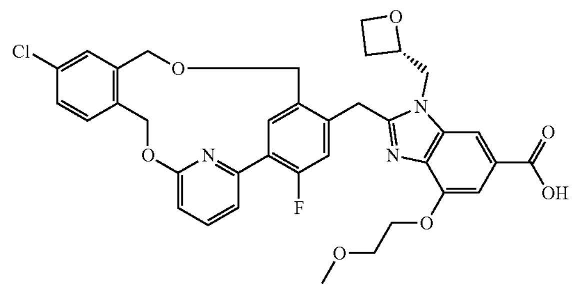 [SMILES: COCCOc1cc(C(=O)O)cc2c1nc(Cc1cc(F)c3cc1COCc1cc(Cl)ccc1COc1cccc-3n1)n2C[C@@H]1CCO1]

Add aqueous LiOH (1 M, 1.6 mL, 1.6 mmol) to a suspension of methyl (S)-2-(($5^4$-chloro-$1^6$-fluoro-3,7-dioxa-2(2,6)-pyridina-1(1,3),5(1,2)-dibenzenacyclooctaphane-$1^4$-yl)methyl)-4-(2-methoxyethoxy)-1-(oxetan-2-ylmethyl)-1H-benzo[d]imidazole-6-carboxylate (285 mg, 0.39 mmol) in a mixture of THE (8.5 mL) and MeOH (4.3 mL). Heat the mixture at 60° C. for 3 h. Concentrate the reaction mixture, add aqueous citric acid (5%), then filter off the solid and wash it with water and ACN. Dry the solid under vacuum at 40° C. to obtain the title compound (285 mg, 100%) as a white solid. ES-MS m/z 674, 676 (M+H).

Example 68

(S)-2-(($5^4$-Cyano-$1^6$-fluoro-3,7-dioxa-2(2,6)-pyridina-1(1,3),5(1,2)-dibenzenacyclooctaphane-$1^4$-yl)methyl)-4-(2-methoxyethoxy)-1-(oxetan-2-ylmethyl)-1H-benzo[d]imidazole-6-carboxylic acid

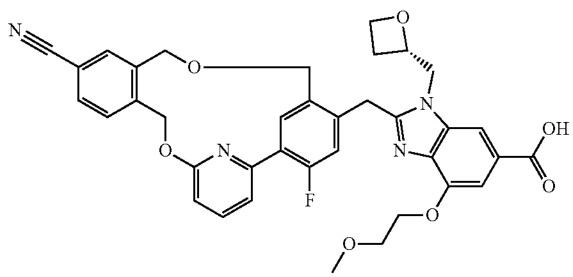 [SMILES: COCCOc1cc(C(=O)O)cc2c1nc(Cc1cc(F)c3cc1COCc1cc(C#N)ccc1COc1cccc-3n1)n2C[C@@H]1CCO1]

Charge a reaction vessel with (S)-2-(($5^4$-chloro-$1^6$-fluoro-3,7-dioxa-2(2,6)-pyridina-1(1,3),5(1,2)-dibenzenacyclooctaphane-$1^4$-yl)methyl)-4-(2-methoxyethoxy)-1-(oxetan-2-ylmethyl)-1H-benzo[d]imidazole-6-carboxylic acid (61 mg, 0.087 mmol), tetrapotassium hexacyanoferrate trihydrate (57 mg, 0.135 mmol), KOAc (19 mg, 0.19 mmol) and chloro(crotyl)(2-dicyclohexylphosphino-2',4',6'-triisopropyl-1,1'-biphenyl) palladium(II) (Pd-170, XPhos Pd(crotyl) Cl, 6.2 mg, 0.009 mmol]. Purge the reaction mixture with $N_2$ and add DMF (1.7 mL) and water (0.9 mL). Purge the mixture again with $N_2$ for 5 min, seal the vessel and stir at 90° C. overnight. Cool the mixture to RT, add aqueous citric acid (5%), filter off the solid and wash with water and ACN. Purify the solid by preparative HPLC [column: XBridge C18 19×150 mm, 5 μm, mobile phase: gradient of 30 to 50% ACN in aqueous $NH_4HCO_3$ (20 mM, pH9) to provide the title compound (9 mg, 16%) as a white solid. ES-MS m/z 665 (M+H).

Example 69

(S)—N-((Cyclopropylmethyl)sulfonyl)-2-(($5^4$-fluoro-$1^6$-methyl-3,9-dioxa-2(2,6)-pyridina-1(1,3),5(1,2)-dibenzenacyclononaphane-$1^4$-yl)methyl)-4-methoxy-1-(oxetan-2-ylmethyl)-1H-benzo[d]imidazole-6-carboxamide

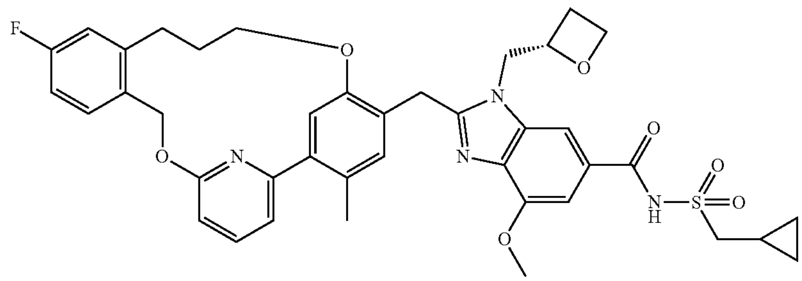 [SMILES: COc1cc(C(=O)NS(=O)(=O)CC2CC2)cc2c1nc(Cc1cc(C)c3cc1OCCCc1cc(F)ccc1COc1cccc-3n1)n2C[C@@H]1CCO1]

To a solution of (S)-4-methoxy-2-(($1^6$-methyl-$5^4$-(fluoro)-3,9-dioxa-2(2,6)-pyridina-1(1,3),5(1,2)-dibenzenacyclononaphane-$1^4$-yl)methyl)-1-(oxetan-2-ylmethyl)-1H-benzo[d]imidazole-6-carboxylic acid (100 mg, 0.16 mmol) in DCM (2 mL) add 4-dimethylaminopyridine (20 mg, 0.16 mmol) cyclopropylmethanesulfonamide (35 mg, 0.26 mmol), TEA (0.1 mL, 0.7 mmol) and purge the mixture gently with $N_2$ for 10 min. Add EDC (50 mg, 0.26 mmol) to the reaction mixture, stir at RT overnight, then heat the reaction at 40° C. for 4 h. Quench the reaction with aqueous citric acid (5%) and dilute with DCM. Separate the phases and the extract the aqueous layer twice with DCM. Combined the organic phases, wash them with saturated aqueous NaCl, dry over $Na_2SO_4$, filter off the solid by filtration and remove the solvent under reduced pressure. Purify the residue by preparative HPLC [column: Xbridge C18 150×19 mm, 5 μm, mobile phase: gradient of 50 to 80% ACN in aqueous $NH_4CO_3$ (20 mM, pH=9)] to give the titled product as a white solid (28 mg, 23.6%) ES-MS m/z 741 (M+H).

Example 70

(S)-2-(($5^4$-Cyano-$1^6$,$5^6$-difluoro-3,8-dioxa-2(2,6)-pyridina-1(1,3),5(1,2)-dibenzenacyclononaphane-$1^4$-yl)methyl)-4-(2-methoxyethoxy)-1-(oxetan-2-ylmethyl)-1H-benzo[d]imidazole-6-carboxylic acid

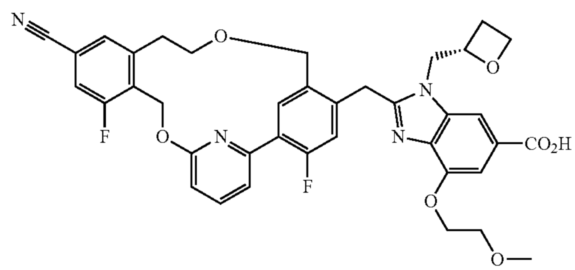 [SMILES: COCCOc1cc(C(=O)O)cc2c1nc(Cc1cc(F)c3cc1COCCc1cc(C#N)cc(F)c1COc1cccc-3n1)n2C[C@@H]1CCO1]

Prepare the title compound essentially as described in Example 68 using (S)-2-(($5^4$-chloro-$1^6$,$5^6$-difluoro-3,8-dioxa-2(2,6)-pyridina-1(1,3),5(1,2)-dibenzenacyclononaphane-$1^4$-yl)methyl)-4-(2-methoxyethoxy)-1-(oxetan-2-ylmethyl)-1H-benzo[d]imidazole-6-carboxylic acid as starting material, using a 2.5:1 mixture of 1,4-dioxane:water as solvent, heating the reaction to 90° C. for 4 h. Purify by preparative HPLC [column: C18 100×30 mm, 5 μm; mobile phase: gradient of 15 to 85% ACN in aqueous formic acid (0.225%)] to afford the title compound as a white solid. ES-MS m/z 697 (M+H).

Example 71

(S)-2-(($5^4$-(3-Fluoro-4-oxopyridin-1(4H)-yl)-3,9-dioxa-2(2,6)-pyridina-1(1,3),5(1,2)-dibenzenacyclononaphane-$1^4$-yl)methyl)-1-(oxetan-2-ylmethyl)-1H-benzo[d]imidazole-6-carboxylic acid

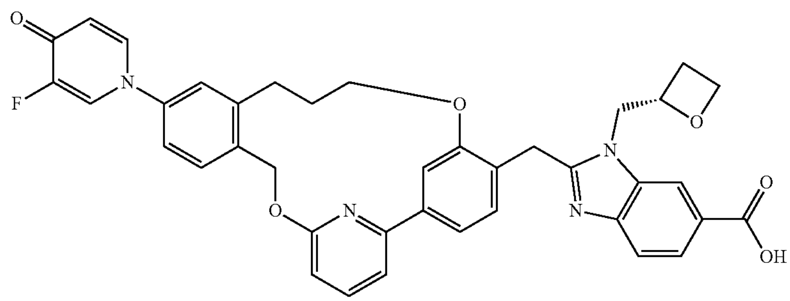 [SMILES: O=C(O)c1ccc2nc(Cc3ccc4cc3OCCCc3cc(-n5ccc(=O)c(F)c5)ccc3COc3cccc-4n3)n(C[C@@H]3CCO3)c2c1]

Charge a reaction vessel with (S)-2-(($5^4$-bromo-3,9-dioxa-2(2,6)-pyridina-1(1,3),5(1,2)-dibenzenacyclononaphane-$1^4$-yl)methyl)-1-(oxetan-2-ylmethyl)-1H-benzo[d]imidazole-6-carboxylic acid (51 mg, 0.079 mmol), 3-fluoropyridin-4-ol (14 mg, 0.12 mmol), copper(I) iodide (1.6 mg, 0.008 mmol) and $K_2CO_3$ (22 mg, 0.156 mmol). Purge the reaction vessel with $N_2$, then add anhydrous DMSO (80 μL) and 2,2,6,6-tetramethyl-3,5-heptanedione (7 μL, 0.033 mmol). Stir the reaction mixture at 120° C. for 9 h. Cool the mixture to RT, add aqueous citric acid (5%), then filter off the solid and wash it with water. Purify by preparative HPLC [column: XBridge C18 19×150 mm, 5 μm; mobile phase: gradient of 30 to 60% ACN in aqueous $NH_4HCO_3$ (20 mM, pH9)] to provide the title compound (10 mg, 18%) as a white solid. ES-MS m/z 673 (M+H).

Example 72

(S)-2-(($5^4$-(4-Methyl-1H-imidazol-1-yl)-3,9-dioxa-2(2,6)-pyridina-1(1,3),5(1,2)-dibenzenacyclononaphane-$1^4$-yl)methyl)-1-(oxetan-2-ylmethyl)-1H-benzo[d]imidazole-6-carboxylic acid

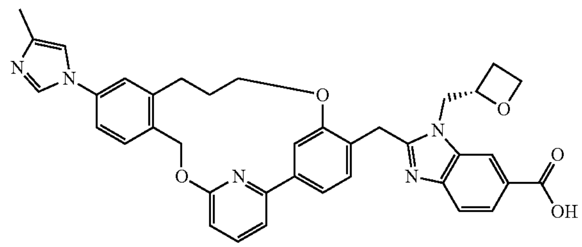 [SMILES: Cc1cn(-c2ccc3c(c2)CCCOc2cc(ccc2Cc2nc4ccc(C(=O)O)cc4n2C[C@@H]2CCO2)-c2cccc(n2)OC3)cn1]

Add anhydrous DMSO (0.06 mL) to a mixture of (S)-2-(($5^4$-bromo-3,9-dioxa-2(2,6)-pyridina-1(1,3),5(1,2)-dibenzenacyclononaphane-$1^4$-yl)methyl)-1-(oxetan-2-ylmethyl)-1H-benzo[d]imidazole-6-carboxylic acid (20 mg, 0.031 mmol), 4-methylimidazole (10 mg, 0.119 mmol), tripotassium phosphate (13 mg, 0.059 mmol), $N^1$,$N^2$-bis(furan-2-ylmethyl)oxalamide (3 mg, 0.012 mmol) and copper(I) oxide (5 mg, 0.034 mmol). Purge the reaction vessel with argon, seal the vessel and heat to 120° C. with stirring for 19 h. Combine the reaction mixture in DCM (20 mL) with a second mixture prepared under similar conditions with bis(tetrabutylammonium iodide)copper(I) iodide (7 mg, 0.006 mmol) in place of copper(I) oxide. Add water (5 mL), 2-propanol (5 mL), aqueous citric acid (5%, 5 mL) and saturated aqueous NaCl (20 mL), then shake the mixture and separate the phases. Extract the aqueous phase using 4:1 DCM:2-propanol (50 mL in two portions). Adjust the aqueous pH to 3 using aqueous tripotassium phosphate and extract again using 4:1 DCM:2-propanol (15 mL). Combine the organic extracts and concentrate under reduced pressure. Purify the residue by reverse-phase chromatography using a gradient of 30 to 60% ACN in aqueous $NH_4HCO_3$ (10 mM, pH=9) to give the title compound (6 mg, 15%) as a solid. ES-MS m/z 642 (M+H).

Example 73

(S)-2-(($5^4$-(1H-Imidazol-1-yl)-3,9-dioxa-2(2,6)-pyridina-1(1,3),5(1,2)-dibenzenacyclononaphane-$1^4$-yl)methyl)-1-(oxetan-2-ylmethyl)-1H-benzo[d]imidazole-6-carboxylic acid

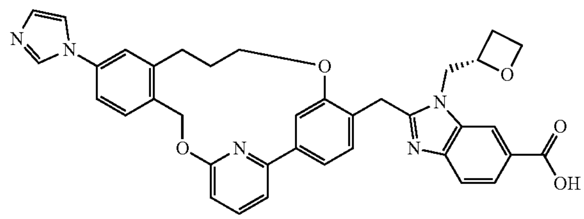 [SMILES: O=C(O)c1ccc2nc(Cc3ccc4cc3OCCCc3cc(-n5ccnc5)ccc3COc3cccc-4n3)n(C[C@@H]3CCO3)c2c1]

Add anhydrous DMSO (0.20 mL) to a mixture of (S)-2-(($5^4$-bromo-3,9-dioxa-2(2,6)-pyridina-1(1,3),5(1,2)-dibenzenacyclononaphane-$1^4$-yl)methyl)-1-(oxetan-2-ylmethyl)-1H-benzo[d]imidazole-6-carboxylic acid (30 mg, 0.046 mmol), imidazole (13 mg, 0.189 mmol), tripotassium phosphate (20 mg, 0.091 mmol), $N^1$,$N^2$-bis(furan-2-ylmethyl)oxalamide (5 mg, 0.02 mmol) and copper(I) oxide (3 mg, 0.02 mmol). Purge the vessel with argon, seal the vessel and then heat to 120° C. with stirring for 20 h. Transfer the reaction mixture to a MeOH-washed strong anion exchange resin cartridge (Isolute© SAX) and elute sequentially with 7:3 MeOH/water, MeOH, DCM, and 1:1 DCM:MeOH with 3% acetic acid. Combine fractions containing the title compound and concentrate under reduced pressure. Dissolve the residue in DMSO and then purify the mixture by reverse-phase chromatography using a gradient of 30 to 60% ACN in aqueous $NH_4HCO_3$ (10 mM, pH=9). Concentrate the appropriate fractions under reduced pressure. Triturate the solid residue in 1:1 DCM:EtOAc (4 mL) and partially concentrate the mixture to remove DCM. Centrifuge the suspension, remove the supernatant liquid and then dry the residue at 50° C. under reduced pressure for 24 h to afford 9.4 mg of the title compound (29% yield) as a white solid. ES-MS m/z 628 (M+H).

Example 74

(S)-1-(Oxetan-2-ylmethyl)-2-(($5^4$-(4-oxopyridin-1(4H)-yl)-3,9-dioxa-2(2,6)-pyridina-1(1,3),5(1,2)-dibenzenacyclononaphane-$1^4$-yl)methyl)-1H-benzo[d]imidazole-6-carboxylic acid

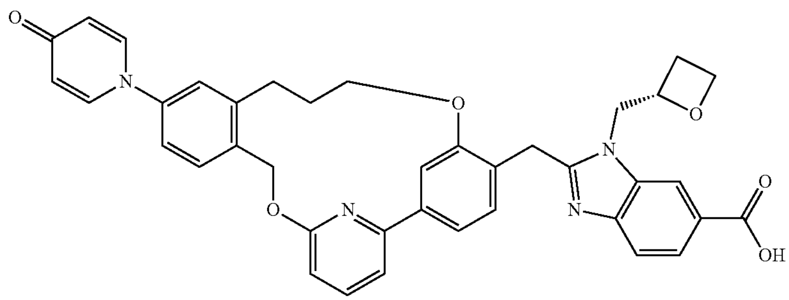 [SMILES: O=C(O)c1ccc2nc(Cc3ccc4cc3OCCCc3cc(-n5ccc(=O)cc5)ccc3COc3cccc-4n3)n(C[C@@H]3CCO3)c2c1]

Add anhydrous DMSO (80 μL) and 2,2,6,6-tetramethyl-3,5-heptanedione (7 μL, 0.033 mmol) to a nitrogen-purged mixture of (S)-2-(($5^4$-bromo-3,9-dioxa-2(2,6)-pyridina-1(1,3),5(1,2)-dibenzenacyclononaphane-$1^4$-yl)methyl)-1-(oxetan-2-ylmethyl)-1H-benzo[d]imidazole-6-carboxylic acid (50 mg, 0.078 mmol), 4-hydroxypyridine (10 mg, 0.102 mmol), copper(I) iodide (1.6 mg, 0.008 mmol) and $K_2CO_3$ (22 mg, 0.156 mmol). Seal the vessel and stir at 120° C. for 16 h. Cool the mixture to RT, add aqueous citric acid (5%), filter off the solid and wash it with water. Purify the solid by preparative HPLC [column: XBridge C18 19×150 mm, 5 μm; mobile phase: gradient of 25 to 55% ACN in aqueous $NH_4HCO_3$ (20 mM, pH=9)], then wash the solid product with MeOH and ACN to give the title compound (11 mg, 18%) as a colorless solid. ES-MS m/z 655 (M+H).

Example 75

(S)-2-(($1^6$-Fluoro-$5^4$-(1-methyl-6-oxo-1,6-dihydropyridin-3-yl)-3,7-dioxa-2(2,6)-pyridina-1(1,3),5(1,2)-dibenzenacyclooctaphane-$1^4$-yl)methyl)-4-(2-methoxyethoxy)-1-(oxetan-2-ylmethyl)-1H-benzo[d]imidazole-6-carboxylic acid

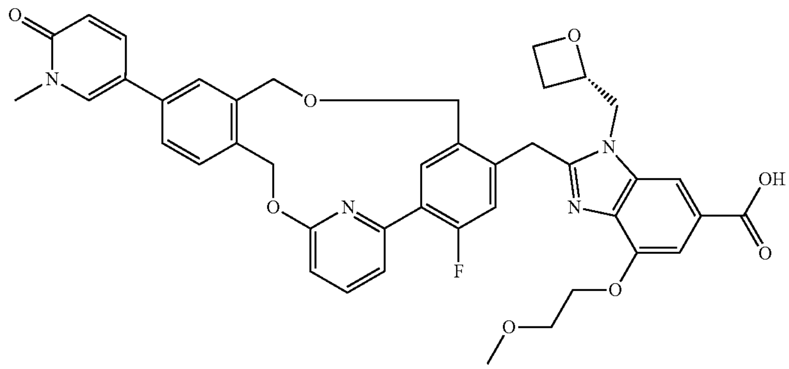 [SMILES: COCCOc1cc(C(=O)O)cc2c1nc(Cc1cc(F)c3cc1COCc1cc(-c4ccc(=O)n(C)c4)ccc1COc1cccc-3n1)n2C[C@@H]1CCO1]

Charge a reaction vessel with (S)-2-(($5^4$-chloro-$1^6$-fluoro-3,7-dioxa-2(2,6)-pyridina-1(1,3),5(1,2)-dibenzenacyclooctaphane-$1^4$-yl)methyl)-4-(2-methoxyethoxy)-1-(oxetan-2-ylmethyl)-1H-benzo[d]imidazole-6-carboxylic acid (61 mg, 0.087 mmol), 1-methyl-5-(4,4,5,5-tetramethyl-1,3,2-dioxaborolan-2-yl)pyridin-2(1H)-one (43 mg, 0.174 mmol) and chloro(crotyl)(2-dicyclohexylphosphino-2',4',6'-triisopropyl-1,1'-biphenyl) palladium(II) (Pd-170, XPhos Pd(crotyl) Cl, 6.2 mg, 0.009 mmol). Purge the vessel with $N_2$, add DMF (860 μL) and aqueous potassium phosphate tribasic (1 M, 260 μL, 0.26 mmol), and stir the mixture at 90° C. for 2.5 h. Cool the mixture to RT, add aqueous citric acid (5%), filter off the solid and wash it with water and ACN. Purify the solid by preparative HPLC [column: XBridge C18, 19×150 mm, 5 μm; mobile phase: gradient of 30 to 60% ACN in $NH_4HCO_3$ (20 mM, pH=9)] to provide the title compound (9.5 mg, 14%) as a pale brown solid. ES-MS m/z 747 (M+H).

Biological Assays

Human GLP-1 Receptor HEK293 Cell cAMP Assay

GLP-1 Receptor functional activity is determined using cAMP formation in an HEK293 clonal cell line expressing human GLP-1R (NCBI accession number NP_002053) at an expression density of 581±94 (n=6) and 104±12 (n=5) fmol/mg protein (determined using [$^{125}$I]GLP-1(7-36)$NH_2$ homologous competition binding analysis). The hGLP-1R receptor expressing cells are treated with compound (20 point concentration-response curve in DMSO, 2.75-fold Labcyte Echo direct dilution, 384 well plate Corning Cat #3570) in DMEM (Gibco Cat #31053) supplemented with 1× GlutaMAX™ (Gibco Cat #35050), 0.1% bovine casein (Sigma C4765-10ML), 250 μM IBMX (3-Isobutyl-1-methylxanthine, Acros Cat #228420010) and 20 mM HEPES (Gibco Cat #15630) in a 20 μL assay volume (final DMSO concentration is 0.5%). After a 30 min incubation at 37° C., the resulting increase in intracellular cAMP is quantitatively determined using the CisBio cAMP Dynamic 2 HTRF Assay Kit (62AM4PEJ). Briefly, cAMP levels within the cell are detected by adding the cAMP-d2 conjugate in cell lysis buffer (10 μL) followed by the antibody anti-cAMP-$Eu^{3+}$-Cryptate, also in cell lysis buffer (10 μL). The resulting competitive assay is incubated for at least 60 min at RT, then detected using a PerkinElmer Envision® instrument with excitation at 320 nm and emission at 665 nm and 620 nm. Envision units (emission at 665 nm/620 nm*10,000) are inversely proportional to the amount of cAMP present and are converted to nM cAMP per well using a cAMP standard curve. The amount of cAMP generated (nM) in each well is converted to a percent of the maximal response observed with human GLP-1(7-36)$NH_2$. A relative $EC_{50}$ value and percent top ($E_{max}$) are derived by non-linear regression analysis using the percent maximal response vs. the concentration of compound added, fitted to a four-parameter logistic equation. The $EC_{50}$ and $E_{max}$ data when the compounds of Examples 1 to 80 are tested in the cAMP assay described above using HEK293 cells expressing 581 and 104 fmol/mg GLP-1R are shown in Tables 1 and 2, respectively. These data indicate that the compounds of Examples 1 to 80 are agonists of the human GLP-1 receptor.

TABLE 1

HEK293 cell line with 581 fmol/mg expression density of GLP-1R, intracellular cAMP response, relative $EC_{50}$ and $E_{max}$

| Example | $EC_{50}$ nM (SEM, n) | Emax % (SEM, n) |
|---|---|---|
| 1 | 19.8 (1.6, n = 11) | 95 (2, n = 11) |
| 2 | 8.05 (1.29, n = 8) | 98 (3, n = 8) |
| 3 | 44.1 (3.8, n = 7) | 102 (4, n = 7) |

TABLE 1-continued

HEK293 cell line with 581 fmol/mg expression density of GLP-1R, intracellular cAMP response, relative $EC_{50}$ and $E_{max}$

| Example | $EC_{50}$ nM (SEM, n) | Emax % (SEM, n) |
|---|---|---|
| 4 | 90.6 (10, n = 7) | 99.2 (4.28, n = 7) |
| 5 | 6.58 (1.44, n = 7) | 109 (4.36, n = 7) |
| 6 | 166 (13.2, n = 8) | 97.2 (3.39, n = 8) |
| 7 | 20.1 (1.59, n = 6) | 104 (2.31, n = 6) |
| 8 | 168 (13.8, n = 6) | 90.5 (2.66, n = 6) |
| 9 | 1.8 (0.162, n = 8) | 118 (3.15, n = 8) |
| 10 | 35.3 (5.55, n = 6) | 107 (3.33, n = 6) |
| 11 | 35 (5.55, n = 6) | 92 (3.95, n = 6) |
| 12 | 20.2 (1.7, n = 8) | 81.8 (2.72, n = 8) |
| 13 | 120 (13.8, n = 6) | 88.5 (14.6, n = 7) |
| 14 | 72.3 (13.7, n = 6) | 109 (9.07, n = 6) |
| 15 | 6.74 (1.66, n = 7) | 105 (3.52, n = 7) |
| 16 | 1.95 (0.192, n = 7) | 125 (5.59, n = 7) |
| 17 | 10.5 (1.7, n = 4) | 121 (4.32, n = 4) |
| 18 | 50.3 (4.89, n = 7) | 115 (1.06, n = 7) |
| 19 | 55.4 (4.79, n = 8) | 103 (2.54, n = 8) |
| 20 | 58 (6.74, n = 6) | 105 (2.78, n = 6) |
| 21 | 35.1 (3.83, n = 4) | 111 (2.5, n = 4) |
| 22 | 2.86 (0.448, n = 7) | 112 (3.81, n = 7) |
| 23 | 69.3 (14.2, n = 9) | 106 (4.01, n = 9) |
| 24 | 2.34 (0.205, n = 5) | 116 (1.38, n = 5) |
| 25 | 317 (n = 1) | 98.3 (n = 1) |
| 26 | 1.66 (0.187, n = 7) | 116 (5.67, n = 7) |
| 27 | 50.7 (10.9, n = 5) | 107 (4.75, n = 5) |
| 28 | 98.4 (21.7, n = 5) | 104 (3.43, n = 5) |
| 29 | 262 (26.8, n = 4) | 92.4 (5.22, n = 4) |
| 30 | 35.6 (5.32, n = 5) | 98.1 (3.78, n = 5) |
| 31 | 70.1 (11.7, n = 4) | 104 (10.4, n = 4) |
| 32 | 178 (6.11, n = 3) | 98.9 (4.91, n = 3) |
| 33 | 40.8 (6.25, n = 4) | 112 (3.19, n = 4) |
| 34 | 167 (28.5, n = 4) | 110 (2.24, n = 4) |
| 35 | 95.8 (10.8, n = 3) | 112 (3.26, n = 3) |
| 36 | 44 (1.34, n = 4) | 108 (7.43, n = 4) |
| 37 | 179 (28.8, n = 4) | 103 (3.15, n = 4) |
| 38 | 300 (n = 1) | 90.1 (n = 1) |
| 39 | 244 (34.7, n = 4) | 99 (1.85, n = 4) |
| 40 | 42.4 (5.82, n = 4) | 110 (6.38, n = 4) |
| 41 | 184 (11.1, n = 4) | 89.1 (3.96, n = 4) |
| 42 | 187 (22.5, n = 3) | 103 (8.87, n = 3) |
| 43 | 48.6 (3.59, n = 5) | 86.9 (3.5, n = 5) |
| 44 | 4.14 (0.98, n = 5) | 112 (6.25, n = 5) |
| 45 | 2.4 (0.625, n = 4) | 122 (3.53, n = 4) |
| 46 | 7.23 (0.755, n = 3) | 107 (8.58, n = 3) |
| 47 | 25.1 (1.86, n = 3) | 110 (4.79, n = 3) |
| 48 | 11.2 (1.88, n = 3) | 108 (3.83, n = 3) |
| 49 | 2.33 (0.412, n = 4) | 112 (3.83, n = 4) |
| 50 | 38.1 (4.02, n = 4) | 115 (4.45, n = 4) |
| 51 | 41 (2.51, n = 4) | 96.7 (6.62, n = 4) |
| 52 | 58.4 (16.1, n = 3) | 108 (6.21, n = 3) |
| 53 | 77.8 (13.9, n = 4) | 104 (11.3, n = 4) |
| 54 | 440 (77.8, n = 3) | 49.5 (2.94, n = 3) |
| 55 | 8.94 (1.11, n = 5) | 113 (3.06, n = 5) |
| 56 | 55.8 (13.2, n = 4) | 85 (6.71, n = 4) |
| 57 | 440 (98.7, n = 4) | 76.2 (1.11, n = 4) |
| 58 | 0.633 (0.0868, n = 4) | 109 (7.7, n = 4) |
| 59 | 262 (29.5, n = 4) | 90.9 (2.1, n = 4) |
| 60 | 0.938 (0.191, n = 5) | 109 (4.24, n = 5) |
| 61 | 18.1 (3.3, n = 4) | 110 (7.36, n = 4) |
| 62 | 285 (46.7, n = 5) | 62.2 (3.62, n = 5) |
| 63 | 29.9 (19.1, n = 3) | 101 (6.22, n = 3) |
| 64 | 2.13 (0.188, n = 4) | 110 (3.43, n = 4) |
| 65 | 1.86 (0.365, n = 4) | 110 (7.21, n = 4) |
| 66 | 13.4 (n = 1) | 118 (n = 1) |
| 67 | 2.13 (0.342, n = 4) | 117 (6.32, n = 4) |
| 68 | 6.82 (n = 1) | 115 (n = 1) |
| 69 | 59.8 (3.77, n = 6) | 71.6 (2.93, n = 6) |
| 70 | 3.11 (n = 1) | 92.3 (n = 1) |
| 71 | 138 (9.94, n = 4) | 68.4 (8.91, n = 4) |
| 72 | 92.5 (11.8, n = 6) | 106 (4.95, n = 6) |
| 73 | 21.3 (3.51, n = 3) | 106 (4.39, n = 3) |
| 74 | 155 (n = 1) | 92.1 (n = 1) |
| 75 | 6.33 (1.29, n = 4) | 93.9 (3.91, n = 4) |
| 76 | 102 (33.1, n = 2) | 99.9 (1.36, n = 2) |

TABLE 1-continued

| HEK293 cell line with 581 fmol/mg expression density of GLP-1R, intracellular cAMP response, relative $EC_{50}$ and $E_{max}$ | | |
|---|---|---|
| Example | $EC_{50}$ nM (SEM, n) | Emax % (SEM, n) |
| 77 | 193 (18.9, n = 3) | 107 (7.26, n = 3) |
| 78 | 95.8 (10.1, n = 4) | 99.8 (4.21, n = 4) |
| 79 | 369 (20, n = 3) | 34.7 (5.13, n = 3) |
| 80 | 130 (25.3, n = 3) | 84.1 (3.1, n = 3) |

TABLE 2

| HEK293 cell line with 104 fmol/mg expression density of GLP-1R, intracellular cAMP response, relative $EC_{50}$ and $E_{max}$ | | |
|---|---|---|
| Example | $EC_{50}$ nM (SEM, n) | $E_{max}$ % (SEM, n) |
| 1 | 59.7 (9.9, n = 7) | 71 (3, n = 7) |
| 2 | 17.5 (3.7, n = 5) | 72 (2, n = 5) |
| 3 | 132 (19, n = 7) | 84 (4, n = 7) |
| 4 | 384 (87.1, n = 7) | 78.7 (1.84, n = 7) |
| 5 | 22.3 (5.33, n = 7) | 81.6 (2.84, n = 7) |
| 6 | 1020 (200, n = 8) | 89.1 (2.35, n = 8) |
| 7 | 96.8 (19.6, n = 6) | 92.9 (1.68, n = 6) |
| 8 | 815 (133, n = 6) | 81.5 (3.83, n = 6) |
| 9 | 5.44 (0.474, n = 8) | 83.1 (1.67, n = 8) |
| 10 | 147 (22, n = 6) | 88.9 (4.9, n = 6) |
| 11 | 194 (15.5, n = 6) | 81 (1.79, n = 6) |
| 12 | 66.3 (3.11, n = 8) | 46.4 (3.52, n = 8) |
| 13 | 542 (54, n = 6) | 74.7 (12.7, n = 7) |
| 14 | 228 (29, n = 6) | 82.5 (2.49, n = 6) |
| 15 | 26.4 (3.64, n = 7) | 82.8 (2.7, n = 7) |
| 16 | 4.02 (0.333, n = 5) | 86.7 (2.6, n = 5) |
| 17 | 38.4 (5.56, n = 4) | 84.6 (6.33, n = 4) |
| 18 | 169 (17.1, n = 7) | 94.9 (4.24, n = 7) |
| 19 | 197 (26.1, n = 8) | 83 (2.25, n = 8) |
| 20 | 226 (33.6, n = 5) | 89.9 (3.24, n = 5) |
| 21 | 133 (25.9, n = 4) | 95.6 (3.62, n = 4) |
| 22 | 10.6 (1.75, n = 7) | 80.9 (2.76, n = 7) |
| 23 | 344 (68.7, n = 9) | 83.7 (3.25, n = 9) |
| 24 | 6.6 (1.03, n = 4) | 89.6 (3.8, n = 4) |
| 25 | 703 (n = 1) | 62.1 (n = 1) |
| 26 | 5.64 (0.655, n = 7) | 91.3 (3.5, n = 7) |
| 27 | 165 (25.4, n = 5) | 82.5 (5.93, n = 5) |
| 28 | 287 (33.3, n = 5) | 74.9 (4.14, n = 5) |
| 29 | 562 (66.1, n = 4) | 59.2 (6.36, n = 4) |
| 30 | 118 (17.3, n = 5) | 77.1 (4.75, n = 5) |
| 31 | 251 (33.7, n = 4) | 88.8 (2.84, n = 4) |
| 32 | 530 (20.8, n = 3) | 70.9 (3.4, n = 3) |
| 33 | 111 (26.1, n = 4) | 85 (2.39, n = 4) |
| 34 | 616 (78.2, n = 4) | 82.3 (4.5, n = 4) |
| 35 | 385 (8.61, n = 3) | 88.1 (2.92, n = 3) |
| 36 | 149 (12.1, n = 4) | 80 (3.2, n = 4) |
| 37 | 506 (57.1, n = 4) | 79.7 (3.52, n = 4) |
| 38 | 613 (n = 1) | 56.9 (n = 1) |
| 39 | 762 (84.7, n = 4) | 76.6 (5.29, n = 4) |
| 40 | 154 (24.3, n = 4) | 85.9 (4.29, n = 4) |
| 41 | 713 (103, n = 4) | 60.3 (4.83, n = 4) |
| 42 | 539 (35.5, n = 3) | 66.4 (4.88, n = 3) |
| 43 | 194 (29.9, n = 5) | 72 (5.72, n = 5) |
| 44 | 16.4 (5.58, n = 5) | 85.5 (3.02, n = 5) |
| 45 | 7.57 (1.86, n = 4) | 87.9 (3.62, n = 4) |
| 46 | 24.6 (5.48, n = 3) | 91.7 (2.68, n = 3) |
| 47 | 116 (15.4, n = 3) | 108 (2.18, n = 3) |
| 48 | 31.5 (2.81, n = 3) | 86.8 (6.89, n = 3) |
| 49 | 8.39 (1.12, n = 4) | 85.5 (4.12, n = 4) |
| 50 | 128 (18.8, n = 4) | 82.8 (5.92, n = 4) |
| 51 | 152 (17.9, n = 4) | 77.1 (8.25, n = 4) |
| 52 | 153 (27.5, n = 3) | 84.3 (1.76, n = 3) |
| 53 | 293 (62.7, n = 4) | 58 (7.97, n = 4) |
| 54 | 654 (62.6, n = 3) | 18.3 (5, n = 3) |
| 55 | 22.8 (2.26, n = 5) | 84.8 (5.59, n = 5) |
| 56 | 131 (27.6, n = 4) | 41.7 (3.43, n = 4) |
| 57 | 1030 (212, n = 4) | 42.1 (2.24, n = 4) |
| 58 | 1.62 (0.195, n = 4) | 90 (6.63, n = 4) |
| 59 | 515 (38.2, n = 4) | 48.4 (6.45, n = 4) |
| 60 | 2.99 (0.356, n = 5) | 87.9 (4.63, n = 5) |

TABLE 2-continued

| HEK293 cell line with 104 fmol/mg expression density of GLP-1R, intracellular cAMP response, relative $EC_{50}$ and $E_{max}$ | | |
|---|---|---|
| Example | $EC_{50}$ nM (SEM, n) | $E_{max}$ % (SEM, n) |
| 61 | 79.1 (10.5, n = 4) | 93.2 (9.3, n = 4) |
| 62 | 737 (41.9, n = 5) | 32.9 (3.9, n = 5) |
| 63 | 112 (72.1, n = 3) | 81.1 (4.02, n = 3) |
| 64 | 5.53 (0.884, n = 4) | 87.3 (2.6, n = 4) |
| 65 | 4.62 (0.69, n = 4) | 98.2 (2.37, n = 4) |
| 66 | 54.5 (n = 1) | 82.5 (n = 1) |
| 67 | 6.88 (0.996, n = 4) | 91.6 (2.82, n = 4) |
| 68 | 8.72 (n = 1) | 98.5 (n = 1) |
| 69 | 103 (14.3, n = 5) | 26.6 (3.01, n = 5) |
| 70 | 12.6 (n = 1) | 95 (n = 1) |
| 71 | 598 (61.9, n = 4) | 52.1 (9.13, n = 4) |
| 72 | 348 (33.8, n = 6) | 90.4 (4.48, n = 6) |
| 73 | 68.5 (2.21, n = 3) | 84.1 (3.4, n = 3) |
| 74 | 533 (n = 1) | 73.3 (n = 1) |
| 75 | 17.4 (3.1, n = 4) | 71.6 (8.14, n = 4) |
| 76 | 359 (113, n = 2) | 78.2 (7.88, n = 2) |
| 77 | 724 (42.4, n = 3) | 83 (5.01, n = 3) |
| 78 | 248 (12.6, n = 4) | 74.1 (3.39, n = 4) |
| 79 | 648 (47.3, n = 3) | 9.53 (2.66, n = 3) |
| 80 | 303 (26, n = 3) | 56 (5.21, n = 3) |

$EC_{50}$, nM = geometric mean followed by SEM (delta method) with the number of observations in parentheses.
$E_{max}$, % = arithmetic mean followed by ± SEM with the number of observations in parentheses for the percent of maximal response to GLP-1(7-36)$NH_2$ at hGLP-1R GLP-1R CHO Cell β-Arrestin Recruitment Assay Activated G-protein coupled receptors can interact with the β-arrestin family of signaling proteins. The potency of compounds for GLP-1R induced arrestin recruitment is determined using the PathHunter Enzyme Fragment Complementation approach substantially as described (von Degenfeld et al., FASEB J., 2007 (14):3819-26 and Hamdouchi et al., J. Med Chem., 2016 59(24):10891-10916). CHO-K1 cells expressing Pro-Link-tagged Human GLP-1R and enzyme-acceptor-tagged β-arrestin-2 may be obtained from DiscoveRx and prepared as assay-ready frozen cells. Test compounds are solubilized in DMSO and serial dilutions are performed using the Echo acoustic dispenser (LabCyte). Assay media is the PathHunter Cell Assay Buffer (DiscoveRx) containing 0.1% w/v hydrolyzed Casein (Sigma). 100 nL of test compound solution is dispensed into 10 μL of assay media in a 384 well plate and then 10 μL of cells in assay media are added to give 5000 cells per well. Plates are incubated for 90 min in a 37° C./5% $CO_2$ incubator and 10 μL of PathHunter detection reagent is added (DiscoveRx) and plates are incubated at RT for 60 min. Luminescence signal is measured. Compound concentration-response curves fit to a four-parameter logistic model to calculate potency as an $EC_{50}$ and percent top ($E_{max}$). Data normalization to % stimulation is performed using DMSO and GLP-1(7-36) as minimum and maximum controls (Campbell et al, Assay Guidance Manual 2017). The potency of a sample compound to stimulate GLP-1R induced β-arrestin recruitment is reported in Table 3.

TABLE 3

| hGLP1R induced β-Arrestin-2 recruitment relative $EC_{50}$ and $E_{max}$ | | |
|---|---|---|
| Example | $EC_{50}$ nM (SEM, n) | $E_{max}$ % (SEM, n) |
| 1 | 213 (36.7, n = 9) | 42.9 (1.85, n = 9) |
| 2 | 133 (6.65, n = 7) | 52.7 (1.78, n = 7) |
| 3 | 320 (29.4, n = 7) | 34 (2.44, n = 7) |
| 12 | >49500 (n = 1) | 9.47 (1.44, n = 7) |

The invention claimed is:

1. A compound of the formula:

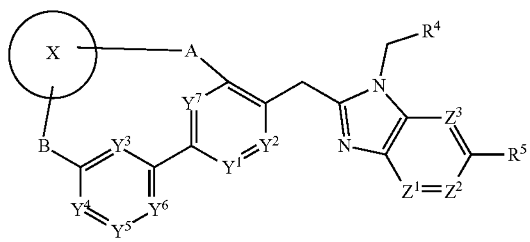

wherein -A- is $—CR_aR^bCR^aR^bCR^bR^bO—$, $—OCR^bR^bCR^aR^bCR^aR^b—$, $—OCR^bR^bCR^bR^bO—$, $—CR^aR^bCR^bR^bOCR^bR^b—$, $—CR^bR^bOCR^bR^bCR_aR^b—$, $—CR^bR^bOCR^bR^b—$, $—CR^aR^bCR^bR^bO—$ or $—OCR^bR^bCR^aR^b—$;

$R^a$ at each occurrence is independently H, halo, $C_1$-$C_2$ alkyl, OH or $C_1$-$C_3$alkoxy;

$R^b$ at each occurrence is independently H, halo or $C_1$-$C_2$alkyl;

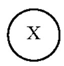

is

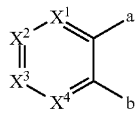

or

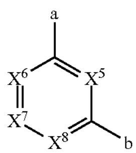

, wherein a is the point of attachment to linker A; b is the point of attachment of linker B;

$X^1$, $X^2$, $X^3$ and $X^4$ are independently N, CH or $CR^1$, wherein no more than two of $X^1$, $X^2$, $X^3$ and $X^4$ are N and no more than two of $X^1$, $X^2$, $X^3$ and $X^4$ are $CR^1$;

$X^5$ is N, CH or $CR^{1a}$, $X^6$, $X^7$ and $X^8$ are independently N, CH or $CR^1$, wherein no more than two of $X^5$, $X^6$, $X^7$ and $X^8$ are N and no more than two of $X^5$, $X^6$, $X^7$ and $X^8$ are $CR^{1a}$ or $CR^1$;

$R^1$ at each occurrence is independently CN; halo; $C_1$-$C_3$alkyl optionally substituted with OH; $C_1$-$C_3$haloalkyl; $C_1$-$C_3$alkoxy; $C_3$-$C_5$cycloalkyl; $—SO_2C_1$-$C_3$alkyl;

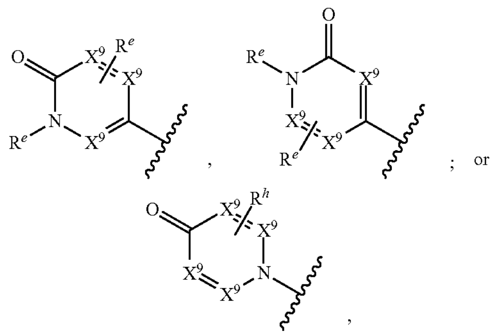

, ; or , wherein each $X^9$ is independently CH or N and no more than one $X^9$ in the ring is N, each $R_e$ is independently selected from: H, $C_1$-$C_3$haloalkyl, halo, $C_3$-$C_5$cycloalkyl and $C_1$-$C_3$alkyl optionally substituted with OH, $R^h$ is H, $C_1$-$C_3$haloalkyl, halo, $C_3$-$C_5$cycloalkyl, OH, $—NR^cR^d$ or $C_1$-$C_3$alkyl optionally substituted with OH; 5- or 6-membered heteroaryl or phenyl wherein the heteroaryl or phenyl is optionally substituted with one or two substituents independently selected from: $C_1$-$C_3$alkoxy, $C_3$-$C_5$cycloalkyl, $—CH_2—C_3$-$C_5$cycloalkyl, $—SO_2C_1$-$C_3$alkyl, $C_4$-$C_5$heterocyclyl, $—CH_2—C_4$-$C_5$heterocyclyl, halo, $C_1$-$C_3$haloalkyl, $C_1$-$C_3$haloalkoxy, CN, $—CONR^cR^d$, $—NR^cR^d$ or $C_1$-$C_3$alkyl optionally substituted with OH;

$R^{1a}$ is CN; halo; $C_1$-$C_3$alkyl optionally substituted with OH; $C_1$-$C_3$haloalkyl; or $C_1$-$C_3$alkoxy;

—B- is $—CH_2O—$, $—OCH_2—$ or $—CH_2NH—$;

$Y^1$, $Y^2$ and $Y^7$ are independently N, CH or $CR_2$, wherein no more than one of $Y^1$, $Y^2$ and $Y^7$ is N and no more than two of $Y^1$, $Y^2$ and $Y^7$ is $CR_2$;

$Y^3$, $Y^4$, $Y^5$ and $Y^6$ are independently N, CH or $CR_2$, wherein no more than two of $Y^3$, $Y^4$, $Y^5$ and $Y^6$ are N and no more than two of $Y^3$, $Y^4$, $Y^5$ and $Y^6$ are $CR_2$;

$R^2$ at each occurrence is independently halo or methyl;

$Z^1$, $Z^2$ and $Z^3$ are independently N, CH or $CR^3$, wherein no more than two of $Z^1$, $Z^2$ and $Z^3$ are N and no more than two of $Z^1$, $Z^2$ and $Z^3$ are $CR^3$;

$R^3$ at each occurrence is independently halo; $C_1$-$C_4$alkyl; $—OC_4$-$C_6$cycloalkyl optionally substituted with $C_1$-$C_2$alkoxy, OH, $C_1$-$C_3$alkyl or $C_1$-$C_3$haloalkyl; $—OC_4$-$C_6$heterocyclyl optionally substituted with $C_1$-$C_2$alkoxy, OH, $C_1$-$C_3$alkyl or $C_1$-$C_3$haloalkyl; or $C_1$-$C_4$alkoxy optionally substituted with one or two substituents selected from: $C_1$-$C_2$alkoxy, OH, $—NR^fR^g$, $—CONR^cR^d$, CN, halo or 5- or 6-membered heteroaryl optionally substituted with $C_1$-$C_3$alkyl;

$R^4$ is

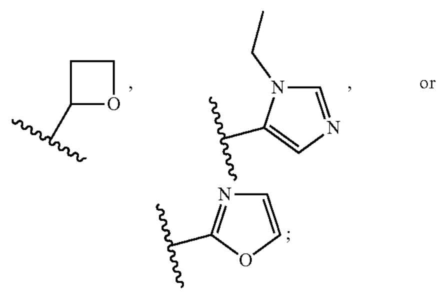

$R^5$ is $—CO_2H$,

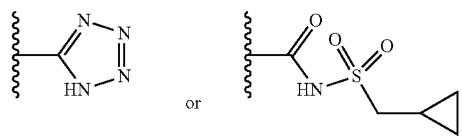

$R^c$ and $R^d$ are each independently H or $C_1$-$C_3$alkyl;

$R^f$ is H or $C_1$-$C_3$alkyl; and $R^g$ is H, $C_1$-$C_3$alkyl, $C_1$-$C_3$haloalkyl, $C_3$-$C_5$cycloalkyl, $C(O)C_1$-$C_3$alkyl, or $C_1$-$C_3$alkyl$C_3$-$C_5$cycloalkyl;

or a pharmaceutically acceptable salt thereof.

2. The compound according to claim 1, wherein the compound is of the formula:

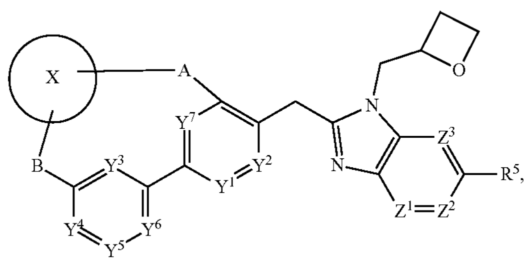

or a pharmaceutically acceptable salt thereof.

3. The compound according to claim 1, wherein

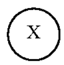

is

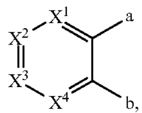

or a pharmaceutically acceptable salt thereof.

4. The compound according to claim 3, wherein $X^1$, $X^3$ and $X^4$ are CH, $X^2$ is $CR^1$ and $R^1$ is CN, Cl, F, $CF_3$,

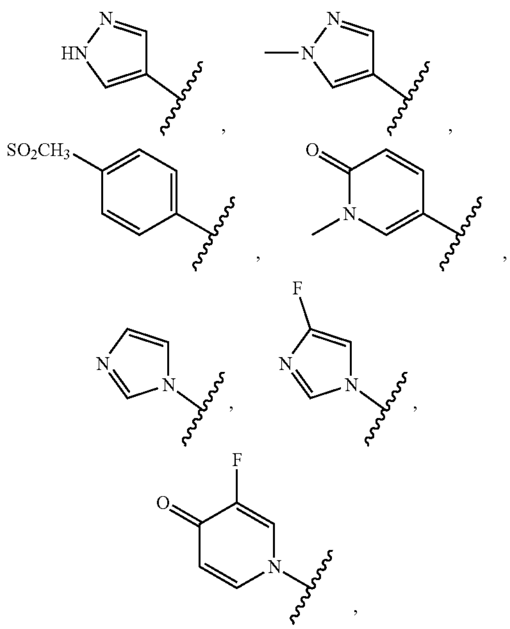

or a pharmaceutically acceptable salt thereof.

5. The compound according to claim 3, wherein $X^1$ is N; $X^2$ is C ($CF_3$); $X^3$ and $X^4$ are CH, or a pharmaceutically acceptable salt thereof.

6. The compound according to claim 3, wherein $X^1$, $X^3$ and $X^4$ are CH; and $X^2$ is N.

7. The compound according to claim 3, wherein $X^1$ and $X^4$ are CH; $X^2$ is C ($CF_3$); and $X^3$ is N.

8. The compound according to claim 3, wherein $X^1$ and $X^3$ are CH; $X^2$ is C (CN); $X^4$ is N.

9. The compound according to claim 3, wherein $X^1$ and $X^3$ are CH; and $X^2$ and $X^4$ are $CR^1$; and each $R^1$ is independently selected from F, Cl and CN, or a pharmaceutically acceptable salt thereof.

10. The compound according to claim 1, wherein

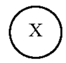

is

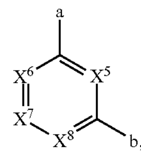

is or a pharmaceutically acceptable salt thereof.

11. The compound according to claim 10, wherein $X^5$, $X^1$ and $X^8$ are CH and $X^6$ is C (CN), or a pharmaceutically acceptable salt thereof.

12. The compound according to claim 10, wherein $X^5$ is N; $X^6$ is C (CN); and $X^7$ and $X^8$ are CH, or a pharmaceutically acceptable salt thereof.

13. The compound according to claim 1, wherein -A- is $—CH_2CH_2CH_2O—$, $—CH_2OCH_2—$, $—CH_2CH_2OCH_2—$, $CH_2OCH_2CH_2—$ or $—CF_2CH_2OCH_2—$, or a pharmaceutically acceptable salt thereof.

14. The compound according to claim 1, wherein —B— is $—CH_2O—$, or a pharmaceutically acceptable salt thereof.

15. The compound according to claim 1, wherein $Y^1$, $Y^2$ and $Y^7$ are all CH, or a pharmaceutically acceptable salt thereof.

16. The compound according to claim 1, wherein $Y^1$ is $CR_2$, $Y^2$ is CH, $Y^7$ is CH and $R^2$ is F, or a pharmaceutically acceptable salt thereof.

17. The compound according to claim 1, wherein $Y^1$ is $CR_2$, $Y^2$ is CH, $Y^7$ is CH and $R^2$ is methyl, or a pharmaceutically acceptable salt thereof.

18. The compound according to claim 1, wherein $Y^3$ is N; and $Y^4$, $Y^5$ are CH; and $Y^6$ is CH or CF, or a pharmaceutically acceptable salt thereof.

19. The compound according to claim 1, wherein $Y^3$, $Y^4$, $Y^5$ and $Y^6$ are all CH, or a pharmaceutically acceptable salt thereof.

20. The compound according to claim 1, wherein $Z^1$ is CH or $CR^3$, and $R^3$ is F, $—OCH_3$, $—OCH_2CH_2OCH_3$, $OCH_2CH_2OH$ or $OCH_2CH_2N(CH_3)_2$, or a pharmaceutically acceptable salt thereof.

21. The compound according to claim 1, wherein $Z^2$ is CH, or a pharmaceutically acceptable salt thereof.

22. The compound according to claim 1, wherein $Z^3$ is CH, or a pharmaceutically acceptable salt thereof.

23. The compound according to claim 1, wherein $R^5$ is $—CO_2H$, or a pharmaceutically acceptable salt thereof.

24. A pharmaceutical composition comprising a compound, or a pharmaceutically acceptable salt thereof, according to claim 1 and at least one pharmaceutically acceptable carrier, diluent, or excipient.

25. A method of treating type II diabetes mellitus in a patient comprising administering to the patient an effective amount of a compound according to claim 1, or a pharmaceutically acceptable salt thereof.

26. A method of lowering blood glucose levels in a patient comprising administering to the patient an effective amount of a compound according to claim 1, or a pharmaceutically acceptable salt thereof.

27. A method of treating hyperglycemia in a patient comprising administering to the patient an effective amount of a compound according to claim 1, or a pharmaceutically acceptable salt thereof.

* * * * *